(12) United States Patent
Purandare et al.

(10) Patent No.: US 8,815,840 B2
(45) Date of Patent: *Aug. 26, 2014

(54) CARBAZOLE AND CARBOLINE KINASE INHIBITORS

(75) Inventors: Ashok Vinayak Purandare, Pennington, NJ (US); Douglas G. Batt, Wilmington, DE (US); Qingjie Liu, Newtown, PA (US); Harold Mastalerz, Guilford, CT (US); Kurt Zimmermann, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 118 days.

This patent is subject to a terminal disclaimer.

(21) Appl. No.: 13/140,184

(22) PCT Filed: Dec. 17, 2009

(86) PCT No.: PCT/US2009/068394
§ 371 (c)(1),
(2), (4) Date: Nov. 21, 2011

(87) PCT Pub. No.: WO2010/080474
PCT Pub. Date: Jul. 15, 2010

(65) Prior Publication Data
US 2012/0058988 A1    Mar. 8, 2012

Related U.S. Application Data

(60) Provisional application No. 61/139,042, filed on Dec. 19, 2008.

(51) Int. Cl.
| | | |
|---|---|---|
| *A61K 31/5377* | (2006.01) |
| *A61K 31/403* | (2006.01) |
| *A61P 7/00* | (2006.01) |
| *A61P 7/02* | (2006.01) |
| *A61P 35/00* | (2006.01) |
| *C07D 403/10* | (2006.01) |
| *C07D 413/08* | (2006.01) |
| *C07D 413/14* | (2006.01) |

(52) U.S. Cl.
USPC .......... 514/210.21; 514/232.8; 540/544; 540/575; 544/130; 544/131; 544/142

(58) Field of Classification Search
USPC .......... 514/210.21, 232.8; 544/142, 131, 130; 540/544, 575
See application file for complete search history.

(56) References Cited

U.S. PATENT DOCUMENTS 5,532,261 A * 7/1996 DiNinno et al. ......... 514/210.14

FOREIGN PATENT DOCUMENTS

WO    WO 2006/034317    3/2006

* cited by examiner

*Primary Examiner* — Kendra D Carter
*Assistant Examiner* — Jason A Deck
(74) *Attorney, Agent, or Firm* — Elliott Korsen; Mary VanAtten

(57) ABSTRACT

The present invention provides compounds of Formula (I)

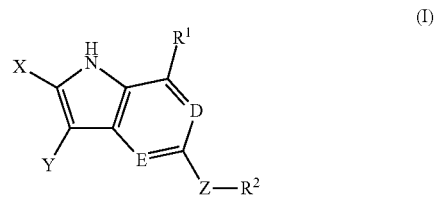

(I)

and pharmaceutically acceptable salts thereof The Formula (I) compounds inhibit tyrosine kinase activity of Jak2, thereby making them useful as antiproliferative agents for the treatment of cancer and other diseases.

6 Claims, No Drawings

CARBAZOLE AND CARBOLINE KINASE INHIBITORS

CROSS REFERENCE TO RELATED APPLICATIONS

The present application is a 371 application of PCT/US2009/068394 filed Dec. 17, 2009, which claims the benefit of U.S. Provisional Application No. 61/139,042, filed Dec. 19, 2008, each of which is incorporated herein by reference in its entirety.

FIELD OF THE INVENTION

This invention relates to novel compounds that are useful as anti-cancer/antiproliferative agents. This invention also relates to a method of using the compounds in the treatment of proliferative diseases, such as cancer, and to pharmaceutical compositions containing the compounds.

BACKGROUND OF THE INVENTION

Efforts to identify new therapeutic approaches to Ph(−) myeloproliferative disease have been bolstered by the observations of constitutive activation of the Jak-Stat signaling pathway in MPD patients. In particular, a single valine to phenylalanine mutation at residue 617 (Jak2-V617F) in Jak2 has been observed in the majority of PV (95%), ET (50-60%) and PMF (50-60%) patients (Table 2, Kralovics et al. (2005); Baxter et al. (2005); Tefferi et al. (2005)). The V617F mutation resides in the region of the Jak2 gene encoding the pseudokinase domain which is thought to function as an autoinhibitory domain to regulate Jak2 tyrosine kinase activity. Mutations in exon 12 of Jak2 which also result in constitutive Jak2 kinase activity are also observed with a lesser frequency (<5% in PV and ET) and are mutually exclusive with Jak2V617F lesions (Pardanari et al. (2007); Scott et al. (2007)). Jak2 is a member of a non-receptor tyrosine kinase family that also includes Jak1, Tyk2 and Jak3 and function as mediators of cytokine receptor signaling (for review see Murray (2007)). Upon cytokine binding to its cognate receptor, receptor-bound Jak family members are activated and phosphorylate a STAT, a latent transcription factor, which upon Jak-mediated phosphorylation undergoes dimerization and translocation to the nucleus to regulate gene expression. Genetic and biochemical studies have established distinct combinations of engagement of a Jak family member with an individual cytokine receptor. For instance, erythropoietin (EPO), thrombopoietin (TPO) and granuolocyte colony stimulating factor (GM-CSF) receptor engagement results in the predominant activation of Jak2 to mediate downstream signaling. Consistent with the pathophysiology of MPD associated with the Jak2-V617F mutation, these cytokines promote the differentiation and expansion of the cell types underlying PV, ET and PMF, respectively. Unlike other genetic activation events, expression of Jak2-V617F is not sufficient to promote transformation in cell based model systems and has been shown to require the co-expression of the type I cytokine receptors, highlighting an important functional co-dependence of the Jak-cytokine receptor interaction (Lu et al. (2005)). Interestingly, activating mutations in the TPO receptor (MPL, tryptophan to leucine substitution at residue 515) have been identified in MPD patients afflicted with Jak2-V617F negative PMF and ET (5% and 1%, respectively) resulting in constitutive Jak2-Stat activation (Pikman et al. (2006)). These observations indicate that Jak-Stat signal transduction can be activated through mutation in MPD at multiple points in the pathway in a mutually exclusive manner and suggest the possible presence of additional pathway mutations in Jak2-V617F and MPL-W515L negative MPD.

Important validation of Jak2 signaling as a driver of Ph(−) MPD emerged from rodent models where Jak2-V617F mutant signaling was reconstituted in the hematopoietic stem cell compartment. Several laboratories demonstrated that viral transduction of Jak2-V617F into mouse bone marrow and subsequent re-implantation into recipient mice reconstituted several aspects human MPD (Wernig et al. (2006); Lacout et al. (2006); Bumm et al. (2006); Zaeleskas et al. (2006)). These features included elevated hematocrit, splenomegaly from extramedullary hematopoiesis, granulocytosis and bone marrow fibrosis all which are also manifested in polycythemia vera. Interestingly, unlike the human condition, thrombocytosis was not observed in these murine models and was suggested to be attributable to secondary genetic events that contribute to platelet expansion (Wernig et al. (2006)). Similar reconstitution of the TPO receptor mutation (MPL-W515L) in rodent bone marrow resulted in a myeloproliferative disease with a more rapid onset than Jak2-V617F animals that was reminiscent of primary myelofribosis including splenomegaly, hepatomegaly, and reticulin fibrosis of bone marrow (Pikman et al. (2006)). Also unlike the Jak2-V617F model, mice expressing MPL-W515L displayed dramatic thrombocytosis perhaps indicating a more dominant function of the receptor activation compared to Jak2-V617 in the expansion of this lineage. Nonetheless, these observations collectively underscore the role of both MPL-W515L and Jak2-V617F as driver mutations underlying the progression of human MPD.

A key question to the genetic basis of MPD is the role of additional genetic events that contribute to disease progression beyond Jak2 and MPL. Several lines of evidence suggest additional genetic alterations in MPD disease progression. In fact, mitotic recombination occurs frequently in MPD patients to generate two Jak2-V617F alleles indicating a selection for cell clones homozygous for the mutated kinase (Levine et al. (2005)). In this regard it will be important to develop conditional Jak2-V617F knock-in animals and to determine the phenotypic consequences of the homozygous versus heterozygous Jak2-V617F burden. Additionally, there is evidence for an inherited germline allele that precedes and predisposes patients to acquire Jak2-V617F (Goerttler et al. (2005); Levine et al. (2006)) as well as loss of chromosomal region 20q in some MPD patients. Although MPD conversion AML is observed clinically at moderate levels and activating Jak chromosomal translocations are observed in leukemia, epidemiological data suggest that it is questionable that Jak2-V617F is a genetic driver in this context suggesting additional genetic alterations are required for full leukemic transformation (Theocharides et al. (2007)). These observations notwithstanding, Jak2 inhibition with small molecule inhibitors is sufficient to modulate disease progression in pre-clinically in animal models suggesting that Jak2 activation is sufficient for maintaining MPD (Paradani et al. (2007)). It will be important to identify these additional genetic alterations and decipher how these genetic changes contribute to the disease progression of PV, ET and PMF in the context of Jak2-V617F and MPL-W515L. It will also be important to implement approaches to identify if other Jak2 pathway components are mutated in MPD patients not associated with the acquisition of Jak2-V617F, Jak2 exon12 or MPL-W515L mutations.

SUMMARY OF THE INVENTION

The present invention provides for compounds of Formula (I), pharmaceutical compositions employing such compounds and for methods of using such compounds.

In accordance with the present invention, are compounds of Formula (I)

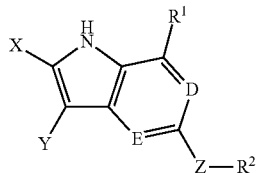

stereoisomers or pharmaceutically acceptable salts, thereof, wherein:
$R^1$ is —$CONH_2$;
D is N or $CR_5$;
E is N, $N^{(+)}$—$O^{(-)}$ or $CR_6$;
X and Y join to form a 5 or 6 membered partially saturated or aromatic carbocyclic ring, substituted with 0-2 $R^4$; or a 5 or 6 membered heterocycle containing 1-2 nitrogen atoms, substituted with 0-2 $R^4$;
Z is a bond, NR, CRR, —CH═CH—, O, or S;
$R^2$ is $C_{3-8}$ cycloalkyl optionally substituted with 0-3 $R^a$, $C_{3-8}$ carbocycle optionally substituted with 0-3 $R^a$, $C_{6-10}$ aryl substituted with 0-3 $R^a$, or a 5-10 membered heterocyclic system containing 1-4 heteroatoms selected from N, O, and S, substituted with 0-3 $R^a$;
$R^4$ is independently hydrogen, halo, $C_{1-6}$ alkyl substituted with 0-3 $R^a$, —CO—$NR^7$—$R^8$, —CO—$NR^7$—$SO_2$—$R^8$, —$(CH_2)_r$O—$R^{10}$, —$(CH_2)_r$$SR^{10}$, —$(CH_2)_r$OC(O)—$R^{10}$, —$NR^7R^8$, —NR—CO—$R^{10}$, —NR—CO—O—$R^9$, NR—CO—$NR^7$—$R^8$, —CO—O—R, $SO_2R^{10}$, a 5-10 membered heterocyclic system containing 1-4 heteroatoms selected from N, O, and S, substituted with 0-3 $R^a$;
$R^5$ and $R^6$ are independently H, halo, or $C_{1-4}$ alkyl;
R is independently H, or $C_{1-4}$ alkyl;
$R^7$ and $R^8$ are independently hydrogen, $C_{1-6}$ alkyl substituted with 0-2 $R^{7a}$, $C_{3-6}$ cycloalkyl substituted with 0-2 $R^{7a}$, a 5-7 membered heterocyclic system containing 1-2 heteroatoms selected from N, O, and S, substituted with 0-2 $R^{7a}$; a 5-6 membered heteroaryl containing 1-2 heteroatoms selected from N, O, and S, substituted with 0-2 $R^{7a}$; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$;
$R^{7a}$ is hydrogen, C═O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle comprising carbon atoms and 1-4 heteroatoms selected from N, O, and $S(O)_p$ substituted with 0-2 $R^a$, alternatively two $R^{7a}$ on adjacent or the same carbon atom form a cyclic acetal of the formula —O—$(CH_2)_n$—O—, wherein n is selected from 1 or 2;
$R^9$ is $C_{1-6}$ alkyl optionally substituted with 0-1$R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$;
$R^{10}$ is hydrogen, $C_{1-6}$ alkyl optionally substituted with 0-1 $R^a$, $C_{3-6}$ cycloalkyl optionally substituted with 0-1 $R^a$, $C_{6-10}$ aryl substituted with 0-3 $R^a$, or a 5-10 membered heterocyclic system containing 1-4 heteroatoms selected from N, O, and S, substituted with 0-3 $R^a$; or
$R^{11}$ and $R^{12}$ are independently hydrogen, $C_{1-6}$ alkyl substituted with 0-1 $R^d$, $C_{3-6}$ cycloalkyl substituted with 0-1 $R^d$, or $(CH_2)_r$-phenyl substituted with 0-1 $R^d$; alternatively $R^{11}$ and $R^{12}$, along with nitrogen atom to which they are attached, join to form a 5-10 membered heterocyclic ring containing 1-4 heteroatoms selected from N, O, and S;
$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle substituted with 0-2 $R^b$, or —$(CH_2)_r$-5-7 membered heterocycle comprising carbon atoms and 1-4 heteroatoms selected from N, O, and $S(O)_p$ substituted with 0-2 $R^b$, alternatively two $R^a$ on adjacent or the same carbon atom form a cyclic acetal of the formula —O—$(CH_2)_n$—O—, or —O—$CF_2$—O—, wherein n is selected from 1 or 2;
$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;
$R^c$ is $C_{1-6}$ alkyl, $C_{3-6}$ cycloalkyl, or $(CH_2)_r$-phenyl;
$R^d$ is hydrogen, F, Cl, Br, $OCF_3$, $CF_3$, CN, $NO_2$, —$OR^e$, —$(CH_2)_rC(O)R^b$, —$NR^eR^e$, —$NR^eC(O)OR^e$, $C_{1-6}$ alkyl, or $(CH_2)_r$-phenyl, pyrrolidinyl, imidazolyl, morpholinyl, pyrrazolyl, 1,4-diazepanyl, piperidinyl substituted with 0-1 $R^f$, 1,4-oxazepanyl, piperazinyl, 1,1-dioxothiomorpholinyl;
$R^e$ is hydrogen, $C_{1-6}$ alkyl, $C_{3-6}$ cycloalkyl, or $(CH_2)_r$-phenyl;
$R^f$ is hydrogen, $C_{1-6}$ alkyl, —$COCH_3$, —$CH_2CH_2$—$COCH_3$, —$CH_2CH_2$—$OCH_3$, or morpholinyl;
r is 0, 1, 2, 3, or 4.

DETAILED DESCRIPTION OF THE INVENTION

In accordance with the present invention, there are disclosed compounds of Formula (I)

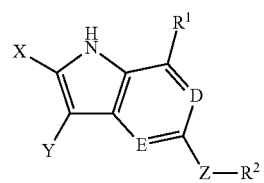

or stereoisomers, tautomers, pharmaceutically acceptable salts, or solvates thereof, wherein:
$R^1$ is —$CONH_2$;
D is N or $CR_5$;
E is N or $CR_6$;
X and Y join to form a 5 or 6 membered partially saturated or aromatic carbocyclic ring, substituted with 0-2 $R^4$; or a 5 or 6 membered heterocycle containing 1-2 nitrogen atoms, substituted with 0-2 $R^4$;
Z is a bond, NR, CRR, O, or S;
$R^2$ is $C_{3-8}$ cycloalkyl optionally substituted with 0-3 $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^4$ is independently halo, —CO—$NR^7$—$R^8$, —CO—$NR^7$—$SO_2$—$R^8$, —$(CH_2)_r$O—$R^{10}$, —$(CH_2)_r$OC(O)—$R^{16}$, —$NR^7R^8$, —NR—CO—$R^{10}$, —NR—CO—O—$R^9$, NR—CO—$NR^7$—$R^8$, —CO—O—R;

$R^5$ and $R^6$ are independently H, or $C_{1-4}$ alkyl;

R is independently H, or $C_{1-4}$ alkyl;

$R^7$ and $R^8$ are independently hydrogen, $C_{1-6}$ alkyl substituted with 0-2 $R^{7a}$, $C_{3-6}$ cycloalkyl substituted with 0-2 $R^{7a}$, a 5-7 membered heterocyclic system containing 1-2 heteroatoms selected from N, O, and S, substituted with 0-2 $R^{7a}$; a 5-6 membered heteroaryl containing 1-2 heteroatoms selected from N, O, and S, substituted with 0-2 $R^{7a}$; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$;

$R^{7a}$ is hydrogen, C=O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OC^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle comprising carbon atoms and 1-4 heteroatoms selected from N, O, and $S(O)_p$ substituted with 0-1 $R^a$, alternatively two $R^{7a}$ on adjacent or the same carbon atom form a cyclic acetal of the formula —O—$(CH_2)_n$—O—, wherein n is selected from 1 or 2;

$R^9$ is $C_{1-6}$ alkyl optionally substituted with 0-1$R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^{10}$ is hydrogen, $C_{1-6}$ alkyl optionally substituted with 0-1 $R^a$, $C_{3-6}$ cycloalkyl optionally substituted with 0-1 $R^a$, $C_{6-10}$ aryl substituted with 0-3 $R^a$, or a 5-10 membered heterocyclic system containing 1-4 heteroatoms selected from N, O, and S, substituted with 0-3 $R^a$; or $R^{11}$ and $R^{12}$ are independently hydrogen, $C_{1-6}$ alkyl substituted with 0-1 $R^d$, $C_{3-6}$ cycloalkyl substituted with 0-1 $R^d$, or $(CH_2)_r$-phenyl substituted with 0-1 $R^d$; alternatively $R^{11}$ and $R^{12}$, along with nitrogen atom to which they are attached, join to form a 5-10 membered heterocyclic ring containing 1-4 heteroatoms selected from N, O, and S;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

r is 0, 1, 2, 3, or 4.

In another embodiment are compounds of Formula (I), wherein:

$R^1$ is —$CONH_2$;

D is N or $CR_5$;

E is N or $CR_6$;

X and Y join to form a 5 or 6 membered partially saturated or aromatic carbocyclic ring, substituted with 0-2 $R^4$; or a 5 or 6 membered heterocycle containing 1-2 nitrogen atoms, substituted with 0-2 $R^4$;

Z is a bond, NR, CRR, O, or S;

$R^2$ is $C_{3-8}$ cycloalkyl optionally substituted with 0-3 $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^4$ is independently halo, —CO—$NR^7$—$R^8$, —CO—$NR^7$—$SO_2$—$R^8$, —$(CH_2)_r$O—$R^{10}$, —$(CH_2)_r$OC(O)—$R^{10}$, —$NR^7R^8$, —NR—CO—$R^{10}$, —NR—CO—O—$R^9$, NR—CO—$NR^7$—$R^8$, —CO—O—R;

$R^5$ and $R^6$ are independently H, or $C_{1-4}$ alkyl;

R is independently H, or $C_{1-4}$ alkyl;

$R^7$ and $R^8$ are independently hydrogen, $C_{1-6}$ alkyl substituted with 0-2 $R^{7a}$, $C_{3-6}$ cycloalkyl substituted with 0-2 $R^{7a}$, a 5-7 membered heterocyclic system containing 1-2 heteroatoms selected from N, O, and S, substituted with 0-2 $R^{7a}$; a 5-6 membered heteroaryl containing 1-2 heteroatoms selected from N, O, and S, substituted with 0-2 $R^{7a}$; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$;

$R^{7a}$ is hydrogen, C=O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle comprising carbon atoms and 1-4 heteroatoms selected from N, O, and $S(O)_p$ substituted with 0-1 $R^a$, alternatively two $R^{7a}$ on adjacent or the same carbon atom form a cyclic acetal of the formula —O—$(CH_2)_n$—O—, wherein n is selected from 1 or 2;

$R^9$ is $C_{1-6}$ alkyl optionally substituted with 0-1$R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^{10}$ is hydrogen, $C_{1-6}$ alkyl optionally substituted with 0-1 $R^a$, $C_{3-6}$ cycloalkyl optionally substituted with 0-1 $R^a$, $C_{6-10}$ aryl substituted with 0-3 $R^a$, or a 5-10 membered heterocyclic system containing 1-4 heteroatoms selected from N, O, and S, substituted with 0-3 $R^a$; or $R^{11}$ and $R^{12}$ are independently hydrogen, $C_{1-6}$ alkyl substituted with 0-1 $R^d$, $C_{3-6}$ cycloalkyl substituted with 0-1 $R^d$, or $(CH_2)_r$-phenyl substituted with 0-1 $R^d$; alternatively $R^{11}$ and $R^{12}$, along with nitrogen atom to which they are attached, join to form a 5-10 membered heterocyclic ring containing 1-4 heteroatoms selected from N, O, and S;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and S(O)$_p$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-2 R$^d$;

R$^c$ is C$_{1-6}$ alkyl, C$_{3-6}$ cycloalkyl, or (CH$_2$)$_r$-phenyl;

R$^d$ is hydrogen, F, Cl, Br, OCF$_3$, CF$_3$, CN, NO$_2$, —OR$^e$, —(CH$_2$)$_r$C(O)R$^b$, —NR$^e$R$^e$, —NR$^e$C(O)OR$^c$, C$_{1-6}$ alkyl, or (CH$_2$)$_r$-phenyl;

R$^e$ is hydrogen, C$_{1-6}$ alkyl, C$_{3-6}$ cycloalkyl, or (CH$_2$)$_r$-phenyl;

r is 0, 1, 2, 3, or 4;

In another embodiment are compounds of Formula (I), wherein:

X and Y join to form a 6 membered partially saturated or aromatic carbocyclic ring, substituted with 0-2 R$^4$; or a 5 or 6 membered heterocycle containing 1-2 nitrogen atoms, substituted with 0-2 R$^4$;

R$^2$ is C$_{6-10}$ aryl substituted with 0-3 R$^a$, or a 5-10 membered heterocyclic system containing 1-4 heteroatoms selected from N, O, and S, substituted with 0-3 R$^a$; and Z is a bond or —CH═CH—.

In another embodiment are compounds of Formula (I), wherein: R$^7$ and R$^8$ are independently hydrogen, C$_{1-6}$ alkyl substituted with 0-2 R$^{7a}$, C$_{3-6}$ cycloalkyl substituted with 0-2 R$^{7a}$, —SO$_2$—R, a 5-7 membered heterocyclic system containing 1-2 heteroatoms selected from N, O, and S, substituted with 0-2 R$^{7a}$; a 5-6 membered heteroaryl containing 1-2 heteroatoms selected from N, O, and S, substituted with 0-2 R$^{7a}$; alternatively R$^7$ and R$^8$, along with nitrogen atom to which they are attached, join to form a 5-10 membered heterocyclic ring containing 0-1 additional heteroatoms selected from N, O or S, substituted with 0-2 R$^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl,

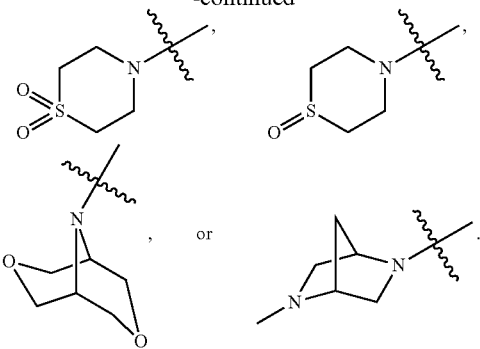

In another embodiment are compounds of Formula (I), wherein R$^7$ and R$^8$ are independently hydrogen, C$_{1-6}$ alkyl substituted with 0-2 R$^{7a}$, C$_{3-6}$ cycloalkyl substituted with 0-2 R$^{7a}$, —SO$_2$—R, a 5-7 membered heterocyclic system containing 1-2 heteroatoms selected from N, O, and S, substituted with 0-2 R$^{7a}$, wherein the heterocyclic system is selected from piperidinyl, pyrrolidinyl, azetidinyl, azepanyl, piperazinyl, morpholinyl, oxazepanyl, and tetrahydropyranyl; a 5-6 membered heteroaryl containing 1-2 heteroatoms selected from N, O, and S, substituted with 0-2 R$^{7a}$, wherein the heteroaryl is pyridinyl, pyrrolidinyl, or imidazolyl; alternatively R$^7$ and R$^8$, along with nitrogen atom to which they are attached, join to form a 5-10 membered heterocyclic ring containing 0-1 additional heteroatoms selected from N, O or S, substituted with 0-2 R$^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl,

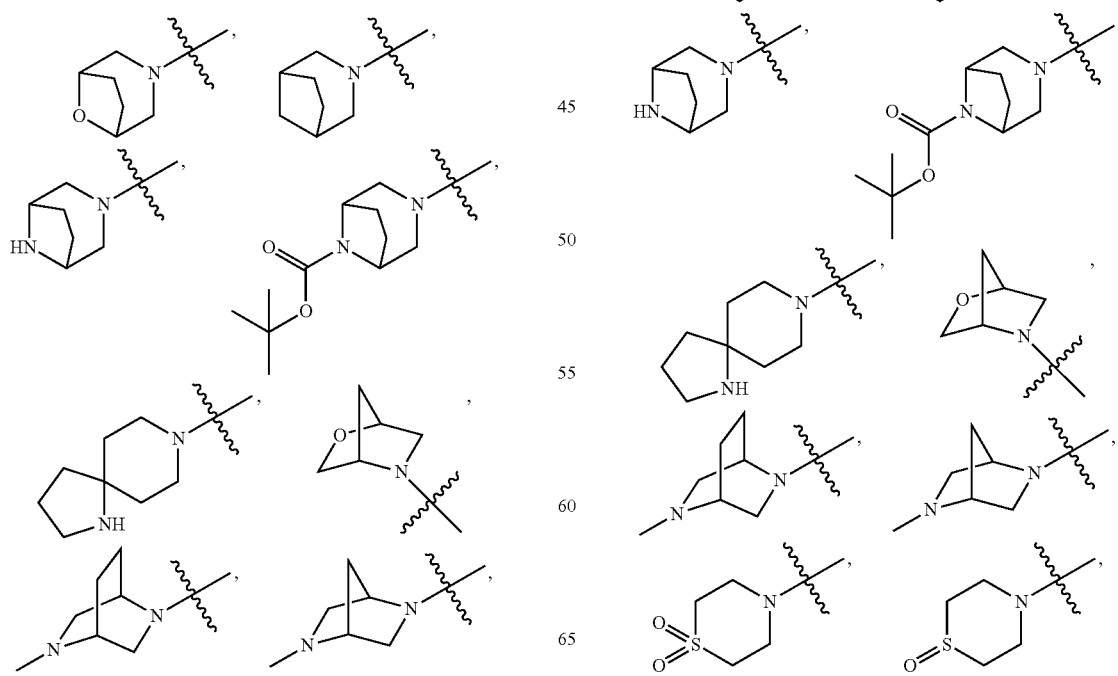

-continued

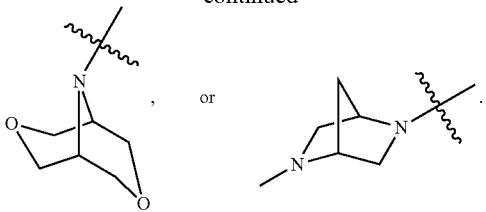

In another embodiment are compounds of Formula (I), wherein $R^{7a}$ is hydrogen, C=O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{12}$, —(CH$_2$)$_r$C(O)NR$^{11}$R$^{12}$, —(CH$_2$)$_r$NR$^b$C(O)R$^c$, —(CH$_2$)$_r$NR$^b$C(O)OR$^c$, —NR$^b$C(O)NR$^{11}$R$^{12}$, —S(O)$_p$NR$^{11}$R$^{12}$, —NR$^b$S(O)$_p$R$^c$, —S(O)R$^c$, —S(O)$_2$R$^c$, C$_{1-6}$ haloalkyl, —(CH$_2$)$_r$-3-14 membered carbocycle substituted with 0-1 R$^a$, or a —(CH$_2$)$_r$-5-7 membered heterocycle comprising carbon atoms and 1-4 heteroatoms selected from N, O, and S(O)$_p$ substituted with 0-2 R$^a$, wherein the heterocycle is selected from morpholinyl, piperazinyl, pyrrolidinyl, piperidinyl, pyrrolidinyl, pyrrolyl, diazepinyl, azetidinyl, imidazolyl, tetrahydropyranyl, azabicyclooctanyl, azabicycloheptanyl, or azaoxobicyclooctanyl; alternatively two R$^{7a}$ on adjacent or the same carbon atom form a cyclic acetal of the formula —O—(CH$_2$)$_n$—O—, wherein n is selected from 1 or 2.

In another embodiment are compounds of Formula (I), wherein:
$R^9$ is C$_{1-6}$ alkyl optionally substituted with 0-1R$^a$, or piperidinyl substituted with 0-3 R$^a$;
$R^{10}$ is hydrogen, C$_{1-6}$ alkyl optionally substituted with 0-1 R$^a$, C$_{3-6}$ cycloalkyl optionally substituted with 0-1 R$^a$, phenyl substituted with 0-3 R$^a$, or a 5-10 membered heterocyclic system containing 1-4 heteroatoms selected from N, O, and S, substituted with 0-3 R$^a$, wherein the heterocycle is selected from piperidinyl, pyrrolidinyl, or tetrahydropyranyl; or
$R^{11}$ and $R^{12}$ are independently hydrogen, C$_{1-4}$ alkyl substituted with 0-1 R$^d$, alternatively $R^{11}$ and $R^{12}$, along with nitrogen atom to which they are attached, join to form a 5-10 membered heterocyclic ring containing 1-4 heteroatoms selected from N, O, and S, wherein the heterocycle is selected from morpholinyl, piperidinyl, pyrrolidinyl or piperazinyl.

In another embodiment are compounds of Formula (I), wherein the compound of formula I is selected from

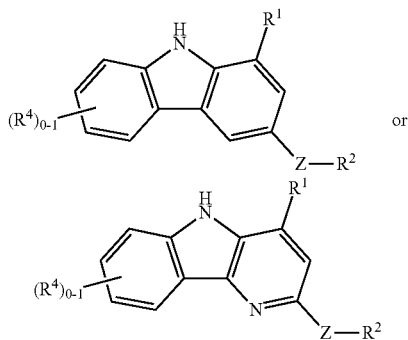

and
Z is a bond or alkenyl.

In another embodiment are compounds of Formula (I), wherein:
D is CR$_5$;
E is N or CR$_6$;
Z is a bond;

$R^2$ is phenyl, naphthyl, pyridyl, benzodioxolyl, any of which are substituted with 0-3 R$^a$;
$R^4$ is independently halo, —CO—NR$^7$-R$^8$, —(CH$_2$)$_r$—O—R$^{10}$, —NR$^7$R$^8$, —NH—CO—R$^{10}$, —NH—CO—O—R$^9$, NH—CO—NR$^7$—R$^8$, —CO—O—R, C$_{1-6}$ alkyl substituted with 0-1 R$^d$, a 5-10 membered heterocyclic system containing 1-4 heteroatoms selected from N, O, and S, substituted with 0-3 R$^a$;
$R^5$ and $R^6$ are H;
$R^7$ and $R^8$ are independently hydrogen; C$_{1-6}$ alkyl substituted with 0-2 R$^{7a}$, wherein the alkyl is selected from methyl, ethyl, or propyl; cyclohexyl substituted with 0-2 R$^{7a}$; —SO$_2$—R; a 5-7 membered heterocyclic system containing 1-2 heteroatoms selected from N, O, and S, substituted with 0-2 R$^{7a}$, wherein the heterocyclic system is selected from piperidinyl, pyrrolidinyl, azetidinyl, and tetrahydropyranyl; alternatively $R^7$ and $R^8$, along with nitrogen atom to which they are attached, join to form a 5-10 membered heterocyclic ring containing 0-1 additional heteroatoms selected from N, O or S, substituted with 0-2 R$^{7a}$, the heterocyclic ring being selected from oxaazobicyclooctanyl, piperidinyl, morpholinyl, oxazabicycloheptanyl, piperazinyl, diazapenyl, pyrrolidinyl,

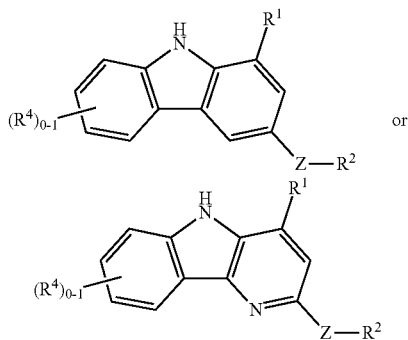

$R^{7a}$ is hydrogen, C=O, F, Cl, Br, CF$_3$, CN, NO$_2$, —(CH$_2$)$_r$OR$^b$, —(CH$_2$)$_r$C(O)R$^b$, —C(O)OR$^b$, —(CH$_2$)$_r$NR$^{11}$R$^{12}$, —(CH$_2$)$_r$C(O)NR$^{11}$R$^{12}$, —(CH$_2$)$_r$NR$^b$C(O)R$^c$, —(CH$_2$)$_r$NR$^b$C(O)OR$^c$, —S(O)$_2$R$^c$, C$_{1-6}$ alkyl, —(CH$_2$)$_r$-phenyl substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$, wherein the heterocycle is selected from piperidinyl, pyridinyl, pyrrolyl, morpholinyl, piperazinyl, imidazoyl, alternatively two R$^{7a}$ on adjacent or the same carbon atom form a cyclic acetal of the formula —O—(CH$_2$)$_n$—O—, wherein n is selected from 1 or 2;

R$^9$ is C$_{1-6}$ alkyl optionally substituted with 0-1 R$^a$, wherein the alkyl is selected from methyl, ethyl, propyl, isopropyl, butyl, and t-butyl; or piperidinyl;

R$^{10}$ is hydrogen, methyl, ethyl, propyl, isopropyl, or butyl; a piperidinyl substituted with 0-1 R$^a$.

In another embodiment are compounds of Formula (I), wherein:

R$^a$ is hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{12}$, —(CH$_2$)$_r$C(O))NR$^{11}$R$^{12}$, —(CH$_2$)$_r$NR$^b$C(O)R$^c$, —(CH$_2$)$_r$NR$^b$C(O)OR$^c$, —NR$^b$C(O)NR$^{11}$R$^{12}$, —S(O)$_p$NR$^{11}$R$^{12}$, —NR$^b$S(O)$_p$R$^c$, —S(O)R$^c$, —S(O)$_2$R$^c$, C$_{1-6}$ alkyl, C$_{1-6}$ haloalkyl, —(CH$_2$)$_r$-3-14 membered carbocycle substituted with 0-2 R$^b$, or —(CH$_2$)$_r$-5-7 membered heterocycle comprising carbon atoms and 1-4 heteroatoms selected from N, O, and S(O)$_p$ substituted with 0-2 R$^b$, wherein the heterocycle is selected from pyrrolidinyl, morpholinyl, pyridinyl, or piperizinyl, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-2 R$^d$;

R$^c$ is C$_{1-6}$ alkyl, C$_{3-6}$ cycloalkyl, or (CH$_2$)$_r$-phenyl;

R$^d$ is hydrogen, F, Cl, Br, OCF$_3$, CF$_3$, CN, NO$_2$, —OR$^e$, —(CH$_2$)$_r$C(O)R$^b$, —NR$^e$R$^e$, —NR$^e$C(O)OR$^c$, C$_{1-6}$ alkyl, or (CH$_2$)$_r$-phenyl, pyrrolidinyl, imidazolyl, morpholinyl, pyrazolyl, 1,4-diazepanyl, piperidinyl substituted with 0-1 R$^f$, 1,4-oxazepanyl, piperazinyl, 1,1-dioxothiomorpholinyl;

R$^e$ is hydrogen, C$_{1-6}$ alkyl, C$_{3-6}$ cycloalkyl or (CH$_2$)$_r$-phenyl;

R$^f$ is hydrogen, C$_{1-6}$ alkyl, —COCH$_3$, —CH$_2$CH$_2$—COCH$_3$, —CH$_2$CH$_2$—OCH$_3$, or morpholinyl;

r is 0, 1, 2, or 3;

In another embodiment are compounds of Formula (I), wherein:

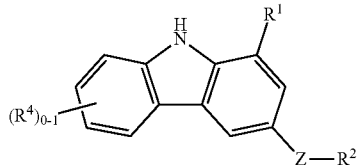

or pharmaceutically acceptable salt thereof.

In another embodiment are compounds of Formula (I), wherein

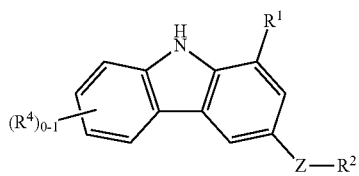

or pharmaceutically acceptable salt thereof, wherein:

Z is a bond;

R$^2$ is phenyl substituted with 0-3 R$^a$, or a 5-10 membered heterocyclic system containing 1-4 heteroatoms selected from N, O, and S, substituted with 0-3 R$^a$, wherein the heterocyclic system is pyridyl, indazolyl, pyrazolyl, furanyl, thiazolyl, indolyl, or thiophenyl;

R$^4$ is independently —CO—NR$^7$—R$^8$, or a 5-10 membered heterocyclic system containing 1-4 heteroatoms selected from N, O, and S, substituted with 0-3 R$^a$, wherein the heterocyclic system is piperidinyl, piperazinyl, pyrrolidinyl, or morpholinyl;

R$^7$ and R$^8$ are independently hydrogen, C$_{1-3}$ alkyl substituted with 0-2 R$^{7a}$; alternatively R$^7$ and R$^8$, along with nitrogen atom to which they are attached, join to form a 5-10 membered morpholinyl, pyrrolidinyl piperazinyl or piperidinyl ring, any of which is substituted with 0-2 R$^{7a}$;

R$^{7a}$ is hydrogen, F, Cl, Br, CN, NO$_2$, —(CH$_2$)$_r$OR$^b$, —C(O)R$^b$, —C(O)OR$^b$, —(CH$_2$)$_r$NR$^{11}$R$^{12}$, R$^b$C(O)OR$^c$, C$_{1-6}$ alkyl substituted with 0-2 R$^a$, —(CH$_2$)$_r$-phenyl substituted with 0-1 R$^a$, or —(CH$_2$)$_r$-5-7 membered heterocycle comprising carbon atoms and 1-4 heteroatoms selected from N, O, and S(O)$_p$ substituted with 0-2 R$^a$ wherein the heterocycle is selected from morpholinyl or piperidinyl, alternatively two R$^{7a}$ on adjacent or the same carbon atom form a cyclic acetal of the formula —O—(CH$_2$)$_n$—O—, wherein n is selected from 1 or 2;

R$^{11}$ and R$^{12}$ are independently hydrogen, C$_{1-4}$ alkyl substituted with 0-1 R$^d$;

R$^a$ is hydrogen, F, Cl, Br, OCF$_3$, CF$_3$, CHF$_2$, CN, —(CH$_2$)$_r$OR$^b$, —C(O)R$^b$, —C(O)OR$^b$, OC(O)R$^b$, —(CH$_2$)$_r$NR$^{11}$R$^{12}$, —(CH$_2$)$_r$C(O)NR$^{11}$R$^{12}$, —(CH$_2$)$_r$NR$^b$C(O)R$^c$, —(CH$_2$)$_r$NR$^b$C(O)OR$^c$, —NR$^b$C(O)NR$^{11}$R$^{12}$, —S(O)$_p$NR$^{11}$R$^{12}$, —NR$^b$S(O)$_p$R$^c$, —S(O)R$^c$, —S(O)$_2$R$^c$, C$_{1-6}$ alkyl, C$_{1-6}$ haloalkyl, —(CH$_2$)$_r$-3-14 membered carbocycle substituted with 0-2 R$^b$, wherein the carbocycle is cyclopropyl or cyclohexyl, or —(CH$_2$)$_r$-5-7 membered heterocycle comprising carbon atoms and 1-4 heteroatoms selected from N, O, and S(O)$_p$ substituted with 0-2 R$^b$, wherein the heterocycle is selected from pyrrolidinyl, morpholinyl, pyridinyl, or piperizinyl, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$haloalkyl, C$_{3-6}$cycloalkyl substituted with 0-2 R$^d$, or (CH$_2$)$_r$-phenyl substituted with 0-2 R$^d$; and R is 0, 1, 2, or 3.

In another embodiment are compounds of Formula (I), wherein:

X and Y join to form a 6 membered partially saturated or aromatic carbocyclic ring, substituted with 0-2 R$^4$; or a 5 or 6 membered heterocycle containing 1-2 nitrogen atoms, substituted with 0-2 R$^4$;

R$^2$ is C$_{6-10}$ aryl substituted with 0-3 R$^a$, or a 5-10 membered heterocyclic system containing 1-4 heteroatoms selected from N, O, and S, substituted with 0-3 R$^a$.

In another embodiment are compounds of Formula (I), wherein R$^7$ and R$^8$ are independently hydrogen, C$_{1-6}$ alkyl substituted with 0-2 R$^{7a}$, C$_{3-6}$cycloalkyl substituted with 0-2 R$^{7a}$, —SO$_2$—R, a 5-7 membered heterocyclic system containing 1-2 heteroatoms selected from N, O, and S, substituted with 0-2 R$^{7a}$; a 5-6 membered heteroaryl containing 1-2 heteroatoms selected from N, O, and S, substituted with 0-2 R$^{7a}$; alternatively R$^7$ and R$^8$, along with nitrogen atom to which they are attached, join to form a 5-10 membered heterocyclic ring containing 0-1 additional heteroatoms selected from N, O or S, substituted with 0-2 R$^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl.

In another embodiment are compounds of Formula (I), wherein R$^7$ and R$^8$ are independently hydrogen, C$_{1-6}$ alkyl substituted with 0-2 R$^{7a}$, C$_{3-6}$cycloalkyl substituted with 0-2

$R^{7a}$, —$SO_2$—R, a 5-7 membered heterocyclic system containing 1-2 heteroatoms selected from N, O, and S, substituted with 0-2 $R^{7a}$, wherein the heterocyclic system is selected from piperidinyl, pyrrolidinyl, azetidinyl, azepanyl, piperazinyl, morpholinyl, oxazepanyl, and tetrahydropyranyl; a 5-6 membered heteroaryl containing 1-2 heteroatoms selected from N, O, and S, substituted with 0-2 $R^{7a}$, wherein the heteroaryl is pyridinyl, pyrrolidinyl, or imidazolyl; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl.

In another embodiment are compounds of Formula (I), wherein $R^{7a}$ is hydrogen, C=O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle substituted with 0-1 $R^a$, or a —$(CH_2)_r$-5-7 membered heterocycle comprising carbon atoms and 1-4 heteroatoms selected from N, O, and $S(O)_p$ substituted with 0-1 $R^a$, wherein the heterocycle is selected from morpholinyl, piperazinyl, pyrrolidinyl, piperidinyl, pyrrolidinyl, pyrrolyl, diazepinyl, azetidinyl, imidazolyl, tetrahydropyranyl, azabicyclooctanyl, azabicycloheptanyl, or azaoxobicyclooctanyl; alternatively two $R^{7a}$ on adjacent or the same carbon atom form a cyclic acetal of the formula —O—$(CH_2)_n$—O—, wherein n is selected from 1 or 2.

In another embodiment are compounds of Formula (I), wherein the compound of Formula (I) is selected from

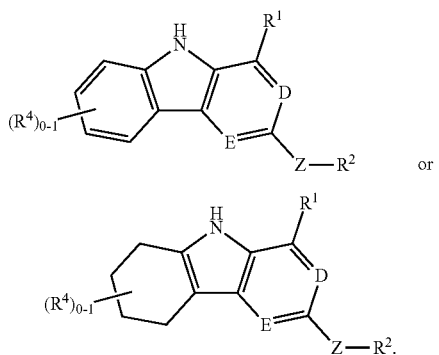

In another embodiment are compounds of Formula (I), wherein the compound of Formula (I) is selected from

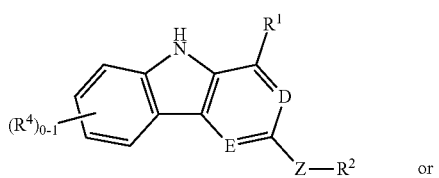

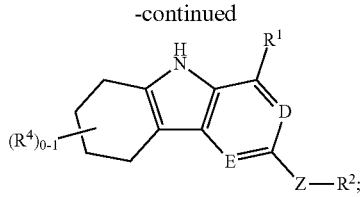

D is $CR_5$;

E is N or $CR_6$;

Z is a bond;

$R^2$ is phenyl, naphthyl, pyridyl, benzodioxolyl, any of which are substituted with 0-3 $R^a$;

$R^4$ is independently halo, —CO—$NR^7$—$R^8$, —O—$R^{10}$, —$NH_2$, —NH—CO—$R^{10}$, —NH—CO—O—$R^9$, NH—CO—$NR^7$—$R^8$, —CO—O—R, $C_{1-6}$ alkyl substituted with 0-1 $R^d$;

$R^5$ and $R^6$ are H;

$R^7$ and $R^8$ are independently hydrogen; $C_{1-6}$ alkyl substituted with 0-2 $R^{7a}$, wherein the alkyl is selected from methyl, ethyl, or propyl; cyclohexyl substituted with 0-2 $R^{7a}$; —$SO_2$—R; a 5-7 membered heterocyclic system containing 1-2 heteroatoms selected from N, O, and S, substituted with 0-2 $R^{7a}$, wherein the heterocyclic system is selected from piperidinyl, pyrrolidinyl, azetidinyl, and tetrahydropyranyl; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, the heterocyclic ring being selected from oxaazobicyclooctanyl, piperidinyl, morpholinyl, oxazabicycloheptanyl, piperazinyl, diazapenyl, pyrrolidinyl;

$R^{7a}$ is hydrogen, C=O, F, Cl, Br, $CF_3$, CN, $NO_2$, —$(CH_2)_rOR^b$, —$(CH_2)_rC(O)R^b$, —$C(O)OR^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$S(O)_2R^c$, $C_{1-6}$ alkyl, —$(CH_2)_r$-phenyl substituted with 0-1 $R^a$, or —$(CH_2)_r$-5-7 membered heterocycle comprising carbon atoms and 1-4 heteroatoms selected from N, O, and $S(O)_p$ substituted with 0-1 $R^a$, wherein the heterocycle is selected from piperidinyl, pyridinyl, pyrrolyl, morpholinyl, piperazinyl, imidazyl, alternatively two $R^7$a on adjacent or the same carbon atom form a cyclic acetal of the formula —O—$(CH_2)_n$—O—, wherein n is selected from 1 or 2;

$R^9$ is $C_{1-6}$ alkyl optionally substituted with 0-1 $R^a$, wherein the alkyl is selected from methyl, ethyl, propyl, isopropyl, butyl, and t-butyl; or piperidinyl;

$R^{10}$ is hydrogen, methyl, ethyl, propyl, isopropyl, or butyl; a piperidinyl substituted with 0-1 $R^a$.

In another embodiment are compounds of Formula (I), wherein the compound of Formula (I) is:

-continued

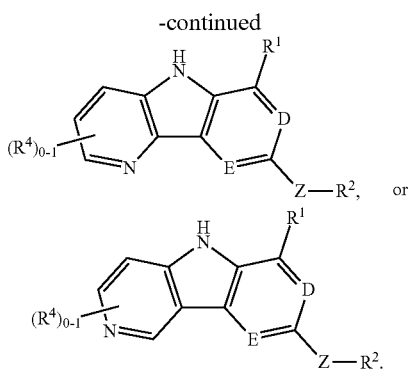

In another embodiment are compounds of Formula (I), wherein the compound of Formula (I) is:

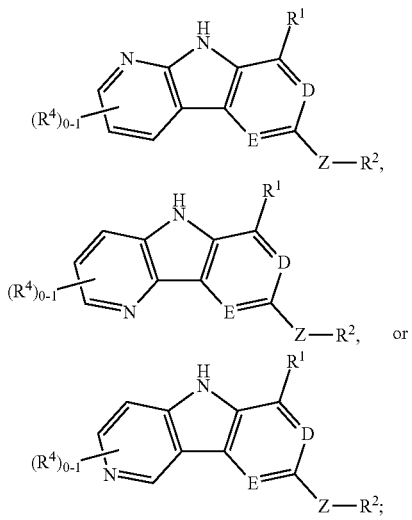

and wherein:
D is $CR_5$;
E is N or $CR_6$.

In another embodiment are compounds of Formula (I), wherein the compound of Formula (I) is:

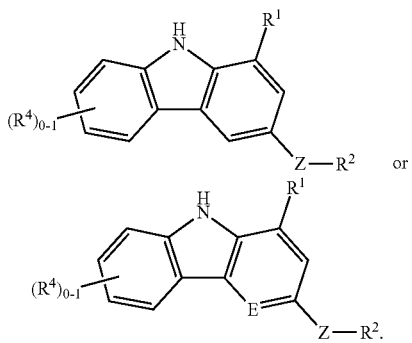

In another embodiment are compounds of Formula (I), wherein X and Y join to form a 6 membered partially saturated or aromatic carbocyclic ring, substituted with 0-2 $R^4$.

In another embodiment are compounds of Formula (I), wherein X and Y join to form a 5 or 6 membered partially saturated or aromatic carbocyclic ring, substituted with 0-2 $R^4$; or a 5 or 6 membered heterocycle containing 1 nitrogen atoms, substituted with 0-2 $R^4$.

In another embodiment are compounds of Formula (I), wherein $R^2$ is phenyl, naphthyl, pyridyl, benzodioxolyl, any of which are substituted with 0-3 $R^a$.

In another embodiment are compounds of Formula (I), wherein $R^4$ is independently halo, —CO—$NR^7$—$R^8$, —O—$R^{10}$, —$NH_2$, —NH—CO—$R^{10}$, —NH—CO—O—$R^9$, NH—CO—$NR^7$—$R^8$, —CO—O—R, $C_{1-6}$ alkyl substituted with 0-1 $R^d$.

In another embodiment are compounds of Formula (I), wherein $R^5$ and $R^6$ are H.

In another embodiment are compounds of Formula (I), wherein $R^7$ and $R^8$ are independently hydrogen; $C_{1-6}$ alkyl substituted with 0-2 $R^{7a}$, wherein the alkyl is selected from methyl, ethyl, or propyl; cyclohexyl substituted with 0-2 $R^{7a}$; —$SO_2$—R; a 5-7 membered heterocyclic system containing 1-2 heteroatoms selected from N, O, and S, substituted with 0-2 $R^{7a}$, wherein the heterocyclic system is selected from piperidinyl, pyrrolidinyl, azetidinyl, and tetrahydropyranyl; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, the heterocyclic ring being selected from oxaazobicyclooctanyl, piperidinyl, morpholinyl, oxazabicycloheptanyl, piperazinyl, diazapenyl, pyrrolidinyl.

In another embodiment are compounds of Formula (I), wherein $R^{7a}$ is hydrogen, C=O, F, Cl, Br, $CF_3$, CN, $NO_2$, —$(CH_2)_rOR^b$, —$(CH_2)_rC(O)R^b$, —$C(O)OR^b$, —$(CH_2)_r$$NR^{11}R^{12}$, —$(CH_2)_rC(O)NR^{11}R^{12}$, —$(CH_2)_rNR^bC(O)R^c$, —$(CH_2)_rNR^bC(O)OR^c$, —$S(O)_2R^c$, $C_{1-6}$ alkyl, —$(CH_2)_r$-phenyl substituted with 0-1 $R^a$, or —$(CH_2)_r$-5-7 membered heterocycle comprising carbon atoms and 1-4 heteroatoms selected from N, O, and $S(O)_p$ substituted with 0-1 $R^a$, wherein the heterocycle is selected from piperidinyl, pyridinyl, pyrrolyl, morpholinyl, piperazinyl, imidazyl, alternatively two $R^{7a}$ on adjacent or the same carbon atom form a cyclic acetal of the formula —O—$(CH_2)_n$—O—, wherein n is selected from 1 or 2.

In another embodiment are compounds of Formula (I), wherein $R^9$ is $C_{1-6}$ alkyl optionally substituted with 0-1 $R^a$, wherein the alkyl is selected from methyl, ethyl, propyl, isopropyl, butyl, and t-butyl; or piperidinyl.

In another embodiment are compounds of Formula (I), wherein $R^{10}$ is hydrogen, methyl, ethyl, propyl, isopropyl, or butyl; a piperidinyl substituted with 0-1 $R^a$.

In another embodiment are compounds of formula (I), wherein the compound is

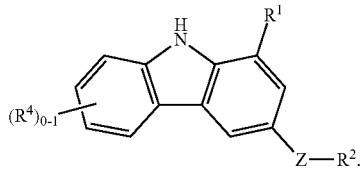

In another embodiment are compounds of formula (I), wherein the compound is

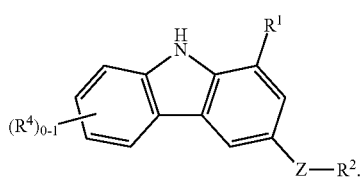

In another embodiment are compounds of formula (I), wherein Z is a bond or —CH=CH—. In another embodiment are compounds of formula (I), wherein Z is a bond.

In another embodiment are compounds of formula (I), wherein $R^2$ is $C_{6-10}$ aryl substituted with 0-3 $R^a$, or a 5-10 membered heterocyclic system containing 1-4 heteroatoms selected from N, O, and S, substituted with 0-3 $R^a$. In another embodiment are compounds of formula (I), wherein $R^2$ is phenyl, naphthyl, pyridyl, benzodioxolyl, any of which are substituted with 0-3 $R^a$. In another embodiment are compounds of formula (I), wherein $R^2$ is phenyl substituted with 0-3 $R^a$, or a 5-10 membered heterocyclic system containing 1-4 heteroatoms selected from N, O, and S, substituted with 0-3 $R^a$, wherein the heterocyclic system is pyridyl, indazolyl, pyrazolyl, furanyl, thiazolyl, indolyl, or thiophenyl.

In another embodiment are compounds of formula (I), wherein $R^4$ is independently halo, —CO—$NR^7$—$R^8$, —$(CH_2)_r$—O—$R^{10}$, —$NR^7R^8$, —NH—CO—$R^{10}$, —NH—CO—O—$R^9$, NH—CO—$NR^7$-$R^8$, —CO—O—R, $C_{1-6}$ alkyl substituted with 0-1 $R^d$, a 5-10 membered heterocyclic system containing 1-4 heteroatoms selected from N, O, and S, substituted with 0-3 $R^a$. In another embodiment are compounds of formula (I), wherein $R^4$ is independently —CO—$NR^7$—$R^8$, or a 5-10 membered heterocyclic system containing 1-4 heteroatoms selected from N, O, and S, substituted with 0-3 $R^a$, wherein the heterocyclic system is piperidinyl, piperazinyl, pyrrolidinyl, or morpholinyl.

In another embodiment are compounds of formula (I), wherein $R^5$ and $R^6$ are H.

In another embodiment are compounds of formula (I), wherein $R^7$ and $R^8$ are independently hydrogen, $C_{1-6}$ alkyl substituted with 0-2 $R^{7a}$, $C_{3-6}$ cycloalkyl substituted with 0-2 $R^{7a}$, —$SO_2$—R, a 5-7 membered heterocyclic system containing 1-2 heteroatoms selected from N, O, and S, substituted with 0-2 $R^{7a}$; a 5-6 membered heteroaryl containing 1-2 heteroatoms selected from N, O, and S, substituted with 0-2 $R^{7a}$; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl,

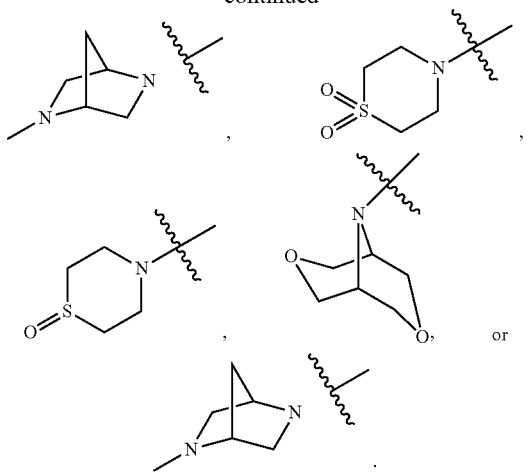

In another embodiment are compounds of formula (I) wherein, $R^7$ and $R^8$ are independently hydrogen, $C_{1-6}$ alkyl substituted with 0-2 $R^{7a}$, $C_{3-6}$ cycloalkyl substituted with 0-2 $R^{7a}$, —$SO_2$—R, a 5-7 membered heterocyclic system containing 1-2 heteroatoms selected from N, O, and S, substituted with 0-2 $R^{7a}$, wherein the heterocyclic system is selected from piperidinyl, pyrrolidinyl, azetidinyl, azepanyl, piperazinyl, morpholinyl, oxazapanyl, and tetrahydropyranyl; a 5-6 membered heteroaryl containing 1-2 heteroatoms selected from N, O, and S, substituted with 0-2 $R^7$a, wherein the heteroaryl is pyridinyl, pyrrolidinyl, or imidazolyl; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, wherein the heterocyclic ring is selected from azetidinyl, pyrrolidinyl, piperidinyl, azepanyl, diazepinyl, piperazinyl, morpholinyl, oxazapanyl, azabicyclooctanyl, azabicycloheptanyl, or azaoxobicyclooctanyl,

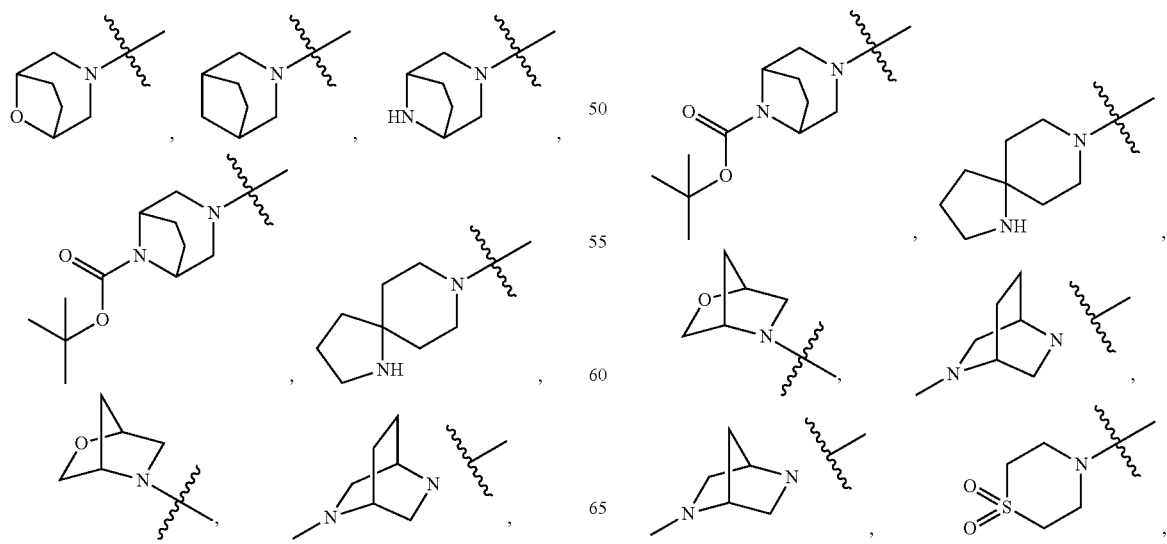

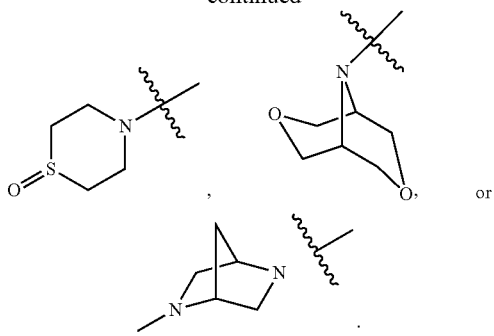
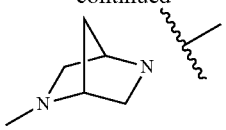

In another embodiment are compounds of formula (I), wherein $R^7$ and $R^8$ are independently hydrogen; $C_{1-6}$ alkyl substituted with 0-2 $R^{7a}$, wherein the alkyl is selected from methyl, ethyl, or propyl; cyclohexyl substituted with 0-2 $R^{7a}$; —$SO_2$—R; a 5-7 membered heterocyclic system containing 1-2 heteroatoms selected from N, O, and S, substituted with 0-2 $R^{7a}$, wherein the heterocyclic system is selected from piperidinyl, pyrrolidinyl, azetidinyl, and tetrahydropyranyl; alternatively $R^7$ and $R^8$, along with nitrogen atom to which they are attached, join to form a 5-10 membered heterocyclic ring containing 0-1 additional heteroatoms selected from N, O or S, substituted with 0-2 $R^{7a}$, the heterocyclic ring being selected from oxaazobicyclooctanyl, piperidinyl, morpholinyl, oxazabicycloheptanyl, piperazinyl, diazapenyl, pyrrolidinyl,

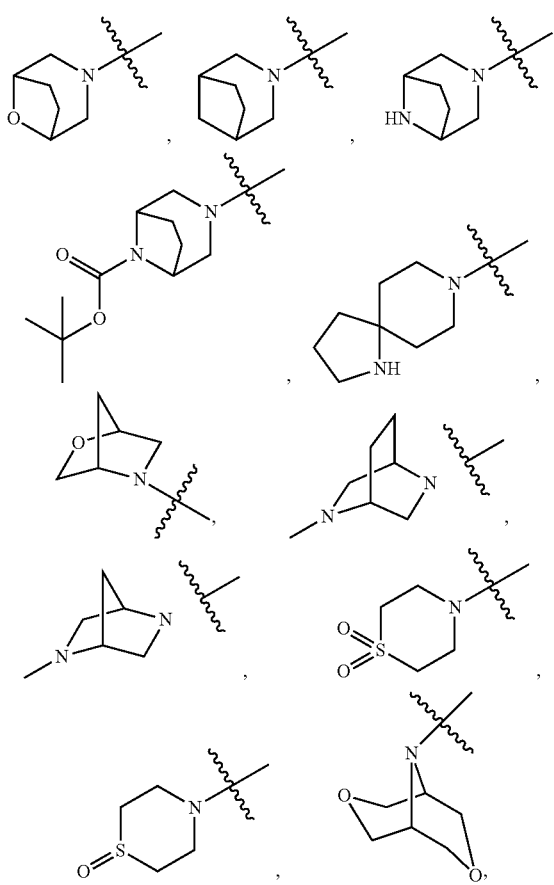

In another embodiment are compounds of formula (I), wherein $R^7$ and $R^8$ are independently hydrogen, $C_{1-3}$ alkyl substituted with 0-2 $R^{7a}$; alternatively $R^7$ and $R^8$, along with nitrogen atom to which they are attached, join to form a 5-10 membered morpholinyl, pyrrolidinyl, piperazinyl or piperidinyl ring, any of which is substituted with 0-2 $R^{7a}$.

In another embodiment are compounds of formula (I), wherein R is independently H, methyl or ethyl.

In another embodiment are compounds of formula (I), wherein $R^7a$ is hydrogen, C=O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS((O)_pF^c$, —$S(O)R^c$, —$S(O)R^c$, —$S(O)_2R^c$, $C_{1-6}$ alkyl, $C_{1-6}$ haloalkyl, —$(CH_2)_r$-3-14 membered carbocycle substituted with 0-1 $R^a$, or a —$(CH_2)_r$-5-7 membered heterocycle comprising carbon atoms and 1-4 heteroatoms selected from N, O, and $S(O)_p$ substituted with 0-2 $R^a$, wherein the heterocycle is selected from morpholinyl, piperazinyl, pyrrolidinyl, piperidinyl, pyrrolidinyl, pyrrolyl, diazepinyl, azetidinyl, imidazolyl, tetrahydropyranyl, azabicyclooctanyl, azabicycloheptanyl, or azaoxobicyclooctanyl; alternatively two $R^{7a}$ on adjacent or the same carbon atom form a cyclic acetal of the formula —O—$(CH_2)_n$—O—, wherein n is selected from 1 or 2.

In another embodiment are compounds of formula (I), wherein $R^7a$ is hydrogen, C=O, F, Cl, Br, $CF_3$, CN, $NO_2$, —$(CH_2)_rOR^b$, —$(CH_2)_rC(O)R^b$, —$C(O)OR^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$S(O)_2R^c$, $C_{1-6}$ alkyl, —$(CH_2)_r$-phenyl substituted with 0-1 $R^a$, or —$(CH_2)_r$-5-7 membered heterocycle comprising carbon atoms and 1-4 heteroatoms selected from N, O, and $S(O)_p$ substituted with 0-1 $R^a$, wherein the heterocycle is selected from piperidinyl, pyridinyl, pyrrolyl, morpholinyl, piperazinyl, imidazoyl, alternatively two $R^{7a}$ on adjacent or the same carbon atom form a cyclic acetal of the formula —O—$(CH_2)_n$—O—, wherein n is selected from 1 or 2;

In another embodiment are compounds of formula (I), wherein $R^{7a}$ is hydrogen, F, Cl, Br, CN, $NO_2$, —$(CH_2)_rOR^b$, —$C(O)R^b$, —$C(O)OR^b$, —$(CH_2)_rNR^{11}R^{12}$, —$NR^bC(O)OR^c$, $C_{1-6}$ alkyl substituted with 0-2 $R^a$, —$(CH_2)_r$-phenyl substituted with 0-1 $R^a$, or —$(CH_2)_r$-5-7 membered heterocycle comprising carbon atoms and 1-4 heteroatoms selected from N, O, and $S(O)_p$ substituted with 0-2 $R^a$ wherein the heterocycle is selected from morpholinyl or piperidinyl, alternatively two $R^{7a}$ on adjacent or the same carbon atom form a cyclic acetal of the formula —O—$(CH_2)_n$—O—, wherein n is selected from 1 or 2.

In another embodiment are compounds of formula (I), wherein $R^9$ is $C_{1-6}$ alkyl optionally substituted with 0-1$R^a$, or piperidinyl substituted with 0-3 $R^a$. In another embodiment are compounds of formula (I), wherein $R^9$ is $C_{1-6}$ alkyl optionally substituted with 0-1 $R^a$, wherein the alkyl is selected from methyl, ethyl, propyl, isopropyl, butyl, and t-butyl; or piperidinyl.

In another embodiment are compounds of formula (I), wherein $R^{10}$ is hydrogen, $C_{1-6}$ alkyl optionally substituted with 0-1 $R^a$, $C_{3-6}$ cycloalkyl optionally substituted with 0-1 $R^a$, phenyl substituted with 0-3 $R^a$, or a 5-10 membered heterocyclic system containing 1-4 heteroatoms selected from N, O, and S, substituted with 0-3 $R^a$, wherein the heterocycle is selected from piperidinyl, pyrrolidinyl, or tetrahydropyranyl. In another embodiment are compounds of formula (I), wherein $R^{10}$ is hydrogen, methyl, ethyl, propyl, isopropyl, or butyl; a piperidinyl substituted with 0-1 $R^a$.

In another embodiment are compounds of formula (I), wherein $R^{11}$ and $R^{12}$ are independently hydrogen, $C_{1-6}$ alkyl substituted with 0-1 $R^d$, $C_{3-6}$ cycloalkyl substituted with 0-1 $R^d$, or $(CH_2)_r$-phenyl substituted with 0-1 $R^d$; alternatively $R^{11}$ and $R^{12}$, along with nitrogen atom to which they are attached, join to form a 5-10 membered heterocyclic ring containing 1-4 heteroatoms selected from N, O, and S. In another embodiment are compounds of formula (I), wherein $R^{11}$ and $R^{12}$ are independently hydrogen, $C_{1-4}$ alkyl substituted with 0-1 $R^d$, alternatively $R^{11}$ and $R^{12}$, along with nitrogen atom to which they are attached, join to form a 5-10 membered heterocyclic ring containing 1-4 heteroatoms selected from N, O, and S, wherein the heterocycle is selected from morpholinyl, piperidinyl, pyrrolidinyl or piperazinyl. In another embodiment are compounds of formula (I), wherein $R^{11}$ and $R^{12}$ are independently hydrogen, $C_{1-4}$ alkyl substituted with 0-1 $R^d$.

In another embodiment, $R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle substituted with 0-2 $R^b$, or —$(CH_2)_r$-5-7 membered heterocycle comprising carbon atoms and 1-4 heteroatoms selected from N, O, and $S(O)_p$ substituted with 0-2 $R^b$, wherein the heterocycle is selected from pyrrolidinyl, morpholinyl, pyridinyl, or piperizinyl, alternatively two $R^a$ on adjacent or the same carbon atom form a cyclic acetal of the formula —O—$(CH_2)_n$—O—, or —O—$CF_2$—O—, wherein n is selected from 1 or 2. In another embodiment, $R^a$ is hydrogen, F, Cl, Br, $OCF_3$, $CF_3$, $CHF_2$, CN, —$(CH_2)_rOR^b$, —$C(O)R^b$, —$C(O)OR^b$, $OC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle substituted with 0-2 $R^b$, wherein the carbocycle is cyclopropyl or cyclohexyl, or —$(CH_2)_r$-5-7 membered heterocycle comprising carbon atoms and 1-4 heteroatoms selected from N, O, and $S(O)_p$ substituted with 0-2 $R^b$, wherein the heterocycle is selected from pyrrolidinyl, morpholinyl, pyridinyl, or piperizinyl, alternatively two $R^a$ on adjacent or the same carbon atom form a cyclic acetal of the formula —O—$(CH_2)_n$—O—, or —O—$CF_2$—O—, wherein n is selected from 1 or 2.

In another embodiment, $R^b$ is hydrogen, $C_{1-6}$ alkyl substituted with 0-2 $R^d$, $C_{1-6}$ haloalkyl, $C_{3-6}$cycloalkyl substituted with 0-2 $R^d$, or $(CH_2)_r$-phenyl substituted with 0-2 $R^d$. In another embodiment, $R^b$ is hydrogen, $C_{1-6}$ alkyl substituted with 0-2 $R^d$, $C_{1-6}$ haloalkyl, $C_{3-6}$cycloalkyl substituted with 0-2 $R^d$, or $(CH_2)_r$-phenyl substituted with 0-2 $R^d$.

In another embodiment, $R^c$ is $C_{1-6}$ alkyl, $C_{3-6}$cycloalkyl, or $(CH_2)_r$-phenyl.

In another embodiment, $R^d$ is hydrogen, F, Cl, Br, $OCF_3$, $CF_3$, CN, $NO_2$, —$OR^e$, —$(CH_2)_rC(O)R^b$, —$NR^eR^e$, —$NR^eC(O)OR^e$, $C_{1-6}$ alkyl, or $(CH_2)_r$-phenyl, pyrrolidinyl, imidazolyl, morpholinyl, pyrrazolyl, 1,4-diazepanyl, piperidinyl substituted with 0-1 $R^f$, 1,4-oxazepanyl, piperazinyl, 1,1-dioxothiomorpholinyl.

In another embodiment, $R^e$ is hydrogen, $C_{1-6}$ alkyl, $C_{3-6}$cycloalkyl, or $(CH_2)_r$-phenyl.

In another embodiment, $R^f$ is hydrogen, $C_{1-6}$ alkyl, —$COCH_3$, —$CH_2CH_2$—$COCH_3$, —$CH_2CH_2$—$OCH_3$, or morpholinyl. In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof In another embodiment, the present invention provides a method for treating proliferative disorders and/or cancer comprising: administering to a patient in need of such treatment a therapeutically effective amount of at least one of the compounds of the present invention or a stereoisomer, tautomer, pharmaceutically acceptable salt, solvate or prodrug thereof, in combination with at least one other anti-cancer agent, or a stereoisomer, tautomer, pharmaceutically acceptable salt, solvate or prodrug thereof In another embodiment, the present invention provides a method for treating proliferative disorders and/or cancer comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method of treating a patient in need of proliferative disorder and/or cancer treatment, comprising: administering a compound of the present invention or a stereoisomer, tautomer, pharmaceutically acceptable salt, solvate, or prodrug form thereof in an amount effective to treat the proliferative disorder and/or cancer.

In another embodiment, the present invention provides a method of treating myeloproliferative diseases(polycythemia vera, essential thrombocytopenia, myelofibrosis), solid tumors of the pancreatic, prostate, lung, head and neck, breast, colon, ovary, gastric cancer as well as other tumor types including multiple myeloma, melanoma, neuroblastoma, glioblastoma and hematological malignancies such as acute myelogenous leukemia.

In another embodiment, the present invention provides a novel method, comprising: administering a compound of the present invention or a stereoisomer, tautomer, pharmaceutically acceptable salt, solvate, or prodrug form thereof in an amount effective to treat a proliferative disorder and/or cancer.

In another embodiment, the present invention provides a compound of the present invention for use in therapy.

In another embodiment, the present invention provides a compound of the present invention for use in therapy for treating a proliferative disorder and/or cancer.

In another embodiment, the present invention also provides the use of a compound of Formula (I) of the present invention for the manufacture of a medicament for the treatment of a proliferative disorder and/or cancer.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. C is and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "cycloalkyl" refers to cyclized alkyl groups, including mono-, bi- or poly-cyclic ring systems. $C_{3-10}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7 membered monocyclic or bicyclic or 7, 8, 9, 10, 11, 12, or 13 membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]

bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7 membered monocyclic or bicyclic or 7, 8, 9, 10, 11, 12, 13, or 14 membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

Also included are smaller heterocyclyls, such as, epoxides and aziridines.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of Formula (I) may exist as a free form (with no ionization) or may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include 13C and 14C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formula (I) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and c) Bundgaard, H., *Adv. Drug Deliv. Rev.*, 8:1-38 (1992);

It should further be understood that solvates (e.g., hydrates) of the compounds of Formula (I) are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa. (1985), which is incorporated herein by reference in its entirety.

UTILITY

The present invention is based on the discovery that certain pyrrolotriazines are inhibitors of protein kinases. More specifically, pyrrolotriazines such as those described in this invention inhibit the protein tyrosine kinase activity of members of the Jak family of receptors, These inhibitors will be useful in the treatment of proliferative diseases that are dependent on signaling by one or more of these receptors. Such diseases include myeloproliferative diseases, solid tumors of the pancreatic, prostate, lung, head and neck, breast, colon, ovary, as well as other tumor types including multiple myeloma, melanoma, neuroblastoma, glioblastoma and hematological malignancies such as acute myelogenous leukemia.

The invention also relates to a pharmaceutical composition of compound of Formula (I), or pharmaceutically acceptable salt thereof, and a pharmaceutically acceptable carrier in the treatment of hyperproliferative disorder in mammal In particular, said pharmaceutical composition is expected to inhibit the growth and/or metastasis of those primary and recurrent solid tumors which are associated with Flt-3 (Fms-like kinase-3), Jak2, Jak3, and JAK1, especially those tumors which are significantly dependent on JAK2, for their growth and spread, including for example, cancers of the blood, thyroid, breast, colon, pancreas, or a variety of tumor types including multiple myeloma, melanoma, neuroblastoma and glioblastoma.

Thus according to a further aspect of the invention there is provided the use of a compound of the Formula (I), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formula (I) or a pharmaceutically acceptable salt thereof as defined herein before.

By virtue of their ability to inhibit Flt-3, Jak2, and Jak3, kinases, compounds of the present invention can be used for the treatment of proliferative diseases, including cancer.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, and teratocarcinoma.

The present invention provides methods for the treatment of leukemia, myeloproliferative diseases (polycythemia vera, essential thrombocytopenia, myelofibrosis), multiple myeloma, colon cancer, breast cancer, and gastric cancer.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of Formula (I) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER[2]

antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; kinase inhibitors, e.g., GLEEVEC® and dasatinib (SPRYCEL®); CASODEX® (bicalutamide, AstraZeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonylpaclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxo-norleucine); ribonucleotide reductase inhibitors; mTOR inhibitors; and hematopoietic growth factors.

Additional cytotoxic agents include cyclophosphamide, doxorubicin, daunorubicin, mitoxantrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formula (I) compounds of the present invention are of interest for their antiproliferative effects. Such compounds of the invention are expected to be useful in a wide range of disease states including cancer, psoriasis, and rheumatoid arthritis.

More specifically, the compounds of Formula (I) are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of Formula (I) are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of Formula (I) may also be useful in the treatment of other cancerous diseases (such as acute myelogenous leukemia).

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formula (I) may also be administered sequentially with known anticancer or cytotoxic agents when a combination formulation is inappropriate. The invention is not limited in the sequence of administration; compounds of Formula (I) may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

DOSAGE AND FORMULATION

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

BIOLOGICAL ASSAYS

JAK2 Tyrosine Kinase Assay

The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM Beta-Glycerolphosphate, 0.015% Brij35 and 4 mM DTT). The reaction was initiated by the combination of JAK2 with substrates and test compounds. The reaction was incubated at room temperature for 60 min. and terminated by adding 45 µl of 35 mM EDTA to each sample. The reaction mixture was analyzed on the Caliper LABCHIP® 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; JAK2 fluorescent peptide, 1.5 µM; JAK2, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis JAK3 Tyrosine Kinase Assay The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM Beta-Glycerolphosphate, 0.015% Brij35 and 4 mM DTT). The reaction was initiated by the combination of JAK3 with substrates and test compounds. The reaction was incubated at room temperature for 60 min. and terminated by adding 45 µl of 35 mM EDTA to each sample. The reaction mixture was analyzed on the Caliper LABCHIP® 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 8 µM; JAK3 fluorescent peptide, 1.5 µM; JAK3, 2.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the JAK2 assay described above. The following results were obtained.

TABLE 1

| Example | JAK2 ($IC_{50}$, uM) |
|---|---|
| 15 | 0.001 |
| 17 | 0.001 |
| 33 | 0.006 |
| 49 | 0.006 |
| 51 | 0.006 |
| 56 | 0.006 |
| 61 | 0.006 |
| 73 | 0.16 |
| 76 | 0.007 |
| 79 | 0.006 |
| 80 | 0.006 |
| 88 | 0.006 |
| 96 | <0.001 |
| 101 | 0.006 |
| 106 | <0.001 |
| 120 | 0.007 |
| 124 | 0.006 |
| 128 | 1.23 |
| 129 | 0.11 |
| 132 | 0.007 |
| 135 | 0.16 |
| 136 | 0.29 |
| 140 | 0.15 |
| 142 | 0.31 |
| 143 | 0.11 |
| 145 | 0.007 |
| 151 | 0.006 |
| 161 | 0.16 |
| 164 | 0.007 |
| 166 | 0.006 |
| 180 | 0.002 |
| 183 | 0.16 |
| 185 | 0.001 |
| 190 | 0.002 |
| 194 | 0.001 |
| 196 | 0.001 |
| 197 | 0.001 |
| 203 | 0.034 |
| 204 | 0.029 |
| 210 | 0.17 |
| 211 | <0.001 |
| 216 | 0.007 |
| 227 | 0.002 |
| 245 | 0.007 |
| 256 | 0.001 |
| 257 | 0.001 |
| 281 | 0.006 |
| 309 | 0.001 |
| 310 | 0.001 |
| 316 | 0.006 |
| 319 | 0.001 |
| 322 | 0.001 |
| 323 | 0.001 |
| 324 | 0.001 |
| 344 | 0.001 |
| 345 | 0.001 |
| 353 | 0.001 |
| 357 | 0.006 |
| 360 | 0.007 |
| 361 | 0.006 |
| 373 | 0.006 |
| 374 | 0.006 |
| 395 | 0.111 |
| 402 | 0.220 |
| 403 | 0.142 |
| 404 | 0.262 |
| 405 | 0.636 |
| 424 | 0.001 |
| 430 | 0.001 |
| 448 | 0.001 |
| 451 | 0.001 |
| 454 | 0.007 |
| 456 | 0.001 |
| 461 | 0.146 |
| 462 | 0.112 |
| 464 | 0.314 |
| 468 | 0.006 |
| 469 | 0.011 |
| 479 | 0.123 |
| 481 | 0.133 |

TABLE 1-continued

| Example | JAK2 (IC$_{50}$, uM) |
|---|---|
| 482 | 0.917 |
| 486 | 0.818 |
| 488 | 0.006 |
| 499 | 0.001 |
| 500 | 0.006 |
| 501 | 0.007 |
| 503 | 0.001 |
| 504 | 0.001 |
| 529 | 0.001 |
| 532 | 0.001 |
| 545 | 0.885 |
| 558 | 0.286 |
| 563 | 1.006 |
| 579 | 0.108 |
| 584 | 0.006 |

Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2,5-diphenyltetrazolium bromide (MTT) dye using the CELL-TITER 96® kit (Promega).

Examples 1-590 have been tested in the JAK2 assay described above and were shown to have activity in that assay with an IC$_{50}$<5 μM.

ABBREVIATIONS

The following abbreviations may be employed in the methods of preparation and Examples:
h=hours
DCM=dichloromethane
THF=tetrahydrofuran
HPLC=high performance liquid chromatography
DIEA=diisopropylethyl amine
i-PrOH=isopropyl alcohol
TFA=trifluoroacetic acid
min=minutes
DMF=dimethylformamide
EDC=N-(3-Dimethylaminopropyl)N'-ethylcarbodiimide
HOBt=hydroxybenzotriazole
NMP=N-methylpyrolidinone
EtOAc=ethyl acetate
AcOH=acetic acid
BOP reagent=benzotriazole-1-yl-oxy-tris-(dimethylamino)-phasphoniumhexafluorophosphate
brine=saturated aqueous sodium chloride solution
Et$_3$N=triethylamine
t$_R$=retention time

METHODS OF PREPARATION

Compounds of general Formula (I) wherein X and Y join to form a 5 or 6 membered saturated or unsaturated optionally substituted ring, Z as bond and R$^2$ as substituted aromatic or heteroaromatic ring were prepared according to general Methods A to F.

Method A (Scheme 1): Suitably halogen substituted hydrazinobenzoic acid such as I (*Molecular Diversity*, 7:161 (2003)) could be condensed with substituted cyclohexanones (II) under acidic condition to give tetrahyroindole carboxylic acids (III) according to the method described in *Chemistry and Pharmaceutical Bulletin*, 52:1071 (2004). Conversion of III to amides IV could be accomplished with ammonium hydroxide in the presence of coupling agent such as EDC and HOBt. Dehydrogenation of IV with DDQ would give carbazoles V. Transition metal mediated coupling of V with suitably functionalized boronic acid or stannane derivative would give VI.

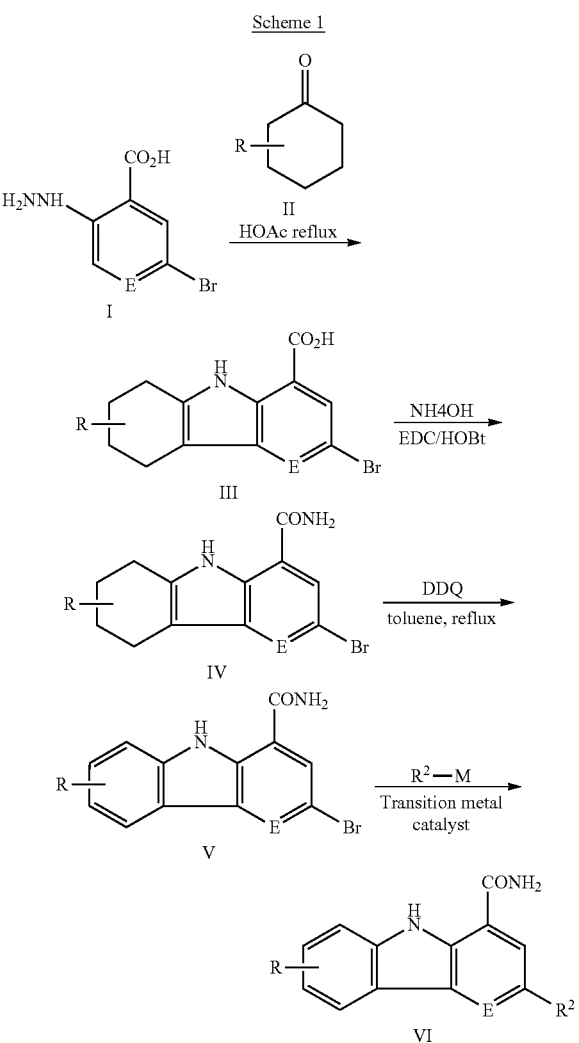

Scheme 1

Method B (Scheme 2): Reaction of fluorobenzene VII with substituted anilines VIII in the presence of base according to the procedure described in *Journal of the Chemical Society, Perkin I*, 1331 (1998) would give diarylamines IX. Transition metal mediated coupling of IX with suitably functionalized boronic acid or stannane derivative would furnish X. Heating X with palladium acetate in acetic acid according to the procedure described in *Journal of Organic Chemistry*, 40:1365 (1975) would give carbazole or carboline (when X=N) VI.

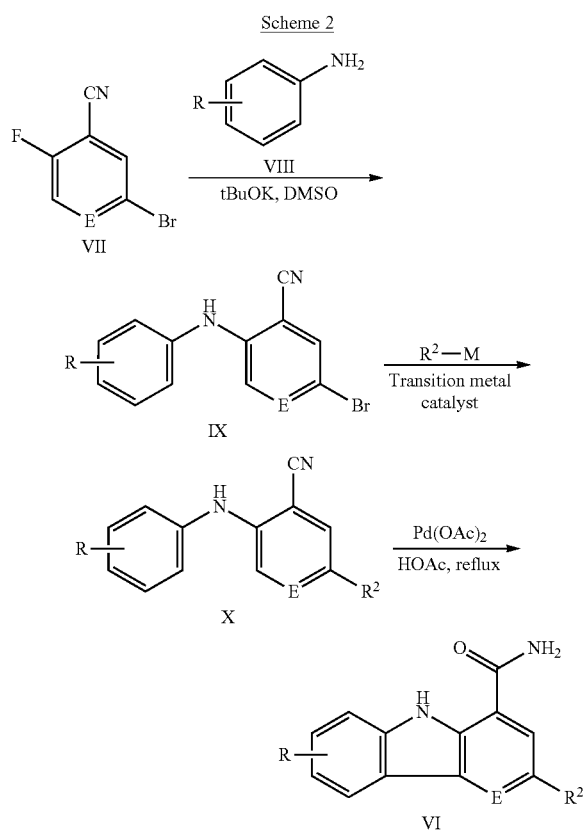

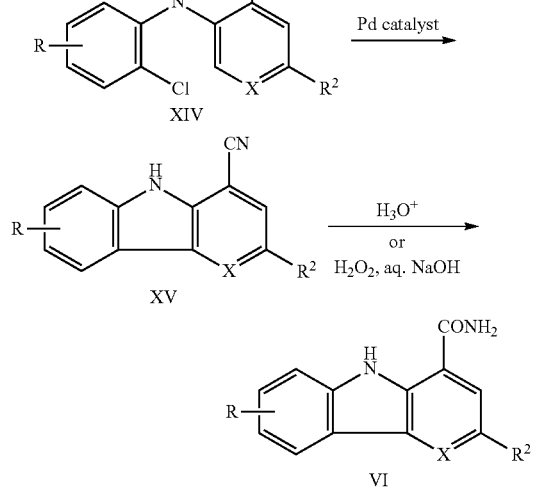

Method D (Scheme 4): Coupling of 2,6-dichloropyridine XVI with a suitably functionalized aromatic or heteroaromatic ring such as boronic acid or stannane derivative would give XVII (*Bioorganic and Medicinal Chemistry Letters*, 1581 (2003)). Reaction of XVII with 2-bromoanilines XVIII would afford N-arylaminopyridines XIX. Palladium-catalyzed conversion of XIX to carbazoles or carbolines (X=N) VI was accomplished using the procedure described in *Journal of the Chemical Society, Perkin I*, 1505 (1999).

Method C (Scheme 3): Transition metal such as Pd mediated coupling of bromoaniline XI with a suitably functionalized aromatic or heteroaromatic ring such as boronic acid or stannane derivative would give biphenyl derivatives XII. Palladium-catalyzed N-arylation (*Tetrahedron*, 11100 (2006)) of XII with substituted iodochlorobenzenes XIII would furnish chlorodiaryl amines XIV. Palladium-catalyzed cyclization of XIV (*Journal of the American Chemical Society*, 581 (2006) and *Angewandte Chemie, Int. Ed.*, 1627 (2007)) would afford carbazoles XV. The nitrile group could be hydrolyzed under acidic or basic conditions to give carbazole carboline (when X=N) amides VI.

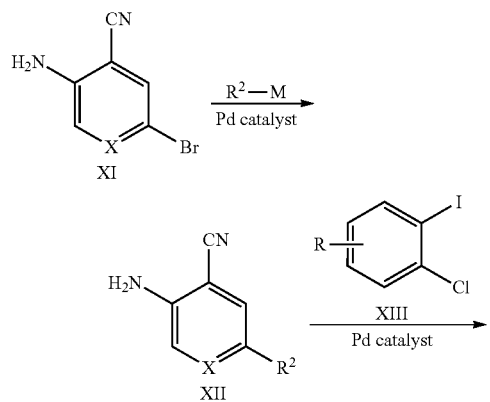

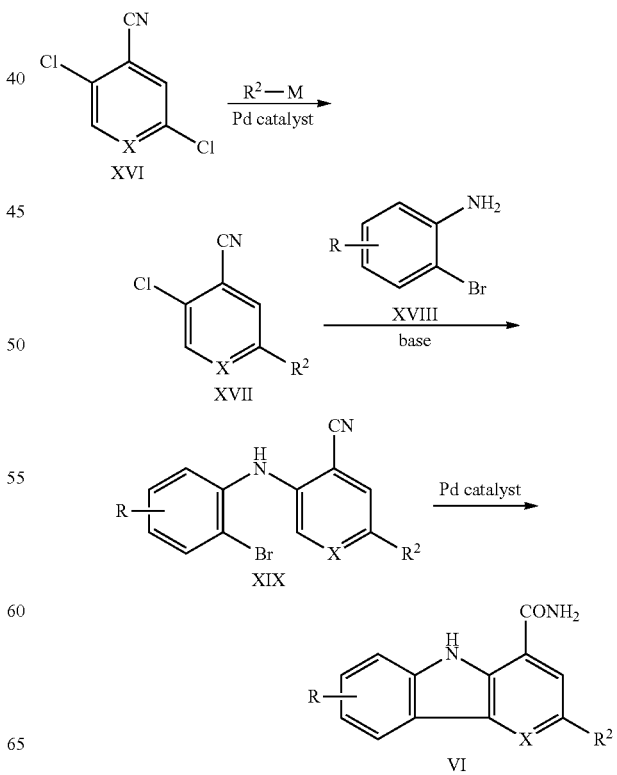

Method E (Scheme 5): Palladium-catalyzed reaction of substituted ketones II with the 3-amino-2-chloroypyridine XX according to the procedure described in *Angewandte Chemie, Int. Ed.*, 4526 (2004) would afford indoles XXI. Transition metal mediated coupling of XXI with a suitably functionalized aromatic or heteroaromatic ring such as boronic acid or stannane derivative would furnish XXII. Dehydrogenation of XXII with DDQ followed by hydrolysis of ester and conversion to the amides VI could be accomplished using known protocols.

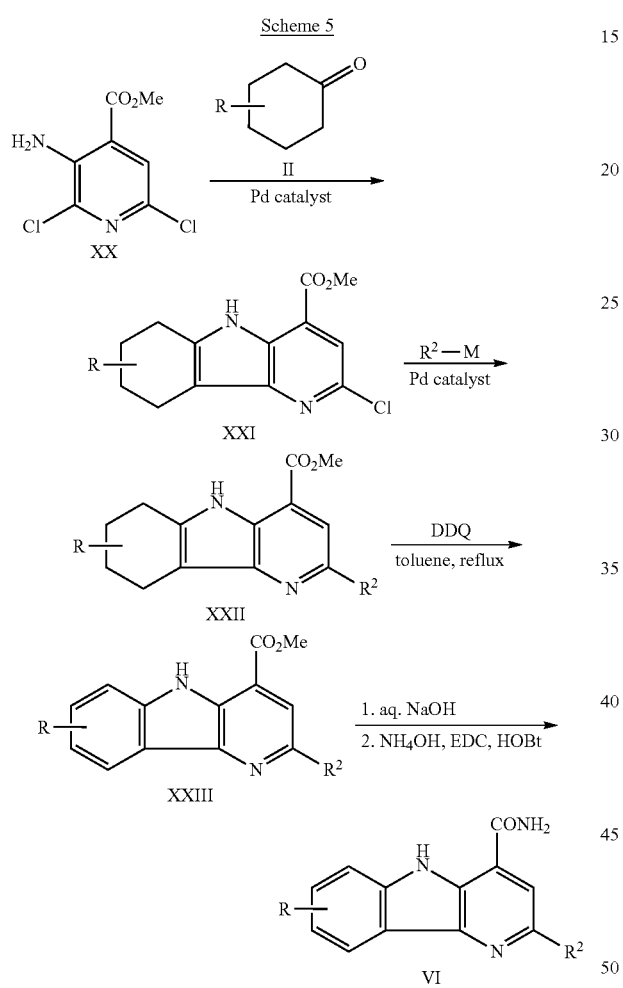

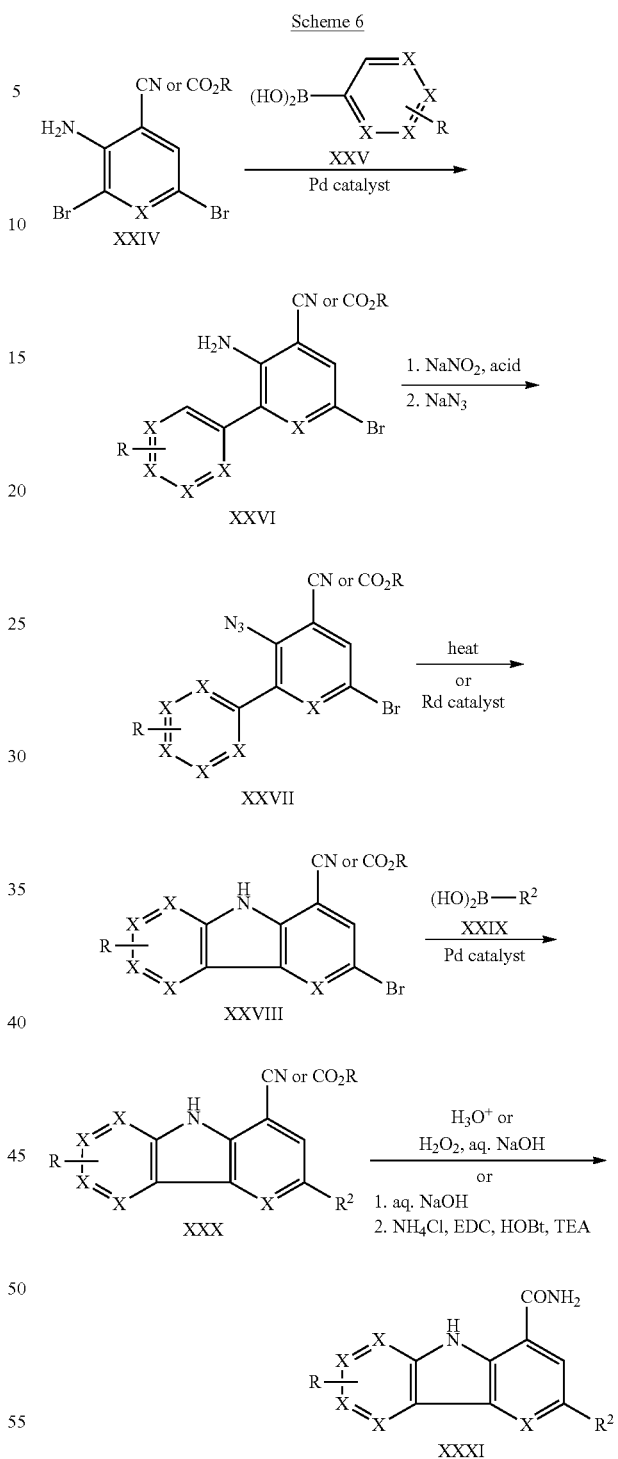

Method F (Scheme 6): Suzuki coupling of the dibromoaniline(X=CH) or dibromopyridine (X=N) XX with substituted aryl boronic acids or heteroaryl boronic acids (X=N or CH) XXV gave XXVI as the major product. Conversion of XXVI to acids (X=N or CH) XXV gave XXVI as the major product. Conversion of XXVI to azides XXVII was followed by cyclization via heating as described in *Tetrahedron*, 10320 (2007) or by using Rd catalysis as described in *Journal of Organic Chemistry*, 74:3225 (2009) to give carbazoles or carbolines XXVIII. Suzuki coupling of XXVIII with substituted aryl boronic acids XXXIX followed by conversion of the nitrile group or ester group of XXX to a carboxamide group gave the tricyclic compounds XXXI.

Further functional group manipulation accomplished using standard synthetic organic transformations. For example, carbazole or carboline (X=N) VI, containing esters readily available using general Methods A to F, could be saponified with aqueous base. The resulting acids XXIX could be converted to amides XXXII by reaction with amines of interest and amide bond forming reagents such as HATU in organic solvents such as DMF (Scheme 7).

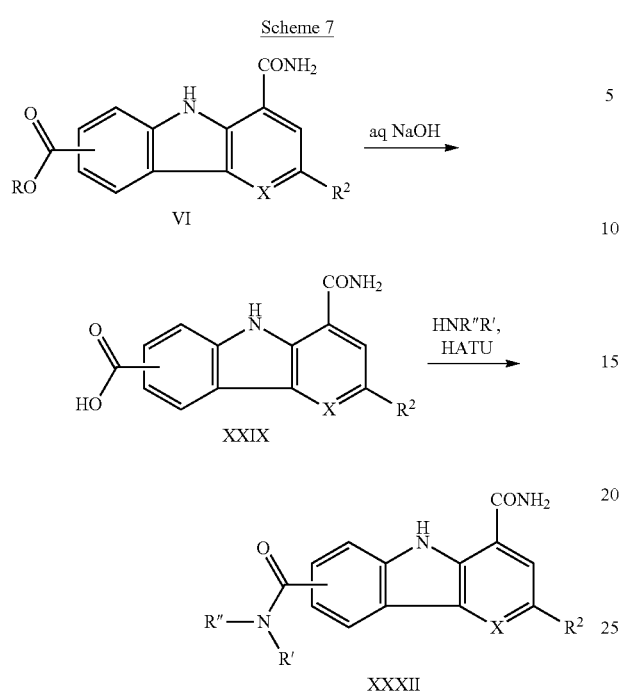

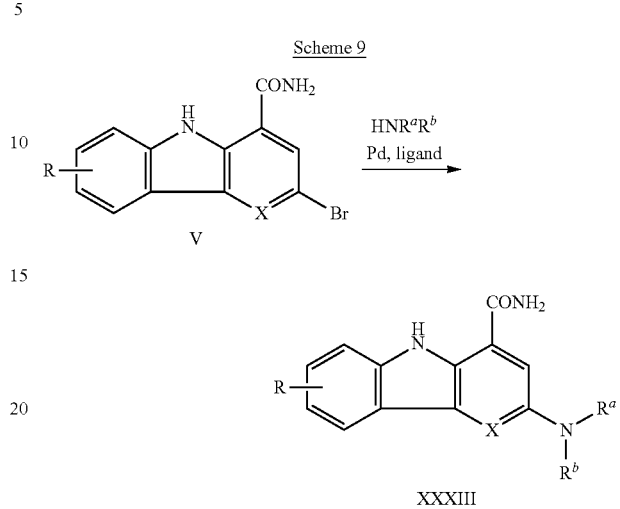

Compounds of general formula VI in which R group is $NR^aR^b$ could be synthesized from intermediate V through Pd mediated coupling with $HNR^aR^b$ (Scheme 9).

Compounds VI containing R=—NHCOY where Y is alkyl, cycloalkyl, aryl or heteroaryl can be synthesized from carboxylic acid XXIX by Curtius rearrangement, deprotection, and amide formation as outlined in Scheme 8.

Compounds of general formula VI in which R group is OR could be synthesized from intermediate V (R=OBzl) by deprotection, Mitsunobu reaction, and carboxamide formation as outlined in Scheme 10.

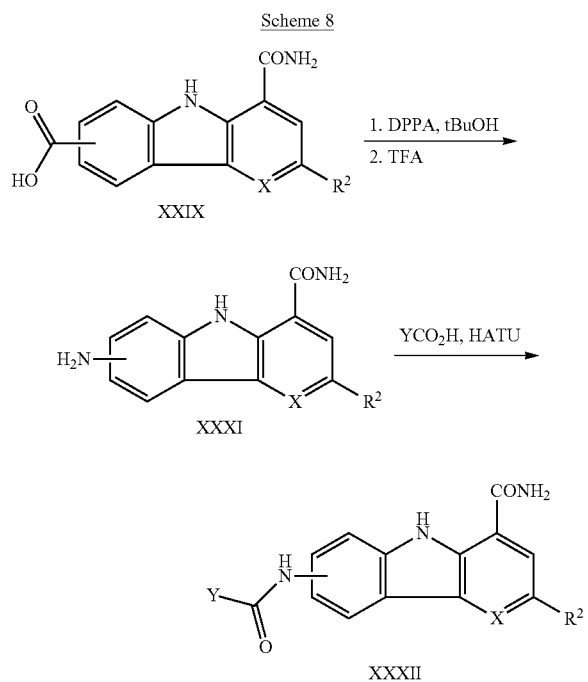

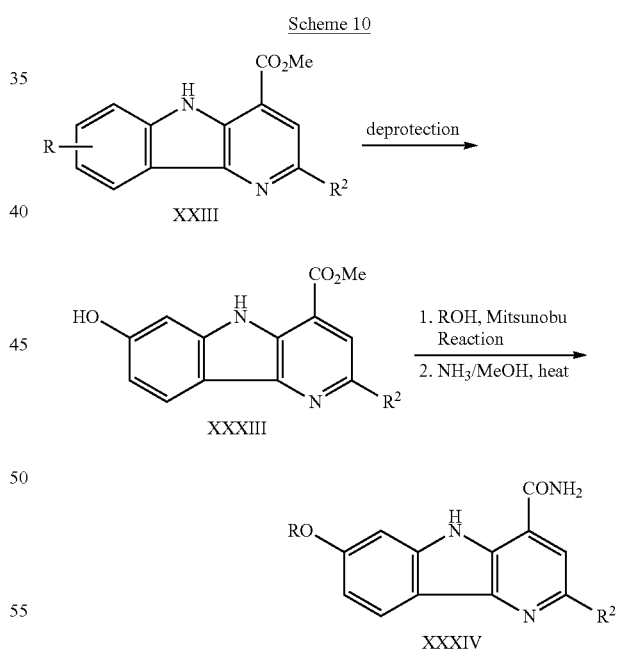

Compounds of general formula VI, in which R is NH—COY where Y is —ORa or $NR^aR^b$, were prepared by reaction of aniline XXXI with activated carbamoyl derivatives.

Compounds of general formula VI in which R group is $CH_2NR^aR^b$ were synthesized from intermediate XXVI (R=CH$_2$OH). Formation of the azide function of XXXV effected concomitant oxidation of the hydroxyl methyl group to an aldehyde group, see: *Synthesis*, 609 (1976) for related oxidations. Rhodium-promoted cyclization, reductive amination, Suzuki coupling, and carboximide formation afforded the product as indicated in Scheme 11.

Scheme 11

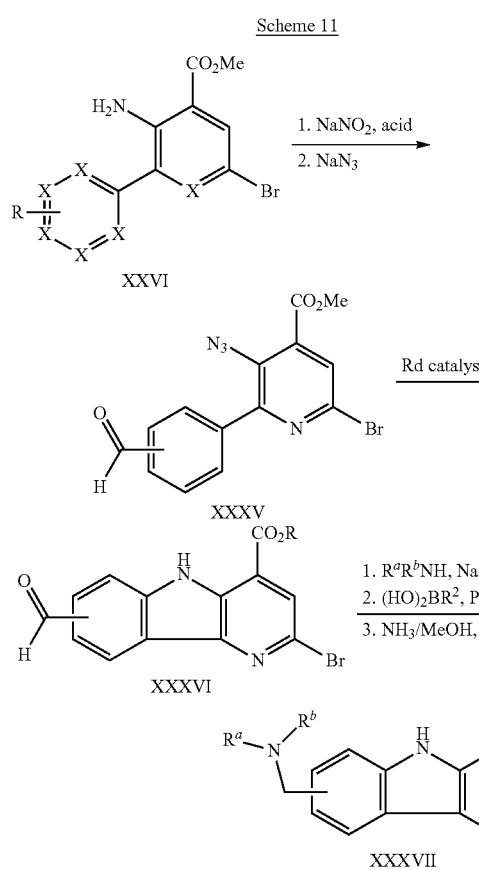

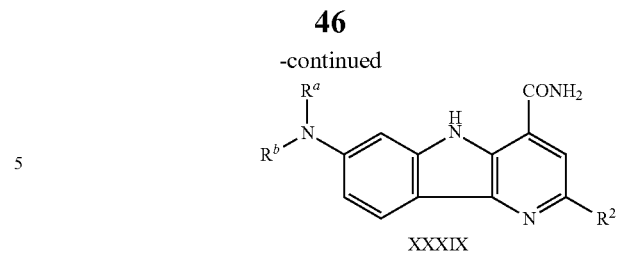

Compounds XXXIX could also be prepared from intermediated XXVIII where R=Cl. Protection followed by a Suzuki reaction gave intermediate XL. Buchwald amination using a procedure like that described in *Journal of Organic Chemistry*, 65:1158 (2000), followed by deprotection and carboxamide formation as outlined in Scheme 13 afforded XXXIX.

Scheme 13

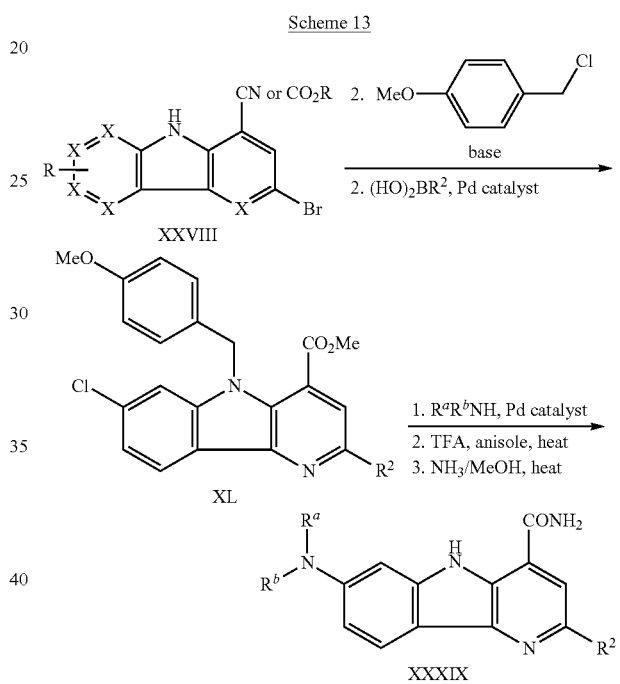

Compounds of general formula VI in which R group is $NR^aR^b$ could be synthesized from intermediate XXXIII. Conversion to a triflate derivative using the procedure described in *Angewandte Chemie, Int. Ed.*, 4961 (2003) followed by protection gave intermediate XXXVIII. Buchwald amination using a procedure like that described in *Journal of Medicinal Chemistry*, 47:2887 (2004), deprotection and carboxamide formation as outlined in Scheme 12 afforded XXXIX.

Scheme 12

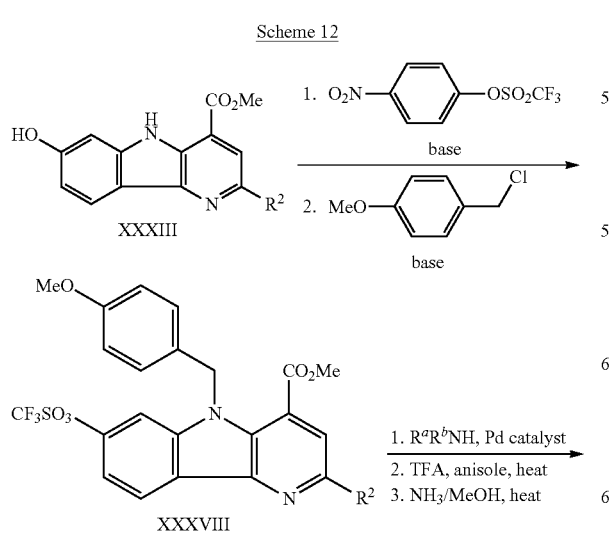

Compounds of general formula VI in which $R^2$ is an aryl ether could be synthesized from intermediate V (R=OBzl) by deprotection, Mitsunobu reaction, and carboxamide formation as outlined in Scheme 14.

Scheme 14

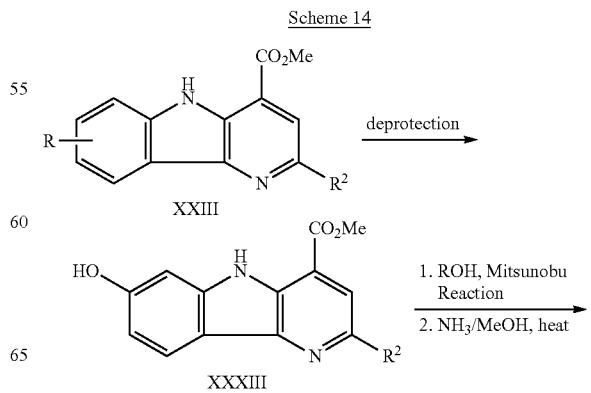

-continued

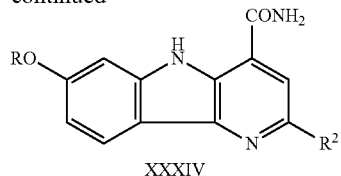

XXXIV

EXAMPLE 1

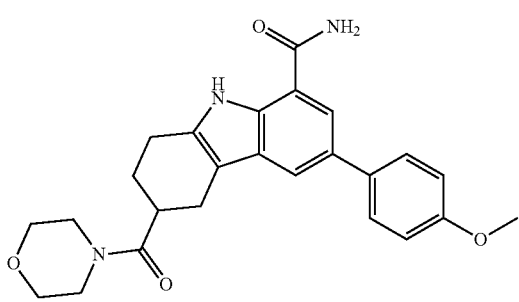 [SMILES: COc1ccc(-c2cc(C(N)=O)c3[nH]c4c(c3c2)CC(C(=O)N2CCOCC2)CC4)cc1]

6-(4-Methoxyphenyl)-3-(morpholine-4-carbonyl)-2,3,4,9-tetrahydro-1H-carbazole-8-carboxamide 1A. Preparation of 6-bromo-3-(ethoxycarbonyl)-2,3,4,9-tetrahydro-1H-carbazole-8-carboxylic acid

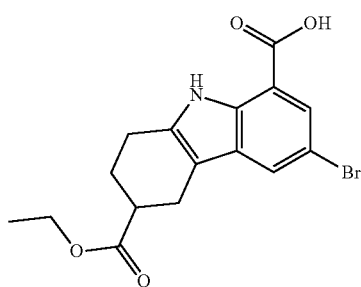 [SMILES: CCOC(=O)C1CCc2[nH]c3c(C(=O)O)cc(Br)cc3c2C1]

To a stirred suspension of 5-bromo-2-hydrazinylbenzoic acid dihydrochloride (3.08 g, 10.13 mmol) in AcOH, (~0.5M) (20 mL) was added ethyl 4-oxocyclohexanecarboxylate (1.759 g, 10.34 mmol) at room temperature. The cream-colored reaction mixture was then stirred under reflux for 4 h. The reaction mixture was cooled to room temperature and concentrated in vacuo to afford a yellow solid. The solid was then dissolved in ethyl acetate, washed with 1N aqueous HCl and brine solution. The organic phase was dried over $Na_2SO_4$ and concentrated to give the crude product, which was then suspended in ether and the yellow solid was collected by filtration, air-dried. Additional quantity was obtained by combining the filtrate followed by silica gel column chromatography (hexane/ethyl acetate=50/50-0/100) to give 2.1 g of 6-bromo-3-(ethoxycarbonyl)-2,3,4,9-tetrahydro-1H-carbazole-8-carboxylic acid. MS (ESI) m/z 367.2 (M+H). $^1$H NMR (DMSO-$d_6$) δ ppm 13.2 (br s, 1H), 10.8 (s, 1H), 7.8 (s, 1H), 7.6 (s, 1H), 3.92 (m, 4H), 3.77 (q, 2H, J=7.8 Hz), 2.52-2.81 (m, 7H), 1.3 (t, 3H).

1B. Preparation of ethyl 6-bromo-8-carbamoyl-2,3,4,9-tetrahydro-1H-carbazole-3-carboxylate

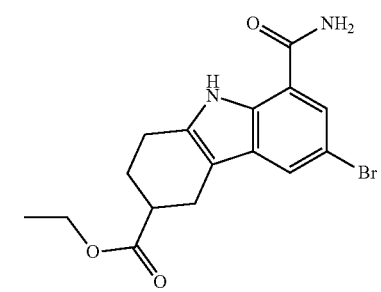 [SMILES: CCOC(=O)C1CCc2[nH]c3c(C(N)=O)cc(Br)cc3c2C1]

To a light suspension of 6-bromo-3-(ethoxycarbonyl)-2,3,4,9-tetrahydro-1H-carbazole-8-carboxylic acid (2.12 g, 5.79 mmol), EDC (1.332 g, 6.95 mmol), and 1-hydroxybenzotriazole hydrate (1.064 g, 6.95 mmol) in THF/$CH_2Cl_2$ (5/1) (100 mL) was added ammonium hydroxide (1.353 mL, 34.7 mmol) and it turned into a thick light yellow suspension and it was stirred at rt overnight. The reaction was concentrated and the residue was dissolved in water/ethyl acetate. The organic phase was separated and washed with brine, dried over $Na_2SO_4$, filtered, concentrated to afford the crude product as a light yellow solid, which was washed with a small amount of ether and air-dried. The crude ethyl 6-bromo-8-carbamoyl-2,3,4,9-tetrahydro-1H-carbazole-3-carboxylate was used as such in the next reaction.

1C. Preparation of 6-bromo-8-carbamoyl-2,3,4,9-tetrahydro-1H-carbazole-3-carboxylic acid

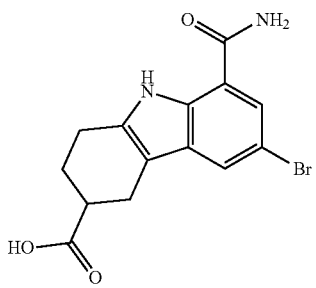 [SMILES: NC(=O)c1cc(Br)cc2c3c([nH]c12)CCC(C(=O)O)C3]

A suspension of ethyl 6-bromo-8-carbamoyl-2,3,4,9-tetrahydro-1H-carbazole-3-carboxylate (0.9 g, 2.464 mmol) and LiOH (0.177 g, 7.39 mmol) in THF/EtOH/$H_2O$ (3/1/1) (25 mL) was stirred at room temperature for 72 hours The reaction mixture was concentrated and the residue was dissolved in water. Aqueous 1M HCl was added to this solution until pH=5 whereupon a light yellow solid precipitated. The solid was collected by filtration, washed with water, air-dried and used as such in the next reaction. LCMS: RT=0.96 min, m/z (M+H) 337.0/339.0.

1D. Preparation of 6-bromo-3-(morpholine-4-carbonyl)-2,3,4,9-tetrahydro-1H-carbazole-8-carboxamide

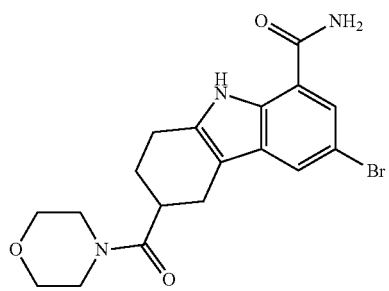 [SMILES: NC(=O)c1cc(Br)cc2c3c([nH]c12)CCC(C(=O)N1CCOCC1)C3]

To a solution of 6-bromo-8-carbamoyl-2,3,4,9-tetrahydro-1H-carbazole-3-carboxylic acid (0.8 g, 2.135 mmol), EDC (0.491 g, 2.56 mmol), and 1-hydroxybenzotriazole hydrate (0.392 g, 2.56 mmol) in THF/CH$_2$Cl$_2$ (5/1) (30 mL) was added morpholine (0.4 mL, 4.27 mmol) and the reaction mixture was stirred at room temperature for 16 hours. The reaction mixture was concentrated and the solid was washed with ethyl acetate, and water. The organic layer was dried over Na$_2$SO$_4$ and concentrated to afford the crude product as a pale solid. The solid was washed with hexane-ethyl acetate to give 800 mg of pure 6-bromo-3-(morpholine-4-carbonyl)-2,3,4,9-tetrahydro-1H-carbazole-8-carboxamide. MS (ESI) m/z 406 (M+H). $^1$H NMR (DMSO-d$_6$) δ ppm 10.9 (s, 1H), 8.2 (bs, 1H), 7.81 (d, 1H), 7.75 (s, 1H), 3.92 (m, 4H), 3.77 (q, 2H, J=7.8 Hz), 2.52-2.81 (m, 7H).

1. Preparation of 6-(4-methoxyphenyl)-3-(morpholine-4-carbonyl)-2,3,4,9-tetrahydro-1H-carbazole-8-carboxamide A suspension of 6-bromo-3-(morpholine-4-carbonyl)-2,3,4,9-tetrahydro-1H-carbazole-8-carboxamide (50 mg, 0.123 mmol), 4-methoxyphenylboronic acid (37.4 mg, 0.246 mmol), K$_2$CO$_3$ (42.5 mg, 0.308 mmol), and PdCl$_2$(dppf)-CH$_2$Cl$_2$ adduct (10.05 mg, 0.012 mmol) in dioxane (3 mL) was sealed in a microwave vial and it was heated in an oil-bath at 120° C. for 16 h. The reaction mixture was concentrated and the crude was purified by preparative HPLC to give 18 mg of 6-(4-methoxyphenyl)-3-(morpholine-4-carbonyl)-2,3,4,9-tetrahydro-1H-carbazole-8-carboxamide as light brown solid. MS (ESI) m/z 434.2 (M+H). $^1$H NMR (methanol-d$_4$) d ppm 7.64-7.73 (m, 2H) 7.52 (d, J=8.8 Hz, 2H) 6.89 (d, J=8.8 Hz, 2H) 3.73 (s, 3H) 3.52-3.67 (m, 8H) 3.00-3.12 (m, 1H) 2.70-2.89 (m, 4H) 1.83-2.09 (m, 2H).

The following compounds in Table 1 have been synthesized utilizing the similar procedures as described in Example 1.

TABLE 1

| Ex. # | Structure | Name | Retention time (min) | MS (ESI) m/z* |
|---|---|---|---|---|
| 2 | 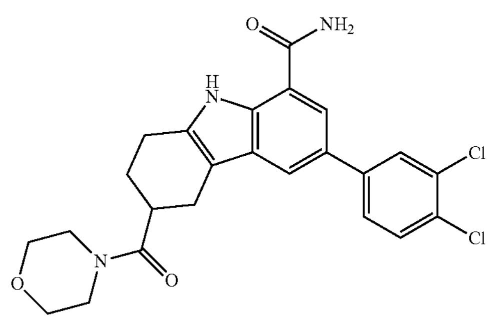 [SMILES: NC(=O)c1cc(-c2ccc(Cl)c(Cl)c2)cc2c3c([nH]c12)CCC(C(=O)N1CCOCC1)C3] | 6-(3,4-dichlorophenyl)-3-(4-morpholinylcarbonyl)-2,3,4,9-tetrahydro-1H-carbazole-8-carboxamide | 1.88 | 472 |
| 3 | 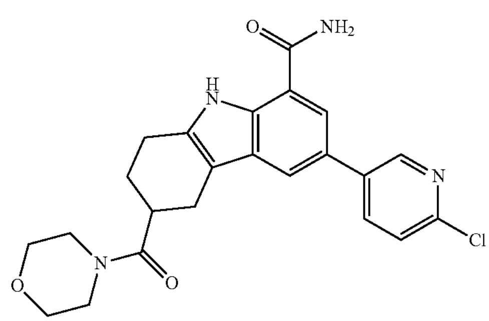 [SMILES: NC(=O)c1cc(-c2ccc(Cl)nc2)cc2c3c([nH]c12)CCC(C(=O)N1CCOCC1)C3] | 6-(6-chloro-3-pyridinyl)-3-(4-morpholinylcarbonyl)-2,3,4,9-tetrahydro-1H-carbazole-8-carboxamide | 1.43 | 439 |

TABLE 1-continued

| Ex. # | Structure | Name | Retention time (min) | MS (ESI) m/z* |
|---|---|---|---|---|
| 4 | 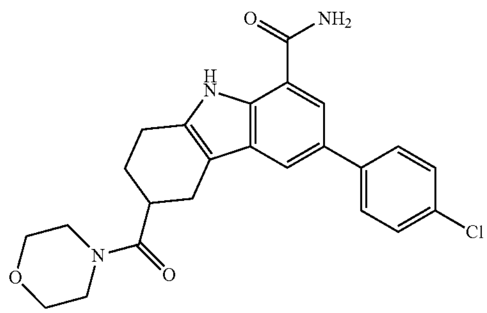 [SMILES: NC(=O)c1cc(-c2ccc(Cl)cc2)cc2c3c([nH]c12)CCC(C(=O)N1CCOCC1)C3] | 6-(4-chlorophenyl)-3-(4-morpholinylcarbonyl)-2,3,4,9-tetrahydro-1H-carbazole-8-carboxamide | 1.43 | 438.3 |
| 5 | 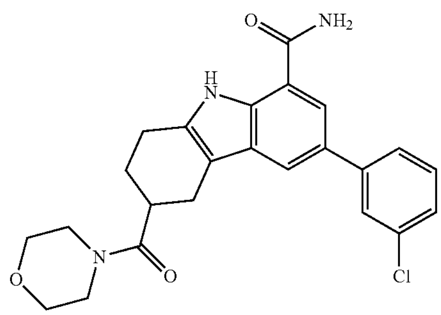 [SMILES: NC(=O)c1cc(-c2cccc(Cl)c2)cc2c3c([nH]c12)CCC(C(=O)N1CCOCC1)C3] | 6-(3-chlorophenyl)-3-(4-morpholinylcarbonyl)-2,3,4,9-tetrahydro-1H-carbazole-8-carboxamide | 1.42 | 438.2 |
| 6 | 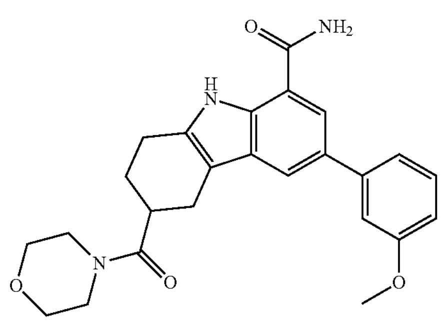 [SMILES: COc1cccc(-c2cc(C(N)=O)c3[nH]c4c(c3c2)CC(C(=O)N2CCOCC2)CC4)c1] | 6-(3-methoxyphenyl)-3-(4-morpholinylcarbonyl)-2,3,4,9-tetrahydro-1H-carbazole-8-carboxamide | 1.31 | 434.1 |
| 7 | 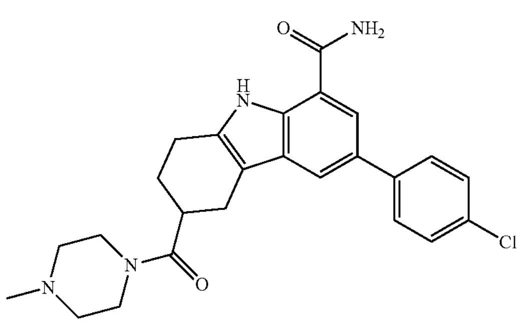 [SMILES: CN1CCN(C(=O)C2CCc3[nH]c4c(C(N)=O)cc(-c5ccc(Cl)cc5)cc4c3C2)CC1] | 6-(4-chlorophenyl)-3-((4-methyl-1-piperazinyl)carbonyl)-2,3,4,9-tetrahydro-1H-carbazole-8-carboxamide | 1.31 | 451.2 |

TABLE 1-continued

| Ex. # | Structure | Name | Retention time (min) | MS (ESI) m/z* |
|---|---|---|---|---|
| 8 | 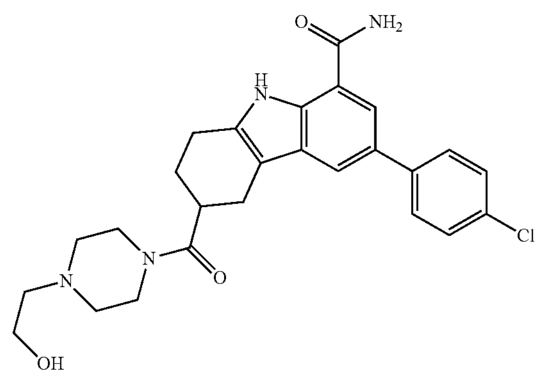 [SMILES: NC(=O)c1cc(-c2ccc(Cl)cc2)cc2c3c([nH]c12)CCC(C(=O)N1CCN(CCO)CC1)C3] | 6-(4-chlorophenyl)-3-((4-(2-hydroxyethyl)-1-piperazinyl)carbonyl)-2,3,4,9-tetrahydro-1H-carbazole-8-carboxamide | 1.25 | 481.2 |
| 9 | 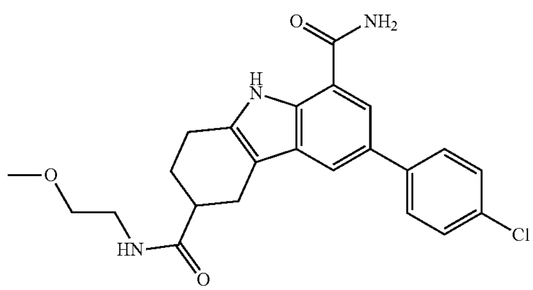 [SMILES: COCCNC(=O)C1CCc2[nH]c3c(C(N)=O)cc(-c4ccc(Cl)cc4)cc3c2C1] | 6-(4-chlorophenyl)-$N^3$-(2-methoxyethyl)-2,3,4,9-tetrahydro-1H-carbazole-3,8-dicarboxamide | 1.40 | 426.2 |
| 10 | 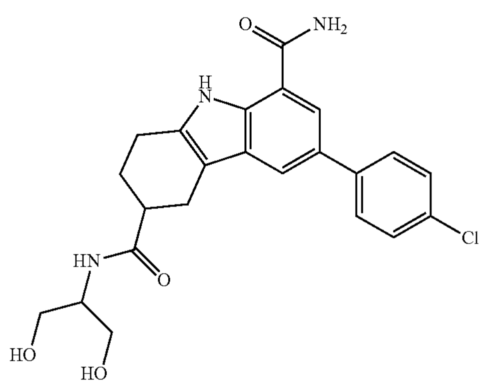 [SMILES: NC(=O)c1cc(-c2ccc(Cl)cc2)cc2c3c([nH]c12)CCC(C(=O)NC(CO)CO)C3] | 6-(4-chlorophenyl)-$N^3$-(1,3-dihydroxypropan-2-yl)-2,3,4,9-tetrahydro-1H-carbazole-3,8-dicarboxamide | 1.18 | 442.2 |
| 11 | 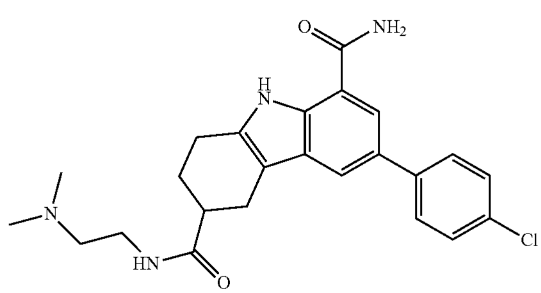 [SMILES: CN(C)CCNC(=O)C1CCc2[nH]c3c(C(N)=O)cc(-c4ccc(Cl)cc4)cc3c2C1] | 6-(4-chlorophenyl)-$N^3$-(2-(dimethylamino)ethyl)-2,3,4,9-tetrahydro-1H-carbazole-3,8-dicarboxamide | 1.19 | 439.3 |

HPLC conditions: Schimadzu HPLC; Column:Ascentis Express C18 4.6 × 50 mm at 45°;

Flow rate: 4 ml/min;

Gradient: 4 min, 0-100% B;

Solvent: A = 5:95 Acetonitrile:Water; B = 95:5 Acetonitrile:Water; Modifier = 10 mM NH$_4$OAc.

*(M + H)$^+$ observed in all cases except the examples where specifically mentioned.

EXAMPLE 12

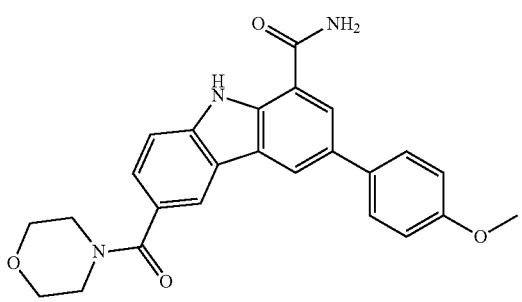 [SMILES: COc1ccc(-c2cc(C(N)=O)c3[nH]c4ccc(C(=O)N5CCOCC5)cc4c3c2)cc1]

3-(4-Methoxyphenyl)-6-(4-morpholinylcarbonyl)-
9H-carbazole-1-carboxamide

12. Preparation of 3-(4-methoxyphenyl)-6-(morpholine-4-carbonyl)-9H-carbazole-1-carboxamide A stirred suspension of 6-(4-methoxyphenyl)-3-(morpholine-4-carbonyl)-2,3,4,9-tetrahydro-1H-carbazole-8-carboxamide (6 mg, 0.014 mmol, Example 1) and 2,3-dichloro-5,6-dicyano-1,4-benzoquinone (9.43 mg, 0.042 mmol) in toluene (2 mL) was heated at reflux for 2 h. The reaction mixture was concentrated, and the crude was purified by prep. HPLC to afford 3 mg of 3-(4-methoxyphenyl)-6-(morpholine-4-carbonyl)-9H-carbazole-1-carboxamide. MS (ESI) m/z 430.2 (M+H). $^1$H NMR (DMSO-$d_6$) δ ppm 11.50 (s, 1H) 8.63 (s, 1H) 8.30 (s, 2H) 8.16-8.24 (m, 1H) 7.77 (d, J=8.79 Hz, 2H) 7.69 (d, J=8.35 Hz, 1H) 7.49 (br. s., 1H) 7.38-7.44 (m, 1H) 7.01 (d, J=8.79 Hz, 2H) 3.76 (s, 3H) 3.55-3.61 (m, 4H) 3.48-3.55 (m, 4H).

The following compounds in Table 1 have been synthesized utilizing the procedures described in Example 12.

TABLE 2

| Ex. # | Structure | Name | Retention time (min) | MS (ESI) m/z* |
|---|---|---|---|---|
| 13 | 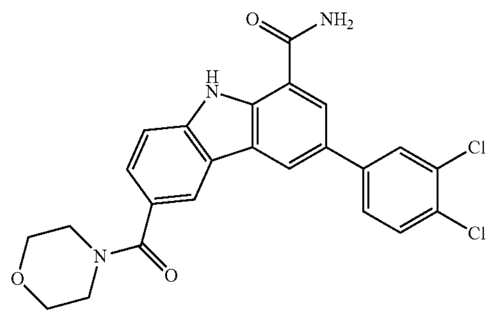 [SMILES: NC(=O)c1cc(-c2ccc(Cl)c(Cl)c2)cc2c1[nH]c1ccc(C(=O)N3CCOCC3)cc12] | 3-(3,4-dichlorophenyl)-6-(morpholine-4-carbonyl)-9H-carbazole-1-carboxamide | 1.60 | 469.2 |
| 14 | 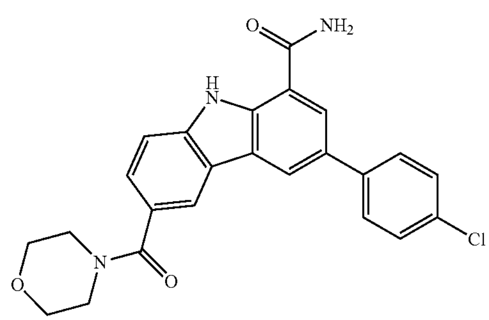 [SMILES: NC(=O)c1cc(-c2ccc(Cl)cc2)cc2c1[nH]c1ccc(C(=O)N3CCOCC3)cc12] | 3-(4-chlorophenyl)-6-(morpholine-4-carbonyl)-9H-carbazole-1-carboxamide | 1.44 | 434.3 |
| 15 | 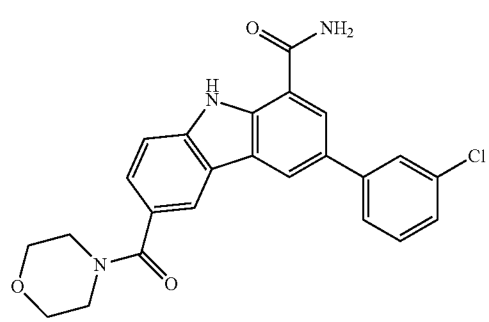 [SMILES: NC(=O)c1cc(-c2cccc(Cl)c2)cc2c1[nH]c1ccc(C(=O)N3CCOCC3)cc12] | 3-(3-chlorophenyl)-6-(morpholine-4-carbonyl)-9H-carbazole-1-carboxamide | 1.45 | 434.5 |

TABLE 2-continued

| Ex. # | Structure | Name | Retention time (min) | MS (ESI) m/z* |
|---|---|---|---|---|
| 16 | 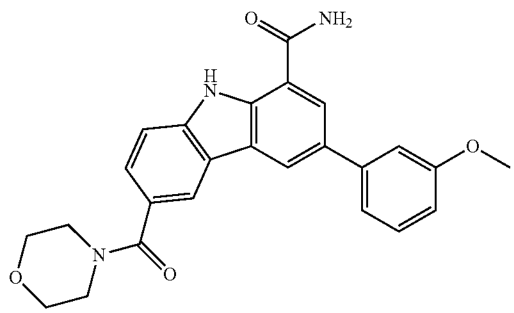 [SMILES: COc1cccc(-c2cc(C(N)=O)c3[nH]c4ccc(C(=O)N5CCOCC5)cc4c3c2)c1] | 3-(3-methoxyphenyl)-6-(morpholine-4-carbonyl)-9H-carbazole-1-carboxamide | 1.33 | 430.2 |
| 17 | 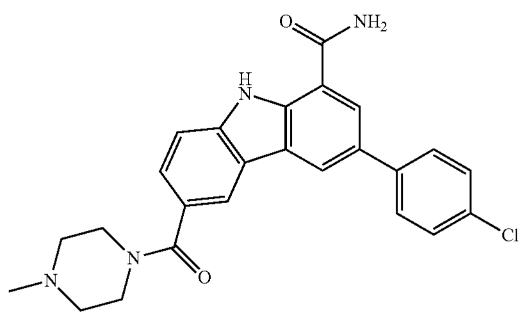 [SMILES: CN1CCN(C(=O)c2ccc3[nH]c4c(C(N)=O)cc(-c5ccc(Cl)cc5)cc4c3c2)CC1] | 3-(4-chlorophenyl)-6-(4-methylpiperazine-1-carbonyl)-9H-carbazole-1-carboxamide | 1.31 | 445.4 |
| 18 | 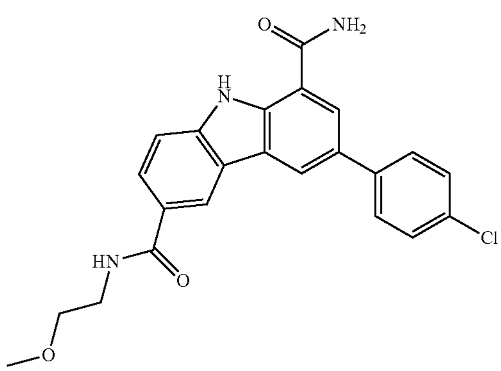 [SMILES: COCCNC(=O)c1ccc2[nH]c3c(C(N)=O)cc(-c4ccc(Cl)cc4)cc3c2c1] | 3-(4-chlorophenyl)-$N^6$-(2-methoxyethyl)-9H-carbazole-1,6-dicarboxamide | 1.44 | 422.4 |
| 19 | 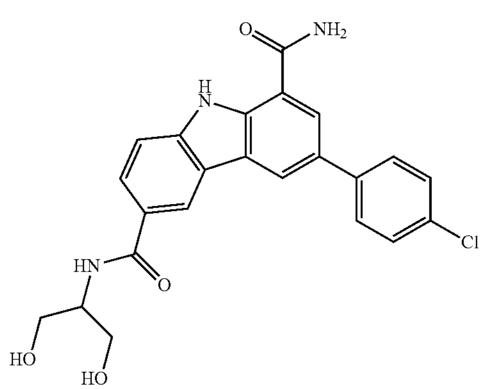 [SMILES: NC(=O)c1cc(-c2ccc(Cl)cc2)cc2c1[nH]c1ccc(C(=O)NC(CO)CO)cc12] | 3-(4-chlorophenyl)-$N^6$-(1,3-dihydroxypropan-2-yl)-9H-carbazole-1,6-dicarboxamide | 1.21 | 438.4 |

TABLE 2-continued

| Ex. # | Structure | Name | Retention time (min) | MS (ESI) m/z* |
|---|---|---|---|---|
| 20 | 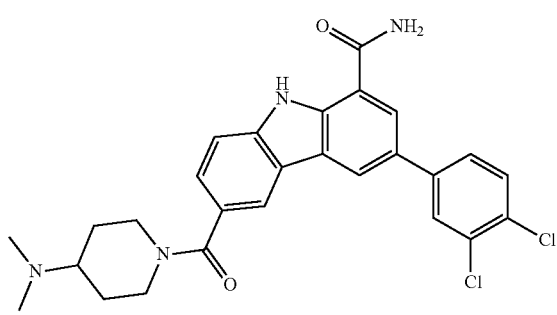 [SMILES: CN(C)C1CCN(C(=O)c2ccc3[nH]c4c(C(N)=O)cc(-c5ccc(Cl)c(Cl)c5)cc4c3c2)CC1] | 3-(4-chlorophenyl)-N[6]-(2-(dimethylamino)ethyl)-9H-carbazole-1,6-dicarboxamide | 1.25 | 435.4 |

HPLC conditions: Schimadzu HPLC; Column:Ascentis Express C18 4.6 × 50 at 45°;
Flow rate: 4 ml/min;
Gradient: 4 min, 0-100% B;
Solvent: A = 5:95 Acetonitrile:Water; B = 95:5 Acetonitrile:Water, Modifier = 10 mM NH$_4$OAc.
*(M + H)$^+$ observed in all cases except the examples where specifically mentioned.

EXAMPLE 21

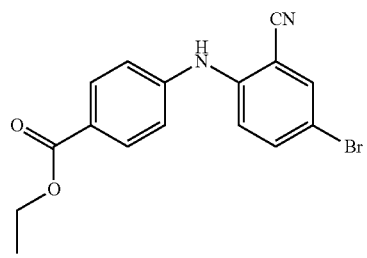 [SMILES: CCOC(=O)c1ccc(Nc2ccc(Br)cc2C#N)cc1]

3-(3,4-Dichlorophenyl)-6-(4-(dimethylamino)piperidine-1-carbonyl)-9H-carbazole-1-carboxamide

21A. Preparation of ethyl 4-(4-bromo-2-cyanophenylamino)benzoate

A flask was charged with 5-bromo-2-fluorobenzonitrile (5 g, 25.00 mmol), ethyl 4-aminobenzoate (4.54 g, 27.5 mmol), and KOtBu (5.11 g, 45.5 mmol). To this was added DMSO (100 mL). After stirring at room temperature for 20 min, the reaction mixture was diluted with ethyl acetate and water. The aqueous was extracted with ethyl acetate, the combined organic was washed with water (3×), brine, dried over MgSO$_4$ and filtered. The filtrate was concentrated. The residue was suspended in ethyl acetate, collected the solid by filtration. Repeated above procedure for several times (each collected solid was checked by LCMS) until the collected solid is pure. The mixture residue was further purified via silica gel chromatography (0-30% ethyl acetate in hexanes) to give total 7.15 g of ethyl 4-(4-bromo-2-cyanophenylamino)benzoate. MS (ESI) m/z 345.2 (M+H). $^1$H NMR (CDCl$_3$) δ ppm 8.02 (2H, d, J=8.55 Hz), 7.65 (1H, d, J=2.44 Hz), 7.53 (1H, dd, J=9.00, 2.29 Hz), 7.25 (1H, d, J=9 Hz), 7.14 (2H, d, Hz), 6.47 (1H, s), 4.36 (2H, q, J=7.22 Hz), 1.38 (3H, t, J=7.17 Hz).

21B. Preparation of ethyl 4-(3',4'-dichloro-3-cyano-biphenyl-4-ylamino)benzoate

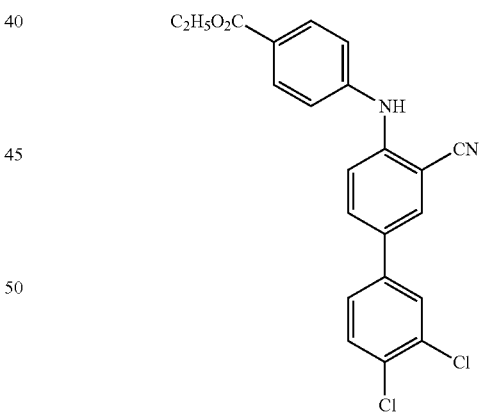

To a suspension of ethyl 4-(4-bromo-2-cyanophenylamino)benzoate (6.33 g, 18.34 mmol), tetrakis(triphenylphosphine)palladium(0) (0.438 g, 0.379 mmol), toluene (60 mL), and 2 M aqueous sodium carbonate (20.81 mL, 41.6 mmol) under nitrogen were added a solution of 3,4-dichlorophenylboronic acid (4.76 g, 24.94 mmol) in MeOH (18 mL) at rt. The resulting reaction mixture was heated at reflux temperature for 4 h. The reaction mixture was cooled to room temperature and diluted with water (100 mL) and ethyl acetate (250 mL). The aqueous phase was extracted with ethyl acetate (100 ml ×2), and the combined organic phase was washed with water (100 ml ×2), diluted (5%) aqueous ammonia (100 mL), and brine (100 mL). The organic phase was dried over Na₂SO₄, filtered, and concentrated. The crude material was suspended in dichloromethane and the solid was collected by filtration, and washed with DCM (5 ml ×2) to afford 5.33 g of ethyl 4-(3',4'-dichloro-3-cyanobiphenyl-4-ylamino)benzoate. MS (ESI) m/z 411.0 (M+H). ¹H NMR (CDCl₃) δ ppm 8.04 (2H, d, J=8.55 Hz), 7.73 (1H, d, J=1.83 Hz), 7.58-7.66 (2H, m), 7.51 (1H, d, J=8.55 Hz), 7.46 (1H, d, J=8.85 Hz), 7.34 (1H, dd, J=8.24, 2.14 Hz), 7.20 (2H, d, J=8.55 Hz), 6.61 (1H, s), 4.37 (2H, q, J=7.12 Hz), 1.39 (3H, t, J=7.17 Hz).

21C. Preparation of ethyl 8-carbamoyl-6-(3,4-dichlorophenyl)-9H-carbazole-3-carboxylate

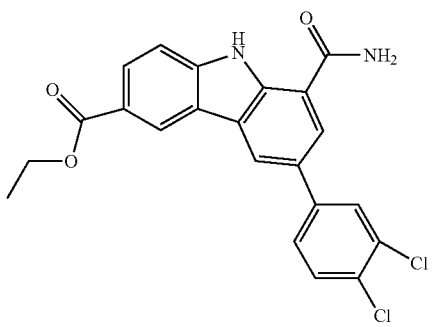 [SMILES: CCOC(=O)c1ccc2[nH]c3c(C(N)=O)cc(-c4ccc(Cl)c(Cl)c4)cc3c2c1]

Ethyl 4-(3',4'-dichloro-3-cyanobiphenyl-4-ylamino)benzoate (410 mg, 0.997 mmol), diacetoxypalladium (560 mg, 2.492 mmol) in glacial acetic acid (20 mL) in a microwave tube (20 mL) were heated in microwave reactors at 160° C. for 4 h. The reaction was cooled to room temperature. The catalyst was filtered off and solid was washed with acetic acid several times. The filtrate was concentrated under reduced pressure and the residue was co-evaporated with toluene (3×). The resulting residue was suspended in ethyl acetate. The solid was collected by filtration and air dried to afford 75.4 mg of ethyl 8-carbamoyl-6-(3,4-dichlorophenyl)-9H-carbazole-3-carboxylate. MS (ESI) m/z 425.1(M–H). ¹H NMR (DMSO-d₆) δ ppmH NMR (DMSO-d₆) d ppm 11.87 (1H, s), 9.00 (2H, m), 8.41 (1H, br. s), 8.40 (1H, d, J=1.22 Hz), 8.30 (1H, d, J=2.14 Hz), 8.06 (1H, dd, J=8.55, 1.53 Hz), 8.01 (1H, dd, J=8.24, 2.14 Hz), 7.82 (1H, d, J=8.55 Hz), 7.78 (1H, d, J=8.55 Hz), 7.65 (1H, br. s.), 4.38 (2H, q, J=7.22 Hz), 1.39 (3H, t, J=7.17 Hz).

21D. Preparation of 8-carbamoyl-6-(3,4-dichlorophenyl)-9H-carbazole-3-carboxylic acid

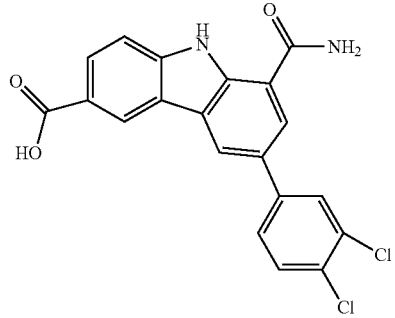 [SMILES: NC(=O)c1cc(-c2ccc(Cl)c(Cl)c2)cc2c1[nH]c1ccc(C(=O)O)cc12]

Ethyl 8-carbamoyl-6-(3,4-dichlorophenyl)-9H-carbazole-3-carboxylate (980 mg, 2.294 mmol), 1 M aqueous sodium hydroxide (5.73 mL, 5.73 mmol) in THF (13 mL)/EtOH (13 mL) was heated in an oil bath at 85° C. for 24 h. The solvent was removed under reduced pressure. The solid was suspended in water (200 mL). To this suspension was added aqueous 1N HCl solution until pH ~2-3. The solid was collected by filtration and dried. The crude was purified using silica gel column chromatography (CH₂Cl₂-MeOH-3 to 50%) to afford 820 mg of 8-carbamoyl-6-(3,4-dichlorophenyl)-9H-carbazole-3-carboxylic acid which was used as such in the next reaction. MS (ESI) m/z 397.2 (M–H). ¹H NMR (DMSO-d₆) δ ppm 12.64 (1H, br. s.), 11.80 (1H, s), 8.83-9.08 (2H, m), 8.42 (1H, br. s.), 8.39 (1H, s), 8.29 (1H, d, J=2.14 Hz), 8.03-8.07 (1H, m), 8.00 (1H, dd, J=8.55, 2.14 Hz), 7.74-7.81 (2H, m), 7.63 (1H, br. s.).

21. Preparation of 3-(3,4-dichlorophenyl)-6-(4-(dimethylamino)piperidine-1-carbonyl)-9H-carbazole-1-carboxamide A solution of 8-carbamoyl-6-(3,4-dichlorophenyl)-9H-carbazole-3-carboxylic acid (20 mg, 0.05 mmol), HATU (22 mg, 0.06 mmol) and N,N'-diisopropylamine (12 mg, 0.15 mmol) in DMF (0.2 ml) was agitated for 16 h at room temperature. The reaction mixture was diluted with methanol and then purified by reverse phase preparative HPLC to give 16 mg of 3-(3,4-dichlorophenyl)-6-(4-(dimethylamino)piperidine-1-carbonyl)-9H-carbazole-1-carboxamide. MS (ESI) m/z 510.2 (M+H). ¹H NMR (DMSO-d₆) δ ppm 11.66 (s, 1H), 8.91 (d, 1H, J=1.2), 8.42 (b, 1H), 8.38 (m, 2H), dd, 8.24 (d, 1H, J=2.3), 7.96 (dd, 1H, J=2.3, 8.4), 7.78 (d, 1H, J=8.3), 7.77 (d, 1H, J=8.3), 7.64 (b, 1H), 7.47 (dd, 1H, J=1.7, 8.4), 4.6-3.7 (b, 2H), 3.15-2.85 (b, 2H), 2.55-2.40 (b, 1H), 2.25 (bs, 6H), 1.9-1.7 (b, 2H), 1.47-1.35 (b, 2H).

The following compounds in Table 3 have been synthesized utilizing the procedures described in Example 21.

TABLE 3

| Ex. # | Structure | Name | Retention time (min) | MS (ESI) m/z* |
|---|---|---|---|---|
| 22 | 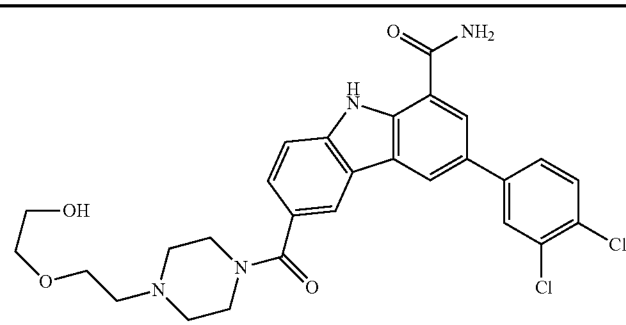 | 3-(3,4-dichlorophenyl)-6-((4-(2-(2-hydroxyethoxy)ethyl)-1-piperazinyl)carbonyl)-9H-carbazole-1-carboxamide | 1.89 | 555.0 |

TABLE 3-continued

| Ex. # | Structure | Name | Retention time (min) | MS (ESI) m/z* |
|---|---|---|---|---|
| 23 | 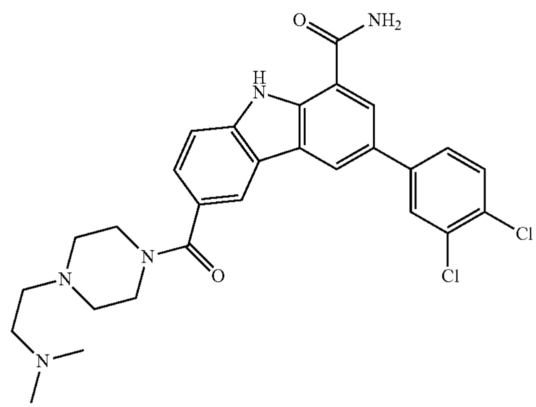 [SMILES: CN(C)CCN1CCN(C(=O)c2ccc3[nH]c4c(C(N)=O)cc(-c5ccc(Cl)c(Cl)c5)cc4c3c2)CC1] | 3-(3,4-dichlorophenyl)-6-((4-(2-(dimethylamino)ethyl)-1-piperazinyl)carbonyl)-9H-carbazole-1-carboxamide | 1.79 | 537.9 |
| 24 | 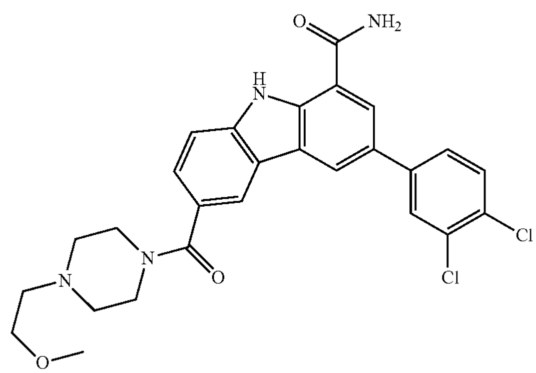 [SMILES: COCCN1CCN(C(=O)c2ccc3[nH]c4c(C(N)=O)cc(-c5ccc(Cl)c(Cl)c5)cc4c3c2)CC1] | 3-(3,4-dichlorophenyl)-6-((4-(2-methoxyethyl)-1-piperazinyl)carbonyl)-9H-carbazole-1-carboxamide | 2.15 | 524.9 |
| 25 | 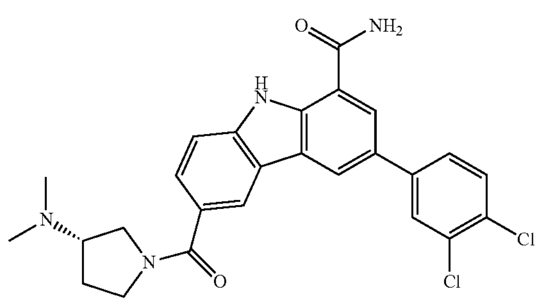 [SMILES: CN(C)[C@H]1CCN(C(=O)c2ccc3[nH]c4c(C(N)=O)cc(-c5ccc(Cl)c(Cl)c5)cc4c3c2)C1] | 3-(3,4-dichlorophenyl)-6-(((3S)-3-(dimethylamino)-1-pyrrolidinyl)carbonyl)-9H-carbazole-1-carboxamide | 2.02 | 495.0 |
| 26 | 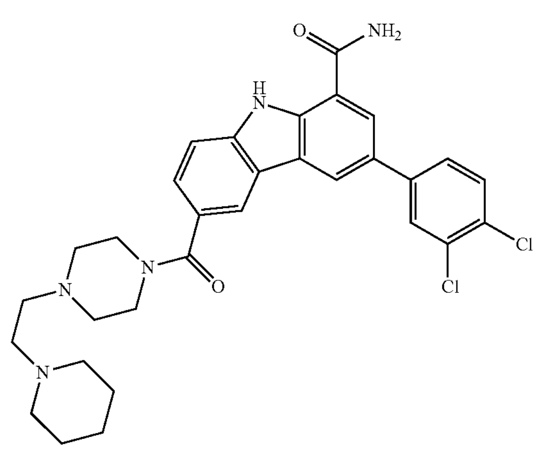 [SMILES: NC(=O)c1cc(-c2ccc(Cl)c(Cl)c2)cc2c1[nH]c1ccc(C(=O)N3CCN(CCN4CCCCC4)CC3)cc12] | 3-(3,4-dichlorophenyl)-6-((4-(2-(1-piperidinyl)ethyl)-1-piperazinyl)carbonyl)-9H-carbazole-1-carboxamide | 1.89 | 578.0 |

TABLE 3-continued

| Ex. # | Structure | Name | Retention time (min) | MS (ESI) m/z* |
|---|---|---|---|---|
| 27 | 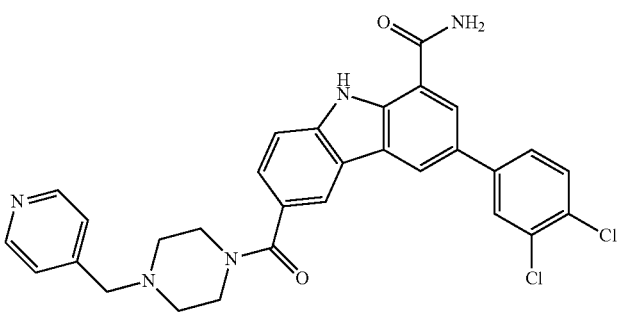 [SMILES: NC(=O)c1cc(-c2ccc(Cl)c(Cl)c2)cc2c1[nH]c1ccc(C(=O)N3CCN(Cc4ccncc4)CC3)cc12] | 3-(3,4-dichlorophenyl)-6-((4-(4-pyridinylmethyl)-1-piperazinyl)carbonyl)-9H-carbazole-1-carboxamide | 2.22 | 558.0 |
| 28 | 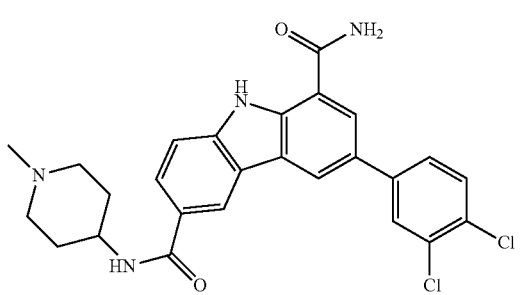 [SMILES: CN1CCC(NC(=O)c2ccc3[nH]c4c(C(N)=O)cc(-c5ccc(Cl)c(Cl)c5)cc4c3c2)CC1] | 3-(3,4-dichlorophenyl)-$N^6$-(1-methyl-4-piperidinyl)-9H-carbazole-1,6-dicarboxamide | 1.80 | 494.9 |
| 29 | 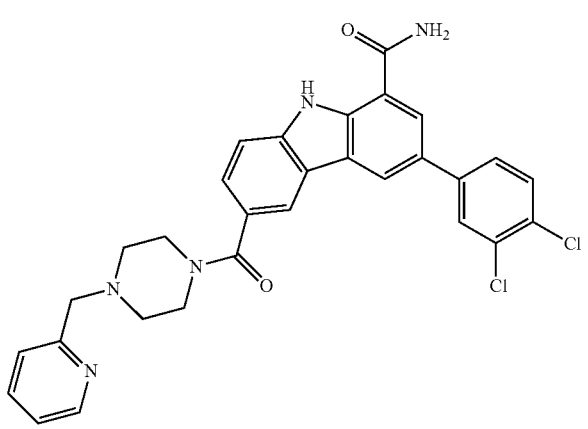 [SMILES: NC(=O)c1cc(-c2ccc(Cl)c(Cl)c2)cc2c1[nH]c1ccc(C(=O)N3CCN(Cc4ccccn4)CC3)cc12] | 3-(3,4-dichlorophenyl)-6-((4-(2-pyridinylmethyl)-1-piperazinyl)carbonyl)-9H-carbazole-1-carboxamide | 2.25 | 557.9 |
| 30 | 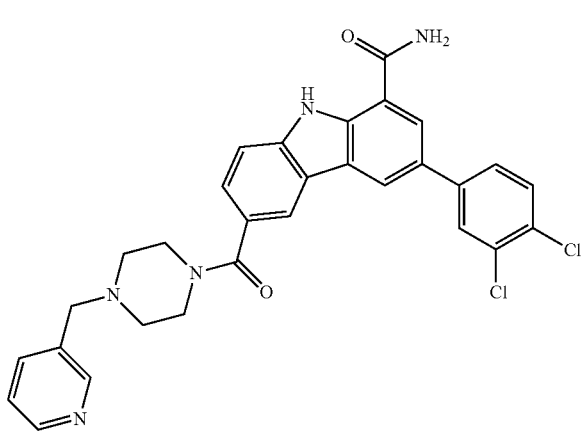 | 3-(3,4-dichlorophenyl)-6-((4-(3-pyridinylmethyl)-1-piperazinyl)carbonyl)-9H-carbazole-1-carboxamide | 2.20 | 557.9 |

TABLE 3-continued

| Ex. # | Structure | Name | Retention time (min) | MS (ESI) m/z* |
|---|---|---|---|---|
| 31 | 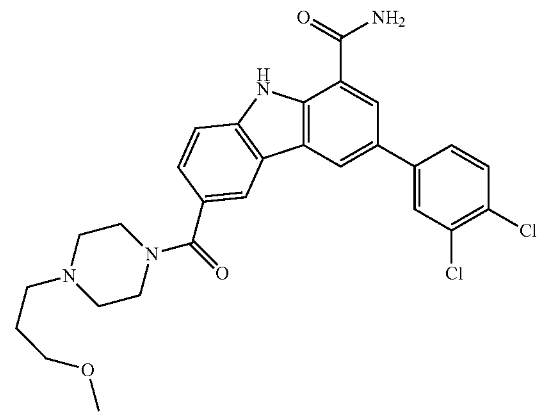 [SMILES: COCCCN1CCN(C(=O)c2ccc3[nH]c4c(C(N)=O)cc(-c5ccc(Cl)c(Cl)c5)cc4c3c2)CC1] | 3-(3,4-dichlorophenyl)-6-((4-(3-methoxypropyl)-1-piperazinyl)carbonyl)-9H-carbazole-1-carboxamide | 2.22 | 539.0 |
| 32 | 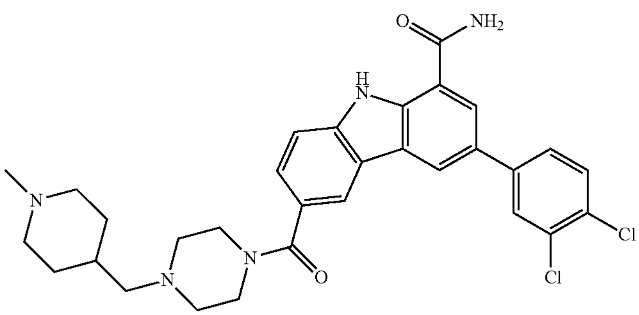 [SMILES: CN1CCC(CN2CCN(C(=O)c3ccc4[nH]c5c(C(N)=O)cc(-c6ccc(Cl)c(Cl)c6)cc5c4c3)CC2)CC1] | 3-(3,4-dichlorophenyl)-6-((4-((1-methyl-4-piperidinyl)methyl)-1-piperazinyl)carbonyl)-9H-carbazole-1-carboxamide | 1.84 | 578.1 |
| 33 | 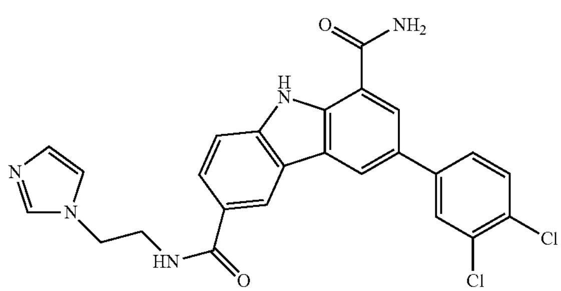 [SMILES: NC(=O)c1cc(-c2ccc(Cl)c(Cl)c2)cc2c1[nH]c1ccc(C(=O)NCCn3ccnc3)cc12] | 3-(3,4-dichlorophenyl)-$N^6$-(2-(1H-imidazol-1-yl)ethyl)-9H-carbazole-1,6-dicarboxamide | 1.96 | 492.0 |
| 34 | 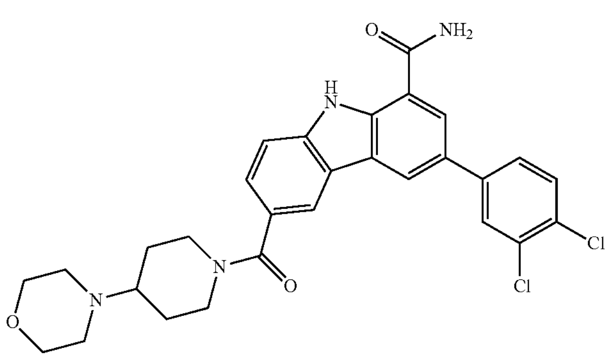 [SMILES: NC(=O)c1cc(-c2ccc(Cl)c(Cl)c2)cc2c1[nH]c1ccc(C(=O)N3CCC(N4CCOCC4)CC3)cc12] | 3-(3,4-dichlorophenyl)-6-((4-(4-morpholinyl)-1-piperidinyl)carbonyl)-9H-carbazole-1-carboxamide | 2.12 | 551.0 |

TABLE 3-continued

| Ex. # | Structure | Name | Retention time (min) | MS (ESI) m/z* |
|---|---|---|---|---|
| 35 | 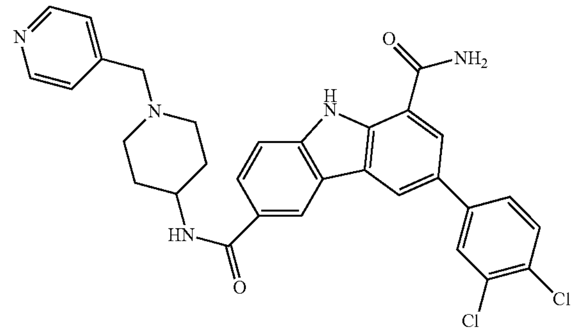 [SMILES: NC(=O)c1cc(-c2ccc(Cl)c(Cl)c2)cc2c1[nH]c1ccc(C(=O)NC3CCN(Cc4ccncc4)CC3)cc12] | 3-(3,4-dichlorophenyl)-$N^6$-(1-(4-pyridinylmethyl)-4-piperidinyl)-9H-carbazole-1,6-dicarboxamide | 2.23 | 572.0 |
| 36 | 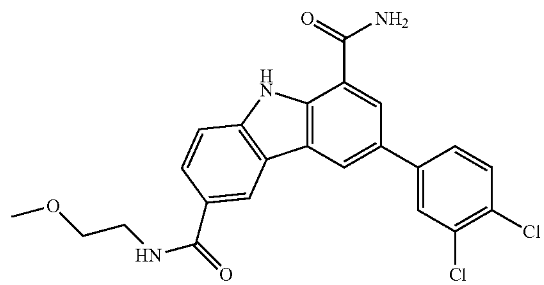 [SMILES: COCCNC(=O)c1ccc2[nH]c3c(C(N)=O)cc(-c4ccc(Cl)c(Cl)c4)cc3c2c1] | 3-(3,4-dichlorophenyl)-$N^6$-(2-methoxyethyl)-9H-carbazole-1,6-dicarboxamide | 2.18 | 455.9 |
| 37 | 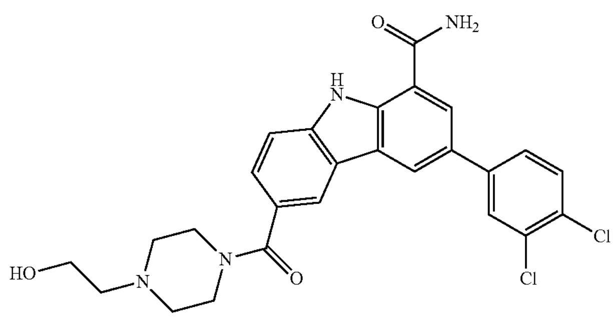 [SMILES: NC(=O)c1cc(-c2ccc(Cl)c(Cl)c2)cc2c1[nH]c1ccc(C(=O)N3CCN(CCO)CC3)cc12] | 3-(3,4-dichlorophenyl)-6-((4-(2-hydroxyethyl)-1-piperazinyl)carbonyl)-9H-carbazole-1-carboxamide | 1.85 | 510.9 |
| 38 | 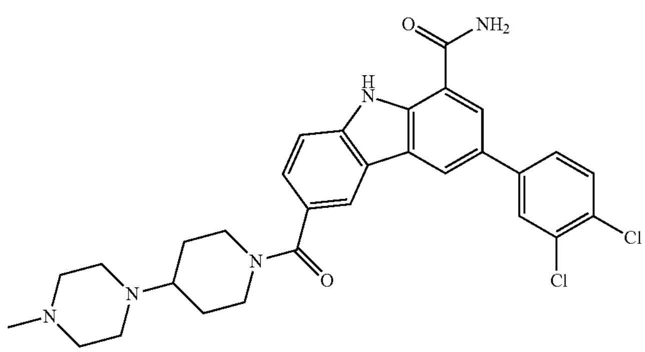 [SMILES: CN1CCN(C2CCN(C(=O)c3ccc4[nH]c5c(C(N)=O)cc(-c6ccc(Cl)c(Cl)c6)cc5c4c3)CC2)CC1] | 3-(3,4-dichlorophenyl)-6-((4-(4-methyl-1-piperazinyl)-1-piperidinyl)carbonyl)-9H-carbazole-1-carboxamide | 1.84 | 564.0 |
| 39 | 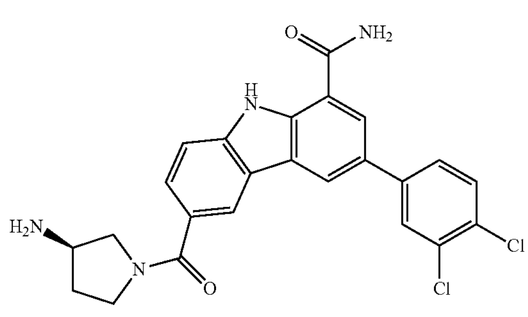 [SMILES: NC(=O)c1cc(-c2ccc(Cl)c(Cl)c2)cc2c1[nH]c1ccc(C(=O)N3CC[C@@H](N)C3)cc12] | 6-(((3R)-3-amino-1-pyrrolidinyl)carbonyl)-3-(3,4-dichlorophenyl)-9H-carbazole-1-carboxamide | 1.68 | 466.9 |

TABLE 3-continued

| Ex. # | Structure | Name | Retention time (min) | MS (ESI) m/z* |
|---|---|---|---|---|
| 40 | 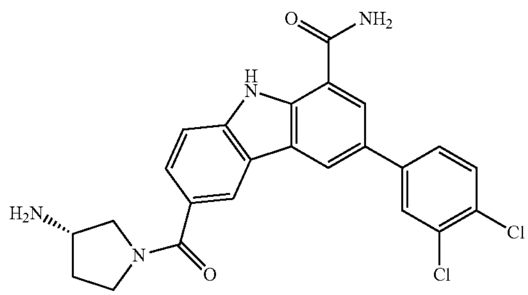 [SMILES: NC(=O)c1cc(-c2ccc(Cl)c(Cl)c2)cc2c1[nH]c1ccc(C(=O)N3CC[C@H](N)C3)cc12] | 6-(((3S)-3-amino-1-pyrrolidinyl)carbonyl)-3-(3,4-dichlorophenyl)-9H-carbazole-1-carboxamide | 1.68 | 466.9 |
| 41 | 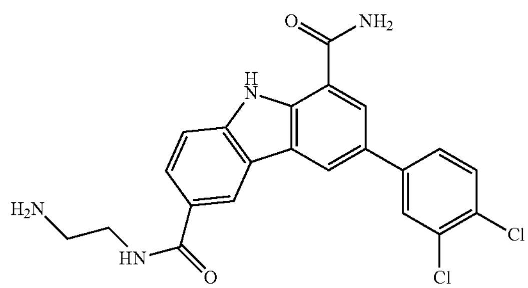 [SMILES: NCCNC(=O)c1ccc2[nH]c3c(C(N)=O)cc(-c4ccc(Cl)c(Cl)c4)cc3c2c1] | $N^6$-(2-aminoethyl)-3-(3,4-dichlorophenyl)-9H-carbazole-1,6-dicarboxamide | 1.66 | 440.9 |
| 42 | 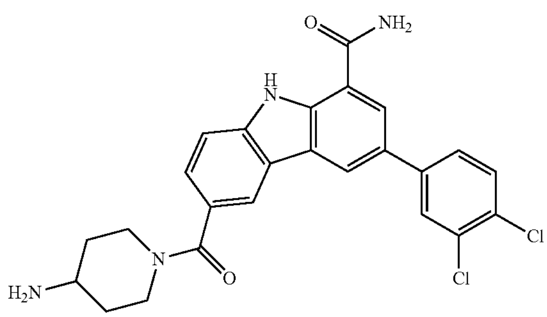 [SMILES: NC(=O)c1cc(-c2ccc(Cl)c(Cl)c2)cc2c1[nH]c1ccc(C(=O)N3CCC(N)CC3)cc12] | 6-((4-amino-1-piperidinyl)carbonyl)-3-(3,4-dichlorophenyl)-9H-carbazole-1-carboxamide | 1.65 | 480.9 |
| 43 | 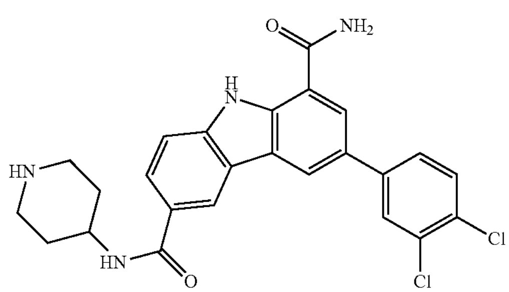 [SMILES: NC(=O)c1cc(-c2ccc(Cl)c(Cl)c2)cc2c1[nH]c1ccc(C(=O)NC3CCNCC3)cc12] | 3-(3,4-dichlorophenyl)-$N^6$-4-piperidinyl-9H-carbazole-1,6-dicarboxamide | 1.71 | 480.9 |
| 44 | 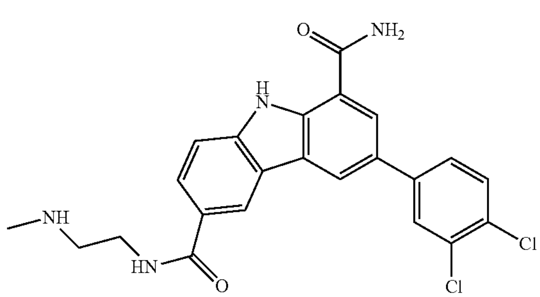 | 3-(3,4-dichlorophenyl)-N~6~-(2-(methylamino)ethyl)-9H-carbazole-1,6-dicarboxamide | 1.71 | 454.9 |

TABLE 3-continued

| Ex. # | Structure | Name | Retention time (min) | MS (ESI) m/z* |
|---|---|---|---|---|
| 45 | 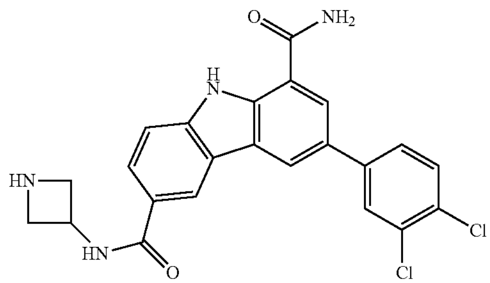 [SMILES: NC(=O)c1cc(-c2ccc(Cl)c(Cl)c2)cc2c1[nH]c1ccc(C(=O)NC3CNC3)cc12] | $N^6$-3-azetidinyl-3-(3,4-dichlorophenyl)-9H-carbazole-1,6-dicarboxamide | 1.70 | 452.9 |
| 46 | 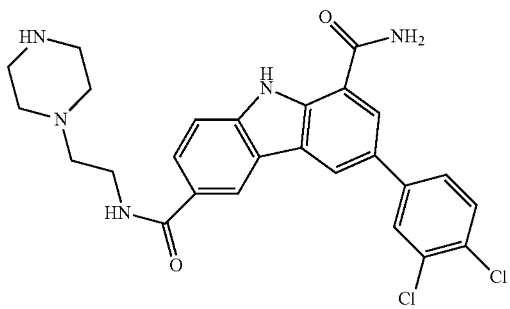 | 3-(3,4-dichlorophenyl)-$N^6$-(2-(1-piperazinyl)ethyl)-9H-carbazole-1,6-dicarboxamide | 1.70 | 509.9 |
| 47 | 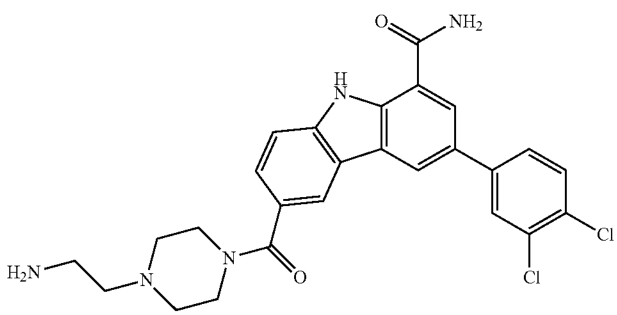 [SMILES: NCCN1CCN(C(=O)c2ccc3[nH]c4c(C(N)=O)cc(-c5ccc(Cl)c(Cl)c5)cc4c3c2)CC1] | 6-((4-(2-aminoethyl)-1-piperazinyl)carbonyl)-3-(3,4-dichlorophenyl)-9H-carbazole-1-carboxamide | 1.69 | 509.9 |
| 48 | 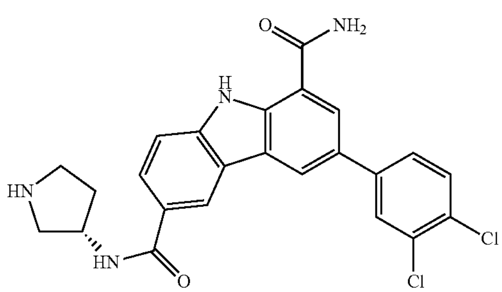 [SMILES: NC(=O)c1cc(-c2ccc(Cl)c(Cl)c2)cc2c1[nH]c1ccc(C(=O)N[C@H]3CCNC3)cc12] | 3-(3,4-dichlorophenyl)-$N^6$-((3S)-3-pyrrolidinyl)-9H-carbazole-1,6-dicarboxamide | 1.72 | 466.9 |
| 49 | 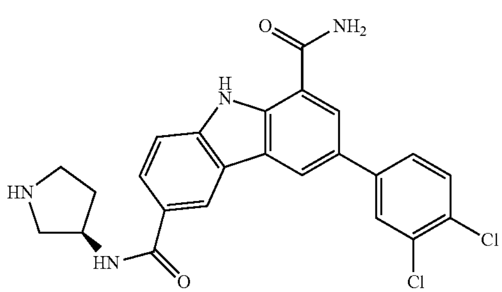 [SMILES: NC(=O)c1cc(-c2ccc(Cl)c(Cl)c2)cc2c1[nH]c1ccc(C(=O)N[C@@H]3CCNC3)cc12] | 3-(3,4-dichlorophenyl)-$N^6$-((3R)-3-pyrrolidinyl)-9H-carbazole-1,6-dicarboxamide | 1.71 | 466.9 |

TABLE 3-continued

| Ex. # | Structure | Name | Retention time (min) | MS (ESI) m/z* |
|---|---|---|---|---|
| 50 | 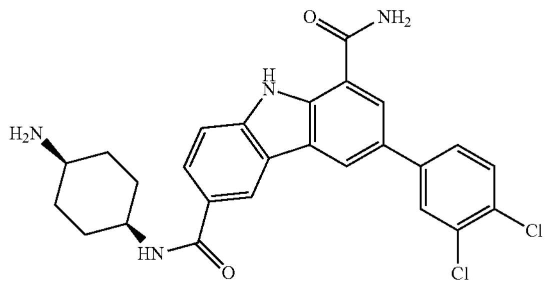 [SMILES: NC(=O)c1cc(-c2ccc(Cl)c(Cl)c2)cc2c1[nH]c1ccc(C(=O)N[C@H]3CC[C@@H](N)CC3)cc12] | $N^6$-(cis-4-aminocyclohexyl)-3-(3,4-dichlorophenyl)-9H-carbazole-1,6-dicarboxamide | 1.73 | 494.9 |
| 51 | 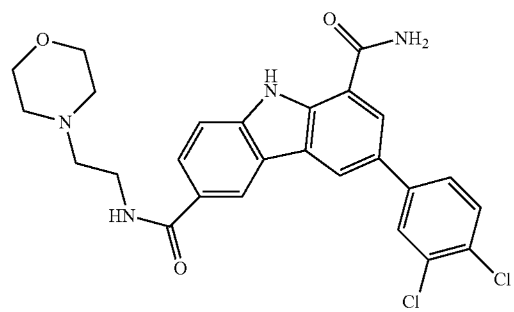 [SMILES: NC(=O)c1cc(-c2ccc(Cl)c(Cl)c2)cc2c1[nH]c1ccc(C(=O)NCCN3CCOCC3)cc12] | 3-(3,4-dichlorophenyl)-$N^6$-(2-(4-morpholinyl)ethyl)-9H-carbazole-1,6-dicarboxamide | 2.06 | 510.9 |
| 52 | 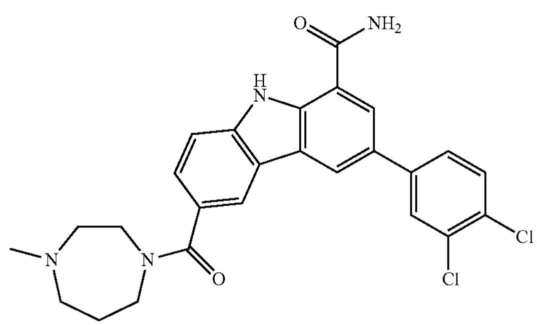 [SMILES: CN1CCCN(C(=O)c2ccc3[nH]c4c(C(N)=O)cc(-c5ccc(Cl)c(Cl)c5)cc4c3c2)CC1] | 3-(3,4-dichlorophenyl)-6-((4-methyl-1,4-diazepan-1-yl)carbonyl)-9H-carbazole-1-carboxamide | 1.94 | 494.9 |
| 53 | 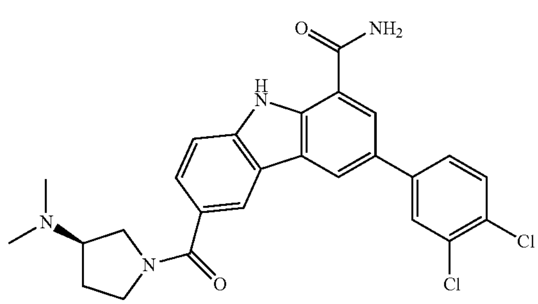 [SMILES: CN(C)[C@@H]1CCN(C(=O)c2ccc3[nH]c4c(C(N)=O)cc(-c5ccc(Cl)c(Cl)c5)cc4c3c2)C1] | 3-(3,4-dichlorophenyl)-6-(((3R)-3-(dimethylamino)-1-pyrrolidinyl)carbonyl)-9H-carbazole-1-carboxamide | 2.05 | 494.9 |

TABLE 3-continued

| Ex. # | Structure | Name | Retention time (min) | MS (ESI) m/z* |
|---|---|---|---|---|
| 54 | 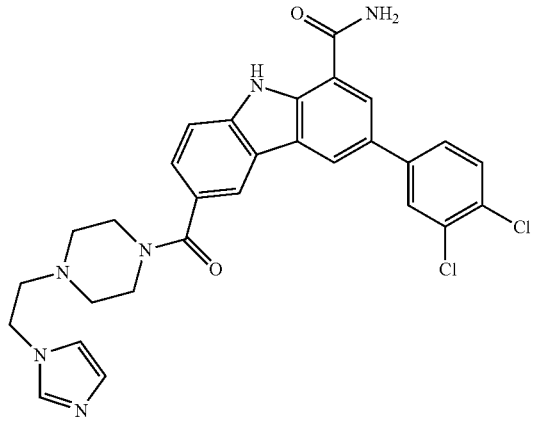 [SMILES: NC(=O)c1cc(-c2ccc(Cl)c(Cl)c2)cc2c1[nH]c1ccc(C(=O)N3CCN(CCn4ccnc4)CC3)cc12] | 3-(3,4-dichlorophenyl)-6-((4-(2-(1H-imidazol-1-yl)ethyl)-1-piperazinyl)carbonyl)-9H-carbazole-1-carboxamide | 2.01 | 560.9 |
| 55 | 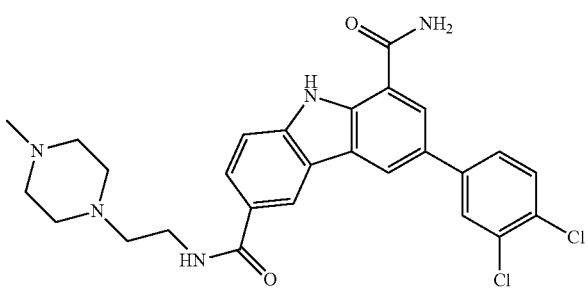 [SMILES: CN1CCN(CCNC(=O)c2ccc3[nH]c4c(C(N)=O)cc(-c5ccc(Cl)c(Cl)c5)cc4c3c2)CC1] | 3-(3,4-dichlorophenyl)-$N^6$-(2-(4-methyl-1-piperazinyl)ethyl)-9H-carbazole-1,6-dicarboxamide | 1.88 | 523.9 |
| 56 | 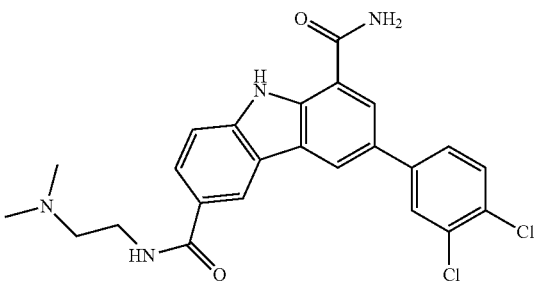 [SMILES: CN(C)CCNC(=O)c1ccc2[nH]c3c(C(N)=O)cc(-c4ccc(Cl)c(Cl)c4)cc3c2c1] | 3-(3,4-dichlorophenyl)-$N^6$-(2-(dimethylamino)ethyl)-9H-carbazole-1,6-dicarboxamide | 1.85 | 468.9 |
| 57 | 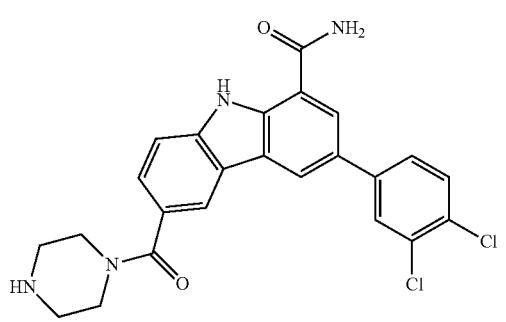 [SMILES: NC(=O)c1cc(-c2ccc(Cl)c(Cl)c2)cc2c1[nH]c1ccc(C(=O)N3CCNCC3)cc12] | 3-(3,4-dichlorophenyl)-6-(1-piperazinylcarbonyl)-9H-carbazole-1-carboxamide | 1.77 | 466.9 |

HPLC conditions: Schimadzu HPLC; Column:Ascentis Express C18 4.6 × 50 at 45°;

Flow rate: 4 ml/min;

Gradient: 4 min, 0-100% B;

Solvent: A = 5:95 Acetonitrile:Water; B = 95:5 Acetonitrile:Water, Modifier = 10 mM NH$_4$OAc.

*(M + H)$^+$ observed in all cases except the examples where specifically mentioned.

EXAMPLE 58

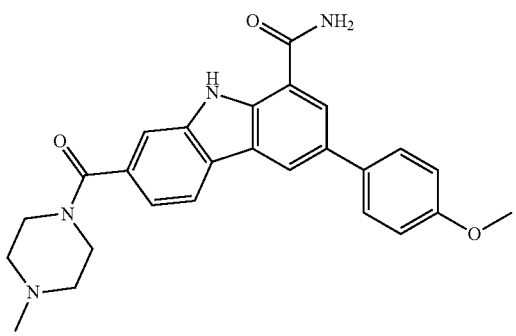 [SMILES: COc1ccc(-c2cc(C(N)=O)c3[nH]c4cc(C(=O)N5CCN(C)CC5)ccc4c3c2)cc1]

3-(4-Methoxyphenyl)-7-(4-methylpiperazine-1-carbonyl)-9H-carbazole-1-carboxamide 58A. Preparation of 6-bromo-2-(ethoxycarbonyl)-2,3,4,9-tetrahydro-1H-carbazole-8-carboxylic acid

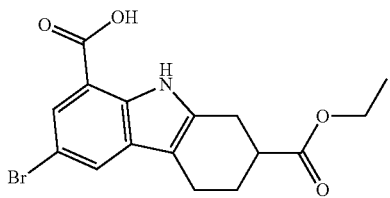 [SMILES: CCOC(=O)C1CCc2c([nH]c3c(C(=O)O)cc(Br)cc23)C1]

A cream colored suspension of 5-bromo-2-hydrazinylbenzoic acid dihydrochloride (6 g, 19.74 mmol) and ethyl 3-oxocyclohexanecarboxylate (3.70 g, 21.71 mmol) in glacial acetic acid, (~0.4M) (45 mL) was heated at reflux for 4h. The reaction mixture turned in to dark yellow suspension. The reaction mixture was cooled to room temperature and it was concentrated to afford a dark yellow solid. The solid was then suspended in ethyl acetate (~50 ml) and the solid was filtered, washed with water and ethyl acetate to give 4.14 g of 6-bromo-2-(ethoxycarbonyl)-2,3,4,9-tetrahydro-1H-carbazole-8-carboxylic acid. MS (ESI) m/z 366.3 (M+H). $^1$H NMR (DMSO-d$_6$) δ ppm 13.4-12.3 (b, 1H), 10.99 (s, 1H), 7.79 (d, 1H, J=1.9 Hz) 7.69 (d, 1H, J=1.8 Hz), 4.08-4.17 (m, 2H), 3.05 (dd, 1H, J=16.5, 5.0), 2.97-2.84 (m, 2H), 2.76-2.69 (m, 1H), 2.67-2.59 (m, 1H), 2.19-2.12 (m, 1H), 1.88-1.78 (m, 1H), 1.21 (t, 3H, J=7.2).

58B. Preparation of ethyl 6-bromo-8-carbamoyl-2,3,4,9-tetrahydro-1H-carbazole-2-carboxylate

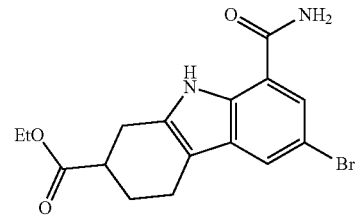 [SMILES: CCOC(=O)C1CCc2c([nH]c3c(C(N)=O)cc(Br)cc23)C1]

To a suspension of 6-bromo-2-(ethoxycarbonyl)-2,3,4,9-tetrahydro-1H-carbazole-8-carboxylic acid (18.5 g, 42.4 mmol), EDC (10.58 g, 55.2 mmol), and 1-hydroxybenzotriazole hydrate (8.45 g, 55.2 mmol) in THF/CH$_2$Cl$_2$ (5/1) (480 mL) was added ammonium hydroxide (9.91 mL, 76 mmol) and it turned into a thick light yellow suspension and it was stirred at room temperature over the weekend. CAUTION: A mild exotherm was observed. The reaction mixture warmed up to 31° C. If reaction is done on larger scale, consider cooling or slow addition of one of the reagents. The reaction mixture was concentrated and then titurated with 500 ml water (sonicate for 2 minutes), then filtered through a medium porosity glass frit. The solids were washed with water and dried in a nitrogen stream to give 15.1 g ethyl 6-bromo-8-carbamoyl-2,3,4,9-tetrahydro-1H-carbazole-2-carboxylate. MS (ESI) m/e-=363/365, m/e+=365/367 [1Br isotope pattern]. $^1$H NMR (DMSO-d$_6$) δ ppm 10.97 (s, 1H), 8.10 (b, 1H), 7.74 (d, 1H, J=1.8), 7.68 (d, 1H, J=1.5), 7.44 (b, 1H), 4.16-4.06 (m, 2H), 3.04 (dd, 1H, J=16.2, 5.0), 2.95-2.83 (m, 2H), 2.75-2.68 (m, 1H), 2.67-2.58 (m, 1H), 2.18-2.12 (m, 1H), 1.87-1.79 (m, 1H), 1.21 (t, 3H, J=7.0).

58C. Preparation of ethyl 6-bromo-8-carbamoyl-9H-carbazole-2-carboxylate

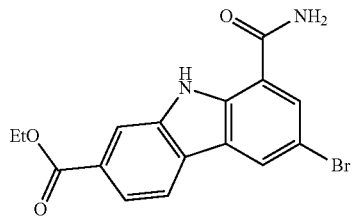

A stirred suspension of ethyl 6-bromo-8-carbamoyl-2,3,4,9-tetrahydro-1H-carbazole-2-carboxylate (3.93 g, 10.76 mmol) and 2,3-dichloro-5,6-dicyano-1,4-benzoquinone (5.37 g, 23.67 mmol) in toluene (60 mL) was heated at reflux for 4 h. The reaction mixture was cooled to room temperature and the solid was filtered, washed with toluene, and air-dried. The solid was suspended in ethyl acetate, the solid filtered, washed with MeOH and air-dried to furnish 4.6 g of ethyl 6-bromo-8-carbamoyl-9H-carbazole-2-carboxylate which was taken as such to the next reaction. MS (ESI) m/z 361.1/363.1 (M+H)$^+$. $^1$H NMR (DMSO-d$_6$) δ ppm 11.76 (s, 1H), 8.60 (d, J=1.76 Hz, 1H), 8.36 (d, J=0.88 Hz, 1H), 8.25 (d, J=8.35 Hz, 1H), 8.23 (br. s., 1H), 8.13 (d, J=1.76 Hz, 1H), 7.73 (dd, J=8.24, 1.43 Hz, 1H), 7.59 (br. s., 1H), 4.29 (q, J=7.18 Hz, 2H), 1.30 (t, J=7.14 Hz, 3H).

58D. Preparation of 6-bromo-8-carbamoyl-9H-carbazole-2-carboxylic acid

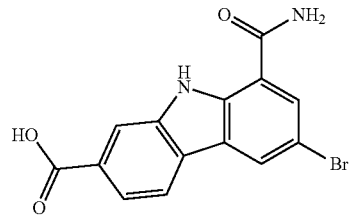 [SMILES: NC(=O)c1cc(Br)cc2c1[nH]c1cc(C(=O)O)ccc12]

A solution of ethyl 6-bromo-8-carbamoyl-9H-carbazole-2-carboxylate (4.7 g, 8.85 mmol) and lithium hydroxide (0.848 g, 35 4 mmol) in THF/EtOH/H$_2$O (3/1/1) (70 mL) was heated at 75° C. overnight. The reaction was concentrated and the resulting yellow solid was suspended in water. To above suspension, was added 1M HCl/conc. HCl until pH=2-3. The light yellow solid was collected by filtration and air-dried to furnish 8.4 g of 6-bromo-8-carbamoyl-9H-carbazole-2-carboxylic acid with ~80% purity. This material was carried forward to the next step. MS (ESI) m/z-=331/363 [M–H]$^-$, 1 Br isotope pattern. HPLC retention time 9.79 min. (Sunfire C18 3.5 μm, 4.6×150 mm column, 15 min gradient, 10-100% B, 1 mL/min. Solvent A: 5% CH$_3$CN-95% H$_2$O-0.1% TFA; Solvent B: 95% CH$_3$CN-5% H$_2$O-0.1% TFA). $^1$H NMR (DMSO-d$_6$) δ ppm 13.0-12.65 (b, 1H), 11.80 (s, 1H), 8.65 (d, 1H, J=1.8), 8.39 (d, 1H, J=0.6), 8.30 (s, 1H), 8.29 (d, 1H, J=8.2), 8.20 (d, 1H, J=1.8), 7.79 (dd, 1H, J=1.5, 8.3), 7.66 (br. s., 1H).

58E. Preparation of 3-bromo-7-(4-methylpiperazine-1-carbonyl)-9H-carbazole-1-carboxamide

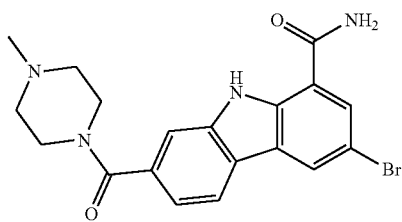 [SMILES: CN1CCN(C(=O)c2ccc3c(c2)[nH]c2c(C(N)=O)cc(Br)cc23)CC1]

To a suspension of 6-bromo-8-carbamoyl-9H-carbazole-2-carboxylic acid (8.47 g, 8.64 mmol), EDC (1.657 g, 8.64 mmol), and 1-hydroxybenzotriazole hydrate (1.324 g, 8.64 mmol) in THF/CH$_2$Cl$_2$ (5/1) (40 mL) was added 1-methylpiperazine (3.84 mL, 34.6 mmol). The reaction mixture turned into a dark pink suspension. The reaction mixture was stirred at room temperature for 16 h. The reaction mixture was concentrated and partitioned between ethyl acetate and water/sat. NaHCO$_3$. The aqueous phase was re-extracted with ethyl acetate. The organic phase was washed with brine, dried over MgSO$_4$ and concentrated to afford the crude product as a dark pink solid, which was purified by silica gel column chromatography (CH$_2$Cl$_2$/2M NH$_3$ in MeOH=100/5-100/7). The product obtained was suspended in ethyl acetate and colorless solid was collected by filtration and air-dried to give 1.78 G of 3-bromo-7-(4-methylpiperazine-1-carbonyl)-9H-carbazole-1-carboxamide. MS (ESI) m/z 415.1 (M+H). $^1$H NMR (DMSO-d$_6$) δ ppm 11.68 (s, 1H) 8.60 (d, J=1.76 Hz, 1H) 8.28 (br. s., 1H 8.24 (d, J=8.13 Hz, 1H), 8.16 (d, J=1.76 Hz, 1H) 7.75 (s, 1H) 7.64 (br. s., 1H) 7.14-7.22 (m, 1H) 3.34-3.75 (m, 4H) 2.24-2.44 (m, 4H) 2.20 (s, 3H).

58. Preparation of 3-(4-methoxyphenyl)-7-(4-methylpiperazine-1-carbonyl)-9H-carbazole-1-carboxamide, (prepared as the TFA salt)

A mixture of 3-bromo-7-(4-methylpiperazine-1-carbonyl)-9H-carbazole-1-carboxamide (25 mg, 0.06 mmol), 4-methoxyphenylboronic acid (13.7 mg, 0.09 mmol), PdCl$_2$ (dppf)—CH$_2$Cl$_2$ adduct (4.92 mg, 6.92 μmol) and potassium carbonate (24.9 mg, 0.18 mmol) in toluene:ethanol (1.5+1 ml) was heated at 160° C. for 30 minutes in microwave oven. The reaction mixture was concentrated and purified using preparative HPLC to give 12 mg of 3-(4-methoxyphenyl)-7-(4-methylpiperazine-1-carbonyl)-9H-carbazole-1-carboxamide, TFA salt. MS (ESI) m/z 443.3 (M+H). $^1$H NMR (DMSO-d$_6$) δ ppm 11.56 (s, 1H) 8.65 (s, 1H) 8.38 (br. s., 1H) 8.26-8.34 (m, 2H) 7.78-7.85 (m, 3H) 7.56 (br. s., 1H) 7.28 (dd, J=8.02, 1.43 Hz, 1H) 7.07 (d, J=8.79 Hz, 2H) 3.82 (s, 3H) 3.23-3.40 (m, 4H) 3.00-3.21 (m, 4H) 2.84 (s, 3H).

The following compounds in Table 4 have been synthesized utilizing the procedures described in Example 58.

TABLE 4

| Ex. # | Structure | Name | Retention time (min) | MS (ESI) m/z* |
|---|---|---|---|---|
| 59 | 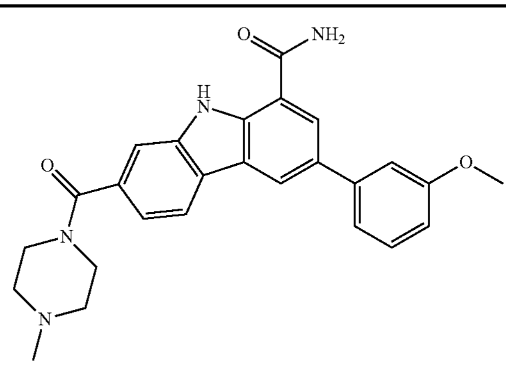 | 3-(3-methoxyphenyl)-7-((4-methyl-1-piperazinyl)carbonyl)-9H-carbazole-1-carboxamide | 1.32 | 443.26 |

TABLE 4-continued

| Ex. # | Structure | Name | Retention time (min) | MS (ESI) m/z* |
|---|---|---|---|---|
| 60 | 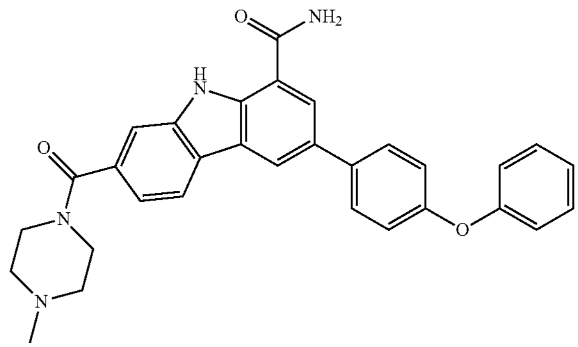 [SMILES: CN1CCN(C(=O)c2ccc3c(c2)[nH]c2c(C(N)=O)cc(-c4ccc(Oc5ccccc5)cc4)cc23)CC1] | 7-((4-methyl-1-piperazinyl)carbonyl)-3-(4-phenoxyphenyl)-9H-carbazole-1-carboxamide | 1.54 | 504.6 |
| 61 | 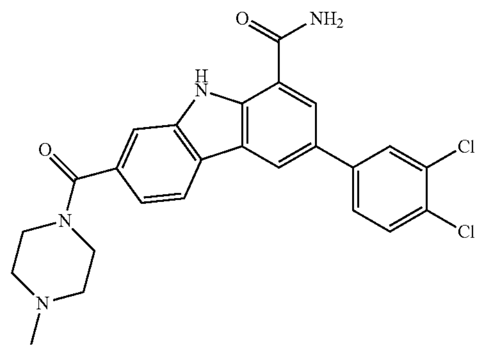 [SMILES: CN1CCN(C(=O)c2ccc3c(c2)[nH]c2c(C(N)=O)cc(-c4ccc(Cl)c(Cl)c4)cc23)CC1] | 3-(3,4-dichlorophenyl)-7-((4-methyl-1-piperazinyl)carbonyl)-9H-carbazole-1-carboxamide | 1.50 | 481.3 |
| 62 | 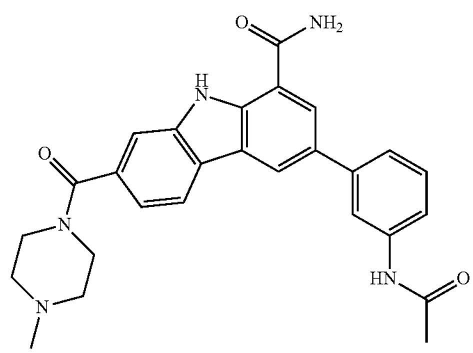 [SMILES: CC(=O)Nc1cccc(-c2cc(C(N)=O)c3[nH]c4cc(C(=O)N5CCN(C)CC5)ccc4c3c2)c1] | 3-(3-acetamidophenyl)-7-((4-methyl-1-piperazinyl)carbonyl)-9H-carbazole-1-carboxamide | 1.09 | 468.2 (M − H)⁻ |
| 63 | 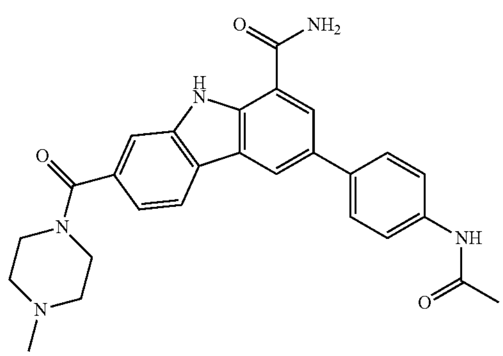 [SMILES: CC(=O)Nc1ccc(-c2cc(C(N)=O)c3[nH]c4cc(C(=O)N5CCN(C)CC5)ccc4c3c2)cc1] | 3-(4-acetamidophenyl)-7-((4-methyl-1-piperazinyl)carbonyl)-9H-carbazole-1-carboxamide | 1.05 | 468.6 (M − H)⁻ |

TABLE 4-continued

| Ex. # | Structure | Name | Retention time (min) | MS (ESI) m/z* |
|---|---|---|---|---|
| 64 | 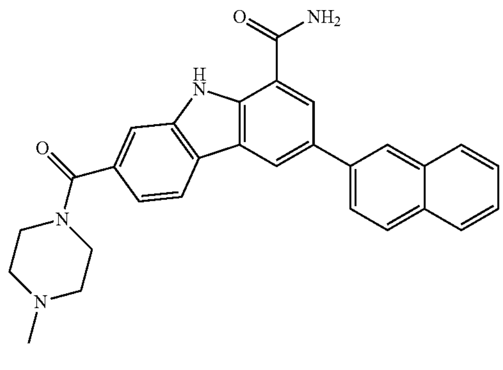 [SMILES: CN1CCN(C(=O)c2ccc3c(c2)[nH]c2c(C(N)=O)cc(-c4ccc5ccccc5c4)cc23)CC1] | 3-(6-methoxy-2-naphthyl)-7-((4-methyl-1-piperazinyl)carbonyl)-9H-carbazole-1-carboxamide | 1.46 | 461.5 (M − H)⁻ |
| 65 | 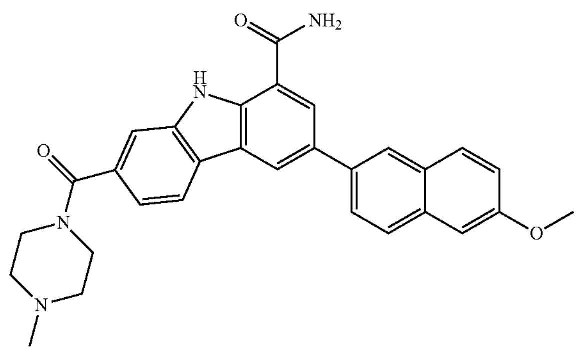 [SMILES: COc1ccc2cc(-c3cc(C(N)=O)c4[nH]c5cc(C(=O)N6CCN(C)CC6)ccc5c4c3)ccc2c1] | 7-((4-methyl-1-piperazinyl)-carbonyl)-3-(2-naphthyl)-9H-carbazole-1-carboxamide | 1.49 | 493.4 |
| 66 | 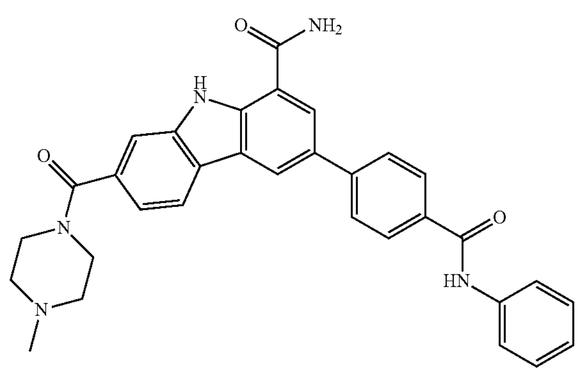 [SMILES: CN1CCN(C(=O)c2ccc3c(c2)[nH]c2c(C(N)=O)cc(-c4ccc(C(=O)Nc5ccccc5)cc4)cc23)CC1] | 7-((4-methyl-1-piperazinyl)carbonyl)-3-(4-(phenylcarbamoyl)phenyl)-9H-carbazole-1-carboxamide | 1.38 | 532.5 |
| 67 | 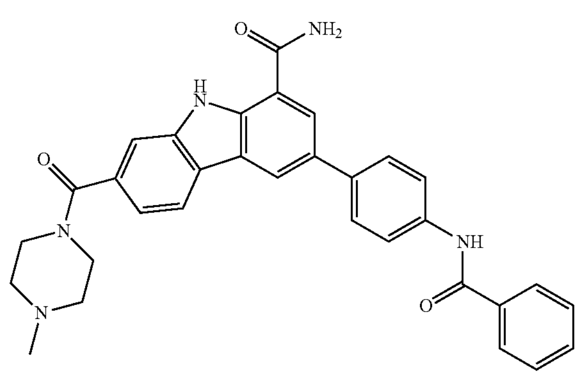 [SMILES: CN1CCN(C(=O)c2ccc3c(c2)[nH]c2c(C(N)=O)cc(-c4ccc(NC(=O)c5ccccc5)cc4)cc23)CC1] | 3-(4-(benzoylamino)phenyl)-7-((4-methyl-1-piperazinyl)carbonyl)-9H-carbazole-1-carboxamide | 1.33 | 530.6 |

TABLE 4-continued

| Ex. # | Structure | Name | Retention time (min) | MS (ESI) m/z* |
|---|---|---|---|---|
| 68 | 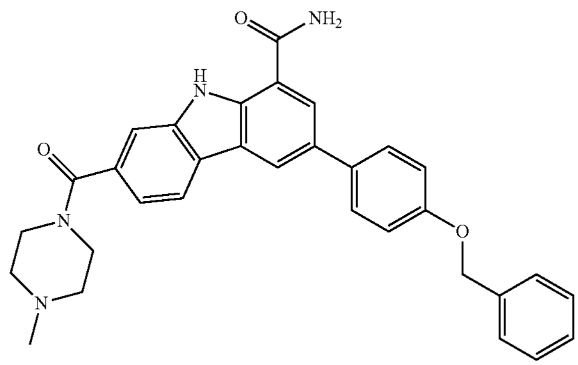 [SMILES: CN1CCN(C(=O)c2ccc3c(c2)[nH]c2c(C(N)=O)cc(-c4ccc(OCc5ccccc5)cc4)cc23)CC1] | 3-(4-(benzyloxy)phenyl)-7-((4-methyl-1-piperazinyl)carbonyl)-9H-carbazole-1-carboxamide | 1.53 | 519.4 |
| 69 | 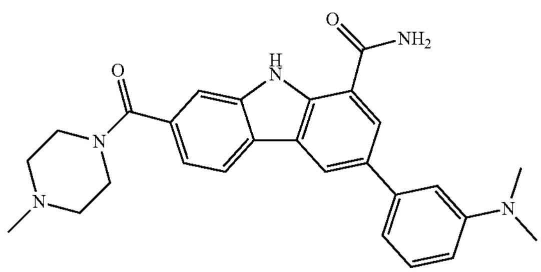 | 3-(3-(dimethylamino)phenyl)-7-((4-methyl-1-piperazinyl)carbonyl)-9H-carbazole-1-carboxamide | 1.24 | 415.2 |
| 70 | 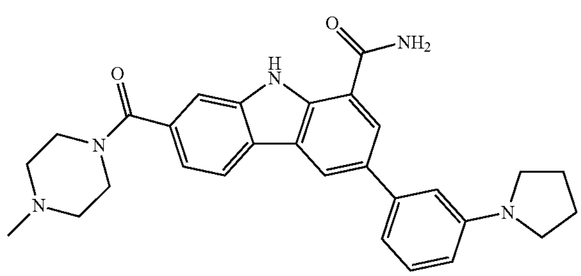 [SMILES: CN1CCN(C(=O)c2ccc3c(c2)[nH]c2c(C(N)=O)cc(-c4cccc(N5CCCC5)c4)cc23)CC1] | 7-((4-methyl-1-piperazinyl)carbonyl)-3-(3-(1-pyrrolidinyl)phenyl)-9H-carbazole-1-carboxamide | 1.76 | 480.4 |
| 71 | 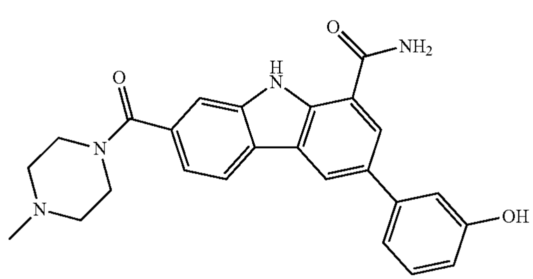 [SMILES: CN1CCN(C(=O)c2ccc3c(c2)[nH]c2c(C(N)=O)cc(-c4cccc(O)c4)cc23)CC1] | 3-(3-hydroxyphenyl)-7-((4-methyl-1-piperazinyl)carbonyl)-9H-carbazole-1-carboxamide | 1.22 | 427.3 |
| 72 | 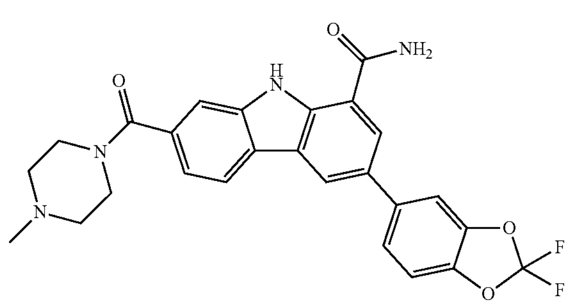 [SMILES: CN1CCN(C(=O)c2ccc3c(c2)[nH]c2c(C(N)=O)cc(-c4ccc5c(c4)OC(F)(F)O5)cc23)CC1] | 3-(2,2-difluoro-1,3-benzodioxol-5-yl)-7-((4-methyl-1-piperazinyl)carbonyl)-9H-carbazole-1-carboxamide | 1.69 | 493.2 |

TABLE 4-continued

| Ex. # | Structure | Name | Retention time (min) | MS (ESI) m/z* |
|---|---|---|---|---|
| 73 | 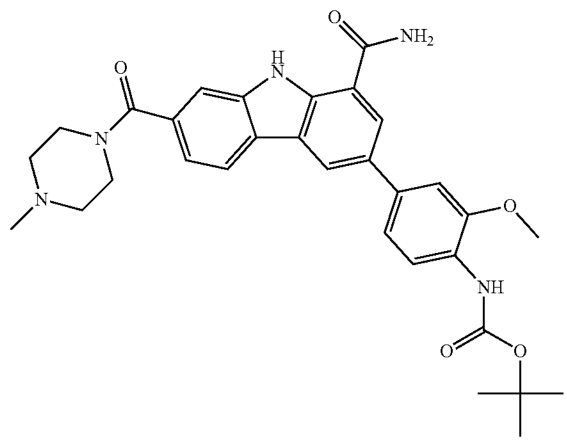 [SMILES: COc1cc(-c2cc(C(N)=O)c3[nH]c4cc(C(=O)N5CCN(C)CC5)ccc4c3c2)ccc1NC(=O)OC(C)(C)C] | tert-butyl (4-(1-carbamoyl-7-((4-methyl-1-piperazinyl)carbonyl)-9H-carbazol-3-yl)-2-methoxyphenyl) carbamate | 1.79 | 556.5 |
| 74 | 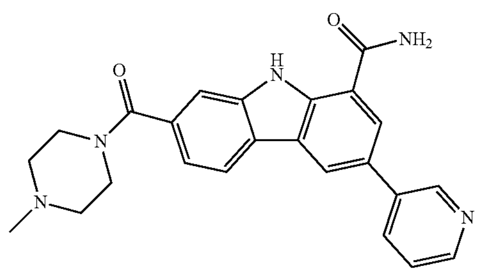 [SMILES: CN1CCN(C(=O)c2ccc3c(c2)[nH]c2c(C(N)=O)cc(-c4cccnc4)cc23)CC1] | 7-((4-methyl-1-piperazinyl)carbonyl)-3-(3-pyridinyl)-9H-carbazole-1-carboxamide | 1.11 | 412.2 (M − H)⁻ |
| 75 | 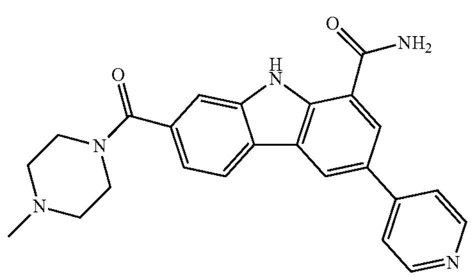 | 7-((4-methyl-1-piperazinyl)carbonyl)-3-(4-pyridinyl)-9H-carbazole-1-carboxamide | 1.06 | 412.2 |
| 76 | 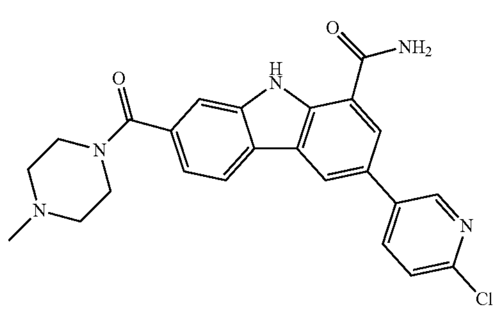 [SMILES: CN1CCN(C(=O)c2ccc3c(c2)[nH]c2c(C(N)=O)cc(-c4ccc(Cl)nc4)cc23)CC1] | 3-(6-chloro-3-pyridinyl)-7-((4-methyl-1-piperazinyl)carbonyl)-9H-carbazole-1-carboxamide | 1.34 | 446.2 |

TABLE 4-continued

| Ex. # | Structure | Name | Retention time (min) | MS (ESI) m/z* |
|---|---|---|---|---|
| 77 | 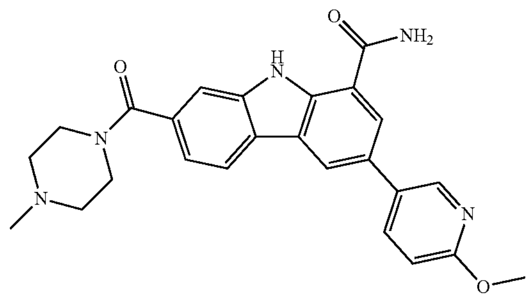 | 3-(6-methoxy-3-pyridinyl)-7-((4-methyl-1-piperazinyl)carbonyl)-9H-carbazole-1-carboxamide | 1.32 | 442.3 |
| 78 | 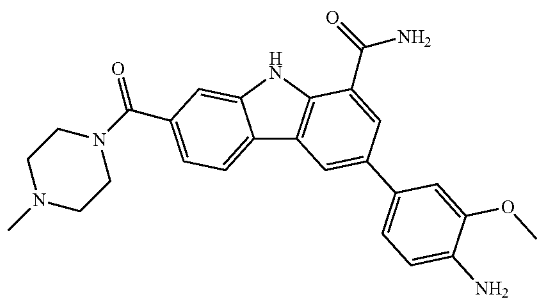 | 3-(4-amino-3-methoxyphenyl)-7-((4-methyl-1-piperazinyl)carbonyl)-9H-carbazole-1-carboxamide | 1.20 | 458.3 |
| 79 | 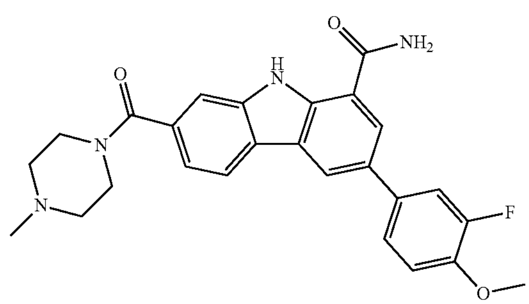 | 3-(3-fluoro-4-methoxyphenyl)-7-((4-methyl-1-piperazinyl)carbonyl)-9H-carbazole-1-carboxamide | 1.67 | 459.3 |
| 80 | 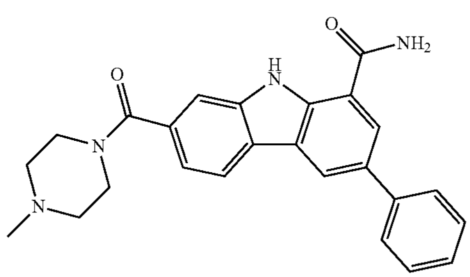 | 7-((4-methyl-1-piperazinyl)carbonyl)-3-phenyl-9H-carbazole-1-carboxamide | 1.59 | 411.3 |
| 81 | 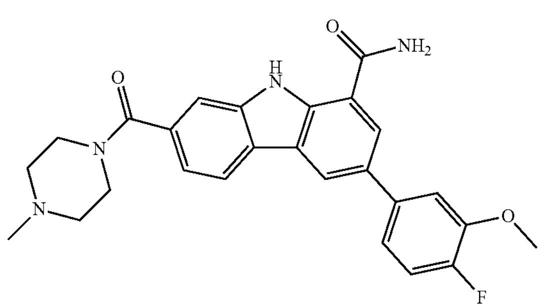 | 3-(4-fluoro-3-methoxyphenyl)-7-((4-methyl-1-piperazinyl)carbonyl)-9H-carbazole-1-carboxamide | 1.63 | 459.39 |

HPLC conditions: Schimadzu HPLC; Column:Ascentis Express C18 4.6 × 50 at 45°;
Flow rate: 4 ml/min;
Gradient: 4 min, 0-100% B;
Solvent: A = 5:95 Acetonitrile:Water; B = 95:5 Acetonitrile:Water, Modifier = 10 mM NH$_4$OAc.
*(M + H)$^+$ Observed in all cases except the examples where specifically mentioned.

EXAMPLE 82

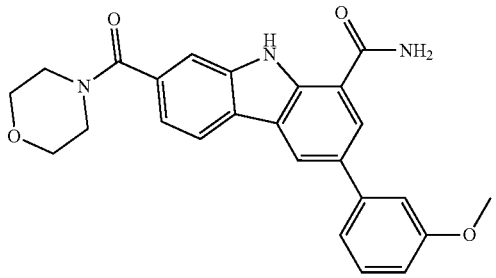 [SMILES: COc1cccc(-c2cc(C(N)=O)c3[nH]c4cc(C(=O)N5CCOCC5)ccc4c3c2)c1]

3-(3-Methoxyphenyl)-7-(4-morpholinylcarbonyl)-9H-carbazole-1-carboxamide

82A. Preparation of ethyl 8-carbamoyl-6-(3-methoxyphenyl)-9H-carbazole-2-carboxylate

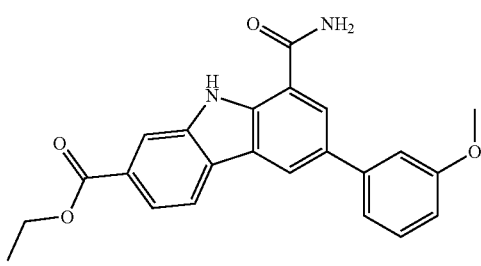 [SMILES: CCOC(=O)c1ccc2c(c1)[nH]c1c(C(N)=O)cc(-c3cccc(OC)c3)cc12]

To a suspension of ethyl 6-bromo-8-carbamoyl-9H-carbazole-2-carboxylate (3.5 g, 6.85 mmol, Example 58C), tetrakis(triphenylphosphine)palladium (0)(0.317 g, 0.274 mmol), toluene (30 mL), and 2 M aqueous sodium carbonate (6.85 mL, 13.70 mmol) under nitrogen were added a solution of 3-methoxyphenylboronic acid (1.457 g, 9.59 mmol) in MeOH (4 mL). The resulting reaction mixture was heated at reflux for 5 h. After cooling to room temperature, it was diluted with a mixture of water (250 mL) and ethyl acetate (250 mL) and the two phases were separated. The aqueous phase was extracted with ethyl acetate (2×200 mL), and the combined organic phases were washed with water (2×200 mL), 5% aqueous NH$_4$OH solution (120 mL), and brine (100 mL). The organic phase was dried over Na$_2$SO$_4$ and the solvent removed. The crude material was suspended in a mixture of DCM and ethyl acetate. The solid was collected by filtration, washed with DCM, and air dried to afford 1.31 g product 82A. The filtrate was mixtured with silica gel and the solvent removed. This was loaded onto a silica gel column and eluted with hexane containing 10 to 50% ethyl acetate to afford additional 1.01 g of product for a total of 2.32 g of crude. MS (ESI) m/z 389.2 (M+H). $^1$H NMR (DMSO-d$_6$) δ ppm 11.73 (1H, s), 8.78 (1H, s), 8.30-8.51 (4H, m), 7.83 (1H, d, J=8.24 Hz), 7.55-7.67 (1H, m), 7.37-7.54 (3H, m), 6.96 (1H, d, J=8.24 Hz), 4.38 (2H, q, J=6.92 Hz), 3.90 (3H, s), 1.39 (3H, t, J=7.02 Hz).

82B. Preparation of 8-carbamoyl-6-(3-methoxyphenyl)-9H-carbazole-2-carboxylic acid

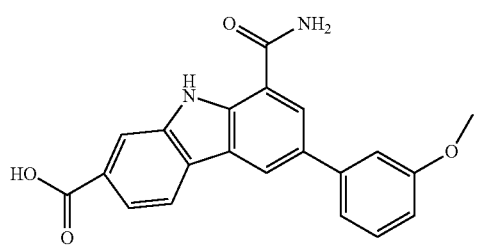 [SMILES: COc1cccc(-c2cc(C(N)=O)c3[nH]c4cc(C(=O)O)ccc4c3c2)c1]

To a solution of ethyl 8-carbamoyl-6-(3-methoxyphenyl)-9H-carbazole-2-carboxylate (2.1 g, 5.41 mmol) in a mixture of THF (40 mL) and MeOH (14 mL) was added a solution of aq. 1 M sodium hydroxide (13.52 mL, 13.52 mmol). The mixture was stirred at room temperature for 2 days. Removal of solvents left a solid which was suspended in water (150 mL), This was acidified with 1N HCl to pH 2-3 and the solid was collected by filtration, washed with H$_2$O(3×20 mL), and dried under vacuum to afford 1.78 gm of the desired product (83% yield). MS (ESI) m/z 361.1 (M+H). $^1$H NMR (DMSO-d$_6$) δ ppm 12.79 (1H, br. s.), 11.70 (1H, s), 8.76 (1H, s), 8.38-8.47 (2H, m), 8.35 (2H, dd, J=4.58, 3.36 Hz), 7.82 (1H, d, J=7.93 Hz), 7.59 (1H, br. s.), 7.40-7.52 (3H, m), 6.96 (1H, dd, J=7.93, 2.14 Hz), 3.89 (3H, s).

Preparation of 3-(3-methoxyphenyl)-7-(4-morpholinylcarbonyl)-9H-carbazole-1-carboxamide A mixture of 8-carbamoyl-6-(3-methoxyphenyl)-9H-carbazole-2-carboxylic acid (36 mg, 0.100 mmol), morpholine (17 mg, 0.2 mmol), EDC (23 mg, 0.12 mmol), HOBt (18 mg, 0.12 mmol) and N-ethyl-N-isopropylpropan-2-amine (0.035 mL, 0.2 mmol) in a mixture of THF (5 mL) and CH$_2$Cl$_2$ (1 mL) was stirred at room temperature overnight. This was diluted with MeOH and the product was isolated by preparative HPLC (100×30 mm Luna C18 column, flow rate 42 ml permin, gradient elution starting with A:B=90:10 and ending with A:B=30:70 [A=10 mM NH$_4$OAc in 5% aqueous acetonitrile; B=10 mM NH$_4$OAc in 95% aqueous acetonitrile] over 20 min) followed by removal of the solvents. This afforded 29 mg of 3-(3-methoxyphenyl)-7-(morpholine-4-carbonyl)-9H-carbazole 1-carboxamide as a solid. MS (ESI) m/z 430.2 (M+H). $^1$H NMR (MeOD) δ ppm 8.42 (1H, s), 8.13 (1H, d, J=7.94 Hz), 8.05 (1H, s), 7.57 (1H, s), 7.32-7.41 (2H, m), 7.29 (1H, d, J=7.63 Hz), 7.21-7.26 (1H, m), 6.85-6.93 (1H, m), 3.88 (3H, s), 3.43-3.84 (8H, m).

The following compounds in Table 5 have been synthesized utilizing the procedures described in Example 82.

TABLE 5

| Ex. # | Structure | Name | Retention time (min) | MS (ESI) m/z* |
|---|---|---|---|---|
| 83 | 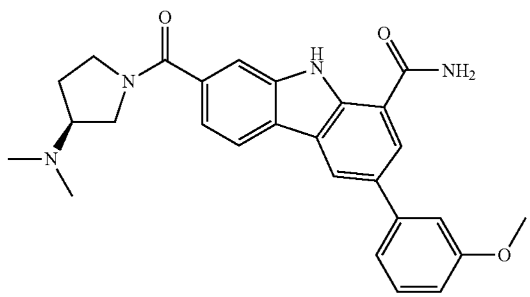 | 7-(((3S)-3-(dimethylamino)-1-pyrrolidinyl)carbonyl)-3-(3-methoxyphenyl)-9H-carbazole-1-carboxamide | 1.78 | 457.2 |
| 84 | 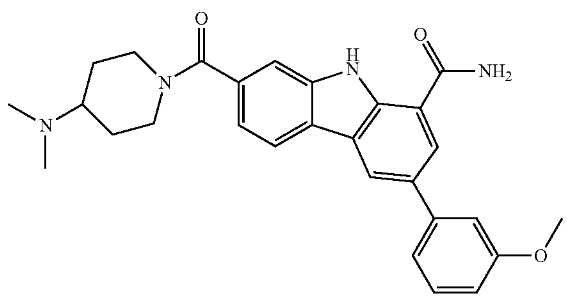 | 7-((4-(dimethylamino)-1-piperidinyl)carbonyl)-3-(3-methoxyphenyl)-9H-carbazole-1-carboxamide | 1.76 | 471.2 |
| 85 | 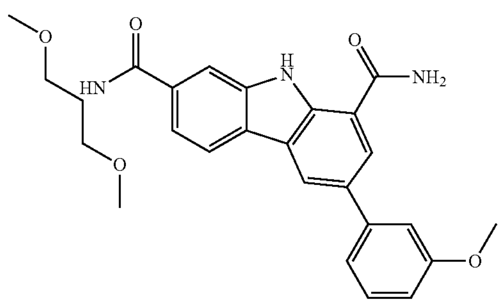 | N7-(2-methoxy-1-(methoxymethyl)ethyl)-3-(3-methoxyphenyl)-9H-carbazole-1,7-dicarboxamide | 2.34 | 462.2 |
| 86 | 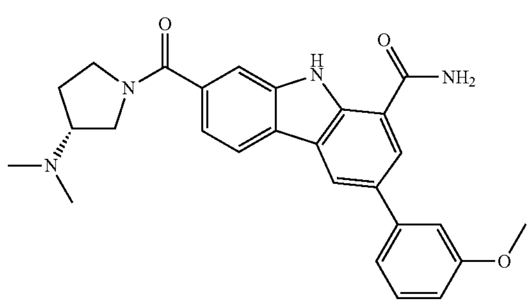 | 7-(((3R)-3-(dimethylamino)-1-pyrrolidinyl)carbonyl)-3-(3-methoxyphenyl)-9H-carbazole-1-carboxamide | 1.74 | 457.2 |
| 87 | 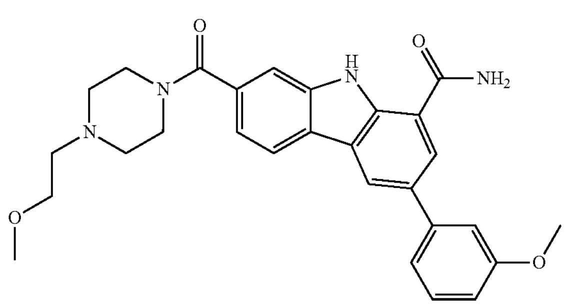 [SMILES: COCCN1CCN(C(=O)c2ccc3c(c2)[nH]c2c(C(N)=O)cc(-c4cccc(OC)c4)cc23)CC1] | 7-((4-(2-methoxyethyl)-1-piperazinyl)carbonyl)-3-(3-methoxyphenyl)-9H-carbazole-1-carboxamide | 1.79 | 487.2 |

US 8,815,840 B2

TABLE 5-continued

| Ex. # | Structure | Name | Retention time (min) | MS (ESI) m/z* |
|---|---|---|---|---|
| 88 | 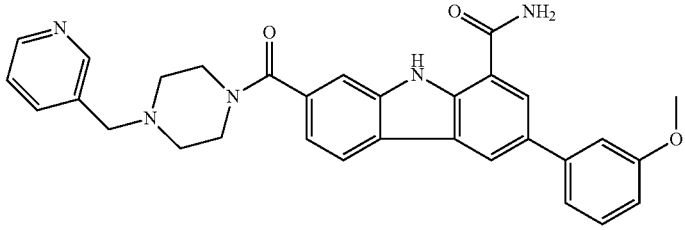 [SMILES: COc1cccc(-c2cc(C(N)=O)c3[nH]c4cc(C(=O)N5CCN(Cc6cccnc6)CC5)ccc4c3c2)c1] | 3-(3-methoxyphenyl)-7-((4-(3-pyridinylmethyl)-1-piperazinyl)carbonyl)-9H-carbazole-1-carboxamide | 3.97 | 520.3 |
| 89 | 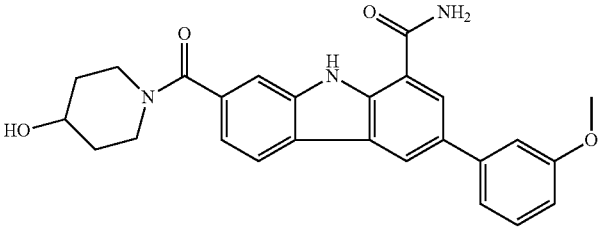 [SMILES: COc1cccc(-c2cc(C(N)=O)c3[nH]c4cc(C(=O)N5CCC(O)CC5)ccc4c3c2)c1] | 7-((4-hydroxy-1-piperidinyl)carbonyl)-3-(3-methoxyphenyl)-9H-carbazole-1-carboxamide | 3.52 | 444.2 |
| 90 | 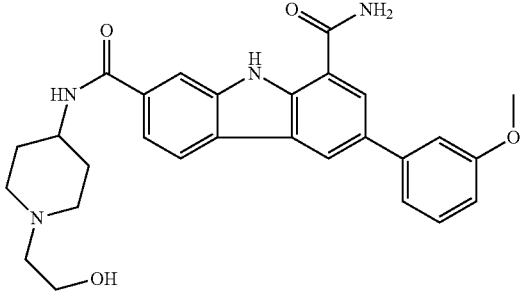 [SMILES: COc1cccc(-c2cc(C(N)=O)c3[nH]c4cc(C(=O)NC5CCN(CCO)CC5)ccc4c3c2)c1] | $N^7$-(1-(2-hydroxyethyl)-4-piperidinyl)-3-(3-methoxyphenyl)-9H-carbazole-1,7-dicarboxamide | 3.54 | 487.32 |
| 91 | 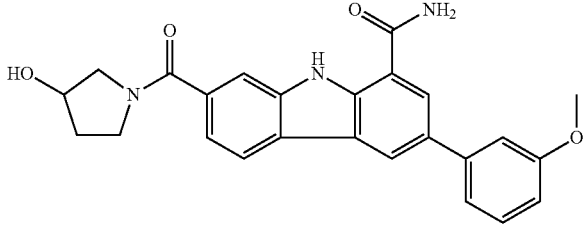 [SMILES: COc1cccc(-c2cc(C(N)=O)c3[nH]c4cc(C(=O)N5CCC(O)C5)ccc4c3c2)c1] | 7-((3-hydroxy-1-pyrrolidinyl)carbonyl)-3-(3-methoxyphenyl)-9H-carbazole-1-carboxamide | 3.49 | 430.2 |
| 92 | 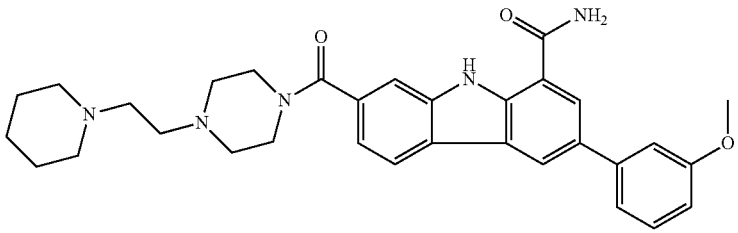 [SMILES: COc1cccc(-c2cc(C(N)=O)c3[nH]c4cc(C(=O)N5CCN(CCN6CCCCC6)CC5)ccc4c3c2)c1] | 3-(3-methoxyphenyl)-7-((4-(2-(1-piperidinyl)ethyl)-1-piperazinyl)carbonyl)-9H-carbazole-1-carboxamide | 3.65 | 540.3 |

TABLE 5-continued

| Ex. # | Structure | Name | Retention time (min) | MS (ESI) m/z* |
|---|---|---|---|---|
| 93 | 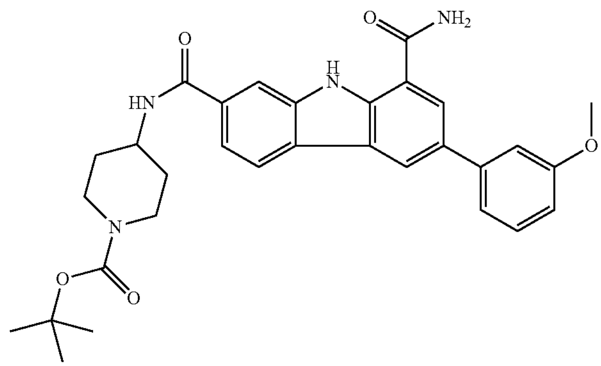 [SMILES: COc1cccc(-c2cc(C(N)=O)c3[nH]c4cc(C(=O)NC5CCN(C(=O)OC(C)(C)C)CC5)ccc4c3c2)c1] | tert-butyl4-(((8-carbamoyl-6-(3-methoxyphenyl)-9H-carbazol-2-yl)carbonyl)amino)-1-piperidinecarboxylate | 4.97 | 543.6 |
| 94 | 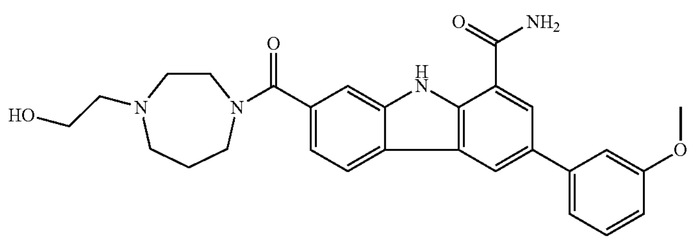 [SMILES: COc1cccc(-c2cc(C(N)=O)c3[nH]c4cc(C(=O)N5CCCN(CCO)CC5)ccc4c3c2)c1] | 7-((4-(2-hydroxyethyl)-1,4-diazepan-1-yl)carbonyl)-3-(3-methoxyphenyl)-9H-carbazole-1-carboxamide | 3.42 | 487.3 |
| 95 | 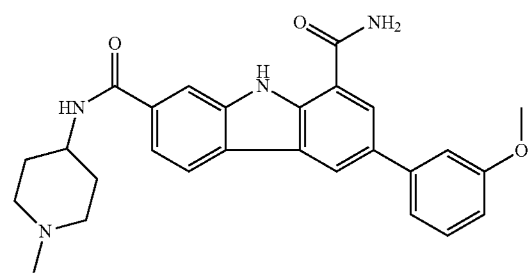 [SMILES: COc1cccc(-c2cc(C(N)=O)c3[nH]c4cc(C(=O)NC5CCN(C)CC5)ccc4c3c2)c1] | 3-(3-methoxyphenyl)-$N^7$-(1-methyl-4-piperidinyl)-9H-carbazole-1,7-dicarboxamide | 3.67 | 457.3 |
| 96 | 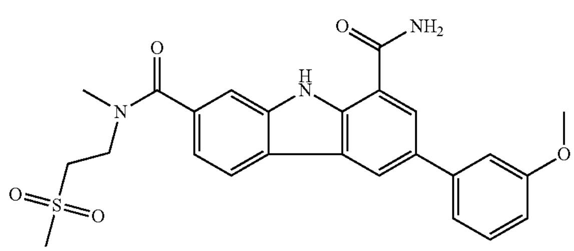 [SMILES: COc1cccc(-c2cc(C(N)=O)c3[nH]c4cc(C(=O)N(C)CCS(C)(=O)=O)ccc4c3c2)c1] | 3-(3-methoxyphenyl)-$N^7$-methyl-$N^7$-(2-(methylsulfonyl)ethyl)-9H-carbazole-1,7-dicarboxamide | 3.75 | 480.2 |
| 97 | 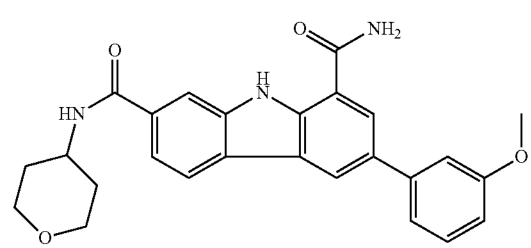 [SMILES: COc1cccc(-c2cc(C(N)=O)c3[nH]c4cc(C(=O)NC5CCOCC5)ccc4c3c2)c1] | 3-(3-methoxyphenyl)-$N^7$-(tetrahydro-2H-pyran-4-yl)-9H-carbazole-1,7-dicarboxamide | 3.89 | 444.2 |

TABLE 5-continued

| Ex. # | Structure | Name | Retention time (min) | MS (ESI) m/z* |
|---|---|---|---|---|
| 98 | 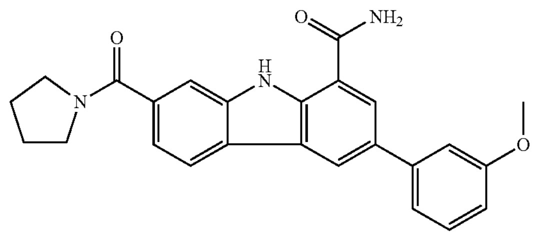 [SMILES: COc1cccc(-c2cc(C(N)=O)c3[nH]c4cc(C(=O)N5CCCC5)ccc4c3c2)c1] | 3-(3-methoxyphenyl)-7-(1-pyrrolidinylcarbonyl)-9H-carbazole-1-carboxamide | 4.26 | 414.2 |
| 99 | 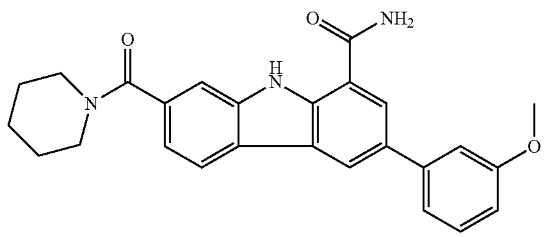 [SMILES: COc1cccc(-c2cc(C(N)=O)c3[nH]c4cc(C(=O)N5CCCCC5)ccc4c3c2)c1] | 3-(3-methoxyphenyl)-7-(1-piperidinylcarbonyl)-9H-carbazole-1-carboxamide | 4.75 | 428.29 |
| 100 | 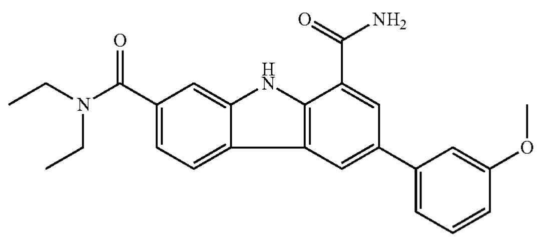 [SMILES: CCN(CC)C(=O)c1ccc2c(c1)[nH]c1c(C(N)=O)cc(-c3cccc(OC)c3)cc12] | $N^7,N^7$-diethyl-3-(3-methoxyphenyl)-9H-carbazole-1,7-dicarboxamide | 4.55 | 416.2 |
| 101 | 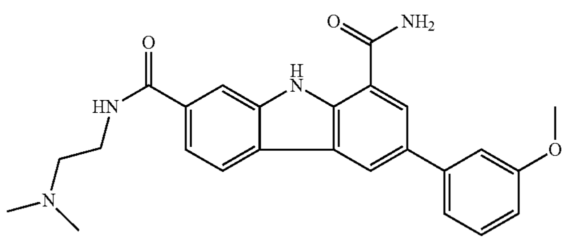 | $N^7$-(2-(dimethylamino)ethyl)-3-(3-methoxyphenyl)-9H-carbazole-1,7-dicarboxamide | 3.72 | 431.3 |
| 102 | 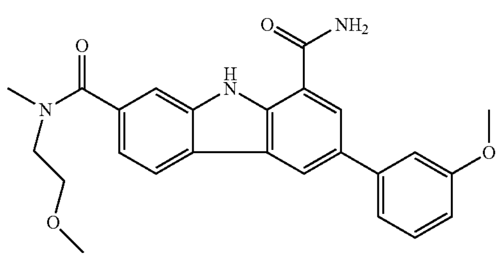 | $N^7$-(2-methoxyethyl)-3-(3-methoxyphenyl)-$N^7$-methyl-9H-carbazole-1,7-dicarboxamide | 4.12 | 432.2 |
| 103 | 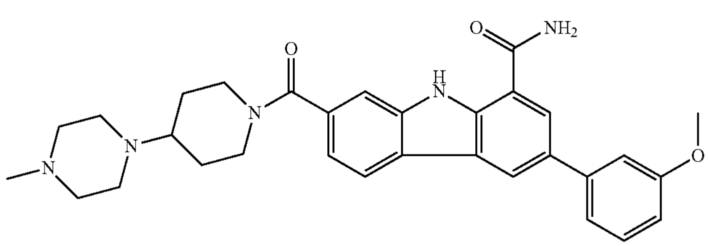 | 3-(3-methoxyphenyl)-7-((4-(4-methyl-1-piperazinyl)-1-piperidinyl)carbonyl)-9H-carbazole-1-carboxamide | 3.64 | 526.3 |

TABLE 5-continued

| Ex. # | Structure | Name | Retention time (min) | MS (ESI) m/z* |
|---|---|---|---|---|
| 104 | 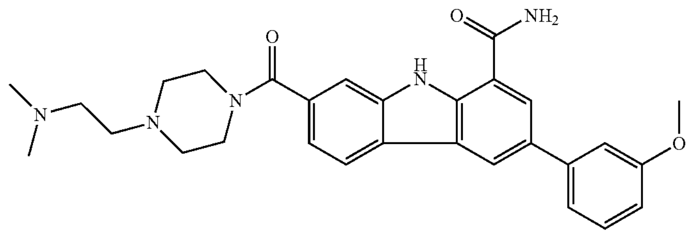 | 7-((4-(2-(dimethylamino) ethyl)-1-piperazinyl) carbonyl)-3-(3-methoxyphenyl)-9H-carbazole-1-carboxamide | 3.59 | 500.3 |
| 105 | 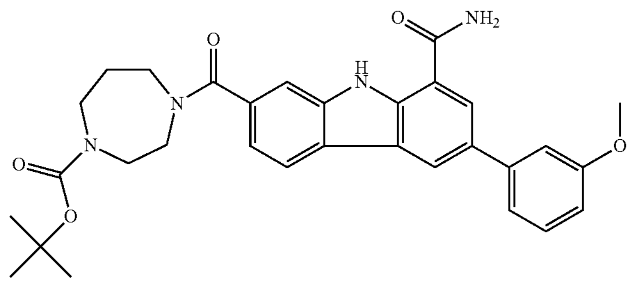 [SMILES: COc1cccc(-c2cc(C(N)=O)c3[nH]c4cc(C(=O)N5CCCN(C(=O)OC(C)(C)C)CC5)ccc4c3c2)c1] | tert-butyl 4-((8-carbamoyl-6-(3-methoxyphenyl)-9H-carbazol-2-yl) carbonyl)-1,4-diazepane-1-carboxylate | 4.94 | 543.3 |
| 106 | 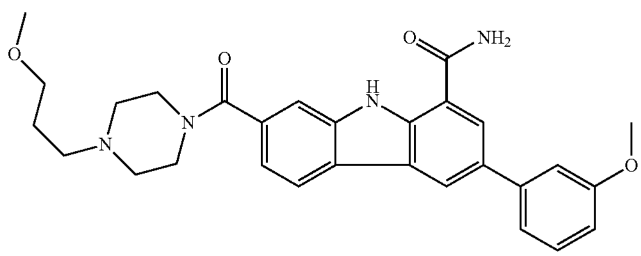 [SMILES: COCCCN1CCN(C(=O)c2ccc3c(c2)[nH]c2c(C(N)=O)cc(-c4cccc(OC)c4)cc23)CC1] | 3-(3-methoxyphenyl)-7-((4-(3-methoxypropyl)-1-piperazinyl)carbonyl)-9H-carbazole-1-carboxamide | 3.93 | 501.3 |
| 107 | 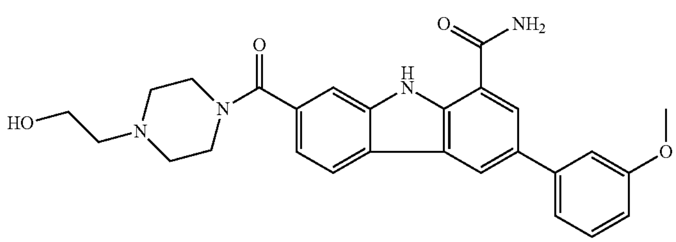 [SMILES: COc1cccc(-c2cc(C(N)=O)c3[nH]c4cc(C(=O)N5CCN(CCO)CC5)ccc4c3c2)c1] | 7-((4-(2-hydroxyethyl)-1-piperazinyl)carbonyl)-3-(3-methoxyphenyl)-9H-carbazole-1-carboxamide | 3.38 | 473.2 |
| 108 | 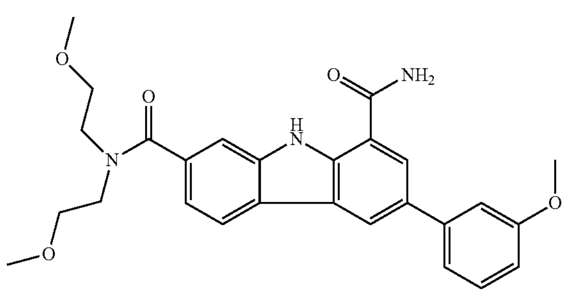 | $N^7,N^7$-bis(2-methoxyethyl)-3-(3-mehoxyphenyl)-9H-carbazole-1,7-dicarboxamide | 4.24 | 476.3 |
| 109 | 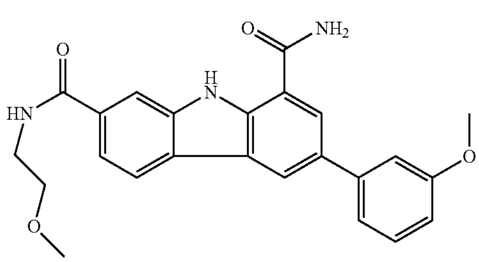 [SMILES: COCCNC(=O)c1ccc2c(c1)[nH]c1c(C(N)=O)cc(-c3cccc(OC)c3)cc12] | $N^7$-(2-methoxyethyl)-3-(3-methoxyphenyl)-9H-carbazole-1,7-dicarboxamide | 3.84 | 418.2 |

TABLE 5-continued

| Ex. # | Structure | Name | Retention time (min) | MS (ESI) m/z* |
|---|---|---|---|---|
| 110 | 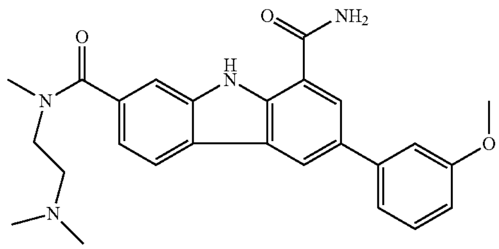 | $N^7$-(2-(dimethylamino)ethyl)-3-(3-methoxyphenyl)-$N^7$-methyl-9H-carbazole-1,7-dicarboxamide | 3.59 | 445.3 |
| 111 | 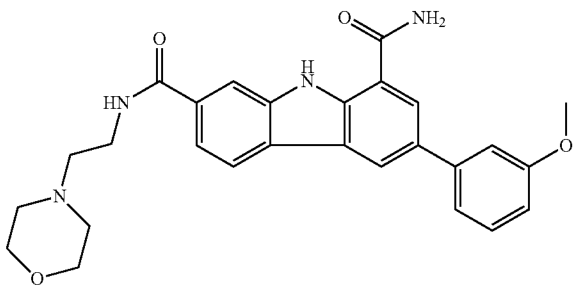 [SMILES: COc1cccc(-c2cc(C(N)=O)c3[nH]c4cc(C(=O)NCCN5CCOCC5)ccc4c3c2)c1] | 3-(3-methoxyphenyl)-$N^7$-(2-(4-morpholinyl)ethyl)-9H-carbazole-1,7-dicarboxamide | 3.66 | 473.2 |
| 112 | 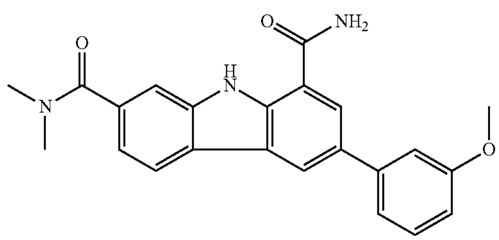 | 3-(3-methoxyphenyl)-$N^7,N^7$-dimethyl-9H-carbazole-1,7-dicarboxamide | 4.03 | 388.2 |
| 113 | 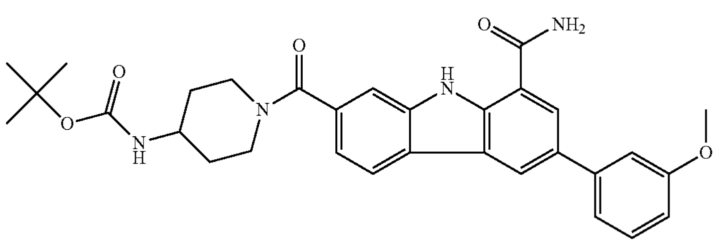 [SMILES: COc1cccc(-c2cc(C(N)=O)c3[nH]c4cc(C(=O)N5CCC(NC(=O)OC(C)(C)C)CC5)ccc4c3c2)c1] | tert-butyl (1-((8-carbamoyl-6-(3-methoxyphenyl)-9H-carbazol-2-yl)carbonyl)-4-piperidinyl)carbamate | 4.8 | 543.3 |
| 114 | 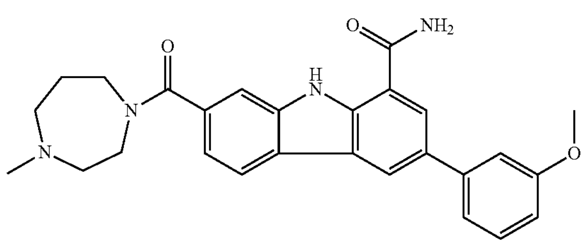 | 3-(3-methoxyphenyl)-7-((4-methyl-1,4-diazepan-1-yl)carbonyl)-9H-carbazole-1-carboxamide | 3.69 | 457.2 |
| 115 | 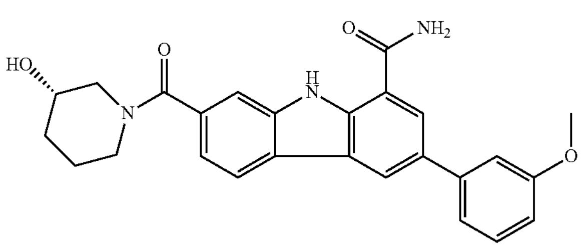 [SMILES: COc1cccc(-c2cc(C(N)=O)c3[nH]c4cc(C(=O)N5CCC[C@H](O)C5)ccc4c3c2)c1] | 7-(((3S)-3-hydroxy-1-piperidinyl)carbonyl)-3-(3-methoxyphenyl)-9H-carbazole-1-carboxamide | 3.77 | 444.2 |

TABLE 5-continued

| Ex. # | Structure | Name | Retention time (min) | MS (ESI) m/z* |
|---|---|---|---|---|
| 116 | 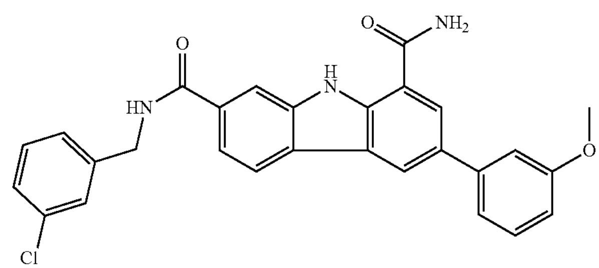 [SMILES: COc1cccc(-c2cc(C(N)=O)c3[nH]c4cc(C(=O)NCc5cccc(Cl)c5)ccc4c3c2)c1] | N7-(3-chlorobenzyl)-3-(3-methoxyphenyl)-9H-carbazole-1,7-dicarboxamide | 5.26 | 484.2 |
| 117 | 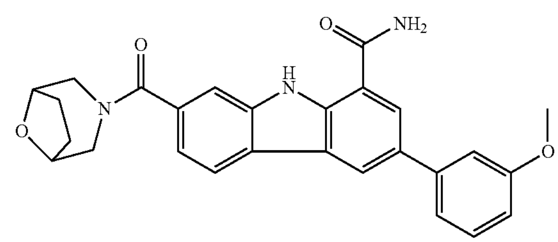 [SMILES: COc1cccc(-c2cc(C(N)=O)c3[nH]c4cc(C(=O)N5CC6CCC(C5)O6)ccc4c3c2)c1] | 3-(3-methoxyphenyl)-7-(8-oxa-3-azabicyclo[3.2.1]oct-3-ylcarbonyl)-9H-carbazole-1-carboxamide | 4.09 | 456.2 |
| 118 | 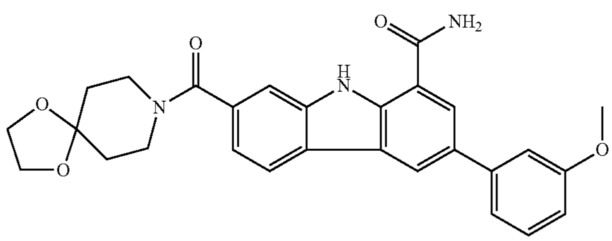 [SMILES: COc1cccc(-c2cc(C(N)=O)c3[nH]c4cc(C(=O)N5CCC6(CC5)OCCO6)ccc4c3c2)c1] | 7-(1,4-dioxa-8-azaspiro[4.5]dec-8-ylcarbonyl)-3-(3-methoxyphenyl)-9H-carbazole-1-carboxamide | 4.28 | 486.2 |
| 119 | 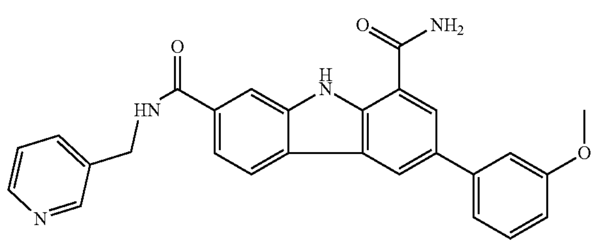 [SMILES: COc1cccc(-c2cc(C(N)=O)c3[nH]c4cc(C(=O)NCc5cccnc5)ccc4c3c2)c1] | 3-(3-methoxyphenyl)-N7-(3-pyridinylmethyl)-9H-carbazole-1,7-dicarboxamide | 3.86 | 451.2 |
| 120 | 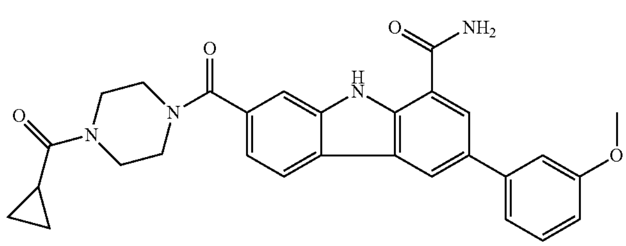 [SMILES: COc1cccc(-c2cc(C(N)=O)c3[nH]c4cc(C(=O)N5CCN(C(=O)C6CC6)CC5)ccc4c3c2)c1] | 7-((4-(cyclopropylcarbonyl)-1-piperazinyl)carbonyl)-3-(3-methoxyphenyl)-9H-carbazole-1-carboxamide | 3.95 | 497.3 |
| 121 | 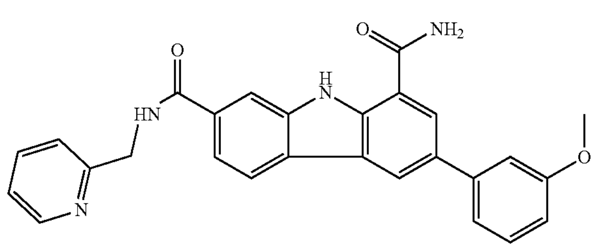 [SMILES: COc1cccc(-c2cc(C(N)=O)c3[nH]c4cc(C(=O)NCc5ccccn5)ccc4c3c2)c1] | 3-(3-methoxyphenyl)-N7-(2-pyridinylmethyl)-9H-carbazole-1,7-dicarboxamide | 4.08 | 451.2 |

TABLE 5-continued

| Ex. # | Structure | Name | Retention time (min) | MS (ESI) m/z* |
|---|---|---|---|---|
| 122 | 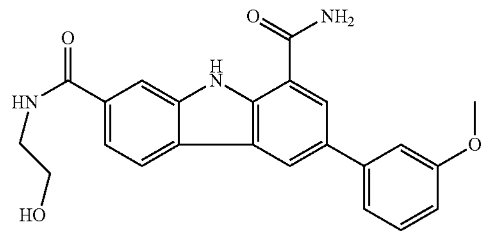 [SMILES: COc1cccc(-c2cc(C(N)=O)c3[nH]c4cc(C(=O)NCCO)ccc4c3c2)c1] | N⁷-(2-hydroxyethyl)-3-(3-methoxyphenyl)-9H-carbazole-1,7-dicarboxamide | 3.46 | 404.2 |
| 123 | 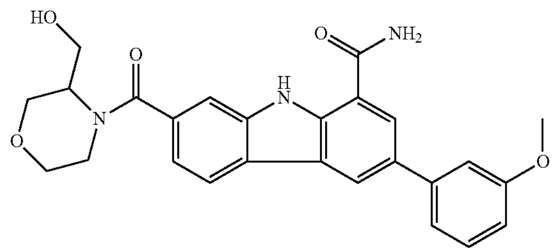 [SMILES: COc1cccc(-c2cc(C(N)=O)c3[nH]c4cc(C(=O)N5CCOCC5CO)ccc4c3c2)c1] | 7-((3-(hydroxymethyl)-4-morpholinyl)carbonyl)-3-(3-methoxyphenyl)-9H-carbazole-1-carboxamide | 3.6 | 460.2 |
| 124 | 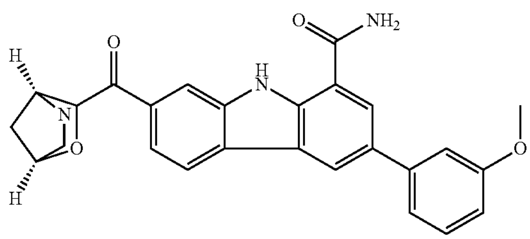 [SMILES: COc1cccc(-c2cc(C(N)=O)c3[nH]c4cc(C(=O)C5O[C@@H]6CN[C@H]5C6)ccc4c3c2)c1] | 3-(3-methoxyphenyl)-7-((1S,4S)-2-oxa-5-azabicyclo[2.2.1]hept-5-ylcarbonyl)-9H-carbazole-1-carboxamide | 3.75 | 442.2 |
| 125 | 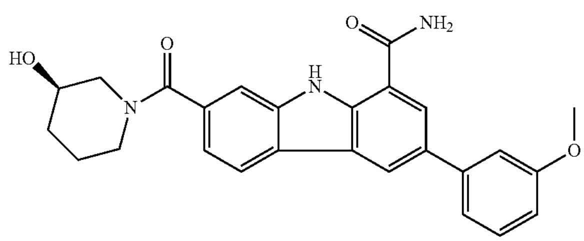 [SMILES: COc1cccc(-c2cc(C(N)=O)c3[nH]c4cc(C(=O)N5CCC[C@@H](O)C5)ccc4c3c2)c1] | 7-(((3R)-3-hydroxy-1-piperidinyl)carbonyl)-3-(3-methoxyphenyl)-9H-carbazole-1-carboxamide | 3.71 | 444.2 |

For Examples 83 to 87 following conditions were used for HPLC and MS analysis: Schimadzu LCT mass spectrometer with 4-way MUX source.

A = 5:95 methanol:Water;

B = 95:5 methanol:Water;

Modifier = 0.1% TFA.

Column: PHENOMENEX ® Luna 3 × 50 mm S10;

Flow rate 4 ml/min;

Gradient 4 min 0-100% B.

For Examples 88 to 125 following conditions were used for HPLC and MS analysis: Waters LCT mass spectrometer with 4-way MUX source.

A = 5:95 ACN:Water;

B = 95:5 ACN:Water;

Modifier = 10 mM NH₄OAc.

Colum: SUPELCO ® Ascentis Express 4.5 × 50 mm 3 um C18.

Flow rate 2 m/min;

Gradient 10 min 0-100% B.

*(M + H)⁺ observed in all cases except the examples where specifically mentioned.

EXAMPLE 126

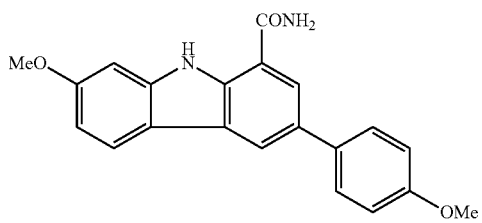 [SMILES: COc1ccc(-c2cc(C(N)=O)c3[nH]c4cc(OC)ccc4c3c2)cc1]

7-Methoxy-3-(4-methoxyphenyl)-9H-carbazole-1-carboxamide

126A. Preparation of 4'-amino-4,4"-dimethoxy-[1,1':3',1"-terphenyl]-5'-carbonitrile

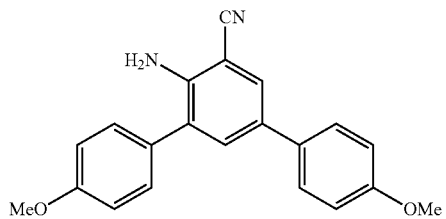 [SMILES: COc1ccc(-c2cc(C#N)c(N)c(-c3ccc(OC)cc3)c2)cc1]

A mixture of 2-amino-3,5-dibromobenzonitrile (250 mg, 0.906 mmol), 4-methoxyphenylboronic acid (330 mg, 2.17 mmol), tetrakis(triphenylphosphine)-palladium(0) (52 mg, 0.045 mmol) and cesium fluoride (661 mg, 4.35 mmol) was placed in a vial and flushed with nitrogen. Dimethoxyethane (4.5 mL) was added and the reaction was heated at 80° C. for 7 hr. After cooling to room temperature, the reaction was partitioned between ethyl acetate and saturated aqueous sodium bicarbonate solution. The organic phase was separated, washed with saturated aqueous sodium bicarbonate solution, brine, and then dried with sodium sulfate. Removal of the solvent followed by silica gel radial chromatography (step gradient elution with hexane containing 0 to 20% ethyl acetate) afforded 4'-amino-4,4"-dimethoxy-[1,1':3',1"-terphenyl]-5'-carbonitrile (267 mg, 89% yield) as an oil. MS (ESI) m/z 331.1 (M+H). $^1$H NMR (CDCl$_3$) δ ppm 7.54 (1H, d, J=2.14 Hz), 7.46 (1H, d, J=2.14 Hz), 7.42 (2H, d, J=8.55 Hz), 7.36 (2H, d, J=8.55 Hz), 7.01 (2H, d, J=8.55 Hz), 6.94 (2H, d, J=8.55 Hz), 4.50 (2H, s), 3.86 (3H, s), 3.83 (3H, s).

126B. Preparation of 4'-azido-4,4"-dimethoxy-[1,1':3',1"-terphenyl]-5'-carbonitrile

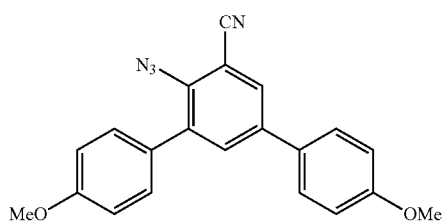 [SMILES: COc1ccc(-c2cc(C#N)c(N=[N+]=[N-])c(-c3ccc(OC)cc3)c2)cc1]

4'-Amino-4,4"-dimethoxy-[1,1':3',1"-terphenyl]-5'-carbonitrile (226 mg, 0.68 mmol) was heated in ethanol (28 mL) to bring most of the material into solution. After cooling to room temperature, 17% aqueous HCl (4 mL) was added and the reaction was cooled in an ice bath. Sodium nitrite (76 mg, 1.09 mmol) was added and the orange-red solution was stirred for 15 min in the ice bath. Sodium azide (71 mg, 1.09 mmol) was then added. After 20 min, the reaction was partitioned between ethyl acetate and sufficient saturated aqueous sodium bicarbonate to neutralize the reaction. The organic phase was separated, washed with brine, and dried with sodium sulfate. Silica gel radial chromatograph using step gradient elution with hexane containing 5 to 20% ethyl acetate afforded 4'-azido-4,4"-dimethoxy-[1,1':3',1"-terphenyl]-5'-carbonitrile (108 mg, 44%) as a solid. $^1$H NMR (500, CDCl$_3$) δ ppm 7.72 (1H, d, J=2.14 Hz), 7.62 (1H, d, J=2.14 Hz), 7.47 (2H, d, J=8.55 Hz), 7.39 (2H, d, J=8.55 Hz), 7.01 (2H, d, J=8.55 Hz), 6.97 (2H, d, J=8.85 Hz), 3.87 (3H, s), 3.84 (3H, s).

126C. Preparation of 7-methoxy-3-(4-methoxyphenyl)-9H-carbazole-1-carbonitrile

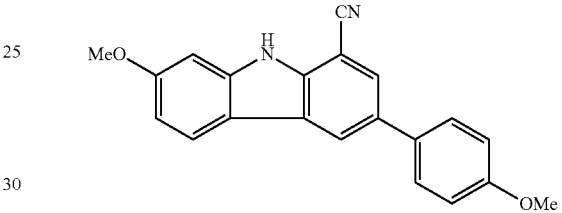

A solution of 4'-azido-4,4"-dimethoxy-[1,1':3',1"-terphenyl]-5'-carbonitrile (108 mg, 0.303 mmol) in 1,2-dichlorobenzene (2 mL) was heated at 180° C. for 0.5 hr. It was allowed to cool to room temperature and diluted with hexane (about 5 mL). The precipitate was collected by filtration and washed with hexane to leave 7-methoxy-3-(4-methoxyphenyl)-9H-carbazole-1-carbonitrile (72 mg, 72% yield) as an off-white solid. MS (ESI) m/z 329.1 (M+H). $^1$H NMR (CDCl$_3$) δ ppm 8.51 (1H, s), 8.28 (1H, s), 7.96 (1H, d, J=8.85 Hz), 7.76 (1H, d, J=1.83 Hz), 7.53-7.59 (2H, m), 7.00-7.04 (2H, m), 6.99 (1H, d, J=2.14 Hz), 6.93 (1H, dd, J=8.70, 2.29 Hz), 3.92 (3H, s), 3.87 (3H, s).

126. Preparation of 7-methoxy-3-(4-methoxyphenyl)-9H-carbazole-1-carboxamide Aqueous sodium carbonate (3 M, 700 μL, 2.10 mmol) and aqueous hydrogen peroxide (30%, 700 μL, 6.79 mmol) were added to a suspension of 7-methoxy-3-(4-methoxyphenyl)-9H-carbazole-1-carbonitrile (69 mg, 0.21 mmol) in ethanol (10 mL). The mixture was heated overnight at 60° C. Sodium hydroxide (84 mg, 2.10 mmol) and additional aqueous hydrogen peroxide (30%, 700 μL, 6.79 mmol) were added and heating was continued for a further 17 hr. The ethanol was removed on the rotary evaporator and the white precipitate was collected by filtration, washed with water, and dried under vacuum. Silica gel radial chromatography using step gradient elution with hexane containing 25 to 100% ethyl acetate gave 7-methoxy-3-(4-methoxyphenyl)-9H-carbazole-1-carboxamide (41 mg, 54% yield) as a white solid. MS (ESI) m/z 347.1 (M+H). $^1$H NMR (DMSO-d$_6$) δ ppm 11.21 (1H, s), 8.45 (1H, d, J=1.22 Hz), 8.29 (1H, br. s.), 8.13 (1H, d, J=1.53 Hz), 8.09 (1H, d, J=8.55 Hz), 7.80 (2H, d, J=8.55 Hz), 7.47 (1H, br. s.), 7.29 (1H, d, J=2.44 Hz), 7.07 (2H, d, J=8.55 Hz), 6.81 (1H, dd, J=8.55, 2.14 Hz), 3.84 (3H, s), 3.83 (3H, s).

EXAMPLE 127

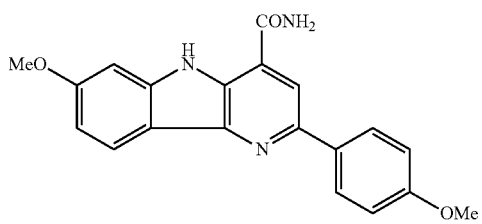

7-Methoxy-2-(4-methoxyphenyl)-5H-pyrido[3,2-b]indole-4-carboxamide

127A. Preparation of 3-amino-2,6-bis(4-methoxyphenyl)isonicotinate

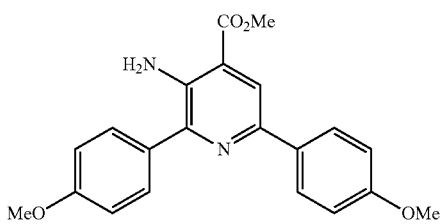

A mixture of methyl 3-amino-2,6-dibromoisonicotinate (500 mg, 1.61 mmol), 4-methoxyphenylboronic acid (588 mg, 3.87 mmol), Tetrakis(triphenylphosphine)-palladium(0) (93 mg, 0.081 mmol) and cesium fluoride (1176 mg, 7.74 mmol) was placed in a vial and flushed with nitrogen. Dimethoxyethane (10 mL) was added and the reaction was heated at 80° C. for 48 hr. After cooling to room temperature, the reaction was partitioned between ethyl acetate and saturated aqueous sodium bicarbonate solution. The organic phase was separated, washed with saturated aqueous sodium bicarbonate solution, brine, and then dried with sodium sulfate. Removal of the solvent followed by silica gel radial chromatography (step gradient elution with hexane containing 0 to 25% ethyl acetate) afforded methyl 3-amino-2,6-bis(4-methoxyphenyl)isonicotinate (258 mg, 0.708 mmol, 43.9% yield) as a yellow oil. MS (ESI) m/z 365.2 (M+H). $^1$H NMR (CDCl$_3$) δ ppm 8.01 (1H, s), 7.91 (2H, d, J=8.85 Hz), 7.66 (2H, d, J=8.55 Hz), 7.02 (2H, d, J=8.55 Hz), 6.94 (2H, d, J=8.85 Hz), 5.93 (2H, br. s.), 3.94 (3H, s), 3.86 (3H, s), 3.83 (3H, s).

127B. Preparation of methyl 3-azido-2,6-bis(4-methoxyphenyl)isonicotinate

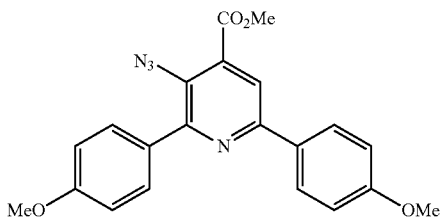 [SMILES: COC(=O)c1cc(-c2ccc(OC)cc2)nc(-c2ccc(OC)cc2)c1N=[N+]=[N-]]

Methyl 3-amino-2,6-bis(4-methoxyphenyl)isonicotinate (234 mg, 0.642 mmol) was dissolved with heating in ethanol (8 mL). After cooling to room temperature, 17% aqueous HCl (4 mL) was added and the reaction was cooled in an ice bath. Sodium nitrite (70.9 mg, 1.027 mmol) was added and the solution turned orange-red. After 25 min, sodium azide (66.8 mg, 1.027 mmol) was added and, after a further 20 min, the reaction was removed from the bath and left stirring at room temperature for 1 hr. The reaction was partitioned between ethyl acetate and sufficient saturated aqueous sodium bicarbonate solution to neutralize the acid. The organic phase was separated, washed with brine, and dried with sodium sulfate. Radial silica gel chromatography (step gradient elution with hexane containing 5 to 20% ethyl acetate) afforded methyl 3-azido-2,6-bis(4-methoxyphenyl)isonicotinate (105 mg, 42% yield) as a yellow solid. MS (ESI) m/z 391.1 (M+H). $^1$H NMR (CDCl$_3$) δ ppm 8.03 (2H, d, J=8.85 Hz), 7.93 (1H, s), 7.83 (2H, d, J=8.85 Hz), 7.02 (2H, d, J=8.85 Hz), 6.98 (2H, d, J=9.16 Hz), 4.03 (3H, s), 3.88 (3H, s), 3.86 (3H, s).

127C. Preparation of methyl 7-methoxy-2-(4-methoxyphenyl)-5H-pyrido[3,2-b]indole-4-carboxylate

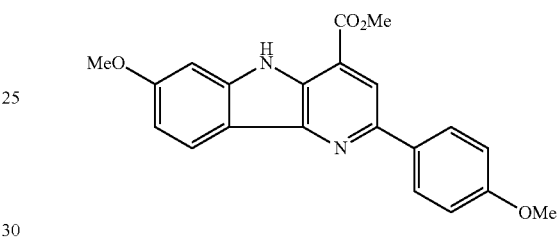

A solution of methyl 3-azido-2,6-bis(4-methoxyphenyl)isonicotinate (230 mg, 0.589 mmol) in 1,2-dichlorobenzene (5 mL) was heated at 170° C. with gas evolution. After 0.5 hr, the solvent was removed under vacuum and silica gel radial chromatography of the residue (step gradient elution with hexane containing 5 to 20% ethyl acetate) afforded methyl 7-methoxy-2-(4-methoxyphenyl)-5H-pyrido[3,2-b]indole-4-carboxylate (153 mg, 72%) as a yellow solid. MS (ESI) m/z 363.1 (M+H). $^1$H NMR (CDCl$_3$) δ ppm 9.39 (1H, s), 8.29 (1H, d, J=8.55 Hz), 8.13 (1H, s), 8.10 (2H, d, J=8.85 Hz), 7.03 (2H, d, J=8.85 Hz), 6.93-6.99 (2H, m), 4.07 (3H, s), 3.93 (3H, s), 3.88 (3H, s).

127D. Preparation of 7-methoxy-2-(4-methoxyphenyl)-5H-pyrido[3,2-b]indole-4-carboxylic acid

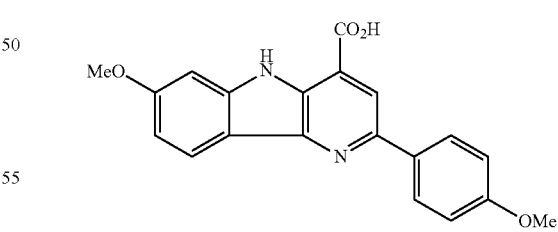

Methyl 7-methoxy-2-(4-methoxyphenyl)-5H-pyrido[3,2-b]indole -4-carboxylate (150 mg, 0 4 mmol) was dissolved in a mixture of tetrahydrofuran (6 mL) and methanol (2 mL) and an aqueous solution of sodium hydroxide (1.0 N, 1.8 mL, 1.8 mmol) was added. After 1 hr the organic solvents were removed on the rotary evaporator and the pH of the aqueous solution was adjusted to about 3 with 6 N aqueous HCl. The resulting precipitate was collected by filtration, washed with water, and dried under vacuum in the presence of KOH to leave 7-methoxy-2-(4-methoxyphenyl)-5H-pyrido[3,2-b]indole-4-carboxylic acid (138 mg, 67% yield) as an orange solid. MS (ESI) m/z 349.1 (M+H). $^1$H NMR (DMSO-$d_6$) δ ppm 11.47 (1H, s), 8.18 (1H, d, J=8.55 Hz), 8.16 (1H, s), 8.13 (2H, d, J=8.55 Hz), 7.29 (1H, d, J=1.83 Hz), 7.10 (2H, d, J=8.85 Hz), 6.94 (1H, dd, J=8.55, 1.83 Hz), 3.89 (3H, s), 3.85 (3H, s).

127. Preparation of 7-methoxy-2-(4-methoxyphenyl)-5H-pyrido[3,2-b]indole-4-carboxamide A mixture of 7-methoxy-2-(4-methoxyphenyl)-5H-pyrido[3,2-b]indole-4-carboxylic acid (60 mg, 0.17 mmol), ammonium chloride (15 mg, 0.28 mmol), N-(3-dimethylaminopropyl)-N'-ethylcarbodiimide hydrochloride (43 mg, 0.22 mmol), and 1-hydroxybenzotriazole hydrate (30 mg, 0.22 mmol) in a vial was flushed with nitrogen and dimethylformamide (0.5 mL) followed by triethylamine (38 μL, 0.28 mmol) were added. After stirring overnight, the reaction was diluted with methanol and the product was isolated by preparative HPLC (100×30 mm Luna C18 column, gradient elution starting with A:B=10:90 and ending with A:B=70:30 [A=10 mM NH$_4$OAc in 5% aqueous acetonitrile; B=10 mM NH$_4$OAc in 95% aqueous acetonitrile] over 20 min) This gave 7-methoxy-2-(4-methoxyphenyl)-5H-pyrido[3,2-b]indole-4-carboxamide (36 mg, 57% yield) as a yellow solid. MS (ESI) m/z 348.0 (M+H). $^1$H NMR (MeOD) δ ppm 8.27 (1H, d, J=8.85 Hz), 8.09 (1H, s), 8.04 (2H, d, J=8.85 Hz), 7.18 (1H, d, J=2.14 Hz), 7.09 (2H, d, J=8.55 Hz), 6.92 (1H, dd, J=8.55, 2.14 Hz), 3.95 (3H, s), 3.90 (3H, s).

EXAMPLE 128

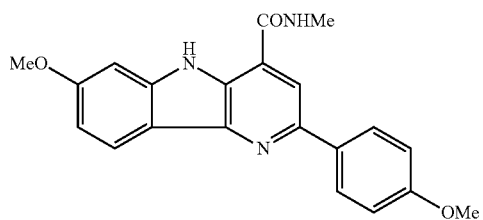

7-Methoxy-2-(4-methoxyphenyl)-N-methyl-5H-pyrido[3,2-b]indole-4-carboxamide

A mixture of 7-methoxy-2-(4-methoxyphenyl)-5H-pyrido[3,2-b]indole-4-carboxylic acid (Example 127D) (60 mg, 0.17 mmol), methylamine hydrochloride (19 mg, 0.28 mmol), N-(3-dimethylaminopropyl)-N'-ethylcarbodiimide hydrochloride (43 mg, 0.22 mmol), and 1-hydroxybenzotriazole hydrate (30 mg, 0.22 mmol) in a vial was flushed with nitrogen and dimethylformamide (0.5 mL) followed by triethylamine (38 μL, 0.28 mmol) were added. After stirring overnight, the reaction was diluted with methanol and the product was isolated by preparative HPLC (100×30 mm Luna C18 column, gradient elution starting with A:B=10:90 and ending with A:B=70:30 [A=10 mM NH$_4$OAc in 5% aqueous acetonitrile; B=10 mM NH$_4$OAc in 95% aqueous acetonitrile] over 20 min) followed by removal of the solvents. This gave 7-methoxy-2-(4-methoxyphenyl)-N-methyl-5H-pyrido[3,2-b]indole-4-carboxamide (41 mg, 63% yield) as a yellow solid. MS (ESI) m/z 362.3 (M+H). $^1$H NMR (MeOD) δ ppm 8.26 (1H, d, J=8.55 Hz), 8.00-8.04 (2H, m), 7.98 (1H, s), 7.17 (1H, d, J=2.14 Hz), 7.07-7.10 (2H, m), 6.92 (1H, dd, J=8.70, 2.29 Hz), 3.94 (3H, s), 3.89 (3H, s), 3.06 (3H, s).

EXAMPLE 129

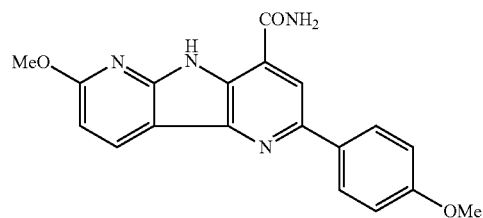

7-Methoxy-2-(4-methoxyphenyl)-5H-pyrido[2',3':4,5]pyrrolo[2,3-b]pyridine-4-carboxamide

129A. Preparation of methyl 3-amino-6-bromo-6'-methoxy-2,3'-bipyridine-4-carboxylate

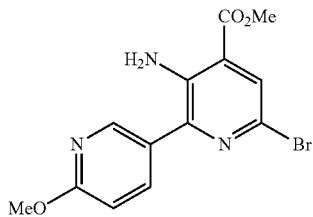

A mixture of methyl 3-amino-2,6-dibromoisonicotinate (300 mg, 0.97 mmol), 6-methoxypyridin-3-ylboronic acid (163 mg, 1.07 mmol), tetrakis(triphenylphosphine)-palladium(0) (56 mg, 0.048 mmol) and cesium fluoride (323 mg, 2.13 mmol) in a vial was flushed with nitrogen. Dimethoxyethane (4.8 mL) was added and the reaction was heated at 80° C. overnight. It was partitioned between ethyl acetate and a saturated aqueous solution of sodium bicarbonate. The organic phase was separated, washed with brine, and dried with sodium sulfate. The solvent removed and the major product was isolated by silica gel radial chromatography (step gradient with hexane containing 5 to 20% ethyl acetate). This gave methyl 3-amino-6-bromo-6'-methoxy-2,3'-bipyridine-4-carboxylate (165 mg, 50% yield) as a yellow solid. MS (ESI) m/z 338 and 340 (M+H). $^1$H NMR (CDCl$_3$) δ ppm 8.45 (1H, d, J=2.14 Hz), 7.82 (1H, dd, J=8.55, 2.44 Hz), 7.80 (1H, s), 6.85 (1H, d, J=8.55 Hz), 5.91 (2H, br. s.), 3.97 (3H, s), 3.92 (3H, s).

129B. Preparation of methyl 3-amino-6'-methoxy-6-(4-methoxyphenyl)-2,3'-bipyridine-4-carboxylate

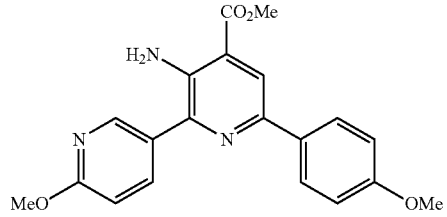 [SMILES: COC(=O)c1cc(-c2ccc(OC)cc2)nc(-c2ccc(OC)nc2)c1N]

A mixture of methyl 3-amino-6-bromo-6'-methoxy-2,3'-bipyridine-4-carboxylate (165 mg, 0.49 mmol), 4-methoxyphenylboronic acid (89 mg, 0.59 mmol), cesium fluoride (178 mg, 1.17 mmol) and tetrakis(triphenylphosphine)palladium(0) (28 mg, 0.024 mmol) in a vial was flushed with nitrogen. Dimethoxyethane (2.4 mL) was added and the reaction was heated at 80° C. overnight. It was partitioned between ethyl acetate and a saturated aqueous solution of sodium bicarbonate. The organic phase was separated, washed with brine, and dried with sodium sulfate. The solvent removed and the major product was isolated by silica gel radial chromatography (step gradient with hexane containing 5 to 20% ethyl acetate). This gave methyl 3-amino-6'-methoxy-6-(4-methoxyphenyl)-2,3'-bipyridine-4-carboxylate (121 mg, 68% yield) as a yellow solid. MS (ESI) m/z 366.1 (M+H). $^1$H NMR (CDCl$_3$) δ ppm 8.57 (1H, d, J=2.44 Hz), 8.05 (1H, s), 7.96 (1H, dd, J=8.55, 2.44 Hz), 7.88-7.93 (2H, m), 6.92-6.97 (2H, m), 6.88 (1H, d, J=8.55 Hz), 5.88 (2H, s), 4.00 (3H, s), 3.96 (3H, s), 3.84 (3H, s).

129C. Preparation of methyl 3-azido-6'-methoxy-6-(4-methoxyphenyl)-2,3'-bipyridine-4-carboxylate

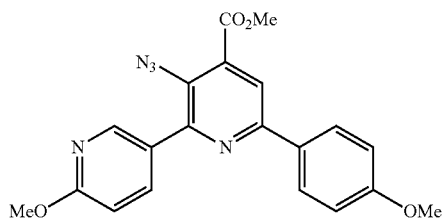 [SMILES: COC(=O)c1cc(-c2ccc(OC)cc2)nc(-c2ccc(OC)nc2)c1N=[N+]=[N-]]

Methyl 3-amino-6'-methoxy-6-(4-methoxyphenyl)-2,3'-bipyridine-4-carboxylate (120 mg, 0.33 mmol) was dissolved in trifluoroacetic acid (1.6 mL) and the solution was cooled in an ice bath. Sodium nitrite (45 mg, 0.66 mmol) was added with stirring to give a dark red suspension. After 30 min, sodium azide (214 mg, 3.3 mmol) was added followed immediately by diethyl ether (1.6 mL). This was stirred in the ice bath for 30 min. and then partially concentrated on the rotary evaporator. The residue was partitioned between ethyl acetate and sufficient saturated aqueous sodium bicarbonate solution (gas evolution) to neutralize the mixture. The organic phase was separated, washed with brine, dried with sodium sulfate, and the solvent removed to leave methyl 3-azido-6'-methoxy-6-(4-methoxyphenyl)-2,3'-bipyridine-4-carboxylate (122 mg, 95% yield) as a yellow solid. MS (ESI) m/z 392.1 (M+H). $^1$H NMR (CDCl$_3$) δ ppm 8.74 (1H, d, J=2.52 Hz), 8.13 (1H, dd, J=8.69, 2.39 Hz), 8.01 (2H, d, J=9.07 Hz), 7.98 (1H, s), 6.97 (2H, d, J=8.81 Hz), 6.85 (1H, d, J=8.81 Hz), 4.03 (3H, s), 4.01 (4H, s), 3.85 (3H, s).

129D. Preparation of 7-methoxy-2-(4-methoxyphenyl)-5H-pyrido[2',3':4,5]pyrrolo[2,3-b]pyridine-4-carboxylate

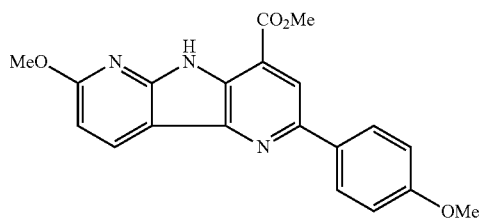 [SMILES: COC(=O)c1cc(-c2ccc(OC)cc2)nc2c1[nH]c1nc(OC)ccc12]

A solution of methyl 3-azido-6'-methoxy-6-(4-methoxyphenyl)-2,3'-bipyridine-4-carboxylate (120 mg, 0.31 mmol) in 1,2-dichlorobenzene (4 mL) was heated at 180° C. for 10 min with gas evolution. The solvent was removed under vacuum and the product was purified by silica gel radial chromatography (step gradient elution with hexane containing 50 to 100% methylene chloride). This gave methyl 7-methoxy-2-(4-methoxyphenyl)-5H-pyrido[2',3':4,5]pyrrolo[2,3-b]pyridine-4-carboxylate (80 mg, 72% yield) as a yellow solid. MS (ESI) m/z 364.1 (M+H). $^1$H NMR (CDCl$_3$) δ ppm 9.61 (1H, s), 8.49 (1H, d, J=8.55 Hz), 8.14 (1H, s), 8.07 (2H, d, J=8.85 Hz), 7.02 (2H, d, J=8.85 Hz), 6.73 (1H, d, J=8.55 Hz), 4.06 (3H, s), 4.04 (3H, s), 3.87 (3H, s).

129E. Preparation of 7-methoxy-2-(4-methoxyphenyl)-5H-pyrido[2',3':4,5]pyrrolo[2,3-b]pyridine-4-carboxylic acid

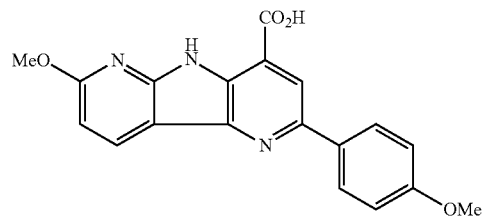 [SMILES: COc1ccc(-c2cc(C(=O)O)c3[nH]c4nc(OC)ccc4c3n2)cc1]

Aqueous sodium hydroxide (1.0 N, 0.66 mL, 0.66 mmol) was added to a solution of methyl 7-methoxy-2-(4-methoxyphenyl)-5H-pyrido[2',3':4,5]pyrrolo[2,3-b]pyridine-4-carboxylate (80 mg, 0.22 mmol) in a mixture of tetrahydrofuran (3 mL) and methanol (1 mL). After 1 hr, the organic solvents were removed on the rotary evaporator. The residue was diluted with water to bring most of the solid into solution and sufficient 1.0 N aqueous HCl was added to bring the pH of the mixture to about 3. After stirring for 0.5 hr, the precipitate was collected, washed with water, and dried under vacuum over solid sodium hydroxide to give 7-methoxy-2-(4-methoxyphenyl)-5H-pyrido[2',3':4,5]pyrrolo[2,3-b]pyridine-4-carboxylic acid (74 mg, 0.212 mmol, 96% yield) as an orange solid. MS (ESI) m/z 350.2 (M+H). $^1$H NMR (DMSO-d$_6$) δ ppm 8.52 (1H, d, J=8.54 Hz), 8.17 (1H, s), 8.09 (2H, d, J=8.85 Hz), 7.07 (2H, d, J=8.85 Hz), 6.78 (1H, d, J=8.24 Hz), 4.02 (3H, s), 3.83 (3H, s).

129. Preparation of 7-methoxy-2-(4-methoxyphenyl)-5H-pyrido[2',3':4,5]pyrrolo[2,3-b]pyridine-4-carboxamide Dimethylformamide (0.6 mL) followed by triethylamine (47 μL, 0.34 mmol) were added to a mixture of 7-methoxy-2-(4-methoxyphenyl)-5H-pyrido[2',3':4,5]pyrrolo[2,3-b]pyridine-4-carboxylic acid (74 mg, 0.21 mmol), N-(3-dimethylaminopropyl)-N'-ethylcarbodiimide hydrochloride (53 mg, 0.28 mmol), 1-hydroxybenzotriazole hydrate (42 mg, 0.28 mmol), and ammonium chloride (18 mg, 0.34 mmol). The reaction mixture was stirred at room temperature for 16 h. The solvent were removed under vacuum and the residue was suspended in about 10 mL of dimethylsulfoxide. The solid was collected by filtration and washed with a little dimethylsulfoxide and water. This was dried under vacuum over solid sodium hydroxide to leave 7-methoxy-2-(4-methoxyphenyl)-5H-pyrido[2',3':4,5]pyrrolo[2,3-b]pyridine-4-carboxamide (51 mg, 66% yield) as a yellow solid. MS (ESI) m/z 349.2 (M+H). $^1$H NMR (DMSO-d$_6$) δ ppm 11.36 (1H, br. s.), 8.49

(2H, d, J=8.06 Hz), 8.26 (1H, s), 8.20 (2H, d, J=8.56 Hz), 7.86 (1H, br. s.), 7.09 (2H, d, J=8.56 Hz), 6.75 (1H, d, J=8.31 Hz), 4.00 (3H, s), 3.84 (3H, s).

EXAMPLE 130

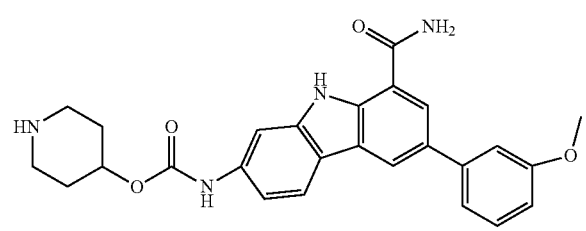 [SMILES: COc1cccc(-c2cc(C(N)=O)c3[nH]c4cc(NC(=O)OC5CCNCC5)ccc4c3c2)c1]

Piperidin-4-yl 8-carbamoyl-6-(3-methoxyphenyl)-9H-carbazol-2-ylcarbamate

To a suspension of 8-carbamoyl-6-(3-methoxyphenyl)-9H-carbazole-2-carboxylic acid (36 mg, 0.100 mmol, Example 82B) and 4 A° molecular sieves (36 mg) in 1,4-dioxane (1.5 mL) at 50° C. was added triethylamine (0.034 mL, 0.247 mmol) and diphenylphosphoryl azide (70.0 mg, 0.247 mmol). The mixture was stirred for 1.5 h and at that point tert-butyl 4-hydroxypiperidine-1-carboxylate (201 mg, 0.999 mmol) was added. The reaction mixture was stirred at 80° C. for 5 h. The reaction was cooled, diluted with ethyl acetate, and filtered. The solvent was removed from the filtrate and the Boc-protected product was isolated by preparative HPLC (100×30 mm Luna C18 column, flow rate 42 ml permin, gradient elution starting with A:B=80:20 and ending with A:B=0:100 [A=10 mM NH$_4$OAc in 5% aqueous acetonitrile; B=10 mM NH$_4$OAc in 95% aqueous acetonitrile] over 20 min) followed by removal of the solvents. It was treated with a mixture of DCM (6 mL) and TFA (3 mL) at rt for 2 h. The solvent was removed and the crude product was purified by preparative HPLC (100×30 mm Luna C18 column, flow rate 42 ml permin, gradient elution starting with A:B=90:10 and ending with A:B=30:70 [A=10 mM NH$_4$OAc in 5% aqueous acetonitrile; B=10 mM NH$_4$OAc in 95% aqueous acetonitrile] over 20 min) The HPLC fractions that contained the product were applied onto a cartridge of PHENOMENEX® Strata-X-C 33 um cation mixed-mode polymer. This was washed with methanol and product was eluted with 2 N solution of ammonia in methanol. Removal of the solvents left 29.4 mg of piperidin-4-yl 8-carbamoyl-6-(3-methoxyphenyl)-9H-carbazol-2-ylcarbamate as a solid. MS (ESI) m/z 459.2 (M+H). $^1$H NMR (MeOD) δ ppm 8.40 (1H, s), 8.11 (1H, s), 8.04 (1H, d, J=8.55 Hz), 7.88 (1H, br. s.), 7.30-7.43 (3H, m), 7.15-7.27 (2H, m), 6.86-6.97 (1H, m), 3.89 (3H, s), 3.37 (1H, s), 3.04-3.14 (2H, m), 2.67-2.80 (2H, m), 2.00 (2H, dd, J=9.00, 4.12 Hz), 1.63-1.74 (2H, m).

The following compounds in Table 6 have been synthesized utilizing the procedures described in Example 130.

TABLE 6

| Ex. # | Structure | Name | Retention time (min) | MS (ESI) m/z* |
|---|---|---|---|---|
| 131 | 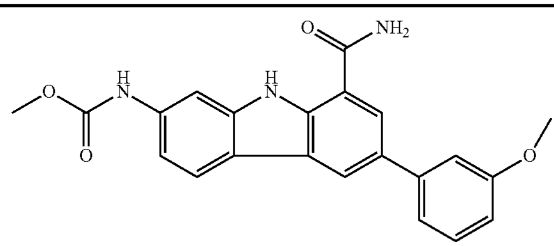 | methyl (8-carbamoyl-6-(3-methoxyphenyl)-9H-carbazol-2-yl)carbamate | 2.303 | 390.1 |
| 132 | 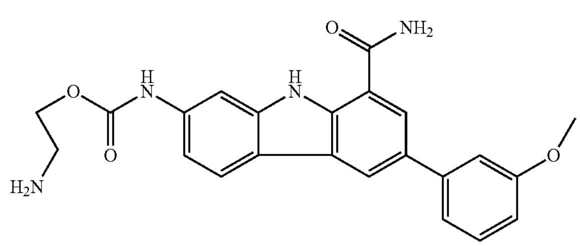 [SMILES: COc1cccc(-c2cc(C(N)=O)c3[nH]c4cc(NC(=O)OCCN)ccc4c3c2)c1] | 2-aminoethyl (8-carbamoyl-6-(3-methoxyphenyl)-9H-carbazol-2-yl)carbamate | 1.825 | 419.2 |
| 133 | 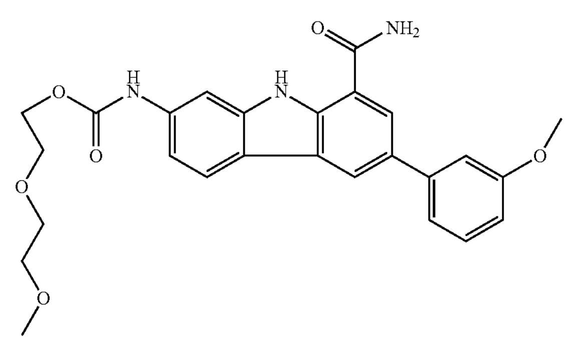 [SMILES: COCCOCCOC(=O)Nc1ccc2c(c1)[nH]c1c(C(N)=O)cc(-c3cccc(OC)c3)cc12] | 2-(2-methoxyethoxy)ethyl (8-carbamoyl-6-(3-methoxyphenyl)-9H-carbazol-2-yl)carbamate | 2.327 | 478.2 |

TABLE 6-continued

| Ex. # | Structure | Name | Retention time (min) | MS (ESI) m/z* |
|---|---|---|---|---|
| 134 | 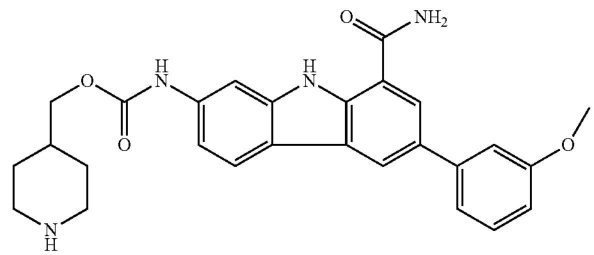 [SMILES: COc1cccc(-c2cc(C(N)=O)c3[nH]c4cc(NC(=O)OCC5CCNCC5)ccc4c3c2)c1] | 4-piperidinylmethyl (8-carbamoyl-6-(3-methoxyphenyl)-9H-carbazol-2-yl)carbamate | 1.932 | 473.2 |
| 135 | 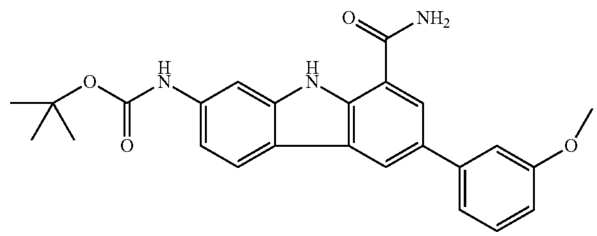 [SMILES: COc1cccc(-c2cc(C(N)=O)c3[nH]c4cc(NC(=O)OC(C)(C)C)ccc4c3c2)c1] | tert-butyl (8-carbamoyl-6-(3-methoxyphenyl)-9H-carbazol-2-yl)carbamate | 2.108 | 430.0 |
| 136 | 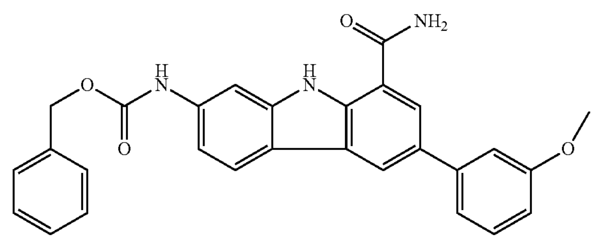 [SMILES: COc1cccc(-c2cc(C(N)=O)c3[nH]c4cc(NC(=O)OCc5ccccc5)ccc4c3c2)c1] | benzyl (8-carbamoyl-6-(3-methoxyphenyl)-9H-carbazol-2-yl)carbamate | 2.142 | 466.2 |

HPLC conditions: Waters Sunfire C18 3.5 um, 4.6 × 150 mm column. Flow = 2 ml/min.
Solvent: A = 0.1% TFA/95% water/5% methanol, Solvent B = 0.1% TFA/5% water/95% methanol. Gradient from 10% B to 100% over 15 minutes, then isocratic 100% B. Detection: UV at 220 nm.
*(M + H)+ observed in all cases except the examples where specifically mentioned.

EXAMPLE 137

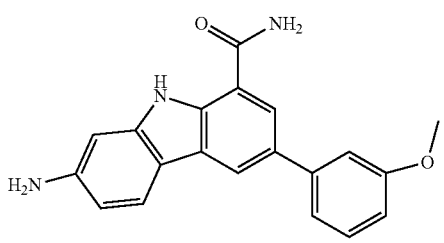 [SMILES: COc1cccc(-c2cc(C(N)=O)c3[nH]c4cc(N)ccc4c3c2)c1]

7-Amino-3-(3-methoxyphenyl)-9H-carbazole-1-carboxamide

A mixture of benzyl 8-carbamoyl-6-(3-methoxyphenyl)-9H-carbazol-2-ylcarbamate (95 mg, 0.204 mmol, Example 136), palladium on carbon (10%) (39.5 mg, 0.037 mmol) and ammonium formate (77 mg, 1.224 mmol) in MeOH (5 mL) was flushed with nitrogen and heated at reflux for 1 hr. The reaction mixture was cooled to room temperature and filtered. The solvent was removed from the filtrate to leave 7-amino-3-(3-methoxyphenyl)-9H-carbazole-1-carboxamide (68 mg, 0.189 mmol, 93% yield) as a solid. MS (ESI) m/z 332.1 (M+H). $^1$H NMR (MeOD) δ ppm 8.31 (1H, d, J=1.53 Hz), 8.02 (1H, d, J=1.53 Hz), 7.89 (1H, d, J=8.24 Hz), 7.26 -7.47 (3H, m), 6.83-7.01 (2H, m), 6.71 (1H, dd, J=8.24, 1.83 Hz), 3.91 (3H, s).

EXAMPLE 138

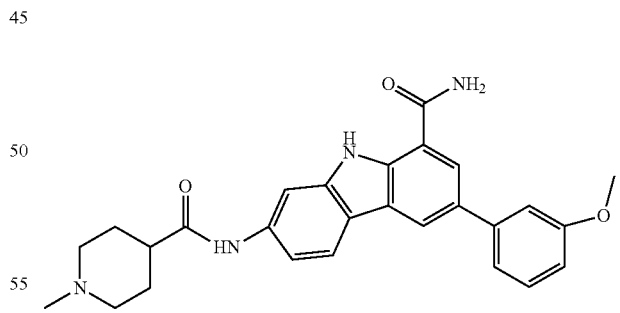

3-(3-Methoxyphenyl)-7-(1-methylpiperidine-4-carboxamido)-9H-carbazole-1-carboxamide To a solution of 1-methylpiperidine-4-carboxylic acid (25.9 mg, 0.181 mmol) in DMF (0.5 mL), were successively added N,N'-diisopropylethylamine (0.053 mL, 0.302 mmol), EDC (23.14 mg, 0.121 mmol) and HOBt (18.49 mg, 0.121 mmol). After stirring at room temperature for 5 min, 7-amino-3-(3-methoxyphenyl)-9H-carbazole-1-carboxamide (20 mg, 0.060 mmol, Example 138) was added. After stirring for 16 h, the reaction was diluted with MeOH, and the product was isolated by preparative HPLC (100×30 mm Luna C18 column, flow rate 42 ml permin, gradient elution starting with A:B=90:10 and ending with A:B=30:70 [A=10 mM NH₄OAc in 5% aqueous acetonitrile; B=10 mM NH₄OAc in 95% aqueous acetonitrile] over 20 min). The HPLC fractions that contained the product were applied onto a PHENOMENEX® Strata-X-C 33 um cation mixed-mode polymer cartridge. This was washed with methanol and product was eluted with 2 N solution of ammonia in methanol. Removal of the solvents gave 18.9 mg of 3-(3-methoxyphenyl)-7-(1-methylpiperidine-4-carboxamido)-9H-carbazole-1-carboxamide as a white solid. MS (ESI) m/z 457.2 (M+H). $^1$H NMR (MeOD) δ ppm 8.43 (1H, s), 8.13 (1H, d, J=1.22 Hz), 8.08 (1H, d, J=8.55 Hz), 8.04 (1H, s), 7.30 -7.43 (3H, m), 7.27 (1H, dd, J=8.39, 1.68 Hz), 6.92 (1H, dd, J=5.49, 2.14 Hz), 3.90 (3H, s), 3.00 (2H, d, J=11.60 Hz), 2.38-2.51 (1H, m), 2.33 (3H, s), 2.06-2.20 (2H, m), 1.85-2.04 (4H, m).

EXAMPLE 139

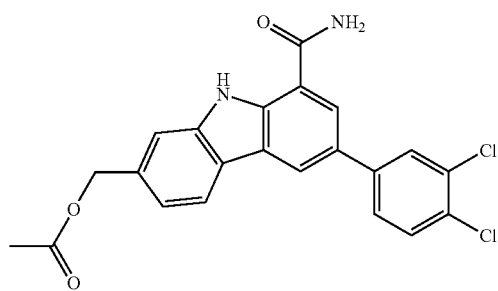 [SMILES: CC(=O)OCc1ccc2c(c1)[nH]c1c(C(N)=O)cc(-c3ccc(Cl)c(Cl)c3)cc12]

(8-Carbamoyl-6-(3,4-dichlorophenyl)-9H-carbazol-2-yl)methyl acetate

139A. Preparation of 3-((triisopropylsilyloxy)methyl)aniline

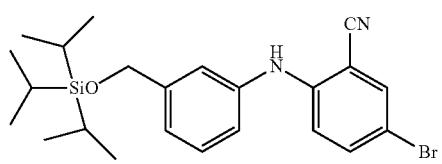

A flask was charged 5-bromo-2-fluorobenzonitrile (5 g, 25.00 mmol), 3-((triisopropylsilyloxy)methyl)aniline (6.99 g, 25.00 mmol), KOtBu (5.11 g, 45.5 mmol). To this was added DMSO (100 mL). After stirring at room temperature for 40 min, the reaction mixture was diluted with ethyl acetate and water. The aqueous was extracted with ethyl acetate, the combined organic was washed with water (3×), brine, dried over MgSO₄, filtered and concentrated. The residue was chromatographed on silica gel eluting with hexane containing 0 to 25% EtOAc to afford 3.9 g product as a solid which was about 60% pure by LC/MS. This was used as such in next step. MS (ESI) m/z 483.1(M+Na).

139B. Preparation of 3',4'-dichloro-4-(3-((triisopropylsilyloxy)methyl)phenylamino)-biphenyl-3-carbonitrile

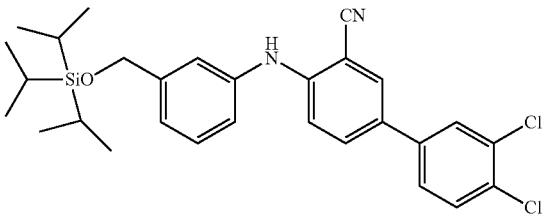

To a suspension of crude 5-bromo-2-(3-((triisopropylsilyloxy)methyl)phenylamino)benzonitrile (3.9 g, 8.49 mmol), tetrakis(triphenylphosphine)palladium(0) (0.438 g, 0.379 mmol), toluene (60 mL), and 2 M aqueous sodium carbonate (9.63 mL, 19.27 mmol) under nitrogen were added a solution of 3,4-dichlorophenylboronic acid (2.203 g, 11.54 mmol) in MeOH (14 mL) at rt. The resulting reaction mixture was heated at reflux for 4 h. After cooling to room temperature, it was diluted with a mixture of water (150 mL) and EtOAc (250 mL) and the two phases were separated. The aqueous phase was extracted with ethyl acetate (2×100 mL), and the combined organic phases were washed with water (2×100 mL), 5% aqueous NH₄OH solution (100 mL), and brine (100 mL). The organic phase was dried over Na2SO4 and the solvent removed. The crude material was purified by chromatography on silica gel, eluting with hexane containing 2%-5% EtOAc afforded 2.42 g of 3',4'-dichloro-4-(3-((triisopropylsilyloxy)methyl)phenylamino)-biphenyl-3-carbonitrile. $^1$H NMR (CDCl₃) δ ppm 7.65 (1H, d, J=1.83 Hz), 7.53-7.58 (2H, m), 7.39 (1H, dd, J=9.00, 2.29 Hz), 7.31 (1H, t, J=7.78 Hz), 7.22 (1H, s), 7.11 (1H, d, J=7.63 Hz), 7.07 (1H, d, J=8.85 Hz), 7.02 (2H, d, J=8.24 Hz), 6.35 (1H, s), 4.82 (2H, s), 1.13-1.22 (3H, m), 1.06-1.11 (18H, m).

139. Preparation of (8-carbamoyl-6-(3,4-dichlorophenyl)-9H-carbazol-2-yl)methyl acetate 3',4'-Dichloro-4-(3-((triisopropylsilyloxy)methyl)phenylamino)biphenyl-3-carbonitrile (267 mg, 0.508 mmol), diacetoxypalladium (285 mg, 1.270 mmol) and glacial acetic acid (15 mL) in a microwave tube (20 mL) were heated in microwave reactors at 160° C. for 3 h. The reaction was cooled to room temperature. The solids were filtered off and washed with acetic acid for several times. The filtrate was concentrated under reduced pressure and the residue was co-evaporated with toluene (3×). The resulting residue was suspended in EtOAc. The solid was collected by filtration and air dried to afford 53 mg (24.4% yield) of (8-carbamoyl-6-(3,4-dichlorophenyl)-9H-carbazol-2-yl)methyl acetate. MS (ESI) m/z 425.2 (M–H). $^1$H NMR (DMSO-d₆) δ ppm 11.53 (1H, s), 8.78 (1H, s), 8.38 (1H, br. s.), 8.34 (1H, d, J=1.22 Hz), 8.26 (1H, d, J=7.94 Hz), 8.23 (1H, d, J=2.14 Hz), 7.95 (1H, dd, J=8.55, 2.14 Hz), 7.77 (1H, d, J=8.55 Hz), 7.75 (1H, s), 7.59 (1H, br. s.), 7.23 (1H, d, J=7.93 Hz), 5.24 (2H, s), 2.11 (3H, s).

EXAMPLE 140

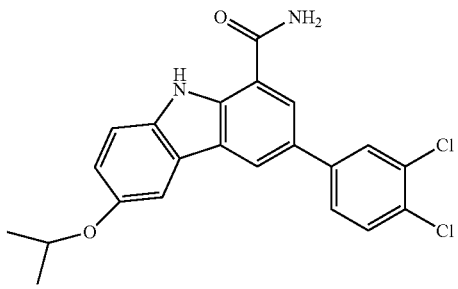 [SMILES: CC(C)Oc1ccc2[nH]c3c(C(N)=O)cc(-c4ccc(Cl)c(Cl)c4)cc3c2c1]

3-(3,4-Dichlorophenyl)-6-isopropoxy-9H-carbazole-1-carboxamide

140A. Preparation of 3',4'-dichloro-4-fluorobiphenyl-3-carbonitrile

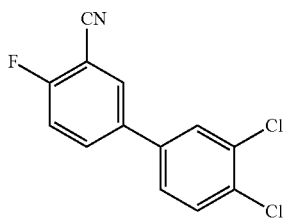 [SMILES: N#Cc1cc(-c2ccc(Cl)c(Cl)c2)ccc1F]

A mixture of 5-bromo-2-fluorobenzonitrile (400 mg, 2.000 mmol) and $(Ph_3P)_4Pd$ (116 mg, 0.100 mmol) were mixed in a microwave tube (20 mL) and flushed with nitrogen. Toluene (5 mL), 2 M aqueous sodium carbonate (2.270 mL, 4.54 mmol) and a solution of 3,4-dichlorophenylboronic acid (519 mg, 2.72 mmol) in MeOH (3 mL) were added. The mixture was heated in an oil bath at 105° C. for 4.5 h. After cooling to room temperature, the reaction was diluted with water (10 mL) and the two phases were separated. The aqueous phase was extracted with ethyl acetate (20 mL), and combined organic phases were washed with water (2×10 mL), 5% aqueous $NH_4OH$ (10 mL), and brine (10 mL). The organic phase was dried over $Na_2SO_4$ and the solvent was removed. The residue was chromatographed on silica gel eluting with hexane containing 0, 2, 3% ethyl acetate to afford 480 mg of product as a white solid which was about 76% pure by LC/MS. This was used as such in the next step.

140B. Preparation of 3',4'-dichloro-4-(4-isopropoxyphenylamino)biphenyl-3-carbonitrile

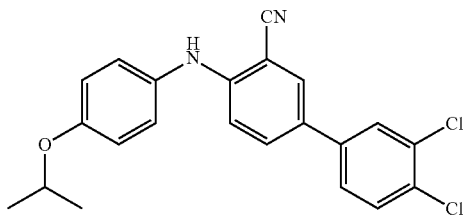 [SMILES: CC(C)Oc1ccc(Nc2ccc(-c3ccc(Cl)c(Cl)c3)cc2C#N)cc1]

A mixture of 3',4'-dichloro-4-fluorobiphenyl-3-carbonitrile (173 mg, 0.650 mmol), 4-isopropoxyaniline (108 mg, 0.715 mmol), and KOtBu (154 mg, 1.375 mmol) in DMSO (4 mL) was stirred at rt for 1.5 h, The mixture was diluted with ethyl acetate, washed with $H_2O$ and brine, and then dried over $Na_2SO_4$. The solvent was removed and the product was purified by silica gel chromatography (eluting with hexane containing 0 to 8% ethyl acetate) followed by preparative HPLC (100×30 mm Luna C18 column, flow rate 42 ml permin, gradient elution starting with A:B=50:50 and ending with A:B=0:100 [A=10 mM $NH_4OAc$ in 5% aqueous acetonitrile; B=10 mM $NH_4OAc$ in 95% aqueous acetonitrile] over 20 min). This afforded 99 mg of 3',4'-dichloro-4-(4-isopropoxyphenylamino)-biphenyl-3-carbonitrile which still contained some impurities according to the LC/MS but was used as such for next step. MS (ESI) m/z 397.1 (M+H).

140. Preparation of 3-(3,4-dichlorophenyl)-6-isopropoxy-9H-carbazole-1-carboxamide The target compound was synthesized utilizing the procedure described in Example 21C. The crude material was purified by preparative HPLC (100×30 mm Luna C18 column, flow rate 42 ml permin, gradient elution starting with A:B=70:30 and ending with A:B=0:100 [A=10 mM $NH_4OAc$ in 5% aqueous acetonitrile; B=10 mM $NH_4OAc$ in 95% aqueous acetonitrile] over 20 min). MS (ESI) m/z 413.1 (M+H). $^1H$ NMR (MeOD) δ ppm 8.55 (1H, d, J=1.53 Hz), 8.19 (1H, d, J=1.53 Hz), 8.02 (1H, d, J=2.14 Hz), 7.72-7.79 (2H, m), 7.63 (1H, d, J=8.55 Hz), 7.52 (1H, d, J=8.55 Hz), 7.11 (1H, dd, J=8.70, 2.29 Hz), 4.60-4.74 (1H, m), 1.39 (6H, d, J=6.10 Hz).

EXAMPLE 141

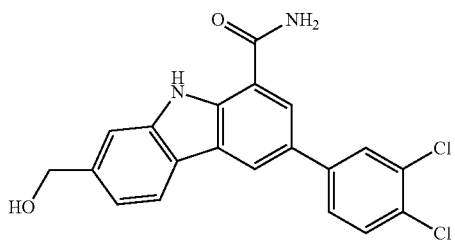 [SMILES: NC(=O)c1cc(-c2ccc(Cl)c(Cl)c2)cc2c1[nH]c1cc(CO)ccc12]

3-(3,4-Dichlorophenyl)-7-(hydroxymethyl)-9H-carbazole-1-carboxamide (8-Carbamoyl-6-(3,4-dichlorophenyl)-9H-carbazol-2-yl) methyl acetate (150 mg, 0.211 mmol, Example 139) was dissolved in a mixture of MeOH (3 mL) and DMF (6 mL). To this solution was added sodium methanolate (140 mg, 0.648 mmol) and the reaction left stirring for 0.5 h. The product was isolated by preparative HPLC (100×30 mm Luna C18 column, flow rate 42 ml permin, gradient elution starting with A:B=90:10 and ending with A:B=30:70 [A=10 mM $NH_4OAc$ in 5% aqueous acetonitrile; B=10 mM $NH_4OAc$ in 95% aqueous acetonitrile] over 20 min) followed by removal of solvent to afford 39 mg of 3-(3,4-dichlorophenyl)-7-(hydroxymethyl)-9H-carbazole-1-carboxamide as a light yellow solid. MS (ESI) m/z 383.1 (M−H). $^1H$ NMR (DMSO-$d_6$) δ ppm 11.44 (1H, s), 8.73 (1H, d, J=1.53 Hz), 8.36 (1H, br. s.), 8.30 (1H, d, J=1.53 Hz), 8.22 (1H, d, J=2.14 Hz), 8.19 (1H, d, J=7.93 Hz), 7.94 (1H, dd, J=8.55, 2.14 Hz), 7.77 (1H, d, J=8.24 Hz), 7.71 (1H, s), 7.56 (1H, br. s.), 7.18 (1H, d, J=7.93 Hz), 5.24 (1H, t, J=5.80 Hz), 4.66 (2H, d, J=5.80 Hz).

EXAMPLE 142

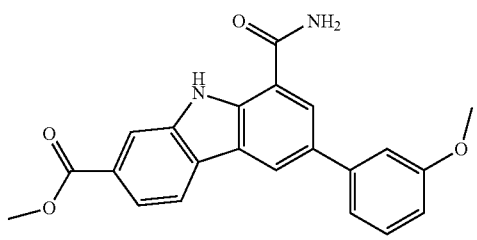

Methyl 8-carbamoyl-6-(3-methoxyphenyl)-9H-carbazole-2-carboxylate

142A. Preparation of 4-amino-3'-methoxybiphenyl-3-carbonitrile

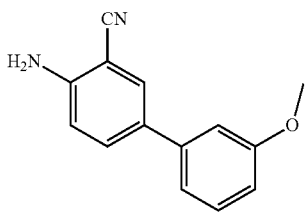 [SMILES: COc1cccc(-c2ccc(N)c(C#N)c2)c1]

142A was synthesized utilizing the procedure described in Example 140A in 91% yield. MS (ESI) m/z 225.1 (M+H). $^1$H NMR (CDCl$_3$) δ ppm 7.60 (1H, d, J=2.14 Hz), 7.56 (1H, dd, J=8.55, 2.14 Hz), 7.32 (1H, t, J=7.93 Hz), 7.06 (1H, d, J=7.93 Hz), 7.00 (1H, d, J=2.14 Hz), 6.86 (1H, dd, J=8.24, 2.75 Hz), 6.80 (1H, d, J=8.55 Hz), 3.85 (3H, s).

142B. Preparation of methyl 3-(3-cyano-3'-methoxybiphenyl-4-ylamino)benzoate

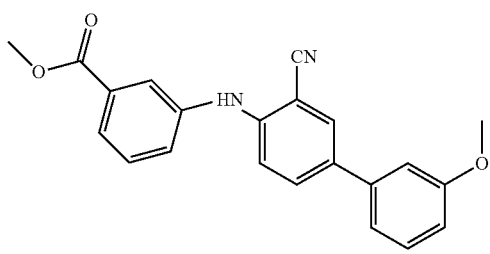

4-Amino-3'-methoxybiphenyl-3-carbonitrile (4.23 g, 18.86 mmol), methyl 3-bromobenzoate (4.87 g, 22.63 mmol), palladium(II) acetate (0.212 g, 0.943 mmol), 9,9-dimethyl-4,5-bis(diphenylphosphino)xanthene (1.091 g, 1.886 mmol) and cesium carbonate (8.60 g, 26.4 mmol) in a pressure vessel was flushed with nitrogen and toluene (75 mL) was added. The mixture was heated at 100° C. overnight. The reaction mixture was filtered and the solid was washed with DCM (2×20 mL). The filtrate was concentrated and the product was purified by flash-chromatography eluting with hexane containing 5 to 20% ethyl acetate. This gave 5.14 g (65% yield) of methyl 3-(3-cyano-3'-methoxybiphenyl-4-ylamino)benzoate. MS (ESI) m/z 359.1 (M+H). $^1$H NMR (CDCl$_3$) δ ppm 7.88 (1H, s), 7.77 (1H, d, J=7.63 Hz), 7.72 (1H, d, J=2.44 Hz), 7.61 (1H, dd, J=8.70, 2.29 Hz), 7.42 (1H, t, J=7.93 Hz), 7.30-7.39 (2H, m), 7.27 (1H, d, J=8.85 Hz), 7.08 (1H, d, J=7.93 Hz), 7.02 (1H, t, J=2.14 Hz), 6.88 (1H, dd, J=8.24, 2.44 Hz), 6.56 (1H, s), 3.91 (3H, s), 3.85 (3H, s).

142. Preparation of methyl 8-carbamoyl-6-(3-methoxyphenyl)-9H-carbazole-2-carboxylate A mixture of methyl 3-(3-cyano-3'-methoxybiphenyl-4-ylamino)benzoate (3.3 g, 9.21 mmol), diacetoxypalladium (5.17 g, 23.02 mmol), and AcOH (150 mL) in a pressure vessel was heated at 130° C. for 48 h. The sold was separated by filtration and washed with several times with HOAc. The filtrate was taken and the HOAc was removed under reduced pressure. The residue was dissolved in a mixture of DCM and MeOH and mixed with silica gel (12 g). After the removal of solvents, the mixture was loaded to a silica gel column and eluted with DCM containing 0 to 1.5% MeOH to afford 140 mg of methyl 8-carbamoyl-6-(3-methoxyphenyl)-9H-carbazole-2-carboxylate. MS (ESI) m/z 375.2 (M+H). $^1$H NMR (MeOD) δ ppm 9.28 (1H, d, J=1.53 Hz), 8.18 (1H, d, J=1.53 Hz), 7.86 (1H, d, J=7.32 Hz), 7.78 (1H, d, J=7.93 Hz), 7.46 (1H, t, J=7.78 Hz), 7.32-7.41 (2H, m), 7.31 (1H, d, J=2.14 Hz), 6.88 (1H, dd, J=7.48, 1.98 Hz), 4.04 (3H, s), 3.89 (3H, s).

EXAMPLE 143

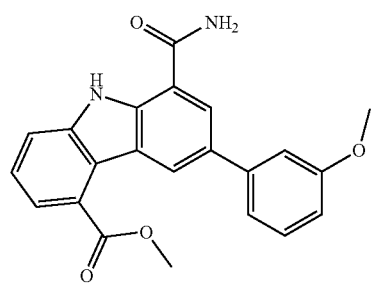 [SMILES: COC(=O)c1cccc2[nH]c3c(C(N)=O)cc(-c4cccc(OC)c4)cc3c12]

Methyl 8-carbamoyl-6-(3-methoxyphenyl)-9H-carbazole-4-carboxylate

Isolated from the crude product during purification of Example 142. MS (ESI) m/z 375.2 (M+H). $^1$H NMR (MeOD) δ ppm 8.49 (1H, s), 8.27 (1H, s), 8.16-8.22 (2H, m), 7.92 (1H, d, J=8.24 Hz), 7.40 (1H, t, J=7.78 Hz), 7.33-7.37 (1H, m), 7.30 (1H, s), 6.92 (1H, d, J=8.24 Hz), 3.97 (3H, s), 3.91 (3H, s).

EXAMPLE 144

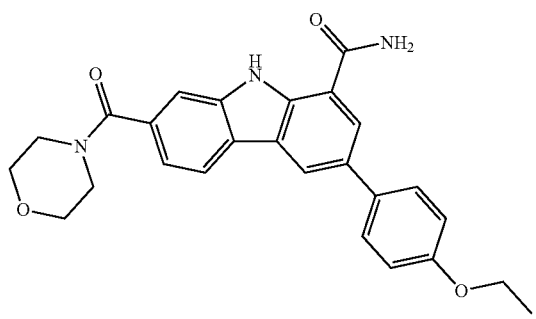 [SMILES: CCOc1ccc(-c2cc(C(N)=O)c3[nH]c4cc(C(=O)N5CCOCC5)ccc4c3c2)cc1]

3-(4-Ethoxyphenyl)-7-(morpholine-4-carbonyl)-9H-carbazole-1-carboxamide

144A. Preparation of 3-bromo-7-(morpholine-4-carbonyl)-9H-carbazole-1-carboxamide

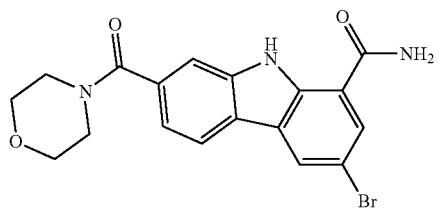 [SMILES: NC(=O)c1cc(Br)cc2c1[nH]c1cc(C(=O)N3CCOCC3)ccc12]

6-Bromo-8-carbamoyl-9H-carbazole-2-carboxylic acid (758 mg, 1.707 mmol, Example 58D) was mixed with morpholine (892 mg, 10.24 mmol), HATU (1947 mg, 5.12 mmol) and DMAP (625 mg, 5.12 mmol) in DMF (8 mL) and stirred for 2 hrs at r.t. The mixture was added slowly to 200 ml H$_2$O while stirring. Resulting mixture was stirred for 10 mins. The resulting yellow precipitate was filtered and air-dried overnight with air-suction to give 546 mg of 3-bromo-7-(morpholine-4-carbonyl)-9H-carbazole-1-carboxamide which was used as such in the next step.

144. Preparation of 3-(4-ethoxyphenyl)-7-(morpholine-4-carbonyl)-9H-carbazole-1-carboxamide 3-Bromo-7-(morpholine-4-carbonyl)-9H-carbazole-1-carboxamide (57 mg, 0.142 mmol), 4-ethoxyphenylboronic acid (35.3 mg, 0.213 mmol), Pd(Ph$_3$P)$_4$ (16.37 mg, 0.014 mmol) and aqueous Na$_2$CO$_3$ (2M) (0.177 mL, 0.354 mmol) were mixed with toluene (2 mL) and MeOH (1 mL) in a sealed microwave tube. The mixture was degassed and filled with N2. then stirred at 100° C. for 12 hrs. The reaction mixture was concentrated and purified using preparative HPLC to give 11.1 mg of titled product. MS (ESI) m/z 444.21 (M+H)$^+$. $^1$H NMR (DMSO-d$_6$) δ ppm 11.53 (s, 1H), 8.64 (s, 1H), 8.37 (bs, 1H), 8.29 (m, 2H), 7.81 (m, 3H), 7.56 (bs, 1H), 7.22 (d, 1H, J=8), 7.07(m, 2H), 4.10 (q, 2H, J=6.9), 3.64 (bm, 8H), 1.37 (t, 3H, J=6.9).

The following compounds in Table 7 have been synthesized utilizing the procedures described in Example 144.

TABLE 7

| Ex. # | Structure | Name | Retention time (min) | MS (ESI) m/z* |
|---|---|---|---|---|
| 145 | 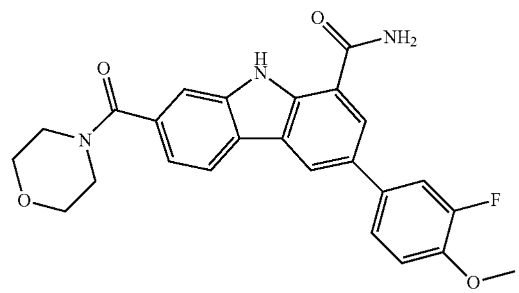 [SMILES: COc1ccc(-c2cc(C(N)=O)c3[nH]c4cc(C(=O)N5CCOCC5)ccc4c3c2)cc1F] | 3-(3-fluoro-4-methoxyphenyl)-7-(4-morpholinylcarbonyl)-9H-carbazole-1-carboxamide | 11.49(c) | 448.17 |
| 146 | 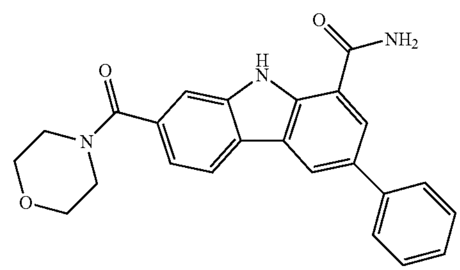 [SMILES: NC(=O)c1cc(-c2ccccc2)cc2c1[nH]c1cc(C(=O)N3CCOCC3)ccc12] | 7-(4-morpholinylcarbonyl)-3-phenyl-9H-carbazole-1-carboxamide | 12.41(c) | 400.18 |
| 147 | 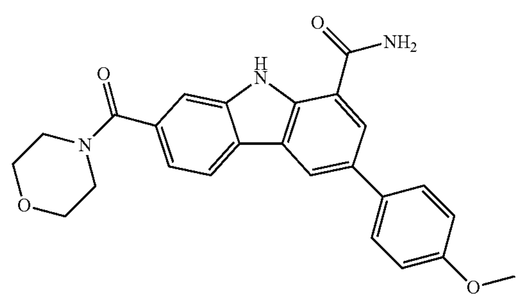 [SMILES: COc1ccc(-c2cc(C(N)=O)c3[nH]c4cc(C(=O)N5CCOCC5)ccc4c3c2)cc1] | 3-(4-methoxyphenyl)-7-(4-morpholinylcarbonyl)-9H-carbazole-1-carboxamide | 11.31(c) | 430.15 |
| 148 | 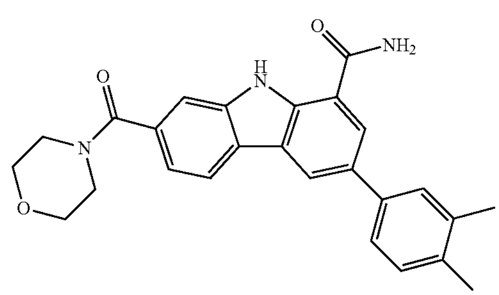 [SMILES: Cc1ccc(-c2cc(C(N)=O)c3[nH]c4cc(C(=O)N5CCOCC5)ccc4c3c2)cc1C] | 3-(3,4-dimethylphenyl)-7-(4-morpholinylcarbonyl)-9H-carbazole-1-carboxamide | 13.35(c) | 428.19 |

TABLE 7-continued

| Ex. # | Structure | Name | Retention time (min) | MS (ESI) m/z* |
|---|---|---|---|---|
| 149 | 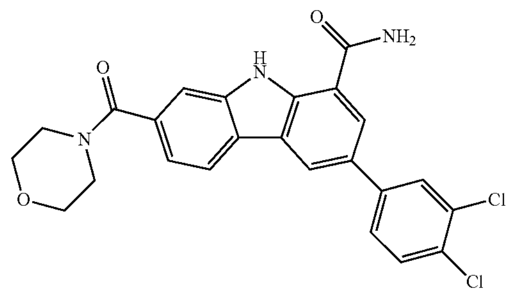 [SMILES: NC(=O)c1cc(-c2ccc(Cl)c(Cl)c2)cc2c1[nH]c1cc(C(=O)N3CCOCC3)ccc12] | 3-(3,4-dichlorophenyl)-7-(4-morpholinylcarbonyl)-9H-carbazole-1-carboxamide | 14.39(c) | 468.06 |
| 150 | 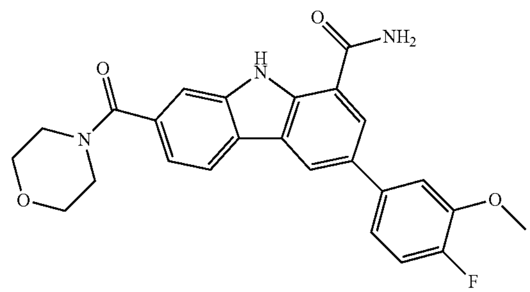 [SMILES: COc1cc(-c2cc(C(N)=O)c3[nH]c4cc(C(=O)N5CCOCC5)ccc4c3c2)ccc1F] | 3-(4-fluoro-3-methoxyphenyl)-7-(4-morpholinylcarbonyl)-9H-carbazole-1-carboxamide | 11.69(c) | 448.20 |
| 151 | 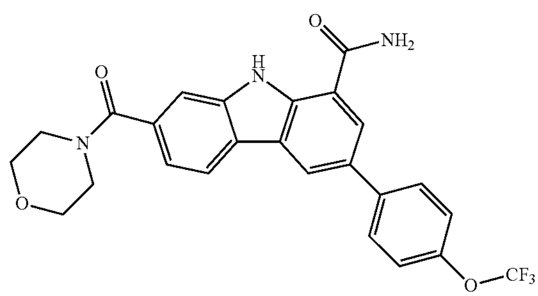 [SMILES: NC(=O)c1cc(-c2ccc(OC(F)(F)F)cc2)cc2c1[nH]c1cc(C(=O)N3CCOCC3)ccc12] | 7-(4-morpholinylcarbonyl)-3-(4-(trifluoromethoxy)phenyl)-9H-carbazole-1-carboxamide | 13.82(c) | 484.13 |
| 152 | 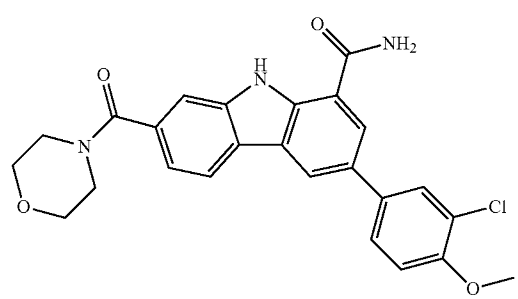 [SMILES: COc1ccc(-c2cc(C(N)=O)c3[nH]c4cc(C(=O)N5CCOCC5)ccc4c3c2)cc1Cl] | 3-(3-chloro-4-methoxyphenyl)-7-(4-morpholinylcarbonyl)-9H-carbazole-1-carboxamide | 12.26(c) | 464.15 |
| 153 | 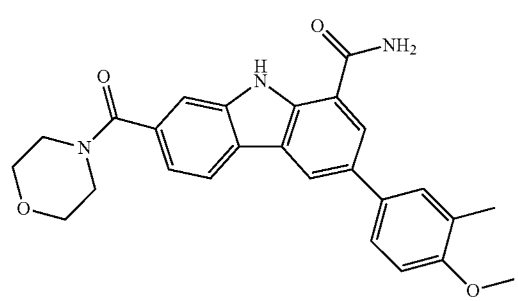 [SMILES: COc1ccc(-c2cc(C(N)=O)c3[nH]c4cc(C(=O)N5CCOCC5)ccc4c3c2)cc1C] | 3-(4-methoxy-3-methylphenyl)-7-(4-morpholinylcarbonyl)-9H-carbazole-1-carboxamide | 12.46(c) | 444.20 |

TABLE 7-continued

| Ex. # | Structure | Name | Retention time (min) | MS (ESI) m/z* |
|---|---|---|---|---|
| 154 | 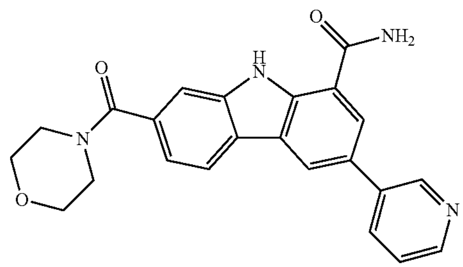 [SMILES: NC(=O)c1cc(-c2cccnc2)cc2c1[nH]c1cc(C(=O)N3CCOCC3)ccc12] | 7-(4-morpholinylcarbonyl)-3-(3-pyridinyl)-9H-carbazole-1-carboxamide | 1.188(d) | 401.16 |
| 155 | 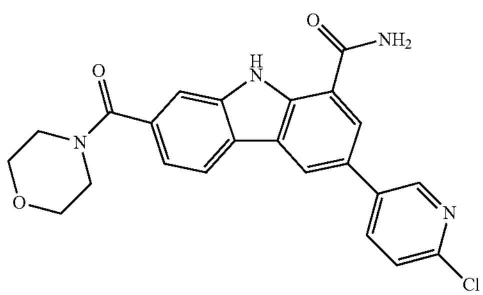 [SMILES: NC(=O)c1cc(-c2ccc(Cl)nc2)cc2c1[nH]c1cc(C(=O)N3CCOCC3)ccc12] | 3-(6-chloro-3-pyridinyl)-7-(4-morpholinylcarbonyl)-9H-carbazole-1-carboxamide | 6.93(c) | 435.13 |
| 156 | 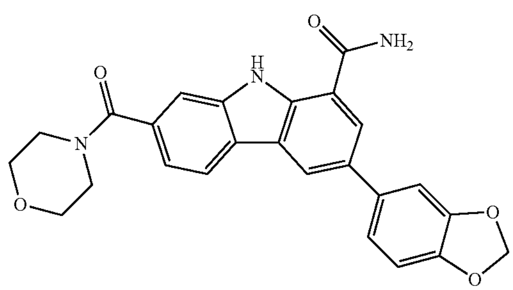 [SMILES: NC(=O)c1cc(-c2ccc3c(c2)OCO3)cc2c1[nH]c1cc(C(=O)N3CCOCC3)ccc12] | 3-(1,3-benzodioxol-5-yl)-7-(4-morpholinylcarbonyl)-9H-carbazole-1-carboxamide | 1.50(d) | 444.18 |
| 157 | 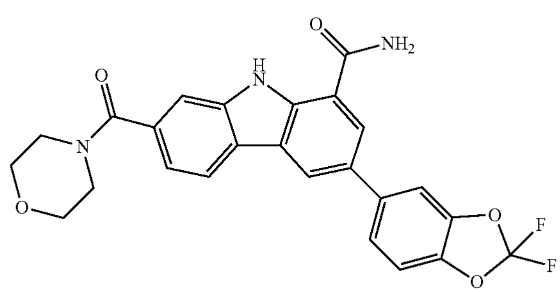 [SMILES: NC(=O)c1cc(-c2ccc3c(c2)OC(F)(F)O3)cc2c1[nH]c1cc(C(=O)N3CCOCC3)ccc12] | 3-(2,2-difluoro-1,3-benzodioxol-5-yl)-7-(4-morpholinylcarbonyl)-9H-carbazole-1-carboxamide | 1.77(d) | 480.13 |
| 158 | 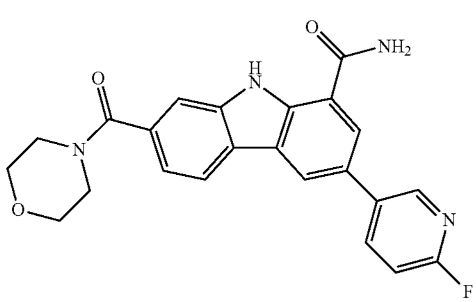 [SMILES: NC(=O)c1cc(-c2ccc(F)nc2)cc2c1[nH]c1cc(C(=O)N3CCOCC3)ccc12] | 3-(6-fluoro-3-pyridinyl)-7-(4-morpholinylcarbonyl)-9H-carbazole-1-carboxamide | 1.31(d) | 419.17 |

TABLE 7-continued

| Ex. # | Structure | Name | Retention time (min) | MS (ESI) m/z* |
|---|---|---|---|---|
| 159 | 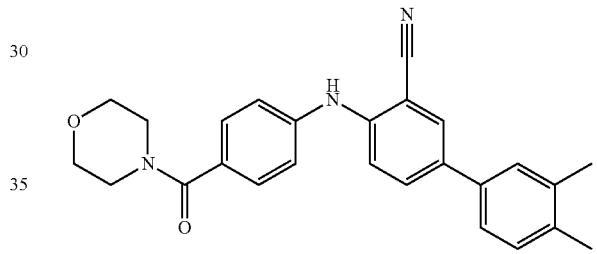 | 3-(6-methoxy-3-pyridinyl)-7-(4-morpholinylcarbonyl)-9H-carbazole-1-carboxamide | 1.37(d) | (M+H)+ 431.19 |

HPLC condition a: Sunfire C18 4.6 × 150 mm column, 20 min gradient, 10-100% B, 1 mL/min. Solvent A: 5% CH$_3$CN - 95% H$_2$O - 0.1% TFA; Solvent B: 95% CH$_3$CN - 5% H$_2$O - 0.1% TFA.
HPLC condition d: XTERRA ® 3.0 × 50 mm S7 column, 3 min gradient, 0-100% B, 4 mL/min. Solvent A: 5% CH$_3$CN - 95% H$_2$O - 10 mm Ammonium Acetate; Solvent B: 95% CH$_3$CN - 5% H$_2$O - 10 mm Ammonium Acetate.
*(M + H)+ observed in all cases except the examples where specifically mentioned.

EXAMPLE 160

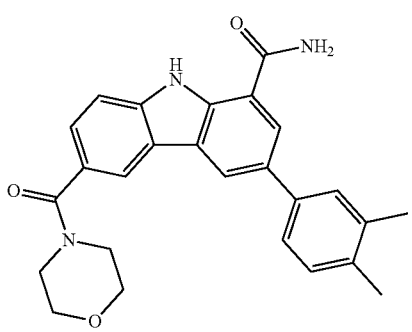 [SMILES: Cc1ccc(-c2cc(C(N)=O)c3[nH]c4ccc(C(=O)N5CCOCC5)cc4c3c2)cc1C]

3-(3,4-Dimethylphenyl)-6-(morpholine-4-carbonyl)-9H-carbazole-1-carboxamide

160A. Preparation of 5-bromo-2-(4-(morpholine-4-carbonyl)phenylamino)benzonitrile

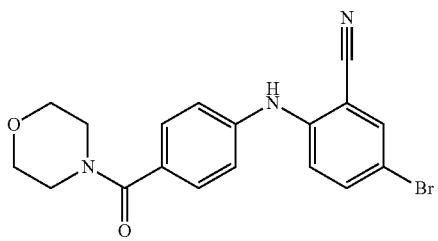 [SMILES: N#Cc1cc(Br)ccc1Nc1ccc(C(=O)N2CCOCC2)cc1]

KOtBu (2.78 g, 24.75 mmol) was dissolved into 20 ml DMSO in a round bottom flask. (4-aminophenyl)(morpholino)methanone (5.10 g, 24.75 mmol) in 10 ml DMSO was added and the resulting mixture was stirred for 35 mins at r.t. The mixture was cooled in an iced bath for 5 mins 5-bromo-2-fluorobenzonitrile (4.5 g, 22.50 mmol) in 10 ml DMSO was added dropwise. Iced bath was removed and the mixture was stirred for 1 hr at r.t. The mixture was diluted with ethyl acetate, 100 ml saturated NH$_4$Cl water solution was added. The organic layer was separated. The water layer was extracted with ethyl acetate. The organic layers were combined and washed with H$_2$O (4×), brine, dried over MgSO$_4$ and concentrated. 8 g crude product (84% purity) was obtained. MS (ESI) m/z 386 (M+H)−. $^1$H NMR (CDCl$_3$) δ ppm 7.61 (d, 1H, J=2.3), 7.47 (dd, 1H, J=9, 2.5), 7.41 (m, 2H), 7.15 (m, 3H), 6.35 (bs, 1H), 3.65 (bm, 8H).

160B. Preparation of 3',4'-dimethyl-4-(4-(morpholine-4-carbonyl)phenylamino)biphenyl-3-carbonitrile 5-Bromo-2-(4-(morpholine-4-carbonyl)phenylamino) benzonitrile (300 mg, 0.777 mmol), Pd(Ph$_3$P)$_4$ (44.9 mg, 0.039 mmol), aqueous 2M Na$_2$CO$_3$ (0.882 mL, 1.763 mmol) were mixed with toluene (4 mL) in a sealed microwave tube. 3,4-dimethylphenylboronic acid (163 mg, 1.087 mmol) in MeOH (2.00 mL) was added to the above mixture. The mixture was heated at 105° C. for 4 hrs in an oil bath. The crude was diluted with CH$_2$Cl$_2$ (100 ml) and washed with water (2×50 ml), brine, dried with MgSO$_4$ and concentrated. 378 mg of crude product (77% purity) was obtained and it will be used as it is.

160. Preparation of 3-(3,4-dimethylphenyl)-6-(morpholine-4-carbonyl)-9H-carbazole-1-carboxamide 3',4'-Dimethyl-4-(4-(morpholine-4-carbonyl)phenylamino)biphenyl-3-carbonitrile (320 mg, 0.777 mmol) and Pd(OAc)$_2$ (0.523 g, 2.331 mmol) were mixed with AcOH (10 mL) in a sealed microwave tube and heated at 130° C. for 12 hrs. The mixture was filtered through a pad of CELITE®, then a ACRODISC® PTFE membrane (0.45 um), rinsed with additional 35 ml AcOH. The filtrate was concentrated and purified using preparative HPLC to give 51.8 mg of titled product. MS (ESI) m/z 428.4 (M+H)+. $^1$H NMR (DMSO-d$_6$) δ ppm 11.59 (s, 1H), 8.74 (s, 1H), 8.38 (bs, 2H), 8.3 (s, 1H), 7.76(d, 1H, J=8.2), 7.71 (s, 1H), 7.63 (d, 1H, J=6.3), 7.57 (bs, 1H), 7.48(d, 1H, J=8.2), 7.27(d, 1H, J=7.6), 3.65-3.59 (bm, 8H), 2.35 (s, 3H),), 2.29 (s, 3H).

The following compounds in Table 8 have been synthesized utilizing the procedures described in Example 160.

TABLE 8

| Ex. # | Structure | Name | Retention time (min) | MS (ESI) m/z* |
|---|---|---|---|---|
| 163 | 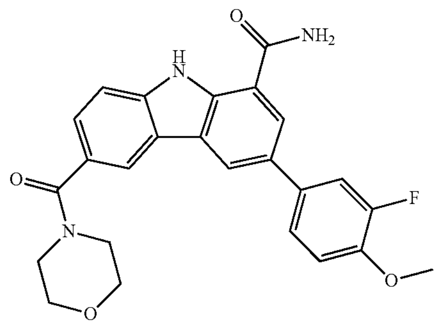 [SMILES: COc1ccc(-c2cc(C(N)=O)c3[nH]c4ccc(C(=O)N5CCOCC5)cc4c3c2)cc1F] | 3-(3-fluoro-4-methoxyphenyl)-6-(4-morpholinylcarbonyl)-9H-carbazole-1-carboxamide | 12.83(a) | 448.37 |
| 164 | 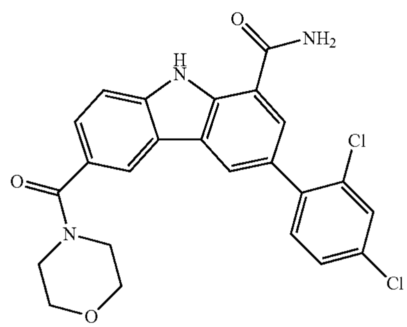 [SMILES: NC(=O)c1cc(-c2ccc(Cl)cc2Cl)cc2c1[nH]c1ccc(C(=O)N3CCOCC3)cc12] | 3-(2,4-dichlorophenyl)-6-(4-morpholinylcarbonyl)-9H-carbazole-1-carboxamide | 14.57(a) | 468.30 |
| 165 | 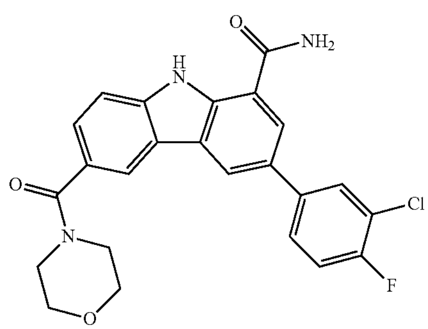 [SMILES: NC(=O)c1cc(-c2ccc(F)c(Cl)c2)cc2c1[nH]c1ccc(C(=O)N3CCOCC3)cc12] | 3-(3-chloro-4-fluorophenyl)-6-(4-morpholinylcarbonyl)-9H-carbazole-1-carboxamide | 14.24(a) | 452.33 |
| 166 | 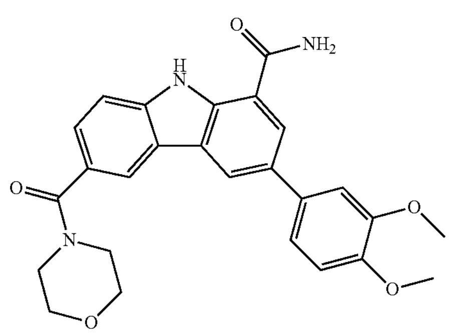 [SMILES: COc1ccc(-c2cc(C(N)=O)c3[nH]c4ccc(C(=O)N5CCOCC5)cc4c3c2)cc1OC] | 3-(3,4-dimethoxyphenyl)-6-(4-morpholinylcarbonyl)-9H-carbazole-1-carboxamide | 11.52(a) | 460.23 |

TABLE 8-continued

| Ex. # | Structure | Name | Retention time (min) | MS (ESI) m/z* |
|---|---|---|---|---|
| 167 | 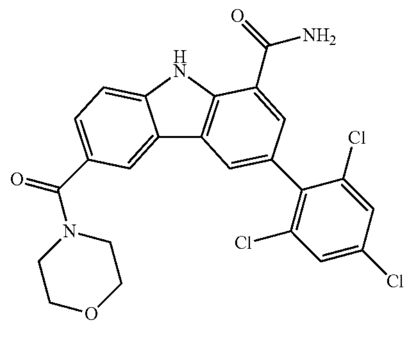 [SMILES: NC(=O)c1cc(-c2c(Cl)cc(Cl)cc2Cl)cc2c1[nH]c1ccc(C(=O)N3CCOCC3)cc12] | 6-(4-morpholinylcarbonyl)-3-(2,4,6-trichlorophenyl)-9H-carbazole-1-carboxamide | 14.82(a) | 500.24 |
| 168 | 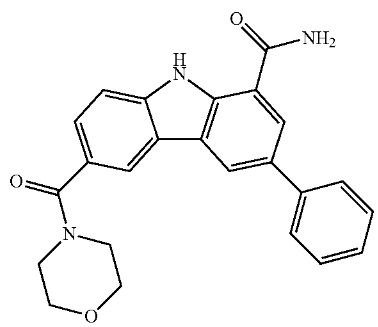 [SMILES: NC(=O)c1cc(-c2ccccc2)cc2c1[nH]c1ccc(C(=O)N3CCOCC3)cc12] | 6-(4-morpholinylcarbonyl)-3-phenyl-9H-carbazole-1-carboxamide | 12.39(a) | 400.23 |
| 169 | 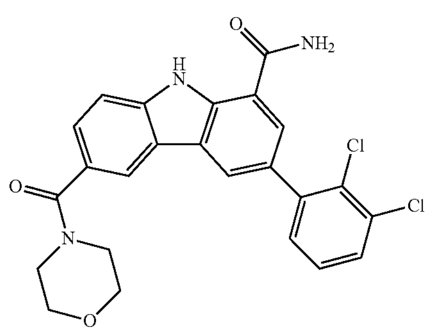 [SMILES: NC(=O)c1cc(-c2cccc(Cl)c2Cl)cc2c1[nH]c1ccc(C(=O)N3CCOCC3)cc12] | 3-(2,3-dichlorophenyl)-6-(4-morpholinylcarbonyl)-9H-carbazole-1-carboxamide | 13.89(a) | 468.12 |
| 170 | 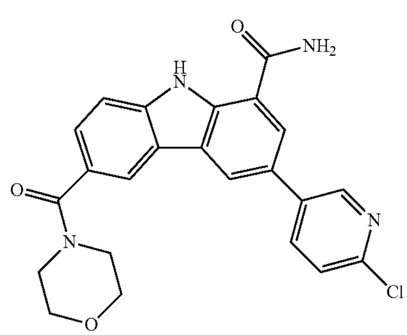 [SMILES: NC(=O)c1cc(-c2ccc(Cl)nc2)cc2c1[nH]c1ccc(C(=O)N3CCOCC3)cc12] | 3-(6-chloro-3-pyridinyl)-6-(4-morpholinylcarbonyl)-9H-carbazole-1-carboxamide | 11.41(a) | 435.15 |

TABLE 8-continued

| Ex. # | Structure | Name | Retention time (min) | MS (ESI) m/z* |
|---|---|---|---|---|
| 171 | 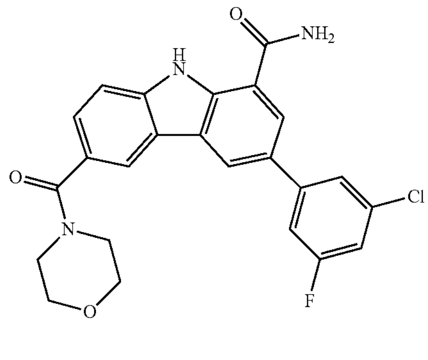 [SMILES: NC(=O)c1cc(-c2cc(F)cc(Cl)c2)cc2c1[nH]c1ccc(C(=O)N3CCOCC3)cc12] | 3-(3-chloro-3-fluorophenyl)-6-(4-morpholinylcarbonyl)-9H-carbazole-1-carboxamide | 12.20(b) | 452.18 |
| 172 | 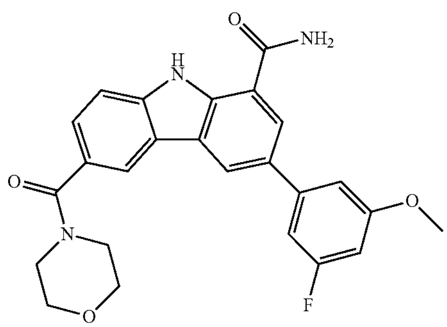 [SMILES: COc1cc(F)cc(-c2cc(C(N)=O)c3[nH]c4ccc(C(=O)N5CCOCC5)cc4c3c2)c1] | 3-(3-fluoro-5-methoxyphenyl)-6-(4-morpholinylcarbonyl)-9H-carbazole-1-carboxamide | 11.29(b) | 448.23 |
| 173 | 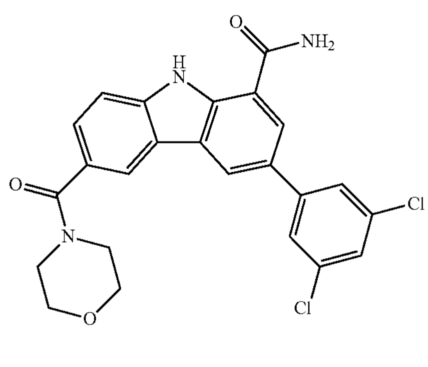 [SMILES: NC(=O)c1cc(-c2cc(Cl)cc(Cl)c2)cc2c1[nH]c1ccc(C(=O)N3CCOCC3)cc12] | 3-(3,5-dichlorophenyl)-6-(4-morpholinylcarbonyl)-9H-carbazole-1-carboxamide | 13.07(b) | 468.14 |
| 174 | 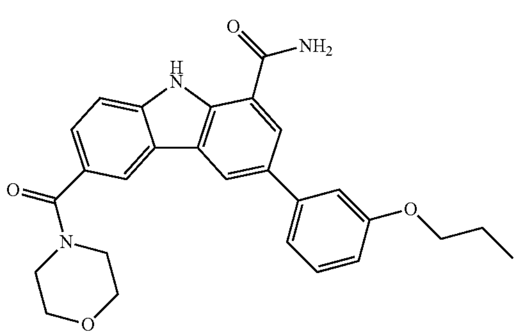 [SMILES: CCCOc1cccc(-c2cc(C(N)=O)c3[nH]c4ccc(C(=O)N5CCOCC5)cc4c3c2)c1] | 6-(4-morpholinylcarbonyl)-3-(3-propoxyphenyl)-9H-carbazole-1-carboxamide | 12.41(b) | 458.25 |

TABLE 8-continued

| Ex. # | Structure | Name | Retention time (min) | MS (ESI) m/z* |
|---|---|---|---|---|
| 175 | 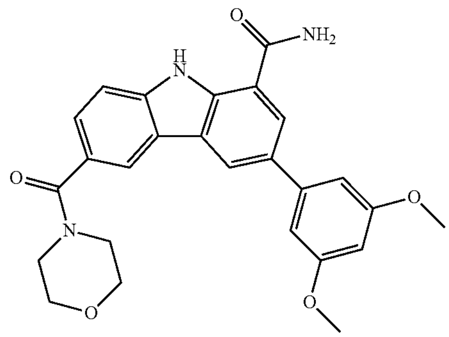 [SMILES: COc1cc(OC)cc(-c2cc(C(N)=O)c3[nH]c4ccc(C(=O)N5CCOCC5)cc4c3c2)c1] | 3-(3,5-dimethoxyphenyl)-6-(4-morpholinylcarbonyl)-9H-carbazole-1-carboxamide | 10.88(b) | 460.22 |
| 176 | 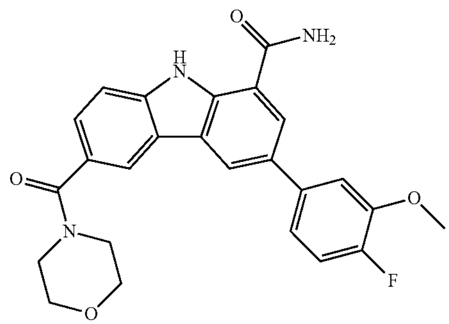 [SMILES: COc1cc(-c2cc(C(N)=O)c3[nH]c4ccc(C(=O)N5CCOCC5)cc4c3c2)ccc1F] | 3-(4-fluoro-3-methoxyphenyl)-6-(4-morpholinylcarbonyl)-9H-carbazole-1-carboxamide | 12.95(a) | 448.18 |

HPLC condition a: Sunfire C18 3.5 u 4.6 × 150 mm column, 20 min gradient, 10-100% B, 1 mL/min. Solvent A: 5% CH₃CN - 95% H₂O - 0.1% TFA; Solvent B: 95% CH₃CN - 5% H₂O - 0.1% TFA.
HPLC condition b: Sunfire C18 3.5 u 4.6 × 150 mm column, 20 min gradient, 10-100% B, 1 mL/min. Solvent A: 5% CH₃CN - 95% H₂O - 0.1% TFA; Solvent B: 95% CH₃CN - 5% H₂O - 0.1% TFA.
*(M + H)⁺ observed in all cases except the examples where specifically mentioned.

EXAMPLE 177

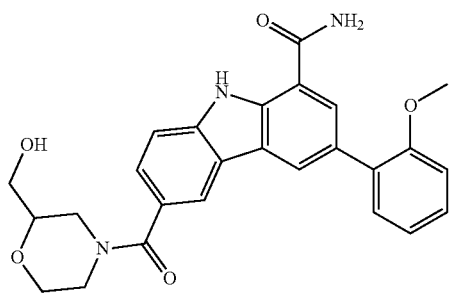 [SMILES: COc1ccccc1-c1cc(C(N)=O)c2[nH]c3ccc(C(=O)N4CCOC(CO)C4)cc3c2c1]

6-(2-(Hydroxymethyl)morpholine-4-carbonyl)-3-(2-methoxyphenyl)-9H-carbazole-1-carboxamide 177A. Preparation of (4-methylpiperazin-1-yl)(4-nitrophenyl)methanone

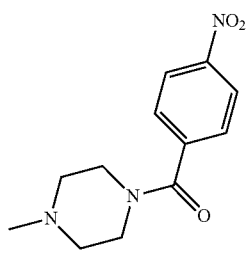

A 1-liter-3-neck flask was loaded with 4-nitrobenzoyl chloride (50.5 g, 267 mmol) and THF (500 ml) and cooled to 0° C. Pyridine (44 ml, 544 mmol), then 1-methyl-piperazine (35 ml, 316 mmol) were added while mechanically stirring at 0° C. After the addition was completed the ice bath was removed and the mixture stirred for 1 hour, while warming to room temperature. A voluminous precipitate forms. The slurry was diluted with dichloromethane and 1 M aq. KOH and the layers separated. The organic layer was washed one more time with 1 M aq. KOH, then with brine and dried over MgSO₄, filtered and concentrated in vacuum. 31.5 g yellow solid (4-methylpiperazin-1-yl)(4-nitrophenyl)methanone were isolated. MS (ESI) m/z 250 (M+H). ¹H NMR (CDCl₃) δ ppm 8.27 (d, 2H, J=7.9), 7.56 (d, 2H, J=7.9), 3.81 (bs, 2H), 3.37 (bs, 2H), 2.50 (bs, 2H), 2.34 (bs, 2H), 2.32 (s, 3H).

177B. Preparation of ((4-aminophenyl)(4-methylpiperazin-1-yl)methanone

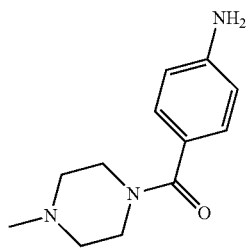 [SMILES: CN1CCN(C(=O)c2ccc([N+](=O)[O-])cc2)CC1]

(4-Methylpiperazin-1-yl)(4-nitrophenyl)methanone (31.5 g, 126 mmol) was dissolved in methanol (150 ml) and transferred into a 500-ml PARR flask. The PARR flask was flushed with nitrogen, then 500 mg Pd/C (10% Pd) were added. The flask was flushed with nitrogen, then hydrogen, then shaken under a pressure of 50 psi of hydrogen for 17 hours. The mixture was filtered through CELITE®, the solid washed with MeOH and concentrated to give 27.2 g beige solid ((4-aminophenyl)(4-methylpiperazin-1-yl)methanone. MS (ESI) m/z 220 (M+H). $^1$H NMR (CDCl$_3$) δ ppm 7.25 (d, 2H, J=7.6), 6.64 (d, 2H, J=7.6), 3.86 (bs, 2H), 3.63 (bs, 4H), 2.40 (bs, 4H), 2.30 (s, 3H).

177C. Preparation of 5-bromo-2-(4-(4-methylpiperazine-1-carbonyl)phenylamino)-benzonitrile

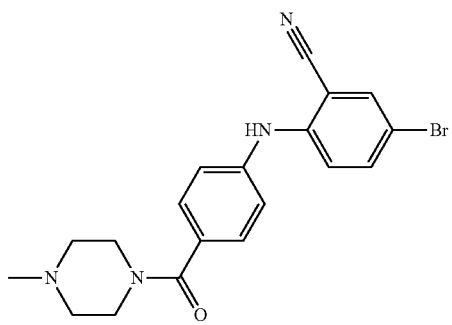 [SMILES: CN1CCN(C(=O)c2ccc(Nc3ccc(Br)cc3C#N)cc2)CC1]

KOtBu (2.81 g, 25.08 mmol) was dissolved in 20 ml DMSO in a round bottom flask. (4-aminophenyl)(4-methylpiperazin-1-yl)methanone (5.0 g, 22.80 mmol) in 30 ml DMSO was added and the resulting mixture was stirred for 15 minutes at r.t. The mixture was cooled in an iced bath for 5 minutes. 5-bromo-2-fluorobenzonitrile (4.6 g, 23.00 mmol) in 20 ml DMSO was added. The ice bath was removed and the mixture stirred for 5 hours while warming to room temperature. Additional KOtBu (2 g, 17.82 mmol) was added and the mixture stirred at room temperature overnight. The mixture was diluted with dichloromethane, extracted twice with water, once with brine, then dried over MgSO$_4$, filtered and concentrated. 8.8 g crude brown oil were isolated. The crude product was recrystallized from dichloromethane+ethyl acetate+hexanes. 5.012 g pale yellow crystals were collected by filtration. The mother liquor was concentrated and purified by chromatography on silica, using a gradient from 100% Solvent A to 50% Solvent A+50% Solvent B. Solvent A: 99% dichloromethane+1% Triethylamine, Solvent B: 99% Ethylacetate+1% Triethylamine. Evaporation of product containing fractions gave additional 1.8 g product of ~70% purity. MS (ESI) m/z 399/401(M+H). $^1$H NMR (CDCl$_3$) δ ppm 7.63 (s, 1H), 7.48 (d, 1H, J=9.2), 7.42 (d, 2H, J=7.9), 7.18-7.14 (m, 3H), 6.41 (s, 1H), 3.80-3.40 (bm, 4H), 2.42 (bs, 4H), 2.32 (s, 3H).

177D. Preparation of 2'-methoxy-4-(4-(4-methylpiperazine-1-carbonyl)phenylamino)-biphenyl-3-carbonitrile

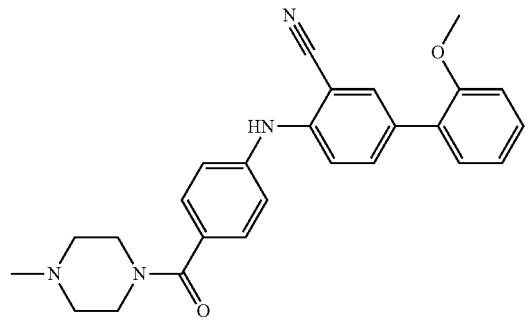 [SMILES: COc1ccccc1-c1ccc(Nc2ccc(C(=O)N3CCN(C)CC3)cc2)c(C#N)c1]

5-Bromo-2-(4-(4-methylpiperazine-1-carbonyl)phenylamino)benzonitrile (100 mg, 0.250 mmol), Pd(Ph$_3$P)$_4$ (14.47 mg, 0.013 mmol), 2-methoxyphenylboronic acid (53.3 mg, 0.351 mmol), aqueous Na$_2$CO$_3$ (0.28 mL, 0.560 mmol), MeOH (0.5 mL) and Toluene (1 mL) were combined in a 2 ml microwave vial, sealed, the vial flushed with nitrogen and heated to 105° C. for 5 hrs in an oil bath. The reaction was poured into a separating funnel loaded with dichloromethane and 0.1 N aq. KOH. The aqueous layer was extracted one more time with dichloromethane, the organic layers combined and washed once with brine, then dried over MgSO$_4$, filtered and concentrated in vacuum. Purification by chromatography on silica Solvent A: 500 ml ethyl acetate+500 ml CH$_2$Cl$_2$+10 ml Et3N; Solvent B: 500 ml ethyl acetate+500 ml CH$_2$Cl$_2$+10 ml Et3N+100 ml MeOH, Gradient from 100% A to 100% B, product elutes at ~25% Solvent B. Combine product containing fractions and evaporate volatiles. 90.1 mg 2'-methoxy-4-(4-(4-methylpiperazine-1-carbonyl)phenylamino)-biphenyl-3-carbonitrile were isolated as a colorless film. MS (ESI) m/z 427 (M+H). $^1$H NMR (CDCl$_3$) δ ppm 7.74 (d, 1H, J=2.2), 7.60 (dd, 1H, J=8.9, 1.9), 7.42 (d, 2H, J=8.5), 7.34 (d, 1H, J=8.9), 7.32 (dt, 1H, J=1.5, ~8, ~8), 7.26 (dd, 1H, J=1.6, ~8), 7.20 (d, 2H, J=8.2), 7.02 (t, 1H, J=7.5), 6.98 (d, 1H, J=8.2), 6.49 (s, 1H), 3.83 (s, 3H), 3.85-3.45 (b, 4H), 2.43 (bs, 4H), 2.32 (s, 3H).

177E. Preparation of 4-(3-cyano-2'-methoxybiphenyl-4-ylamino)benzoic acid

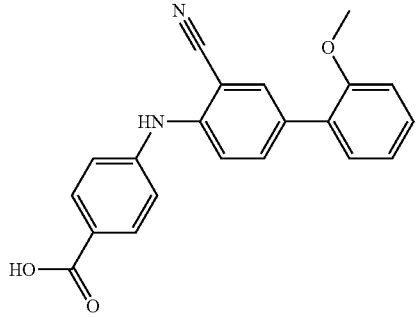 [SMILES: COc1ccccc1-c1ccc(Nc2ccc(C(=O)O)cc2)c(C#N)c1]

2'-Methoxy-4-(4-(4-methylpiperazine-1-carbonyl)phenylamino)biphenyl-3-carbonitrile (75 mg, 0.171 mmol) was dissolved in dioxane (6 ml) in a 20 ml microwave vial, HCl (1M aqueous, 6 ml, 6.00 mmol) was added, the vial sealed and heated for 90 minutes to 130° C. After evaporation of volatiles the crude was suspended in water, sonicated briefly, and the product collected by filtration. Solids were washed with water and dried under a stream of nitrogen. 65.9 mg white solid 4-(3-cyano-2'-methoxybiphenyl-4-ylamino)benzoic acid were isolated (>95% pure by UV-HPLC, excess amount over 100% yield is likely water) and used without further purification. MS (ESI) m/z 343 (M–H).

177F. Preparation of 8-carbamoyl-6-(2-methoxyphenyl)-9H-carbazole-3-carboxylic acid

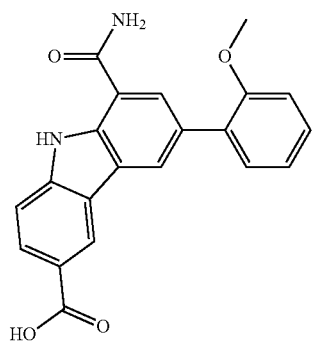 [SMILES: COc1ccccc1-c1cc(C(N)=O)c2[nH]c3ccc(C(=O)O)cc3c2c1]

A 5 ml microwave vial was loaded with 4-(3-cyano-2'-methoxybiphenyl-4-ylamino)benzoic acid (63 mg, 0.161 mmol), Acetic Acid (4 ml) and Palladium(II) acetate (106 mg, 0.472 mmol), sealed and heated to 130° C. for 12 hours. The reaction mixture was filtered through a 0.45 um Nylon filter, the filter rinsed with acetic acid and the collected liquids evaporated. 31.5 mg of 8-carbamoyl-6-(2-methoxyphenyl)-9H-carbazole-3-carboxylic acid were isolated as a brown film and used without further purification. MS (ESI) m/z 359 (M–H).

177. Preparation of 6-(2-(hydroxymethyl)morpholine-4-carbonyl)-3-(2-methoxyphenyl)-9H-carbazole-1-carboxamide

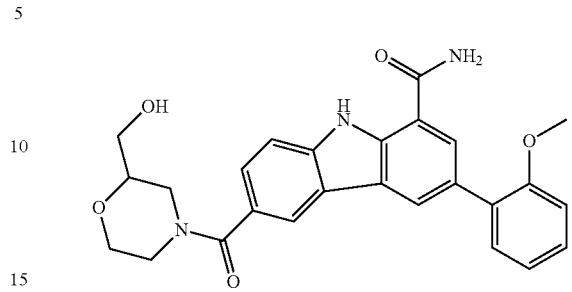

8-Carbamoyl-6-(2-methoxyphenyl)-9H-carbazole-3-carboxylic acid (31.5 mg, 0.061 mmol), HATU (75 mg, 0.197 mmol), DMAP (25 mg, 0.205 mmol), morpholin-2-ylmethanol (35 mg, 0.299 mmol) and DMF (3 ml) were combined and stirred at room temperature for 18 hours. The reaction mixture was filtered through a 0.45 um Nylon filter and purified by prep HPLC chromatography (water/$CH_3CN$/$NH_4OAc$ eluent system). Product containing fractions were collected and evaporated in SPEEDVAC®. 13.4 mg 6-(2-(hydroxymethyl)morpholine-4-carbonyl)-3-(2-methoxyphenyl)-9H-carbazole-1-carboxamide were isolated as an off-white solid. MS (ESI) m/z 460 [M+H]. $^1$H NMR ($CD_3OD$) δ ppm 8.45 (d, 1H, J=1.5), 8.27 (bs, 1H), 8.09 (d, 1H, J=1.5), 7.71 (d, 1H, J=8.6), 7.56 (dd, 1H, J=8.4, 1.7), 7.47 (dd, 1H, J=7.5, 1.7), 7.37 (dt, 1H, J~8, ~8, 1.7), 7.14 (d, 1H, J=8.5), 7.09 (dt, 1H, J=0.9, 7.5, 7.5), 4.05-3.90 (b, 2H), 3.86 (s, 3H), 3.70-3.55 (b, 4H), 3.5-3.0 (b, 3H).

The following compounds in Table 9 have been synthesized utilizing the procedures described for Example 177.

TABLE 9

| Ex. # | Structure | Name | Retention time (min) | MS (ESI) m/z* |
|---|---|---|---|---|
| 178 | 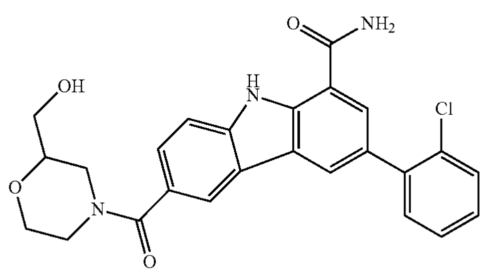 [SMILES: NC(=O)c1cc(-c2ccccc2Cl)cc2c1[nH]c1ccc(C(=O)N3CCOC(CO)C3)cc12] | 3-(2-chlorophenyl)-6-(2-(hydroxymethyl)morpholine-4-carbonyl)-9H-carbazole-1-carboxamide | 10.04 | 464 |
| 179 | 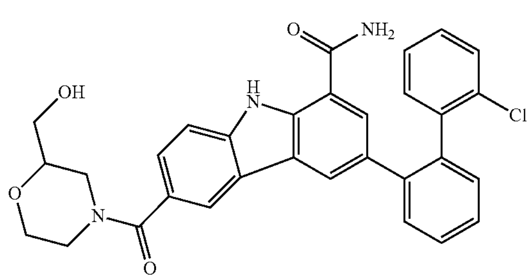 [SMILES: NC(=O)c1cc(-c2ccccc2-c2ccccc2Cl)cc2c1[nH]c1ccc(C(=O)N3CCOC(CO)C3)cc12] | 3-(2'-chlorobiphenyl-2-yl)-6-(2-(hydroxymethyl)morpholine-4-carbonyl)-9H-carbazole-1-carboxamide | 9.58 | 540 |

TABLE 9-continued

| Ex. # | Structure | Name | Retention time (min) | MS (ESI) m/z* |
|---|---|---|---|---|
| 180 | 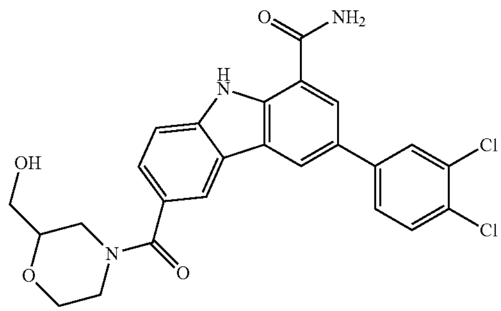 [SMILES: NC(=O)c1cc(-c2ccc(Cl)c(Cl)c2)cc2c1[nH]c1ccc(C(=O)N3CCOC(CO)C3)cc12] | 3-(3,4-dichlorophenyl)-6-(2-(hydroxymethyl) morpholine-4-carbonyl)-9H-carbazole-1-carboxamide | 9.64 | 498 |
| 181 | 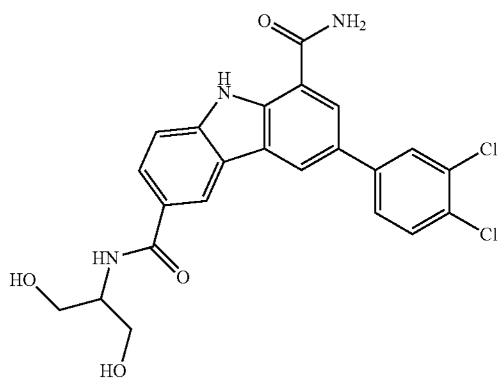 [SMILES: NC(=O)c1cc(-c2ccc(Cl)c(Cl)c2)cc2c1[nH]c1ccc(C(=O)NC(CO)CO)cc12] | 3-(3,4-dichlorophenyl)-$N^6$-(1,3-dihydroxypropan-2-yl)-9H-carbazole-1,6-dicarboxamide | 13.48 | 472 |
| 182 | 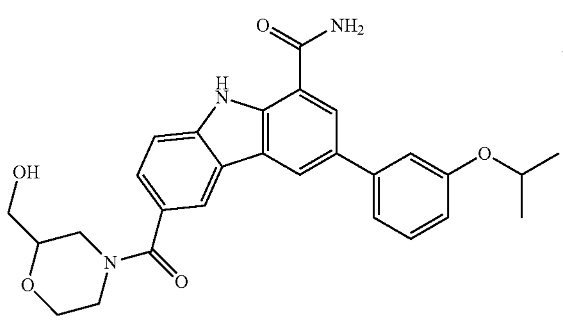 [SMILES: CC(C)Oc1cccc(-c2cc(C(N)=O)c3[nH]c4ccc(C(=O)N5CCOC(CO)C5)cc4c3c2)c1] | 6-(2-(hydroxymethyl) morpholine-4-carbonyl)-3-(3-isopropoxyphenyl)-9H-carbazole-1-carboxamide | 9.02 | 488 |
| 183 | 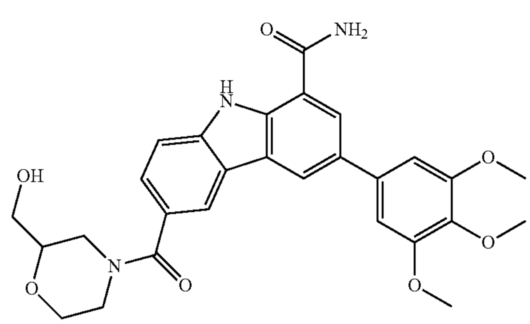 [SMILES: COc1cc(-c2cc(C(N)=O)c3[nH]c4ccc(C(=O)N5CCOC(CO)C5)cc4c3c2)cc(OC)c1OC] | 6-(2-(hydroxymethyl) morpholine-4-carbonyl)-3-(3,4,5-trimethoxyphenyl)-9H-carbazole-1-carboxamide | 11.07 | 520 |

TABLE 9-continued

| Ex. # | Structure | Name | Retention time (min) | MS (ESI) m/z* |
|---|---|---|---|---|
| 184 | 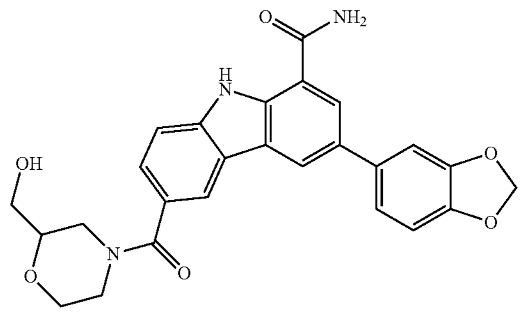 [SMILES: NC(=O)c1cc(-c2ccc3c(c2)OCO3)cc2c1[nH]c1ccc(C(=O)N3CCOC(CO)C3)cc12] | 3-(benzo[d][1,3]dioxol-5-yl)-6-(2-(hydroxymethyl)morpholine-4-carbonyl)-9H-carbazole-1-carboxamide | 7.66 | 474 |
| 185 | 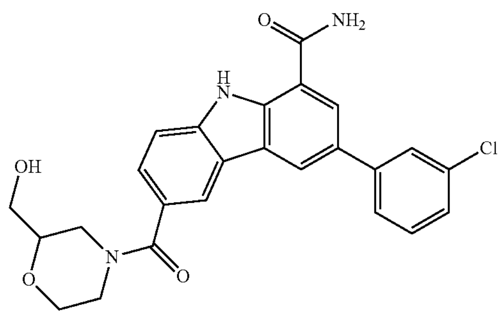 [SMILES: NC(=O)c1cc(-c2cccc(Cl)c2)cc2c1[nH]c1ccc(C(=O)N3CCOC(CO)C3)cc12] | 3-(3-chlorophenyl)-6-(2-(hydroxymethyl)morpholine-4-carbonyl)-9H-carbazole-1-carboxamide | 8.75 | 464 |
| 186 | 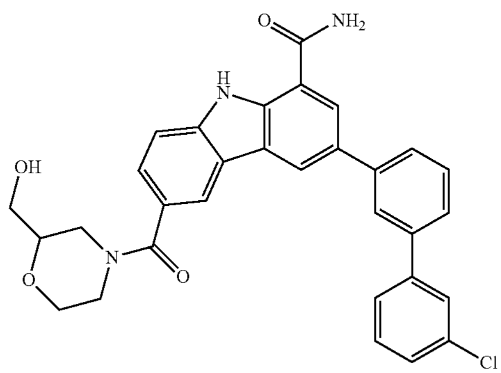 [SMILES: NC(=O)c1cc(-c2cccc(-c3cccc(Cl)c3)c2)cc2c1[nH]c1ccc(C(=O)N3CCOC(CO)C3)cc12] | 3-(3'-chlorobiphenyl-3-yl)-6-(2-(hydroxymethyl)morpholine-4-carbonyl)-9H-carbazole-1-carboxamide | 10.93 | 540 |

HPLC conditions: Waters Sunfire C18 3.5 um, 4.6 × 150 mm column. Flow = 2 ml/min.
Solvent: A = 0.1% TFA/95% water/5% methanol, Solvent B = 0.1% TFA/5% water/95% methanol. Gradient from 10% B to 100% over 15 minutes, then isocratic 100% B. Detection: UV at 220 nm.
*(M + H)⁺ observed in all cases except the examples where specifically mentioned.

EXAMPLE 187

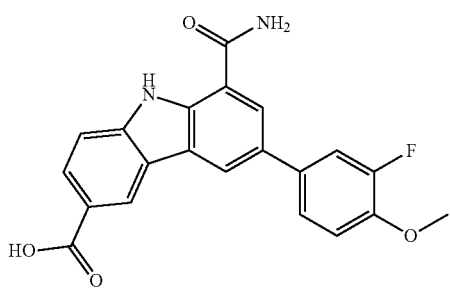 [SMILES: COc1ccc(-c2cc(C(N)=O)c3[nH]c4ccc(C(=O)O)cc4c3c2)cc1F]

8-Carbamoyl-6-(3-fluoro-4-methoxyphenyl)-9H-carbazole-3-carboxylic acid

187A. Preparation of tert-butyl 4-(4-nitrobenzoyl)piperazine-1-carboxylate

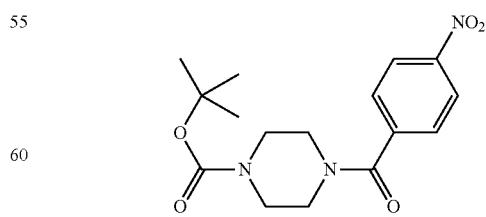

A 500 ml round bottom flask was loaded with 4-nitrobenzoyl chloride (10.2 g, 53.9 mmol) and dichloromethane (100 ml) and cooled to 0° C. Pyridine (10 ml, 124 mmol) was added, followed by tert-butyl piperazine-1-carboxylate (10.2 g, 54.8 mmol) (solid, in portions) while stirring at 0° C. After the addition was completed, the ice bath was removed and the reaction mixture stirred while allowing the reaction to warm to room temperature overnight. The mixture was poured into a separating funnel loaded with 250 ml ethyl acetate and 250 ml 1N aq. HCl. The layers were separated, the organic layer washed one more time with 1 M aq. HCl, then with sat. aq. NaHCO$_3$ solution (2×), then brine (1×), then dried over MgSO$_4$, filtered and concentrated in vacuum. 12.9 g tert-butyl 4-(4-nitrobenzoyl)piperazine-1-carboxylate were isolated as a white solid. MS (ESI) m/z 280 (M+H—C$_4$H$_8$), 236 (M+H-BOC). $^1$H NMR (CDCl$_3$) δ ppm 8.28 (d, 2H, J=8.6), 7.57 (d, 2H, J=8.6), 3.76 (bs, 2H), 3.53 (bs, 2H), 3.39 (bs, 2H), 3.33 (bs, 2H), 1.46 (s, 9H).

187B. Preparation of tert-butyl 4-(4-aminobenzoyl)piperazine-1-carboxylate

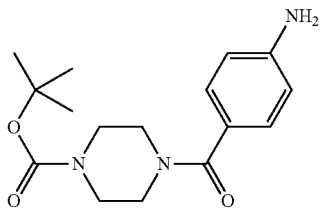 [SMILES: CC(C)(C)OC(=O)N1CCN(C(=O)c2ccc([N+](=O)[O-])cc2)CC1]

tert-Butyl 4-(4-nitrobenzoyl)piperazine-1-carboxylate (12.9 g, 38.5 mmol) was dissolved in methanol (150 ml) and transferred into a 500-ml PARR flask. The flask was flushed with nitrogen, 10% Pd/C (0.38 g, 0.357 mmol) was added, flushed again with nitrogen, then hydrogen, then hydrogenate for 17 hours while shaking. (H2 pressure 50 psi). The reaction mixture was filtered through CELITE®, the CELITE® washed with MeOH and the collected liquids concentrated in vacuum. 11.67 g of tert-butyl 4-(4-amino-benzoyl)piperazine-1-carboxylate were isolated as a beige solid. MS (ESI) m/z 306 (M+H). $^1$H NMR (CDCl$_3$) δ ppm 7.25 (d, 2H, J=7.7), 6.64 (d, 2H, J=7.7), 3.89 (bs, 2H), 3.58 (bs, 4H), 4.43 (bs, 4H), 1.46 (s, 9H).

187C. Preparation of tert-butyl 4-(4-(4-bromo-2-cyanophenylamino)-benzoyl)piperazine-1-carboxylate

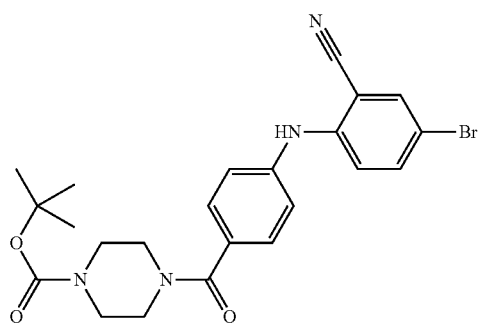 [SMILES: CC(C)(C)OC(=O)N1CCN(C(=O)c2ccc(Nc3ccc(Br)cc3C#N)cc2)CC1]

KOtBu (2.81 g, 25.08 mmol) was dissolved into 20 ml DMSO in a round bottom flask. tert-butyl 4-(4-aminobenzoyl)piperazine-1-carboxylate (7 g, 22.92 mmol) in 30 ml DMSO was added and the resulting mixture was stirred for 15 minutes at room temperature, then cooled in an iced bath for 5 minutes. 5-bromo-2-fluorobenzonitrile (4.6 g, 23.00 mmol) in 20 ml DMSO was added. The ice bath was removed and the mixture stirred for 5 hours while warming to room temperature. LCMS showed product and unreacted starting materials. Additional KOtBu (2 g, 17.82 mmol) was added and the reaction stirred at room temperature overnight. The mixture was transferred into a separating funnel that was loaded with dichloromethane and dilute aq. NH$_4$Cl solution. The layers were separated, the organic layer washed one more time with water, then brine, dried over Mg5O$_4$, filtered and concentrated in vacuum. The crude was dissolved in dichloromethane, and refluxed while adding ethyl acetate until the solution becomes cloudy, then allowed to stand and cool to room temperature. The product precipitated and was collected by filtration. 6.40 g tert-butyl 4-(4-(4-bromo-2-cyanophenylamino)-benzoyl) piperazine-1-carboxylate were isolated as a white solid. The mother liquor was concentrated in vacuum and purified by column chromatography on silica, gradient from 100% dichloromethane to 50% ethyl acetate in dichloromethane. Product containing fractions were combined and evaporate to give additional 0.90 g product as a pale yellow solid. MS (ESI) m/z 485/487 (1 Br isotope pattern) (M+H), 429/431 (1 Br isotope pattern) (M+H—C$_4$H$_8$). $^1$H NMR (CDCl$_3$) δ ppm 7.64 (s, 1H), 7.50 (d, 1H, J=9.2), 7.42 (d, 2H, J=8.3), 7.19-7.15 (m, 3H), 6.39 (s, 1H), 3.80-3.40 (b, 8H), 1.47 (s, 9H).

187D. Preparation of tert-butyl 4-(4-(3-cyano-3'-fluoro-4'-methoxybiphenyl-4-ylamino)benzoyl)piperazine-1-carboxylate

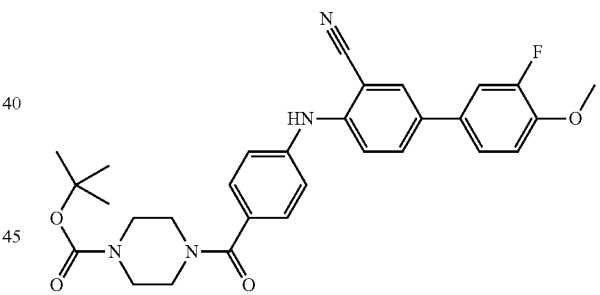

A 125 ml pressure flask was loaded with tert-butyl 4-(4-(4-bromo-2-cyanophenylamino)benzoyl)piperazine-1-carboxylate (6.55 g, 13.49 mmol), 3-fluoro-4-methoxyphenylboronic acid (2.75 g, 16.19 mmol) and Pd(Ph$_3$P)$_4$ (0.43 g, 0.372 mmol). Toluene (45 mL), MeOH (22.50 mL) and a 2 molar solution of Na$_2$CO$_3$ (16.87 mL, 33.7 mmol) were added, the flask flushed with nitrogen, sealed and heated to 105° C. for 5 hours. The reaction mixture was poured into a separating funnel loaded with water and dichloromethane, the layers separated and the aqueous layer extracted one more time with dichloromethane. The combined organic layers were washed with brine and dried over MgSO$_4$, filtered and concentrated in vacuum. The crude product was purified by column chromatography on silica. Gradient from 100% CH$_2$Cl$_2$ to 67% CH$_2$Cl$_2$+33 ethyl acetate. Product containing fractions were combined and concentrated in vacuum. 6.88 g tert-butyl 4-(4-(3-cyano-3'-fluoro-4'-methoxybiphenyl-4-ylamino)benzoyl)-piperazine-1-carboxylate were isolated as a pale yellow foam of ~80% purity. The material was used in then next step without further purification. MS (ESI) m/z 529 (M−H).

187E. Preparation of 4-(3-cyano-3'-fluoro-4'-methoxybiphenyl-4-ylamino)benzoic acid

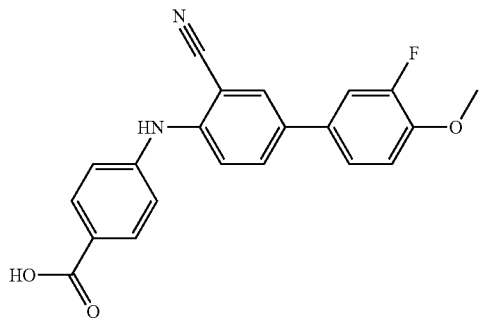 [SMILES: COc1ccc(-c2ccc(Nc3ccc(C(=O)O)cc3)c(C#N)c2)cc1F]

tert-Butyl 4-(4-(3-cyano-3'-fluoro-4'-methoxybiphenyl-4-ylamino)benzoyl)piperazine-1-carboxylate (6.88 g, 10.37 mmol) was dissolved in dioxane (100 ml) in a 350 ml pressure flask. Aqueous HCl (1N, 100 ml, 100 mmol) was added and the reaction heated to 130° C. for 2 hours. A white precipitate formed. The reaction mixture was concentrated to a volume of ~50 ml and filtered. The collected solid was washed with water and dried under a nitrogen stream. 4.62 g 4-(3-cyano-3'-fluoro-4'-methoxybiphenyl-4-ylamino)benzoic acid were collected as an off-white solid. The material was used without further purification. MS (ESI) m/z 361 (M−H).

187. Preparation of 8-carbamoyl-6-(3-fluoro-4-methoxyphenyl)-9H-carbazole-3-carboxylic acid A 350 ml pressure flask was loaded with 4-(3-cyano-3'-fluoro-4'-methoxybiphenyl-4-ylamino)benzoic acid (4.52 g, 9.73 mmol), acetic Acid (200 mL) and palladium(II) acetate (4.37 g, 19.46 mmol), sealed and heated to 130° C. for 12 hours. The mixture was filtered through CELITE®, the solids washed with acetic acid and the collected filtrate concentrated in vacuum. 2.14 g brown solid 8-carbamoyl-6-(3-fluoro-4-methoxyphenyl)-9H-carbazole-3-carboxylic acid were isolated and used without further purification. HPLC retention time 9.26 min (HPLC conditions as in Table 9 and Table 10). MS (ESI) m/z [M−H]⁻ 477.

The following compounds in Table 10 have been synthesized from 187 utilizing the amide coupling procedure described in Example 177.

TABLE 10

| Ex. # | Structure | Name | Retention time (min) | MS (ESI) m/z* |
|---|---|---|---|---|
| 188 | 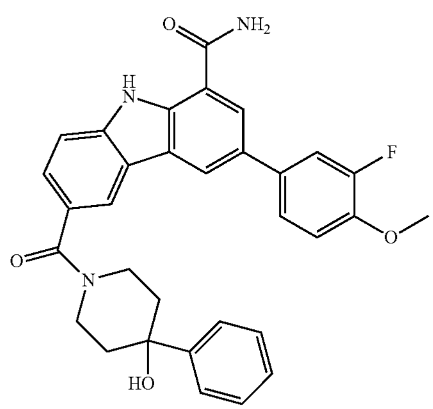 [SMILES: COc1ccc(-c2cc(C(N)=O)c3[nH]c4ccc(C(=O)N5CCC(O)(c6ccccc6)CC5)cc4c3c2)cc1F] | 3-(3-fluoro-4-methoxyphenyl)-6-(4-hydroxy-4-phenylpiperidine-1-carbonyl)-9H-carbazole-1-carboxamide | 10.15 | 538 |
| 189 | 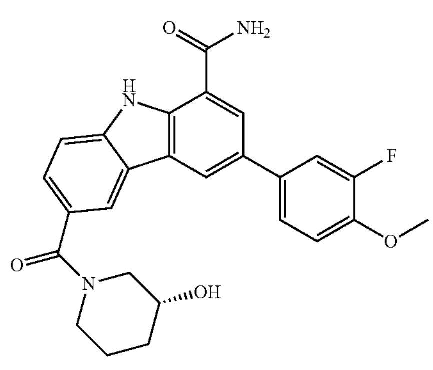 [SMILES: COc1ccc(-c2cc(C(N)=O)c3[nH]c4ccc(C(=O)N5CCC[C@@H](O)C5)cc4c3c2)cc1F] | (R)-3-(3-fluoro-4-methoxyphenyl)-6-(3-hydroxypiperidine-1-carbonyl)-9H-carbazole-1-carboxamide | 8.33 | 462 |

TABLE 10-continued

| Ex. # | Structure | Name | Retention time (min) | MS (ESI) m/z* |
|---|---|---|---|---|
| 190 | 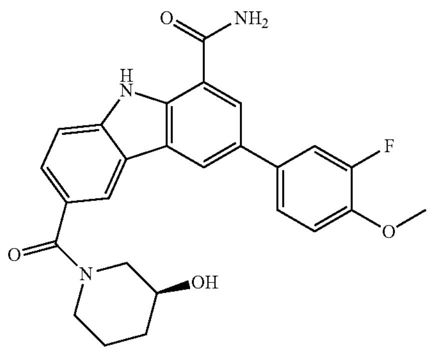 [SMILES: COc1ccc(-c2cc(C(N)=O)c3[nH]c4ccc(C(=O)N5CCC[C@H](O)C5)cc4c3c2)cc1F] | (S)-3-(3-fluoro-4-methoxyphenyl)-6-(3-hydroxypiperidine-1-carbonyl)-9H-carbazole-1-carboxamide | 8.42 | 462 |
| 191 | 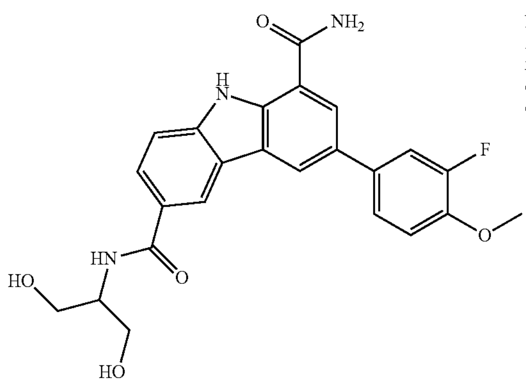 [SMILES: COc1ccc(-c2cc(C(N)=O)c3[nH]c4ccc(C(=O)NC(CO)CO)cc4c3c2)cc1F] | $N^6$-(1,3-dihydroxypropan-2-yl)-3-(3-fluoro-4-methoxyphenyl)-9H-carbazole-1,6-dicarboxamide | 7.02 | 452 |
| 192 | 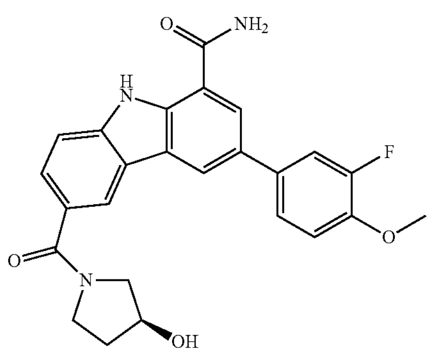 [SMILES: COc1ccc(-c2cc(C(N)=O)c3[nH]c4ccc(C(=O)N5CC[C@H](O)C5)cc4c3c2)cc1F] | (S)-3-(3-fluoro-4-methoxyphenyl)-6-(3-hydroxypiperidine-1-carbonyl)-9H-carbazole-1-carboxamide | 7.61 | 448 |
| 193 | 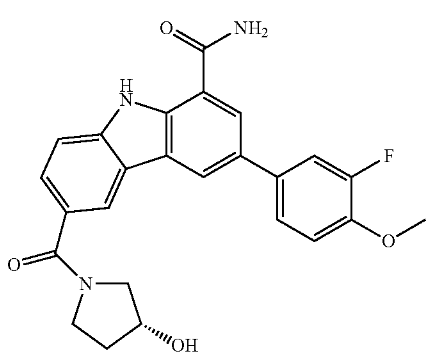 [SMILES: COc1ccc(-c2cc(C(N)=O)c3[nH]c4ccc(C(=O)N5CC[C@@H](O)C5)cc4c3c2)cc1F] | (R)-3-(3-fluoro-4-methoxyphenyl)-6-(3-hydroxypyrrolidine-1-carbonyl)-9H-carbazole-1-carboxamide | 7.71 | 448 |

TABLE 10-continued

| Ex. # | Structure | Name | Retention time (min) | MS (ESI) m/z* |
|---|---|---|---|---|
| 194 | 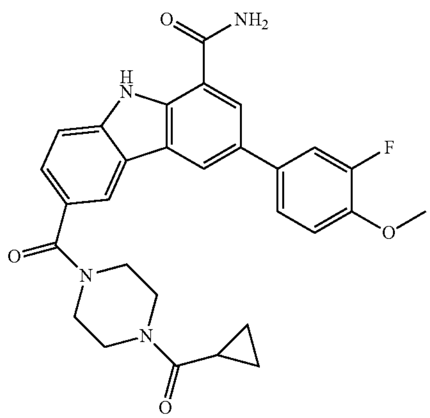 [SMILES: COc1ccc(-c2cc(C(N)=O)c3[nH]c4ccc(C(=O)N5CCN(C(=O)C6CC6)CC5)cc4c3c2)cc1F] | 6-(4-(cyclopropanecarbonyl)piperazine-1-carbonyl)-3-(3-fluoro-4-methoxyphenyl)-9H-carbazole-1-carboxamide | 8.88 | 515 |
| 195 | 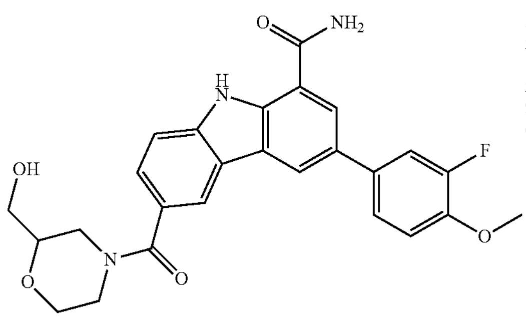 | 3-(3-fluoro-4-methoxyphenyl)-6-(2-(hydroxymethyl)morpholine-4-carbonyl)-9H-carbazole-1-carboxamide | 7.79 | 478 |
| 196 | 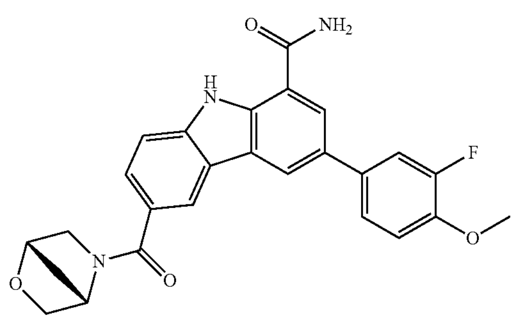 [SMILES: COc1ccc(-c2cc(C(N)=O)c3[nH]c4ccc(C(=O)N5C[C@@H]6C[C@H]5CO6)cc4c3c2)cc1F] | 6-((1S,4S)-2-oxa-5-azabicyclo[2.2.1]heptane-5-carbonyl)-3-(3-fluoro-4-methoxyphenyl)-9H-carbazole-1-carboxamide | 8.67 | 460 |
| 197 | 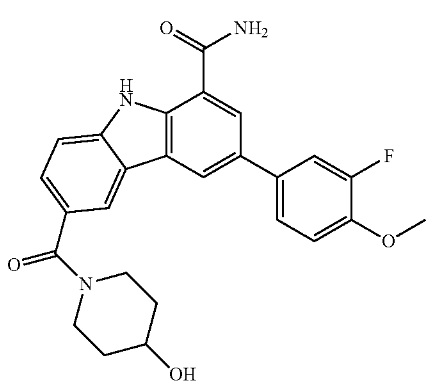 [SMILES: COc1ccc(-c2cc(C(N)=O)c3[nH]c4ccc(C(=O)N5CCC(O)CC5)cc4c3c2)cc1F] | 3-(3-fluoro-4-methoxyphenyl)-6-(4-hydroxypiperidine-1-carbonyl)-9H-carbazole-1-carboxamide | 7.85 | 462 |

TABLE 10-continued

| Ex. # | Structure | Name | Retention time (min) | MS (ESI) m/z* |
|---|---|---|---|---|
| 198 | 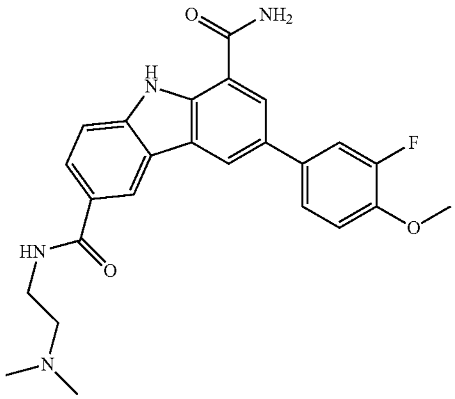 | $N^6$-(2-(dimethylamino)ethyl)-3-(3-fluoro-4-methoxyphenyl)-9H-carbazole-1,6-dicarboxamide | 6.02 | 449 |

HPLC conditions: Waters Sunfire C18 3.5 um, 4.6 × 150 mm column. Flow = 2 ml/min.
Solvent: A = 0.1% TFA/95% water/5% methanol, Solvent B = 0.1% TFA/5% water/95% methanol. Gradient from 10% B to 100% over 15 minutes, then isocratic 100% B. Detection: UV at 220 nm.
*(M + H)+ observed in all cases except the examples where specifically mentioned.

EXAMPLE 199

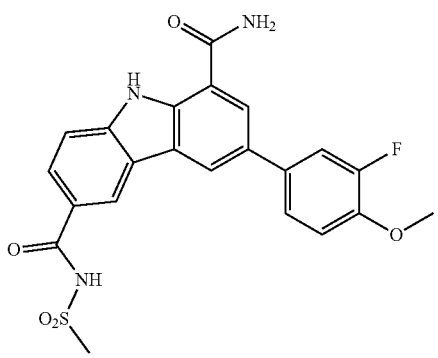 [SMILES: COc1ccc(-c2cc(C(N)=O)c3[nH]c4ccc(C(=O)NS(C)(=O)=O)cc4c3c2)cc1F]

3-(3-Fluoro-4-methoxyphenyl)-$N^6$-(methylsulfonyl)-9H-carbazole-1,6-dicarboxamide To a solution of 8-carbamoyl-6-(3-fluoro-4-methoxyphenyl)-9H-carbazole-3-carboxylic acid (53 mg, 0.070 mmol, Example 187) in DMF (1 ml) was added DMAP (63 mg, 0.516 mmol), then EDC (128 mg, 0.668 mmol) and methanesulfonamide (92 mg, 0.967 mmol) and the mixture stirred at room temperature for 18 hours. The reaction mixture was filtered through a 0.45 um Nylon filter and purified by prep HPLC (water/CH$_3$CN/NH$_4$OAc eluent system). Product containing fractions were evaporated to give 17.5 mg 3-(3-fluoro-4-methoxyphenyl)-$N^6$-(methylsulfonyl)-9H-carbazole-1,6-dicarboxamide as an off-white solid. HPLC retention time 11.10 min (HPLC conditions as in Table 9 and Table 10). MS (ESI) m/z [M−H]$^-$ 454; [M+H]$^+$ 456. $^1$H NMR (CD$_3$OD) δ ppm 8.88 (s, 1H), 8.53 (d, 1H, J=1.3), 8.16 (m, 2H), 7.63-7.55 (m, 3H), 7.22 (t, 1H, 8.5), 3.96 (s, 3H), 3.25 (s, 3H).

EXAMPLE 200

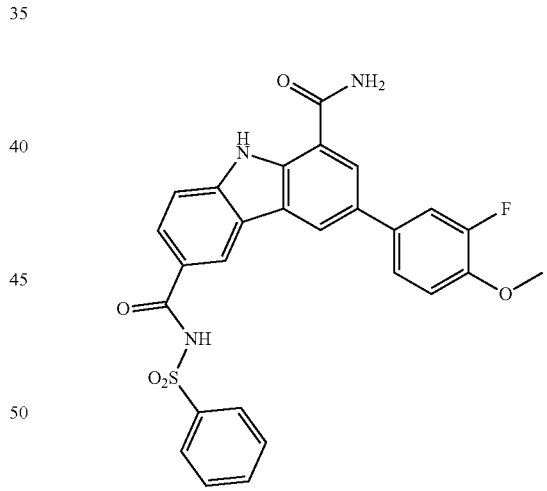

3-(3-Fluoro-4-methoxyphenyl)-$N^6$-(phenylsulfonyl)-9H-carbazole-1,6-dicarboxamide Following the procedure described in Example 199. using benzenesulfonamide instead of methylsulfonamide. HPLC retention time 11.25 min (HPLC conditions as in Table 9 and Table 10). MS (ESI) m/z [M−H]$^-$ 516; [M+H]$^+$ 518.

EXAMPLE 201

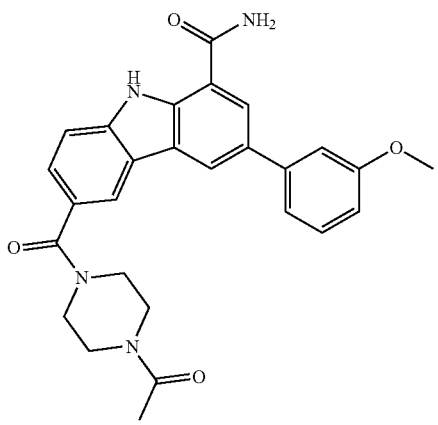 [SMILES: COc1cccc(-c2cc(C(N)=O)c3[nH]c4ccc(C(=O)N5CCN(C(C)=O)CC5)cc4c3c2)c1]

6-(4-Acetylpiperazine-1-carbonyl)-3-(3-methoxyphenyl)-9H-carbazole-1-carboxamide 201A. Preparation of 3'-methoxy-4-(4-(4-methylpiperazine-1-carbonyl)phenylamino)-biphenyl-3-carbonitrile

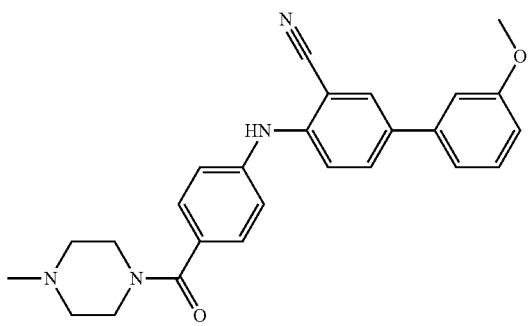 [SMILES: COc1cccc(-c2ccc(Nc3ccc(C(=O)N4CCN(C)CC4)cc3)c(C#N)c2)c1]

3'-Methoxy-4-(4-(4-methylpiperazine-1-carbonyl)phenylamino)-biphenyl-3-carbonitrile was prepared as described for Example 177D, using 3-methoxyphenylboronic acid. MS (ESI) m/z [M+H]$^+$ 427.

201. Preparation of 6-(4-acetylpiperazine-1-carbonyl)-3-(3-methoxyphenyl)-9H-carbazole-1-carboxamide

201

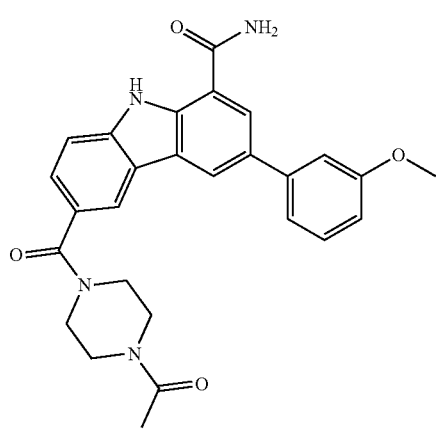

201B

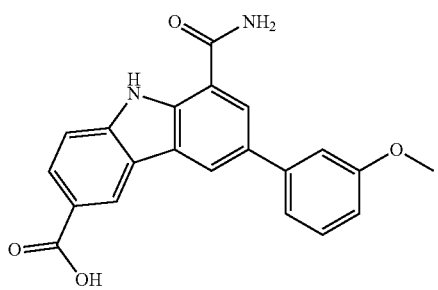

A 5 ml microwave vial was loaded with 3'-methoxy-4-(4-(4-methylpiperazine-1-carbonyl)phenylamino)biphenyl-3-carbonitrile (102 mg, 0.191 mmol, Example 201A), diacetoxypalladium (134 mg, 0.597 mmol) and acetic acid (4 ml) and heated for 3.5 hours to 120° C. LCMS analysis shows largest peak (by UV) to be m/e+=454, consistent with oxidation of N-methyl group to N-formyl and exchange of formyl to acetyl, but no oxidative cyclization of diphenylamine to the carbazole. The reaction mixture was heated to 135° C. for additional 10 hours. Palladium(II)acetate (115 mg, 0.512 mmol) was added and the reaction mixture heated to 130° C. for 24 hours. The reaction mixture was filtered through a 0.45 um Nylon filter and the crude purified by prep HPLC (water/CH$_3$CN/NH$_4$OAc eluent system). Product containing fractions were collected and concentrated in vacuum. 12.4 mg of 201B (off-white solid) and 6.7 mg 6-(4-acetylpiperazine-1-carbonyl)-3-(3-methoxyphenyl)-9H-carbazole-1-carboxamide (off-white solid) were isolated.

Analytical Data for Example 201:
HPLC retention time 7.14 min (HPLC conditions as in Table 5 and Table 6), MS (ESI) m/z [M−H]$^-$ 469; [M+H]$^-$ 471. HPLC retention time 7.14 min (HPLC conditions: Waters Sunfire C18 3.5 um, 4.6×150 mm column. Flow=2 ml/min. Solvent A=0.1% TFA/95% water/5% methanol, Solvent B=0.1% TFA/5% water/95% methanol. Gradient from 10%B to 100%B over 12 minutes, then isocratic 100% B. Detection: UV at 220 nm.).

Analytical Data for 201B:
MS (ESI) m/z [M−H]$^-$ 359; [M+H]$^+$ 361.

EXAMPLE 202

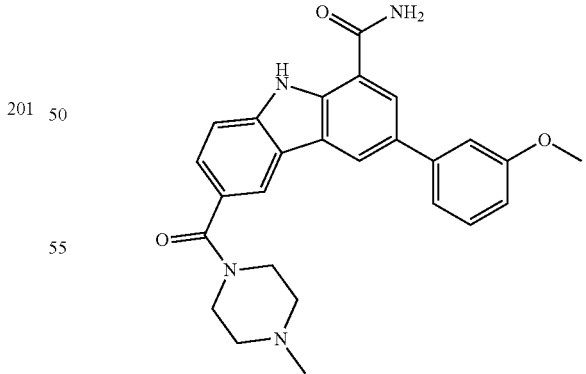

3-(3-Methoxyphenyl)-6-(4-methylpiperazine-1-carbonyl)-9H-carbazole-1-carboxamide 3-(3-Methoxyphenyl)-6-(4-methylpiperazine-1-carbonyl)-9H-carbazole-1-carboxamide was prepared from byproduct 201B (obtained during preparation of Example 201) using the amide coupling procedure described for Example 177. MS (ESI) m/z [M−H]⁻ 441; [M+H]⁺ 443. ¹H NMR (CD₃OD) δ ppm 8.62 (d, 1H, J=1.6), 8.34 (d, 1H, J=0.9), 8.25 (d, 1H, J=1.8), 7.71 (d, 1H, J=8.6), 7.55 (dd, 1H, J=8.4, 1.7), 7.43-7.37 (m, 3H), 6.95 (dt, 1H, J=6.7, 2.4, 2.4), 3.93 (s, 3H), 3.77 (b, 4H), 2.57 (b, 4H), 2.38 (s, 3H).

EXAMPLE 203

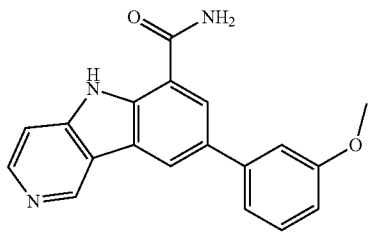 [SMILES: COc1cccc(-c2cc(C(N)=O)c3[nH]c4ccncc4c3c2)c1]

8-(3-Methoxyphenyl)-5H-pyrido[4,3-b]indole-6-carboxamide, HCl

203A. Preparation of 4-fluoro-3'-methoxybiphenyl-3-carbonitrile

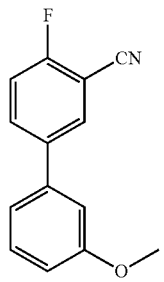

To a stirred suspension of 5-bromo-2-fluorobenzonitrile (1.00 g, 5.0 mmol), tetrakis (triphenylphosphine)palladium (0) (0.44 g, 0.38 mmol), toluene (16 mL) and (2M) aqueous sodium carbonate (5.67 mL, 11.35 mmole) under nitrogen was added a solution of 3-methoxyphenylboronic acid (1.00 g, 6.80 mmole) in methanol (3 mL) at room temperature. The reaction mixture was stirred under reflux for 12 h. The reaction mixture was cooled to room temperature and partitioned between water and ethyl acetate. The layers were separated and the organics were filtered. The organics were washed with water, (5%) aqueous ammonia, and brine solution. The organic phase was dried over Na₂SO₄ and concentrated to give the crude product. The crude material was purified by silica gel column chromatography (hexane/ethyl acetate=100/0–70/30) to afford 0.98 g, of 4-fluoro-3'-methoxybiphenyl-3-carbonitrile. MS (ESI) m/z 228.3 (M+H). ¹H NMR (CDCl₃) d ppm 7.73-7.83 (2H, m), 7.38 (1H, t, J=7.93 Hz), 7.23-7.30 (1H, m), 7.08 (1H, d, J=7.63 Hz), 7.01 (1H, t, J=1.98 Hz), 6.94 (1H, dd, J=8.24, 2.44 Hz), 3.86 (3H, s).

203B. Preparation of 3'-methoxy-4-(pyridine-4-ylamino)biphenyl-3-carbonitrile

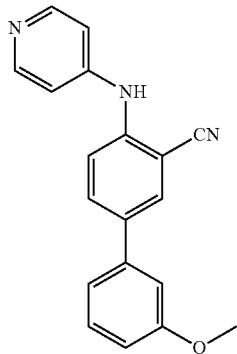 [SMILES: COc1cccc(-c2ccc(Nc3ccncc3)c(C#N)c2)c1]

To a solution of 4-fluoro-3'-methoxybiphenyl-3-carbonitrile (0.50 g, 2.20 mmol) in DMSO (4 mL) was added pyridine-4-amine (0.23 g, 2.42 mmol) and KOtBu (0.15 g, 1.38 mmol). The reaction stirred under nitrogen at room temperature for 12 h. The reaction mixture was partitioned between water and ethyl acetate, the layers were separated, the organics were washed with water, brine solution, dried over Na₂SO₄ and concentrated to give the crude product. The crude material was purified by silica gel column chromatography (DCM/(2M)NH₄-MeOH=100/0–95/5) to afford 0.53 g of 3'-methoxy-4-(pyridine-4-ylamino)biphenyl-3-carbonitrile. MS (ESI) m/z 302.2 (M+H). ¹H NMR MeOD) d ppm 8.24 (2H, d, J=6.41 Hz), 8.01 (1H, d, J=2.44 Hz), 7.93 (1H, dd, J=8.70, 2.29 Hz), 7.61 (1H, d, J=8.55 Hz), 7.40 (1H, t, J=7.93 Hz), 7.17-7.30 (2H, m), 6.92-7.05 (3H, m), 3.88 (3H, s).

203. Preparation of 8-(3-methoxyphenyl)-5H-pyrido[4,3-b]indole-6-carboxamide, HCl To a 5 mL microwave vial 3'-methoxy-4-(pyridine-4-ylamino)biphenyl-3-carbonitrile (60.0 mg, 0.20 mmol), diacetoxypalladium (89.0 mg, 0.40 mmol) and AcOH (2 mL) were added. The vessel was sealed, and the reaction stirred at 160° C. 1 h. The reaction mixture was filtered and purified by preparative HPLC (100×30 mm Luna C18 column, flow rate 42 ml permin, gradient elution starting with A:B=80:20 and ending with A:B=0:100 [A=10% MeOH, 90% water, 0.1% TFA; B=90% MeOH, 10% water, 0.1% TFA] over 20 min). The HPLC fractions that contained the product were applied onto a cartridge of PHENOMENEX® Strata-X-C 33 um cation mixed-mode polymer. This was washed with methanol and the product was eluted with a 2N solution of ammonia in methanol. The solvents were removed and the product was converted to the HCl salt by adding a (1 eq) solution of 1N HCl in methanol. The solvents were removed to afford 10.00 mg of 8-(3-methoxyphenyl)-5H-pyrido[4,3-b]indole-6-carboxamide, HCl. MS (ESI) m/z 318.2 (M+H). ¹H NMR MeOD) d ppm 9.67 (1H, s), 8.86 (1H, d, J=1.53 Hz), 8.60 (1H, d, J=6.71 Hz), 8.49 (1H, d, J=1.53 Hz), 8.07 (1H, d, J=6.71 Hz), 7.37-7.51 (3H, m), 6.95-7.06 (1H, m), 3.93 (3H, s).

EXAMPLE 204

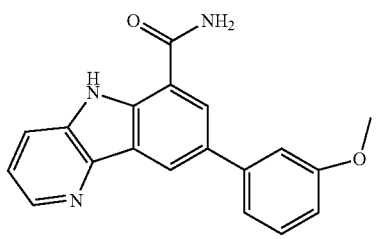 [SMILES: COc1cccc(-c2cc(C(N)=O)c3[nH]c4cccnc4c3c2)c1]

8-(3-Methoxyphenyl)-5H-pyrido[3,2-b]indole-6-carboxamide, HCl

204A. Preparation of 3'-methoxy-4-(pyridine-3-ylamino)biphenyl-3-carbonitrile

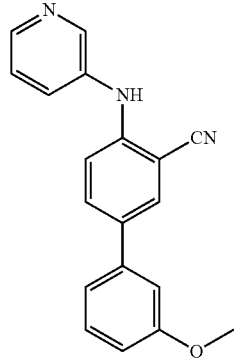 [SMILES: COc1cccc(-c2ccc(Nc3cccnc3)c(C#N)c2)c1]

To a solution of 4-fluoro-3'-methoxybiphenyl-3-carbonitrile (0.60 g, 2.64 mmol, Example 203A) in DMSO (4 mL) was added pyridine-3-amine (0.27 g, 2.90 mmol) and KOtBu (0.15 g, 1.38 mmol). The reaction stirred under nitrogen at room temperature 12 h. The reaction mixture was partitioned between water and ethyl acetate, the layers were separated, the organics were washed with water, brine solution, dried over $Na_2SO_4$ and concentrated to give the crude product. The crude material was purified by silica gel column chromatography (DCM/(2M)$NH_4$-MeOH=100/0–95/5) to afford 0.53 g of 3'-methoxy-4-(pyridine-3-ylamino)biphenyl-3-carbonitrile. MS (ESI) m/z 302.2 (M+H). $^1$H NMR (MeOD) d ppm 8.43 (1H, d, J=2.75 Hz), 8.19 (1H, dd, J=4.88, 1.22 Hz), 7.91 (1H, d, J=2.14 Hz), 7.81 (1H, dd, J=8.70, 2.29 Hz), 7.56-7.73 (1H, m), 7.32-7.47 (3H, m), 7.11-7.23 (2H, m), 6.94(1H, dd, J=8.24, 2.44 Hz), 3.87 (3H, s).

204. Preparation of 8-(3-methoxyphenyl)-5H-pyrido[3,2-b]indole-6-carboxamide, (prepared as the HCl salt)

To a 5 mL microwave vial 3'-methoxy-4-(pyridine-3-ylamino)biphenyl-3-carbonitrile (100.0 mg, 0.33 mmol), diacetoxypalladium (149.0 mg, 0.66 mmol) and AcOH (2 mL) were added. The vessel was sealed, and the reaction stirred at 160° C. 1 h. The reaction mixture was filtered and purified by preparative HPLC (100×30 mm Luna C18 column, flow rate 42 ml permin, gradient elution starting with A:B=80:20 and ending with A:B=0:100 [A=10% MeOH, 90% water, 0.1% TFA; B=90% MeOH, 10% water, 0.1% TFA] over 20 min). The HPLC fractions that contained the product were applied onto a cartridge of PHENOMENEX® Strata-X-C 33 um cation mixed-mode polymer. This was washed with methanol and the product was eluted with a 2N solution of ammonia in methanol. The solvents were removed and the product was converted to the HCl salt by adding a (1 eq) solution of 1N HCl in methanol. The solvents were removed to afford 12.00 mg of 8-(3-methoxyphenyl)-5H-pyrido[3,2-b]indole-6-carboxamide, carboxamide, HCl. MS (ESI) m/z 318.2 (M+H). $^1$H NMR (MeOD) d ppm 8.77-8.85 (3H, m), 8.62 (1H, d, J=1.83 Hz), 8.06 (1H, dd, J=8.24, 5.80 Hz), 7.48 (1H, t, J=7.93 Hz), 7.39-7.44 (2H, m), 7.04 (1H, dd, J=8.09, 1.68 Hz), 3.93 (3H, s).

EXAMPLE 205

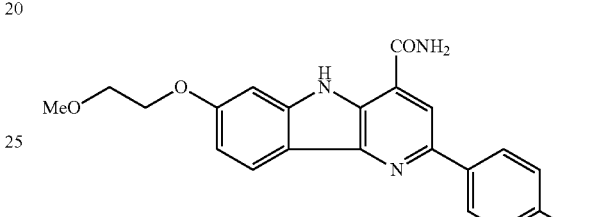

7-(2-Methoxyethoxy)-2-(4-methoxyphenyl)-5H-pyrido[3,2-b]indole-4-carboxamide

205A. Preparation of methyl 3-amino-2-(4-(benzyloxy)-phenyl)-6-bromoisonicotinate

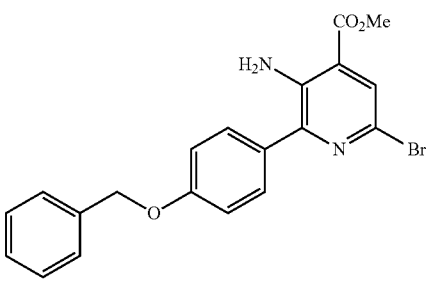 [SMILES: COC(=O)c1cc(Br)nc(-c2ccc(OCc3ccccc3)cc2)c1N]

A flask containing a mixture of methyl 3-amino-2,6-dibromoisonicotinate (1000 mg, 3.23 mmol), 4-(benzyloxy)phenylboronic acid (883 mg, 3.87 mmol), cesium fluoride (1176 mg, 7.74 mmol) and tetrakis(triphenylphosphine)-palladium (0) (224 mg, 0.194 mmol) was flushed with nitrogen. Dimethoxyethane (16 mL) was added and the reaction was heated at 80° C. for 18 hr. The reaction was then partitioned between EtOAc and water. The organic phase was separated, washed with brine, dried with sodium sulfate, and the solvent removed. Radial silica gel chromatography (step gradient elution with hexane containing 30 to 20% methylene chloride) afforded 1055 mg of methyl 3-amino-2-(4-(benzyloxy)-phenyl)-6-bromoisonicotinate as a yellow solid. MS (ESI) m/z 415.1 (M+H). $^1$H NMR (CDCl$_3$) δ ppm 7.77 (1H, s), 7.55

(2H, d, J=8.55 Hz), 7.31-7.46 (5H, m), 7.06 (2H, d, J=8.55 Hz), 5.95 (2H, br. s.), 5.12 (2H, s), 3.92 (3H, s).

205B. Preparation of methyl 3-amino-2-(4-(benzyloxy)phenyl)-6-(4-methoxyphenyl)-isonicotinate

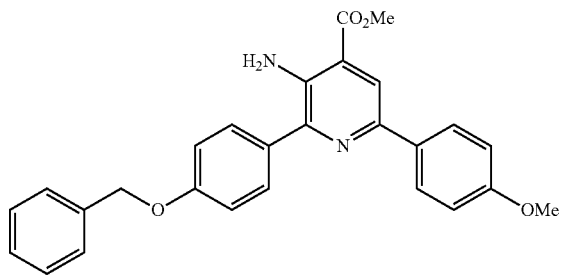 [SMILES: COC(=O)c1cc(-c2ccc(OC)cc2)nc(-c2ccc(OCc3ccccc3)cc2)c1N]

A flask containing dicyclohexyl(2',6'-dimethoxybiphenyl-2-yl)phosphine (132 mg, 0.322 mmol), methyl 3-amino-2-(4-(benzyloxy)phenyl)-6-bromoisonicotinate (665 mg, 1.61 mmol), 4-methoxyphenylboronic acid (293 mg, 1.93 mmol), palladium(II) acetate (36.1 mg, 0.161 mmol), and potassium phosphate tribasic (1025 mg, 4.83 mmol) was flushed with nitrogen. Tetrahydrofuran (16 mL) was added and the reaction was heated at reflux overnight. The reaction was partitioned between EtOAc and water. The organic phase was separated, washed with brine, dried with sodium sulfate and the solvent removed. Radial silica gel chromatography (step gradient elution with hexane containing 0 to 10% EtOAc) afforded 556 mg of methyl 3-amino-2-(4-(benzyloxy)phenyl)-6-(4-methoxyphenyl)-isonicotinate as a yellow oil. MS (ESI) m/z 441.2 (M+H). $^1$H NMR (CDCl$_3$) δ ppm 8.01 (1H, s), 7.92 (2H, d, J=8.85 Hz), 7.67 (2H, d, J=8.85 Hz), 7.44-7.48 (2H, m), 7.40 (2H, t, J=7.63 Hz), 7.35 (1H, d, J=7.32 Hz), 7.10 (2H, d, J=8.85 Hz), 6.94 (2H, d, J=8.85 Hz), 5.94 (2H, br. s.), 5.13 (2H, s), 3.95 (3H, s), 3.83 (3H, s).

205C. Preparation of methyl 3-azido-2-(4-hydroxyphenyl)-6-(4-methoxyphenyl)-isonicotinate and methyl 3-azido-2-(4-(benzyloxy)phenyl)-6-(4-methoxyphenyl)-isonicotinate

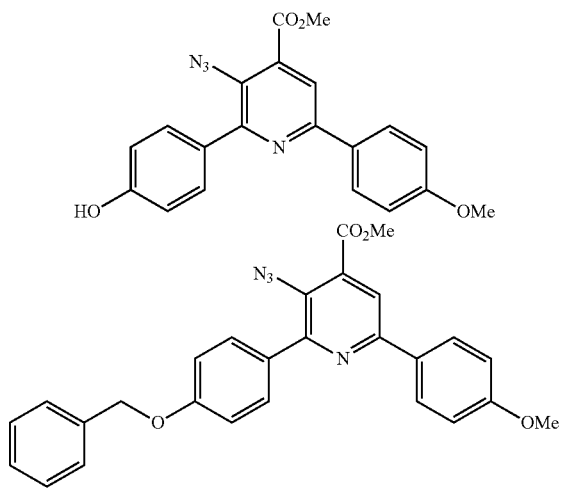

Methyl 3-amino-2-(4-(benzyloxy)phenyl)-6-(4-methoxyphenyl)-isonicotinate (556 mg, 1.262 mmol) was dissolved in trifluoroacetic acid (6 mL) and the yellow solution cooled in an ice bath. Solid sodium nitrite (174 mg, 2.52 mmol) was added with stirring to give a dark red mixture. After 30 min, solid sodium azide (821 mg, 12.6 mmol) was added followed by diethyl ether (6 mL). The light red mixture was stirred in the ice bath for 30 min. The reaction was concentrated on the rotary evaporator and was then partitioned between EtOAc and sufficient saturated aqueous NaHCO$_3$ solution (gas evolution) to neutralize the acid. The organic phase was separated, washed with brine, dried with sodium sulfate, and the solvent removed. Radial silica gel chromatography (step gradient elution with hexane containing 0 to 20% EtOAc) afforded the two major products as oils:

Methyl 3-azido-2-(4-(benzyloxy)phenyl)-6-(4-methoxyphenyl)isonicotinate (356 mg): MS (ESI) m/z 467.2 (M+H). $^1$H NMR (CDCl$_3$) δ ppm 8.00-8.06 (2H, m), 7.94 (1H, s), 7.81-7.86 (2H, m), 7.44-7.49 (2H, m), 7.37-7.43 (2H, m), 7.31-7.36 (1H, m), 7.08-7.13 (2H, m), 6.94-7.01 (2H, m), 5.15 (2H, s), 3.99-4.06 (3H, m), 4.03 (3H, s), 3.87 (3H, s);

Methyl 3-azido-2-(4-hydroxyphenyl)-6-(4-methoxyphenyl)isonicotinate (83 mg): MS (ESI) m/z 377.1 (M+H). $^1$H NMR (CDCl$_3$) δ ppm 8.01 (2H, d, J=8.85 Hz), 7.93 (1H, s), 7.76 (2H, d, J=8.55 Hz), 6.98 (2H, d, J=8.55 Hz), 6.93 (2H, d, J=8.24 Hz), 5.48 (1H, br. s.), 4.03 (3H, s), 3.86 (3H, s).

205D. Preparation of methyl 3-azido-2-(4-(2-methoxyethoxy)phenyl)-6-(4-methoxyphenyl)-isonicotinate

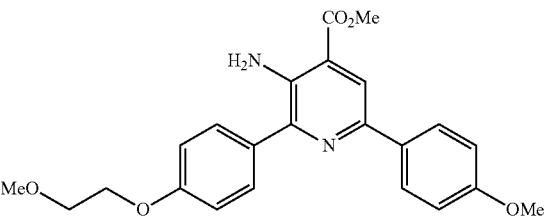 [SMILES: COCCOc1ccc(-c2nc(-c3ccc(OC)cc3)cc(C(=O)OC)c2N)cc1]

A mixture of methyl 3-azido-2-(4-hydroxyphenyl)-6-(4-methoxyphenyl)isonicotinate (83 mg, 0.221 mmol), cesium carbonate (359 mg, 1.10 mmol), and 2-bromoethyl methyl ether (0.062 mL, 0.662 mmol) in acetonitrile (1 mL) was heated at 75° C. for 5 hr. The reaction was partitioned between EtOAc and water. The organic phase was separated and washed with brine, dried with sodium sulfate and the solvent removed. Radial silica gel chromatography (step gradient elution with hexane containing 0 to 30% EtOAc) afforded 42 mg of methyl 3-azido-2-(4-(2-methoxyethoxy)phenyl)-6-(4-methoxyphenyl)isonicotinate as an oil. MS (ESI) m/z 435.1 (M+H). $^1$H NMR (CDCl$_3$) δ ppm 8.02 (2H, d, J=8.55 Hz), 7.93 (1H, s), 7.78-7.86 (2H, m), 7.05 (2H, d, J=8.85 Hz), 6.98 (2H, d, J=8.85 Hz), 4.16-4.24 (2H, m), 4.02 (3H, s), 3.85 (3H, s), 3.75-3.81 (2H, m), 3.47 (3H, s).

205E. Preparation of methyl 7-(2-methoxyethoxy)-2-(4-methoxyphenyl)-5H-pyrido[3,2-b]indole-4-carboxylate

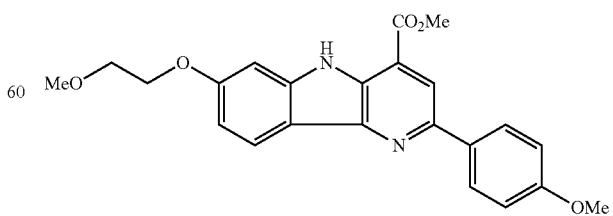

A solution of methyl 3-azido-2-(4-(2-methoxyethoxy)phenyl)-6-(4-methoxyphenyl)-isonicotinate (42 mg, 0.097 mmol) in 1,2-dichlorobenzene (2 mL) was heated at 160° C. for 10 min. The solvent was removed under a stream of nitrogen and the residue was purified by radial chromatography (step gradient elution with hexane containing 10 to 50% EtOAc) to give methyl 7-(2-methoxyethoxy)-2-(4-methoxyphenyl)-5H-pyrido[3,2-b]indole-4-carboxylate (28 mg) as a solid. MS (ESI) m/z 407.2 (M+H). $^1$H NMR (CDCl$_3$) δ ppm 9.38 (1H, s), 8.29 (1H, d, J=8.24 Hz), 8.13 (1H, s), 8.10 (2H, d, J=8.55 Hz), 7.03 (2H, d, J=8.55 Hz), 6.94-7.02 (2H, m), 4.19-4.28 (2H, m), 4.07 (3H, s), 3.88 (3H, s), 3.79-3.84 (2H, m), 3.49 (3H, s).

205. Preparation of 7-(2-methoxyethoxy)-2-(4-methoxyphenyl)-5H-pyrido[3,2-b]indole-4-carboxamide A suspension of methyl 7-(2-methoxyethoxy)-2-(4-methoxyphenyl)-5H-pyrido[3,2-b]indole-4-carboxylate (28 mg, 0.069 mmol) in 7 N ammonia in MeOH (3mL) in a sealed microwave vial was heated at 60° C. for 22 hr. The solvent was removed and the residue was purified by radial chromatography (step gradient elution with DCM containing 2 to 4% MeOH) to give 7-(2-methoxyethoxy)-2-(4-methoxyphenyl)-5H-pyrido[3,2-b]indole-4-carboxamide (20 mg). MS (ESI) m/z 392.1 (M+H). $^1$H NMR (MeOD) δ ppm 8.26 (1H, d, J=8.55 Hz), 8.07 (1H, s), 8.01-8.06 (2H, m), 7.16 (1H, d, J=2.14 Hz), 7.06-7.11 (2H, m), 6.94 (1H, d, J=8.55 Hz), 4.21-4.29(2H, m), 3.89(3H, s), 3.83 (2H, dd), 3.45-3.51 (3H, s).

EXAMPLE 206

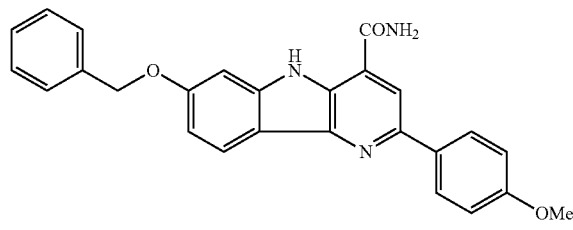 [SMILES: COc1ccc(-c2cc(C(N)=O)c3[nH]c4cc(OCc5ccccc5)ccc4c3n2)cc1]

7-(Benzyloxy)-2-(4-methoxyphenyl)-5H-pyrido[3,2-b]indole-4-carboxamide

A solution of methyl 3-azido-2-(4-(benzyloxy)phenyl)-6-(4-methoxyphenyl)isonicotinate (Example 205C, 356 mg, 0.763 mmol) in 1,2-dichlorobenzene (10 mL) was heated at 165° C. for 20 min. The solvent was removed under a stream of nitrogen to leave crude methyl 7-(benzyloxy)-2-(4-methoxyphenyl)-5H-pyrido[3,2-b]indole-4-carboxylate as a yellow solid: $^1$H NMR (CDCl$_3$) δ ppm 9.37 (1H, s), 8.29 (1H, d, J=8.85 Hz), 8.13 (1H, s), 8.07-8.12 (2H, m), 7.47-7.51 (2H, m), 7.38-7.44 (2H, m), 7.31-7.37 (1H, m), 7.00-7.05 (3H, m), 5.19 (2H, s), 4.07 (3H, s), 3.88 (3H, s). This was suspended in a solution of 7 N ammonia in methanol (12 mL) and heated in a sealed microwave vial at 60° C. for 36 hr. The solvent was removed and the residue was dissolved in methylene chloride. An equal volume of hexane was added and the precipitate was collected by filtration. This gave 160 mg of 7-(benzyloxy)-2-(4-methoxyphenyl)-5H-pyrido[3,2-b]indole-4-carboxamide as a yellow solid. MS (ESI) m/z 424.1 (M+H). $^1$H NMR (DMSO-d$_6$) δ ppm 11.38 (1H, s), 8.55 (1H, br. s.), 8.28 (1H, s), 8.23 (2H, d, J=8.85 Hz), 8.12 (1H, d, J=8.55 Hz), 7.83 (1H, br. s.), 7.49-7.57 (2H, m), 7.44 (2H, t, J=7.48 Hz), 7.31-7.40 (2H, m), 7.10 (2H, d, J=8.85 Hz), 6.97 (1H, dd, J=8.70, 2.29 Hz), 5.22 (2H, s), 3.85 (3H, s).

EXAMPLE 207

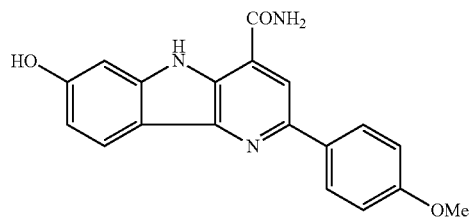 [SMILES: COc1ccc(-c2cc(C(N)=O)c3[nH]c4cc(O)ccc4c3n2)cc1]

7-Hydroxy-2-(4-methoxyphenyl)-5H-pyrido[3,2-b]indole-4-carboxamide

A mixture of 7-(benzyloxy)-2-(4-methoxyphenyl)-5H-pyrido[3,2-b]indole-4-carboxamide (Example 206, 155 mg, 0.366 mmol), 10% palladium on activated carbon (75 mg) and ammonium formate (115 mg, 1.83 mmol) was heated at reflux for 2 hr. Filtration followed by removal of the solvent form the filtrate. The residue was suspended in methylene chloride and filtration afforded 7-hydroxy-2-(4-methoxyphenyl)-5H-pyrido[3,2-b]indole-4-carboxamide (109 mg) as a yellow solid. MS (ESI) m/z 334.1 (M+H). $^1$H NMR (DMSO-d$_6$) δ ppm 11.23 (1H, br. s.), 9.75 (1H, br. s.), 8.52 (1H, br. s.), 8.17-8.26 (3H, m), 8.01 (1H, d, J=8.24 Hz), 7.79 (1H, br. s.), 7.04-7.13 (3H, m), 6.74 (1H, dd, J=8.39, 1.98 Hz), 3.85 (3H, s).

EXAMPLE 208

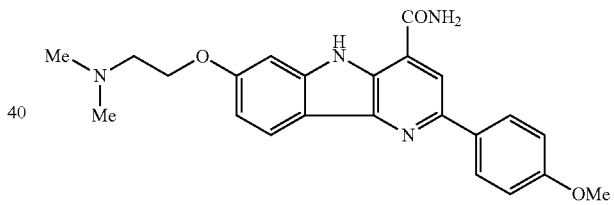

7-(2-(Dimethylamino)ethoxy)-2-(4-methoxyphenyl)-5H-pyrido[3,2-b]indole-4-carboxamide Diethyl azodicarboxylate (0.057 mL, 0.360 mmol) was added to an ice-cooled solution of triphenylphosphine (94 mg, 0.360 mmol) in dry THF (1 mL). The bath was removed and a solution of 7-hydroxy-2-(4-methoxyphenyl)-5H-pyrido[3,2-b]indole-4-carboxamide (Example 207, 60 mg, 0.180 mmol) and 2-(dimethylamino)ethanol (24 mg, 0.270 mmol) in dry THF (1 mL) was added after 15 minutes. After stirring for 2 hr at room temperature, the reaction was quenched with brine and extracted with EtOAc. The extracts were dried with sodium sulfate and the solvent was removed. Radial silica gel chromatography of the residue (step gradient elution with methylene chloride containing 10 to 60% methanol) followed by SCX cartridge purification gave 7-(2-(dimethylamino)ethoxy)-2-(4-methoxyphenyl)-5H-pyrido[3,2-b]indole-4-carboxamide (12 mg) as a yellow glass. MS (ESI) m/z 405.1 (M+H). $^1$H NMR (DMSO-d$_6$) δ ppm 11.34 (1H, br. s.), 8.56 (1H, s), 8.28 (1H, s), 8.23 (2H, d, J=8.85 Hz), 8.10 (1H, d, J=8.55 Hz), 7.83 (1H, s), 7.28 (1H, d, J=2.14 Hz), 7.10

(2H, d, J=8.85 Hz), 6.89 (1H, dd, J=8.55, 2.44 Hz), 4.15 (2H, t, J=5.95 Hz), 3.85 (3H, s), 2.70 (2H, t, J=5.80 Hz), 2.27 (6H, s).

EXAMPLE 209

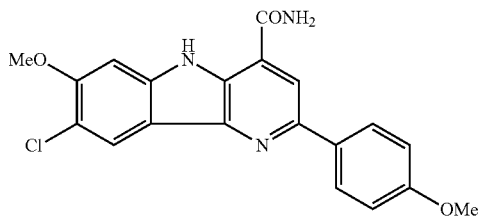

8-Chloro-7-methoxy-2-(4-methoxyphenyl)-5H-pyrido[3,2-b]indole-4-carboxamide

209A. Preparation of methyl 3-amino-6-bromo-2-(3-chloro-4-methoxyphenyl)-isonicotinate

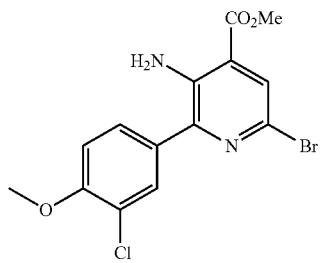 [SMILES: COC(=O)c1cc(Br)nc(-c2ccc(OC)c(Cl)c2)c1N]

A vial containing a mixture of methyl 3-amino-2,6-dibromoisonicotinate (500 mg, 1.613 mmol), 3-chloro-4-methoxyphenylboronic acid (301 mg, 1.613 mmol), cesium fluoride (588 mg, 3.87 mmol), and tetrakis(triphenylphosphine)palladium(0) (112 mg, 0.097 mmol) was flushed with nitrogen. Dimethoxyethane (8 mL) was added and the reaction was heated at 80° C. for 18 hr. It was then partitioned between EtOAc and water and the organic phase was separated, washed with brine, dried with sodium sulfate, and the solvent removed. Radial silica gel chromatography (step gradient elution with hexane containing 25 to 40% methylene chloride) afforded methyl 3-amino-6-bromo-2-(3-chloro-4-methoxyphenyl)isonicotinate (181 mg) as a yellow solid. MS (ESI) m/z 373.0 (M+H). $^1$H NMR (CDCl$_3$) δ ppm 7.79 (1H, s), 7.66 (1H, d, J=2.14 Hz), 7.52 (1H, dd, J=8.55, 2.14 Hz), 7.02 (1H, d, J=8.55 Hz), 5.94 (2H, br. s.), 3.95 (3H, s), 3.92 (3H, s).

209B. Preparation of methyl 3-azido-6-bromo-2-(3-chloro-4-methoxyphenyl)-isonicotinate

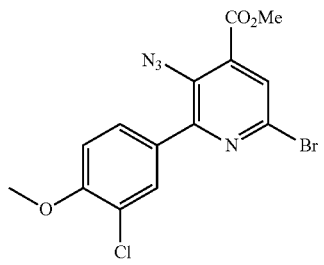 [SMILES: COC(=O)c1cc(Br)nc(-c2ccc(OC)c(Cl)c2)c1N=[N+]=[N-]]

Methyl 3-amino-6-bromo-2-(3-chloro-4-methoxyphenyl) isonicotinate (181 mg, 0.487 mmol) was dissolved in trifluoroacetic acid (2.4 mL) and cooled in an ice bath. Solid sodium nitrite (67 mg, 0.97 mmol) was added with stirring to give a dark red mixture. After 10 minutes, solid sodium azide (317 mg, 4.87 mmol) was added followed by diethyl ether (2.4 mL). This was stirred in the ice bath for 10 minutes and then partitioned between EtOAc and sufficient saturated aqueous NaHCO$_3$ solution (gas evolution) to neutralize the acid. The organic phase was separated, washed with brine, dried with sodium sulfate, and the solvent removed. The gave methyl 3-azido-6-bromo-2-(3-chloro-4-methoxyphenyl)isonicotinate (161 mg) as a yellow solid. MS (ESI) m/z 398.9 (M+H). $^1$H NMR (CDCl$_3$) δ ppm 7.85 (1H, d, J=2.14 Hz), 7.75 (1H, s), 7.71 (1H, dd, J=8.55, 2.14 Hz), 7.01 (1H, d, J=8.55 Hz), 4.01 (3H, s), 3.96 (3H, s).

209C. Preparation of methyl 2-bromo-8-chloro-7-methoxy-5H-pyrido[3,2-b]indole-4-carboxylate

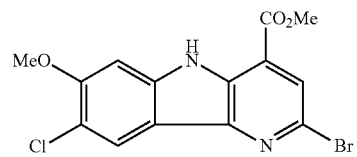 [SMILES: COC(=O)c1cc(Br)nc2c1[nH]c1cc(OC)c(Cl)cc12]

1,2-Dichloroethane (0.1 mL) was added to a mixture of methyl 3-azido-6-bromo-2-(3-chloro-4-methoxyphenyl) isonicotinate (56 mg, 0.14 mmol), rhodium octanoate dimer (11 mg, 0.014 mmol) and crushed 4 A° molecular sieves (56 mg) in a microwave vial. The vial was sealed and heated at 60° C. overnight. The reaction was diluted with dichloromethane, filtered, and the solvents removed from the filtrate. Radial silica gel chromatography (step gradient with hexane containing 50 to 100% methylene chloride) of the residue afforded methyl 2-bromo-8-chloro-7-methoxy-5H-pyrido[3,2-b]indole-4-carboxylate (29 mg). MS (ESI) m/z 370.9 (M+H). $^1$H NMR (CDCl$_3$) δ ppm 9.51 (1H, br. s.), 8.31 (1H, s), 7.89 (1H, s), 6.99 (1H, s), 4.05 (3H, s), 4.01 (3H, s).

209D. Preparation of methyl 8-chloro-7-methoxy-2-(4-methoxyphenyl)-5H-pyrido[3,2-b]indole-4-carboxylate

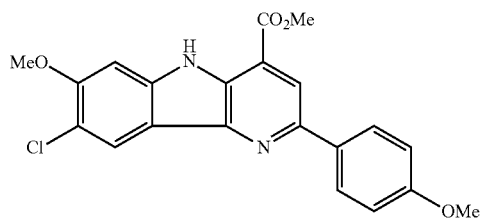 [SMILES: COC(=O)c1cc(-c2ccc(OC)cc2)nc2c1[nH]c1cc(OC)c(Cl)cc12]

A vial containing dicyclohexyl(2',6'-dimethoxybiphenyl-2-yl)phosphine (6 mg, 0.015 mmol), 4-methoxyphenylboronic acid (14 mg, 0.093 mmol), methyl 2-bromo-8-chloro-7-methoxy-5H-pyrido[3,2-b]indole-4-carboxylate (29 mg, 0.077 mmol), palladium(II) acetate (1.7 mg, 7.7 μmol), and potassium phosphate tribasic (49.1 mg, 0.231 mmol) was flushed with nitrogen. Tetrahydrofuran (1 mL) was added and the reaction was heated at 80° C. overnight. The reaction was partitioned between EtOAc and water. The organic phase was separated, washed with brine, dried with sodium sulfate, and the solvents removed. Radial silica gel chromatography (elution with DCM) afforded methyl 8-chloro-7-methoxy-2-(4-methoxyphenyl)-5H-pyrido[3,2-b]indole-4-carboxylate (29 mg). MS (ESI) m/z 397.0 (M+H). $^1$H NMR (CDCl$_3$) δ ppm 9.31 (1H, s), 8.31 (1H, s), 8.00-8.12 (3H, m), 6.99-7.07 (2H, m), 6.90 (1H, s), 4.03 (3H, s), 3.96 (3H, s), 3.88 (3H, s).

209E. Preparation of 8-chloro-7-methoxy-2-(4-methoxyphenyl)-5H-pyrido[3,2-b]indole-4-carboxamide

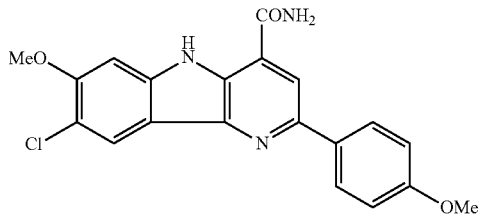 [SMILES: COc1ccc(-c2cc(C(N)=O)c3[nH]c4cc(OC)c(Cl)cc4c3n2)cc1]

A suspension of methyl 8-chloro-7-methoxy-2-(4-methoxyphenyl)-5H-pyrido[3,2-b]indole-4-carboxylate (29 mg, 0.073 mmol) in a 7 N solution of ammonia in MeOH (7 mL) in a sealed microwave vial was heated at 80° C. for 24 hr. The solvents were removed and preparative HPLC (100×30 mm Luna C18 column, gradient elution with A:B=30:70 to A:B=0:100 [A=10 mM NH₄OAc in 5% aqueous CH₃CN; B=10 mM NH₄OAc in 95% aqueous CH₃CN] over 20 min) afforded 8-chloro-7-methoxy-2-(4-methoxyphenyl)-5H-pyrido[3,2-b]indole-4-carboxamide (16 mg) as a yellow solid. MS (ESI) m/z 380.1 (M+H). $^1$H NMR (MeOD) δ ppm 8.36 (1H, s), 8.13 (1H, s), 8.06 (2H, d, J=8.85 Hz), 7.31 (1H, s), 7.10 (2H, d, J=8.85 Hz), 4.03 (3H, s), 3.90 (3H, s).

EXAMPLE 210

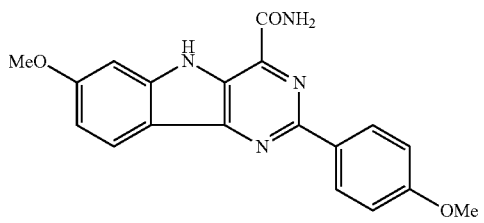 [SMILES: COc1ccc(-c2nc(C(N)=O)c3[nH]c4cc(OC)ccc4c3n2)cc1]

7-Methoxy-2-(4-methoxyphenyl)-5H-pyrimido[5,4-b]indole-4-carboxamide

210A. Preparation of methyl 2,6-dihydroxy-5-nitropyrimidine-4-carboxylate

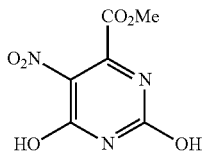

Potassium 2,6-dihydroxy-5-nitropyrimidine-4-carboxylate (25 gm, 105 mmol) was dissolved in MeOH (75 mL) and sulphuric acid (21 mL) was added dropwise. The reaction was heated at reflux overnight. After cooling to room temperature, the precipitate was collected by filtration, washed with water, and dried to give methyl 2,6-dihydroxy-5-nitropyrimidine-4-carboxylate (17.1 g) as a white solid. $^1$H NMR (DMSO-d₆) δ ppm 12.04 (2H, br. s.), 3.90 (3H, s).

210B. Preparation of methyl 2,6-dichloro-5-nitropyrimidine-4-carboxylate

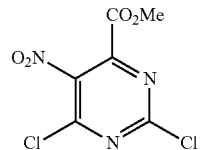 [SMILES: COC(=O)c1nc(Cl)nc(Cl)c1[N+](=O)[O-]]

N,N-Diethylaniline (13 mL, 82 mmol) was added with stirring to a mixture of methyl 2,6-dihydroxy-5-nitropyrimidine-4-carboxylate (10 gm, 47 mmol) in phosphorous oxychloride (40 mL). This heated at reflux for 20 minutes and then the excess phosphorous oxychloride was removed under vacuum. The dark oily residue was poured into a mixture of ice and water with stirring and the mixture was extracted with ethyl acetate. The organic phase was separated, washed twice with 0.5 N HCl solution, saturated aqueous NaHCO₃ solution, brine, dried over sodium sulfate and the solvent removed. This gave methyl 2,6-dichloro-5-nitropyrimidine-4-carboxylate (9.5 gm) as a brown solid. $^1$H NMR (CDCl₃) δ ppm 4.02 (3H, s).

210C. Preparation of methyl 5-amino-2,6-dichloropyrimidine-4-carboxylate

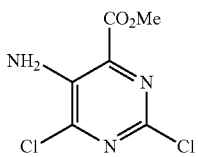

A mixture of methyl 2,6-dichloro-5-nitropyrimidine-4-carboxylate (5 gm, 20 mmol) and powdered iron (5 gm) in acetic acid (40 mL) was heated at 60° C. There was a vigorous exotherm within 5 minutes and the reaction was allowed to cool to room temperature. The acetic acid was removed and the residue was suspended in a mixture of water and diethyl ether. This was filtered and the solid was washed with diethyl ether. The organic phase was separated, washed with saturated aqueous NaHCO₃ solution (twice) and brine, dried over sodium sulfate, and the solvent removed to leave methyl 5-amino-2,6-dichloropyrimidine-4-carboxylate (2.1 gm) as a yellow brown solid. MS (ESI) m/z 222.0 and 224.0 (M+H). $^1$H NMR (CDCl₃) δ ppm 6.20 (2H, br. s.), 3.99 (3H, s).

210D. Preparation of methyl 5-amino-2,6-bis(4-methoxyphenyl)pyrimidine-4-carboxylate

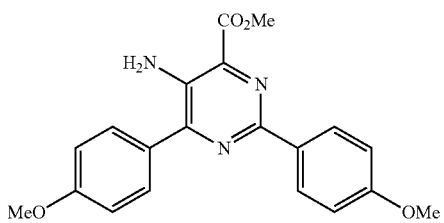

Mixture of 4-methoxyphenylboronic acid (616 mg, 4.05 mmol), methyl 5-amino-2,6-dichloropyrimidine-4-carboxylate (300 mg, 1.35 mmol), powdered potassium phosphate tribasic (1291 mg, 6.08 mmol), 2-dicyclohexylphosphino-2', 4',6'-triisopropylbiphenyl (161 mg, 0.338 mmol), and palladium(II) acetate (30 mg, 0.14 mmol) in a microwave vial was flushed with nitrogen. Tetrahydrofuran (4 mL) was added, the vial was sealed, and the reaction was heated at 80° C. overnight. The reaction was partitioned between water and ethyl acetate. The organic phase was separated, washed with brine, dried over sodium sulfate and the solvents removed. Radial silica gel chromatography (step gradient elution with hexane containing 50 to 100% methylene chloride) afforded methyl 5-amino-2,6-bis(4-methoxyphenyl)pyrimidine-4-carboxylate (393 mg) as a yellow foam. MS (ESI) m/z 366.1 (M+H). $^1$H NMR (CDCl$_3$) δ ppm 8.27-8.37 (2H, m), 7.71-7.83 (2H, m), 7.01-7.12 (2H, m), 6.86-7.01 (2H, m), 5.93 (2H, br. s.), 4.02 (3H, s), 3.89 (3H, s), 3.85 (3H, s).

210E. Preparation of methyl 5-azido-2,6-bis(4-methoxyphenyl)pyrimidine-4-carboxylate

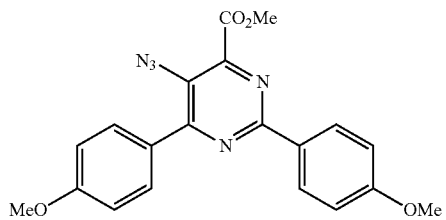 [SMILES: COC(=O)c1nc(-c2ccc(OC)cc2)nc(-c2ccc(OC)cc2)c1N=[N+]=[N-]]

Methyl 5-amino-2,6-bis(4-methoxyphenyl)pyrimidine-4-carboxylate (393 mg, 1.08 mmol) was dissolved in trifluoroacetic acid (5 mL) and the yellow solution was cooled in an ice bath. Solid sodium nitrite (148 mg, 2.15 mmol) was added with stirring to give a dark red mixture. After 10 minutes, solid sodium azide (699 mg, 10.8 mmol) was added followed by diethyl ether (5 mL). After and additional 20 minutes the reaction was partitioned between EtOAc and sufficient saturated aqueous NaHCO$_3$ solution (gas evolution) to neutralize the acid. The organic phase was separated, washed with brine, dried with sodium sulfate, and the solvent removed to leave methyl 5-azido-2,6-bis(4-methoxyphenyl)pyrimidine-4-carboxylate (350 mg) as a solid. $^1$H NMR (CDCl$_3$) δ ppm 8.42 (2H, d, J=9.16 Hz), 8.02 (2H, d, J=9.16 Hz), 7.03 (2H, d, J=8.85 Hz), 6.96 (2H, d, J=9.16 Hz), 4.07 (3H, s), 3.88 (3H, s), 3.85 (3H, s).

210F. Preparation of methyl 7-methoxy-2-(4-methoxyphenyl)-5H-pyrimido[5,4-b]-indole-4-carboxylate

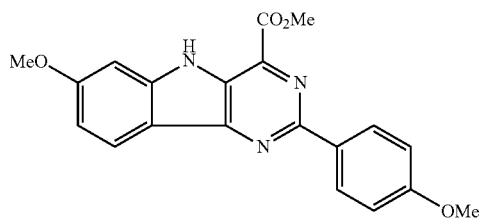 [SMILES: COC(=O)c1nc(-c2ccc(OC)cc2)nc2c1[nH]c1cc(OC)ccc12]

1,2-Dichloroethane (0.25 mL) was added to a mixture of methyl 5-azido-2,6-bis(4-methoxyphenyl)pyrimidine-4-carboxylate (154 mg, 0.393 mmol), rhodium octanoate dimer (31 mg, 0.039 mmol) and crushed 4 A° molecular sieves (154 mg) in a microwave vial. The vial was sealed and heated at 60° C. overnight. This was diluted with mixture of dichloromethane and EtOAc (9:1), filtered, and the solvent removed from the filtrate. Radial silica chromatography (step gradient elution with methylene chloride containing 0 to 5% EtOAc) afforded methyl 7-methoxy-2-(4-methoxyphenyl)-5H-pyrimido[5,4-b]indole-4-carboxylate (100 mg) as a yellow solid. MS (ESI) m/z 364.0 (M+H). $^1$H NMR (DMSO-d$_6$) δ ppm 11.68 (1H, s), 8.48 (2H, d, J=8.85 Hz), 8.23 (1H, d, J=8.85 Hz), 7.24 (1H, d, J=2.14 Hz), 7.11 (2H, d, J=8.85 Hz), 6.99 (1H, dd, J=8.85, 2.14 Hz), 4.09 (3H, s), 3.93 (3H, s), 3.86 (3H, s).

Preparation of 7-methoxy-2-(4-methoxyphenyl)-5H-pyrimido[5,4-b]indole-4-carboxamide A suspension of methyl 7-methoxy-2-(4-methoxyphenyl)-5H-pyrimido[5,4-b]indole-4-carboxylate (97 mg, 0.27 mmol) in a 7 N solution of ammonia in MeOH (10 mL) in a sealed microwave vial was heated at 80° C. overnight. The solvent was removed and the residue was suspended in EtOAc. Filtration gave 7-methoxy-2-(4-methoxyphenyl)-5H-pyrimido[5,4-b]indole-4-carboxamide (58 mg) as a yellow solid. MS (ESI) m/z 349.0 (M+H). $^1$H NMR (DMSO-d$_6$) δ ppm 11.68 (1H, br. s.), 8.59-8.73 (3H, m), 8.20 (1H, d, J=8.85 Hz), 8.05 (1H, s), 7.29 (1H, d, J=2.14 Hz), 7.08 (2H, d, J=8.85 Hz), 6.96 (1H, dd, J=8.70, 2.29 Hz), 3.90 (3H, s), 3.87 (3H, s).

EXAMPLE 211

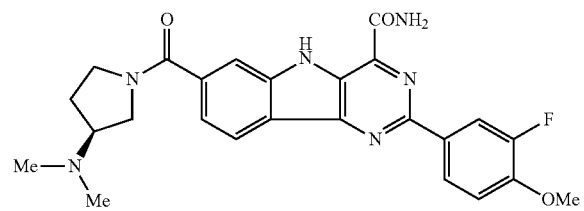 [SMILES: COc1ccc(-c2nc(C(N)=O)c3[nH]c4cc(C(=O)N5CC[C@H](N(C)C)C5)ccc4c3n2)cc1F]

(S)-7-(3-(Dimethylamino)pyrrolidine-1-carbonyl)-2-(3-fluoro-4-methoxyphenyl)-5H-pyrido[3,2-b]indole-4-carboxamide 211A. Preparation of methyl 3-amino-6-bromo-2-(4-(methoxycarbonyl)phenyl)-isonicotinate

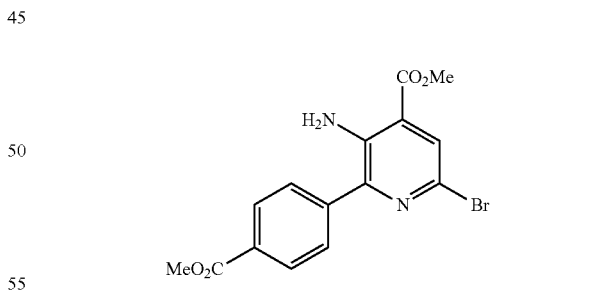

A mixture of methyl 3-amino-2,6-dibromoisonicotinate (5.00 g, 16.1 mmol), 4-methoxycarbonylphenylboronic acid (2.90 gm, 16.1 mmol), and tetrakis-(triphenylphosphine)palladium(0) (0.932 g, 0.807 mmol) in a flask was flushed with nitrogen. Toluene (70 mL), MeOH (14 mL), and a 2 N aqueous solution of sodium carbonate (18 mL, 37 mmol) were added and the reaction was heated in a 120° C. oil bath for 4 hr. The reaction mixture was partitioned between EtOAc and saturated aqueous sodium bicarbonate solution. The organic phase was separated, washed with saturated aqueous sodium bicarbonate, and brine. It was dried with sodium sulfate and the solvents removed. Flash silica gel chromatography (elution with hexane containing 10% EtOAc) afforded methyl 3-amino-6-bromo-2-(4-(methoxycarbonyl)phenyl)isonicotinate (2.0 gm). MS (ESI) m/z 365.0 and 367.0 (M+H). $^1$H NMR (CDCl$_3$) δ ppm 8.15 (2H, d, J=8.24 Hz), 7.84 (1H, s), 7.71 (2H, d, J=8.24 Hz), 5.94 (2H, br. s.), 3.94 (6H, d, J=5.19 Hz).

211B. Preparation of methyl 3-amino-6-(3-fluoro-4-methoxyphenyl)-2-(4-(methoxycarbonyl)phenyl)-isonicotinate

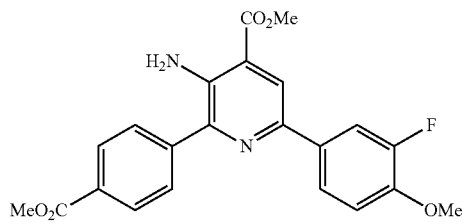 [SMILES: COC(=O)c1ccc(-c2nc(-c3ccc(OC)c(F)c3)cc(C(=O)OC)c2N)cc1]

A mixture of methyl 3-amino-6-bromo-2-(4-(methoxycarbonyl)phenyl)-isonicotinate (2.00 g, 5.48 mmol), 3-fluoro-4-methoxyphenylboronic acid (0.931 g, 5.48 mmol), and tetrakis(triphenylphosphine)palladium(0) (0.316 g, 0.274 mmol) in a flask was flushed with nitrogen. Toluene (25 mL), MeOH (5 mL) and a 2 N aqueous solution of sodium carbonate (6.2 mL, 12.4 mmol) was added and the reaction was heated in a 125° C. oil bath for 2 hr. The reaction was partitioned between EtOAc and a saturated aqueous solution of sodium bicarbonate. The organic phase was separated and washed with a saturated aqueous solution of sodium bicarbonate and brine. It was dried with sodium sulfate and the solvents removed. Flash silica gel chromatography (elution with hexane containing 10% EtOAc) afforded methyl 3-amino-6-(3-fluoro-4-methoxyphenyl)-2-(4-(methoxycarbonyl)phenyl)isonicotinate (1.8 g). MS (ESI) m/z 411.2 (M+H). $^1$H NMR (CDCl$_3$) δ ppm 8.18 (2H, d, J=8.24 Hz), 8.06 (1H, s), 7.81 (2H, d, J=8.24 Hz), 7.74 (1H, dd, J=12.97, 1.98 Hz), 7.68 (1H, d, J=8.85 Hz), 6.99 (1H, t, J=8.70 Hz), 5.98 (2H, br. s.), 3.97 (3H, s), 3.96 (3H, s), 3.92 (3H, s).

211C. Preparation of methyl 3-azido-6-(3-fluoro-4-methoxyphenyl)-2-(4-(methoxycarbonyl)phenyl) isonicotinate

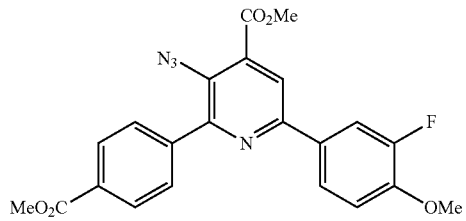 [SMILES: COC(=O)c1ccc(-c2nc(-c3ccc(OC)c(F)c3)cc(C(=O)OC)c2N=[N+]=[N-])cc1]

Methyl 3-amino-6-(3-fluoro-4-methoxyphenyl)-2-(4-(methoxycarbonyl)phenyl)-isonicotinate (1.00 g, 2.44 mmol) was dissolved in trifluoroacetic acid (12 mL) and the yellow solution was cooled in an ice bath. Powdered sodium nitrite (0.336 gm, 4.87 mmol) was added with stirring to give a dark red mixture. After 30 min, powdered sodium azide (1.59 g, 24.4 mmol) was added followed by diethyl ether (12 mL). The light red mixture was stirred in the ice bath for 30 min. The reaction was partitioned between EtOAc and sufficient saturated aqueous NaHCO$_3$ solution (gas evolution) to neutralize the acid. The organic phase was washed with brine, dried with sodium sulfate, and the solvent removed. Flash silica gel chromatography (elution with a 1:1 mixture of methylene chloride and EtOAc) afforded methyl 3-azido-6-(3-fluoro-4-methoxyphenyl)-2-(4-(methoxycarbonyl)phenyl)isonicotinate (1.06 gm). $^1$H NMR (CDCl$_3$) δ ppm 8.17 (2H, d, J=7.93 Hz), 8.01 (1H, s), 7.91 (2H, d, J=7.93 Hz), 7.82-7.88 (1H, m), 7.79 (1H, d, J=8.55 Hz), 7.04 (1H, t, J=8.55 Hz), 4.05 (3H, s), 3.96 (3H, s), 3.94 (3H, s).

211C. Preparation of dimethyl 2-(3-fluoro-4-methoxyphenyl)-5H-pyrido[3,2-b]indole-4,7-dicarboxylate

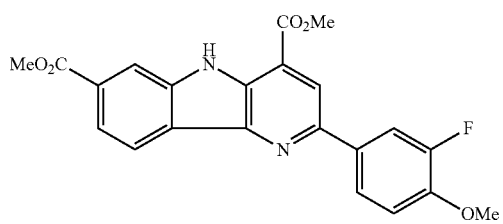 [SMILES: COC(=O)c1ccc2c(c1)[nH]c1c(C(=O)OC)cc(-c3ccc(OC)c(F)c3)nc12]

A solution of methyl 3-azido-6-(3-fluoro-4-methoxyphenyl)-2-(4-(methoxycarbonyl)phenyl)isonicotinate (1.06 g, 2.43 mmol) in 1,2-dichlorobenzene (30 mL) was heated under reflux for 5 minutes. Removal of the solvent followed by flash silica gel chromatography (elution with hexane containing 15% EtOAc) afforded dimethyl 2-(3-fluoro-4-methoxyphenyl)-5H-pyrido[3,2-b]indole-4,7-dicarboxylate (0.77 gm). MS (ESI) m/z 409.1 (M+H). $^1$H NMR (DMSO-d$_6$) δ ppm 11.86 (1H, br. s.), 8.29-8.47 (3H, m), 8.11 (1H, dd, J=13.12, 2.14 Hz), 7.97-8.06 (1H, m), 7.92(1H, d, J=8.24 Hz), 7.32 (1H, t, J=8.85 Hz), 4.09 (3H, s), 3.95 (3H, s), 3.94 (3H, s).

211D. Preparation of methyl 4-carbamoyl-2-(3-fluoro-4-methoxyphenyl)-5H-pyrido[3,2-b]indole-7-carboxylate

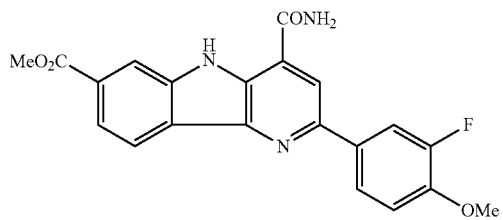 [SMILES: COC(=O)c1ccc2c(c1)[nH]c1c(C(N)=O)cc(-c3ccc(OC)c(F)c3)nc12]

A solution of dimethyl 2-(3-fluoro-4-methoxyphenyl)-5H-pyrido[3,2-b]indole-4,7-dicarboxylate (612 mg, 1.50 mmol) in a mixture of tetrahydrofuran (24 ml), MeOH (8 ml) and 1 N aqueous sodium hydroxide (2.4 ml, 2.4 mmol) was stirred at room temperature for 30 minutes and then neutralized with 1 N aqueous HCl. The organic solvents were removed on the rotary evaporator and the residue was dissolved in water and acidified to about pH 3 with 1 N aqueous HCl. This was chilled in an ice bath and the precipitate was collected by filtration and dried. LC/MS indicated that the major component of this was 2-(3-fluoro-4-methoxyphenyl)-7-(methoxycarbonyl)-5H-pyrido[3,2-b]indole-4-carboxylic acid [MS (ESI) m/z 395.0 (M+H); retention time 2.75 min; Xbridge S10 4.6×50 mm column; flow rate=4 mL/min; gradient from 0% B to 100% B over 3 min; Solvent A=0.1% TFA/95% water/5% methanol, Solvent B=0.1% TFA/5% water 95% methanol]. Dimethylformamide (5 mL) was added to a mixture of a portion of this material (400 mg, about 1.01 mmol), ammonium chloride (0.163 gm, 3.04 mmol), 1-(3-dimethylaminopropyl)-3-ethylcarbodimide hydrochloride (0.583 g, 3.04 mmol), and 1-hydroxybenzotriazole hydrate (0.411 g, 3.04 mmol). After stirring for a few minutes, triethylamine (0.42 mL, 3.0 mmol) was added and the reaction was left stirring overnight. It was diluted with EtOAc, washed with water and dried with sodium sulfate. The solvent was removed and the residue was suspended in warm (40° C.) methylene chloride for 10 minutes and then filtered to gave methyl 4-carbamoyl-2-(3-fluoro-4-methoxyphenyl)-5H-pyrido[3,2-b]indole-7-carboxylate (0.35 g) as a yellow solid. $^1$H NMR (DMSO-d$_6$) δ ppm 11.90 (1H, s), 8.64 (1H, br. s.), 8.51 (1H, s), 8.44 (1H, s), 8.39 (1H, d, J=8.24 Hz), 8.09-8.22 (2H, m), 7.97 (1H, br. s.), 7.89 (1H, d, J=8.24 Hz), 7.36 (1H, t, J=8.70 Hz), 3.95 (3H, s), 3.93 (3H, s).

211E. Preparation of 4-carbamoyl-2-(3-fluoro-4-methoxyphenyl)-5H-pyrido[3,2-b]indole-7-carboxylic acid

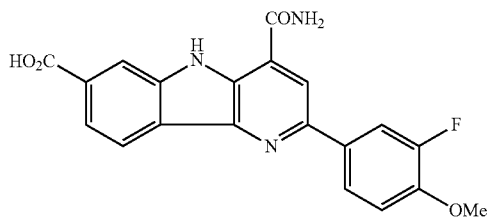 [SMILES: COc1ccc(-c2cc(C(N)=O)c3[nH]c4cc(C(=O)O)ccc4c3n2)cc1F]

A solution of methyl 4-carbamoyl-2-(3-fluoro-4-methoxyphenyl)-5H-pyrido[3,2-b]indole-7-carboxylate (75 mg, 0.19 mmol) in a mixture of THF (3 ml), MeOH (1 ml) and 1 N aqueous sodium hydroxide (3.0 ml, 3.0 mmol) was stirred at room temperature for 24 hr. This was neutralized with 1 N aqueous HCl and the organic solvents were removed on the rotary evaporator. The residue was dissolved in water and acidified to about pH 3 with 1 N aqueous HCl. The mixture was chilled in an ice bath and the precipitate was collected by filtration and dried to give 4-carbamoyl-2-(3-fluoro-4-methoxyphenyl)-5H-pyrido[3,2-b]indole-7-carboxylic acid (70 mg) as a yellow solid. MS (ESI) m/z 380.0 (M+H). $^1$H NMR (DMSO-d$_6$) δ ppm 11.87 (1H, s), 8.64 (1H, br. s.), 8.50 (1H, s), 8.41 (1H, s), 8.36 (1H, d, J=7.93 Hz), 8.11-8.21 (2H, m), 7.96(1H, br. s.), 7.87 (1H, d, J=8.24 Hz), 7.36 (1H, t, J=8.85 Hz), 3.95 (3H, s).

Preparation of (S)-7-(3-(dimethylamino)pyrrolidine-1-carbonyl)-2-(3-fluoro-4-methoxyphenyl)-5H-pyrido[3,2-b]indole-4-carboxamide

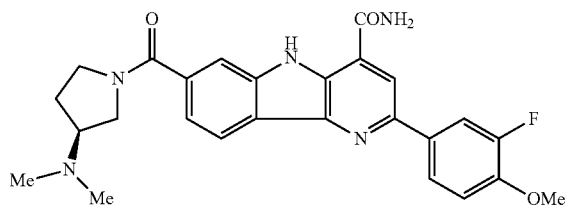 [SMILES: COc1ccc(-c2cc(C(N)=O)c3[nH]c4cc(C(=O)N5CC[C@H](N(C)C)C5)ccc4c3n2)cc1F]

Dimethylformamide (5 mL) was added to a mixture of 4-carbamoyl-2-(3-fluoro-4-methoxyphenyl)-5H-pyrido[3,2-b]indole-7-carboxylic acid (70 mg, 0.19 mmol), (3S)-(+3-(dimethylamino)pyrrolidine (0.070 mL, 0.55 mmol), 1-(3-dimethylaminopropyl)-3-ethylcarbodiimide hydrochloride (106 mg, 0.554 mmol), and 1-hydroxybenzotriazole hydrate (75 mg, 0.55 mmol). After stirring for a few minutes, triethylamine (0.077 mL, 0.55 mmol) was added and the reaction was left stirring overnight. It was diluted with EtOAc, washed with water, dried with sodium sulfate and the solvent was removed. The residue was suspended in DCM at 40° C. for 10 min and then filtered to gave (S)-7-(3-(dimethylamino)pyrrolidine-1-carbonyl)-2-(3-fluoro-4-methoxyphenyl)-5H-pyrido[3,2-b]indole-4-carboxamide (40 mg) as a yellow solid.

MS (ESI) m/z 476.2 (M+H). $^1$H NMR (DMSO-d$_6$) δ ppm 11.71 (1H, br. s.), 8.62 (1H, br. s.), 8.47 (1H, s), 8.30 (1H, dd, J=7.48, 4.43 Hz), 8.09-8.21 (2H, m), 7.92 (2H, m), 7.42 (1H, m), 7.36 (1H, m), 3.95 (3H, s), 3.64-3.82 (1H, m), 3.47-3.63 (2H, m), 3.36 (1H, m), 2.61-2.83 (1H, m), 2.22 (3H, s), 2.11 (3H, s), 2.03 (1 H, br. s.), 1.68-1.85 (1H, m).

EXAMPLE 212

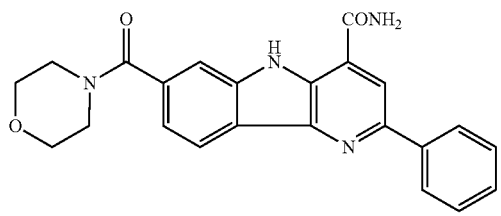 [SMILES: NC(=O)c1cc(-c2ccccc2)nc2c1[nH]c1cc(C(=O)N3CCOCC3)ccc12]

7-(Morpholine-4-carbonyl)-2-phenyl-5H-pyrido[3,2-b]indole-4-carboxamide

212A. Preparation of (4-iodophenyl)(morpholino)methanone

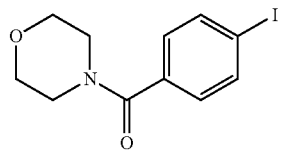 [SMILES: O=C(c1ccc(I)cc1)N1CCOCC1]

1-(3-Dimethylaminopropyl)-3-ethylcarbodimide hydrochloride (12.1 g, 62.9 mmol), 1-hydroxybenzotriazole hydrate (9.63 g, 62.9 mmol), and morpholine (9.13 g, 105 mmol) was added to a solution of 4-iodobenzoic acid (13 g, 52.4 mmol) in a mixture of THF (250 mL) and methylene chloride (50 mL). After stirred at 25° C. for 20 hr, the solvent was removed and flash silica gel chromatography (step gradient elution with methylene chloride containing 0 to 3% MeOH) afforded (4-iodophenyl)(morpholino)-methanone (15.1 g). MS (ESI) m/z 317.9 (M+H). $^1$H NMR (CDCl$_3$) δ ppm 7.76 (2H, d, J=8.24 Hz), 7.14 (2H, d, J=8.24 Hz), 3.23-4.00 (8H, m).

212B. Preparation of 4-(morpholine-4-carbonyl)phenylboronic acid

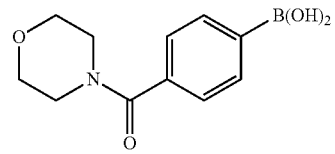 [SMILES: O=C(c1ccc(B(O)O)cc1)N1CCOCC1]

Isopropylmagnesium chloride (27.8 mL, 2 M in THF, 55.6 mmol) was added to a solution of bis(2-dimethylaminoethyl) ether (10.5 mL, 55.6 mmol) in THF (230 mL) 15° C. After 20 minutes, (4-iodophenyl)-(morpholino)methanone (14.7 g, 46.4 mmol) was added and the reaction was removed from the cooling bath. After 1 hr, another 0.8 eq of isopropylmagnesium chloride was added. Trimethyl borate (10.6, 93 mmol) was added after 15 minutes, and after stirring 40 min, the reaction was quenched with 150 ml 1 N aqueous HCl. After stirring at room temperature for 2 hr, THF was removed on the rotary evaporator and the residue was extracted three times with EtOAc. The organic extracts were dried with Na$_2$SO$_4$. The solvent was removed and the residue was twice suspended in toluene and the solvent removed on the rotary evaporator. The resulting white solid was suspended in hexane and this was heated at reflux for 5 minutes. After cooling to room temperature, the white solid was collected by filtration and air-dried to afford 4-(morpholine-4-carbonyl)phenylboronic acid (8.7 g). MS (ESI) m/z 236.1 (M+H). ¹H NMR (MeOD) δ ppm 7.78 (2H, d, J=7.30 Hz), 7.36 (2H, d, J=8.06 Hz), 3.72-3.41 (8H, m).

212C. Preparation of methyl 3-amino-6-bromo-2-(4-(morpholine-4-carbonyl)phenyl)-isonicotinate

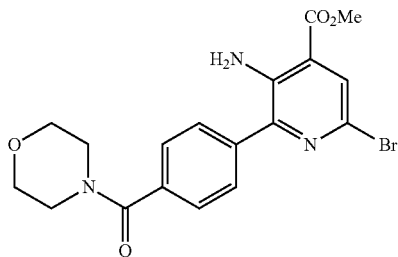 [SMILES: COC(=O)c1cc(Br)nc(-c2ccc(C(=O)N3CCOCC3)cc2)c1N]

A mixture of methyl 3-amino-2,6-dibromoisonicotinate (11.4 g, 36.6 mmol), 4-(morpholine-4-carbonyl)phenylboronic acid (8.7 g, 33.3 mmol), and powdered sodium carbonate (8.12 g, 77 mmol) in a mixture of toluene (90 mL) and methanol (30 mL) was degassed and then backfilled with nitrogen twice. Tetrakis(triphenylphosphine)-palladium(0) (1.93 g, 1.67 mmol) was added and the reaction was degassed and backfilled with nitrogen. After stirred in a 110° C. oil bath for 64 hr, the reaction was cooled and then partitioned between EtOAc and saturated aqueous sodium bicarbonate. The organic phase was separated and washed with saturated aqueous sodium bicarbonate, brine, and then dried over sodium sulfate and the solvents removed. The residue was suspended in EtOAc and the solid was collected by filtration and washed with EtOAc to give methyl 3-amino-6-bromo-2-(4-(morpholine-4-carbonyl)phenyl)-isonicotinate (3.29 gm, 24%). Flash silica gel chromatography of the filtrate (step gradient elution with hexane containing 10 to 20% EtOAc and then methylene chloride containing 1 to 4% MeOH) gave additional 4.63 g (33%) of pure product and 2.2 g of material that contained 65% of the product according to LC/MS. MS (ESI) m/z 418 and 420 (M−H). ¹H NMR (CDCl₃) δ ppm 7.83 (1H, s), 7.68 (2H, d, J=8.24 Hz), 7.52 (2H, d, J=7.93 Hz), 5.93 (2H, br. s.), 3.92 (3H, s), 3.78 (4H, br. s.), 3.62 (2H, br. s.), 3.46 (2H, br. s.).

212D. Preparation of methyl 3-azido-6-bromo-2-(4-(morpholine-4-carbonyl)phenyl)-isonicotinate

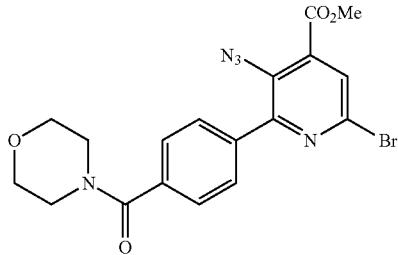 [SMILES: COC(=O)c1cc(Br)nc(-c2ccc(C(=O)N3CCOCC3)cc2)c1N=[N+]=[N-]]

Methyl 3-amino-6-bromo-2-(4-(morpholine-4-carbonyl)phenyl)isonicotinate (2.00 gm, 4.76 mmol) was dissolved in trifluoroacetic acid (26 mL) and the yellow solution was cooled in an ice-bath. Powdered sodium nitrite (0.657 gm, 9.52 mmol) was added with stirring to give a dark red mixture. After 30 minutes, powdered sodium azide (3.09 gm, 47.6 mmol) was added followed by diethyl ether (26 mL). The light red mixture was stirred in the ice-bath for 30 minutes. The reaction was partitioned between EtOAc and sufficient saturated aqueous NaHCO₃ solution (gas evolution) to neutralize the acid. The organic phase was washed with brine, dried over sodium sulfate, and concentrated to about 50 mL on the rotary evaporator. The resulting solid was collected by filtration and washed three times with EtOAc to give methyl 3-azido-6-bromo-2-(4-(morpholine-4-carbonyl)phenyl) isonicotinate (5.86 gm, 72% yield). Removal of the solvent from the filtrate followed by flash silica gel chromatography (step gradient elution with methylene chloride containing 0 to 2% MeOH) afforded another 1.58 gm of product. MS (ESI) m/z 446 and 448 (M+H). ¹H NMR (CDCl₃) δ ppm 7.82-7.80 (3H, m), 7.49-7.53 (2H, m), 4.02 (3H, s), 3.69-3.88 (4H, m), 3.57-3.70 (2H, m), 3.40-3.53 (2H, m).

212E. Preparation of methyl 2-bromo-7-(morpholine-4-carbonyl)-5H-pyrido[3,2-b]indole-4-carboxylate

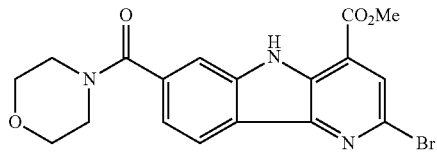 [SMILES: COC(=O)c1cc(Br)nc2c1[nH]c1cc(C(=O)N3CCOCC3)ccc12]

A solution of methyl 3-azido-6-bromo-2-(4-(morpholine-4-carbonyl)phenyl)-isonicotinate (7.2 g, 16.1 mmol) in 1,2-dichlorobenzene (115 mL) was placed in a 180° C. oil bath and stirred for 10 minutes. The solvent was removed, the residue suspended in methylene chloride, and the solid collected by filtration. This was resuspended in methylene chloride and filtered to afford methyl 2-bromo-7-(morpholine-4-carbonyl)-5H-pyrido[3,2-b]indole-4-carboxylate (3.02 gm, 45% yield). Removal of the solvent from filtrate followed by flash silica gel chromatography (step gradient elution with methylene chloride containing 0 to 3% MeOH) afforded another 1.02 gm (15% yield) of product. MS (ESI) m/z 416 and 418 (M+H). ¹H NMR (MeOD) δ ppm 8.39 (1H, d, J=7.94 Hz), 8.08 (1H, s), 7.78 (1H, s), 7.41 (1H, d, J=7.93 Hz), 4.12 (3H, s), 3.61-3.95 (6H, m), 3.46-3.61 (2H, m).

212F. Preparation of methyl 7-(morpholine-4-carbonyl)-2-phenyl-5H-pyrido[3,2-b]indole-4-carboxylate

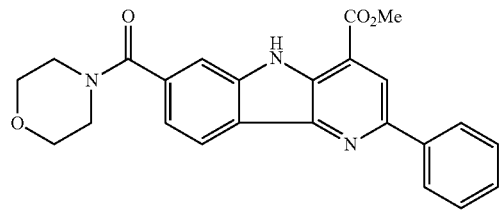 [SMILES: NC(=O)c1cc(-c2ccccc2)nc2c1[nH]c1cc(C(=O)N3CCOCC3)ccc12]

A mixture of phenylboronic acid (92 mg, 0.75 mmol), methyl 2-bromo-7-(morpholine-4-carbonyl)-5H-pyrido[3,2-b]indole-4-carboxylate (150 mg, 0.359 mmol), finely powdered potassium phosphate tribasic (183 mg, 0.861 mmol), 2-dicyclohexylphosphino-2',4',6'-triisopropylbiphenyl (56.8 mg, 0.119 mmol), and palladium(II) acetate (11 mg, 0.047 mmol) in a vial was flushed with nitrogen. Tetrahydrofuran (3 mL) was added and the reaction was heated at 80° C. overnight. It was partitioned between water and methylene chloride. The organic phase was separated, washed with brine, and dried over sodium sulfate. Removal of the solvents followed by radial silica gel chromatography (step gradient elution with methylene chloride containing 0 to 2% MeOH) afforded methyl 7-(morpholine-4-carbonyl)-2-phenyl-5H-pyrido[3,2-b]indole-4-carboxylate (112 mg) as a solid. MS (ESI) m/z 416.1 (M+H). $^1$H NMR (CDCl$_3$) δ ppm 9.82 (1H, s), 8.40 (1H, d, J=7.93 Hz), 8.25 (1H, s), 8.12 (2H, d, J=7.63 Hz), 7.60 (1H, s), 7.48 (2H, t, J=7.63 Hz), 7.36-7.42 (1H, m), 7.32 (1H, d, J=7.93 Hz), 4.03 (3H, s), 3.38-3.95 (8H, m).

212G. Preparation of 7-(morpholine-4-carbonyl)-2-phenyl-5H-pyrido[3,2-b]indole-4-carboxamide

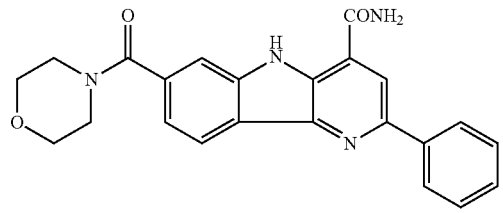

A mixture of methyl 7-(morpholine-4-carbonyl)-2-phenyl-5H-pyrido[3,2-b]indole-4-carboxylate (112 mg, 0.270 mmol) in a 7 N solution of ammonia in MeOH (3 mL) in a sealed microwave tube was heated in an oil bath at 70° C. for 3 days. The solid was collected by filtration and washed with MeOH to give 7-(-(morpholine-4-carbonyl)-2-phenyl-5H-pyrido[3,2-b]indole-4-carboxamide (73 mg, 68% yield). The solvent was removed from the filtrate and preparative HPLC of the residue (100×30 mm Luna C18 column; flow rate=42 mL/min; gradient elution from 15 to 100% B over 20 minutes; Solvent A=10 mM NH$_4$OAc in 95% water:5% acetonitrile; B=10 mM NH$_4$OAc in 5% water:95% acetonitrile) afforded another 9 mg of product. MS (ESI) m/z 401.1 (M+H). $^1$H NMR (DMSO-d$_6$) δ ppm 11.75 (1H, br. s.), 8.66 (1H, br. s.), 8.51 (1H, s), 8.28-8.35 (3H, m), 7.93 (1H, br. s.), 7.82 (1H, s), 7.52-7.60 (2H, m), 7.45 (1H, t, J=6.71 Hz), 7.32 (1H, dd, J=8.09, 1.37 Hz), 3.35-3.88 (8H, m).

The compounds listed in Table 11 were synthesized using procedures similar to that described for Example 212.

TABLE 11

| Ex. # | Structure | Name | Retention time (min) | MS (ESI) m/z (M + H) |
|---|---|---|---|---|
| 213 | 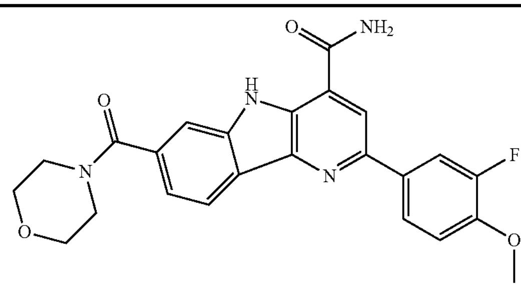 | 2-(3-fluoro-4-methoxyphenyl)-7-(4-morpholinylcarbonyl)-5H-pyrido[3,2-b]indole-4-carboxamide | 1.98* | 449.1 |
| 214 | 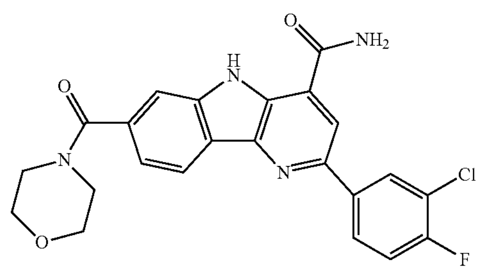 [SMILES: NC(=O)c1cc(-c2ccc(F)c(Cl)c2)nc2c1[nH]c1cc(C(=O)N3CCOCC3)ccc12] | 2-(3-chloro-4-fluorophenyl)-7-(4-morpholinylcarbonyl)-5H-pyrido[3,2-b]indole-4-carboxamide | 1.56** | 453.1 |
| 215 | 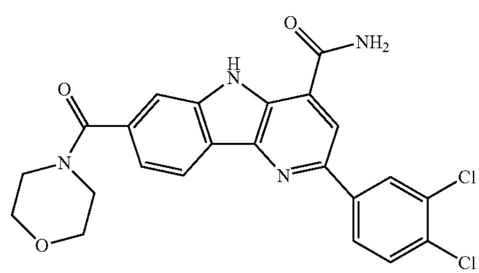 [SMILES: NC(=O)c1cc(-c2ccc(Cl)c(Cl)c2)nc2c1[nH]c1cc(C(=O)N3CCOCC3)ccc12] | 2-(3,4-dichlorophenyl)-7-(morpholine-4-carbonyl)-5H-pyrido[3,2-b]indole-4-carboxamide | 1.72** | 469.0 |
| 216 | 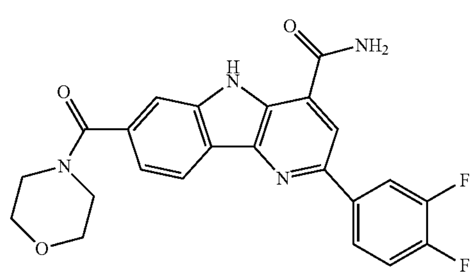 [SMILES: NC(=O)c1cc(-c2ccc(F)c(F)c2)nc2c1[nH]c1cc(C(=O)N3CCOCC3)ccc12] | 2-(3,4-difluorophenyl)-7-(4-morpholinylcarbonyl)-5H-pyrido[3,2-b]indole-4-carboxamide | 3.85* | 437.1 |

TABLE 11-continued

| Ex. # | Structure | Name | Retention time (min) | MS (ESI) m/z (M + H) |
|---|---|---|---|---|
| 217 | 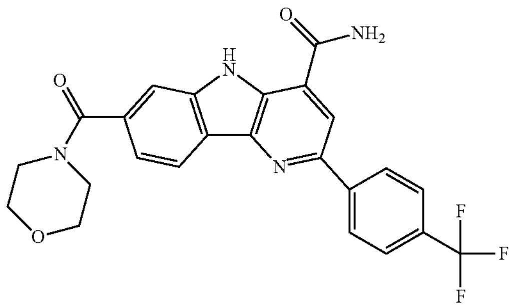 [SMILES: NC(=O)c1cc(-c2ccc(C(F)(F)F)cc2)nc2c1[nH]c1cc(C(=O)N3CCOCC3)ccc12] | 7-(4-morpholinylcarbonyl)-2-(4-(trifluoromethyl)phenyl)-5H-pyrido[3,2-b]indole-4-carboxamide | 2.39* | 469.1 |
| 218 | 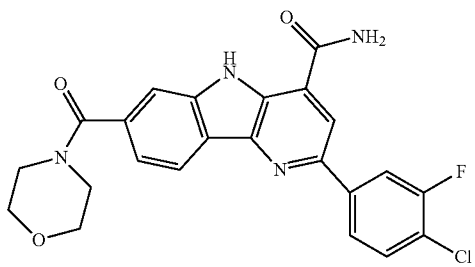 [SMILES: NC(=O)c1cc(-c2ccc(Cl)c(F)c2)nc2c1[nH]c1cc(C(=O)N3CCOCC3)ccc12] | 2-(4-chloro-3-fluorophenyl)-7-(4-morpholinylcarbonyl)-5H-pyrido[3,2-b]indole-4-carboxamide | 2.79* | 453.0 |
| 219 | 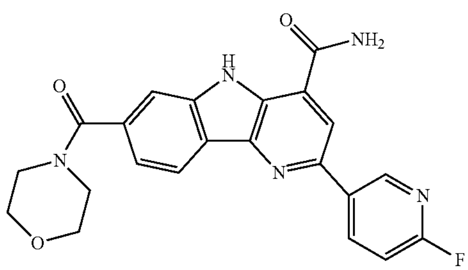 [SMILES: NC(=O)c1cc(-c2ccc(F)nc2)nc2c1[nH]c1cc(C(=O)N3CCOCC3)ccc12] | 2-(6-fluoropyridin-3-yl)-8-(morpholine-4-carbonyl)-5H-pyrido[3,2-b]indole-4-carboxamide | 1.17** | 420.1 |
| 220 | 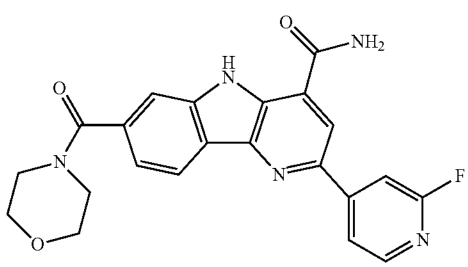 [SMILES: NC(=O)c1cc(-c2ccnc(F)c2)nc2c1[nH]c1cc(C(=O)N3CCOCC3)ccc12] | 2-(2-fluoro-4-pyridinyl)-7-(4-morpholinylcarbonyl)-5H-pyrido[3,2-b]indole-4-carboxamide | 1.21** | 420.1 |
| 221 | 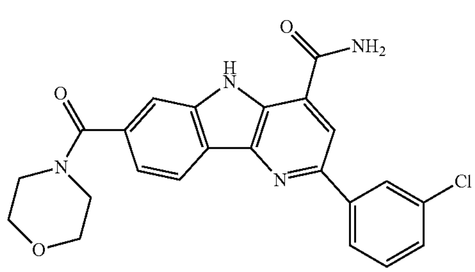 [SMILES: NC(=O)c1cc(-c2cccc(Cl)c2)nc2c1[nH]c1cc(C(=O)N3CCOCC3)ccc12] | 2-(3-chlorophenyl)-7-(4-morpholinylcarbonyl)-5H-pyrido[3,2-b]indole-4-carboxamide | 1.52** | 435.1 |

TABLE 11-continued

| Ex. # | Structure | Name | Retention time (min) | MS (ESI) m/z (M + H) |
|---|---|---|---|---|
| 222 | 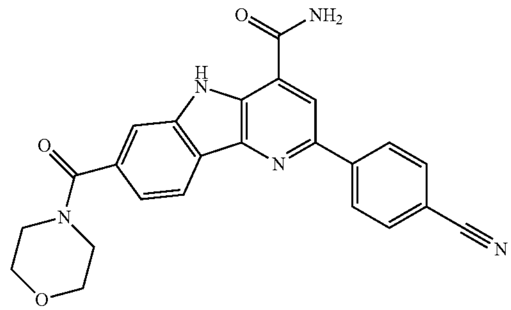 [SMILES: N#Cc1ccc(-c2cc(C(N)=O)c3[nH]c4cc(C(=O)N5CCOCC5)ccc4c3n2)cc1] | 2-(4-cyanophenyl)-7-(4-morpholinylcarbonyl)-5H-pyrido[3,2-b]indole-4-carboxamide | 1.31** | 426.1 |
| 223 | 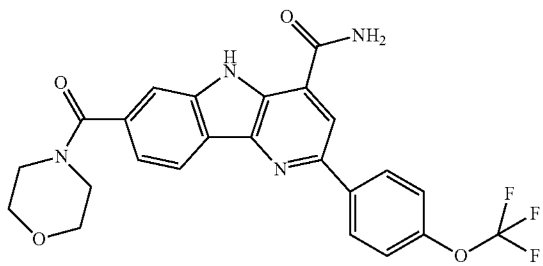 [SMILES: NC(=O)c1cc(-c2ccc(OC(F)(F)F)cc2)nc2c1[nH]c1cc(C(=O)N3CCOCC3)ccc12] | 7-(4-morpholinylcarbonyl)-2-(4-(trifluoromethoxy)phenyl)-5H-pyrido[3,2-b]indole-4-carboxamide | 1.64** | 485.0 |
| 224 | 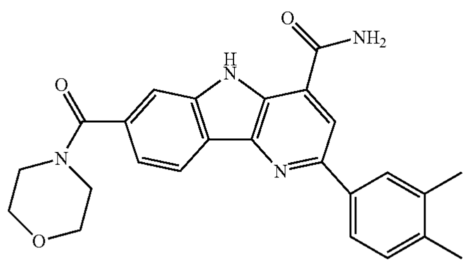 [SMILES: Cc1ccc(-c2cc(C(N)=O)c3[nH]c4cc(C(=O)N5CCOCC5)ccc4c3n2)cc1C] | 2-(3,4-dimethylphenyl)-7-(4-morpholinylcarbonyl)-5H-pyrido[3,2-b]indole-4-carboxamide | 1.51** | 429.1 |
| 225 | 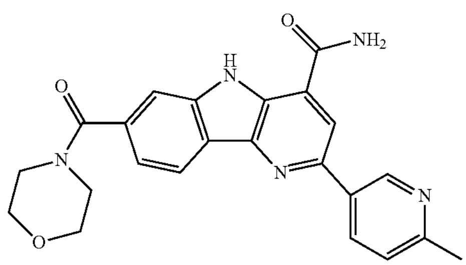 [SMILES: Cc1ccc(-c2cc(C(N)=O)c3[nH]c4cc(C(=O)N5CCOCC5)ccc4c3n2)cn1] | 2-(6-methyl-3-pyridinyl)-7-(4-morpholinylcarbonyl)-5H-pyrido[3,2-b]indole-4-carboxamide | 1.15** | 416.2 |
| 226 | 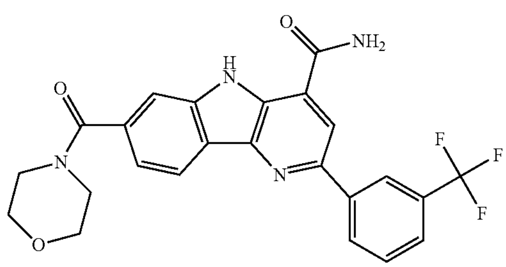 [SMILES: NC(=O)c1cc(-c2cccc(C(F)(F)F)c2)nc2c1[nH]c1cc(C(=O)N3CCOCC3)ccc12] | 7-(4-morpholinylcarbonyl)-2-(3-(trifluoromethyl)phenyl)-5H-pyrido[3,2-b]indole-4-carboxamide | 1.22** | 469.1 |

TABLE 11-continued

| Ex. # | Structure | Name | Retention time (min) | MS (ESI) m/z (M + H) |
|---|---|---|---|---|
| 227 | 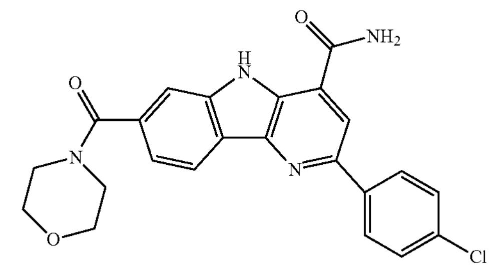 [SMILES: NC(=O)c1cc(-c2ccc(Cl)cc2)nc2c1[nH]c1cc(C(=O)N3CCOCC3)ccc12] | 2-(4-chlorophenyl)-7-(4-morpholinylcarbonyl)-5H-pyrido[3,2-b]indole-4-carboxamide | 1.53** | 435.1 |
| 228 | 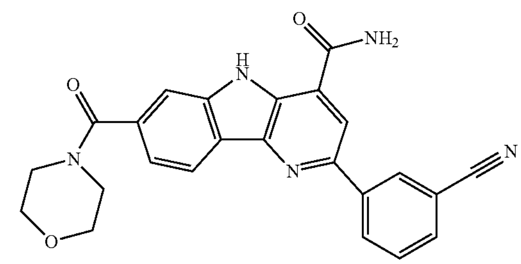 [SMILES: N#Cc1cccc(-c2cc(C(N)=O)c3[nH]c4cc(C(=O)N5CCOCC5)ccc4c3n2)c1] | 2-(3-cyanophenyl)-7-(4-morpholinylcarbonyl)-5H-pyrido[3,2-b]indole-4-carboxamide | 1.35** | 426.1 |
| 229 | 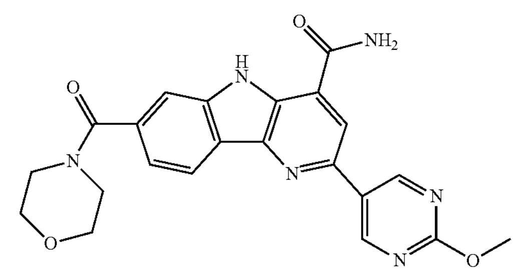 [SMILES: COc1ncc(-c2cc(C(N)=O)c3[nH]c4cc(C(=O)N5CCOCC5)ccc4c3n2)cn1] | 2-(2-methoxy-5-pyrimidinyl)-7-(4-morpholinylcarbonyl)-5H-pyrido[3,2-b]indole-4-carboxamide | 1.09** | 433.2 |
| 230 | 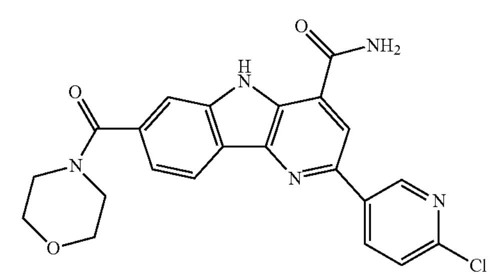 [SMILES: NC(=O)c1cc(-c2ccc(Cl)nc2)nc2c1[nH]c1cc(C(=O)N3CCOCC3)ccc12] | 2-(6-chloro-3-pyridinyl)-7-(4-morpholinylcarbonyl)-5H-pyrido[3,2-b]indole-4-carboxamide | 1.27** | 436.1 |
| 231 | 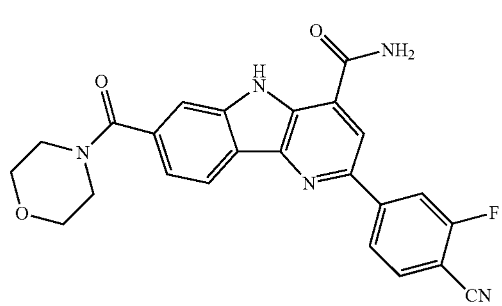 [SMILES: N#Cc1ccc(-c2cc(C(N)=O)c3[nH]c4cc(C(=O)N5CCOCC5)ccc4c3n2)cc1F] | 2-(4-cyano-3-fluorophenyl)-7-(morpholine-4-carbonyl)-5H-pyrido[3,2-b]indole-4-carboxamidecarboxamide | 1.43** | 444.1 |

TABLE 11-continued

| Ex. # | Structure | Name | Retention time (min) | MS (ESI) m/z (M + H) |
|---|---|---|---|---|
| 232 | 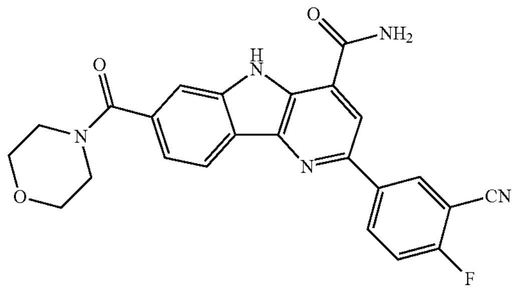 [SMILES: N#Cc1cc(-c2cc(C(N)=O)c3[nH]c4cc(C(=O)N5CCOCC5)ccc4c3n2)ccc1F] | 2-(3-cyano-4-fluorophenyl)-7-(morpholine-4-carbonyl)-5H-pyrido[3,2-b]indole-4-carboxamide | 1.44* | 444.1 |
| 233 | 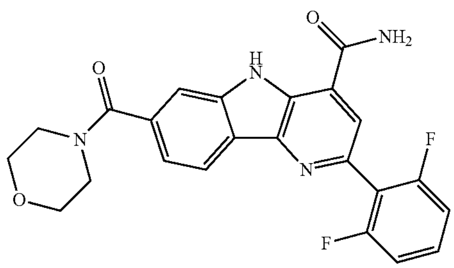 [SMILES: NC(=O)c1cc(-c2c(F)cccc2F)nc2c1[nH]c1cc(C(=O)N3CCOCC3)ccc12] | 2-(2,6-difluorophenyl)-7-(morpholine-4-carbonyl)-5H-pyrido[3,2-b]indole-4-carboxamide | 1.70* | 437.06 |
| 234 | 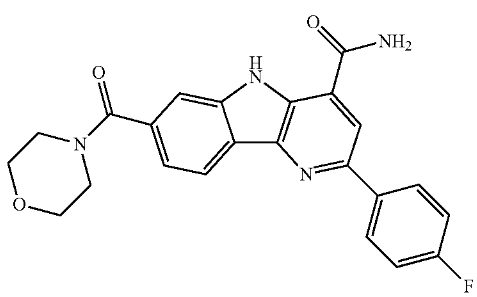 [SMILES: NC(=O)c1cc(-c2ccc(F)cc2)nc2c1[nH]c1cc(C(=O)N3CCOCC3)ccc12] | 2-(4-fluorophenyl)-7-(morpholine-4-carbonyl)-5H-pyrido[3,2-b]indole-4-carboxamide | 1.37** | 419.1 |
| 235 | 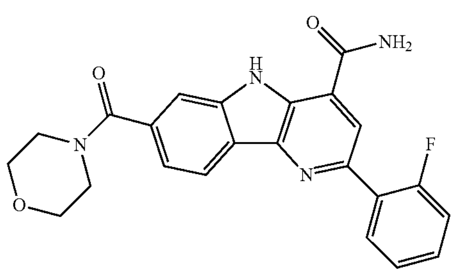 [SMILES: NC(=O)c1cc(-c2ccccc2F)nc2c1[nH]c1cc(C(=O)N3CCOCC3)ccc12] | 2-(2-fluorophenyl)-7-(morpholine-4-carbonyl)-5H-pyrido[3,2-b]indole-4-carboxamidecarboxamide | 1.81* | 419.09 |
| 236 | 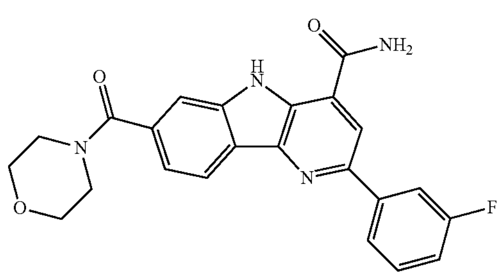 [SMILES: NC(=O)c1cc(-c2cccc(F)c2)nc2c1[nH]c1cc(C(=O)N3CCOCC3)ccc12] | 2-(3-fluorophenyl)-7-(morpholine-4-carbonyl)-5H-pyrido[3,2-b]indole-4-carboxamide | 1.40** | 419.0 |

TABLE 11-continued

| Ex. # | Structure | Name | Retention time (min) | MS (ESI) m/z (M + H) |
|---|---|---|---|---|
| 237 | 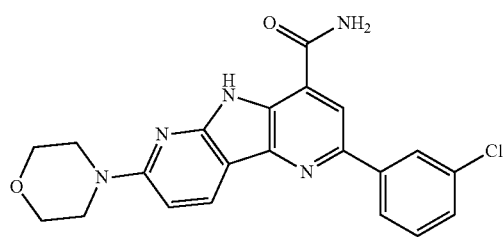 [SMILES: NC(=O)c1cc(-c2cccc(Cl)c2)nc2c1[nH]c1nc(N3CCOCC3)ccc12] | 2-(2-chlorophenyl)-7-(morpholine-4-carbonyl)-5H-pyrido[3,2-b]indole-4-carboxamide | 1.29** | 434.8 |

HPLC conditions: Schimadzu HPLC with:
*PHENOMENEX ® Luna S10 3.0 × 50 mm column; Flow rate: 4 ml/min; Gradient: 0 to 100% B over 3 min; Solvent: A = 5:95 Methanol:Water;
B = 95:5 Methanol:Water; Modifier = 0.1% trifluoroacetic acid.
**PHENOMENEX ® Luna C18 3.0 × 50 mm column; Flow rate: 5 ml/min; Gradient: 0 to 100% B over 3 min; Solvent: A = 5:95 Acetonitrile:Water;
B = 95:5 Acetonitrile:Water; Modifier = 10 mM NH₄OAc.

EXAMPLE 238

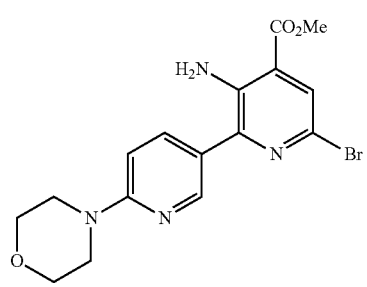 [SMILES: COC(=O)c1cc(Br)nc(-c2ccc(N3CCOCC3)nc2)c1N]

2-(3-Chlorophenyl)-7-(4-morpholinyl)-5H-pyrido[2',3':4,5]pyrrolo[2,3-b]pyridine-4-carboxamide

238A. Preparation of methyl 3-amino-6-bromo-6'-morpholino-2,3'-bipyridine-4-carboxylate

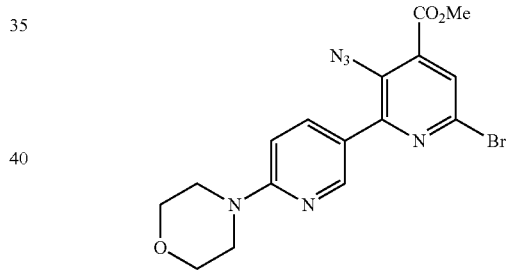

A mixture of 4-(5-(4,4,5,5-tetramethyl-1,3,2-dioxaborolan-2-yl)pyridin-2-yl)morpholine (400 mg, 1.379 mmol), methyl 3-amino-2,6-dibromoisonicotinate (427 mg, 1.379 mmol), tetra(triphenylphospine)palladium(0) (159 mg, 0.138 mmol), K₂CO₃ (762 mg, 5.51 mmol) in a microwave vial was flushed with nitrogen and DMF (4.0 mL) was added. The vial was sealed heated at 100° C. overnight. The reaction was diluted with EtOAc and water to give a precipitate. This was collected by filtration, washed with water and EtOAc to leave methyl 3-amino-6-bromo-6'-morpholino-2,3'-bipyridine-4-carboxylate (232 mg, 0.590 mmol, 42.8% yield) as a light green solid. $^1$H NMR (400 MHz, chloroform-d) δ ppm 8.49 (1H, d, J=1.76 Hz), 7.70-7.82 (2H, m), 6.71 (1H, d, J=8.81 Hz), 5.93 (2H, br. s.), 3.91 (3H, s), 3.76-3.86 (4H, m), 3.46-3.63 (4H, m).

238B. Preparation of methyl 3-azido-6-bromo-6'-morpholino-2,3'-bipyridine-4-carboxylate Methyl 3-amino-6-bromo-6'-morpholino-2,3'-bipyridine-4-carboxylate (230 mg, 0.59 mmol) was dissolved in TFA (2.9 mL) and the solution was cooled in an ice bath. Solid sodium nitrite (89 mg, 1.29 mmol) was added slowly with stirring to give a red solution. After 30 min, powdered sodium azide (380 mg, 5.85 mmol) was added in portions with gas evolution. Et₂O (29 mL) was added with stirring after 0.5 hr, water was added and the mixture was extracted with EtOAc. The combined organic extracts were washed with, water (3×), saturated Na₂CO₃ solution (until the aqueous phase was basic), and brine (1×). After drying the solvent with sodium sulfate, the solvent was removed. Flash chromatography (step gradient elution with DCM containing 0 to 20% EtOAc) afforded methyl 3-azido-6-bromo-6'-morpholino-2,3'-bipyridine-4-carboxylate (240 mg, 0.57 mmol, 98% yield) yellow solid. $^1$H NMR (500 MHz, chloroform-d) δ ppm 8.73 (1H, d, J=2.44 Hz), 7.99 (1H, dd, J=9.00, 2.59 Hz), 7.71 (1H, s), 6.68 (1H, d, J=8.85 Hz), 4.00 (3H, s), 3.79-3.86 (4H, m), 3.59-3.66 (4H, m).

238C. Preparation of methyl 2-bromo-7-(4-morpholinyl)-5H-pyrido[2',3':4,5]pyrrolo[2,3-b]pyridine-4-carboxylate

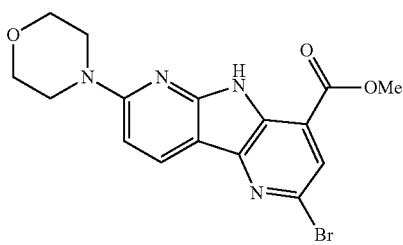 [SMILES: COC(=O)c1cc(Br)nc2c1[nH]c1nc(N3CCOCC3)ccc12]

1,2-Dichloroethane (0.4 mL) was added to a mixture of methyl 3-azido-6-bromo-6'-morpholino-2,3'-bipyridine-4-carboxylate (240 mg, 0.572 mmol), rhodium octanoate dimer (35.7 mg, 0.046 mmol) and crushed 4 A° molecular sieves (500 mg gm) and heated overnights at 80° C. The reaction was diluted with THF and filtered. The collected solid was washed with multiple portions of boiling THF to extract all of the product. The solvent was removed from the combined filtrates and the residue was suspended in MeOH and the product was collected by filtration. This left methyl 2-bromo-7-(4-morpholinyl)-5H-pyrido[2',3':4,5]pyrrolo[2,3-b]pyridine-4-carboxylate (167 mg, 0.427 mmol, 745% yield) as a yellow solid. $^1$H NMR (500 MHz, DMSO-$d_6$) δ ppm 11.75 (1H, s), 8.30 (1H, d, J=8.85 Hz), 7.72 (1H, s), 6.91 (1H, d, J=8.85 Hz), 4.01 (3H, s), 3.74 (8H, dd, J=15.56, 4.88 Hz).

238D. Preparation of methyl 2-(3-chlorophenyl)-7-(4-morpholinyl)-5H-pyrido[2',3':4,5]pyrrolo[2,3-b]pyridine-4-carboxylate

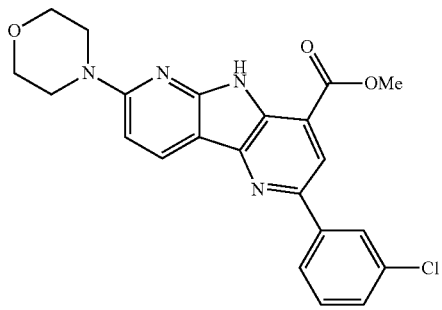 [SMILES: COC(=O)c1cc(-c2cccc(Cl)c2)nc2c1[nH]c1nc(N3CCOCC3)ccc12]

A mixture of 3-chlorophenylboronic acid (48.0 mg, 0.307 mmol), methyl 2-bromo-7-(4-morpholinyl)-5H-pyrido[2',3': 4,5]pyrrolo[2,3-b]pyridine-4-carboxylate (100 mg, 0.256 mmol), finely powdered potassium phosphate tribasic (130 mg, 0.613 mmol), dicyclohexyl(2',6'-dimethoxybiphenyl-2-yl)phosphine (21 mg, 0.051 mmol), and Pd(OAc)$_2$ (5.7 mg, 0.026 mmol) in a microwave vial was flushed with nitrogen. THF (1.3 mL) was added, the vial was capped, and the reaction was heated in a 70° C. oil bath for 24 hr. After cooling, it was partitioned between EtOAc and water. The organic phase was extracted with brine and dried with sodium sulfate. The solvents were removed and radial chromatography (step gradient elution with DCM containing 0 to 50% EtOAc) afforded methyl 2-(3-chlorophenyl)-7-(4-morpholinyl)-5H-pyrido[2',3':4,5]pyrrolo[2,3-b]pyridine-4-carboxylate (55 mg, 0.130 mmol, 51% yield). MS (ESI) m/z 423.11 (M+H). $^1$H NMR (500 MHz, chloroform-d) δ ppm 9.51 (1H, s), 8.43 (1H, d, J=8.55 Hz), 8.16 (1H, t, J=1.83 Hz), 8.13 (1H, s), 7.99 (1H, d, J=7.93 Hz), 7.42 (1H, t, J=7.78 Hz), 7.33-7.38 (1H, m), 6.67 (1H, d, J=8.85 Hz), 4.08 (3H, s), 3.84-3.91 (4H, m), 3.67-3.75 (4H, m).

238E. Preparation of 2-(3-chlorophenyl)-7-(4-morpholinyl)-5H-pyrido[2',3':4,5]pyrrolo[2,3-b]pyridine-4-carboxamide A solution of methyl 2-(3-chlorophenyl)-7-(4-morpholinyl)-5H-pyrido[2',3':4,5]pyrrolo[2,3-b]pyridine-4-carboxylate (50 mg, 0.12 mmol) in a solution of 7 N NH$_3$ in MeOH (5 mL) in a sealed microwave vial was heated at 80° C. for 48 hr. Filtration gave 2-(3-chlorophenyl)-7-(4-morpholinyl)-5H-pyrido[2',3':4,5]pyrrolo[2,3-b]pyridine-4-carboxamide (10 mg, 0.022 mmol, 19% yield) as a yellow solid. MS (ESI) m/z 408 (M+H). $^1$H NMR (DMSO-$d_6$) δ ppm 10.97 (s, 1H), 8.53 (br. s., 1H), 8.19-8.44 (m, 4H), 7.88 (br. s., 1H), 7.41-7.63 (m, 2H), 6.87 (br. s., 1H), 3.56-3.88 (m, 8H).

EXAMPLE 239

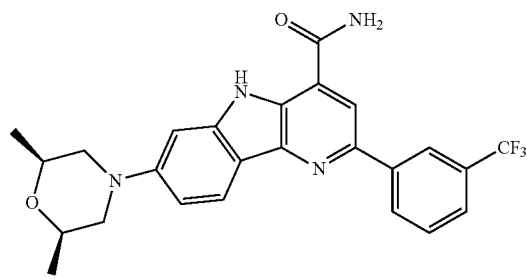 [SMILES: C[C@@H]1CN(c2ccc3c(c2)[nH]c2c(C(N)=O)cc(-c4cccc(C(F)(F)F)c4)nc23)C[C@H](C)O1]

7-((2S,6R)-2,6-Dimethylmorpholino)-2-(3-(trifluoromethyl)phenyl)-5H-pyrido[3,2-b]indole-4-carboxamide 239A. Preparation of methyl 3-amino-2-(4-(benzyloxy)phenyl)-6-bromoisonicotinate

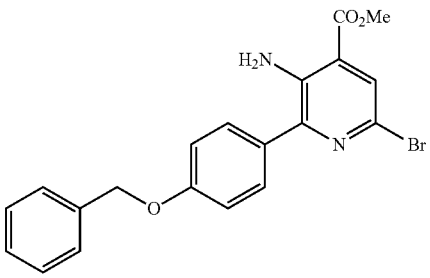 [SMILES: COC(=O)c1cc(Br)nc(-c2ccc(OCc3ccccc3)cc2)c1N]

A mixture of 4-(benzyloxy)phenylboronic acid (3.53 g, 15.5 mmol), methyl 3-amino-2,6-dibromoisonicotinate (4.0 g, 12.9 mmol), tetrakis(triphenylphosphine)-palladium(0) (0.90 g, 0.77 mmol), sodium carbonate (3.28 g, 31.0 mmol) was flushed with nitrogen and toluene (32 mL), and MeOH (11 mL) were added. The reaction was heated at reflux under nitrogen for 24 hr. It was partitioned between EtOAc and water. The organic phase was washed with brine, dried with sodium sulfate and the solvent removed. Radial chromatography (step gradient elution with hexane containing 20 to 80% DCM) afforded methyl 3-amino-2-(4-(benzyloxy)phenyl)-6-bromoisonicotinate (3.28 g, 7.94 mmol, 62% yield) as a yellow solid. MS (ESI) m/z 415.0 (M+H). ¹H NMR (500 MHz, chloroform-d) δ ppm 7.77 (1H, s), 7.52-7.58 (2H, m), 7.41-7.46 (2H, m), 7.36-7.41 (2H, m), 7.30-7.36 (1H, m), 7.04-7.09 (2H, m), 5.95 (2H, br. s.), 3.92 (3H, s).

239B. Preparation of methyl 3-azido-2-(4-(benzyloxy)phenyl)-6-bromoisonicotinate

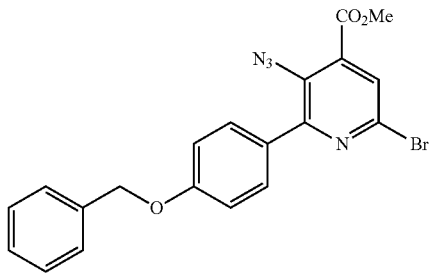

Methyl 3-amino-2-(4-(benzyloxy)phenyl)-6-bromoisonicotinate (3.28 g, 7.94 mmol) was dissolved in TFA (40 mL) and the yellow solution was cooled in an ice bath. Solid sodium nitrite (1.1 g, 15.9 mmol) was added with stirring to give a red mixture with gas evolution. After 20 min, solid sodium azide (5.16 g, 79 mmol) was added over 5 min followed immediately by Et₂O (40 mL). After 20 minutes water was added and the mixture was extracted with EtOAc. The combined organic phases were washed with water (3×), and saturated Na₂CO₃ solution (until the aqueous phase was basic) and brine. After drying the solvent with sodium sulfate, the solvent was removed. Flash chromatography (step gradient elution with hexane containing 10 to 40% DCM) afforded methyl 3-azido-2-(4-(benzyloxy)phenyl)-6-bromoisonicotinate (2.23 g, 5.08 mmol, 64% yield). ¹H NMR (500 MHz, chloroform-d) δ ppm 7.68-7.79 (3H, m), 7.29-7.49 (5H, m), 7.06 (2H, d, J=8.55 Hz), 4.00 (3H, s).

239C. Preparation of methyl 7-(benzyloxy)-2-bromo-5H-pyrido[3,2-b]indole-4-carboxylate

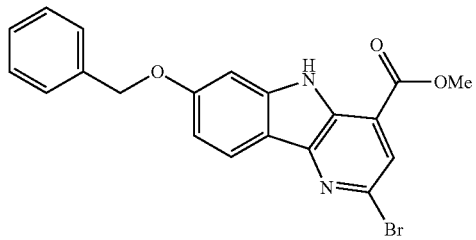 [SMILES: COC(=O)c1cc(Br)nc2c1[nH]c1cc(OCc3ccccc3)ccc12]

1,2-Dichloroethane (3.5 mL) was added to a mixture of methyl 3-azido-2-(4-(benzyloxy)phenyl)-6-bromoisonicotinate (2.28 g, 5.19 mmol), rhodium octanoate dimer (0.101 g, 0.130 mmol) and crushed 4 A° molecular sieves (2.2 gm). This was heated at 60° C. for 6 hr. The reaction was diluted with a mixture of DCM:MeOH=3:1 and filtered. The collected solid was washed with additional DCM:MeOH mixture to dissolve any remaining product. The solvent was removed from the filtrate and the residue was suspended in MeOH. The product was collected by filtration and washed with a little MeOH to leave methyl 7-(benzyloxy)-2-bromo-5H-pyrido[3,2-b]indole-4-carboxylate (1.72 g, 4.18 mmol, 81% yield) as a yellow solid. MS (ESI) m/z 412.9 (M+H). ¹H NMR (400 MHz, chloroform-d) δ ppm 9.45 (1H, br. s.), 8.22 (1H, d, J=8.81 Hz), 7.87 (1H, s), 7.43-7.50 (2H, m), 7.37-7.44 (2H, m), 7.30-7.37 (1H, m), 6.96-7.06 (2H, m), 5.18 (2H, s), 4.04 (3H, s).

239D. Preparation of methyl 7-(benzyloxy)-2-(3-(trifluoromethyl)phenyl)-5H-pyrido[3,2-b]indole-4-carboxylate

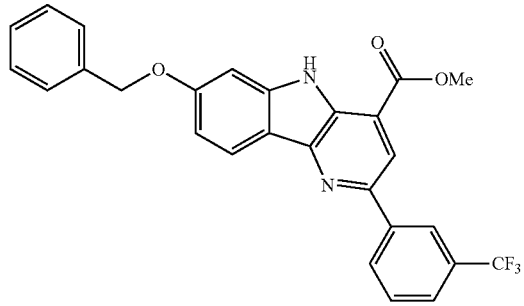 [SMILES: COC(=O)c1cc(-c2cccc(C(F)(F)F)c2)nc2c1[nH]c1cc(OCc3ccccc3)ccc12]

A mixture of 3-(trifluoromethyl)phenylboronic acid (0.59 g, 3.1 mmol), methyl 7-(benzyloxy)-2-bromo-5H-pyrido[3,2-b]indole-4-carboxylate (1.07 g, 2.60 mmol), powdered potassium phosphate tribasic (1.33 g, 6.24 mmol), dicyclohexyl(2',6'-dimethoxybiphenyl-2-yl)phosphine (0.214 g, 0.520 mmol), and Pd(OAc)₂ (0.058 g, 0.260 mmol) in a microwave vial was flushed with nitrogen. THF (13 mL) was added, the vial was capped, and the reaction was heated in a 70° C. oil bath for 24 hr. It was partitioned between EtOAc and water. The organic phase was washed with water and brine, dried with sodium sulfate, and the solvent removed. Silica gel chromatography (step gradient elution with DCM containing 50 to 25% hexane) afforded methyl 7-(benzyloxy)-2-(3-(trifluoromethyl)phenyl)-5H-pyrido[3,2-b]indole-4-carboxylate (1.03 g, 2.16 mmol, 83% yield) as a tan solid. MS (ESI) m/z 477.1 (M+H). ¹H NMR (500 MHz, chloroform-d) δ ppm 9.47 (1H, s), 8.44 (1H, s), 8.30-8.37 (2H, m), 8.21 (1H, s), 7.57-7.67 (2H, m), 7.49 (2H, d, J=7.32 Hz), 7.42 (2H, t, J=7.48 Hz), 7.32-7.38 (1H, m), 7.03-7.09 (2H, m), 5.21 (2H, s), 4.10 (3H, s).

239E. Preparation of methyl 7-hydroxy-2-(3-(trifluoromethyl)phenyl)-5H-pyrido[3,2-b]indole-4-carboxylate

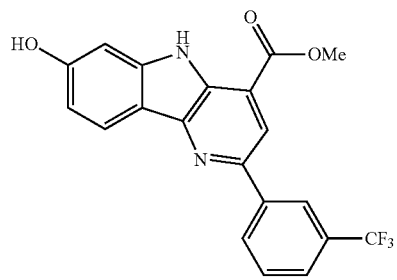 [SMILES: COC(=O)c1cc(-c2cccc(C(F)(F)F)c2)nc2c1[nH]c1cc(O)ccc12]

A solution of methyl 7-(benzyloxy)-2-(3-(trifluoromethyl)phenyl)-5H-pyrido[3,2-b]indole-4-carboxylate (1.0 g, 2.1 mmol) in TFA (8.3 mL) and water (2.3 mL) was heated at 90°

C. for 3 hrs. The solvent was removed to leave an orange solid. This was suspended in DCM:hexane=1:1 and then collected by filtration to give crude methyl 7-hydroxy-2-(3-(trifluoromethyl)phenyl)-5H-pyrido [3,2-b]indole-4-carboxylate (0.9 g) as a yellow solid that was used as such. MS (ESI) m/z 387.09 (M+H). $^1$H NMR (500 MHz, DMSO-d$_6$) δ ppm 11.49 (1H, s), 8.53 (1H, s), 8.49 (1H, d, J=7.02 Hz), 8.30 (1H, s), 8.11 (1H, d, J=8.24 Hz), 7.75-7.80 (2H, m), 7.13 (1H, d, J=1.83 Hz), 6.81 (1H, dd, J=8.39, 1.98 Hz), 4.07 (3H, s).

239F. Preparation of methyl 2-(3-(trifluoromethyl)phenyl)-7-(trifluoromethylsulfonyloxy)-5H-pyrido[3,2-b]indole-4-carboxylate

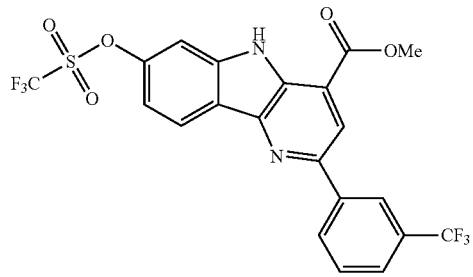 [SMILES: COC(=O)c1cc(-c2cccc(C(F)(F)F)c2)nc2c1[nH]c1cc(OS(=O)(=O)C(F)(F)F)ccc12]

A suspension of methyl 7-hydroxy-2-(3-(trifluoromethyl)phenyl)-5H-pyrido[3,2-b]indole-4-carboxylate (800 mg, 2.07 mmol), 4-nitrophenyl trifluoromethanesulfonate (842 mg, 3.11 mmol), and potassium carbonate (859 mg, 6.21 mmol) in DMF (12 ml) was stirred at RT for 3 hr. The reaction was partitioned between water and EtOAc. The organic phase was separated and washed with water (5×) and brine. It was dried with sodium sulfate and the solvent was removed. Column chromatography (step gradient elution with hexane containing 20 to 80% DCM) afforded methyl 2-(3-(trifluoromethyl)phenyl)-7-(trifluoromethylsulfonyloxy)-5H-pyrido[3,2-b]indole-4-carboxylate (548 mg, 1.06 mmol, 51% yield) as a light yellow solid. MS (ESI) m/z 587.09 (M+H). $^1$H NMR (500 MHz, chloroform-d) δ ppm 9.76 (1H, s), 8.51 (1H, d, J=8.55 Hz), 8.44 (1H, s), 8.31-8.38 (2H, m), 7.60-7.72 (2H, m), 7.51 (1H, d, J=2.14 Hz), 7.29 (1H, dd, J=8.55, 2.14 Hz), 4.13 (3H, s).

239G. Preparation of methyl 5-(4-methoxybenzyl)-2-(3-(trifluoromethyl)phenyl)-7-(trifluoromethylsulfonyloxy)-5H-pyrido[3,2-b]indole-4-carboxylate

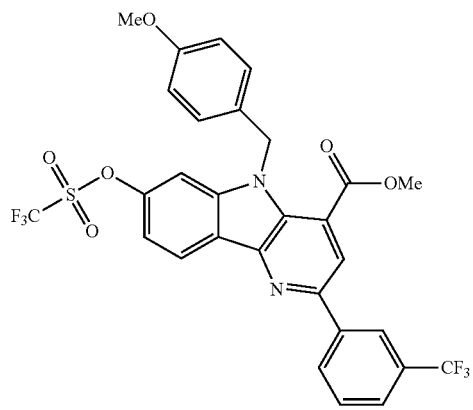 [SMILES: COC(=O)c1cc(-c2cccc(C(F)(F)F)c2)nc2c3ccc(OS(=O)(=O)C(F)(F)F)cc3n(Cc3ccc(OC)cc3)c12]

Sodium hydride (22 mg, 0.54 mmol, 60% dispersion in oil) was added to an ice-cooled stirred solution of methyl 2-(3-(trifluoromethyl)phenyl)-7-(trifluoromethylsulfonyloxy)-5H-pyrido[3,2-b]indole-4-carboxylate (200 mg, 0.386 mmol) in DMF (4 ml). This was left stirring until gas evolution stopped. 1-(bromomethyl)-4-methoxybenzene (0.072 ml, 0.502 mmol) was added and the reaction was kept in the ice bath for 2 hr. After an additional 1 hr at RT, the reaction was quenched with a saturated aqueous solution of NH$_4$Cl solution and extracted with EtOAc. The organic extracts were washed with water (5×), brine, and dried with sodium sulfate. Removal of the solvent, followed by radial chromatography (step gradient elution with hexane containing 0 to 5% DCM) afforded methyl 5-(4-methoxybenzyl)-2-(3-(trifluoromethyl)phenyl)-7-(trifluoromethylsulfonyloxy)-5H-pyrido[3,2-b]indole-4-carboxylate (91 mg, 0.14 mmol, 37% yield). MS (ESI) m/z 639.1 (M+H). $^1$H NMR (500 MHz, chloroform-d) δ ppm 8.55 (1H, d, J=8.55 Hz), 8.42 (1H, s), 8.33 (1H, d, J=7.63 Hz), 8.08 (1H, s), 7.59-7.71 (2H, m), 7.40 (1H, d, J=2.14 Hz), 7.29 (1H, dd, J=8.55, 2.14 Hz), 6.88 (2H, d, J=8.85 Hz), 6.76 (2H, d, J=8.85 Hz), 5.71 (2H, s), 3.86 (3H, s), 3.73 (3H, s).

239H. Preparation of methyl 7-((2S,6R)-2,6-dimethylmorpholino)-5-(4-methoxybenzyl)-2-(3-(trifluoromethyl)phenyl)-5H-pyrido[3,2-b]indole-4-carboxylate

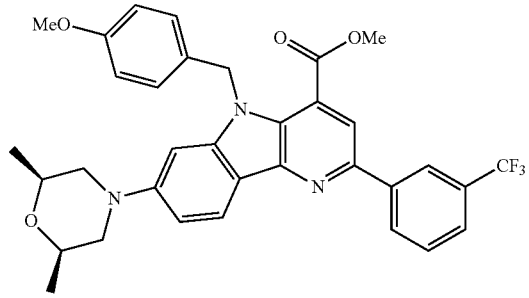 [SMILES: COC(=O)c1cc(-c2cccc(C(F)(F)F)c2)nc2c3ccc(N4C[C@@H](C)O[C@@H](C)C4)cc3n(Cc3ccc(OC)cc3)c12]

A microwave vial containing a mixture of methyl 5-(4-methoxybenzyl)-2-(3-(trifluoromethyl)phenyl)-7-(trifluoromethylsulfonyloxy)-5H-pyrido[3,2-b]indole-4-carboxylate (51 mg, 0.08 mmol), cis-2,6-dimethylmorpholine (9.8 μL, 0.080 mmol), powdered potassium phosphate, tribasic (51 mg, 0.240 mmol), biphenyl-2-yldi-tert-butylphosphine (11 mg, 0.036 mmol), and Pd(OAc)$_2$ (2.7 mg, 0.012 mmol) was flushed with nitrogen. DME (160 μL) was added and the vial was sealed and heated at 80° C. for 24 hr. The reaction was then partitioned between EtOAc and water and the organic phase was washed with brine and dried with sodium sulfate. The solvent was removed and the residue was chromatographed (step gradient elution with hexane containing 50 to 100% DCM) to afford methyl 7-((2S,6R)-2,6-dimethylmorpholino)-5-(4-methoxybenzyl)-2-(3-(trifluoromethyl)phenyl)-5H-pyrido[3,2-b]indole-4-carboxylate (27 mg, 0.045 mmol, 56% yield) as a yellow oil. MS (ESI) m/z 604.40 (M+H). $^1$H NMR (500 MHz, chloroform-d) δ ppm 8.40 (1H, s), 8.28-8.35 (2H, m), 7.88 (1H, s), 7.56-7.65 (2H, m), 7.03 (1H, dd, J=8.70, 1.98 Hz), 6.89 (2H, d, J=8.55 Hz), 6.81 (1H, d, J=1.83 Hz), 6.72-6.77 (2H, m), 5.66 (2H, s), 3.80-3.89 (2H, m), 3.80 (3H, s), 3.72 (3H, s), 3.54-3.62 (2H, m), 2.54 (2H, m), 1.28 (6H, d, J=6.1).

239I. Preparation of methyl 7-((2S,6R)-2,6-dimethylmorpholino)-2-(3-(trifluoromethyl)phenyl)-5H-pyrido[3,2-b]indole-4-carboxylate

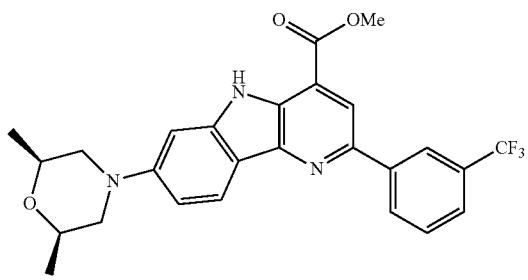 [SMILES: COC(=O)c1cc(-c2cccc(C(F)(F)F)c2)nc2c1[nH]c1cc(N3C[C@@H](C)O[C@@H](C)C3)ccc12]

TFA (3 mL) was added to a mixture of methyl 7-((2S,6R)-2,6-dimethylmorpholino)-5-(4-methoxybenzyl)-2-(3-(trifluoromethyl)phenyl)-5H-pyrido[3,2-b]indole-4-carboxylate (27 mg, 0.045 mmol) and anisole (0.049 mL, 0.45 mmol) in a vial. The vial was sealed and heated at 60° C. for 3 hr and then 70° C. for an additional 4 hr. The solvent was removed and the residue was dissolved in EtOAc. This was washed with saturated aqueous NaHCO₃ solution, brine, and then dried with sodium sulfate. Removal of the solvents followed by radial chromatography (step gradient elution with DCM containing 50 to 0% hexane followed by 10% EtOAc) to afforded methyl 7-((2S,6R)-2,6-dimethylmorpholino)-2-(3-(trifluoromethyl)phenyl)-5H-pyrido[3,2-b]indole-4-carboxylate (16 mg, 0.034 mmol, 75% yield) as a yellow oil. MS (ESI) m/z 484.1 (M+H). ¹H NMR (400 MHz, chloroform-d) d ppm 9.41 (1H, s), 8.42 (1H, s), 8.32 (1H, d, J=7.30 Hz), 8.27 (1H, d, J=8.56 Hz), 8.16 (1H, s), 7.55-7.66 (2H, m), 7.00 (1H, dd, J=8.81, 2.01 Hz), 6.92 (1H, d, J=2.01 Hz), 4.08 (3H, s), 3.85 (2H, ddd, J=10.45, 6.30, 2.39 Hz), 3.63 (2H, d, J=10.58 Hz), 2.51-2.61 (2H, m), 1.30 (6H, d, J=6.04 Hz).

239J. Preparation of 7-((2S,6R)-2,6-dimethylmorpholino)-2-(3-(trifluoromethyl)phenyl)-5H-pyrido[3,2-b]indole-4-carboxamide A suspension of methyl 7-((2S,6R)-2,6-dimethylmorpholino)-2-(3-(trifluoromethyl)phenyl)-5H-pyrido[3,2-b]indole-4-carboxylate (16 mg, 0.033 mmol) in 7 N NH₃ in MeOH (5 mL) in a sealed microwave vial was heated at 80° C. for 48 hr. Removal of the solvent followed by preparative HPLC (100×30 mm Luna C18 column, gradient elution with A:B=75:25 to A:B=25:75 [A=95% H₂O:5% MeOH:0.1% TFA; B=5% H₂O:95% MeOH:0.1% TFA] over 20 min) followed by SCX capture and release with 2 N NH₃ in MeOH afforded 7-((2S,6R)-2,6-dimethylmorpholino)-2-(3-(trifluoromethyl)phenyl)-5H-pyrido[3,2-b]indole-4-carboxamide (12.9 mg, 0.026 mmol, 79% yield) as an orange solid. MS (ESI) m/z 469.28 (M+H). ¹H NMR (500 MHz, MeOD) δ ppm 8.47 (1H, s), 8.39 (1H, t, J=4.27 Hz), 8.23 (1H, d, J=8.55 Hz), 8.20 (1H, s), 7.72 (2H, d, J=4.27 Hz), 7.07-7.11 (1H, m), 7.01-7.08 (1H, m), 3.80-3.91 (2H, m), 3.70-3.76 (2H, m), 2.43-2.53 (2H, m), 1.29 (6H, d, J=6.41 Hz).

EXAMPLE 240

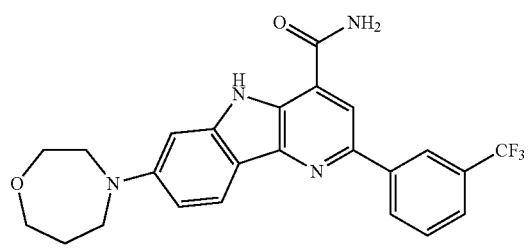 [SMILES: NC(=O)c1cc(-c2cccc(C(F)(F)F)c2)nc2c1[nH]c1cc(N3CCCOCC3)ccc12]

7-(1,4-Oxazepan-4-yl)-2-(3-(trifluoromethyl)phenyl)-5H-pyrido[3,2-b]indole-4-carboxamide This was similarly prepared from methyl 5-(4-methoxybenzyl)-2-(3-(trifluoromethyl)phenyl)-7-(trifluoromethylsulfonyloxy)-5H-pyrido[3,2-b]indole-4-carboxylate and 1,4-oxazepane. MS (ESI) m/z 455.25 (M+H). ¹H NMR (500 MHz, MeOD) δ ppm 8.45 (1H, br. s.), 8.32-8.41 (1H, m), 8.20 (1H, d, J=8.85 Hz), 8.15 (1H, s), 7.68-7.78 (2H, m), 6.85-6.98 (2H, m), 3.90-3.98 (2H, m), 3.78-3.86 (4H, m), 3.71-3.77 (2H, m), 2.05-2.16 (2H, m).

EXAMPLE 241

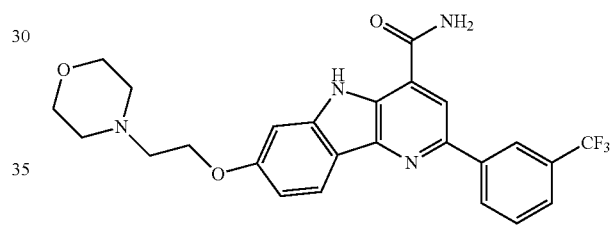

7-(2-Morpholinoethoxy)-2-(3-(trifluoromethyl)phenyl)-5H-pyrido[3,2-b]indole-4-carboxamidee

241A. Preparation of methyl 2-bromo-7-hydroxy-5H-pyrido[3,2-b]indole-4-carboxylate

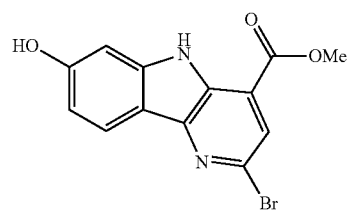 [SMILES: COC(=O)c1cc(Br)nc2c1[nH]c1cc(O)ccc12]

A solution of methyl 7-(benzyloxy)-2-bromo-5H-pyrido[3,2-b]indole-4-carboxylate (25 mg, 0.061 mmol) in TFA (0.5 mL) was heated at 80° C. for 20 min. The solvent was removed to leave a solid. This was suspended in a mixture of EtOAc and hexane and the solid was collected by filtration to give methyl 2-bromo-7-hydroxy-5H-pyrido[3,2-b]indole-4-carboxylate (10 mg, 0.031 mmol, 51% yield). MS (ESI) m/z 320.9 (M+H). ¹H NMR (400 MHz, MeOD) δ ppm 8.03 (1H, d, J=8.56 Hz), 7.79 (1H, s), 6.99 (1H, d, J=1.76 Hz), 6.79 (1H, dd, J=8.56, 2.27 Hz), 4.00-4.07 (3H, m).

241B. Preparation of methyl 2-bromo-7-(2-morpholinoethoxy)-5H-pyrido[3,2-b]indole-4-carboxylate

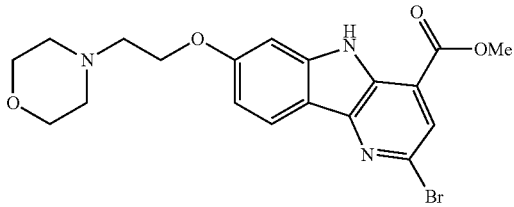 [SMILES: COC(=O)c1cc(Br)nc2c1[nH]c1cc(OCCN3CCOCC3)ccc12]

Diethyl azodicarboxylate (790 µL, 5.0 mmol) was added to a solution of triphenylphosphine (1.31 g, 5.0 mmol), methyl 2-bromo-7-hydroxy-5H-pyrido[3,2-b]indole-4-carboxylate (800 mg, 2.49 mmol) and 2-morpholinoethanol (610 µL, 5.0 mmol) in dry THF (12 mL) at room temperature under nitrogen. After 1 hr, the reaction was partitioned between EtOAc and water and the organic phase was washed with brine and dried over sodium sulfate. The solvent was removed and the residue was taken up in a 1:1 mixture of DCM:MeOH and the product was captured on a SCX cartridge and released with a 1:1 mixture of 2 N $NH_3$ in MeOH:DCM. The solvent was removed and the product was purified by radial chromatography (step gradient elution with DCM containing 0 to 3% MeOH) to afford methyl 2-bromo-7-(2-morpholinoethoxy)-5H-pyrido[3,2-b]indole-4-carboxylate (577 mg, 1.33 mmol, 53% yield) as a tan solid. MS (ESI) m/z 434.0 (M+H). $^1$H NMR (400 MHz, chloroform-d) δ ppm 9.48 (1H, s), 8.21 (1H, d, J=9.32 Hz), 7.88 (1H, s), 6.89-7.00 (2H, m), 4.22 (2H, t, J=5.67 Hz), 4.04 (3H, s), 3.70-3.80 (3H, m), 3.69-3.81 (4H, m), 2.86 (2H, t, J=5.67 Hz), 2.55-2.65 (4H, m).

241C. Preparation of 7-(2-morpholinoethoxy)-2-(3-(trifluoromethyl)phenyl)-5H-pyrido[3,2-b]indole-4-carboxamide A mixture of 3-(trifluoromethyl)phenylboronic acid (51 mg, 0.27 mmol), methyl 2-bromo-7-(2-morpholinoethoxy)-5H-pyrido[3,2-b]indole-4-carboxylate (90 mg, 0.21 mmol), powdered potassium phosphate tribasic (114 mg, 0.539 mmol), dicyclohexyl(2',6'-dimethoxybiphenyl-2-yl)phosphine (17 mg, 0.041 mmol), and Pd(OAc)$_2$ (4.7 mg, 0.021 mmol) in a microwave vial was flushed with nitrogen. THF (1 mL) was added, the vial was capped, and the reaction was heated in a 70° C. oil bath for 18 hr. Additional Pd(OAc)$_2$ (4.7 mg, 0.021 mmol) and dicyclohexyl(2',6'-dimethoxybiphenyl-2-yl)phosphine (17 mg, 0.041 mmol) were added, the vial was resealed, and heating was continued for 16 hr. The reaction was filtered and the collected solid was washed with THF. The filtrate was applied onto an SCX column and washed with DCM and then MeOH. Release with 2 N $NH_3$ in MeOH afforded crude methyl 7-(2-morpholinoethoxy)-2-(3-(trifluoromethyl)phenyl)-5H-pyrido[3,2-b]indole-4-carboxylate (107 mg). This was suspended in 7 N $NH_3$ in MeOH (5 mL) in a sealed microwave vial and heated at 80° C. overnight. Preparative HPLC (100×30 mm Luna C18 column, gradient elution with A:B=30:70 to A:B=0:100 [A=10 mM $NH_4$OAc in 5% aqueous $CH_3$CN; B=10 mM $NH_4$OAc in 95% aqueous $CH_3$CN] over 20 min) followed by removal of the solvents on a SPEEDVAC® gave 7-(2-morpholinoethoxy)-2-(3-(trifluoromethyl)phenyl)-5H-pyrido[3,2-b]indole-4-carboxamide (48 mg, 0.094 mmol, 44% yield) as a yellow solid. MS (ESI) m/z 483.1 (M–H). $^1$H NMR (500 MHz, DMSO-d$_6$) δ ppm 11.51 (1H, s), 8.62 (3H, s), 8.47 (1H, s), 8.16 (1H, d, J=8.55 Hz), 7.92 (1H, s), 7.69-7.83 (2H, m), 7.31 (1H, d, J=1.53 Hz), 6.92 (1H, dd, J=8.70, 1.68 Hz), 4.19 (2H, t, J=5.49 Hz), 3.61 (4H, t, J=4.43 Hz), 2.77 (2H, t, J=5.49 Hz), 2.51 (4H, br. s.).

EXAMPLE 242

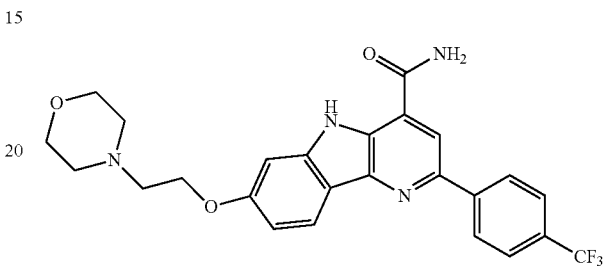

7-(2-Morpholinoethoxy)-2-(4-(trifluoromethyl)phenyl)-5H-pyrido[3,2-b]indole-4-carboxamide This was similarly prepared from methyl 2-bromo-7-(2-morpholinoethoxy)-5H-pyrido[3,2-b]indole-4-carboxylate and 4-(trifluoromethyl)phenylboronic acid. MS (ESI) m/z 485.0 (M+H). $^1$H NMR (500 MHz, DMSO-d$_6$) δ ppm 11.51 (1H, br. s.), 8.61 (1H, br. s.), 8.51 (2H, d, J=8.24 Hz), 8.47 (1H, s), 8.14 (1H, d, J=8.55 Hz), 7.90 (3H, d, J=8.24 Hz), 7.31 (1H, d, J=1.83 Hz), 6.92 (1H, dd, J=8.55, 1.83 Hz), 4.20 (2H, t, J=5.65 Hz), 3.61 (4H, t, J=4.58 Hz), 2.77 (2H, t, J=5.80 Hz), 2.42-2.58 (4H, m).

EXAMPLE 243

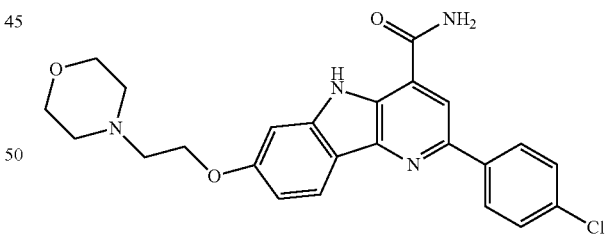

2-(4-Chlorophenyl)-7-(2-morpholinoethoxy)-5H-pyrido[3,2-b]indole-4-carboxamide

This was similarly prepared from methyl 2-bromo-7-(2-morpholinoethoxy)-5H-pyrido[3,2-b]indole-4-carboxylate and 4-chlorophenylboronic acid. MS (ESI) m/z 451.1 (M+H). $^1$H NMR (400 MHz, chloroform-d) δ ppm 9.90 (1H, s), 8.26 (1H, d, J=9.32 Hz), 7.96-8.07 (2H, m), 7.64 (1H, s), 7.39-7.50 (2H, m), 6.86-7.02 (2H, m), 6.17-6.70 (1H, m), 5.62-6.16 (1H, m), 4.22 (2H, t, J=5.67 Hz), 3.70-3.81 (4H, m), 2.86 (2H, t, J=5.79 Hz), 2.54-2.66 (4H, m).

EXAMPLE 244

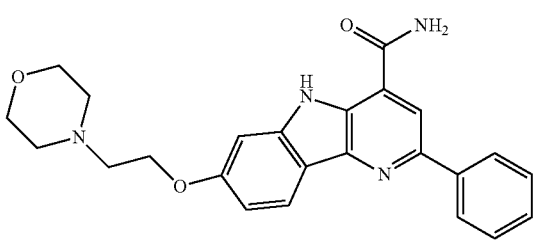 [SMILES: NC(=O)c1cc(-c2ccccc2)nc2c1[nH]c1cc(OCCN3CCOCC3)ccc12]

7-(2-Morpholinoethoxy)-2-phenyl-5H-pyrido[3,2-b]indole-4-carboxamide

This was similarly prepared from methyl 2-bromo-7-(2-morpholinoethoxy)-5H-pyrido[3,2-b]indole-4-carboxylate and phenylboronic acid. MS (ESI) m/z 415.1 (M−H). $^1$H NMR (500 MHz, MeOD) d ppm 8.24-8.29 (1H, m), 8.12-8.16 (1H, m), 8.10 (2H, d, J=8.24 Hz), 7.49-7.56 (2H, m), 7.39-7.46 (1H, m), 7.16 (1H, d, J=2.14 Hz), 6.89-6.97 (1H, m), 4.26 (2H, t, J=5.49 Hz), 3.72-3.78 (4H, m), 2.84-2.91 (2H, m), 2.65 (4H, br. s.).

EXAMPLE 245

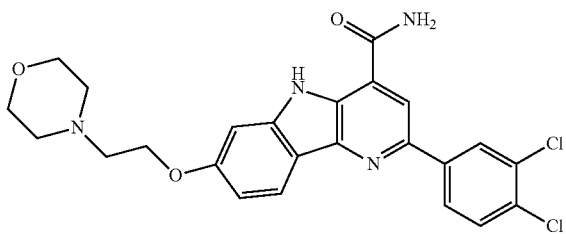 [SMILES: NC(=O)c1cc(-c2ccc(Cl)c(Cl)c2)nc2c1[nH]c1cc(OCCN3CCOCC3)ccc12]

7-(2-Morpholinoethoxy)-2-phenyl-5H-pyrido[3,2-b]indole-4-carboxamide

This was similarly prepared from methyl 2-bromo-7-(2-morpholinoethoxy)-5H-pyrido[3,2-b]indole-4-carboxylate and 3,4-dichlorophenylboronic acid. MS (ESI) m/z 485.0 (M+H). $^1$H NMR (500 MHz, DMSO-$d_6$) δ ppm 11.52 (1H, s), 8.57 (1H, s), 8.53 (1H, d, J=2.14 Hz), 8.43 (1H, s), 8.31 (1H, dd, J=8.55, 2.14 Hz), 8.15 (1H, d, J=8.55 Hz), 7.91 (1H, s), 7.81 (1H, d, J=8.55 Hz), 7.30 (1H, d, J=2.44 Hz), 6.92 (1H, dd, J=8.70, 2.29 Hz), 4.20 (2H, t, J=5.65 Hz), 3.57-3.65 (4H, m), 2.78 (2H, t, J=5.80 Hz), 2.49-2.54 (4H, m).

EXAMPLE 246

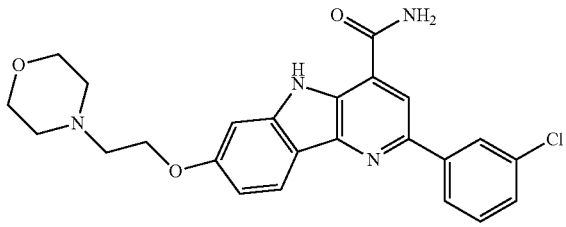 [SMILES: NC(=O)c1cc(-c2cccc(Cl)c2)nc2c1[nH]c1cc(OCCN3CCOCC3)ccc12]

7-(2-Morpholinoethoxy)-2-phenyl-5H-pyrido[3,2-b]indole-4-carboxamide

This was similarly prepared from methyl 2-bromo-7-(2-morpholinoethoxy)-5H-pyrido[3,2-b]indole-4-carboxylate and 3-chlorophenylboronic acid. MS (ESI) m/z 451.0 (M+H). $^1$H NMR (500 MHz, DMSO-$d_6$) δ ppm 11.49 (1H, br. s.), 8.59 (1H, br. s.), 8.41 (1H, s), 8.35 (1H, s), 8.28 (1H, d, J=7.94 Hz), 8.15 (1H, d, J=8.55 Hz), 7.89 (1H, s), 7.57 (1H, t, J=7.78 Hz), 7.44-7.50 (1H, m), 7.30 (1H, d, J=2.14 Hz), 6.91 (1H, dd, J=8.55, 2.14 Hz), 4.20 (2H, t, J=5.65 Hz), 3.58-3.64 (4H, m), 2.77 (2H, t, J=5.65 Hz), 2.48-2.57 (4H, m).

EXAMPLE 247

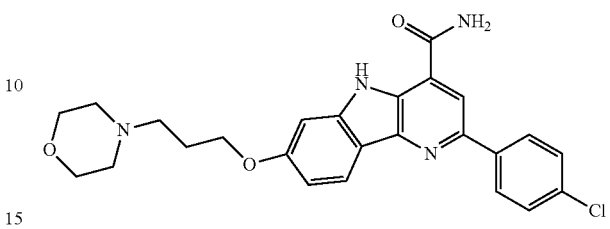

2-(4-Chlorophenyl)-7-(3-morpholinopropoxy)-5H-pyrido[3,2-b]indole-4-carboxamide

247A. Preparation of methyl 7-(benzyloxy)-2-(4-chlorophenyl)-5H-pyrido[3,2-b]indole-4-carboxylate

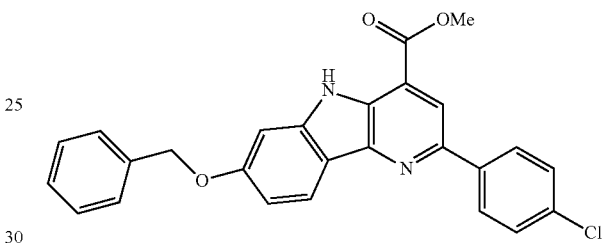

A mixture of 4-chlorophenylboronic acid (388 mg, 2.48 mmol) methyl 7-(benzyloxy)-2-bromo-5H-pyrido[3,2-b]indole-4-carboxylate (850 mg, 2.07 mmol), powdered potassium phosphate tribasic (1053 mg, 4.96 mmol), dicyclohexyl-(2',6'-dimethoxybiphenyl-2-yl)-phosphine (85 mg, 0.21 mmol), and Pd(OAc)$_2$ (23.2 mg, 0.103 mmol) in a flask was flushed with nitrogen. THF (10 mL) was added and the reaction was heated at reflux for 24 hr. It was partitioned between EtOAc and water. The organic phase was separated and the aqueous phase was extracted with EtOAc. The combined organic phases were washed with brine, dried with sodium sulfate and the solvent was removed. Radial chromatography (step gradient elution with hexane containing 0 to 50% DCM) afforded impure methyl 7-(benzyloxy)-2-(4-chlorophenyl)-5H-pyrido[3,2-b]indole-4-carboxylate (709 mg) as a yellow solid. MS (ESI) m/z 443.0 (M+H).

247B. Preparation of methyl 2-(4-chlorophenyl)-7-hydroxy-5H-pyrido[3,2-b]indole-4-carboxylate

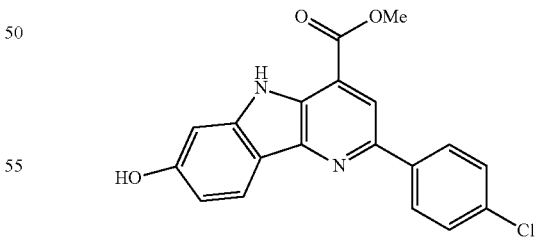

An solution of methyl 7-(benzyloxy)-2-(4-chlorophenyl)-5H-pyrido[3,2-b]indole-4-carboxylate (709 mg, 1.60 mmol) in trifluoroacetic acid (15 mL) was heated at 70° C. for 30 min. The solvent was removed and the residue was suspended in a mixture of EtOAc (25 mL) and hexane (50 mL). The suspended solid was collected by filtration and washed with the EtOAc/hexane mixture. This gave impure methyl 2-(4-chlorophenyl)-7-hydroxy-5H-pyrido[3,2-b]indole-4-carboxylate (573 mg). MS (ESI) m/z 353.0 (M+H).

247C. Preparation of methyl 2-(4-chlorophenyl)-7-(3-morpholinopropoxy)-5H-pyrido[3,2-b]indole-4-carboxylate

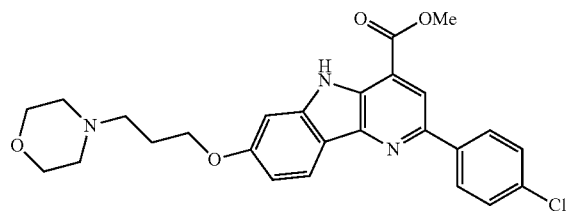 [SMILES: NC(=O)c1cc(-c2ccc(Cl)cc2)nc2c1[nH]c1cc(OCCCN3CCOCC3)ccc12]

Diethyl azodicarboxylate (90 μL, 0.57 mmol) was added to a solution of triphenylphosphine (149 mg, 0.567 mmol), methyl 2-(4-chlorophenyl)-7-hydroxy-5H-pyrido[3,2-b]indole-4-carboxylate (100 mg, 0.283 mmol) and 3-morpholinopropan-1-ol (78 μL, 0.57 mmol) in dry THF (1.4 mL) at RT under nitrogen. After 1 hr, the reaction was quenched with a little water and the product was captured on an SCX cartridge, washed with MeOH and DCM, and then released with 2 N $NH_3$ in MeOH. Radial chromatography (step gradient elution with DCM containing 0 to 1% MeOH) afforded impure methyl 2-(4-chlorophenyl)-7-(3-morpholinopropoxy)-5H-pyrido[3,2-b]indole-4-carboxylate (75 mg) as a yellow solid. MS (ESI) m/z 480.0 (M+H).

247. Preparation of 2-(4-chlorophenyl)-7-(3-morpholinopropoxy)-5H-pyrido[3,2-b]indole-4-carboxamide A suspension of crude methyl 2-(4-chlorophenyl)-7-(3-morpholinopropoxy)-5H-pyrido[3,2-b]indole-4-carboxylate (75 mg, 0.16 mmol) in 7 N $NH_3$ in MeOH (4 mL) in a sealed microwave vial was heated at 80° C. overnight. The product was isolated by preparative HPLC (100×30 mm Luna C18 column, gradient elution with A:B=30:70 to A:B=0:100 [A=10 mM $NH_4OAc$ in 5% aq. $CH_3CN$; B=10 mM $NH_4OAc$ in 95% aq. $CH_3CN$] over 20 min) followed by removal of the solvents on the SPEEDVAC® to leave 2-(4-chlorophenyl)-7-(3-morpholinopropoxy)-5H-pyrido[3,2-b]indole-4-carboxamide (34.6 mg, 0.071 mmol, 45% yield) as a yellow solid. MS (ESI) m/z 465.0 (M+H). $^1$H NMR (400 MHz, DMSO-$d_6$) δ ppm 11.45 (1H, s), 8.57 (1H, s), 8.37 (1H, s), 8.28-8.33 (2H, m), 8.11 (1H, d, J=8.56 Hz), 7.87 (1H, s), 7.54-7.63 (2H, m), 7.28 (1H, d, J=2.27 Hz), 6.88 (1H, dd, J=8.69, 2.14 Hz), 4.11 (2H, t, J=6.29 Hz), 3.59 (4H, br. s.), 2.45 (2H, br. s.), 2.32-2.45 (4H, m), 1.96 (2H, br. s.).

EXAMPLE 248

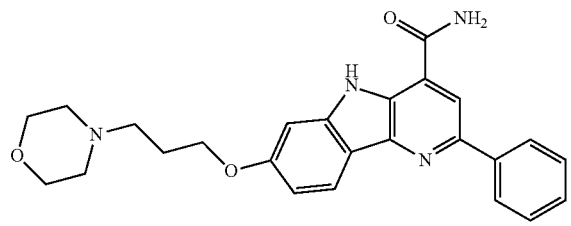 [SMILES: NC(=O)c1cc(-c2ccccc2)nc2c1[nH]c1cc(OCCCN3CCOCC3)ccc12]

7-(3-Morpholinopropoxy)-2-phenyl-5H-pyrido[3,2-b]indole-4-carboxamide

This was similarly prepared from methyl 7-(benzyloxy)-2-bromo-5H-pyrido[3,2-b]indole-4-carboxylate and 4-chlorophenylboronic acid. MS (ESI) m/z 431.1 (M+H). $^1$H NMR (400 MHz, chloroform-d) d ppm 9.88 (1H, s), 8.28 (1H, d, J=8.56 Hz), 8.00-8.15 (2H, m), 7.67 (1H, s), 7.49 (2H, t, J=7.55 Hz), 7.40 (1H, d, J=7.55 Hz), 6.85-7.02 (2H, m), 6.45 (1H, br. s.), 5.88 (1H, br. s.), 4.13 (2H, t, J=6.30 Hz), 3.61-3.77 (4H, m), 2.41-2.66 (6H, m), 1.94-2.10 (2H, m).

EXAMPLE 249

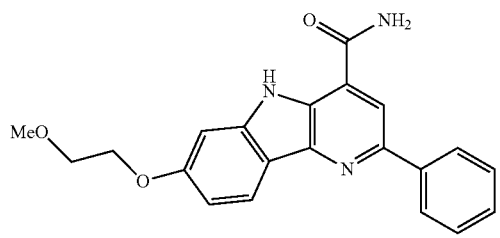 [SMILES: COCCOc1ccc2c(c1)[nH]c1c(C(N)=O)cc(-c3ccccc3)nc12]

7-(2-Methoxyethoxy)-2-phenyl-5H-pyrido[3,2-b]indole-4-carboxamide

249A. Preparation of methyl 7-(benzyloxy)-2-phenyl-5H-pyrido[3,2-b]indole-4-carboxylate

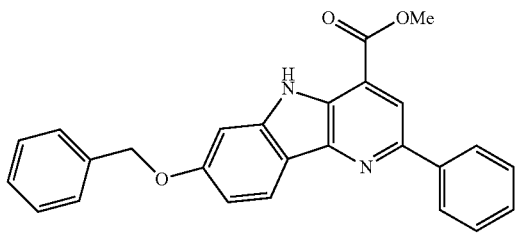 [SMILES: COC(=O)c1cc(-c2ccccc2)nc2c1[nH]c1cc(OCc3ccccc3)ccc12]

A flask containing dicyclohexyl-(2',6'-dimethoxybiphenyl-2-yl)-phosphine (0.419 g, 1.02 mmol), methyl 7-(benzyloxy)-2-bromo-5H-pyrido[3,2-b]indole-4-carboxylate (2.1 g, 5.1 mmol), phenylboronic acid (0.747 g, 6.13 mmol), $Pd(OAc)_2$ (0.115 g, 0.511 mmol), and powdered potassium phosphate tribasic (3.25 g, 15.3 mmol) was flushed with nitrogen. THF (16 mL) was added and the reaction was heated at reflux overnight. It was partitioned between EtOAc and water and the organic phase was separated, washed with brine, and dried with sodium sulfate. Removal of the solvents followed by chromatography (step gradient elution with hexane containing 25 to 70% DCM) afforded methyl 7-(benzyloxy)-2-phenyl-5H-pyrido[3,2-b]indole-4-carboxylate (1.09 g, 2.67 mmol, 52% yield) as a yellow solid. MS (ESI) m/z 407.2 (M−H). $^1$H NMR (500 MHz, chloroform-d) d ppm 9.43 (1H, s), 8.32 (1H, d, J=9.16 Hz), 8.20 (1H, s), 8.12-8.19 (2H, m), 7.46-7.54 (4H, m), 7.32-7.44 (4H, m), 7.02-7.07 (2H, m), 5.21 (2H, s), 4.08 (3H, s).

249B. Preparation of 7-(benzyloxy)-2-phenyl-5H-pyrido[3,2-b]indole-4-carboxamide

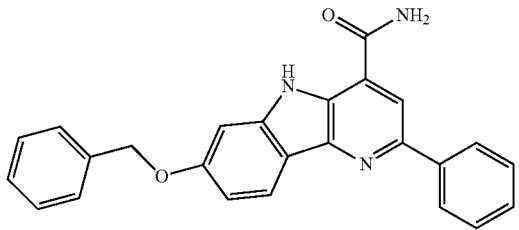 [SMILES: NC(=O)c1cc(-c2ccccc2)nc2c1[nH]c1cc(OCc3ccccc3)ccc12]

A suspension of methyl 7-(benzyloxy)-2-phenyl-5H-pyrido[3,2-b]indole-4-carboxylate (1008 mg, 2.47 mmol) in 7 N $NH_3$ in MeOH (36 mL) in a sealed microwave vial was heated at 80° C. for 24 hr. The product crystallized from the reaction mixture on cooling and was collected by filtration and washed with MeOH. This gave 7-(benzyloxy)-2-phenyl-5H-pyrido[3,2-b]indole-4-carboxamide (880 mg, 2.24 mmol, 91% yield) as a yellow solid. MS (ESI) m/z 394.1

(M+H). ¹H NMR (500 MHz, chloroform-d) d ppm 9.87 (1H, s), 8.27-8.35 (1H, m), 8.09 (3H, d, J=7.02 Hz), 7.68 (1H, s), 7.47-7.55 (5H, m), 7.41 (4H, t, J=7.63 Hz), 7.31-7.37 (1H, m), 7.00-7.08 (3H, m), 5.20 (2H, s).

249C. Preparation of 7-hydroxy-2-phenyl-5H-pyrido[3,2-b]indole-4-carboxamide

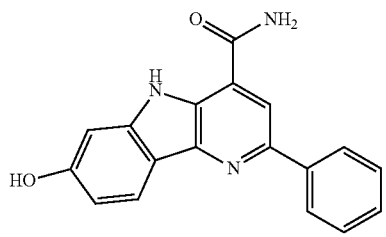 [SMILES: NC(=O)c1cc(-c2ccccc2)nc2c1[nH]c1cc(O)ccc12]

A mixture of 7-(benzyloxy)-2-phenyl-5H-pyrido[3,2-b]indole-4-carboxamide (880 mg, 2.237 mmol), 10% Pd on carbon (400 mg) and ammonium formate (705 mg, 11.2 mmol) in ethanol (50 mL) was heated at reflux for 1 hr. Filtration followed by removal of the solvent from the filtrate left 7-hydroxy-2-phenyl-5H-pyrido[3,2-b]indole-4-carboxamide (658 mg, 2.17 mmol, 97% yield) as a yellow solid. MS (ESI) m/z 304.0 (M+H). ¹H NMR (500 MHz, DMSO-d₆) d ppm 11.30 (1H, br. s.), 9.77 (1H, br. s.), 8.54 (1H, br. s.), 8.30 (1H, s), 8.27 (2H, d, J=7.32 Hz), 8.03 (1H, d, J=8.24 Hz), 7.80 (1H, br. s.), 7.53 (2H, t, J=7.63 Hz), 7.41 (1H, s), 7.36-7.46 (1H, m), 7.14-7.15 (1H, m), 7.14-7.14 (1H, m), 7.12 (1H, d, J=1.83 Hz), 6.75 (1H, dd, J=8.55, 2.14 Hz).

249. Preparation of 7-(2-methoxyethoxy)-2-phenyl-5H-pyrido[3,2-b]indole-4-carboxamide Diethyl azodicarboxylate (0.073 mL, 0.46 mmol) was added to a mixture of 7-hydroxy-2-phenyl-5H-pyrido[3,2-b]indole-4-carboxamide (70 mg, 0.23 mmol), 2-methoxyethanol (0.036 mL, 0.46 mmol), and triphenylphosphine (121 mg, 0.462 mmol) in dry THF (1 mL) at RT under nitrogen. After 2 hr the reaction was diluted with MeOH and the product was isolated by preparative HPLC (100×30 mm Luna C18 column, gradient elution with B=10% to B=70% [A=10 mM NH₄OAc in 5% aq CH₃CN; B=10 mM NH₄OAc in 95% aq CH₃CN] over 20 min) followed by removal of the solvents on a SPEEDVAC®. This gave 7-(2-methoxyethoxy)-2-phenyl-5H-pyrido[3,2-b]indole-4-carboxamide (27.8 mg, 0.074 mmol, 32% yield) as a yellow solid. MS (ESI) m/z 362.1 (M+H). ¹H NMR (500 MHz, DMSO-d₆) δ ppm 11.42 (1H, s), 8.57 (1H, br. s.), 8.36 (1H, s), 8.22-8.33 (2H, m), 8.13 (1H, d, J=8.55 Hz), 7.85 (1H, br. s.), 7.54 (2H, t, J=7.63 Hz), 7.37-7.47 (1H, m), 7.30 (1H, d, J=2.14 Hz), 6.91 (1H, dd, J=8.70, 2.29 Hz), 4.12-4.24 (2H, m), 3.66-3.79 (2H, m), 3.36 (3H, s).

EXAMPLE 250

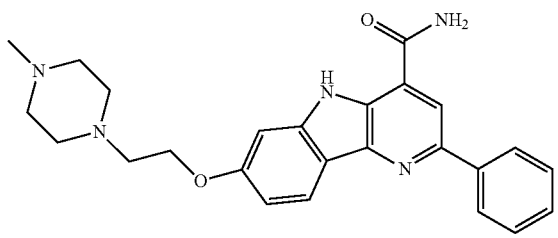 [SMILES: CN1CCN(CCOc2ccc3c(c2)[nH]c2c(C(N)=O)cc(-c4ccccc4)nc23)CC1]

7-(2-(4-Methylpiperazin-1-yl)ethoxy)-2-phenyl-5H-pyrido[3,2-b]indole-4-carboxamide This was similarly prepared from 7-hydroxy-2-phenyl-5H-pyrido[3,2-b]indole-4-carboxamide and 2-(4-methylpiper-azin-1-yl)ethanol. MS (ESI) m/z 430.1 (M+H). ¹H NMR (400 MHz, MeOD) δ ppm 8.20-8.27 (1H, m), 8.12 (1H, s), 8.04-8.09 (2H, m), 7.46-7.53 (2H, m), 7.37-7.42 (1H, m), 7.12-7.16 (1H, m), 6.87-6.94 (1H, m), 4.18-4.27 (2H, m), 2.87 (2H, t, J=5.41 Hz), 2.42-2.77 (6H, m), 2.27 (3H, s).

EXAMPLE 251

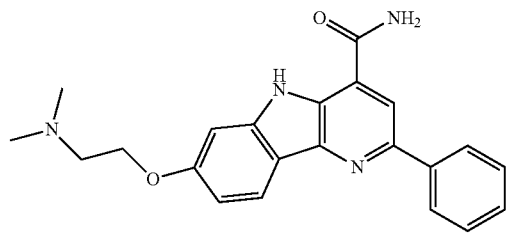 [SMILES: CN(C)CCOc1ccc2c(c1)[nH]c1c(C(N)=O)cc(-c3ccccc3)nc12]

7-(2-(Dimethylamino)ethoxy)-2-phenyl-5H-pyrido[3,2-b]indole-4-carboxamide

This was similarly prepared from 7-hydroxy-2-phenyl-5H-pyrido[3,2-b]indole-4-carboxamide and 2-(dimethylamino)ethanol. MS (ESI) m/z 375.1 (M+H). ¹H NMR (500 MHz, MeOD) δ ppm 8.25-8.33 (1H, m), 8.16 (1H, s), 8.08-8.13 (2H, m), 7.53 (2H, t, J=7.78 Hz), 7.44 (1H, t, J=7.32 Hz), 7.20 (1H, d, J=2.14 Hz), 6.98 (1H, dd, J=8.85, 2.14 Hz), 4.30 (2H, t, J=5.34 Hz), 3.01 (2H, t, J=5.34 Hz), 2.52 (6H, s).

EXAMPLE 252

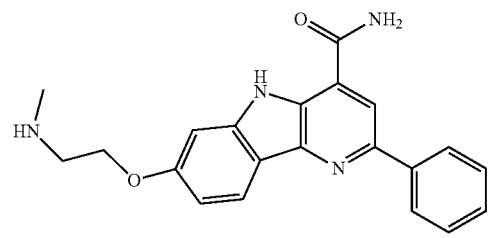 [SMILES: CNCCOc1ccc2c(c1)[nH]c1c(C(N)=O)cc(-c3ccccc3)nc12]

7-(2-(Methylamino)ethoxy)-2-phenyl-5H-pyrido[3,2-b]indole-4-carboxamide

This was similarly prepared from 7-hydroxy-2-phenyl-5H-pyrido[3,2-b]indole-4-carboxamide and tert-butyl 2-hydroxyethyl(methyl)carbamate except that the crude product was deprotected with a mixture of MeOH (1 mL) and conc. HCl (1 mL) before purification. MS (ESI) m/z 361.12 (M+H). ¹H NMR (500 MHz, MeOD) δ ppm 8.29 (1H, d, J=8.85 Hz), 8.16 (1H, s), 8.11 (2H, d, J=7.02 Hz), 7.54 (2H, t, J=7.78 Hz), 7.44 (1H, t, J=7.32 Hz), 7.21 (1H, d, J=2.14 Hz), 6.98 (1H, dd, J=8.70, 2.29 Hz), 4.25 (2H, t, J=5.19 Hz), 3.05 (2H, t, J=5.19 Hz), 2.51 (3H, s).

EXAMPLE 253

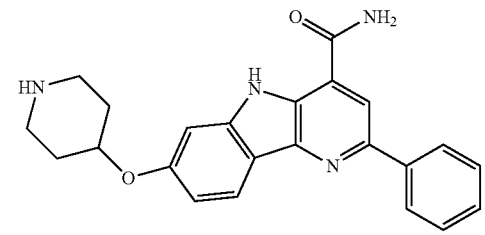 [SMILES: NC(=O)c1cc(-c2ccccc2)nc2c1[nH]c1cc(OC3CCNCC3)ccc12]

2-Phenyl-7-(piperidin-4-yloxy)-5H-pyrido[3,2-b]indole-4-carboxamide

This was similarly prepared from 7-hydroxy-2-phenyl-5H-pyrido[3,2-b]indole-4-carboxamide and tert-butyl 4-hydroxypiperidine-1-carboxylate. MS (ESI) m/z 387.1 (M+H). $^1$H NMR (500 MHz, DMSO-$d_6$) δ ppm 11.35 (1H, br. s.), 8.57 (1H, s), 8.36 (1H, s), 8.28 (2H, d, J=7.02 Hz), 8.12 (1H, d, J=8.55 Hz), 7.84 (1H, s), 7.54 (2H, t, J=7.63 Hz), 7.42 (1H, t, J=7.32 Hz), 7.32 (1H, d, J=2.14 Hz), 6.91 (1H, dd, J=8.85, 2.14 Hz), 4.43-4.57 (1H, m), 3.05 (2H, ddd, J=12.67, 4.27, 4.12 Hz), 2.61-2.74 (2H, m), 1.98-2.11 (2H, m), 1.91 (3H, s), 1.50-1.68 (2H, m).

EXAMPLE 254

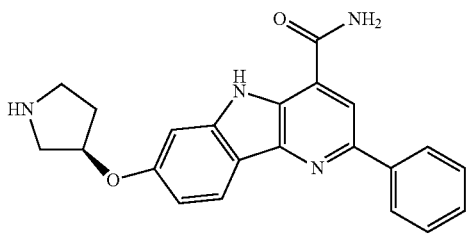 [SMILES: NC(=O)c1cc(-c2ccccc2)nc2c1[nH]c1cc(O[C@@H]3CCNC3)ccc12]

(R)-2-Phenyl-7-(pyrrolidin-3-yloxy)-5H-pyrido[3,2-b]indole-4-carboxamide

This was similarly prepared from 7-hydroxy-2-phenyl-5H-pyrido[3,2-b]indole-4-carboxamide and (S)-tert-butyl 3-hydroxypyrrolidine-1-carboxylate. MS (ESI) m/z 373.1 (M+H). $^1$H NMR (500 MHz, MeOD) δ ppm 8.28 (1H, d, J=8.85 Hz), 8.16 (1H, s), 8.11 (2H, d, J=7.02 Hz), 7.54 (2H, t, J=7.63 Hz), 7.44 (1H, t, J=7.32 Hz), 7.17 (1H, d, J=2.14 Hz), 6.92 (1H, dd, J=8.85, 2.14 Hz), 5.05-5.13 (1H, m), 3.14-3.23 (3H, m), 3.00 (1H, ddd, J=11.22, 8.32, 4.88 Hz), 2.16-2.27 (1H, m), 2.05-2.15 (1H, m).

EXAMPLE 255

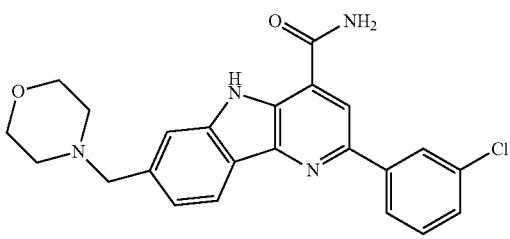 [SMILES: NC(=O)c1cc(-c2cccc(Cl)c2)nc2c1[nH]c1cc(CN3CCOCC3)ccc12]

2-(3-Chlorophenyl)-7-(morpholinomethyl)-5H-pyrido[3,2-b]indole-4-carboxamide

255A. Preparation of methyl 3-amino-6-bromo-2-(4-(hydroxymethyl)phenyl)isonicotinate

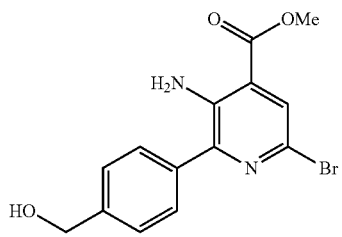 [SMILES: COC(=O)c1cc(Br)nc(-c2ccc(CO)cc2)c1N]

A mixture of 4-(hydroxymethyl)phenylboronic acid (2.35 g, 15.5 mmol), methyl 3-amino-2,6-dibromoisonicotinate (4.0 g, 12.9 mmol), tetrakistriphenylphosphine palladium(0) (0.895 g, 0.774 mmol), sodium carbonate (3.28 g, 31.0 mmol) was flushed with nitrogen and toluene (32.3 mL), and MeOH (10.75 mL) were added. The reaction was heated at reflux under nitrogen for 24 hr. It was partitioned between EtOAc and water. The organic phase was washed with brine, dried with sodium sulfate, and the solvents removed. The organic phase was washed with brine, dried with sodium sulfate and the solvent removed. The residue was chromatographed (step gradient elution with DCM containing 0 to 20% EtOAc afforded methyl 3-amino-6-bromo-2-(4-(hydroxymethyl) phenyl)isonicotinate (1.99 g, 5.90 mmol, 46% yield) as a yellow fluffy solid. MS (ESI) m/z 336.8 (M+H). $^1$H NMR (500 MHz, chloroform-d) δ ppm 7.80 (1H, s), 7.61 (2H, d, J=8.24 Hz), 7.48 (2H, d, J=7.93 Hz), 5.94 (2H, br. s.), 4.75 (2H, d, J=5.80 Hz), 3.92 (3H, s), 1.72 (1H, t, J=5.80 Hz).

255B. Methyl 3-azido-6-bromo-2-(4-formylphenyl)isonicotinate

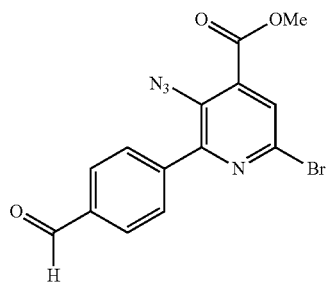 [SMILES: COC(=O)c1cc(Br)nc(-c2ccc(C=O)cc2)c1N=[N+]=[N-]]

Methyl 3-amino-6-bromo-2-(4-(hydroxymethyl)phenyl) isonicotinate (5.7 g, 16.91 mmol) was dissolved in TFA (85 mL) and the solution was cooled in an ice bath. Sodium nitrite (2.57 g, 37 2 mmol) was added slowly with stirring to give a yellow solution with gas evolution. After 40 min, gas evolution had ceased and solid sodium azide (10.99 g, 169 mmol) was added in portions over about 5 min with gas evolution. $Et_2O$ (85 mL) was slowly added and a precipitate formed. After stirring for 0.5 hr, water was added and the mixture was extracted with EtOAc. The combined organic phases were washed with water (3x) and brine (1x) and then saturated $Na_2CO_3$ solution (until the aqueous phase was basic) and brine (1x). After drying the solvent with sodium sulfate, the solvent was removed. Flash chromatography (step gradient elution with DCM containing 40 to 0% hexane and then 10% EtOAc) afforded methyl 3-azido-6-bromo-2-(4-formylphenyl)isonicotinate (4.45 g, 12.3 mmol, 73% yield) as a fluffy yellow solid. $^1$H NMR (500 MHz, chloroform-d) δ ppm 10.10 (1H, s), 7.96-8.04 (2H, m), 7.90-7.96 (2H, m), 7.86 (1H, s), 4.03 (3H, s).

255C. Preparation of methyl 2-bromo-7-formyl-5H-pyrido[3,2-b]indole-4-carboxylate

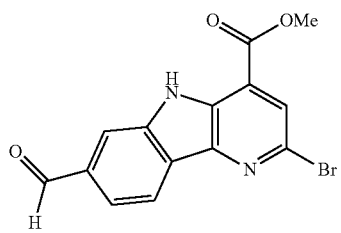 [SMILES: COC(=O)c1cc(Br)nc2c1[nH]c1cc(C=O)ccc12]

1,2-Dichloroethane (760 μL) was added to a mixture of methyl 3-azido-6-bromo-2-(4-formylphenyl)isonicotinate (412 mg, 1.14 mmol), rhodium octanoate dimer (71 mg, 0.091 mmol) and crushed 4A° molecular sieves (0.4 gm) in an microwave vial.

This was sealed and heated at 80° C. for 24 hr. The reaction was diluted with THF and the solid collected by filtration. This was washed with multiple portions of boiling THF to extract remaining product. The solvent was removed from the combined filtrates and the residue was suspended in MeOH. Filtration gave methyl 2-bromo-7-formyl-5H-pyrido[3,2-b]indole-4-carboxylate (292 mg, 0.877 mmol, 77% yield) as a light green solid. MS (ESI) m/z 334.7 (M+H). $^1$H NMR (400 MHz, DMSO-d$_6$) δ ppm 12.17 (1H, s), 10.19 (1H, s), 8.38 (1H, d, J=8.06 Hz), 8.28 (1H, s), 8.00 (1H, s), 7.85 (1H, dd, J=8.18, 1.13 Hz), 4.05 (3H, s).

255D Preparation of methyl 2-bromo-7-(morpholinomethyl)-5H-pyrido[3,2-b]indole-4-carboxylate

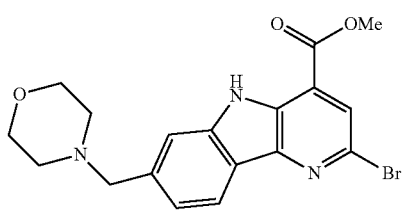 [SMILES: COC(=O)c1cc(Br)nc2c1[nH]c1cc(CN3CCOCC3)ccc12]

A suspension of methyl 2-bromo-7-formyl-5H-pyrido[3,2-b]indole-4-carboxylate (150 mg, 0.450 mmol) in DMF (1 mL) was stirred for 5 min and then diluted with DCM (10 mL). Morpholine (0.047 mL, 0.540 mmol) was added and the suspension was cooled in an ice bath. Sodium triacetoxyborohydride (258 mg, 1.21 mmol) was added and the suspension was left stirring for 1 hr. Acetic acid (0.052 mL, 0.90 mmol) was then added and the bath removed. The reaction was left stirring at RT for 7 hr and then diluted with DCM and washed with sat. aq. NaHCO$_3$ solution followed by water (2×). After drying with sodium sulfate, the solvent was removed. Radial chromatography (step gradient elution with DCM containing 2 to 4% MeOH) afforded methyl 2-bromo-7-(morpholinomethyl)-5H-pyrido[3,2-b]indole-4-cearboxylate (75 mg, 0.19 mmol, 41% yield) as off white solid. MS (ESI) m/z 402.0 (M+H). $^1$H NMR (400 MHz, chloroform-d) δ ppm 9.56 (1H, br. s.), 8.31 (1H, d, J=8.31 Hz), 7.99 (1H, s), 7.56 (1H, s), 7.35 (1H, dd, J=8.06, 1.26 Hz), 4.09 (3H, s), 3.73-3.79 (4H, m), 3.71 (2H, s), 2.47-2.59 (4H, m).

255E. Preparation of methyl 2-(3-chlorophenyl)-7-(morpholinomethyl)-5H-pyrido[3,2-b]indole-4-carboxylate

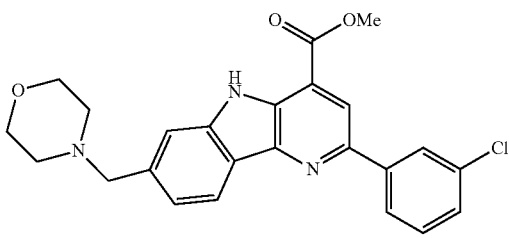 [SMILES: COC(=O)c1cc(-c2cccc(Cl)c2)nc2c1[nH]c1cc(CN3CCOCC3)ccc12]

A mixture of 3-chlorophenylboronic acid (34 mg, 0.22 mmol), methyl 2-bromo-7-(morpholinomethyl)-5H-pyrido[3,2-b]indole-4-carboxylate (75 mg, 0.19 mmol), powdered potassium phosphate tribasic (95 mg, 0.45 mmol), dicyclohexyl(2',6'-dimethoxybiphenyl-2-yl)phosphine (15 mg, 0.037 mmol), and Pd(OAc)$_2$ (4.2 mg, 0.019 mmol) in a microwave vial was flushed with nitrogen. THF (928 μL) was added, the vial was capped, and the reaction was heated in a 70° C. oil bath for 24 hr. The reaction was partitioned between EtOAc and water. The organic phase was extracted with brine and dried with sodium sulfate. The solvents were removed and radial chromatography (step gradient elution with DCM containing 0 to 2% MeOH) afforded methyl 2-(3-chlorophenyl)-7-(morpholinomethyl)-5H-pyrido[3,2-b]indole-4-carboxylate (59 mg, 0.14 mmol, 73% yield) as a yellow oil. MS (ESI) m/z 435.9 (M+H). $^1$H NMR (400 MHz, chloroform-d) δ ppm 9.54 (1H, s), 8.40 (1H, d, J=8.06 Hz), 8.26 (1H, s), 8.23 (1H, t, J=1.76 Hz), 8.06 (1H, dt, J=7.74, 1.42 Hz), 7.56 (1H, s), 7.46 (1H, t, J=7.68 Hz), 7.33-7.43 (2H, m), 4.13 (3H, s), 3.75-3.80 (4H, m), 3.73 (2H, s), 2.51-2.58 (4H, m).

255. Preparation of 2-(3-chlorophenyl)-7-(morpholinomethyl)-5H-pyrido[3,2-b]indole-4-carboxamide A mixture of methyl 2-(3-chlorophenyl)-7-(morpholinomethyl)-5H-pyrido[3,2-b]indole-4-carboxylate (59 mg, 0.14 mmol) and 7 N NH$_3$ in MeOH (3 mL) in a sealed microwave vial was heated at 80° C. overnight. The solvent was removed and preparative HPLC (100×30 mm Luna C18 column, gradient elution with A:B=75:25 to A:B=25:75 [A=95% H$_2$O: 5% MeOH:0.1% TFA; B=5% H$_2$O:95% MeOH:0.1% TFA] over 20 min) SCX capture and release with 2 N NH$_3$ in MeOH afforded 2-(3-chlorophenyl)-7-(morpholinomethyl)-5H-pyrido[3,2-b]indole-4-carboxamide (18 mg, 0.041 mmol, 30% yield) as a white crystalline solid. MS (ESI) m/z 420.8 (M+H). $^1$H NMR (400 MHz, DMSO-d$_6$) δ ppm 11.60 (1H, br. s.), 8.60 (1H, s), 8.47 (1H, s), 8.35 (1H, t, J=1.76 Hz), 8.29 (1H, d, J=8.31 Hz), 8.22 (1H, d, J=8.06 Hz), 7.91 (1H, s), 7.72 (1H, s), 7.58 (1H, t, J=7.81 Hz), 7.44-7.51 (1H, m), 7.26 (1H, dd, J=8.06, 1.26 Hz), 3.64 (2H, s), 3.57-3.63 (4H, m), 2.42 (4H, d, J=2.01 Hz).

EXAMPLE 256

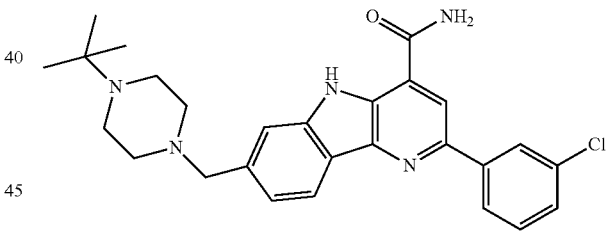

7((4-tert-Butyl-1-piperazinyl)methyl)-2-(3-chlorophenyl)-5H-pyrido[3,2-b]indole-4-carboxamide 256A. Preparation of methyl 2-(3-chlorophenyl)-7-formyl-5H-pyrido[3,2-b]indole-4-carboxylate

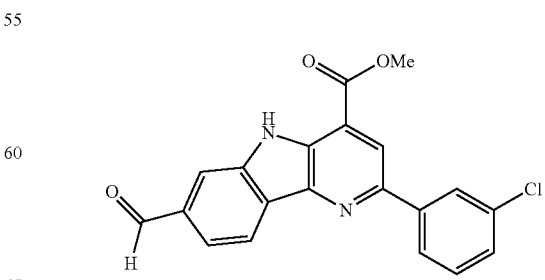

A mixture of 3-chlorophenylboronic acid (73.8 mg, 0.472 mmol), methyl 2-bromo-7-formyl-5H-pyrido[3,2-b]indole- 4-carboxylate (131 mg, 0.393 mmol), powdered potassium phosphate tribasic (200 mg, 0.944 mmol), dicyclohexyl(2',6'-dimethoxybiphenyl-2-yl)phosphine (32.3 mg, 0.079 mmol), and Pd(OAc)$_2$ (8.8 mg, 0.039 mmol) in a microwave vial was flushed with nitrogen. THF (2 mL) was added, the vial was capped and the reaction was heated in a 70° C. oil bath for 24 hr. The reaction was partitioned between EtOAc (10 mL) and water (10 mL). The precipitate was collected by filtration, washed with EtOAc and water and air dried to leave methyl 2-(3-chlorophenyl)-7-formyl-5H-pyrido[3,2-b]indole-4-carboxylate (88 mg, 0.24 mmol, 61% yield) as a yellow solid. MS (ESI) m/z 364.99 (M+H). $^1$H NMR (400 MHz, DMSO-d$_6$) δ ppm 12.04 (1H, br. s.), 10.18 (1H, s), 8.47 (1H, d, J=8.06 Hz), 8.41 (1H, s), 8.28 (1H, s), 8.25 (1H, s), 8.17 (1 H, d, J=7.55 Hz), 7.83 (1H, d, J=8.06 Hz), 7.56 (1H, t, J=7.81 Hz), 7.47-7.53 (1H, m), 4.07 (3H, s).

256B. Preparation of methyl 7-((4-tert-butylpiperazin-1-yl)methyl)-2-(3-chlorophenyl)-5H-pyrido[3,2-b]indole-4-carboxylate

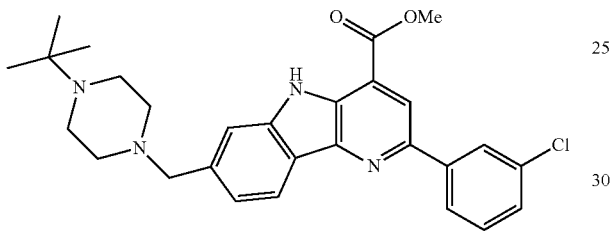

A suspension of methyl 2-(3-chlorophenyl)-7-formyl-5H-pyrido[3,2-b]indole-4-carboxylate (80 mg, 0.22 mmol) in DMF (1 mL) was stirred for 5 min and then diluted with DCM (10 mL). 1-tert-butylpiperazine (38 mg, 0.26 mmol) was added and the suspension was cooled in an ice bath. Sodium triacetoxyborohydride (125 mg, 0.592 mmol) was added and the suspension was left stirring for 0.5 hr. Acetic acid (0.025 mL, 0.44 mmol) was then added and the bath removed. The reaction was left stirring at RT overnight, diluted with DCM, and washed with sat. aq. NaHCO$_3$ solution followed by water (2×). After drying with sodium sulfate, the solvent was removed and radial chromatography (step gradient elution with DCM containing 0 to 3% MeOH) afforded methyl 7-((4-tert-butylpiperazin-1-yl)methyl)-2-(3-chlorophenyl)-5H-pyrido[3,2-b]indole-4-carboxylate (45 mg, 0.092 mmol, 42% yield) as a yellow solid. MS (ESI) m/z 491.19 (M+H). $^1$H NMR (500 MHz, chloroform-d) δ ppm 9.49 (1H, s), 8.36 (1H, d, J=7.94 Hz), 8.24 (1H, s), 8.20 (1H, s), 8.04 (1H, d, J=7.63 Hz), 7.53 (1H, t, J=7.78 Hz), 7.35-7.39 (1H, m), 7.33 (1H, d, J=7.93 Hz), 4.09 (3H, s), 3.70 (2H, s), 2.63 (8H, br. s.), 1.07 (9H, s).

256 Preparation of 7-((4-tert-butylpiperazin-1-yl)methyl)-2-(3-chlorophenyl)-5H-pyrido[3,2-b]indole-4-carboxamide A suspension of methyl 7-((4-tert-butylpiperazin-1-yl)methyl)-2-(3-chlorophenyl)-5H-pyrido[3,2-b]indole-4-carboxylate (45 mg, 0.092 mmol) and 7 N NH$_3$ in MeOH (5 mL) in a sealed microwave vial was heated at 80° C. overnight. The solvent was removed and preparative HPLC (100×30 mm Luna C18 column, gradient elution with A:B=75:25 to A:B=25:75 [A=95% H$_2$O:5% MeOH:0.1% TFA; B=5% H$_2$O:95% MeOH:0.1% TFA] over 20 min) SCX capture and release with 2 N NH$_3$ in MeOH afforded 7-((4-tert-butylpiperazin-1-yl)methyl)-2-(3-chlorophenyl)-5H-pyrido[3,2-b]indole-4-carboxamide (28 mg, 0.055 mmol, 60% yield) as a film. MS (ESI) m/z 476.1 (M+H). $^1$H NMR (500 MHz, MeOD) δ ppm 8.35 (1H, d, J=7.94 Hz), 8.28 (1H, s), 8.22 (1H, d, J=1.53 Hz), 8.09 (1H, d, J=7.93 Hz), 7.64 (1H, s), 7.51 (1H, t, J=7.93 Hz), 7.40-7.45 (1H, m), 7.32 (1H, d, J=7.93 Hz), 3.73 (2H, s), 2.66-2.79 (4H, m), 2.52-2.66 (4H, m), 1.11 (9H, s).

EXAMPLE 257

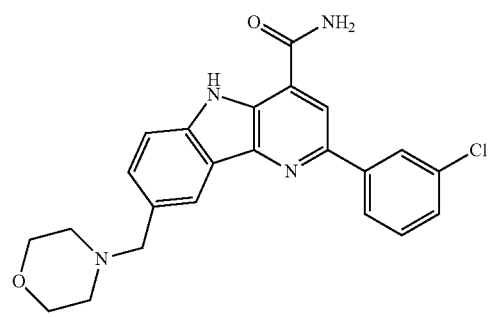 [SMILES: NC(=O)c1cc(-c2cccc(Cl)c2)nc2c1[nH]c1ccc(CN3CCOCC3)cc12]

2-(3-Chlorophenyl)-8-(morpholinomethyl)-5H-pyrido[3,2-b]indole-4-carboxamide

257A. Preparation of methyl 3-amino-6-bromo-2-(3-(hydroxymethyl)phenyl)isonicotinate

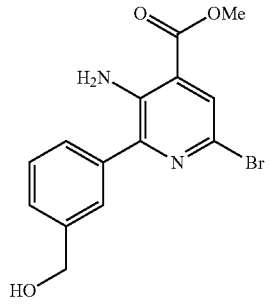 [SMILES: COC(=O)c1cc(Br)nc(-c2cccc(CO)c2)c1N]

A flask containing a mixture of 3-(hydroxymethyl)phenylboronic acid (0.88 g, 5.79 mmol), methyl 3-amino-2,6-dibromoisonicotinate (1.5 g, 4 8 mmol), tetrakistriphenylphosphine Pd(0) (0.335 g, 0.290 mmol), sodium carbonate (1.23 g, 11.6 mmol) was flushed with nitrogen and toluene (12 mL), and MeOH (4 mL) were added. The reaction was heated at reflux under nitrogen for 48 hr. It was partitioned between EtOAc and water and the organic phase was separated, washed with brine, dried with sodium sulfate, and the solvent removed. Chromatography (step gradient elution with DCM containing 0 to 15% EtOAc) afforded methyl 3-amino-6-bromo-2-(3-(hydroxymethyl)phenyl)isonicotinate (1.4 g, 4.2 mmol, 86% yield) as a yellow solid. MS (ESI) m/z 339.02 (M+H). $^1$H NMR (400 MHz, chloroform-d) δ ppm 7.80 (1H, s), 7.58 (1H, s), 7.40-7.55 (3H, m), 5.94 (2H, br. s.), 4.74 (2H, d, J=5.79 Hz), 3.92 (3H, s), 1.77 (1H, t, J=5.92 Hz).

257B Preparation of methyl 3-azido-6-bromo-2-(3-formylphenyl)isonicotinate

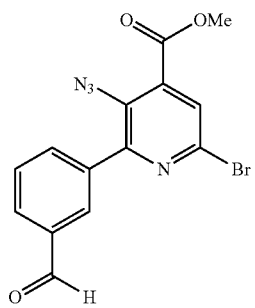 [SMILES: COC(=O)c1cc(Br)nc(-c2cccc(C=O)c2)c1N=[N+]=[N-]]

Methyl 3-amino-6-bromo-2-(3-(hydroxymethyl)phenyl)isonicotinate (1.35 g, 4.00 mmol) was dissolved in TFA (20 mL) and the yellow solution was cooled in an ice bath. Solid sodium nitrite (0.553 g, 8.01 mmol) was added with stirring to give a yellow solution with gas evolution. After 30 min, sodium azide (2.60 g, 40 0 mmol) was added over 5 min followed immediately by Et$_2$O (20 mL). A precipitate formed and, after 0.5 hr, water was added and the mixture was extracted with EtOAc. The organic phases were washed with water (3×), brine (1×), and then saturated Na$_2$CO$_3$ solution (until the aqueous phase was basic) and brine (1×). After drying with sodium sulfate, the solvent was removed. Flash chromatography (step gradient elution with DCM containing 20% hexane, DCM and DCM containing 5% EtOAc) afforded methyl 3-azido-6-bromo-2-(3-formylphenyl)isonicotinate (0.90 g, 2.5 mmol, 63% yield) as a tan solid. $^1$H NMR (400 MHz, chloroform-d) δ ppm 10.09 (1H, s), 8.27 (1H, t, J=1.51 Hz), 8.01-8.07 (1H, m), 7.98 (1H, ddd, J=7.68, 1.51, 1.38 Hz), 7.84 (1H, s), 7.65 (1H, t, J=7.68 Hz), 4.02 (3H, s).

257C. Preparation of methyl 2-bromo-8-formyl-5H-pyrido[3,2-b]indole-4-carboxylate

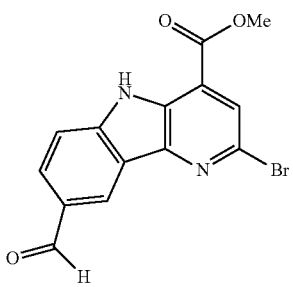 [SMILES: COC(=O)c1cc(Br)nc2c1[nH]c1ccc(C=O)cc12]

1,2-Dichloroethane (1.7 mL) was added to a mixture of methyl 3-azido-6-bromo-2-(3-formylphenyl)isonicotinate (903 mg, 2.50 mmol), rhodium octanoate dimer (156 mg, 0.20 mmol) and crushed 4A° molecular sieves (0.9 gm) in an flask. This was heated at 80° C. for 18 hr. The reaction was diluted THF and filtered. The collected solid was washed with multiple portions of boiling THF to complete extraction of the product. The solvent was removed from the combined filtrates, the residue was suspended in MeOH, and the product was collected by filtration. This left methyl 2-bromo-8-formyl-5H-pyrido[3,2-b]indole-4-carboxylate (484 mg, 1.45 mmol, 58% yield) as a grey solid. MS (ESI) m/z 334.91 (M+H). $^1$H NMR (400 MHz, DMSO-d$_6$) δ ppm 12.25 (1H, s), 10.12 (1H, s), 8.80 (1H, s), 8.11 (1H, d, J=9.32 Hz), 7.98 (1H, s), 7.88 (1H, d, J=8.56 Hz), 3.33 (3H, s).

257D. Preparation of methyl 2-bromo-8-(morpholinomethyl)-5H-pyrido[3,2-b]indole-4-carboxylate

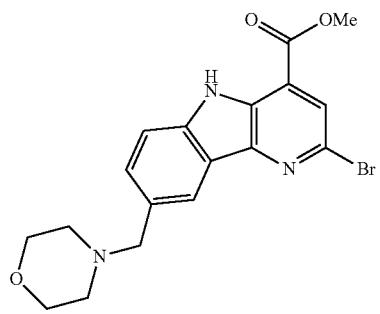 [SMILES: COC(=O)c1cc(Br)nc2c1[nH]c1ccc(CN3CCOCC3)cc12]

A suspension of methyl 2-bromo-8-formyl-5H-pyrido[3,2-b]indole-4-carboxylate (200 mg, 0.600 mmol) in DMF (1 mL) was stirred for 5 min and then diluted with DCM (10 mL). Morpholine (0.063 mL, 0.720 mmol) was added and the suspension was cooled in an ice bath. Sodium triacetoxyborohydride (344 mg, 1.62 mmol) was added and the suspension was left stirring for 0.5 hr. Acetic acid (0.069 mL, 1.20 mmol) was then added and the bath removed. The reaction was left stirring at RT overnight. It was diluted with DCM and washed with sat. aq. NaHCO$_3$ solution followed by water (2×). After drying with sodium sulfate, the solvent was removed and radial chromatography (step gradient elution with DCM containing 0 to 3% MeOH) afforded methyl 2-bromo-8-(morpholinomethyl)-5H-pyrido[3,2-b]indole-4-carboxylate (143 mg, 0.354 mmol, 59% yield) as dark green solid. MS (ESI) m/z 436.10 (M+H). $^1$H NMR (400 MHz, chloroform-d) δ ppm 9.55 (1H, br. s.), 8.27 (1H, s), 7.94 (1H, s), 7.56 (1H, dd, J=8.31, 1.51 Hz), 7.45 (1H, d, J=8.31 Hz), 4.04 (3H, s), 3.66-3.74 (4H, m), 3.64 (2H, s), 2.46 (4H, br. s.).

257E. Preparation of 2-(3-chlorophenyl)-8-(morpholinomethyl)-5H-pyrido[3,2-b]indole-4-carboxamide A mixture of methyl 2-(3-chlorophenyl)-8-(morpholinomethyl)-5H-pyrido[3,2-b]indole-4-carboxylate (68 mg, 0.15 mmol) and 7 N NH$_3$ in MeOH (5 mL) in a sealed microwave vial was heated at 80° C. overnight. The solvent was removed and preparative HPLC (100×30 mm Luna C18 column, gradient elution with A:B=75:25 to A:B=25:75 [A=95% H$_2$O: 5% MeOH:0.1% TFA; B=5% H$_2$O:95% MeOH:0.1% TFA] over 20 min) SCX capture and release with 2 N NH$_3$ in MeOH afforded 2-(3-chlorophenyl)-8-(morpholinomethyl)-5H-pyrido[3,2-b]indole-4-carboxamide (33 mg, 0.073 mmol, 47% yield) as a white crystalline solid. MS (ESI) m/z 421.08 (M+H). $^1$H NMR (400 MHz, MeOD) d ppm 8.32 (1H, s), 8.26 (1H, s), 8.21 (1H, t, J=1.76 Hz), 8.04-8.09 (1H, m), 7.58-7.62 (1H, m), 7.51-7.56 (1H, m), 7.48 (1H, t, J=7.93 Hz), 7.37-7.42 (1H, m), 3.65-3.74 (6H, m), 2.48-2.57 (4H, m).

EXAMPLE 258

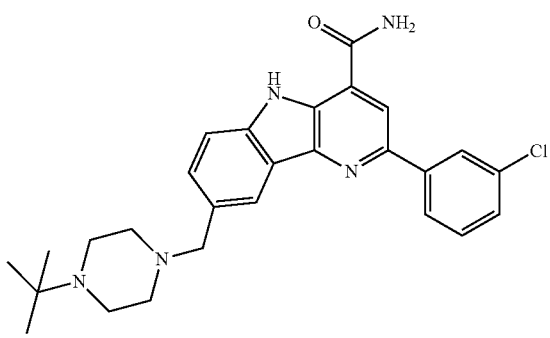 [SMILES: CC(C)(C)N1CCN(Cc2ccc3[nH]c4c(C(N)=O)cc(-c5cccc(Cl)c5)nc4c3c2)CC1]

8-((4-tert-Butylpiperazin-1-yl)methyl)-2-(3-chlorophenyl)-5 H-pyrido[3,2-b]indole-4-carboxamide This was similarly prepared from 2-bromo-8-formyl-5 H-pyrido[3,2-b]indole-4-carboxylate and 1-tert-butylpiperazine. MS (ESI) m/z 476.17 (M+H). $^1$H NMR (400 MHz, MeOD) δ ppm 8.32 (1H, s), 8.26 (1H, s), 8.22 (1H, t, J=1.76 Hz), 8.04-8.10 (1H, m), 7.57-7.62 (1H, m), 7.50-7.55 (1H, m), 7.48 (1H, t, J=7.81 Hz), 7.37-7.42 (1H, m), 3.72 (2H, s), 2.51-2.74 (8H, m), 1.06 (9H, s).

EXAMPLE 259

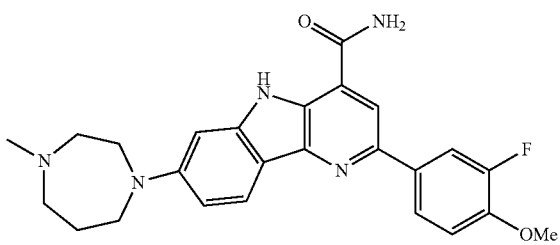 [SMILES: COc1ccc(-c2cc(C(N)=O)c3[nH]c4cc(N5CCCN(C)CC5)ccc4c3n2)cc1F]

2-(3-Fluoro-4-methoxyphenyl)-7-(4-methyl-1,4-diazepan-1-yl)-5 H-pyrido[3,2-b]indole-4-carboxamide

259A. Preparation of methyl 3-Amino-6-bromo-2-(4-chlorophenyl)isonicotinate

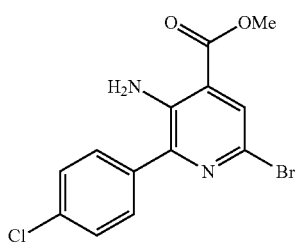 [SMILES: COC(=O)c1cc(Br)nc(-c2ccc(Cl)cc2)c1N]

A mixture of 4-chlorophenylboronic acid (3.03 g, 19.4 mmol), methyl 3-amino-2,6-dibromoisonicotinate (5.0 g, 16 1 mmol), tetrakistriphenylphosphine palladium (0) (1.12 g, 0.968 mmol), sodium carbonate (4.10 g, 38 7 mmol) was flushed with nitrogen, toluene (40 mL), and MeOH (13 mL) were added and the reaction was heated in a 93° C. for 30 hr. This was partitioned between EtOAc and water and the organic phase was washed with brine, dried with sodium sulfate, and the solvent removed. Silica gel chromatography (step gradient elution with DCM containing 75 to 0% hexane) afforded methyl 3-amino-6-bromo-2-(4-chlorophenyl)isonicotinate (3.86 g, 11 3 mmol, 70% yield) as a yellow fluffy solid. MS (ESI) m/z 343.02 (M+H). $^1$H NMR (500 MHz, chloroform-d) δ ppm 7.81 (1H, s), 7.54-7.60 (2H, m), 7.43-7.49 (2H, m), 5.91 (2H, br.s.), 3.93 (3H, s).

259B. Preparation of methyl 3-azido-6-bromo-2-(4-chlorophenyl)isonicotinate

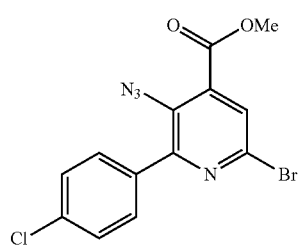 [SMILES: COC(=O)c1cc(Br)nc(-c2ccc(Cl)cc2)c1N=[N+]=[N-]]

Methyl 3-amino-6-bromo-2-(4-chlorophenyl)isonicotinate (3.86g, 11 3 mmol) was dissolved in TFA (57 mL) and the solution was cooled in an ice bath. Solid sodium nitrite (1.72 g, 24 9 mmol) was added slowly with stirring to give a brown solution with gas evolution. After 30 min solid sodium azide (7.35 g, 113 mmol) was added in portions over 5 min with gas evolution. Et$_2$O (57 mL) was slowly added and a precipitate formed. After stirring for 0.5 h, water was added and the mixture was extracted with EtOAc. The combined organic phases were washed with water (3×) and brine (1×) and then saturated aqueous Na$_2$CO$_3$ solution (so that the aqueous phase was basic) and brine (1×). After drying with sodium sulfate, the solvent was removed to leave methyl 3-azido-6-bromo-2-(4-chlorophenyl)isonicotinate (2.41 g, 6.56 mmol, 58.0% yield) as a fluffy yellow solid. $^1$H NMR (400 MHz, chloroform-d) δ ppm 7.79 (1H, s), 7.68-7.73 (2H, m), 7.42-7.47 (2H, m), 4.00 (3H, s).

259C. Preparation of methyl 2-bromo-7-chloro-5H-pyrido[3,2-b]indole-4-carboxylate

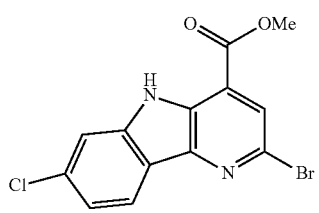 [SMILES: COC(=O)c1cc(Br)nc2c1[nH]c1cc(Cl)ccc12]

1.2-Dichloroethane (4.4 mL) was added to a mixture of methyl 3-azido-6-bromo-2-(4-chlorophenyl)isonicotinate (2.42 g, 6.58 mmol), rhodium octanoate dimer (0.41 g, 0.53 mmol) and crushed 4A° molecular sieves (2.5 gm) and heated at 80° C. for 24 hr. The reaction was diluted with THF and filtered. The collected solid was washed with multiple portions of hot THF to extract remaining product. The solvent was removed from the combined filtrates and the residue was suspended in MeOH and the product was collected by filtration to leave methyl 2-bromo-7-chloro-5H-pyrido[3,2-b]indole-4-carboxylate (1.92 g, 5.65 mmol, 86% yield) as a gray solid. MS (ESI) m/z 340.99 (M+H). $^1$H NMR (500 MHz, DMSO-d$_6$) δ ppm 11.89 (1H, s), 8.19 (1H, d, J=8.24 Hz), 7.92 (1H, s), 7.76 (1H, d, J=1.53 Hz), 7.35 (1H, dd, J=8.55, 1.83 Hz), 4.04 (3H, s).

259D Preparation of methyl 7-chloro-2-(3-fluoro-4-methoxyphenyl)-5H-pyrido[3,2-b]indole-4-carboxylate

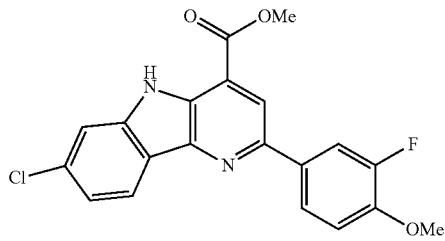 [SMILES: COC(=O)c1cc(-c2ccc(OC)c(F)c2)nc2c1[nH]c1cc(Cl)ccc12]

A flask containing a mixture of 3-fluoro-4-methoxyphenylboronic acid (0.901 g, 5.30 mmol), methyl 2-bromo-7-chloro-5H-pyrido[3,2-b]indole-4-carboxylate (1.5 g, 4.4 mmol), powdered potassium phosphate tribasic (2.25 g, 10 6 mmol), dicyclohexyl(2',6'-dimethoxybiphenyl-2-yl)phosphine (0.363 g, 0.883 mmol), and Pd(OAc)$_2$ (0.099 g, 0.44 mmol) was flushed with nitrogen, THF (22 mL) was added, and the reaction was heated at 70° C. for 20 hr. This was partitioned between EtOAc and water and the organic phase was washed with water and brine and then dried with sodium sulfate. Removal of the solvent followed by silica gel chromatography (step gradient elution with DCM containing 75 to 0% hexane) afforded methyl 7-chloro-2-(3-fluoro-4-methoxyphenyl)-5H-pyrido[3,2-b]indole-4-carboxylate (1.29 g, 3.35 mmol, 76% yield) as a light green solid. MS (ESI) m/z 385.13 (M+H). $^1$H NMR (500 MHz, DMSO-d$_6$) δ ppm 11.89 (1H, s), 8.19 (1H, d, J=8.24 Hz), 7.92 (1H, s), 7.76 (1H, d, J=1.53 Hz), 7.35 (1H, dd, J=8.55, 1.83 Hz), 4.04 (3H, s).

259E Preparation of methyl 2-bromo-7-chloro-5-(4-methoxybenzyl)-5H-pyrido[3,2-b]indole-4-carboxylate

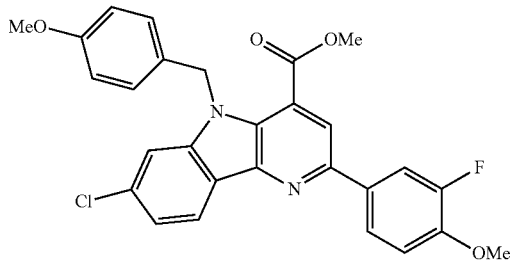 [SMILES: COC(=O)c1cc(-c2ccc(OC)c(F)c2)nc2c3ccc(Cl)cc3n(Cc3ccc(OC)cc3)c12]

1-(Chloromethyl)-4-methoxybenzene (0.72 ml, 5.36 mmol) and sodium iodide (0.80 g, 5 4 mmol) were added to a stirred suspension of methyl 7-chloro-2-(3-fluoro-4-methoxyphenyl)-5H-pyrido[3,2-b]indole-4-carboxylate (1.03 g, 2.68 mmol) and K$_2$CO$_3$ (1.11 g, 8.03 mmol) in DMF (10 ml) at RT. After 2 days this was diluted with EtOAc, washed with water (5×) and brine, and then dried with sodium sulfate. Removal of the solvent followed by radial silica gel chromatography (step gradient elution with hexane containing 0 to 50% DCM) afforded impure methyl 7-chloro-2-(3-fluoro-4-methoxyphenyl)-5-(4-methoxybenzyl)-5H-pyrido[3,2-b]indole-4-carboxylate (820 mg, 1.62 mmol, 61% yield) as a yellow solid that was used as such. MS (ESI) m/z 505.29 (M+H). $^1$H NMR (500 MHz, chloroform-d) δ ppm 8.38 (2H, d, J=8.24 Hz), 7.92-7.97 (3H, m), 7.85 (1H, dd, J=8.55, 1.22 Hz), 7.46 (1H, s), 7.34 (1H, dd, J=8.24, 1.53 Hz), 7.06 (1H, t, J=8.70 Hz), 6.86 (2H, d, J=8.24 Hz), 6.75 (2H, d, J=8.55 Hz), 5.66 (2H, s), 3.95 (3H, s), 3.81 (3H, s), 3.73 (3H, s).

259F Preparation of 2-(3-fluoro-4-methoxyphenyl)-7-(4-methyl-1,4-diazepan-1-yl)-5H-pyrido[3,2-b]indole-4-carboxamide A microwave vial containing a mixture of methyl 7-chloro-2-(3-fluoro-4-methoxyphenyl)-5-(4-methoxybenzyl)-5H-pyrido[3,2-b]indole-4-carboxylate (60 mg, 0.12 mmol), 1-methyl-1,4-diazepane (41 mg, 0.36 mmol), biphenyl-2-yldi-tert-butylphosphine (14 mg, 0.048 mmol), and Pd(OAc)$_2$ (5.3 mg, 0.024 mmol) was flushed with nitrogen. Toluene (0.5 mL) was added and the vial was sealed and heated at 110° C. for 20 hr. The reaction was partitioned between EtOAc and water, the organic phase was washed with brine and the product was captured on an SCX column, washed with MeOH and then removed with 2 N NH$_3$ in MeOH. The solvent was removed to leave crude methyl 2-(3-fluoro-4-methoxyphenyl)-5-(4-methoxybenzyl)-7-(4-methyl-1,4-diazepan-1-yl)-5H-pyrido[3,2-b]indole-4-carboxylate (47 mg). This was placed in a microwave vial, TFA (3 mL) and anisole (0.088 mL, 0.81 mmol) were added. The vial sealed and heated at 70° C. for 3 hr. The solvents were removed and the residue was dissolved in MeOH and applied onto an SCX column. This was washed with MeOH and product was released with 2 N NH$_3$ in MeOH to leave crude methyl 2-(3-fluoro-4-methoxyphenyl)-7-(4-methyl-1,4-diazepan-1-yl)-5H-pyrido[3,2-b]indole-4-carboxylate (37 mg). This was suspended in 7 N NH$_3$ in MeOH (5 mL) and heated at 80° C. for 15 hr. Preparative HPLC (100×30 mm Luna C18 column, gradient elution with A:B=100:0 to A:B=40:60 [A=95% H$_2$O:5% MeOH:0.1% TFA; B=5% H$_2$O:95% MeOH:0.1% TFA] over 20 min) followed by SCX capture and release with 2 N NH$_3$ in MeOH afforded 2-(3-fluoro-4-methoxyphenyl)-7-(4-methyl-1,4-diazepan-1-yl)-5H-pyrido[3,2-b]indole-4-carboxamide (3.2 mg, 6.8 μmol, 7% yield overall) as an orange solid. MS (ESI) m/z 448.29 (M+H). $^1$H NMR (500 MHz, MeOD) δ ppm 8.24 (1H, d, J=8.85 Hz), 8.06 (1H, s), 7.82- 7.94 (2H, m), 7.24 (1H, t, J=8.55 Hz), 6.97 (1H, d, J=2.14 Hz), 6.91 (1H, dd, J=8.85, 2.44 Hz), 3.97 (5H, br. s.), 3.73 (2H, t, J=5.95 Hz), 3.38-3.66 (4H, m), 3.00 (3H, s), 2.28-2.43 (2H, m).

The Examples in the following table were similarly prepared.

TABLE 12

| Ex. # | Structure | Name | Retention time (min) | MS (ESI) m/z M + H+ |
|---|---|---|---|---|
| 260 | 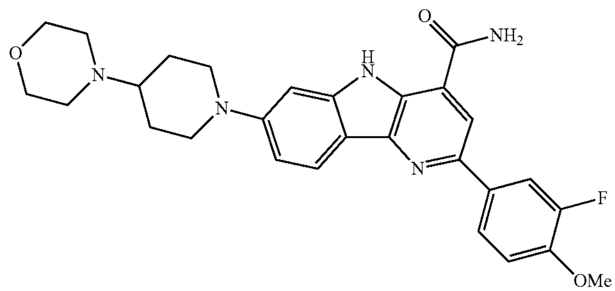 [SMILES: COc1ccc(-c2cc(C(N)=O)c3[nH]c4cc(N5CCC(N6CCOCC6)CC5)ccc4c3n2)cc1F] | 2-(3-fluoro-4-methoxyphenyl)-7-(4-morpholinopiperidin-1-yl)-5H-pyrido[3,2-b]indole-4-carboxamide | 1.73 | 504 |
| 261 | 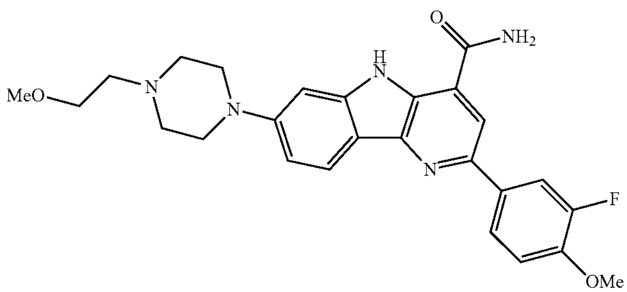 [SMILES: COCCN1CCN(c2ccc3c(c2)[nH]c2c(C(N)=O)cc(-c4ccc(OC)c(F)c4)nc23)CC1] | 2-(3-fluoro-4-methoxyphenyl)-7-(4-(2-methoxyethyl)piperazin-1-yl)-5H-pyrido[3,2-b]indole-4-carboxamide | 1.73 | 478.15 |
| 262 | 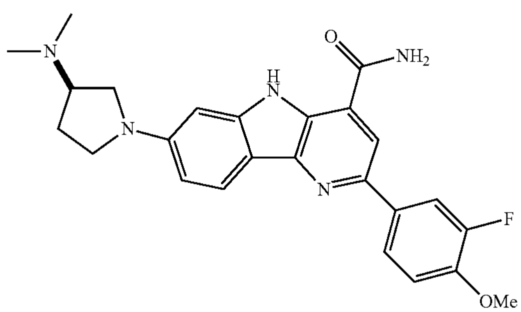 [SMILES: COc1ccc(-c2cc(C(N)=O)c3[nH]c4cc(N5CC[C@@H](N(C)C)C5)ccc4c3n2)cc1F] | (R)-7-(3-(dimethylamino) pyrrolidin-1-yl)-2-(3-fluoro-4-methoxyphenyl)-5H-pyrido[3,2-b]indole-4-carboxamide | 1.54 | 448.14 |
| 263 | 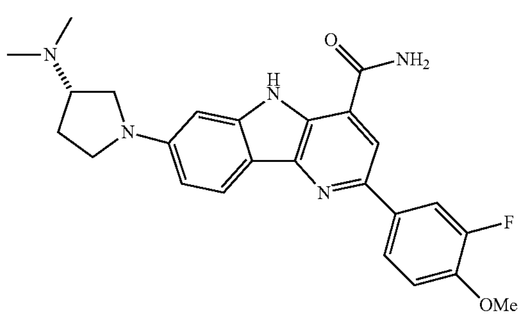 [SMILES: COc1ccc(-c2cc(C(N)=O)c3[nH]c4cc(N5CC[C@H](N(C)C)C5)ccc4c3n2)cc1F] | (S)-7-(3-(dimethylamino) pyrrolidin-1-yl)-2-(3-fluoro-4-methoxyphenyl)-5H-pyrido[3,2-b]indole-4-carboxamide | 1.54 | 448.14 |
| 264 | 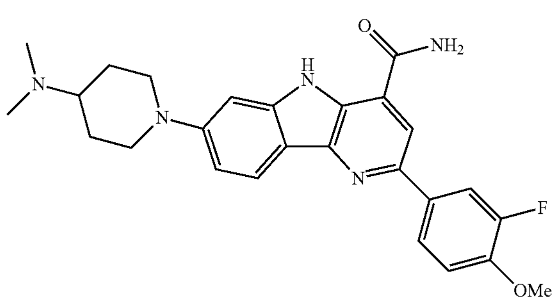 [SMILES: COc1ccc(-c2cc(C(N)=O)c3[nH]c4cc(N5CCC(N(C)C)CC5)ccc4c3n2)cc1F] | 7-(4-(dimethylamino) piperidin-1-yl)-2-(3-fluoro-4-methoxyphenyl)-5H-pyrido[3,2-b]indole-4-carboxamide | 1.67 | 461.00 |

HPLC condition: PHENOMENEX ® Luna S10 3 × 550 mm column, 4 min gradient, 0-100% B, 4 mL/min. Solvent A: 95% MeOH –5% H₂O - 0.1% TFA; Solvent B: 5% MeOH - 95% H₂O - 0.1% TFA.

EXAMPLE 265

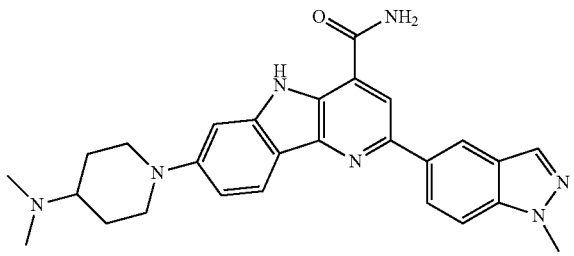 [SMILES: CN(C)C1CCN(c2ccc3c(c2)[nH]c2c(C(N)=O)cc(-c4ccc5c(cnn5C)c4)nc23)CC1]

7-(4-(Dimethylamino)piperidin-1-yl)-2-(1-methyl-1H-indazol-5-yl)-5H-pyrido[3,2-b]indole-4-carboxamide 265A Preparation of methyl 2-bromo-7-chloro-5-(4-methoxybenzyl)-5H-pyrido[3,2-b]indole-4-carboxylate

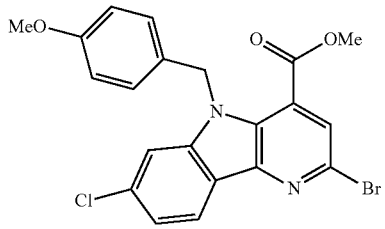 [SMILES: COC(=O)c1cc(Br)nc2c3ccc(Cl)cc3n(Cc3ccc(OC)cc3)c12]

NaH (0.62 g, 15 mmol, 60% oil dispersion) was added to a stirred solution of methyl 2-bromo-7-chloro-5H-pyrido[3,2-b]indole-4-carboxylate (3.5 g, 10.3 mmol) in dry DMF (30 mL) under nitrogen in an ice bath. After 5 min, 1-(chloromethyl)-4-methoxybenzene (1.82 mL, 13 4 mmol) was added and the reaction was removed from the bath and left stirring at RT overnight. The reaction was diluted with EtOAc, washed with water (4×) and then brine. Removal of the solvent followed by step gradient silica gel radial chromatography with hexane containing 25 to 50% DCM afforded impure methyl 2-bromo-7-chloro-5-(4-methoxybenzyl)-5H-pyrido[3,2-b]indole-4-carboxylate (4.0 g) as a light yellow fully solid that was used as such. MS (ESI) m/z 460.95 (M+H). $^1$H NMR (500 MHz, chloroform-d) δ ppm 8.31 (1H, d, J=8.24 Hz), 7.69 (1H, s), 7.47 (1H, d, J=1.53 Hz), 7.34 (1H, dd, J=8.39, 1.68 Hz), 6.78-6.82 (2H, m), 6.73-6.76 (2H, m), 5.63 (2H, s), 3.78 (3H, s), 3.73 (3H, s).

265B. Preparation of methyl 7-chloro-5-(4-methoxybenzyl)-2-(1-methyl-1H-indazol-5-yl)-5H-pyrido[3,2-b]indole-4-carboxylate

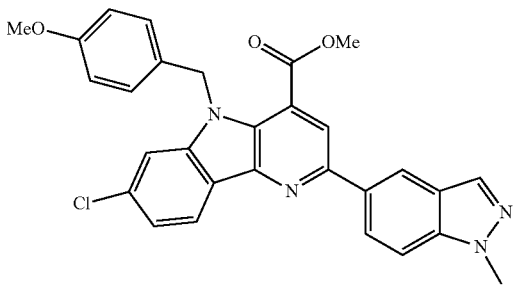 [SMILES: COC(=O)c1cc(-c2ccc3c(cnn3C)c2)nc2c3ccc(Cl)cc3n(Cc3ccc(OC)cc3)c12]

A flask containing a mixture of 1-methyl-1H-indazol-5-ylboronic acid (590 mg, 3.35 mmol), methyl 2-bromo-7-chloro-5-(4-methoxybenzyl)-5H-pyrido[3,2-b]indole-4-carboxylate (1.19 g, 2.58 mmol), powdered potassium phosphate tribasic (1.31 g, 6.19 mmol), dicyclohexyl(2',6'-dimethoxybiphenyl-2-yl)phosphine (0.212 g, 0.516 mmol), and Pd(OAc)$_2$ (0.058 g, 0.258 mmol) was flushed with nitrogen. THF (10 mL) was added and the reaction was heated at 70° C. for 15 hr. The reaction was partitioned between EtOAc and water. The organic phase was washed with water and brine, dried with sodium sulfate, and the solvent was removed. Silica gel chromatography (step gradient elution with DCM containing 0 to 3% EtOAc) afforded methyl 7-chloro-5-(4-methoxybenzyl)-2-(1-methyl-1H-indazol-5-yl)-5H-pyrido[3,2-b]indole-4-carboxylate (720 mg, 1.41 mmol, 55% yield) as a solid. MS (ESI) m/z 511.14 (M+H). $^1$H NMR (500 MHz, chloroform-d) δ ppm 8.47 (1H, s), 8.42 (1H, d, J=8.24 Hz), 8.27 (1H, dd, J=8.55, 1.53 Hz), 8.07 (2H, d, J=2.14 Hz), 7.50 (1H, d, J=8.55 Hz), 7.46 (1H, s), 7.35 (1H, dd, J=8.24, 1.53 Hz), 6.86-6.91 (2H, m), 6.76 (2H, d, J=8.85 Hz), 5.67 (2H, s), 4.12 (3H, s), 3.82 (3H, s), 3.73 (3H, s).

265C. Preparation of 7-(4-(dimethylamino)piperidin-1-yl)-2-(1-methyl-1H-indazol-5-yl)-5H-pyrido[3,2-b]indole-4-carboxamide A microwave vial containing a mixture of methyl 7-chloro-5-(4-methoxybenzyl)-2-(1-methyl-1H-indazol-5-yl)-5H-pyrido[3,2-b]indole-4-carboxylate (100 mg, 0.196 mmol), biphenyl-2-yldi-tert-butylphosphine (23 mg, 0.078 mmol), potassium phosphate tribasic (125 mg, 0.587 mmol), and Pd(OAc)$_2$ (9 mg, 0.04 mmol) was flushed with nitrogen. Toluene (0.8 mL) was added and the vial was sealed and heated at 110° C. for 15 hr. The reaction was partitioned between EtOAc and water. The organic phase was washed with brine and applied onto on an SCX column. This was washed with EtOAc and then MeOH. Release with 2N NH$_3$ in MeOH followed by washing with DCM gave crude methyl 7-(4-(dimethylamino)piperidin-1-yl)-5-(4-methoxybenzyl)-2-(1-methyl-lH-indazol-5-yl)-5H-pyrido[3,2-b]indole-4-carboxylate (102 mg). This was dissolve in TFA (5 mL), anisole (0.19 mL, 1 7 mmol) was added, and the reaction was heated at 75° C. for 4 hr. Solvents were removed and the residue was dissolved in MeOH and applied onto a SCX column and washed with MeOH. Release with 2N NH$_3$ in MeOH left crude methyl 7-(4-(dimethylamino)piperidin-1-yl)-2-(1-methyl-1H-indazol-5-yl)-5H-pyrido[3,2-b]indole-4-carboxylate (83 mg). This was suspended in 7N NH$_3$ in MeOH (7 mL) was heated at 80° C. for 24 hr in a sealed microwave vial. Preparative HPLC (Luna Axia 100×30 mm C18 column, Solvent A=10% Methanol, 90% H$_2$O, 0.1% TFA; Solvent B=90% Methanol, 10% H$_2$O, 0.1% TFA, 0 to 70% B gradient at a flow rate of 42 mL/min over 20 min) followed by SCX capture and release with 2N NH$_3$ in MeOH left 7-(4-(dimethylamino)piperidin-1-yl)-2-(1-methyl-1H-indazol-5-yl)-5H-pyrido[3,2-b]indole-4-carboxamide (36 mg, 0.072 mmol, 42% yield) as a solid. MS (ESI) m/z 468.28 (M+H). $^1$H NMR (400 MHz, DMSO-d$_6$) δ ppm 11.15 (1H, s), 8.61 (1H, s), 8.55 (1H, s), 8.39 (1H, dd, J=8.94, 1.64 Hz), 8.33 (1H, s), 8.17 (1H, s), 8.05 (1H, d, J=8.56 Hz), 7.81 (1H, s), 7.77 (1H, d, J=9.06 Hz), 7.21 (1H, d, J=2.01 Hz), 6.99 (1H, dd, J=8.81, 2.27 Hz), 4.10 (3H, s), 3.84 (2H, d, J=12.84 Hz), 3.14-3.21 (1H, m), 2.74-2.87 (2H, m), 2.23 (6H, s), 1.89 (2H, d, J=10.32 Hz), 1.46-1.60 (2H, m).

The Examples in the following table were similarly prepared.

US 8,815,840 B2

TABLE 13

| Ex. # | Structure | Name | Retention time (min) | MMS (ESI) m/z M + H+ |
|---|---|---|---|---|
| 266 | 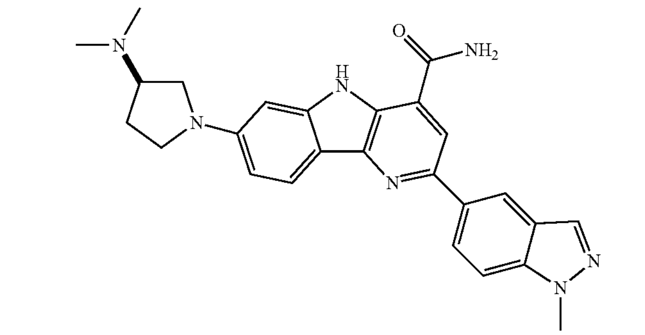 [SMILES: CN(C)[C@@H]1CCN(c2ccc3c(c2)[nH]c2c(C(N)=O)cc(-c4ccc5c(cnn5C)c4)nc23)C1] | (R)-7-(3-(dimethylamino) pyrrolidin-1-yl)-2-(1-methyl-1H-indazol-5-yl)-5H-pyrido[3,2-b]indole-4-carboxamide | 1.17(a) | 454.25 |
| 267 | 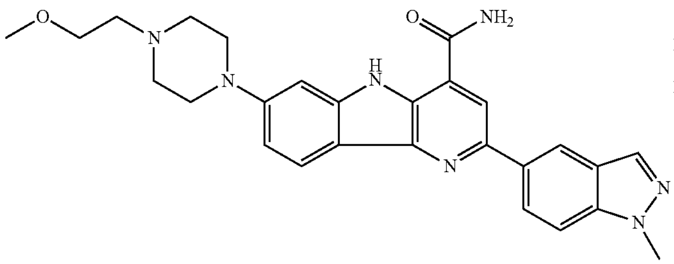 [SMILES: COCCN1CCN(c2ccc3c(c2)[nH]c2c(C(N)=O)cc(-c4ccc5c(cnn5C)c4)nc23)CC1] | 7-(4-(2-methoxyethyl) piperazin-1-yl)-2-(1-methyl-1H-indazol-5-yl)-5H-pyrido[3,2-b]indole-4-carboxamide | 1.51(b) | 484.4 |

HPLC condition a: PHENOMENEX ® Luna S10 3 × 50 mm column, 3 min gradient, 0-100% B, 4 mL/min. Solvent A: 95% MeOH –5% H₂O - 0.1% TFA; Solvent B: 5% MeOH - 95% H₂O - 0.1% TFA.
HPLC condition b: PHENOMENEX ® Luna C18 3 × 50 mm column, 2 min gradient, 0-100% B, 4 mL/min. Solvent A: 5% CH₃CN - 95% H₂O - 10 mM Ammonium Acetate; Solvent B: 95% CH₃CN - 5% H₂O - 10 mM Ammonium Acetate.

EXAMPLE 268

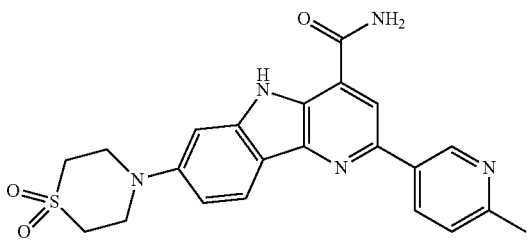 [SMILES: Cc1ccc(-c2cc(C(N)=O)c3[nH]c4cc(N5CCS(=O)(=O)CC5)ccc4c3n2)cn1]

7-(1,1-Dioxido-4-thiomorpholinyl)-2-(6-methyl-3-pyridinyl)-5H-pyrido[3,2-b]indole-4-carboxamide 268A Preparation of methyl 7-chloro-5-(4-methoxybenzyl)-2-(6-methylpyridin-3-yl)-5H-pyrido[3,2-b]indole-4-carboxylate

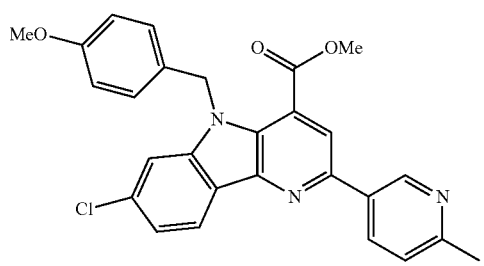 [SMILES: COC(=O)c1cc(-c2ccc(C)nc2)nc2c3ccc(Cl)cc3n(Cc3ccc(OC)cc3)c12]

A flask containing a mixture of 6-methylpyridin-3-ylboronic acid (0.592 g, 4.32 mmol), methyl 2-bromo-7-chloro-5-(4-methoxybenzyl)-5H-pyrido[3,2-b]indole-4-carboxylate (1.24 g, 2.70 mmol), powdered potassium phosphate tribasic (1.38 g, 6.48 mmol), dicyclohexyl(2',6'-dimethoxybiphenyl-2-yl)phosphine (0.222 g, 0.540 mmol), and Pd(OAc)₂ (0.061 g, 0.270 mmol) was flushed with nitrogen. THF (10 mL) was added and the reaction was heated at 70° C. for 15 hr. This was partitioned between EtOAc and water. The organic phase was washed with water and brine, dried with sodium sulfate, and the solvent was removed. Silica gel chromatography (step gradient elution with DCM containing 0 to 3% EtOAc) afforded methyl 7-chloro-5-(4-methoxybenzyl)-2-(6-methylpyridin-3-yl)-5H-pyrido[3,2-b]indole-4-carboxylate (360 mg, 0.763 mmol, 28% yield) as a solid. MS (ESI) m/z 472.12 (M+H). ¹H NMR (500 MHz, chloroform-d) δ ppm 9.18 (1H, s), 8.33-8.42 (2H, m), 7.98 (1H, s), 7.47 (1H, s), 7.34 (1H, d, J=8.24 Hz), 7.28 (1H, d, J=7.93 Hz), 6.86 (2H, d, J=8.24 Hz), 6.75 (2H, d, J=8.55 Hz), 5.66 (2H, s), 3.78-3.84 (3H, m), 3.69-3.74 (3H, m), 2.63 (3H, s).

268B. Preparation of 7-(1,1-dioxido-4-thiomorpholinyl)-2-(6-methyl-3-pyridinyl)-5H-pyrido[3,2-b]indole-4-carboxamide A microwave vial containing a mixture of biphenyl-2-yl-dicyclohexylphosphine (13 mg, 0.037 mmol), thiomorpholine 1,1 dioxide (30 mg, 0.22 mmol), methyl 7-chloro-5-(4-methoxybenzyl)-2-(6-methylpyridin-3-yl)-5H-pyrido[3,2-b]indole-4-carboxylate (88 mg, 0.186 mmol), potassium phosphate, tribasic (59 mg, 0.28 mmol), and tris(dibenzylideneacetone)dipalladium(0) (8.5 mg, 9.3 µmol) was flushed with nitrogen. DME (0.4 mL) was added and the vial was sealed and heated at 100° C. overnight. The reaction was partitioned between EtOAc and water. The organic phase was washed with brine and the product was captured on an SCX column, washed with EtOAc and MeOH and then removed with 2N NH$_3$ in MeOH and DCM. The solvent was removed and the crude methyl 7-(1,1-dioxido-4-thiomorpholinyl)-5-(4-methoxybenzyl)-2-(6-methylpyridin-3-yl)-5H-pyrido[3,2-b]indole-4-carboxylate (74 mg). This was dissolved in TFA (5 mL), anisole (0.142 mL, 1.30 mmol) was added, and the reaction was heated at 75° C. for 4 hr. Solvents were removed and the product was captured on an SCX column, washed with MeOH, and released with 2N NH$_3$ in MeOH to leave crude methyl 7-(1,1-dioxido-4-thiomorpholinyl)-2-(6-methylpyridin-3-yl)-5H-pyrido[3,2-b]indole-4-carboxylate (61 mg). It was suspended in 7 N NH$_3$ in MeOH (7 mL) and heated at 85° C. for 17 hr in a sealed microwave vial. Preparative HPLC (100×30 mm Luna C18 column, gradient elution with A:B=100:0 to A:B=40:60 [A=95% H$_2$O:5% MeOH:0.1% TFA; B=5% H$_2$O:95% MeOH:0.1% TFA] over 20 min) followed by SCX capture and release with 2 N NH$_3$ in MeOH afforded 7-(1,1-dioxido-4-thiomorpholinyl)-2-(6-methyl-3-pyridinyl)-5H-pyrido[3,2-b]indole-4-carboxamide (14 mg, 0.031 mmol, 23% yield) as a yellow solid. MS (ESI) m/z 436.10 (M+H). $^1$H NMR (400 MHz, DMSO-d$_6$) δ ppm 11.29 (1H, br. s.), 9.31 (1H, d, J=2.01 Hz), 8.54 (1H, s), 8.49(1H, dd, J=8.18, 2.39 Hz), 8.35 (1H, s), 8.10 (1H, d, J=8.81 Hz), 7.87 (1H, s), 7.41 (1H, d, J=8.31 Hz), 7.31 (1H, d, J=2.27 Hz), 7.07 (1H, dd, J=8.81, 2.01 Hz), 3.87 (4H, d, J=4.78 Hz), 3.22 (4H, d, J=4.03 Hz), 2.55 (3H, s).

The Examples in the following table were similarly prepared.

TABLE 14

| Ex. # | Structure | Name | Retention time (min) | MMS (ESI) m/z M + H$^+$ |
|---|---|---|---|---|
| 269 | 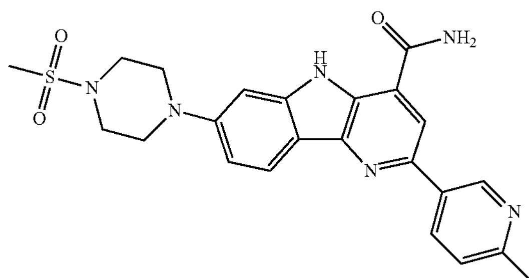 | 2-(6-methylpyridin-3-yl)-7-(4-(methylsulfonyl)piperazin-1-yl)-5H-pyrido[3,2-b]indole-4-carboxamide | 1.58(a) | 465.15 |
| 270 | 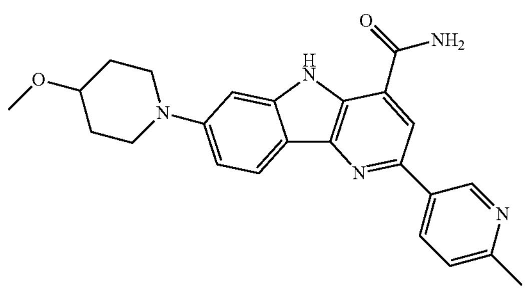 | 7-(4-methoxypiperidin-1-yl)-2-(6-methylpyridin-3-yl)-5H-pyrido[3,2-b]indole-4-carboxamide | 1.26(a) | 416.17 |
| 271 | 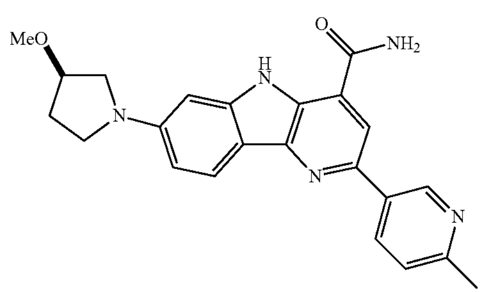 [SMILES: CO[C@@H]1CCN(c2ccc3c(c2)[nH]c2c(C(N)=O)cc(-c4ccc(C)nc4)nc23)C1] | (R)-7-(3-methoxypyrrolidin-1-yl)-2-(6-methylpyridin-3-yl)-5H-pyrido[3,2-b]indole-4-carboxamide | 1.82(a) | 402.13 |
| 272 | 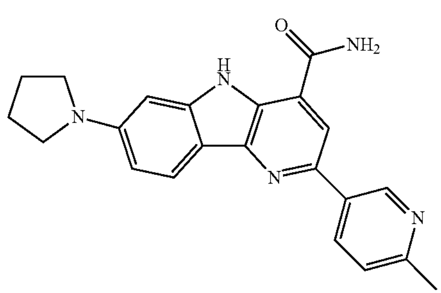 [SMILES: Cc1ccc(-c2cc(C(N)=O)c3[nH]c4cc(N5CCCC5)ccc4c3n2)cn1] | 2-(6-methylpyridin-3-yl)-7-(pyrrolidin-1-yl)-5H-pyrido[3,2-b]indole-4-carboxamide | 1.93(a) | 372.13 |

TABLE 14-continued

| Ex. # | Structure | Name | Retention time (min) | MMS (ESI) m/z M + H+ |
|---|---|---|---|---|
| 273 | 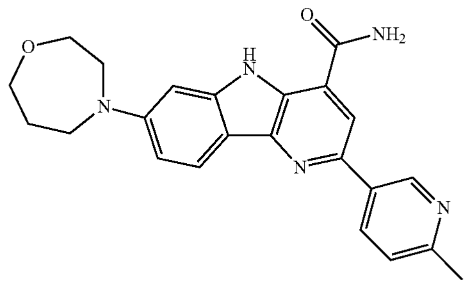 [SMILES: Cc1ccc(-c2cc(C(N)=O)c3[nH]c4cc(N5CCCOCC5)ccc4c3n2)cn1] | 2-(6-methylpyridin-3-yl)-7-(1,4-oxazepan-4-yl)-5H-pyrido[3,2-b]indole-4-carboxamide | 1.66(a) | 402.16 |
| 274 | 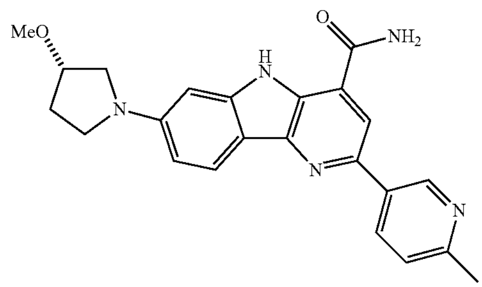 [SMILES: CO[C@H]1CCN(c2ccc3c(c2)[nH]c2c(C(N)=O)cc(-c4ccc(C)nc4)nc23)C1] | (S)-7-(3-methoxypyrrolidin-1-yl)-2-(6-methylpyridin-3-yl)-5H-pyrido[3,2-b]indole-4-carboxamide | 1.82(a) | 402.13 |
| 275 | 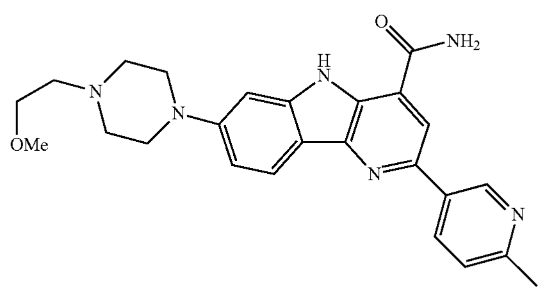 [SMILES: COCCN1CCN(c2ccc3c(c2)[nH]c2c(C(N)=O)cc(-c4ccc(C)nc4)nc23)CC1] | 7-(4-(2-methoxyethyl)piperazin-1-yl)-2-(6-methylpyridin-3-yl)-5H-pyrido[3,2-b]indole-4-carboxamide | 1.09(b) | 445.14 |
| 276 | 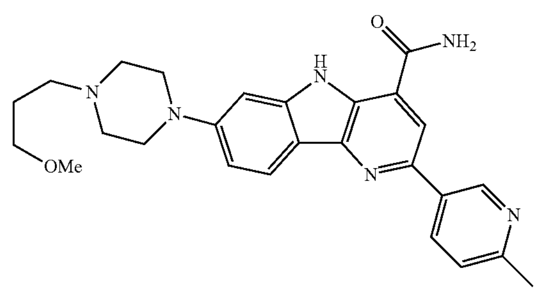 [SMILES: COCCCN1CCN(c2ccc3c(c2)[nH]c2c(C(N)=O)cc(-c4ccc(C)nc4)nc23)CC1] | 7-(4-(3-methoxypropyl)piperazin-1-yl)-2-(6-methylpyridin-3-yl)-5H-pyrido[3,2-b]indole-4-carboxamide | 1.13(b) | 459.18 |
| 277 | 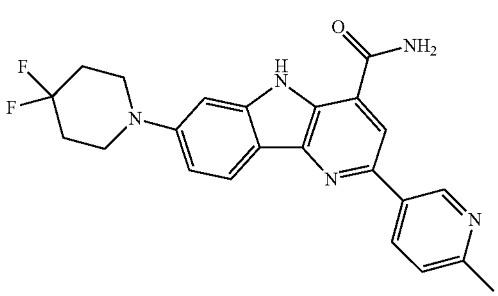 [SMILES: Cc1ccc(-c2cc(C(N)=O)c3[nH]c4cc(N5CCC(F)(F)CC5)ccc4c3n2)cn1] | 7-(4,4-difluoropiperidin-1-yl)-2-(6-methylpyridin-3-yl)-5H-pyrido[3,2-b]indole-4-carboxamide | 1.67(b) | 422.12 |

TABLE 14-continued

| Ex. # | Structure | Name | Retention time (min) | MMS (ESI) m/z M + H⁺ |
|---|---|---|---|---|
| 278 | 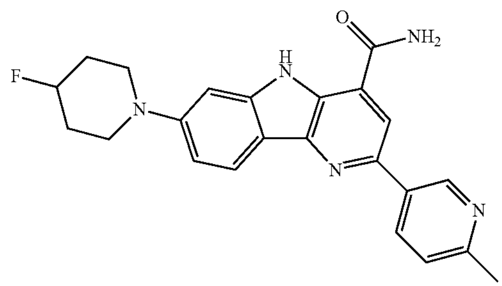 [SMILES: Cc1ccc(-c2cc(C(N)=O)c3[nH]c4cc(N5CCC(F)CC5)ccc4c3n2)cn1] | 7-(4-fluoropiperidin-1-yl)-2-(6-methylpyridin-3-yl)-5H-pyrido[3,2-b]indole-4-carboxamide | 1.34(a) | 404.10 |
| 279 | 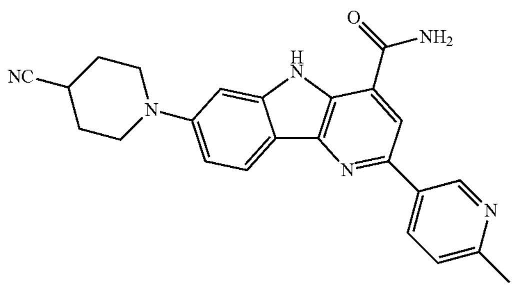 [SMILES: Cc1ccc(-c2cc(C(N)=O)c3[nH]c4cc(N5CCC(C#N)CC5)ccc4c3n2)cn1] | 7-(4-cyanopiperidin-1-yl)-2-(6-methylpyridin-3-yl)-5H-pyrido[3,2-b]indole-4-carboxamide | 1.67(a) | 411.12 |
| 280 | 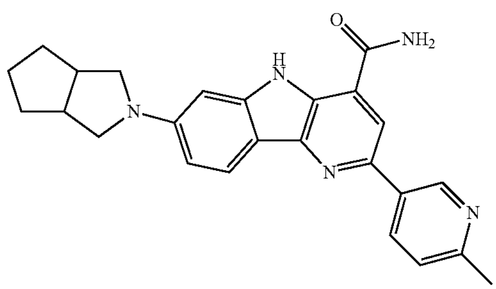 [SMILES: Cc1ccc(-c2cc(C(N)=O)c3[nH]c4cc(N5CC6CCCC6C5)ccc4c3n2)cn1] | 7-(hexahydrocyclopenta[c]pyrrol-2(1H)-yl)-2-(6-methylpyridin-3-yl)-5H-pyrido[3,2-b]indole-4-carboxamide | 1.34(a) | 412.1 |
| 281 | 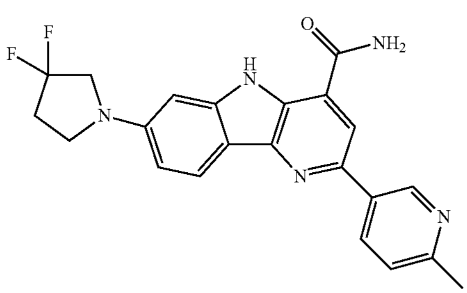 [SMILES: Cc1ccc(-c2cc(C(N)=O)c3[nH]c4cc(N5CCC(F)(F)C5)ccc4c3n2)cn1] | 7-(3,3-difluoropyrrolidin-1-yl)-2-(6-methylpyridin-3-yl)-5H-pyrido[3,2-b]indole-4-carboxamide | 2.08(a) | 408.10 |
| 282 | 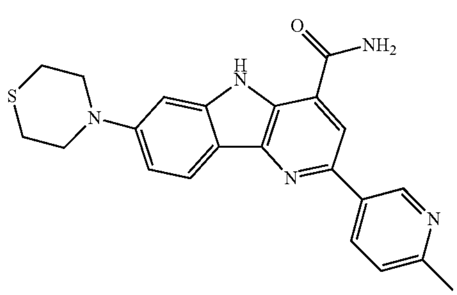 [SMILES: Cc1ccc(-c2cc(C(N)=O)c3[nH]c4cc(N5CCSCC5)ccc4c3n2)cn1] | 2-(6-methylpyridin-3-yl)-7-thiomorpholino-5H-pyrido[3,2-b]indole-4-carboxamide | 1.68(a) | 404.07 |

TABLE 14-continued

| Ex. # | Structure | Name | Retention time (min) | MMS (ESI) m/z M + H+ |
|---|---|---|---|---|
| 283 | 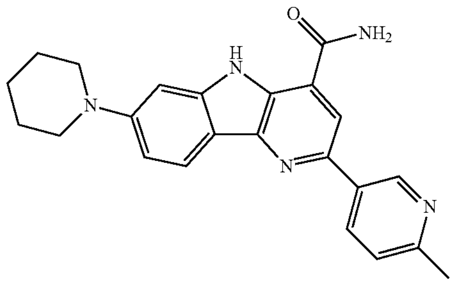 [SMILES: Cc1ccc(-c2cc(C(N)=O)c3[nH]c4cc(N5CCCCC5)ccc4c3n2)cn1] | 2-(6-methylpyridin-3-yl)-7-(piperidin-1-yl)-5H-pyrido[3,2-b]indole-4-carboxamide | 1.14(a) | 386.16 |
| 284 | 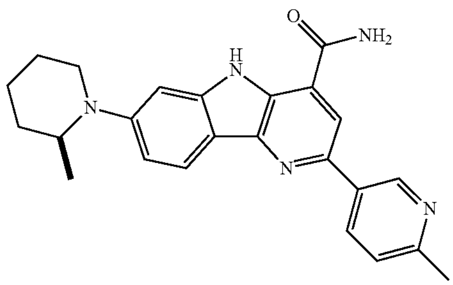 [SMILES: Cc1ccc(-c2cc(C(N)=O)c3[nH]c4cc(N5CCCC[C@@H]5C)ccc4c3n2)cn1] | (S)-7-(2-methylpiperidin-1-yl)-2-(6-methylpyridin-3-yl)-5H-pyrido[3,2-b]indole-4-carboxamide | 1.18(a) | 400.14 |
| 285 | 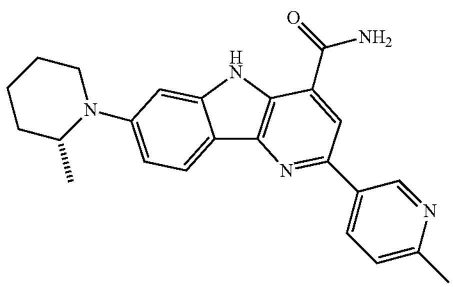 [SMILES: Cc1ccc(-c2cc(C(N)=O)c3[nH]c4cc(N5CCCC[C@H]5C)ccc4c3n2)cn1] | (R)-7-(2-methylpiperidin-1-yl)-2-(6-methylpyridin-3-yl)-5H-pyrido[3,2-b]indole-4-carboxamide | 1.18(a) | 400.14 |
| 286 | 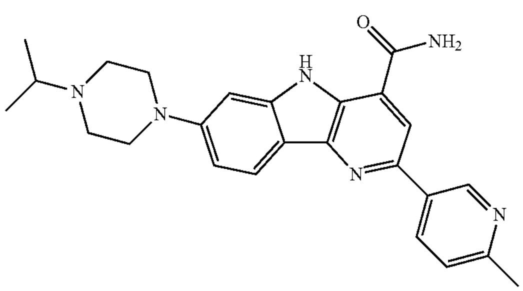 [SMILES: Cc1ccc(-c2cc(C(N)=O)c3[nH]c4cc(N5CCN(C(C)C)CC5)ccc4c3n2)cn1] | 7-(4-isopropylpiperazin-1-yl)-2-(6-methylpyridin-3-yl)-5H-pyrido[3,2-b]indole-4-carboxamide | 1.12(a) | 429.16 |
| 287 | 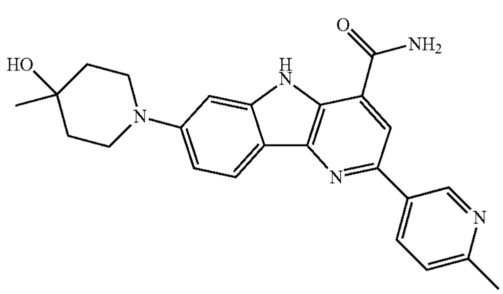 | 7-(4-hydroxy-4-methylpiperidin-1-yl)-2-(6-methylpyridin-3-yl)-5H-pyrido[3,2-b]indole-4-carboxamide | 1.05(a) | 416.10 |

HPLC condition a: PHENOMENEX ® Luna S10 3 × 50 mm column, 4 min gradient, 0-100% B, 4 mL/min. Solvent A: 95% MeOH −5% $H_2O$ - 0.1% TFA; Solvent B: 5% MeOH - 95% $H_2O$ - 0.1% TFA.
HPLC condition b: PHENOMENEX ® Luna C18 3 × 50 mm column, 3 min gradient, 0-100% B, 4 mL/min. Solvent A: 95% MeOH −5% $H_2O$ - 0.1% TFA; Solvent B: 5% MeOH - 95% $H_2O$ - 0.1% TFA.

EXAMPLE 288

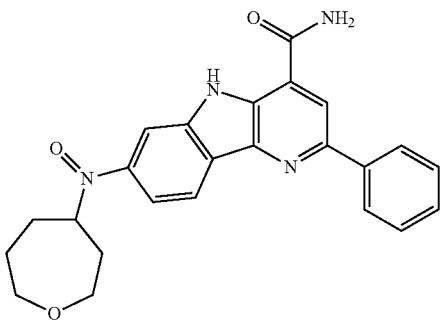

7-(1,4-Oxazepan-4-ylcarbonyl)-2-phenyl-5H-pyrido[3,2-b]indole-4-carboxamide

288A. Preparation of methyl 3-amino-6-bromo-2-(4-(isopropoxycarbonyl)phenyl)isonicotinate

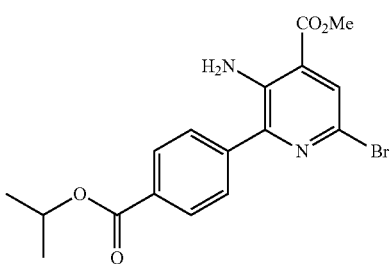 [SMILES: COC(=O)c1cc(Br)nc(-c2ccc(C(=O)OC(C)C)cc2)c1N]

A mixture of 4-isopropoxycarbonylphenylboronic acid (0.98 g, 4 7 mmol), sodium carbonate (1.02 g, 9.58 mmol), tetrakistriphenylphosphine palladium (0) (0.205 g, 0.177 mmol), and methyl 3-amino-2,6-dibromoisonicotinate (1.1 g, 3 6 mmol) in a vial was flushed with nitrogen. Toluene (12 mL) and methanol (4 mL) were added and the reaction stirred at 110° C. for 16 h. The reaction mixture was partitioned between EtOAc and sat. aq. sodium bicarbonate solution. The organic phase was washed with sat. aq. sodium bicarbonate solution, brine, and dried with sodium sulfate. Removal of the solvents followed by silica gel chromatography (step gradient elution with hexane containing 0 to 20% EtOAc afforded methyl 3-amino-6-bromo-2-(4-(isopropoxycarbonyl)phenyl)isonicotinate (1.04 g, 2.59 mmol, 73% yield). MS (ESI) m/z 393.00 (M+H). $^1$H NMR (500 MHz, chloroform-d) δ ppm 8.14 (2H, d, J=8.24 Hz), 7.84 (1H, s), 7.69 (2H, d, J=8.24 Hz), 5.94 (2H, br. s.), 5.27 (1H, dt, J=12.51, 6.26 Hz), 3.93 (3H, s), 1.38 (6H, d, J=6.10 Hz).

288B. Preparation of methyl 3-azido-6-bromo-2-(4-(isopropoxycarbonyl)phenyl)isonicotinate

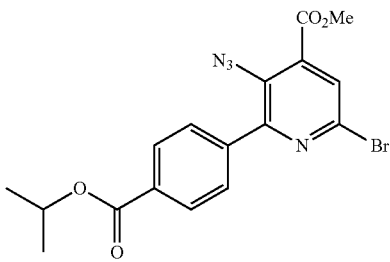 [SMILES: COC(=O)c1cc(Br)nc(-c2ccc(C(=O)OC(C)C)cc2)c1N=[N+]=[N-]]

Methyl 3-amino-6-bromo-2-(4-(isopropoxycarbonyl)phenyl)isonicotinate (1.0 g, 2.54 mmol) was dissolved in TFA (15 mL) and the yellow solution was cooled in an ice bath. Sodium nitrite (0.351 g, 5.09 mmol) was added with stirring to give a dark yellow mixture. After 30 min, sodium azide (1.65 g, 25.4 mmol) was added followed immediately by Et$_2$O (15 mL). The light yellow mixture was stirred in the ice bath for 30 min. It was partitioned between EtOAc and sufficient sat. aq. NaHCO$_3$ solution to neutralize the acid. The organic phase was washed with brine, dried with sodium sulfate, and the solvent removed to leave methyl 3-azido-6-bromo-2-(4-(isopropoxycarbonyl)phenyl)isonicotinate (1.0 gm, 2.3 mmole, 92% yield). $^1$H NMR (500 MHz, chloroform-d) δ ppm 8.13 (2H, d, J=8.24 Hz), 7.82 (2H, d, J=4.58 Hz), 7.80 (1H, s), 5.24-5.30 (1H, m), 4.01 (3H, s), 1.38 (6H, d, J=6.10 Hz).

288C. Preparation of 7-isopropyl 4-methyl 2-bromo-5H-pyrido[3,2-b]indole-4,7-dicarboxylate

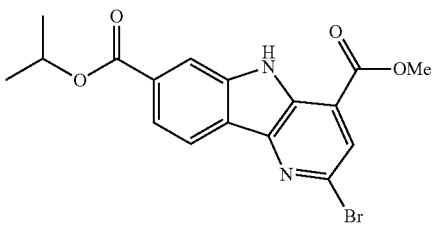 [SMILES: COC(=O)c1cc(Br)nc2c1[nH]c1cc(C(=O)OC(C)C)ccc12]

A solution of methyl 3-azido-6-bromo-2-(4-(isopropoxycarbonyl)phenyl)-isonicotinate (1.0 g, 2 4 mmol) in 1,2-dichlorobenzene (30 mL) was heated under reflux for 5min. After removal of the solvent under reduced pressure the residue was purified by silica gel chromatography (elution with hexane containing 30% EtOAc) to afford 7-isopropyl 4-methyl 2-bromo-5H-pyrido[3,2-b]indole-4,7-dicarboxylate (0.48 g, 1.20 mmol, 50% yield). MS (ESI) m/z 391.1 (M+H). $^1$H NMR (500 MHz, DMSO-d$_6$) δ ppm 12.05 (1H, br. s.), 8.42 (1H, s), 8.33 (1H, d, J=8.24 Hz), 8.01 (1H, d, J=1.22 Hz), 7.91 (1H, d, J=8.24 Hz), 5.22 (1H, quin, J=6.03 Hz), 4.06 (3H, s), 1.39 (6H, d, J=6.10 Hz).

288D Preparation of 7-isopropyl 4-methyl 2-phenyl-5H-pyrido[3,2-b]indole-4,7-dicarboxylate

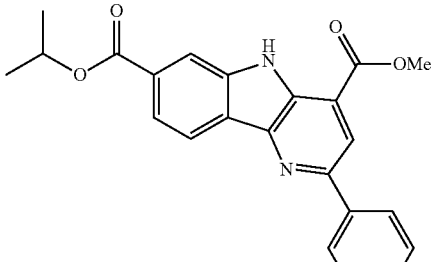

A flask containing a mixture of phenylboronic acid (0.935 g, 7.67 mmol), 7-isopropyl 4-methyl 2-bromo-5H-pyrido[3,2-b]indole-4,7-dicarboxylate (1.00 g, 2.56 mmol), powdered potassium phosphate tribasic (2.387 g, 11.25 mmol), 2-dicyclohexylphosphino-2',4',6'-tri-iso-propyl-1,1'-biphenyl (0.244 g, 0.511 mmol), and Pd(OAc)$_2$ (0.057 g, 0.256 mmol)

was flushed with nitrogen. THF (8 mL) was added and the mixture was heated at 80° C. for 3 hr. The mixture was diluted with EtOAc, washed with water, dried with sodium sulfate, and the solvents removed. Silica gel chromatography (step gradient elution with hexane containing 50% to 100% DCM) afforded 7-isopropyl 4-methyl 2-phenyl-5H-pyrido[3,2-b]indole-4,7-dicarboxylate (0.7 g, 1.8 mmol, 68% yield). MS (ESI) m/z 388.99 (M+H). $^1$H NMR (500 MHz, chloroform-d) δ ppm 9.68 (1H, s), 8.52 (1H, d, J=8.24 Hz), 8.39 (1H, s), 8.30 (1H, s), 8.21 (2H, d, J=7.32 Hz), 8.08 (1H, d, J=8.24 Hz), 7.56 (2H, t, J=7.63 Hz), 7.41-7.51 (1H, m), 5.36 (1H, dt, J=12.51, 6.26 Hz), 4.14 (3H, s), 1.46 (6H, d, J=6.41 Hz).

288E Preparation of 7-(isopropoxycarbonyl)-2-phenyl-5H-pyrido[3,2-b]indole-4-carboxylic acid

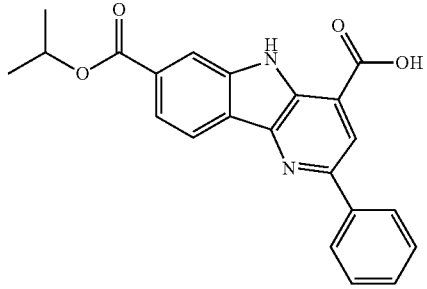 [SMILES: CC(C)OC(=O)c1ccc2c(c1)[nH]c1c(C(=O)O)cc(-c3ccccc3)nc12]

A solution of 7-isopropyl 4-methyl 2-phenyl-5H-pyrido[3,2-b]indole-4,7-dicarboxylate (380 mg, 0.978 mmol) in a mixture of THF (5.6 mL), MeOH (1.9 mL) and 1 N aqueous sodium hydroxide solution (2.0 mL, 2.0 mmol) was stirred at 25° C. for 15 min. The reaction was treated with 1 N aqueous HCl (0.52 mL) and the organic solvents were removed. The residue was diluted with water and acidified to about pH 3.0 with 1 N aqueous HCl to give an yellow gel-like precipitate. This was chilled in an ice bath and the precipitate was collected by filtration, washed with water and dried to leave impure 7-(isopropoxycarbonyl)-2-phenyl-5H-pyrido[3,2-b]indole-4-carboxylic acid (395 mg). MS (ESI) m/z 375.09 (M+H). $^1$H NMR (500 MHz, DMSO-d$_6$) δ ppm 11.88 (1H, s), 8.35-8.50 (3H, m), 8.25 (2H, d, J=7.94 Hz), 7.83-7.96 (1H, m), 7.56 (2H, t, J=7.78 Hz), 7.46 (1H, t, J=7.17 Hz), 5.22 (1H, quin, J=6.26 Hz), 1.40 (6H, d, J=6.10 Hz).

288F. Preparation of isopropyl 4-carbamoyl-2-phenyl-5H-pyrido[3,2-b]indole-7-carboxylate

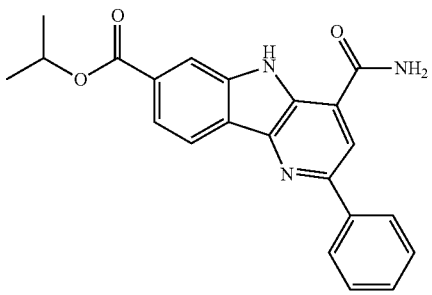 [SMILES: CC(C)OC(=O)c1ccc2c(c1)[nH]c1c(C(N)=O)cc(-c3ccccc3)nc12]

Dry DMF (10 mL) was added to a mixture of 7-(isopropoxycarbonyl)-2-phenyl-5H-pyrido[3,2-b]indole-4-carboxylic acid (0.95 g, 2.54 mmol), NH$_4$Cl (0.41 g, 7.6 mmol), EDC (1.46 g, 7.61 mmol), and 1-hydroxybenzotriazole hydrate (1.03 g, 7.61 mmol). After stirring for a few minutes, TEA (1.06 mL, 7.61 mmol) was added and the reaction left stirred overnight. It was diluted with water (200 ml) and the precipitate was collected by filtration, washed with water and dried to leave isopropyl 4-carbamoyl-2-phenyl-5H-pyrido[3,2-b]indole-7-carboxylate (0.925 g, 2.28 mmol, 90% yield) as a yellow solid. MS (ESI) m/z 374.04 (M+H). $^1$H NMR (500 MHz, DMSO-d$_6$) δ ppm 11.89 (1H, s), 8.66 (1H, br. s.), 8.54 (1H, s), 8.46 (1H, s), 8.38 (1H, d, J=8.24 Hz), 8.33 (2H, d, J=7.32 Hz), 7.92-7.99 (1H, m), 7.88 (1H, dd, J=8.24, 1.22 Hz), 7.57 (2H, t, J=7.63 Hz), 7.46 (1H, t, J=7.32 Hz), 5.22 (1H, dt, J=12.51, 6.26 Hz), 1.39 (6H, d, J=6.41 Hz).

288G Preparation of 4-carbamoyl-2-phenyl-5H-pyrido[3,2-b]indole-7-carboxylic acid

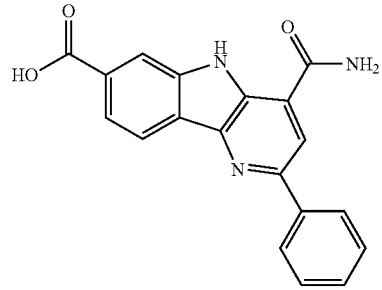 [SMILES: NC(=O)c1cc(-c2ccccc2)nc2c1[nH]c1cc(C(=O)O)ccc12]

A solution of isopropyl 4-carbamoyl-2-phenyl-5H-pyrido[3,2-b]indole-7-carboxylate (2 g, 5.36 mmol) in a mixture of THF (36 ml), MeOH (15 ml) and 1 N aqueous NaOH (12 ml, 120 mmol) was stirred at 25° C. overnight. The organic solvents were removed and the residue was dissolved in water, washed with DCM (20 mL), and acidified to about pH 3 with 1 N aqueous HCl to give a yellow gel-like precipitate. This was chilled in an ice bath and the precipitate was collected by filtration, washed with water, and dried to leave 4-carbamoyl-2-phenyl-5H-pyrido[3,2-b]indole-7-carboxylic acid (2.1 g, 5.1 mmol, 95% yield). MS (ESI) m/z 332.00 (M+H). $^1$H NMR (500 MHz, MeOD) δ ppm 8.67 (1H, d, J=8.55 Hz), 8.58-8.64 (1H, m), 8.54 (1H, s), 8.03-8.17 (3H, m), 7.67-7.79 (3H, m).

288. Preparation of 7-(1,4-oxazepane-4-carbonyl)-2-phenyl-5H-pyrido[3,2-b]indole-4-carboxamide A mixture of 1,4-oxazepane (15 mg, 0.15 mmol), 4-carbamoyl-2-phenyl-5H-pyrido[3,2-b]indole-7-carboxylic acid (50 mg, 0.15 mmol), and N-ethyl-N-isopropylpropan-2-amine (0.071 mL, 0.41 mmol) in dry DMF (1.3 mL) was stirring for a few minutes and then benzotriazol-1-yloxytris(dimethylamino)phosphonium hexafluorophosphate (80 mg, 0.18 mmol) was added. After 1 hr, the reaction was diluted with MeOH and preparative HPLC (PHENOMENEX® Luna 30×100 mm C18, Solvent A=10% acetonitrile -90% H$_2$O—0.1% TFA; Solvent B=90% acetonitrile—10% H$_2$O —0.1% TFA, 10-70% B gradient over 18 min) afforded 7-(1,4-oxazepane-4-carbonyl)-2-phenyl-5H-pyrido[3,2-b]indole-4-carboxamide (45 mg, 0.11 mmol, 70% yield) as a yellow solid. MS (ESI) m/z 415.09 (M+H). $^1$H NMR (500 MHz, DMSO-d$_6$) δ ppm 11.75 (1H, br. s.), 8.65 (1H, br. s.), 8.50 (1H, s), 8.31 (3H, d, J=7.63 Hz), 7.92 (1H, br. s.), 7.78 (1H, br. s.), 7.56 (2H, t, J=7.63 Hz), 7.45 (1H, t, J=7.32 Hz), 7.28 (1H, d, J=7.63 Hz), 3.77 (5H, br. s.), 3.65 (1H, br. s.), 3.50 (2H, br. s.), 1.94 (1H, br. s.), 1.79 (1H, br. s.).

The Examples in the following table were similarly prepared.

TABLE 15

| Ex. # | Structure | Name | Retention time (min) | MS (ESI) m/z M + H+ |
|---|---|---|---|---|
| 289 | 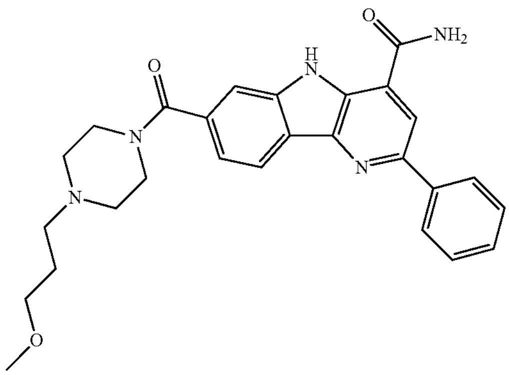 [SMILES: COCCCN1CCN(C(=O)c2ccc3c(c2)[nH]c2c(C(N)=O)cc(-c4ccccc4)nc23)CC1] | 7-(4-(3-methoxypropyl) piperazine-1-carbonyl)-2-phenyl-5H-pyrido[3,2-b]indole-4-carboxamide | 1.67(a) | 472.15 |
| 290 | 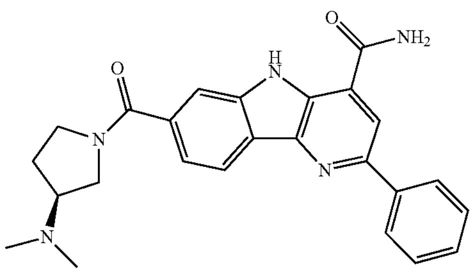 [SMILES: CN(C)[C@H]1CCN(C(=O)c2ccc3c(c2)[nH]c2c(C(N)=O)cc(-c4ccccc4)nc23)C1] | (S)-7-(3-(dimethylamino) pyrrolidine-1-carbonyl)-2-phenyl-5H-pyrido[3,2-b]indole-4-carboxamide | 1.58(a) | 428.1 |
| 291 | 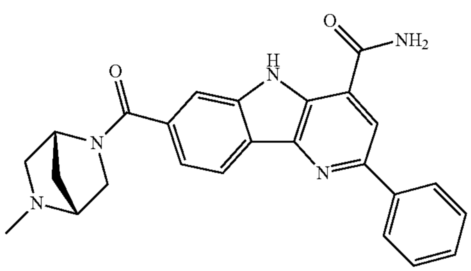 [SMILES: CN1C[C@H]2C[C@@H]1CN2C(=O)c1ccc2c(c1)[nH]c1c(C(N)=O)cc(-c3ccccc3)nc12] | 7-((1S,4S)-5-methyl-2,5-diazabicyclo[2.2.1]heptane-2-carbonyl)-2-phenyl-5H-pyrido[3,2-b]indole-4-carboxamide | 1.27(b) | 426.04 |
| 292 | 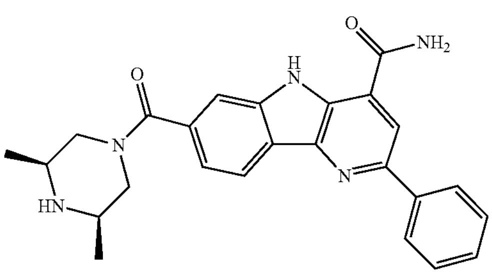 [SMILES: C[C@@H]1CN(C(=O)c2ccc3c(c2)[nH]c2c(C(N)=O)cc(-c4ccccc4)nc23)C[C@H](C)N1] | 7-((3S,5R)-3,5-dimethylpiperazine-1-carbonyl)-2-phenyl-5H-pyrido[3,2-b]indole-4-carboxamide | 1.39(b) | 428.08 |
| 293 | 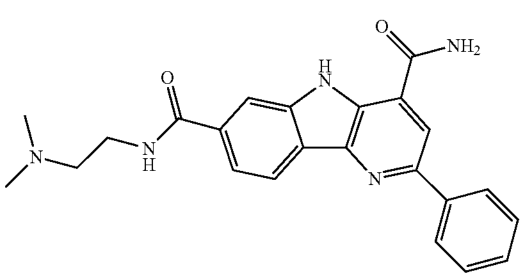 [SMILES: CN(C)CCNC(=O)c1ccc2c(c1)[nH]c1c(C(N)=O)cc(-c3ccccc3)nc12] | N7-(2-(dimethylamino)ethyl)-2-phenyl-5H-pyrido[3,2-b]indole-4,7-dicarboxamide | 1.40(b) | 402.11 |

TABLE 15-continued

| Ex. # | Structure | Name | Retention time (min) | MS (ESI) m/z M + H+ |
|---|---|---|---|---|
| 294 | 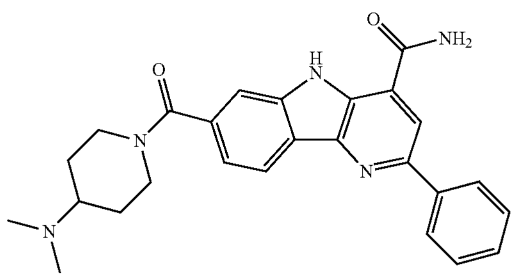 [SMILES: CN(C)C1CCN(C(=O)c2ccc3c(c2)[nH]c2c(C(N)=O)cc(-c4ccccc4)nc23)CC1] | 7-(4-(dimethylamino) piperidine-1-carbonyl)-2-phenyl-5H-pyrido[3,2-b]indole-4-carboxamide | 1.47(c) | 442.1 |
| 295 | 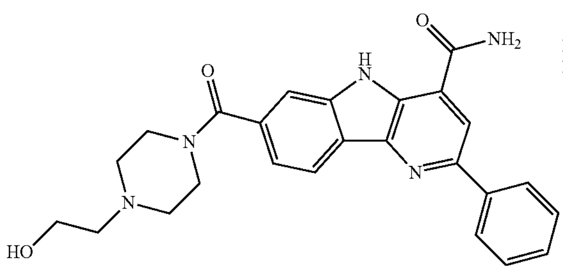 [SMILES: NC(=O)c1cc(-c2ccccc2)nc2c1[nH]c1cc(C(=O)N3CCN(CCO)CC3)ccc12] | 7-(4-(2-hydroxyethyl) piperazine-1-carbonyl)-2-phenyl-5H-pyrido[3,2-b]indole-4-carboxamide | 1.28(c) | 441.1 |
| 296 | 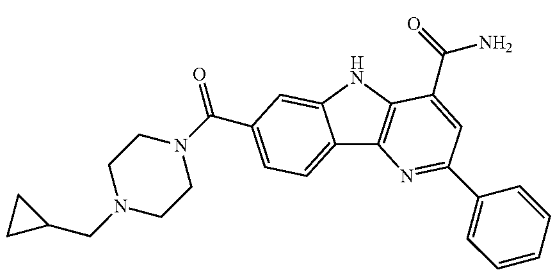 [SMILES: NC(=O)c1cc(-c2ccccc2)nc2c1[nH]c1cc(C(=O)N3CCN(CC4CC4)CC3)ccc12] | 7-(4-(cyclopropylmethyl) piperazine-1-carbonyl)-2-phenyl-5H-pyrido[3,2-b]indole-4-carboxamide | 1.39(b) | 454.11 |
| 297 | 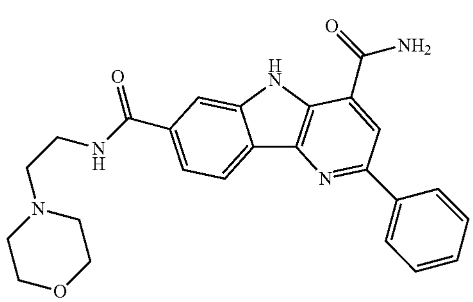 [SMILES: NC(=O)c1cc(-c2ccccc2)nc2c1[nH]c1cc(C(=O)NCCN3CCOCC3)ccc12] | N$^7$-(2-morpholinoethyl)-2-phenyl-5H-pyrido[3,2-b]indole-4,7-dicarboxamide | 1.42(b) | 444.08 |
| 298 | 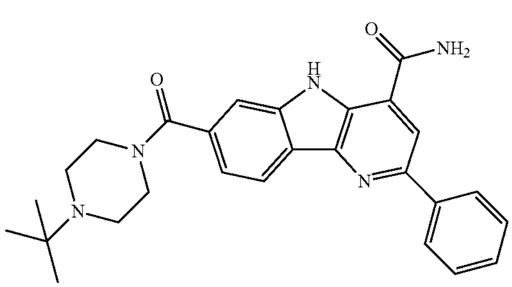 [SMILES: CC(C)(C)N1CCN(C(=O)c2ccc3c(c2)[nH]c2c(C(N)=O)cc(-c4ccccc4)nc23)CC1] | 7-(4-tert-butyl piperazine-1-carbonyl)-2-phenyl-5H-pyrido[3,2-b]indole-4-carboxamide | 1.47(c) | 456.1 |

TABLE 15-continued

| Ex. # | Structure | Name | Retention time (min) | MS (ESI) m/z M + H[+] |
|---|---|---|---|---|
| 299 | 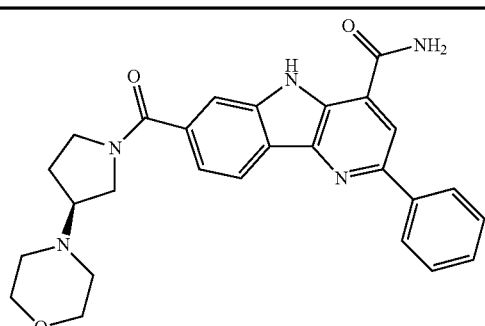 | (S)-7-(3-morpholinopyrrolidine-1-carbonyl)-2-phenyl-5H-pyrido[3,2-b]indole-4-carboxamide | 1.58(a) | 470.11 |
| 300 | 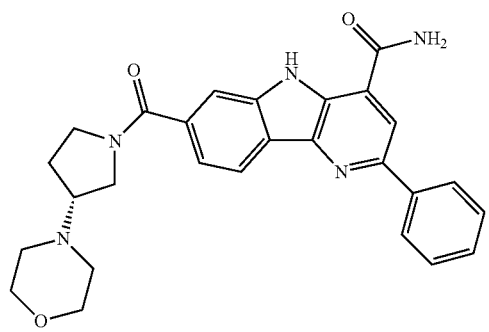 [SMILES: NC(=O)c1cc(-c2ccccc2)nc2c1[nH]c1cc(C(=O)N3CC[C@@H](N4CCOCC4)C3)ccc12] | (R)-7-(3-morpholinopyrrolidine-1-carbonyl)-2-phenyl-5H-pyrido[3,2-b]indole-4-carboxamide | 1.58(a) | 470.11 |

HPLC condition a: Xbridge S10 4.6 × 50 mm column, 3 min gradient, 0-100% B, 4 mL/min. Solvent A: 95% MeOH –5% H₂O - 0.1% TFA; Solvent B: 5% MeOH - 95% H₂O - 0.1% TFA.
HPLC condition b: PHENOMENEX ® Luna S10 3 × 50 mm column, 3 min gradient, 0-100% B, 4 mL/min. Solvent A: 95% MeOH –5% H₂O - 0.1% TFA; Solvent B: 5% MeOH - 95% H₂O - 0.1% TFA.
HPLC condition c: PHENOMENEX ® Luna C18 3 × 50 mm column, 3 min gradient, 0-100% B, 4 mL/min. Solvent A: 5% CH₃CN - 95% H₂O - 10 mM Ammonium Acetate; Solvent B: 95% CH₃CN - 5% H₂O - 10 mM Ammonium Acetate.

The following compounds were also similarly prepared except that an N-Boc protecting group was removed with TFA:DCM=1:1 prior to purification of the product.

TABLE 16

| Ex. # | Structure | Name | Retention time (min) | MS (ESI) m/z M + H[+] |
|---|---|---|---|---|
| 301 | 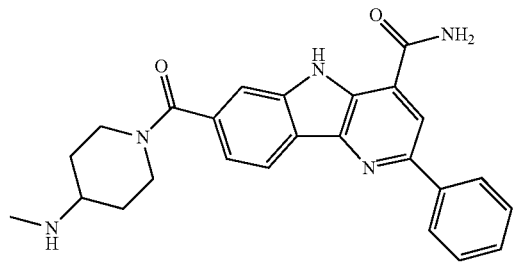 [SMILES: CNC1CCN(C(=O)c2ccc3c(c2)[nH]c2c(C(N)=O)cc(-c4ccccc4)nc23)CC1] | 7-(4-(methylamino)piperidine-1-carbonyl)-2-phenyl-5H-pyrido[3,2-b]indole-4-carboxamide | 1.31(a) | 428.2 |

TABLE 16-continued

| Ex. # | Structure | Name | Retention time (min) | MS (ESI) m/z M + H+ |
|---|---|---|---|---|
| 302 | 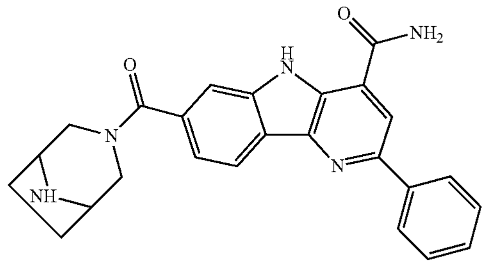 [SMILES: NC(=O)c1cc(-c2ccccc2)nc2c1[nH]c1cc(C(=O)N3CC4CCC(C3)N4)ccc12] | 7-(3,8-diazabicyclo[3.2.1]octane-3-carbonyl)-2-phenyl-5H-pyrido[3,2-b]indole-4-carboxamide | 1.35(b) | 426.04 |
| 303 | 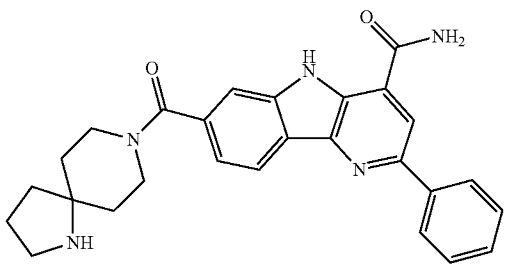 [SMILES: NC(=O)c1cc(-c2ccccc2)nc2c1[nH]c1cc(C(=O)N3CCC4(CCCN4)CC3)ccc12] | 7-(1,8-diazaspiro[4.5]dec-8-ylcarbonyl)-2-phenyl-5H-pyrido[3,2-b]indole-4-carboxamide | 1.40(b) | 454.11 |

HPLC condition a: Xbridge S10 4.6 × 50 mm column, 3 min gradient, 0-100% B, 4 mL/min. Solvent A: 95% MeOH –5% H₂O - 0.1% TFA; Solvent B: 5% MeOH - 95% H₂O - 0.1% TFA.
HPLC condition b: PHENOMENEX ® Luna S10 3 × 150 mm column, 3 min gradient, 0-100% B, 4 mL/min. Solvent A: 95% MeOH –5% H₂O - 0.1% TFA; Solvent B: 5% MeOH - 95% H₂O - 0.1% TFA.

EXAMPLE 304

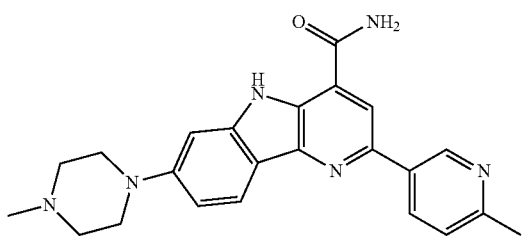

7-(4-Methylpiperazin-1-yl)-2-(6-methylpyridin-3-yl)-5H-pyrido[3,2-b]indole-4-carboxamide

304A. Preparation of methyl 3-amino-6-bromo-2-(4-nitrophenyl)isonicotinate

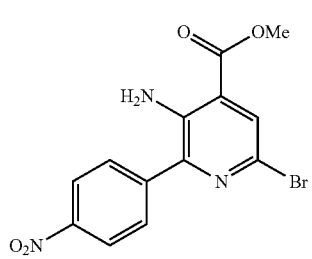 [SMILES: COC(=O)c1cc(Br)nc(-c2ccc([N+](=O)[O-])cc2)c1N]

A flask containing a mixture of 4-nitrophenylboronic acid (5.5 g, 32 9 mmol), sodium carbonate (10.3 g, 97 mmol), tetrakistriphenyphosphine palladium(0) (1.86 g, 1.61 mmol), and methyl 3-amino-2,6-dibromoisonicotinate (10 g, 32 3 mmol) was flushed with nitrogen, 1,4-dioxane (60.0 mL) followed by methanol (20 mL) were added, and the reaction heated at 110° C. for 16 h. The reaction mixture was partitioned between EtOAc and water. The organic phase was washed with sat. aq. Sodium bicarbonate solution and brine, dried with sodium sulfate, and the solvents removed. The residue was suspended and a mixture of EtOAc:hexane=1:4 and then filtered to give methyl 3-amino-6-bromo-2-(4-nitrophenyl)isonicotinate (9.3 g, 21 mmol, 66% yield). MS (ESI) m/z 354.04 (M+H). $^1$H NMR (500 MHz, chloroform-d) δ ppm 8.37 (2 H, d, J=8.85 Hz), 7.91 (1H, s), 7.88 (2H, d, J=8.85 Hz), 5.98 (2H, br. s.), 3.98 (3H, s).

304B. Preparation of methyl 3-azido-6-bromo-2-(4-nitrophenyl)isonicotinate

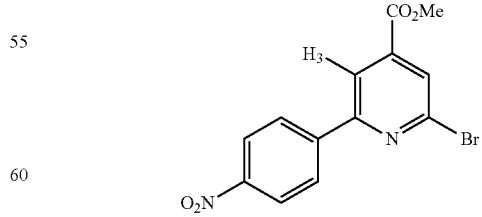

Methyl 3-amino-6-bromo-2-(4-nitrophenyl)isonicotinate (7.2 g, 20 5 mmol) was dissolved in TFA (70 mL) and the yellow solution was cooled in an ice bath. Sodium nitrite (2.82 g, 40.9 mmol) was added in small portions with stirring to give a dark yellow mixture. After 30 min, sodium azide (13.29 g, 204 mmol) was added in small portions followed by Et₂O (20 mL). The light yellow mixture was stirred in the ice-bath for 30 min and then partitioned between DCM and water. The organic phase washed with water (3×250 mL), sat. aq. Na₂CO₃ solution (3×250 mL), brine, dried with sodium sulfate, and the solvent removed. Silica gel chromatography (30% THF in DCM) afforded methyl 3-azido-6-bromo-2-(4-nitrophenyl)isonicotinate (6.8 g, 16.5 mmol, 81% yield). ¹H NMR (500 MHz, DMSO-d₆) δ ppm 8.37 (2H, d, J=8.85 Hz), 8.06 (1H, s), 8.02 (2H, d, J=9.16 Hz), 3.97 (3H, s).

304C. Preparation of methyl 2-bromo-7-nitro-5H-pyrido[3,2-b]indole-4-carboxylate

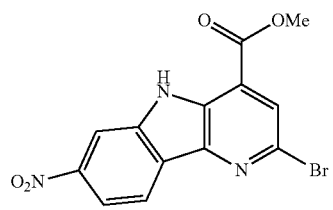 [SMILES: COC(=O)c1cc(Br)nc2c1[nH]c1cc([N+](=O)[O-])ccc12]

1,2-Dichloroethane (30 mL) was added to a mixture of methyl 3-azido-6-bromo-2-(4-nitrophenyl)isonicotinate (6.5 g, 17 2 mmol), rhodium octanoate dimer (0.669 g, 0.859 mmol) and crushed 4A° molecular sieves (6.5 g). The reaction heated at 80° C. for 14 hr. The crude mixture was diluted with THF and filtered. The collected solid were then extracted with additional hot THF. The solvents were removed from the combined filtrates and the residue was suspended in methanol, filtered and air dried to leave methyl 2-bromo-7-nitro-5H-pyrido[3,2-b]indole-4-carboxylate (5.0 g, 13.4 mmol, 78% yield). MS (ESI) m/z 351.91 (M+H). ¹H NMR (500 MHz, DMSO-d₆) δ ppm 12.31 (1H, br. s.), 8.63 (1H, d, J=2.14 Hz), 8.45 (1H, d, J=8.55 Hz), 8.17 (1H, dd, J=8.55, 2.14 Hz), 8.08 (1H, s), 4.07 (3H, s).

304D. Preparation of methyl 7-amino-2-bromo-5H-pyrido[3,2-b]indole-4-carboxylate

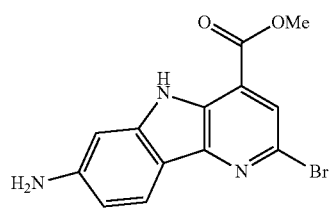

A mixture of methyl 2-bromo-7-nitro-5H-pyrido[3,2-b]indole-4-carboxylate (1.5 g, 4.3 mmol) and raney nickel (1.5 g, 26 mmol, W. R. Grace 2800 slurry in water) in EtOH (30 mL) under H₂ (balloon) was stirred for 16 hr. Filtration and removal of the solvent from the filtrate afforded methyl 7-amino-2-bromo-5H-pyrido[3,2-b]indole-4-carboxylate (1.1 g, 2.8 mmol, 66% yield) as a solid. MS (ESI) m/z 322.2 (M+H). ¹H NMR (500 MHz, DMSO-d₆) δ ppm 11.27 (1H, s), 7.79 (1H, d, J=8.55 Hz), 7.62 (1H, s), 6.79 (1H, d, J=1.83 Hz), 6.61 (1H, dd, J=8.55, 1.83 Hz), 5.84 (2H, s), 4.00 (3H, s).

304E. Preparation of methyl 2-bromo-7-(4-methylpiperazin-1-yl)-5H-pyrido[3,2-b]indole-4-carboxylate

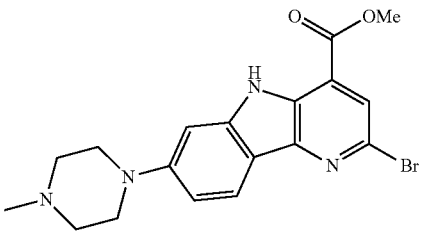 [SMILES: COC(=O)c1cc(Br)nc2c1[nH]c1cc(N3CCN(C)CC3)ccc12]

A mixture of methyl 7-amino-2-bromo-5H-pyrido[3,2-b]indole-4-carboxylate (1.0 g, 3.1 mmol), 2-chloro-N-(2-chloroethyl)-N-methylethanamine hydrochloride (1.20 g, 6.25 mmol) and sodium carbonate (1.66 g, 15 6 mmol) in t-BuOH (40 mL) was heated at reflux overnight. The reaction was partitioned between EtOAc and water and the organic phase was washed with sat. aq. NaHCO₃ solution, water, and brine. After drying with sodium sulfate, the solvents were removed and silica gel chromatography (elution with 5% MeOH in DCM) afforded methyl 2-bromo-7-(4-methylpiperazin-1-yl)-5H-pyrido[3,2-b]indole-4-carboxylate (900 mg, 2.14 mmol, 69% yield). MS (ESI) m/z 405.14 (M+H); LCMS Ret Time: 1.995 min; Xbridge S10 4.6×50 mm column, 3 min gradient, 0-100% B, 4 mL/min. Solvent A: 95% MeOH—5% H₂O—0.1% TFA; Solvent B: 5% MeOH—95% H₂O—0.1% TFA.

304F. Preparation of 2-bromo-7-(4-methylpiperazin-1-yl)-5H-pyrido[3,2-b]indole-4-carboxamide

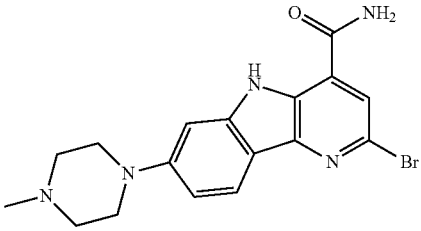 [SMILES: CN1CCN(c2ccc3c(c2)[nH]c2c(C(N)=O)cc(Br)nc23)CC1]

A mixture of methyl 2-bromo-7-(4-methylpiperazin-1-yl)-5H-pyrido[3,2-b]indole-4-carboxylate (300 mg, 0.744 mmol) and 7 N NH₃ in MeOH (5 mL) in a sealed microwave vial was heated in an oil bath at 80° C. for 16 h. After cooling to RT, the solid was collected by filtration, washed with MeOH, and air-dried to afford 2-bromo-7-(4-methylpiperazin-1-yl)-5H-pyrido[3,2-b]indole-4-carboxamide (200 mg, 0.489 mmol, 66% yield). MS (ESI) m/z 390.0 (M+H); LCMS Ret Time: 1.242 min; PHENOMENEX® Luna S10 4.6×50 mm column, 3 min gradient, 0-100% B, 5 mL/min. Solvent A: 10% MeOH—90% H₂O—0.1% TFA; Solvent B: 90% MeOH—10% H₂O—0.1% TFA.

304. Preparation of 2-(1-methyl-1H-pyrazol-4-yl)-7-(4-methylpiperazin-1-yl)-5H-pyrido[3,2-b]indole-4-carboxamide A microwave vial containing a mixture of 2-bromo-7-(4-methylpiperazin-1-yl)-5H-pyrido[3,2-b]indole-4-carboxamide (50 mg, 0.13 mmol), 1-methyl-4-(4,4,5,5-tetramethyl-1,3,2-dioxaborolan-2-yl)-1H-pyrazole (54 mg, 0.26 mmol), PdCl$_2$(dppf)-CH$_2$Cl$_2$ adduct (11 mg, 0.013 mmol), and 2 N aq. Na$_2$CO$_3$ (0.32 mL, 0.64 mmol) was flushed with nitrogen. DME (5 mL) was added and the vial was sealed and heated at 100° C. in an oil bath for 2 hrs. The reaction was diluted with MeOH, filtered, and the solid was washed with MeOH. The solvents were removed from the combined filtrates and preparative HPLC (PHENOMENEX® Luna C18 30×100 10u Column, Solvent A=10 mM NH$_4$OAc in 95% water:5% acetonitrile; B=10 mM NH$_4$OAc in 5% water:95% acetonitrile; 30 to 100% B over 20 min at 30 mL/min. SCX capture and release with 2 N NH$_3$ in MeOH gave 2-(1-methyl-1H-pyrazol-4-yl)-7-(4-methylpiperazin-1-yl)-5H-pyrido[3,2-b]indole-4-carboxamide (27 mg, 0.066 mmol, 51% yield) as a yellow solid. MS (ESI) m/z 401.27 (M+H). $^1$H NMR (500 MHz, acetone) d ppm 10.66 (1H, br. s.), 9.34 (1H, d, J=1.83 Hz), 8.50 (1H, dd, J=8.09, 2.29 Hz), 8.32 (1H, s), 8.16 (1H, d, J=8.85 Hz), 8.11 (1H, br. s.), 7.36 (1H, d, J=8.24 Hz), 7.30 (1H, d, J=1.83 Hz), 7.12 (1H, br. s.), 7.08 (1H, dd, J=8.70, 2.29 Hz), 3.33-3.40 (4H, m), 2.78 (4H, br. s.), 2.57 (3H, s), 2.31 (3H, s).

The Examples in the following table were similarly prepared.

TABLE 17

| Ex. # | Structure | Name | Retention time (min) | MS (ESI) m/z M + H$^+$ |
|---|---|---|---|---|
| 305 | 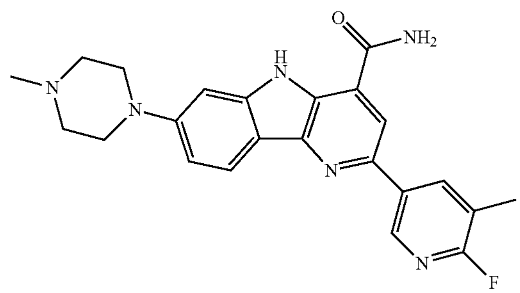 | 2-(6-fluoro-5-methylpyridin-3-yl)-7-(4-methylpiperazin-1-yl)-5H-pyrido[3,2-b]indole-4-carboxamide | 1.61 | 419.30 |
| 306 | 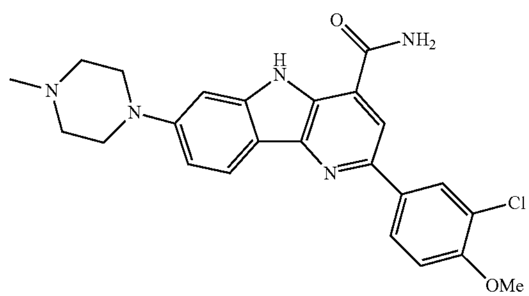 [SMILES: COc1ccc(-c2cc(C(N)=O)c3[nH]c4cc(N5CCN(C)CC5)ccc4c3n2)cc1Cl] | 2-(3-chloro-4-methoxyphenyl)-7-(4-methylpiperazin-1-yl)-5H-pyrido[3,2-b]indole-4-carboxamide | 1.69 | 450.26 |
| 307 | 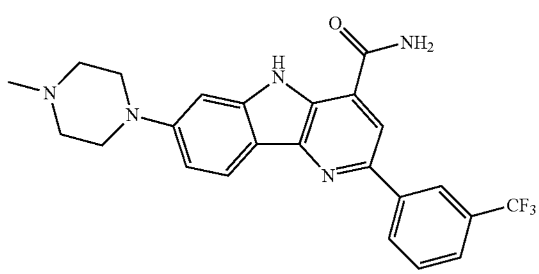 [SMILES: CN1CCN(c2ccc3c(c2)[nH]c2c(C(N)=O)cc(-c4cccc(C(F)(F)F)c4)nc23)CC1] | 7-(4-methylpiperazin-1-yl)-2-(3-(trifluoromethyl)phenyl)-5H-pyrido[3,2-b]indole-4-carboxamidecarboxamide | 2.04 | 454.26 |
| 308 | 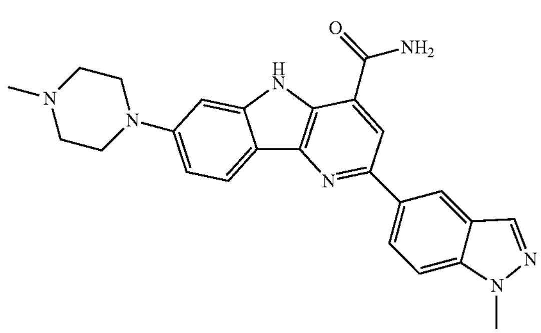 [SMILES: CN1CCN(c2ccc3c(c2)[nH]c2c(C(N)=O)cc(-c4ccc5c(cnn5C)c4)nc23)CC1] | 2-(1-methyl-1H-indazol-5-yl)-7-(4-methylpiperazin-1-yl)-5H-pyrido[3,2-b]indole-4-carboxamide | 1.33 | 440.29 |

TABLE 17-continued

| Ex. # | Structure | Name | Retention time (min) | MS (ESI) m/z M + H+ |
|---|---|---|---|---|
| 309 | 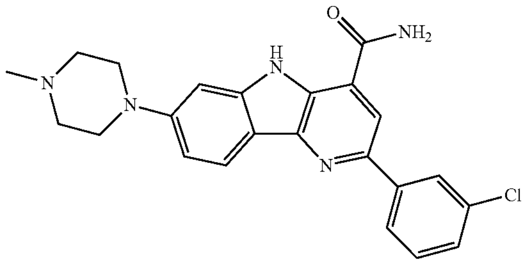 [SMILES: CN1CCN(c2ccc3c(c2)[nH]c2c(C(N)=O)cc(-c4cccc(Cl)c4)nc23)CC1] | 2-(3-chlorophenyl)-7-(4-methylpiperazin-1-yl)-5H-pyrido[3,2-b]indole-4-carboxamide | 1.88 | 420.22 |
| 310 | 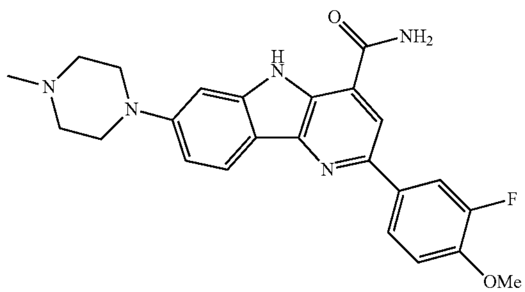 [SMILES: COc1ccc(-c2cc(C(N)=O)c3[nH]c4cc(N5CCN(C)CC5)ccc4c3n2)cc1F] | 2-(3-fluoro-4-methoxyphenyl)-7-(4-methylpiperazin-1-yl)-5H-pyrido[3,2-b]indole-4-carboxamide | 1.52 | 434.18 |

HPLC: Xbridge S10 4.6 × 50 mm column, 3 min gradient, 0-100% B, 4 mL/min. Solvent A: 95% MeOH −5% H₂O - 0.1% TFA; Solvent B: 5% MeOH - 95% H₂O - 0.1% TFA.

EXAMPLE 311

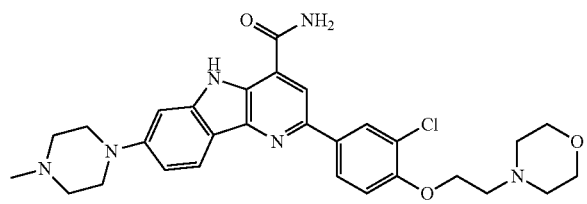 [SMILES: CN1CCN(c2ccc3c(c2)[nH]c2c(C(N)=O)cc(-c4ccc(OCCN5CCOCC5)c(Cl)c4)nc23)CC1]

2-(3-Chloro-4-(2-morpholinoethoxy)phenyl)-7-(4-methylpiperazin-1-yl)-5H-pyrido[3,2-b]indole-4-carboxamide 311A. Preparation of methyl 2-(3-chloro-4-hydroxyphenyl)-7-(4-methylpiperazin-1-yl)-5H-pyrido[3,2-b]indole-4-carboxylate

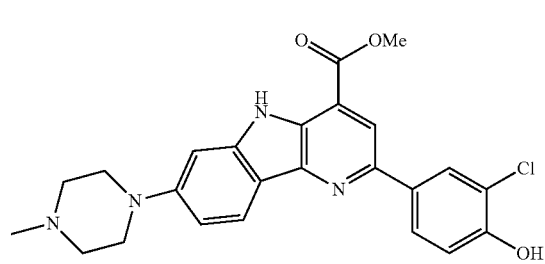 [SMILES: COC(=O)c1cc(-c2ccc(O)c(Cl)c2)nc2c1[nH]c1cc(N3CCN(C)CC3)ccc12]

A microwave vial containing a mixture of 3-chloro-4-hydroxyphenylboronic acid (64 mg, 0.37 mmol), methyl 2-bromo-7-(4-methylpiperazin-1-yl)-5H-pyrido[3,2-b]indole-4-carboxylate (50 mg, 0.12 mmol), powdered potassium phosphate tribasic (116 mg, 0.546 mmol), 2-dicyclohexylphosphino-2',4',6'-tri-iso-propyl-1,1'-biphenyl (12 mg, 0.025 mmol), and Pd(OAc)₂ (2.8 mg, 0.012 mmol) was flushed with nitrogen. THF (0.5 mL) was added, the vial was sealed, and the reaction was heated at 80° C. for 3 hr. Preparative HPLC (100×30 mm Luna C18 column, Solvent A=10% Methanol, 90% H₂O, 0.1% TFA; Solvent B=90% Methanol, 10% H₂O, 0.1% TFA; 10-60% B at 42 mL/min over 20 min) of the reaction mixture followed by SCX capture and release with 2 N NH₃ in MeOH gave methyl 2-(3-chloro-4-hydroxyphenyl)-7-(4-methylpiperazin-1-yl)-5H-pyrido[3,2-b]indole-4-carboxylate (30 mg, 0.043 mmol, 34.9% yield. MS (ESI) m/z 451.10 (M+H).

311B. Preparation of 2-(3-chloro-4-hydroxyphenyl)-7-(4-methylpiperazin-1-yl)-5H-pyrido[3,2-b]indole-4-carboxamide

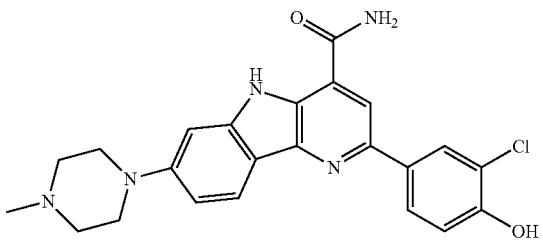 [SMILES: CN1CCN(c2ccc3c(c2)[nH]c2c(C(N)=O)cc(-c4ccc(O)c(Cl)c4)nc23)CC1]

A mixture of methyl 2-(3-chloro-4-hydroxyphenyl)-7-(4-methylpiperazin-1-yl)-5H-pyrido[3,2-b]indole-4-carboxylate (100 mg, 0.222 mmol) and 7N NH₃ in MeOH (5 mL) in a sealed microwave vessel was heated in an oil bath at 80° C.

for 16 h. After cooling to RT, the solid was collected by filtration, and washed with MeOH, and air-dried to afford 2-(3-chloro-4-hydroxyphenyl)-7-(4-methylpiperazin-1-yl)-5H-pyrido[3,2-b]indole-4-carboxamide (75 mg, 0.16 mmol, 74% yield). MS (ESI) m/z 436.10 (M+H).

311C. Preparation of 2-(3-chloro-4-(2-morpholinoethoxy)phenyl)-7-(4-methylpiperazin-1-yl)-5H-pyrido[3,2-b]indole-4-carboxamide Diethyl azodicarboxylate (0.076 mL, 0.48 mmol) was added to a solution of triphenylphosphine (126 mg, 0.482 mmol), 2-(3-chloro-4-hydroxyphenyl)-7-(4-methylpiperazin-1-yl)-5H-pyrido[3,2-b]indole-4-carboxamide (70 mg, 0.16 mmol) and 2-morpholinoethanol (0.039 mL, 0.32 mmol) in dry THF (2 mL) in an oven-dried vial at RT under nitrogen. After stirring for 12 h, preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min). SCX capture and release with 2 N NH$_3$ in MeOH afforded 2-(3-chloro-4-(2-morpholinoethoxy)phenyl)-7-(4-methylpiperazin-1-yl)-5H-pyrido[3,2-b]indole-4-carboxamide (25 mg, 0.041 mmol, 26% yield) as a yellow solid. $^1$H NMR and LCMS are consistent with the desired material. MS (ESI) m/z 549.23 (M+H). $^1$H NMR (500 MHz, chloroform-d) δ ppm 9.83 (1H, s), 8.27 (1H, d, J=8.55 Hz), 8.16 (1H, d, J=1.53 Hz), 8.00 (1H, dd, J=8.24, 1.83 Hz), 7.60 (1H, s), 7.08 (1H, d, J=8.24 Hz), 7.02 (1H, dd, J=8.70, 1.98 Hz), 6.93-6.96 (1H, m), 4.26-4.30 (2H, m), 3.76-3.81 (4H, m), 3.40-3.45 (4H, m), 2.90-2.95 (2H, m), 2.65-2.73 (8H, m), 2.44 (3H, s).

EXAMPLE 312

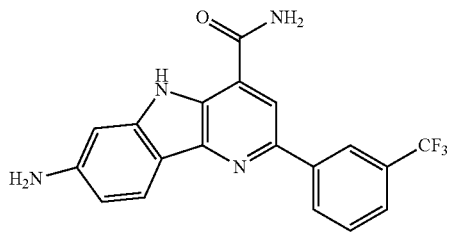

7-Amino-2-(3-(trifluoromethyl)phenyl)-5H-pyrido[3,2-b]indole-4-carboxamide

312A. Preparation of methyl 3-amino-2-(4-nitrophenyl)-6-(3-(trifluoromethyl)phenyl)isonicotinate

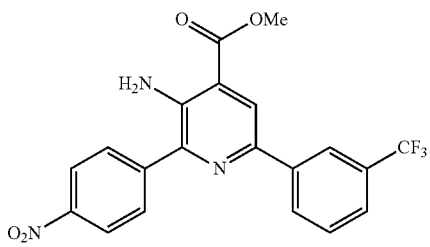 [SMILES: COC(=O)c1cc(-c2cccc(C(F)(F)F)c2)nc(-c2ccc([N+](=O)[O-])cc2)c1N]

A flask containing a mixture of methyl 3-amino-6-bromo-2-(4-nitrophenyl)isonicotinate (1.70 g, 4.83 mmol), 3-(trifluoromethyl)phenylboronic acid (1.83 g, 9.66 mmol), powdered potassium phosphate tribasic (3.38 g, 15 9 mmol), 2-dicyclohexylphosphino-2',4',6'-tri-iso-propyl-1,1'-biphenyl (0.460 g, 0.966 mmol), and Pd(OAc)$_2$ (0.108 g, 0.483 mmol) was flushed with nitrogen. THF (20 mL) was added and the mixture was heated at reflux under nitrogen for 2 hr. The mixture was diluted with EtOAc and washed with water and brine. After drying with Na$_2$SO$_4$, the solvents removed and the residue was suspended in a mixture of 20% EtOAc in hexane. Filtration afforded methyl 3-amino-2-(4-nitrophenyl)-6-(3-(trifluoromethyl)phenyl)-isonicotinate (1.0 g, 2.2 mmol, 46% yield). MS (ESI) m/z 417.99 (M+H). $^1$H NMR (400 MHz, chloroform-d) δ ppm 8.39-8.47 (2H, m), 8.22-8.27 (2H, m), 8.19 (1H, d, J=7.55 Hz), 7.93-8.03 (2H, m), 7.54-7.65 (2H, m), 6.13 (2H, br. s.), 4.04 (3H, s).

312B. Preparation of methyl 3-azido-2-(4-nitrophenyl)-6-(3-(trifluoromethyl)phenyl)isonicotinate

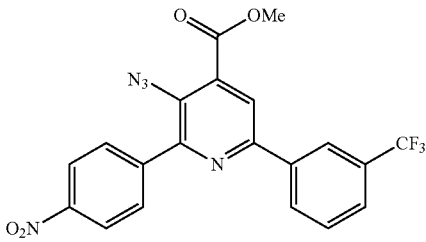 [SMILES: COC(=O)c1cc(-c2cccc(C(F)(F)F)c2)nc(-c2ccc([N+](=O)[O-])cc2)c1N=[N+]=[N-]]

A mixture of methyl 3-amino-2-(4-nitrophenyl)-6-(3-(trifluoromethyl)phenyl)isonicotinate (1 g, 2 4 mmol) in concentrated hydrochloric acid (20 mL, 37%) was cooled in an ice bath and a solution of sodium nitrite (0.99 g, 14.4 mmol) in water (0.5 ml) was added in small portions. The orange-red solution was stirred for 20 min and then a solution of sodium azide (0.94 g, 14.4 mmol) in water (0.5 mL) was added in portions. A precipitate formed and, after 30 min, the reaction was partitioned between DCM and water. The organic phase was washed with brine (2×50 mL), sat. aq. Na$_2$CO$_3$ solution, water, brine and then dried with sodium sulfate. Removal of the solvent followed by silica gel chromatography (elution with 40% EtOAc in hexane) afforded methyl 3-azido-2-(4-nitrophenyl)-6-(3-(trifluoromethyl)phenyl)-isonicotinate (1.0 g, 2 1 mmol, 89% yield). $^1$H NMR (500 MHz, chloroform-d) δ ppm 8.40 (2H, d, J=9.2), 8.33 (s, 1H), 8.29 (d, 1H, J=8.3), 8.22 (s, 1H), 8.07 (d, 2H, J=8.9), 7.74 (d, 1H, J=7.3), 7.66 (t, 1H, J=7.6), 4.12 (3H, s).

312C. Preparation of methyl 7-nitro-2-(3-(trifluoromethyl)phenyl)-5H-pyrido[3,2-b]indole-4-carboxylate

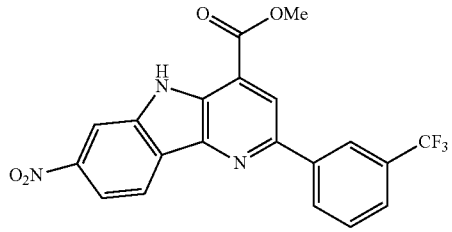 [SMILES: COC(=O)c1cc(-c2cccc(C(F)(F)F)c2)nc2c1[nH]c1cc([N+](=O)[O-])ccc12]

1,2-Dichloroethane (10 mL) was added to a mixture of methyl 3-azido-2-(4-nitrophenyl)-6-(3-(trifluoromethyl)phenyl)isonicotinate (1.0 g, 2.3 mmol), rhodium octanoate dimer (0.125 g, 0.161 mmol) and crushed 4A° molecular sieves (1.0 g). The reaction was heated at 80° C. for 20 hr. The crude mixture was diluted with DCM and silica gel chromatography (step gradient elution with DCM containing 0 to 20% MeOH) afforded methyl 7-nitro-2-(3-(trifluoromethyl)phenyl)-5H-pyrido[3,2-b]indole-4-carboxylate (400 mg, 0.963 mmol, 43% yield). MS (ESI) m/z 416.09 (M+H). $^1$H NMR (500 MHz, DMSO-d$_6$) δ ppm 12.24 (1H, br s), 8.42-8.72 (5H, m), 8.16 (1H, dd, J=8.55, 1.83 Hz), 7.82 (2H, ddd, J=15.11, 7.78, 7.63 Hz), 4.10 (3H, s).

312D. Preparation of 7-nitro-2-(3-(trifluoromethyl)phenyl)-5H-pyrido[3,2-b]indole-4-carboxamidete

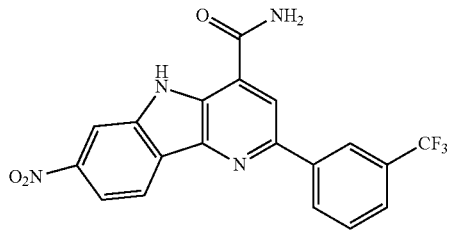 [SMILES: NC(=O)c1cc(-c2cccc(C(F)(F)F)c2)nc2c1[nH]c1cc([N+](=O)[O-])ccc12]

A suspension of methyl 7-nitro-2-(3-(trifluoromethyl)phenyl)-5H-pyrido[3,2-b]indole-4-carboxylate (250 mg, 0.602 mmol) in 7 N NH$_3$ in MeOH (5 mL) in a sealed microwave vial was heated in an oil bath at 80° C. for 16 h. After cooling to RT, the solid was collected by filtration and washed with MeOH to afford 7-nitro-2-(3-(trifluoromethyl)phenyl)-5H-pyrido[3,2-b]indole-4-carboxamide (200 mg, 0.475 mmol, 79% yield). MS (ESI) m/z 401.1 (M+H). $^1$H NMR (500 MHz, DMSO-d$_6$) δ ppm 12.26 (1H, br. s.), 8.62-8.81 (5H, m), 8.54 (1H, d, J=8.85 Hz), 8.03-8.19 (2H, m), 7.75-7.88 (2H, m).

312 Preparation of 7-amino-2-(3-(trifluoromethyl)phenyl)-5H-pyrido[3,2-b]indole-4-carboxamide A mixture of 7-nitro-2-(3-(trifluoromethyl)phenyl)-5H-pyrido[3,2-b]indole-4-carboxamide (200 mg, 0.500 mmol) and Pd-C (200 mg, 0.188 mmol)in MeOH (5 mL) under a H$_2$ balloon was stirred for 3 hr. Filtration followed by preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min) and SCX capture and release with 2 N NH$_3$ in MeOH afforded 7-amino-2-(3-(trifluoromethyl)phenyl)-5H-pyrido[3,2-b]indole-4-carboxamide (80 mg, 0.21 mmol, 41% yield). MS (ESI) m/z 371.09 (M+H). $^1$H NMR (500 MHz, DMSO-d$_6$) δ ppm 11.16 (1H, d, J=4.58 Hz), 8.58 (2H, br. s.), 8.51 (1H, br. s.), 8.25-8.37 (1H, m), 7.86-7.99 (1H, m), 7.75 (3H, d, J=6.10 Hz), 6.82 (1H, d, J=3.36 Hz), 6.48-6.67 (1H, m), 5.61 (2H, br. s.).

EXAMPLE 313

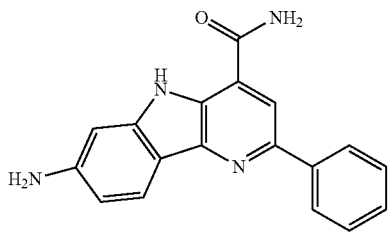 [SMILES: NC(=O)c1cc(-c2ccccc2)nc2c1[nH]c1cc(N)ccc12]

7-Amino-2-phenyl-5H-pyrido[3,2-b]indole-4-carboxamide

This was similarly prepared as Example 312. MS (ESI) m/z 303.07 (M+H). $^1$H NMR (500 MHz, DMSO-d$_6$) δ ppm 11.05 (1H, s), 8.46 (1H, br. s.), 8.25 (2H, d, J=8.24 Hz), 8.19 (1H, s), 7.87 (1H, d, J=8.24 Hz), 7.73 (1H, br. s.), 7.51 (2H, t, J=7.78 Hz), 7.39 (1H, t, J=7.32 Hz), 6.82 (1H, d, J=1.83 Hz), 6.57 (1H, dd, J=8.24, 1.83 Hz), 5.55 (2H, s).

EXAMPLE 314

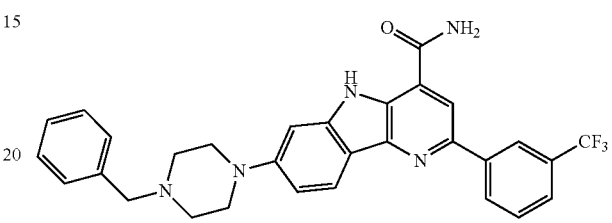

7-(4-Benzylpiperazin-1-yl)-2-(3-(trifluoromethyl)phenyl)-5H-pyrido[3,2-b]indole-4-carboxamide A mixture of 7-amino-2-(3-(trifluoromethyl)phenyl)-5H-pyrido[3,2-b]indole-4-carboxamide (70 mg, 0.189 mmol), N-benzyl-2-chloro-N-(2-chloroethyl)ethanamine hydrochloride (102 mg, 0.378 mmol) and Na$_2$CO$_3$ (100 mg, 0.945 mmol) in t-BuOH (2 mL) was heated at reflux overnight. Preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min) and SCX capture and release with 2 N NH$_3$ in MeOH afforded 7-(4-benzylpiperazin-1-yl)-2-(3-(trifluoromethyl)phenyl)-5H-pyrido[3,2-b]indole-4-carboxamide (50 mg, 0.090 mmol, 48% yield). MS (ESI) m/z 530.29 (M+H). $^1$H NMR (500 MHz, DMSO-d$_6$) δ ppm 11.33 (1H, s), 8.54-8.64 (3H, m), 8.41 (1H, s), 8.07 (1H, d, J=8.85 Hz), 7.88 (1H, br. s.), 7.72-7.80 (2H, m), 7.35-7.41 (4H, m), 7.26-7.32 (1H, m), 7.22 (1H, d, J=1.83 Hz), 7.01 (1H, dd, J=8.85, 1.83 Hz), 3.57 (2H, s), 3.30 (4H, d, J=3.97 Hz), 2.59 (4H, d, J=3.97 Hz).

EXAMPLE 315

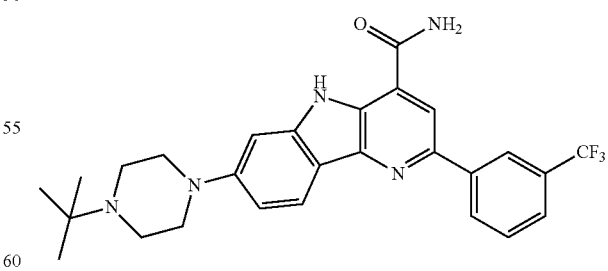

7-(4-tert-Butylpiperazin-1-yl)-2-(3-(trifluoromethyl)phenyl)-5H-pyrido[3,2-b]indole-4-carboxamide A mixture of 7-amino-2-(3-(trifluoromethyl)phenyl)-5H-pyrido[3,2-b]indole-4-carboxamide (90 mg, 0.243 mmol), N,N-bis(2-chloroethyl)-2-methylpropan-2-amine hydrochloride (114 mg, 0.486 mmol) and Na$_2$CO$_3$ (129 mg, 1.22 mmol) in t-BuOH (2 mL) was heated at reflux overnight. Purification by HPLC gave 7-(4-tert-butylpiperazin-1-yl)-2-(3-(trifluoromethyl)phenyl)-5H-pyrido[3,2-b]indole-4-carboxamide (40 mg, 0.077 mmol, 32% yield). MS (ESI) m/z 496.2 (M+H). $^1$H NMR (500 MHz, DMSO-d$_6$) δ ppm 11.30 (1H, s), 8.60 (2H, d, J=1.53 Hz), 8.56 (1H, br. s.), 8.40 (1H, s), 8.07 (1H, d, J=8.55 Hz), 7.85 (1H, br. s.), 7.74-7.78 (2H, m), 7.20 (1H, d, J=1.83 Hz), 7.00 (1H, dd, J=8.85, 2.14 Hz), 3.23-3.28 (4H, m), 2.71 (4H, d, J=4.27 Hz), 1.08 (9H, s).

EXAMPLE 316

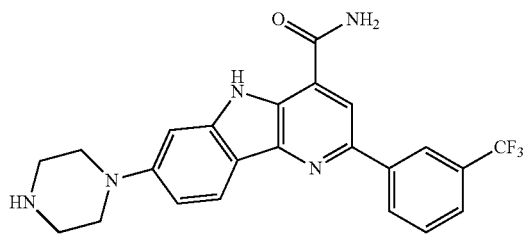 [SMILES: NC(=O)c1cc(-c2cccc(C(F)(F)F)c2)nc2c1[nH]c1cc(N3CCNCC3)ccc12]

7-(Piperazin-1-yl)-2-(3-(trifluoromethyl)phenyl)-5H-pyrido[3,2-b]indole-4-carboxamide A mixture of 7-(4-benzylpiperazin-1-yl)-2-(3-(trifluoromethyl)phenyl)-5H-pyrido[3,2-b]indole-4-carboxamide (20 mg, 0.038 mmol), 10% Pd on carbon (7 mg) and ammonium formate (12 mg, 0.19 mmol) in MeOH (3 mL) was heated at reflux for 0.5 hr. The reaction was cooled to RT, diluted with DCM and filtered. The solvents were removed to leave 7-(piperazin-1-yl)-2-(3-(trifluoromethyl)phenyl)-5H-pyrido[3,2-b]indole-4-carboxamide (9 mg, 0.02 mmol, 52% yield). MS (ESI) m/z 440.16 (M+H). $^1$H NMR (500 MHz, DMSO-d$_6$) δ ppm 11.32 (1H, s), 8.53-8.65 (3H, m), 8.41 (1H, s), 8.07 (1H, d, J=8.85 Hz), 7.88 (1H, s), 7.69-7.83 (2H, m), 7.21 (1H, d, J=1.83 Hz), 7.00 (1H, dd, J=8.70, 1.98 Hz), 3.13-3.25 (4H, m), 2.82-3.00 (4H, m).

EXAMPLE 317

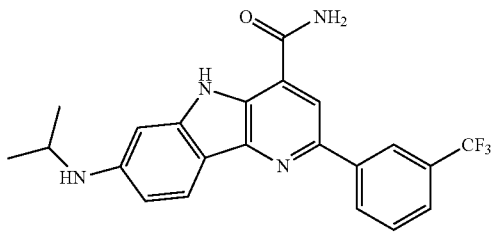 [SMILES: CC(C)Nc1ccc2c(c1)[nH]c1c(C(N)=O)cc(-c3cccc(C(F)(F)F)c3)nc12]

7-(Isopropylamino)-2-(3-(trifluoromethyl)phenyl)-5H-pyrido[3,2-b]indole-4-carboxamide A suspension of 7-amino-2-(3-(trifluoromethyl)phenyl)-5H-pyrido[3,2-b]indole-4-carboxamide (30 mg, 0.081 mmol), propan-2-one (0.118 mL, 1.62 mmol), and sodium triacetoxyborohydride (172 mg, 0.810 mmol) in a mixture of DCM/THF (2/1) (3 mL) was stirred at RT overnight. The mixture was diluted with MeOH and preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min) followed by SCX capture and release with 2 N NH$_3$ in MeOH afforded 7-(isopropylamino)-2-(3-(trifluoromethyl)phenyl)-5H-pyrido[3,2-b]indole-4-carboxamide (20 mg, 0.045 mmol, 55% yield). MS (ESI) m/z 413.20 (M+H). $^1$H NMR (400 MHz, DMSO-d$_6$) δ ppm 11.13 (1H, s), 8.58 (2H, s), 8.51 (1H, s), 8.29 (1H, s), 7.90 (1H, d J=8.56 Hz), 7.81 (1H, s), 7.68-7.77 (2H, m), 6.80 (1H, d, J=1.76 Hz), 6.60 (1H, dd, J=8.56, 2.01 Hz), 6.00 (1H, d, J=7.55 Hz), 3.53-3.68 (1H, m), 1.21 (6H, d, J=6.30 Hz).

EXAMPLE 318

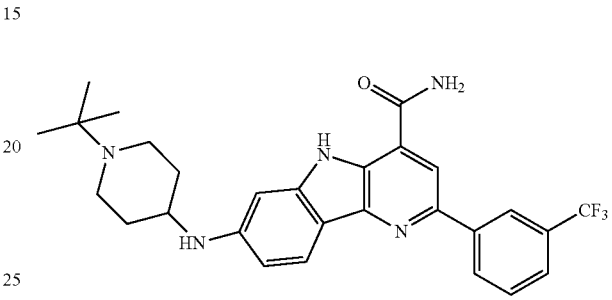

7-(1-tert-Butylpiperidin-4-ylamino)-2-(3-(trifluoromethyl)phenyl)-5H-pyrido[3,2-b]indole-4-carboxamide This was similarly prepared from 7-amino-2-(3-(trifluoromethyl)phenyl)-5H-pyrido[3,2-b]indole-4-carboxamide and 1-(t-butyl)piperidin-4-one. MS (ESI) m/z 510.35 (M+H). $^1$H NMR (500 MHz, DMSO-d$_6$) δ ppm 11.10 (1H, s), 8.55-8.63 (2H, m), 8.51 (1H, br. s.), 8.30 (1H, s), 7.90 (1H, d, J=8.55 Hz), 7.80 (1H, br. s.), 7.70-7.78 (2H, m), 6.85 (1H, d, J=1.83 Hz), 6.63 (1H, dd, J=8.70, 1.98 Hz), 6.04 (1H, d, J=7.63 Hz), 3.23 (1H, dd, J=10.22, 3.81 Hz), 2.95-3.08 (2H, m), 2.21 (2H, t, J=10.99 Hz), 2.02 (2H, d, J=12.82 Hz), 1.34-1.52 (2H, m), 1.06 (9H, s).

EXAMPLE 319

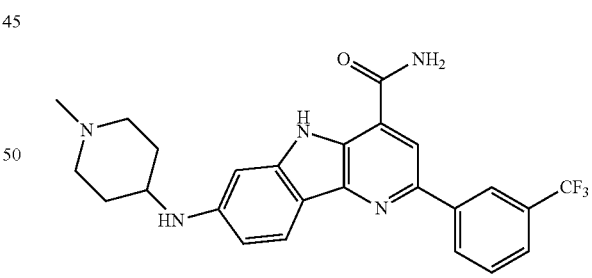

7-(1-Methylpiperidin-4-ylamino)-2-(3-(trifluoromethyl)phenyl)-5H-pyrido[3,2-b]indole-4-carboxamide This was similarly prepared 7-amino-2-(3-(trifluoromethyl)phenyl)-5H-pyrido[3,2-b]indole-4-carboxamide and 1-methylpiperidin-4-one. MS (ESI) m/z 468.30 (M+H); HPLC retention time of 1.85 min with Xbridge S10 4.6×50 mm column, 3 min gradient, 0-100% B, 4 mL/min. Solvent A: 95% MeOH—5% H$_2$O—0.1% TFA; Solvent B: 5% MeOH—95% H$_2$O—0.1% TFA.

EXAMPLE 320

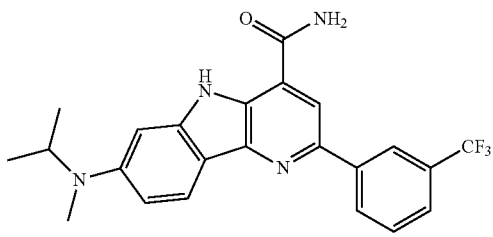 [SMILES: CC(C)N(C)c1ccc2c(c1)[nH]c1c(C(N)=O)cc(-c3cccc(C(F)(F)F)c3)nc12]

7-(Isopropyl(methyl)amino)-2-(3-(trifluoromethyl)phenyl)-5H-pyrido[3,2-b]indole-4-carboxamide A suspension of 7-(isopropylamino)-2-(3-(trifluoromethyl)phenyl)-5H-pyrido[3,2-b]indole-4-carboxamide (13 mg, 0.032 mmol), formaldehyde (0.023 mL, 0.315 mmol, 37% aq. solution), and sodium triacetoxyborohydride (33 mg, 0.16 mmol) in a mixture of DCM/THF (2/1) (0.3 mL) was stirred at RT overnight. The crude reaction was diluted with MeOH and preparative HPLC (100×30 mm Luna C18 column, Solvent A=10% Methanol, 90% H₂O, 0.1% TFA; Solvent B=90% Methanol, 10% H₂O, 0.1% TFA, 10-60% B at 42 mL/min over 20 min) followed by SCX capture and release with 2 N NH₃ in MeOH afforded 7-(isopropyl(methyl)amino)-2-(3-(trifluoromethyl)phenyl)-5H-pyrido[3,2-b]indole-4-carboxamide (6 mg, 0.011 mmol, 38% yield). MS (ESI) m/z 427.13 (M+H). ¹H NMR (500 MHz, DMSO-d₆) δ ppm 11.17 (1H, br. s.), 8.60 (2H, d, J=1.53 Hz), 8.54 (1H, br. s.), 8.35 (1H, s), 8.03 (1H, d, J=8.85 Hz), 7.83 (1H, br. s), 7.73-7.78 (2H, m), 7.07 (1H, d, J=2.14 Hz), 6.87 (1H, dd, J=8.85, 2.14 Hz), 4.24 (septupled, 1H, J=6.6), 2.82 (3H, s), 1.21 (6H, d, J=6.41 Hz).

EXAMPLE 321

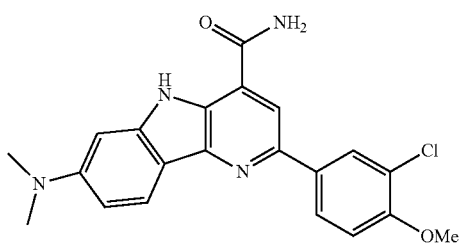 [SMILES: COc1ccc(-c2cc(C(N)=O)c3[nH]c4cc(N(C)C)ccc4c3n2)cc1Cl]

2-(3-Chloro-4-methoxyphenyl)-7-(dimethylamino)-5H-pyrido[3,2-b]indole-4-carboxamide 321A. Preparation of methyl 7-amino-2-bromo-5H-pyrido[3,2-b]indole-4-carboxylate

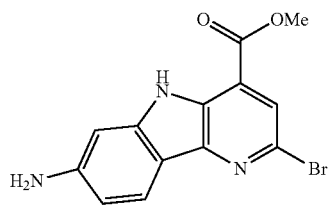

A suspension of methyl 2-bromo-7-nitro-5H-pyrido[3,2-b]indole-4-carboxylate (1.00 g, 2.86 mmol) and Raney nickel (1.0 g, 17 mmol, 2800 nickel slurry in water) was stirred in THF (50 mL) under H₂ (balloon) for 1.5 hr. This was filtered and the filter cake was washed with warn THF (100 mL). Removal of the solvent left methyl 7-amino-2-bromo-5H-pyrido[3,2-b]indole-4-carboxylate (700 mg, 2.08 mmol, 73% yield) as a solid. MS (ESI) m/z 321.94 (M+H). ¹H NMR (500 MHz, DMSO-d₆) δ ppm 11.27 (1H, br. s.), 7.78 (1H, d), 7.62 (1H, s), 6.79 (1H, br. s.), 6.60 (1H, d, J=8.5), 5 84 (2H, br. s.), 4.00 (3H, s).

321B. Preparation of 7-amino-2-bromo-5H-pyrido[3,2-b]indole-4-carboxamide

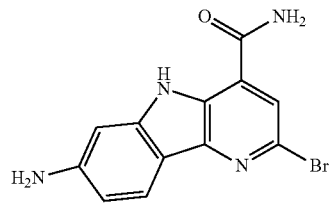

A mixture of methyl 7-amino-2-bromo-5H-pyrido[3,2-b]indole-4-carboxylate (700 mg, 2.19 mmol) and 7 N NH₃ in MeOH (5 mL) in a sealed microwave vial was heated in an oil bath at 80° C. for 16 h. After cooled to RT, the solid was collected by filtration and washed with MeOH, to afford 7-amino-2-bromo-5H-pyrido[3,2-b]indole-4-carboxamide (500 mg, 1.15 mmol, 53% yield). MS (ESI) m/z 306.96 (M+H). ¹H NMR (500 MHz, DMSO-d₆) δ ppm 11.18 (1H, br. s.), 8.33 (1H, br. s.), 7.79 (1H, br. s.), 7.71-7.77 (2H, m), 6.79 (1H, s), 6.52-6.60 (1H, m), 5.70 (2H, br. s.).

321C. Preparation of 2-bromo-7-(dimethylamino)-5H-pyrido[3,2-b]indole-4-carboxamide

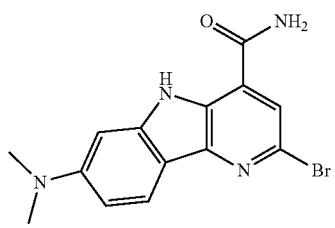 [SMILES: CN(C)c1ccc2c(c1)[nH]c1c(C(N)=O)cc(Br)nc12]

Sodium cyanoborohydride (0.655 mL, 0.655 mmol, 1.0 M in THF) was added to a mixture of 7-amino-2-bromo-5H-pyrido[3,2-b]indole-4-carboxamide (100 mg, 0.262 mmol), formaldehyde (0.21 mL, 2.6 mmol, 37% aq. solution), and acetic acid (0.45 mL, 0.79 mmol), in a mixture of MeOH (1 mL) and THF (1 mL). After stirring for 1 hr, this was diluted with MeOH and preparative HPLC (PHENOMENEX® Luna C18 30×100 10u Column, Solvent A=10 mM NH₄OAc in 95% water:5% acetonitrile; B=10 mM NH₄OAc in 5% water: 95% acetonitrile, 30 to 100% B over 20 min at 30 mL/min) followed by SCX capture and release with 2 N solution NH₃ in MeOH afforded 2-bromo-7-(dimethylamino)-5H-pyrido[3,2-b]indole-4-carboxamide (70 mg, 0.17 mmol, 66% yield) as a yellow solid. MS (ESI) m/z 333.02 (M+H). ¹H NMR (500 MHz, DMSO-d₆) δ ppm 11.24 (1H, s), 8.37 (1H, br. s.), 7.91 (1H, d, J=8.85 Hz), 7.82 (2H, s), 6.95 (1H, s), 6.80 (1H, dd, J=8.85, 2.14 Hz), 3.04 (6H, s).

321. Preparation of 2-(3-chloro-4-methoxyphenyl)-7-(dimethylamino)-5H-pyrido[3,2-b]indole-4-carboxamide A microwave vial containing a mixture of 2-bromo-7-(dimethylamino)-5H-pyrido[3,2-b]indole-4-carboxamide (30 mg, 0.090 mmol), 3-chloro-4-methoxyphenylboronic acid (34 mg, 0.18 mmol), PdCl$_2$(dppf)-CH$_2$Cl$_2$ adduct (7.4 mg, 9.0 μmol) was flushed with nitrogen. DME (1.5 mL) and Na$_2$CO$_3$ (0.23 mL, 0.45 mmol, 2.0 M aq. solution) were added and the vial was sealed and heated at 100° C. in an oil bath for 2 hrs. This was diluted with DMF and preparative HPLC (PHENOMENEX® Luna C18 30×100 10u Column, Solvent A=10 mM NH$_4$OAc in 95% water:5% acetonitrile; B=10 mM NH$_4$OAc in 5% water:95% acetonitrile, 30 to 100% B over 20 min at 30 mL/min) followed by SCX capture and release with 2 N solution NH$_3$ in MeOH afforded 2-(3-chloro-4-methoxyphenyl)-7-(dimethylamino)-5H-pyrido[3,2-b]indole-4-carboxamide (30 mg, 0.072 mmol, 80% yield) as a yellow solid. MS (ESI) m/z 395.12 (M+H). $^1$H NMR (500 MHz, DMSO-d$_6$) δ ppm 11.10 (1H, s), 8.49 (1H, s), 8.33 (1H, d, J=2.14 Hz), 8.16-8.27 (2H, m), 8.02 (1H, d, J=8.55 Hz), 7.78 (1H, s), 7.31 (1H, d, J=8.55 Hz), 6.99 (1H, d, J=2.14 Hz), 6.79 (1H, dd, J=8.85, 2.14 Hz), 3.95 (3H, s), 3.04 (6H, s).

EXAMPLE 322

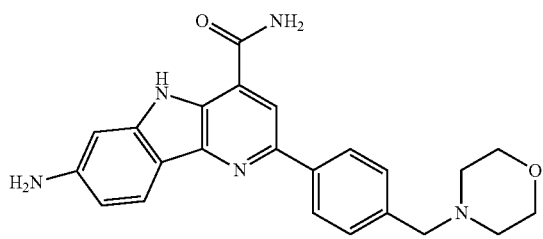 [SMILES: NC(=O)c1cc(-c2ccc(CN3CCOCC3)cc2)nc2c1[nH]c1cc(N)ccc12]

7-Amino-2-(4-(morpholinomethyl)phenyl)-5H-pyrido[3,2-b]indole-4-carboxamide

A microwave vial containing 7-amino-2-bromo-5H-pyrido[3,2-b]indole-4-carboxamide (150 mg, 0.393 mmol), 4-(4-(4,4,5,5-tetramethyl-1,3,2-dioxaborolan-2-yl)benzyl)morpholine (238 mg, 0.787 mmol), PdCl$_2$(dppf)-CH$_2$Cl$_2$ adduct (32 mg, 0.039 mmol) was flushed with nitrogen. DME (2 mL) and Na$_2$CO$_3$ (0.98 mL, 2.0 mmol, 2.0 N aq. solution) were added and the vial was sealed and heated at 100° C. for 2 hrs. This was diluted with DMF and preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min) followed by SCX capture and release with 2 N NH$_3$ in MeOH afforded 7-amino-2-(4-(morpholinomethyl)phenyl)-5H-pyrido[3,2-b]indole-4-carboxamide (90 mg, 0.20 mmol, 51% yield) as a yellow solid. MS (ESI) m/z 402.16 (M+H); HPLC retention time of 0.87 min with Xbridge S10 4.6×50 mm column, 3 min gradient, 0-100% B, 4 mL/min. Solvent A: 95% MeOH—5% H$_2$O—0.1% TFA; Solvent B: 5% MeOH—95% H$_2$O—0.1% TFA.

EXAMPLE 323

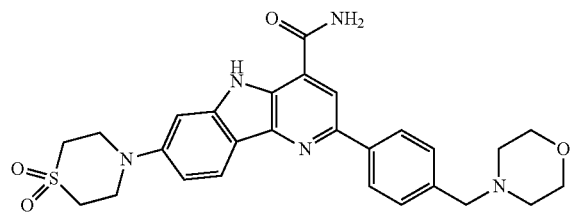 [SMILES: NC(=O)c1cc(-c2ccc(CN3CCOCC3)cc2)nc2c1[nH]c1cc(N3CCS(=O)(=O)CC3)ccc12]

7-(1,1-Dioxido-4-thiomorpholinyl)-2-(4-(4-morpholinylmethyl)phenyl)-5H-pyrido[3,2-b]indole-4-carboxamide A mixture of 7-amino-2-(4-(morpholinomethyl)phenyl)-5H-pyrido[3,2-b]indole-4-carboxamide (50 mg, 0.125 mmol), vinyl sulfone (0.13 mL, 1 3 mmol) in 2-propanol (3 mL) was stirred at 100° C. overnight. The solvent was removed and preparative HPLC (100×30 mm Luna C18 column, Solvent A=10% Methanol, 90% H$_2$O, 0.1% TFA; Solvent B=90% Methanol, 10% H$_2$O, 0.1% TFA, 10-60% B at 42 mL/min over 20 min) followed by SCX capture and release with 2 N NH$_3$ in MeOH afforded 7-(1,1-dioxido-4-thiomorpholinyl)-2-(4-(4-morpholinylmethyl)phenyl)-5H-pyrido[3,2-b]indole-4-carboxamide (6 mg, 10.97 μmol, 8.81% yield). MS (ESI) m/z 520.22 (M+H). $^1$H NMR (500 MHz, DMSO-d$_6$) δ ppm 11.22 (1H, s), 8.54 (1H, br. s.), 8.30 (1H, s), 8.22 (2H, d, J=8.24 Hz), 8.09 (1H, d, J=8.55 Hz), 7.82 (1H,s),7.46 (2H, d, J=7.93 Hz), 7.32 (1H, d, J=2.14 Hz), 7.07 (1H, dd, J=8.85, 2.14 Hz), 3.88 (4H, br. s.), 3.58-3.65 (4H, m), 3.55 (2H, s), 3.20-3.27 (4H, m), 2.41 (4H, br. s.).

EXAMPLE 324

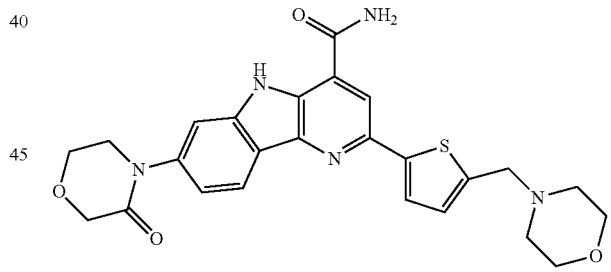

2-(5-(Morpholinomethyl)thiophen-2-yl)-7-(3-oxomorpholino)-5H-pyrido[3,2-b]indole-4-carboxamide

324A. Preparation of 2-bromo-7-(3-oxomorpholino)-5H-pyrido[3,2-b]indole-4-carboxamide

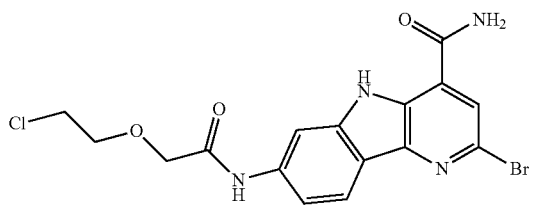 [SMILES: NC(=O)c1cc(Br)nc2c1[nH]c1cc(NC(=O)COCCCl)ccc12]

A mixture of 7-amino-2-bromo-5H-pyrido[3,2-b]indole-4-carboxamide (200 mg, 0.655 mmol) and 2-(2-chloroethoxy)acetyl chloride (113 mg, 0.721 mmol) in toluene (1.5 mL) was stirred at 100° C. for 12 hr. The solvent was removed and preparative HPLC (100×30 mm Luna C18 column, Solvent A=10% Methanol, 90% H₂O, 0.1% TFA; Solvent B=90% Methanol, 10% H₂O, 0.1% TFA, 10-60% B at 42 mL/min over 20 min) followed by SCX capture and release with 2 N NH₃ in MeOH left 2-bromo-7-(2-(2-chloroethoxy)acetamido)-5H-pyrido[3,2-b]indole-4-carboxamide (80 mg, 0.19 mmol, 29% yield) as a yellow solid. MS (ESI) m/z 426.97 (M+H). ¹H NMR (500 MHz, DMSO-d₆) δ ppm 11.73 (1H, s), 9.99 (1H, s), 8.44 (1H, br. s.), 8.24 (1H, s), 8.09 (1H, d, J=8.55 Hz), 7.98 (1H, s), 7.91 (1H, br. s.), 7.49 (1H, d, J=9.46 Hz), 4.21 (2H, s), 3.86 (4H, s).

324B. Preparation of 7-amino-2-bromo-5H-pyrido[3,2-b]indole-4-carboxamide

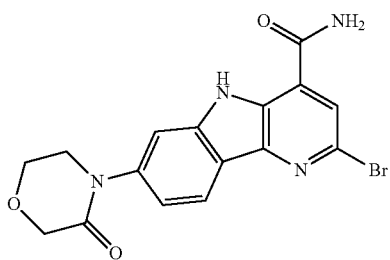 [SMILES: NC(=O)c1cc(Br)nc2c1[nH]c1cc(N3CCOCC3=O)ccc12]

A mixture of 2-bromo-7-(2-(2-chloroethoxy)acetamido)-5H-pyrido[3,2-b]indole-4-carboxamide (40 mg, 0.094 mmol) and potassium carbonate (27 mg, 0.20 mmol) in acetonitrile (2.5 mL) was stirred at 100° C. for 3 hr. The solvent was removed and preparative HPLC (100×30 mm Luna C18 column, Solvent A=10% Methanol, 90% H₂O, 0.1% TFA; Solvent B=90% Methanol, 10% H₂O, 0.1% TFA, 10-60% B at 42 mL/min over 20 min) followed by SCX capture and release with 2 N NH₃ in MeOH left 2-bromo-7-(3-oxomorpholino)-5H-pyrido[3,2-b]indole-4-carboxamide (30 mg, 0.073 mmol, 78% yield) as a yellow solid. MS (ESI) m/z 389.02 (M+H). ¹H NMR (500 MHz, DMSO-d₆) δ ppm 11.84 (1H, br. s.), 8.06-8.32 (1H, m), 7.89 (2H, br. s.), 7.52-7.76 (2H, m), 7.23 (1H, br. s.), 4.16-4.36 (2H, m), 3.94-4.13 (2H, m), 3.74-3.90 (2H, m).

324. Preparation of 2-(5-(morpholinomethyl)thiophen-2-yl)-7-(3-oxomorpholino)-5H-pyrido[3,2-b]indole-4-carboxamide A mixture of 2-bromo-7-(3-oxomorpholino)-5H-pyrido[3,2-b]indole-4-carboxamide (30 mg, 0.077 mmol), 4-((5-(4,4,5,5-tetramethyl-1,3,2-dioxaborolan-2-yl)thiophen-2-yl)methyl)morpholine (48 mg, 0.15 mmol), PdCl₂(dppf)-CH₂Cl₂ adduct (6 mg, 8 µmol) was flushed with nitrogen. DME (1.5 mL) and Na₂CO₃ (0.19 mL, 0.39 mmol, 2.0 N aq. solution) were added and the vial was sealed and heated at 100° C. for 2 hrs. This was diluted with DMF and preparative HPLC (100×30 mm Luna C18 column, Solvent A=10% Methanol, 90% H₂O, 0.1% TFA; Solvent B=90% Methanol, 10% H₂O, 0.1% TFA, 10-60% B at 42 mL/min over 20 min) followed by SCX capture and release with 2 N NH₃ in MeOH afforded 2-(5-(morpholinomethyl)thiophen-2-yl)-7-(3-oxomorpholino)-5H-pyrido[3,2-b]indole-4-carboxamide (23 mg, 0.046 mmol, 60% yield) as a yellow solid. MS (ESI) m/z 492.15 (M+H). ¹H NMR (500 MHz, DMSO-d₆) δ ppm 11.67 (1H, s), 8.54 (1H, s), 8.37 (1H, s), 8.20 (1H, d, J=8.24 Hz), 7.92 (1H, s), 7.74 (1H, d, J=1.83 Hz), 7.67 (1H, d, J=3.66 Hz), 7.30 (1H, dd, J=8.24, 1.83 Hz), 7.05 (1H, d, J=3.66 Hz), 4.27 (2H, s), 4.01-4.07 (2H, m), 3.79-3.88 (2H, m), 3.73 (2H, s), 3.63 (4H, t, J=4.73 Hz), 2.47 (4H, br. s.).

EXAMPLE 325

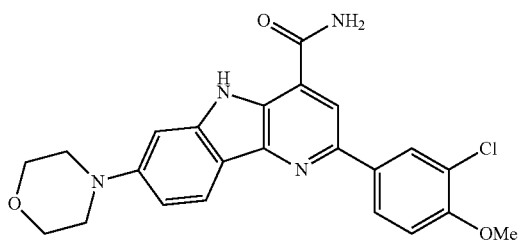 [SMILES: COc1ccc(-c2cc(C(N)=O)c3[nH]c4cc(N5CCOCC5)ccc4c3n2)cc1Cl]

2-(3-Chloro-4-methoxyphenyl)-7-morpholino-5H-pyrido[3,2-b]indole-4-carboxamide

325A. Preparation of methyl 3-amino-6-bromo-2-(4-morpholinophenyl)isonicotinate

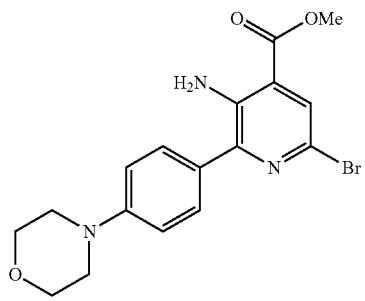 [SMILES: COC(=O)c1cc(Br)nc(-c2ccc(N3CCOCC3)cc2)c1N]

A mixture of 4-morpholinophenylboronic acid (5.0 g, 24 mmol), sodium carbonate (6.91 g, 65.2 mmol), tetrakistriphenylphosphine palladium (0) (1.40 g, 1.21 mmol), and methyl 3-amino-2,6-dibromoisonicotinate (7.86 g, 25 4 mmol) in a pressure flask was flushed with nitrogen. Toluene (60 mL) and methanol (20 mL) were added and the flask was sealed heated at 110° C. for 44 h. After cooling to RT, the solid was collected by filtration and washed with sat. aq. NaHCO₃ solution, water, and dried to give methyl 3-amino-6-bromo-2-(4-morpholinophenyl)-isonicotinate (7.32 gm, 77%). MS (ESI) m/z 392.15 (M+H). ¹H NMR (500 MHz, chloroform-d) δ ppm 7.78 (1H, s), 7.58 (2H, d, J=8.85 Hz), 7.01 (2H, d, J=8.85 Hz), 6.00 (2H, br. s.), 3.94 (3H, s), 3.88-3.92 (4H, m), 3.22-3.28 (4H, m).

325B. Preparation of methyl 3-azido-6-bromo-2-(4-morpholinophenyl)isonicotinate

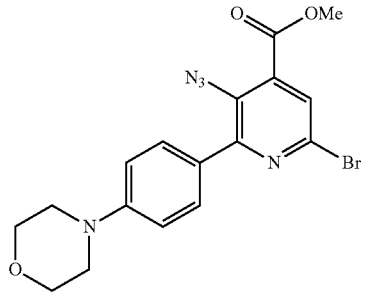 [SMILES: COC(=O)c1cc(Br)nc(-c2ccc(N3CCOCC3)cc2)c1N=[N+]=[N-]]

Methyl 3-amino-6-bromo-2-(4-morpholinophenyl)isonicotinate (2.0 g, 5.1 mmol) was quickly dissolved in TFA (25 mL) and the light brown solution was cooled in an ice-bath. Solid sodium nitrite (0.405 g, 5.86 mmol) was added in small portions over 5 min with stirring to give a dark red mixture. After 30 min, solid sodium azide (1.24 g, 19.1 mmol) was added over 1 min followed by Et$_2$O (25 mL). The mixture was stirred in the ice-bath for 30 min. Water was added and the mixture was extracted with EtOAc. The combined organic phases were washed with water (3×), brine, sat. aq. NaHCO$_3$ solution (until aq. phases were basic), and brine (1×). After drying with sodium sulfate, the solvent was removed and silica gel chromatography (step gradient elution with hexane containing 5, 10, 15, 20% EtOAc) to afford methyl 3-azido-6-bromo-2-(4-morpholinophenyl)isonicotinate (1.27 g, 3.04 mmol, 60% yield) as a solid. $^1$H NMR (500 MHz, chloroform-d) δ ppm 7.77 (2H, d, J=9.16 Hz), 7.70 (1H, s), 6.99 (2H, d, J=9.16 Hz), 4.02 (3H, s), 3.87-3.92 (4H, m), 3.26-3.31 (4H, m).

325C. Preparation of methyl 2-bromo-7-morpholino-5H-pyrido[3,2-b]indole-4-carboxylate

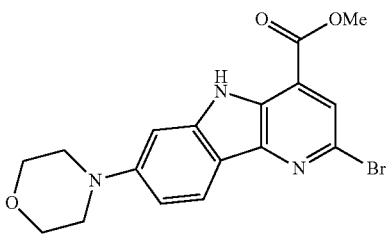 [SMILES: COC(=O)c1cc(Br)nc2c1[nH]c1cc(N3CCOCC3)ccc12]

1,2-Dichloroethane (14 mL) was added to a mixture of methyl 3-azido-6-bromo-2-(4-morpholinophenyl)isonicotinate (4.66 g, 11 1 mmol), rhodium octanoate dimer (0.521 g, 0.669 mmol) and crushed 4A° molecular sieves (4.66 g) and this was heated at 85° C. for 26 hr. It was diluted with DCM, filtered, and the solid was washed with multiple portions of DCM. The solvent was removed from the combined filtrate and the residue was suspended in MeOH. The solid was collected by filtration, washed with MeOH, and dried to leave methyl 2-bromo-7-morpholino-5H-pyrido[3,2-b]indole-4-carboxylate (4.05 g, 10.4 mmol, 93% yield) as a yellow solid. MS (ESI) m/z 390.11 (M+H). $^1$H NMR (500 MHz, chloroform-d) δ ppm 9.43 (1H, br. s.), 8.20 (1H, d, J=8.85 Hz), 7.86 (1H, s), 7.00 (1H, dd, J=8.70, 1.68 Hz), 6.89 (1H, s), 4.06 (3H, s), 3.91-3.96 (4H, m), 3.32-3.37 (4H, m).

325D. Preparation of 2-bromo-7-morpholino-5H-pyrido[3,2-b]indole-4-carboxamide

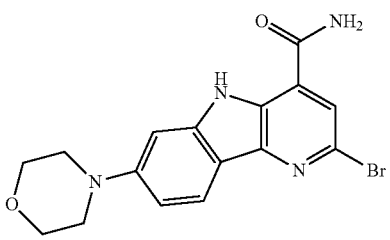

Methyl 2-bromo-7-morpholino-5H-pyrido[3,2-b]indole-4-carboxylate (3.0 g, 7.69 mmol) was mixed with 7 N NH$_3$ in MeOH (80 mL) in a pressure bottle. This was sealed and heated at 75° C. for 47 hrs. It was cooled to RT and the solid was collected by filtration, washed with MeOH, and air dried to afford 2-bromo-7-morpholino-5H-pyrido[3,2-b]indole-4-carboxamide (2.64 g, 6.33 mmol, 82% yield) as a yellow solid. MS (ESI) m/z 375.09 (M+H). $^1$H NMR (500 MHz, DMSO-d$_6$) δppm 11.41 (1H, s), 8.42 (1H, br. s.), 7.96 (1H, d, J=8.85 Hz), 7.85-7.91 (2H, m), 7.19 (1H, d, J=1.83 Hz), 7.03 (1H, dd, J=8.70, 1.98 Hz), 3.72-3.85 (4H, m), 3.16-3.25 (4H, m).

325. Preparation of 2-(3-chloro-4-methoxyphenyl)-7-morpholino-5H-pyrido[3,2-b]indole-4-carboxamide A mixture of 2-bromo-7-morpholino-5H-pyrido[3,2-b]indole-4-carboxamide (50 mg, 0.120 mmol), 3-chloro-4-methoxyphenylboronic acid (33.5 mg, 0.180 mmol), PdCl$_2$(dppf)-CH$_2$Cl$_2$ adduct (9.8 mg, 0.012 mmol) in a microwave vial was flushed with nitrogen. DME (2 mL) and aq. Na$_2$CO$_3$ solution (0.30 mL, 0.60 mmol, 2.0 M) were added and the vial was sealed and heated at 100° C. for 3.5 hr. Preparative HPLC (100×30 mm Luna C18 column, Solvent A=10% Methanol, 90% H$_2$O, 0.1% TFA; Solvent B=90% Methanol, 10% H$_2$O, 0.1% TFA, 10 to 70% gradient over 20 min at 42 mL/min) followed by SCX capture and release with 2 N NH$_3$ in MeOH gave 2-(3-chloro-4-methoxyphenyl)-7-morpholino-5H-pyrido[3,2-b]indole-4-carboxamide (10 mg, 0.023 mmol, 19% yield) as a solid. MS (ESI) m/z 437.21 (M+H). $^1$H NMR (500 MHz, DMSO-d$_6$) δ ppm 11.24 (1H, s), 8.53 (1H, s), 8.35 (1H, d, J=2.14 Hz), 8.27 (1H, s), 8.24 (1H, dd, J=8.55, 2.14 Hz), 8.08 (1H, d, J=8.85 Hz), 7.82 (1H, s), 7.31 (1H, d, J=8.85 Hz), 7.22 (1H, d, J=2.14 Hz), 7.01 (1H, dd, J=8.55, 2.14 Hz), 3.95 (3H, s), 3.78-3.85 (4H, m), 3.22-3.27 (4H, m).

EXAMPLE 326

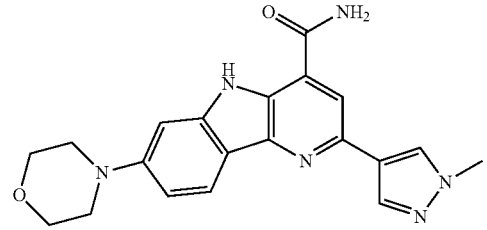 [SMILES: Cn1cc(-c2cc(C(N)=O)c3[nH]c4cc(N5CCOCC5)ccc4c3n2)cn1]

2-(1-Methyl-1H-pyrazol-4-yl)-7-morpholino-5H-pyrido[3,2-b]indole-4-carboxamide

2-Bromo-7-morpholino-5H-pyrido[3,2-b]indole-4-carboxamide (50 mg, 0.12 mmol), 1-methyl-4-(4,4,5,5-tetramethyl-1,3,2-dioxaborolan-2-yl)-1H-pyrazole (50 mg, 0.24 mmol), and PdCl$_2$(dppf)-CH$_2$Cl$_2$ adduct (9.79 mg, 0.012 mmol) in a microwave vial was flushed with nitrogen. DME (2 mL) and aq. Na$_2$CO$_3$ solution (0.30 mL, 0.60 mmol, 2.0 M) were added, the vial sealed, and heated at 100° C. for 3.5 hr. Preparative HPLC (100×30 mm Luna C18 column, Solvent A=10% Methanol, 90% H$_2$O, 0.1% TFA; Solvent B=90% Methanol, 10% H$_2$O, 0.1% TFA, 10 to 70% gradient over 20 min at 42 mL/min) followed by SCX capture and release with 2 N NH$_3$ in MeOH gave 2-(1-methyl-1H-pyrazol-4-yl)-7-morpholino-5H-pyrido[3,2-b]indole-4-carboxamide (30 mg, 0.075 mmol, 63% yield) as a solid. MS (ESI) m/z 377.20 (M+H). $^1$H NMR (500 MHz, DMSO-d$_6$) δ ppm 11.12 (1H, s), 8.36 (1H, br. s.), 8.25 (1H, s), 8.05 (1H, s), 8.01 (1H, s), 7.99 (1H, d, J=8.85 Hz), 7.79 (1H, s), 7.19 (1H, d, J=2.14 Hz), 6.98 (1H, dd, J=8.85, 2.14 Hz), 3.93 (3H, s), 3.77-3.84 (4H, m), 3.20-3.25 (4H, m).

The Examples in the following table were similarly prepared.

TABLE 18

| Ex. # | Structure | Name | Retention time (min) | MS (ESI) m/z M + H+ |
|---|---|---|---|---|
| 327 | 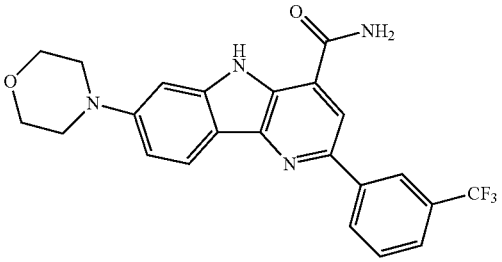 [SMILES: NC(=O)c1cc(-c2cccc(C(F)(F)F)c2)nc2c1[nH]c1cc(N3CCOCC3)ccc12] | 7-morpholino-3-(3-(trifluoromethyl)phenyl)-9H-carbazole-1-carboxamide | 2.43(a) | 440.16 |
| 328 | 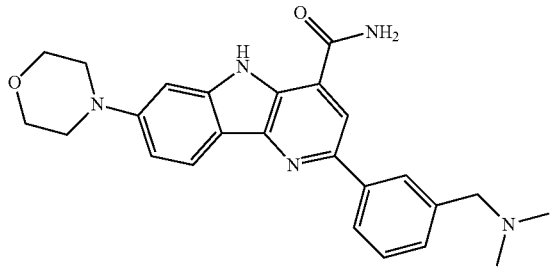 [SMILES: CN(C)Cc1cccc(-c2cc(C(N)=O)c3[nH]c4cc(N5CCOCC5)ccc4c3n2)c1] | 2-(3-((dimethylamino)methyl)phenyl)-7-morpholino-5H-pyrido[3,2-b]indole-4-carboxamide | 1.52(c) | 430.5 |
| 329 | 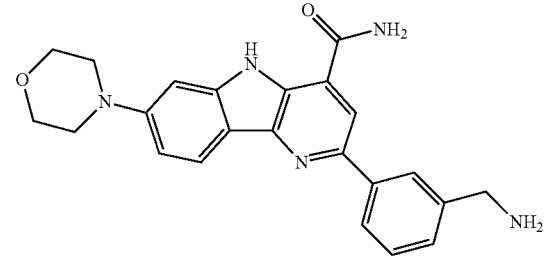 [SMILES: NCc1cccc(-c2cc(C(N)=O)c3[nH]c4cc(N5CCOCC5)ccc4c3n2)c1] | 2-(3-(aminomethyl)phenyl)-7-morpholino-5H-pyrido[3,2-b]indole-4-carboxamide | 1.47(c) | 402.5 |
| 330 | 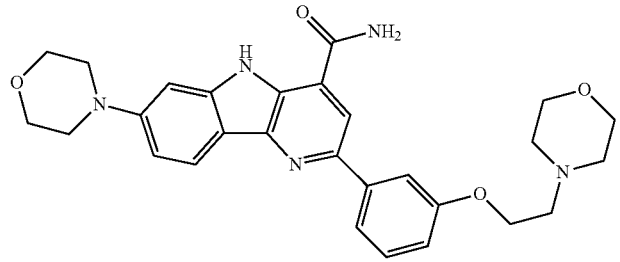 [SMILES: NC(=O)c1cc(-c2cccc(OCCN3CCOCC3)c2)nc2c1[nH]c1cc(N3CCOCC3)ccc12] | 7-morpholino-2-(3-(2-morpholinoethoxy)phenyl)-5H-pyrido[3,2-b]indole-4-carboxamide | 1.33(b) | 502.38 |
| 331 | 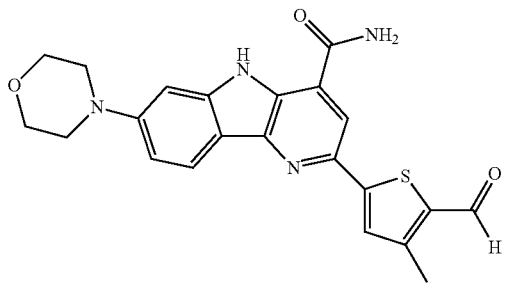 [SMILES: Cc1cc(-c2cc(C(N)=O)c3[nH]c4cc(N5CCOCC5)ccc4c3n2)sc1C=O] | 2-(5-formyl-4-methylthiophen-2-yl)-7-morpholino-5H-pyrido[3,2-b]indole-4-carboxamide | 2.07(b) | 421.20 |

TABLE 18-continued

| Ex. # | Structure | Name | Retention time (min) | MS (ESI) m/z M + H+ |
|---|---|---|---|---|
| 332 | 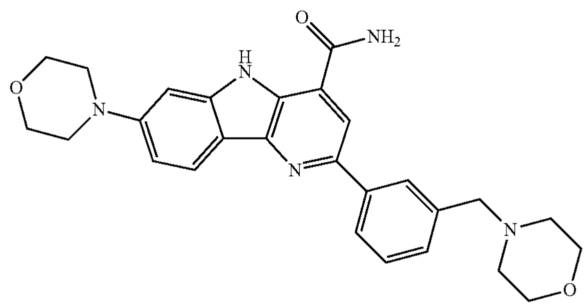 [SMILES: NC(=O)c1cc(-c2cccc(CN3CCOCC3)c2)nc2c1[nH]c1cc(N3CCOCC3)ccc12] | 7-morpholino-2-(3-(morpholinomethyl)phenyl)-5H-pyrido[3,2-b]indole-4-carboxamide | 1.24(b) | 472.24 |
| 333 | 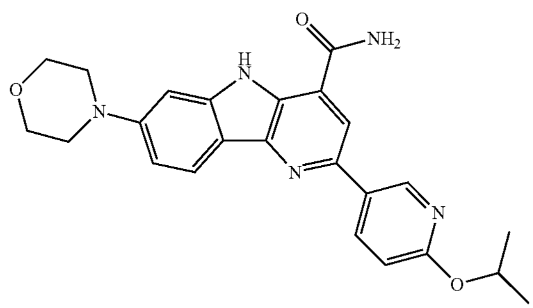 [SMILES: CC(C)Oc1ccc(-c2cc(C(N)=O)c3[nH]c4cc(N5CCOCC5)ccc4c3n2)cn1] | 2-(6-isopropoxypyridin-3-yl)-7-morpholino-5H-pyrido[3,2-b]indole-4-carboxamidecarboxamide | 2.00(b) | 432.15 |
| 334 | 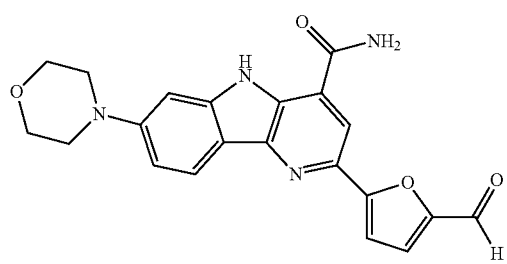 [SMILES: NC(=O)c1cc(-c2ccc(C=O)s2)nc2c1[nH]c1cc(N3CCOCC3)ccc12] | 2-(5-formylfuran-2-yl)-7-morpholino-5H-pyrido[3,2-b]indole-4-carboxamide | 1.78(b) | 391.17 |
| 335 | 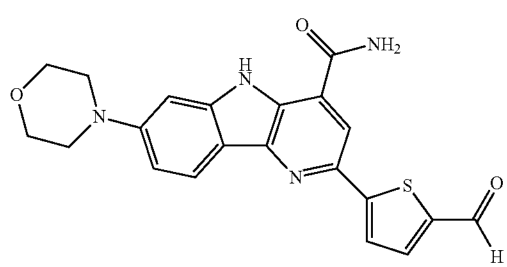 | 2-(5-formylthiophen-3-yl)-7-morpholino-5H-pyrido[3,2-b]indole-4-carboxamide | 1.73(b) | 407.17 |
| 336 | 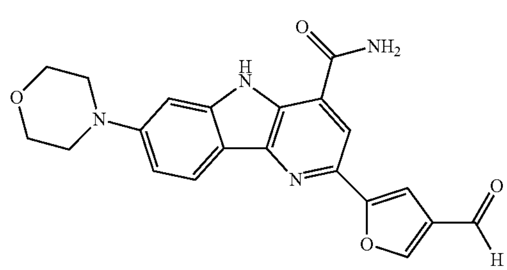 [SMILES: NC(=O)c1cc(-c2cc(C=O)co2)nc2c1[nH]c1cc(N3CCOCC3)ccc12] | 2-(4-formylfuran-2-yl)-7-morpholino-5H-pyrido[3,2-b]indole-4-carboxamide | 1.61(b) | 391.19 |

TABLE 18-continued

| Ex. # | Structure | Name | Retention time (min) | MS (ESI) m/z M + H+ |
|---|---|---|---|---|
| 337 | 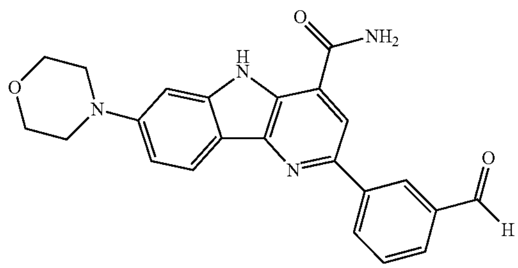 [SMILES: NC(=O)c1cc(-c2cccc(C=O)c2)nc2c1[nH]c1cc(N3CCOCC3)ccc12] | 2-(3-formylphenyl)-7-morpholino-5H-pyrido[3,2-b]indole-4-carboxamide | 1.45(b) | 401.15 |
| 338 | 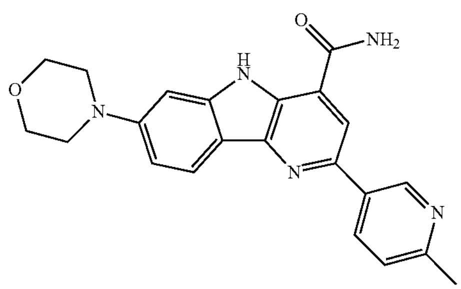 [SMILES: Cc1ccc(-c2cc(C(N)=O)c3[nH]c4cc(N5CCOCC5)ccc4c3n2)cn1] | 2-(6-methylpyridin-3-yl)-7-morpholino-5H-pyrido[3,2-b]indole-4-carboxamide | 1.28(b) | 388.16 |
| 339 | 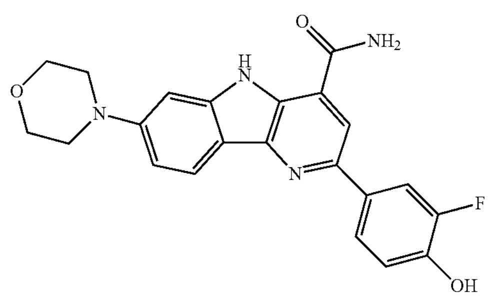 [SMILES: NC(=O)c1cc(-c2ccc(O)c(F)c2)nc2c1[nH]c1cc(N3CCOCC3)ccc12] | 2-(3-fluoro-4-hydroxyphenyl)-7-morpholino-5H-pyrido[3,2-b]indole-4-carboxamide | 1.54(b) | 407.20 |
| 340 | 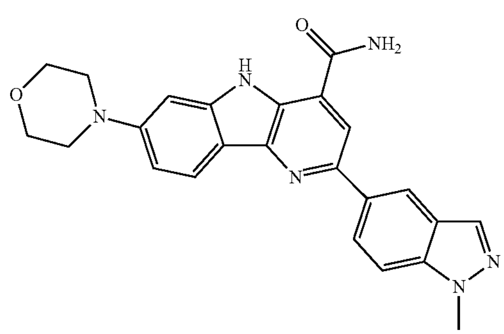 [SMILES: Cn1ncc2cc(-c3cc(C(N)=O)c4[nH]c5cc(N6CCOCC6)ccc5c4n3)ccc21] | 2-(1-methyl-1H-indazol-5-yl)-7-morpholino-5H-pyrido[3,2-b]indole-4-carboxamide | 1.65(b) | 427.14 |
| 341 | 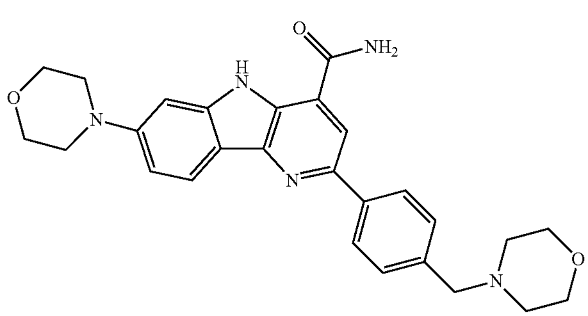 [SMILES: NC(=O)c1cc(-c2ccc(CN3CCOCC3)cc2)nc2c1[nH]c1cc(N3CCOCC3)ccc12] | 7-morpholino-2-(4-(morpholinomethyl)phenyl)-5H-pyrido[3,2-b]indole-4-carboxamide | 1.17(b) | 472.3 |

TABLE 18-continued

| Ex. # | Structure | Name | Retention time (min) | MS (ESI) m/z M + H+ |
|---|---|---|---|---|
| 342 | 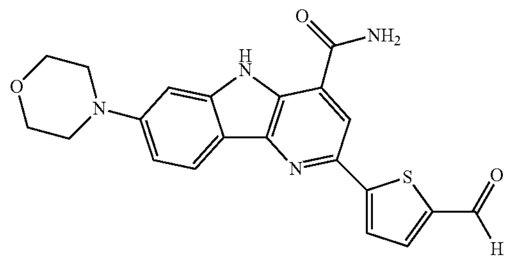 [SMILES: NC(=O)c1cc(-c2ccc(C=O)s2)nc2c1[nH]c1cc(N3CCOCC3)ccc12] | 7-morpholino-2-(4-(morpholinomethyl)phenyl)-5H-pyrido[3,2-b]indole-4-carboxamide | 1.91(b) | 407.16 |
| 343 | 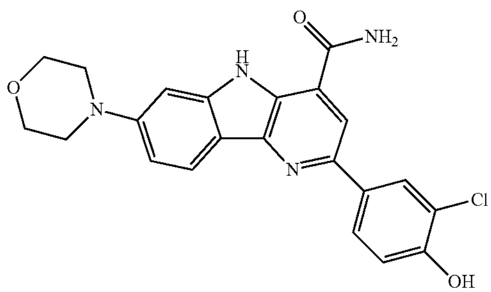 [SMILES: NC(=O)c1cc(-c2ccc(O)c(Cl)c2)nc2c1[nH]c1cc(N3CCOCC3)ccc12] | 2-(3-chloro-4-hydroxyphenyl)-7-morpholino-5H-pyrido[3,2-b]indole-4-carboxamide | 1.61(c) | 423.4 |
| 344 | 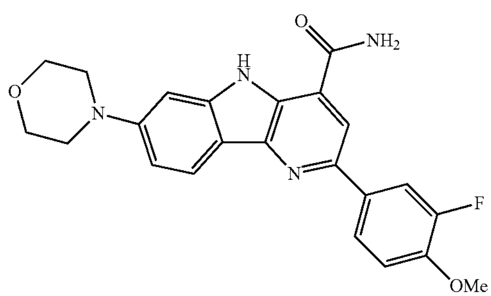 [SMILES: COc1ccc(-c2cc(C(N)=O)c3[nH]c4cc(N5CCOCC5)ccc4c3n2)cc1F] | 2-(3-fluoro-4-methoxyphenyl)-7-morpholino-5H-pyrido[3,2-b]indole-4-carboxamide | 1.79(b) | 421.25 |
| 345 | 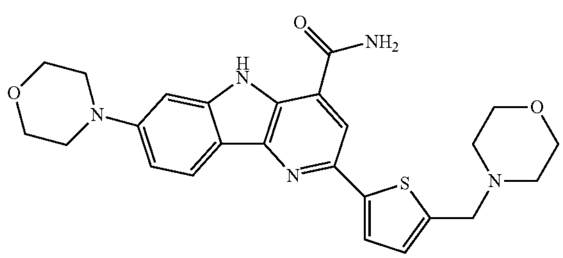 [SMILES: NC(=O)c1cc(-c2ccc(CN3CCOCC3)s2)nc2c1[nH]c1cc(N3CCOCC3)ccc12] | 7-morpholino-2-(5-(morpholinomethyl)thiophen-2-yl)-5H-pyrido[3,2-b]indole-4-carboxamide | 1.27(b) | 478.21 |
| 346 | 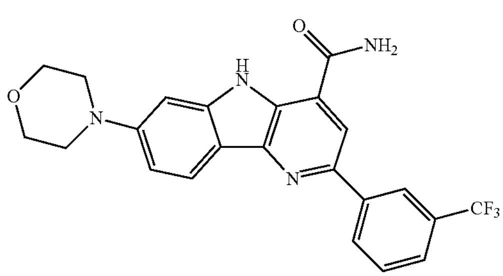 [SMILES: NC(=O)c1cc(-c2cccc(C(F)(F)F)c2)nc2c1[nH]c1cc(N3CCOCC3)ccc12] | 7-morpholino-2-(3-(trifluoromethyl)phenyl)-5H-pyrido[3,2-b]indole-4-carboxamide | 2.44(a) | 441.21 |

TABLE 18-continued

| Ex. # | Structure | Name | Retention time (min) | MS (ESI) m/z M + H+ |
|---|---|---|---|---|
| 347 | 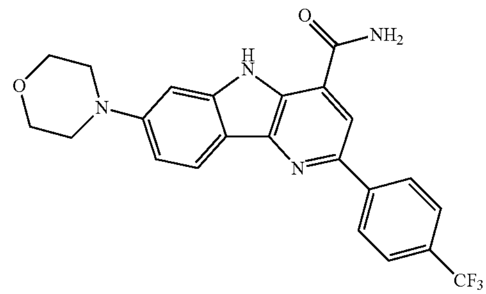 [SMILES: NC(=O)c1cc(-c2ccc(C(F)(F)F)cc2)nc2c1[nH]c1cc(N3CCOCC3)ccc12] | 7-morpholino-2-(4-(trifluoromethyl)phenyl)-5H-pyrido[3,2-b]indole-4-carboxamide | 2.51(a) | 441.21 |
| 348 | 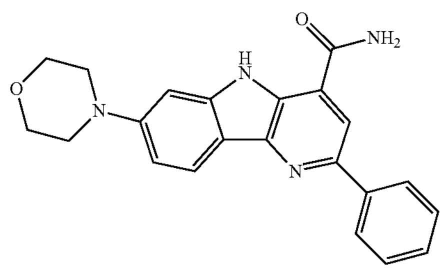 [SMILES: NC(=O)c1cc(-c2ccccc2)nc2c1[nH]c1cc(N3CCOCC3)ccc12] | 7-morpholino-2-phenyl-5H-pyrido[3,2-b]indole-4-carboxamide | 1.84(a) | 373.11 |
| 349 | 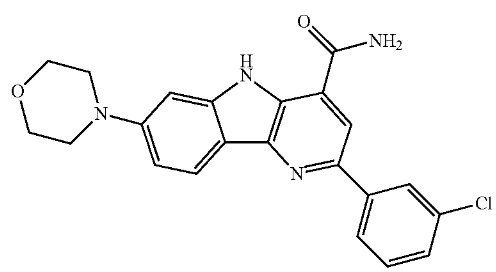 [SMILES: NC(=O)c1cc(-c2cccc(Cl)c2)nc2c1[nH]c1cc(N3CCOCC3)ccc12] | 2-(3-chlorophenyl)-7-morpholino-5H-pyrido[3,2-b]indole-4-carboxamide | 2.68(a) | 407.25 |
| 350 | 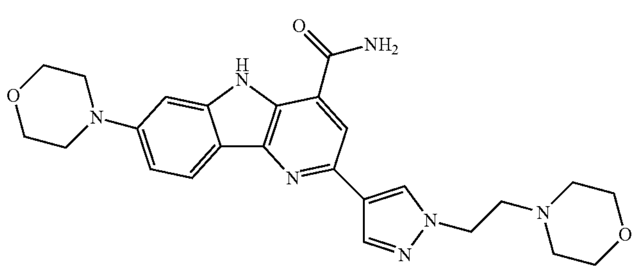 [SMILES: NC(=O)c1cc(-c2cnn(CCN3CCOCC3)c2)nc2c1[nH]c1cc(N3CCOCC3)ccc12] | 7-morpholino-2-(1-(2-morpholinoethyl)-1H-pyrazol-4-yl)-5H-pyrido[3,2-b]indole-4-carboxamide | 1.08(a) | 476.37 |

HPLC condition a: Xbridge S10 4.6 × 50 mm column, 3 min gradient, 0-100% B, 4 mL/min. Solvent A: 95% MeOH –5% H$_2$O - 0.1% TFA; Solvent B: 5% MeOH - 95% H$_2$O - 0.1% TFA.

HPLC condition b: PHENOMENEX ® Luna S10 3 × 50 mm column, 3 min gradient, 0-100% B, 4 mL/min. Solvent A: 95% MeOH –5% H$_2$O - 0.1% TFA; Solvent B: 5% MeOH - 95% H$_2$O - 0.1% TFA.

HPLC condition c: PHENOMENEX ® Luna C18 3 × 50 mm column, 2 min gradient, 0-100% B, 1 mL/min. Solvent A: 5% CH$_3$CN - 95% H$_2$O - 10 mM Ammonium Acetate; Solvent B: 95% CH$_3$CN - 5% H$_2$O - 10 mM Ammonium Acetate.

EXAMPLE 351

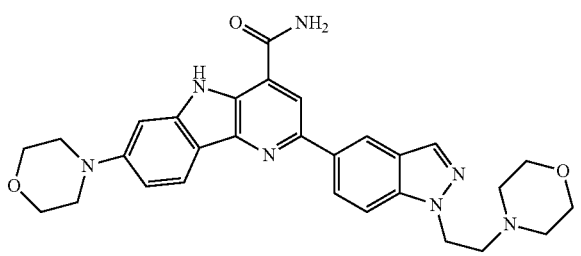 [SMILES: NC(=O)c1cc(-c2ccc3c(cnn3CCN3CCOCC3)c2)nc2c1[nH]c1cc(N3CCOCC3)ccc12]

7-Morpholino-2-(1-(2-morpholinoethyl)-1H-indazol-5-yl)-5H-pyrido[3,2-b]indole-4-carboxamide

351A. Preparation of 5-bromo-1-(2-chloroethyl)-1H-indazole

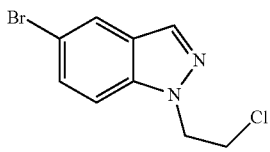 [SMILES: ClCCn1ncc2cc(Br)ccc21]

A mixture of 5-bromo-1H-indazole (900 mg, 4.57 mmol), 1-bromo-2-chloroethane (1.31 g, 9.14 mmol) and K$_2$CO$_3$ (1.89 g, 13 7 mmol) in DMF (40 mL) in a sealed pressure flask was heated at 40° C. for 10 h. Additional 1.3 g 1-bromo-2-chloroethane (1.31 g, 9.14 mmol), and K$_2$CO$_3$ (1.89 g, 13 7 mmol) were then added and heating was continued for 3 h. This was filtered, the solvent removed from the filtrate, and the residue chromatographed on silica gel (step gradient elution with hexane containing 0, 5, 10 and 20% EtOAc) afforded (in order of elution): 5-bromo-1-(2-chloroethyl)-1H-indazole (690 mg, 2.66 mmol, 58% yield). MS (ESI) m/z 260.95 (M+H). $^1$H NMR (500 MHz, chloroform-d) δ ppm 7.99 (1H, s), 7.88 (1H, s), 7.46-7.52 (1H, m), 7.36 (1H, d, J=8.85 Hz), 4.67 (2H, t, J=6.26 Hz), 3.97 (2H, t, J=6.26 Hz). 5-bromo-2-(2-chloroethyl)-2H-indazole (360 mg, 1.39 mmol, 30% yield). MS (ESI) m/z 260.95 (M+H). $^1$H NMR (500 MHz, chloroform-d) δ ppm 7.98 (1H, s), 7.85 (1H, s), 7.60 (1H, d, J=9.16 Hz), 7.37 (1H, d, J=9.16 Hz), 4.69-4.74 (2H, m), 4.02-4.07 (2H, m).

351B. Preparation of 4-(2-(5-bromo-1H-indazol-1-yl)ethyl)morpholine

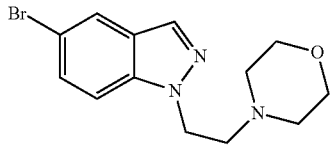 [SMILES: Brc1ccc2c(cnn2CCN2CCOCC2)c1]

A mixture of 5-bromo-1-(2-chloroethyl)-1H-indazole (500 mg, 1.93 mmol), potassium iodide (1.28 mg, 7.71 mmol) and morpholine (1.0 mL, 12 mmol) in NMP (3 mL) in a sealed vial was heated at 70° C. overnight. Preparative HPLC (100×30 mm Luna C18 column, Solvent A=10% Methanol, 90% H$_2$O, 0.1% TFA; Solvent B=90% Methanol, 10% H$_2$O, 0.1% TFA, elution gradient of 0 to 60% B over 20 min at 42 mL/min) afforded 4-(2-(5-bromo-1H-indazol-1-yl)ethyl) morpholine (549 mg, 1.77 mmol, 92% yield) as a solid. MS (ESI) m/z 311.98 (M+H). $^1$H NMR (500 MHz, chloroform-d) δ ppm 7.89 (1H, s), 7.81 (1H, s), 7.38-7.42 (1H, m), 7.29 (1H, d, J=8.85 Hz), 4.44 (2H, t, J=6.87 Hz), 3.58-3.63 (4H, m), 2.82 (2H, t, J=6.87 Hz), 2.41-2.48 (4H, m).

351. Preparation of 7-morpholino-2-(1-(2-morpholinoethyl)-1H-indazol-5-yl)-5H-pyrido[3,2-b]indole-4-carboxamide A microwave vial containing a mixture of 4-(2-(5-bromo-1H-indazol-1-yl)ethyl)morpholine (549 mg, 1.77 mmol), 4,4,4',4',5,5,5',5'-octamethyl-2,2'-bi(1,3,2-dioxaborolane) (494 mg, 1.95 mmol), potassium acetate (347 mg, 3.54 mmol) and PdCl$_2$(dppf)-CH$_2$Cl$_2$ adduct (72 mg, 0.088 mmol) was flushed with nitrogen. Dioxane (4.5 mL) was added, the vial was sealed and heated at 100° C. for 5 hrs. This was diluted with EtOAc, washed with water and brine, and dried over MgSO$_4$. Removal of the solvent left crude 4-(2-(5-(4,4,5,5-tetramethyl-1,3,2-dioxaborolan-2-yl)-1H-indazol-1-yl) ethyl)morpholine (1 gm) as a oil which was used as such. A microwave vial containing a mixture of 2-bromo-7-morpholino-5H-pyrido[3,2-b]indole-4-carboxamide (50 mg, 0.120 mmol), crude 4-(2-(5-(4,4,5,5-tetramethyl-1,3,2-dioxaborolan-2-yl)-1H-indazol-1-yl)ethyl)morpholine (83 mg, 0.17 mmol), and PdCl$_2$(dppf)-CH$_2$Cl$_2$ adduct (9.8 mg, 0.012 mmol), was flushed with nitrogen. DME (2 mL) and aq. Na$_2$CO$_3$ (0.30 mL, 0.60 mmol, 2.0 M) were added and the vial was sealed and heated at 100° for 6 hrs. Preparative HPLC (100×30 mm Luna C18 column, Solvent A=10% Methanol, 90% H$_2$O, 0.1% TFA; Solvent B=90% Methanol, 10% H$_2$O, 0.1% TFA, elution gradient of 0 to 60% B over 20 min at 42 mL/min) followed by SCX capture and release with 2 N NH$_3$ in MeOH afforded 7-morpholino-2-(1-(2-morpholinoethyl)-1H-indazol-5-yl)-5H-pyrido[3,2-b]indole-4-carboxamide (35 mg, 0.067 mmol, 56% yield) as a solid. MS (ESI) m/z 526.24 (M+H). $^1$H NMR (500 MHz, DMSO-d$_6$) δ ppm 11.21 (1H, s), 8.61 (1H, s), 8.55 (1H, br. s.), 8.37 (1H, dd, J=9.16, 1.53 Hz), 8.35 (1H, s), 8.19 (1H, s), 8.10 (1H, d J=8.85 Hz), 7.79-7.86 (2H, m), 7.23 (1H, d, J=1.83 Hz), 7.02 (1H, dd, J=8.70, 1.98 Hz), 4.58 (2H, t, J=6.56 Hz), 3.77-3.87 (4H, m), 3.49-3.56 (4H, m), 3.21-3.27 (4H, m), 2.82 (2H, t, J=6.56 Hz), 2.41-2.49 (4H, m).

EXAMPLE 352

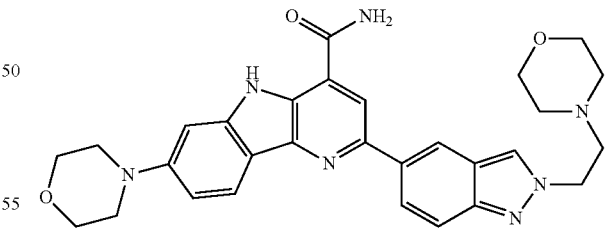

7-Morpholino-2-(1-(2-morpholinoethyl)-1H-indazol-5-yl)-5H-pyrido[3,2-b]indole-4-carboxamide This was similarly prepared from 5-bromo-2-(2-chloroethyl)-2H-indazole and 2-bromo-7-morpholino-5H-pyrido[3,2-b]indole-4-carboxamide. MS (ESI) m/z 526.24 (M+H). $^1$H NMR (500 MHz, DMSO-d$_6$) δ ppm 11.20 (1H, s), 8.50-8.61 (3H, m), 8.34 (1H, s), 8.26 (1H, d, J=9.15 Hz), 8.09 (1H, d, J=8.85 Hz), 7.80 (1H, br. s.), 7.73 (1H, d, J=9.16 Hz), 7.22

(1H, s), 7.01 (1H, d, J=8.55 Hz), 4.59 (2H, t, J=6.26 Hz), 3.77-3.87 (4H, m), 3.56-3.61 (4H, m), 3.20-3.27 (4H, m), 2.91 (2H, t, J=6.41 Hz), 2.42-2.48 (4H, m).

EXAMPLE 353

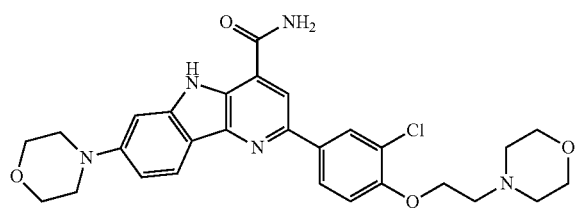 [SMILES: NC(=O)c1cc(-c2ccc(OCCN3CCOCC3)c(Cl)c2)nc2c1[nH]c1cc(N3CCOCC3)ccc12]

2-(3-Chloro-4-(2-morpholinoethoxy)phenyl)-7-morpholino-5H-pyrido[3,2-b]indole-4-carboxamide Diethyl azodicarboxylate (0.012 mL, 0.074 mmol) was added to a solution of triphenylphosphine (19 mg, 0.074 mmol), 2-(3-chloro-4-hydroxyphenyl)-7-morpholino-5H-pyrido[3,2-b]indole-4-carboxamide (16 mg, 0.037 mmol) and 2-morpholinoethanol (9.0 µL, 0.074 mmol) in dry THF (0.5 mL) at RT under nitrogen. After stirring overnight, the solvent was removed and preparative HPLC (PHENOMENEX® Luna C18 30×100 10u Column, Solvent A=10 mM NH$_4$OAc in 95% water:5% acetonitrile; B=10 mM NH$_4$OAc in 5% water:95% acetonitrile, gradient of 10 to 100% B over 25 min at 30 mL/min) followed by SCX capture and release with 2 N NH$_3$ in MeOH afforded 2-(3-chloro-4-(2-morpholinoethoxy)phenyl)-7-morpholino-5H-pyrido[3,2-b]indole-4-carboxamide (4.9 mg, 8.2 nmol, 22% yield) as a solid. MS (ESI) m/z 536.38 (M+H). $^1$H NMR (400 MHz, DMSO-d$_6$) δ ppm 11.26 (1H, s), 8.54 (1H, s), 8.34 (1H, d, J=2.01 Hz), 8.27 (1H, s), 8.21 (1H, dd, J=8.69, 2.14 Hz), 8.07 (1H, d, J=8.56 Hz), 7.84 (1H, s), 7.32 (1H, d, J=8.81 Hz), 7.20 (1H, d, J=2.01 Hz), 7.00 (1H, dd, J=8.81, 2.01 Hz), 4.26 (2H, t, J=5.79 Hz), 3.74-3.85 (4H, m), 3.53-3.66 (4H, m), 3.18-3.28 (4H, m), 2.78 (2H, t, J=5.67 Hz), 2.52-2.59 (4H, m).

The Examples in the following table were similarly prepared.

TABLE 19

| Ex. # | Structure | Name | Retention time (min) | MS (ESI) m/z M + H$^+$ |
|---|---|---|---|---|
| 354 | 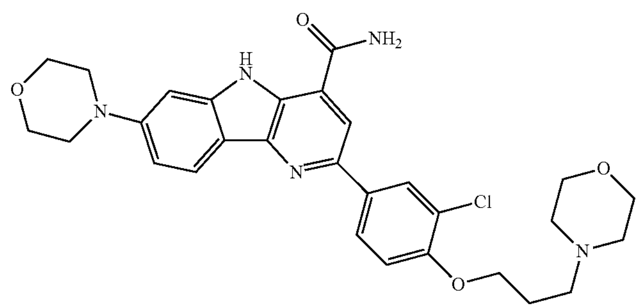 [SMILES: NC(=O)c1cc(-c2ccc(OCCCN3CCOCC3)c(Cl)c2)nc2c1[nH]c1cc(N3CCOCC3)ccc12] | 2-(3-chloro-4-(3-morpholinopropoxy)phenyl)-7-morpholino-5H-pyrido[3,2-b]indole-4-carboxamide | 11.51 | 550.37 |
| 355 | 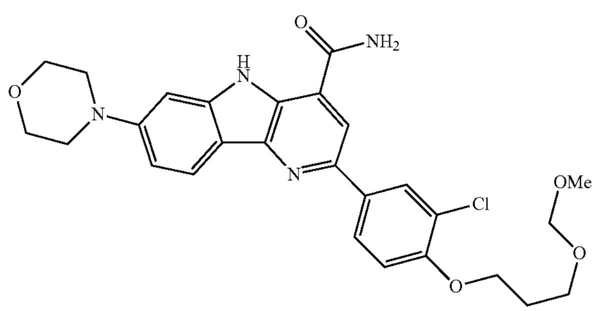 [SMILES: COCOCCCOc1ccc(-c2cc(C(N)=O)c3[nH]c4cc(N5CCOCC5)ccc4c3n2)cc1Cl] | 2-(3-chloro-4-(2-(2-methoxyethoxy)ethoxy)phenyl)-7-morpholino-5H-pyrido[3,2-b]indole-4-carboxamide | 2.00 | 525.15 |
| 356 | 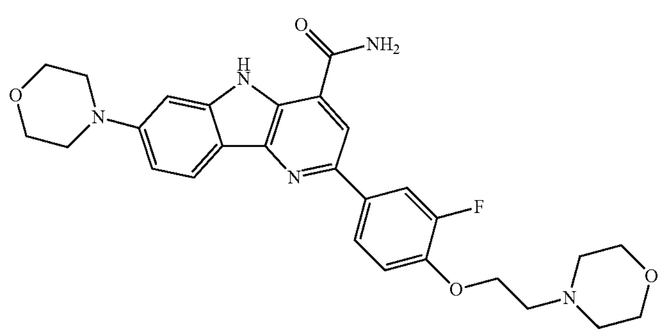 [SMILES: NC(=O)c1cc(-c2ccc(OCCN3CCOCC3)c(F)c2)nc2c1[nH]c1cc(N3CCOCC3)ccc12] | 2-(3-fluoro-4-(2-morpholinoethoxy)phenyl)-7-morpholino-5H-pyrido[3,2-b]indole-4-carboxamide | 1.33 | 520.38 |

TABLE 19-continued

| Ex. # | Structure | Name | Retention time (min) | MS (ESI) m/z M + H+ |
|---|---|---|---|---|
| 357 | 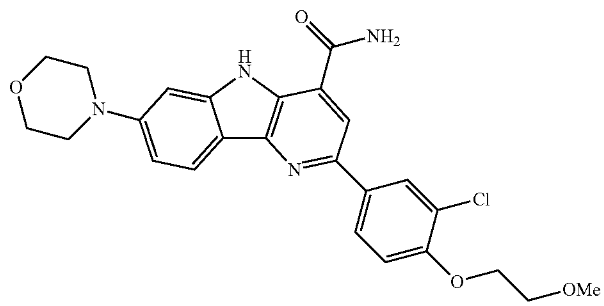 [SMILES: COCCOc1ccc(-c2cc(C(N)=O)c3[nH]c4cc(N5CCOCC5)ccc4c3n2)cc1Cl] | 2-(3-chloro-4-(2-methoxyethoxy)phenyl)-7-morpholino-5H-pyrido[3,2-b]indole-4-carboxamide | 1.98 | 481.29 |
| 358 | 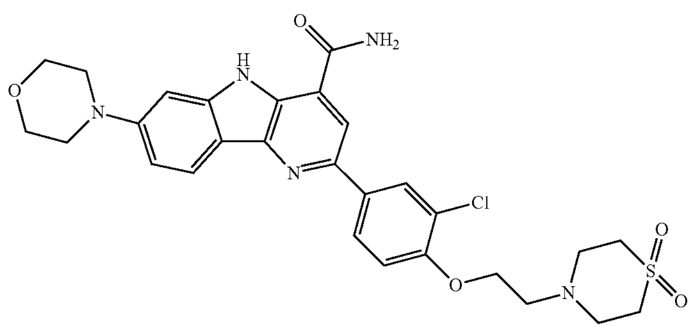 [SMILES: NC(=O)c1cc(-c2ccc(OCCN3CCS(=O)(=O)CC3)c(Cl)c2)nc2c1[nH]c1cc(N3CCOCC3)ccc12] | 2-(3-chloro-4-(2-(1,1-dioxido-4-thiomorpholinyl)ethoxy)phenyl)-7-(4-morpholinyl)-5H-pyrido[3,2-b]indole-4-carboxamide | 1.62 | 584.33 |

HPLC conditions: PHENOMENEX ® Luna S10 3 × 50 mm column, 3 min gradient, 0-100% B, 4 mL/min. Solvent A: 95% MeOH −5% H₂O - 0.1% TFA; Solvent B: 5% MeOH - 95% H₂O - 0.1% TFA.

The following compounds were also similarly prepared except that an N-Boc protecting group was removed with TFA:DCM=1:1 prior to final purification of the product.

TABLE 20

| Ex. # | Structure | Name | Retention time (min) | MS (ESI) m/z M + H+ |
|---|---|---|---|---|
| 359 | 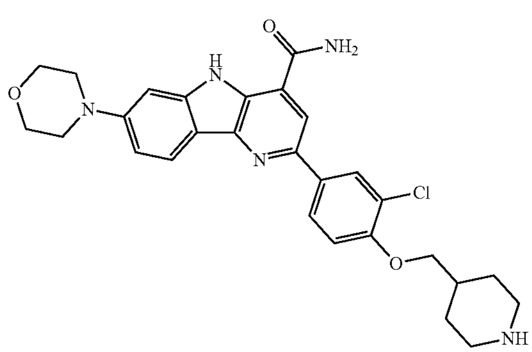 [SMILES: NC(=O)c1cc(-c2ccc(OCC3CCNCC3)c(Cl)c2)nc2c1[nH]c1cc(N3CCOCC3)ccc12] | 2-(3-chloro-4-(piperidin-4-ylmethoxy)phenyl)-7-morpholino-5H-pyrido[3,2-b]indole-4-carboxamide | 1.61 | 520.20 |

TABLE 20-continued

| Ex. # | Structure | Name | Retention time (min) | MS (ESI) m/z M + H+ |
|---|---|---|---|---|
| 360 | 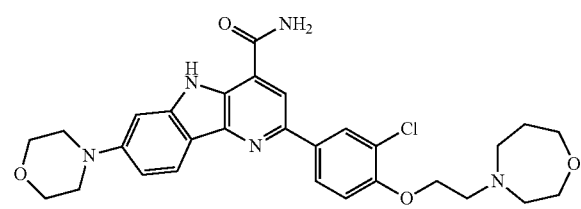 [SMILES: NC(=O)c1cc(-c2ccc(OCCN3CCCOCC3)c(Cl)c2)nc2c1[nH]c1cc(N3CCOCC3)ccc12] | 2-(3-chloro-4-(piperidin-4-yloxy)phenyl)-7-morpholino-5H-pyrido[3,2-b]indole-4-carboxamide | 1.57 | 506.16 |

HPLC conditions: PHENOMENEX ® Luna S10 3 × 50 mm column, 3 min gradient, 0-100% B, 4 mL/min. Solvent A: 95% MeOH – 5% H₂O – 0.1% TFA; Solvent B: 5% MeOH – 95% H₂O – 0.1% TFA.

EXAMPLE 361

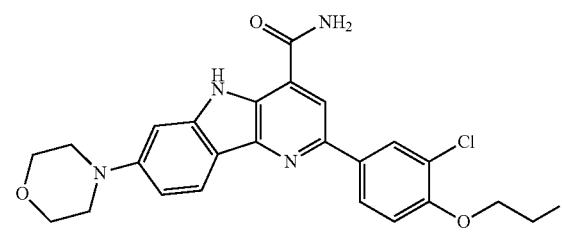

2-(4-(2-(1,4-Oxazepan-4-yl)ethoxy)-3-chlorophenyl)-7-morpholino-5H-pyrido[3,2-b]indole-4-carboxamide 361A. Preparation of 2-(3-chloro-4-(2-chloroethoxy)phenyl)-7-morpholino-5H-pyrido[3,2-b]indole-4-carboxamide A mixture of 2-(3-chloro-4-hydroxyphenyl)-7-morpholino-5H-pyrido[3,2-b]indole-4-carboxamide (120 mg, 0.284 mmol), 1-bromo-2-chloroethane (67 μL, 1.42 mmol) and K₂CO₃ (196 mg, 1.42 mmol) in DMF (4.8 mL) in a vial was heated at 40° C. for 3 h. Preparative HPLC (100×30 mm Luna C18 column, Solvent A=10% Methanol, 90% H₂O, 0.1% TFA; Solvent B=90% Methanol, 10% H₂O, 0.1% TFA; gradient of 0 to 100% B over 10 min at 42 mL/min) followed by SCX capture and release with 2 N NH₃ in MeOH left 2-(3-chloro-4-(2-chloroethoxy)phenyl)-7-morpholino-5H-pyrido[3,2-b]indole-4-carboxamide (94 mg, 0.19 mmol, 68% yield) as a yellow solid. MS (ESI) m/z 485.22 (M+H). ¹H NMR (500 MHz, DMSO-d₆) δ ppm 11.25 (1H, s), 8.53 (1H, s), 8.36 (1H, d, J=2.44 Hz), 8.28 (1H, s), 8.23 (1H, dd, J=8.70, 2.29 Hz), 8.08 (1H, d, J=8.55 Hz), 7.83 (1H, s), 7.34 (1H, d, J=8.85 Hz), 7.22 (1H, d, J=2.14 Hz), 7.01 (1H, dd, J=8.85, 2.14 Hz), 4.43-4.48 (2H, m), 4.01-4.05 (2H, m), 3.78-3.84 (4H, m), 3.21-3.27 (4H, m).

361. Preparation of 2-(4-(2-(1,4-oxazepan-4-yl)ethoxy)-3-chlorophenyl)-7-morpholino-5H-pyrido[3,2-b]indole-4-carboxamide A mixture of 2-(3-chloro-4-(2-chloroethoxy)phenyl)-7-morpholino-5H-pyrido[3,2-b]indole-4-carboxamide (20 mg, 0.041 mmol), potassium iodide (14 mg, 0.082 mmol), K₂CO₃ (11 mg, 0.082 mmol) and homomorpholine hydrochloride (23 mg, 0.17 mmol) in DMSO (0.2 mL) in a vial was heated at 70° C. for 40 hrs. Preparative HPLC (100×30 mm Luna C18 column, Solvent A=10% Methanol, 90% H₂O, 0.1% TFA; Solvent B=90% Methanol, 10% H₂O, 0.1% TFA, gradient of 0 to 60% B over 20 min at 42 mL/min) followed by SCX capture and release with 2 N NH₃ in MeOH afforded 2-(4-(2-(1,4-oxazepan-4-yl)ethoxy)-3-chlorophenyl)-7-morpholino-5H-pyrido[3,2-b]indole-4-carboxamide (16 mg, 0.029 mmol, 71% yield) as a yellow solid. MS (ESI) m/z 550.24 (M+H). ¹H NMR (500 MHz, MeOD) δ ppm 8.22 (1H, d, J=8.85 Hz), 8.16 (1H, d, J=2.14 Hz), 8.06 (1H, s), 7.99 (1H, dd, J=8.55, 2.44 Hz), 7.19 (1H, d, J=8.85 Hz), 7.10 (1H, d, J=2.14 Hz), 7.03 (1H, dd, J=8.85, 2.14 Hz), 4.27 (2H, t, J=5.34 Hz), 3.86-3.94 (4H, m), 3.76-3.85 (4H, m), 3.27-3.31 (4H, m), 3.10 (2H, t, J=5.34 Hz), 2.94-3.02 (4H, m), 1.97 (2H, m).

The Examples in the following table were similarly prepared.

TABLE 21

| Ex. # | Structure | Name | Retention time (min) | MMS (ESI) m/z M + H+ |
|---|---|---|---|---|
| 362 | 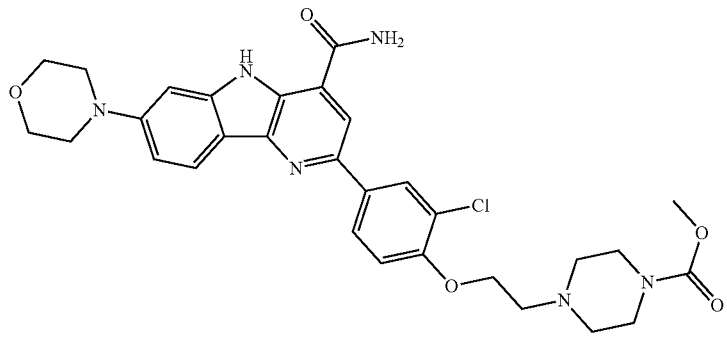 [SMILES: COC(=O)N1CCN(CCOc2ccc(-c3cc(C(N)=O)c4[nH]c5cc(N6CCOCC6)ccc5c4n3)cc2Cl)CC1] | methyl 4-(2-(4-(4-carbamoyl-7-morpholino-5H-pyrido[3,2-b]indol-2-yl)-2-chlorophenoxy)ethyl)piperazine-1-carboxylate | 1.57 | 593.19 |
| 363 | 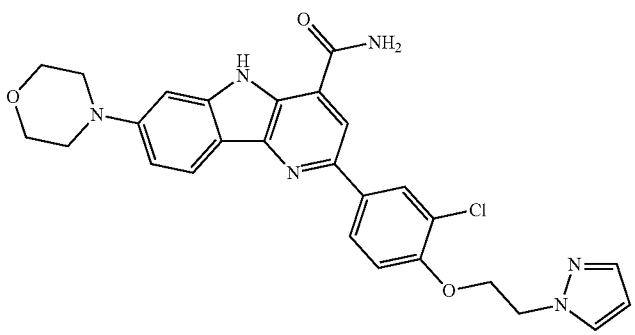 [SMILES: NC(=O)c1cc(-c2ccc(OCCn3cccn3)c(Cl)c2)nc2c1[nH]c1cc(N3CCOCC3)ccc12] | 2-(4-(2-(1H-pyrazol-1-yl)ethoxy)-3-chlorophenyl)-7-morpholino-5H-pyrido[3,2-b]indole-4-carboxamide | 2.06 | 517.20 |
| 364 | 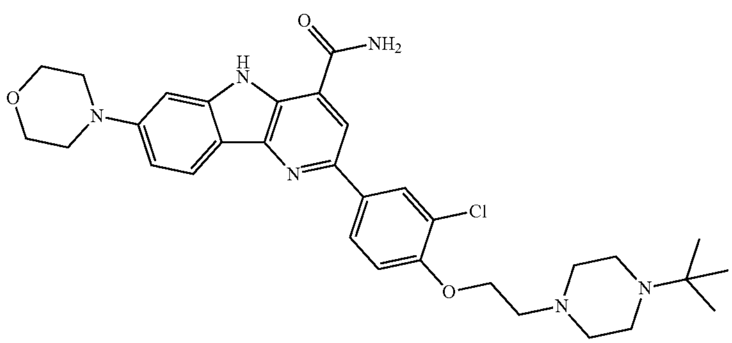 [SMILES: CC(C)(C)N1CCN(CCOc2ccc(-c3cc(C(N)=O)c4[nH]c5cc(N6CCOCC6)ccc5c4n3)cc2Cl)CC1] | 2-(4-(2-(4-tert-butylpiperazin-1-yl)ethoxy)-3-chlorophenyl)-7-morpholino-5H-pyrido[3,2-b]indole-4-carboxamide | 1.49 | 591.42 |
| 365 | 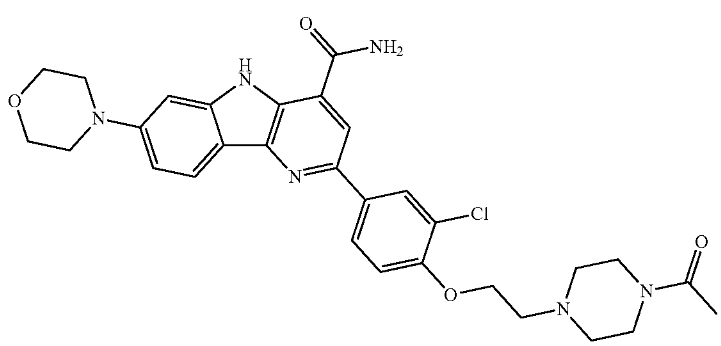 [SMILES: CC(=O)N1CCN(CCOc2ccc(-c3cc(C(N)=O)c4[nH]c5cc(N6CCOCC6)ccc5c4n3)cc2Cl)CC1] | 2-(4-(2-(4-acetylpiperazin-1-yl)ethoxy)-3-chlorophenyl)-7-morpholino-5H-pyrido[3,2-b]indole-4-carboxamide | 1.42 | 577.16 |

TABLE 21-continued

| Ex. # | Structure | Name | Retention time (min) | MMS (ESI) m/z M + H+ |
|---|---|---|---|---|
| 366 | 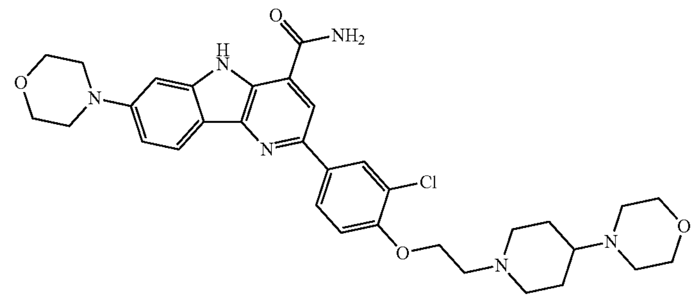 [SMILES: NC(=O)c1cc(-c2ccc(OCCN3CCC(N4CCOCC4)CC3)c(Cl)c2)nc2c1[nH]c1cc(N3CCOCC3)ccc12] | 2-(3-chloro-4-(2-(4-morpholinopiperidin-1-yl)ethoxy)phenyl)-7-morpholino-5H-pyrido[3,2-b]indole-4-carboxamide | 1.33 | 619.24 |
| 367 | 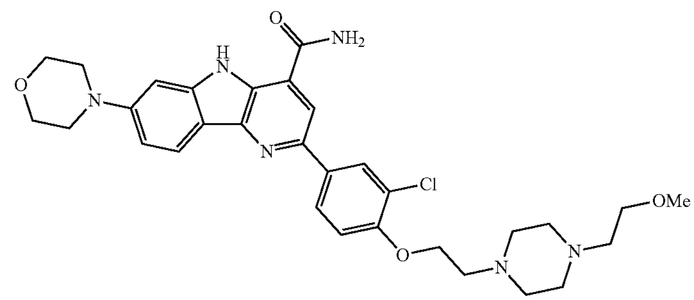 [SMILES: COCCN1CCN(CCOc2ccc(-c3cc(C(N)=O)c4[nH]c5cc(N6CCOCC6)ccc5c4n3)cc2Cl)CC1] | 2-(3-chloro-4-(2-(4-(2-methoxy-ethyl)piperazin-1-yl)ethoxy)phenyl)-7-morpholino-5H-pyrido[3,2-b]indole-4-carboxamide | 1.49 | 593.21 |
| 368 | 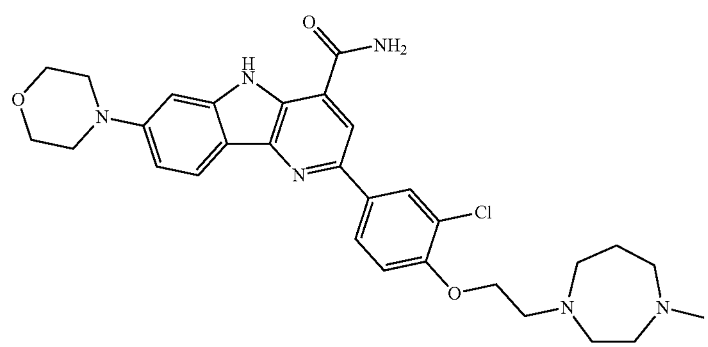 [SMILES: CN1CCCN(CCOc2ccc(-c3cc(C(N)=O)c4[nH]c5cc(N6CCOCC6)ccc5c4n3)cc2Cl)CC1] | 2-(3-chloro-4-(2-(4-methyl-1,4-diazepan-1-yl)ethoxy)phenyl)-7-morpholino-5H-pyrido[3,2-b]indole-4-carboxamide | 1.30 | 563.21 |
| 369 | 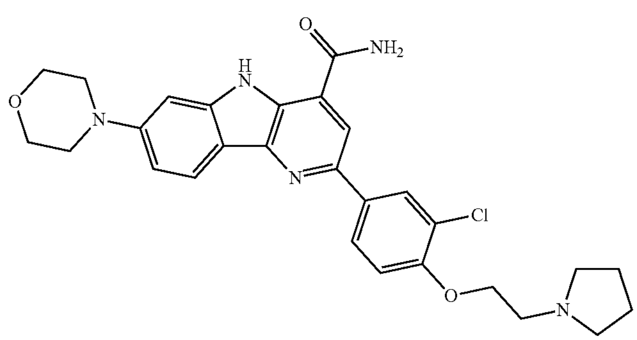 [SMILES: NC(=O)c1cc(-c2ccc(OCCN3CCCC3)c(Cl)c2)nc2c1[nH]c1cc(N3CCOCC3)ccc12] | 2-(3-chloro-4-(2-(pyrrolidin-1-yl)ethoxy)phenyl)-7-morpholino-5H-pyrido[3,2-b]indole-4-carboxamide | 1.53 | 520.37 |

TABLE 21-continued

| Ex. # | Structure | Name | Retention time (min) | MMS (ESI) m/z M + H+ |
|---|---|---|---|---|
| 370 | 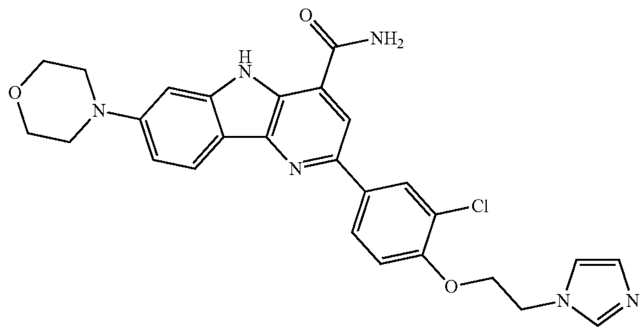 [SMILES: NC(=O)c1cc(-c2ccc(OCCn3ccnc3)c(Cl)c2)nc2c1[nH]c1cc(N3CCOCC3)ccc12] | 2-(4-(2-(1H-imidazol-1-yl)ethoxy)-3-chlorophenyl)-7-morpholino-5H-pyrido[3,2-b]indole-4-carboxamide | 1.47 | 517.19 |
| 371 | 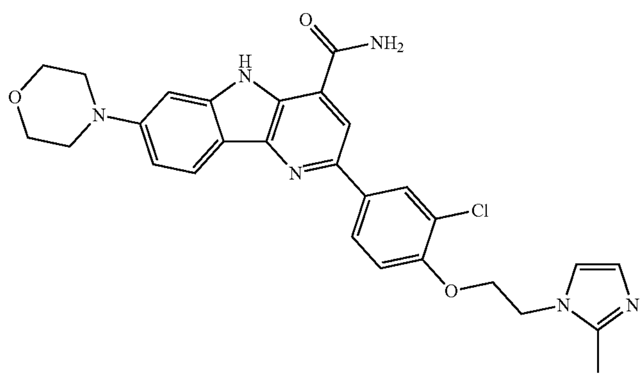 [SMILES: Cc1nccn1CCOc1ccc(-c2cc(C(N)=O)c3[nH]c4cc(N5CCOCC5)ccc4c3n2)cc1Cl] | 2-(3-chloro-4-(2-(2-methyl-1H-imidazol-1-yl)ethoxy)phenyl)-7-morpholino-5H-pyrido[3,2-b]indole-4-carboxamide | 1.50 | 531.24 |

HPLC conditions: PHENOMENEX ® Luna S10 3 × 50 mm column, 3 min gradient, 0-100% B, 4 mL/min. Solvent A: 95% MeOH – 5% H₂O – 0.1% TFA; Solvent B: 5% MeOH – 95% H₂O – 0.1% TFA.

EXAMPLE 372

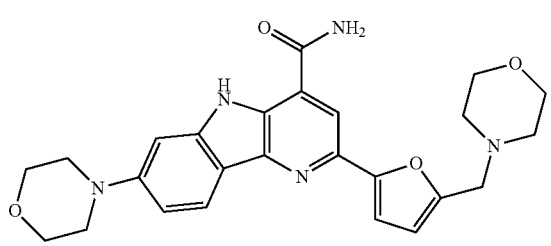 [SMILES: NC(=O)c1cc(-c2ccc(CN3CCOCC3)o2)nc2c1[nH]c1cc(N3CCOCC3)ccc12]

7-Morpholino-2-(5-(morpholinomethyl)furan-2-yl)-5H-pyrido[3,2-b]indole-4-carboxamide A suspension of 2-(5-formylfuran-2-yl)-7-morpholino-5H-pyrido[3,2-b]indole-4-carboxamide (14 mg, 0.022 mmol), morpholine (19 uL, 0.22 mmol), and sodium triacetoxyborohydride (24 mg, 0.11 mmol) in 1,2-dichloroethane (0.3 mL) was stirred at RT overnight. Preparative HPLC (100×30 mm Luna C18 column, Solvent A=10% Methanol, 90% H₂O, 0.1% TFA; Solvent B=90% Methanol, 10% H₂O, 0.1% TFA; gradient of 0 to 60% B over 10 min at 42 mL/min) followed by SCX capture and release with 2 N NH₃ in MeOH gave 7-morpholino-2-(5-(morpholinomethyl)furan-2-yl)-5H-pyrido[3,2-b]indole-4-carboxamide (7.8 mg, 0.016 mmol, 44% yield). MS (ESI) m/z 462.33 (M+H). ¹H NMR (500 MHz, chloroform-d) δ ppm 8.27 (1H, d, J=8.55 Hz), 7.98 (1H, s), 7.11 (1H, d, J=3.05 Hz), 6.98 (1H, dd, J=8.70, 1.98 Hz), 6.91 (1H, d, J=1.83 Hz), 6.42 (1H, d, J=3.36 Hz), 3.88-3.98 (4H, m), 3.75-3.84 (4H, m), 3.65 (2H, s), 3.29-3.38 (4H, m), 2.53-2.69 (4H, m).

The Examples in the following table were similarly prepared.

TABLE 22

| Ex. # | Structure | Name | Retention time (min) | MS (ESI) m/z M + H+ |
|---|---|---|---|---|
| 373 | 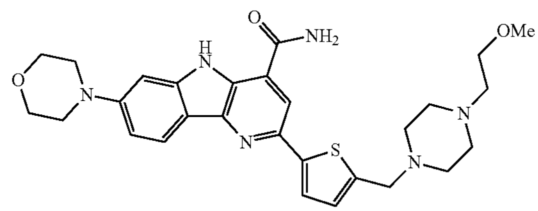 [SMILES: COCCN1CCN(Cc2ccc(-c3cc(C(N)=O)c4[nH]c5cc(N6CCOCC6)ccc5c4n3)s2)CC1] | 2-(5-((4-(2-methoxyethyl)piperazin-1-yl)methyl)thiophen-2-yl)-7-morpholino-5H-pyrido[3,2-b]indole-4-carboxamide | 1.36 | 535.40 |
| 374 | 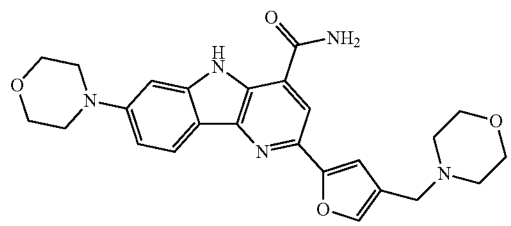 [SMILES: NC(=O)c1cc(-c2cc(CN3CCOCC3)co2)nc2c1[nH]c1cc(N3CCOCC3)ccc12] | 7-morpholino-2-(4-(morpholinomethyl)furan-2-yl)-5H-pyrido[3,2-b]indole-4-carboxamide | 1.19 | 462.32 |
| 375 | 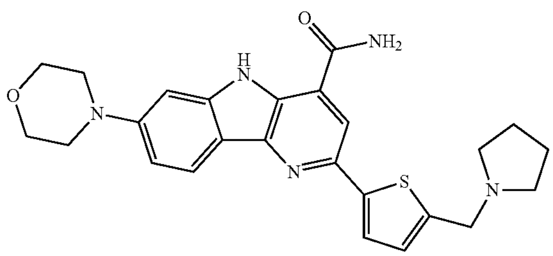 [SMILES: NC(=O)c1cc(-c2ccc(CN3CCCC3)s2)nc2c1[nH]c1cc(N3CCOCC3)ccc12] | 7-morpholino-2-(5-(pyrrolidin-1-ylmethyl)thiophen-2-yl)-5H-pyrido[3,2-b]indole-4-carboxamide | 1.34 | 462.32 |

HPLC conditions: PHENOMENEX ® Luna S10 3 × 50 mm column, 3 min gradient, 0-100% B, 4 mL/min. Solvent A: 95% MeOH – 5% H$_2$O – 0.1% TFA; Solvent B: 5% MeOH – 95% H$_2$O – 0.1% TFA.

EXAMPLE 376

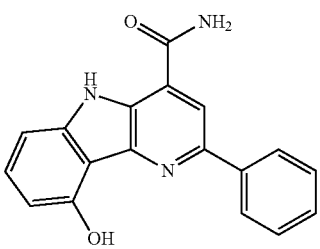 [SMILES: NC(=O)c1cc(-c2ccccc2)nc2c1[nH]c1cccc(O)c12]

9-Hydroxy-2-phenyl-5H-pyrido[3,2-b]indole-4-carboxamide

376A. Preparation of methyl 9-(benzyloxy)-2-bromo-5H-pyrido[3,2-b]indole-4-carboxylate

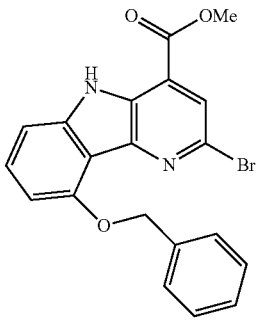 [SMILES: COC(=O)c1cc(Br)nc2c1[nH]c1cccc(OCc3ccccc3)c12]

A flask containing a mixture of methyl 3-amino-2,6-dibromoisonicotinate (3.00 g, 9.68 mmol), 2-benzyloxybenzeneboronic acid (2.52 g, 11.1 mmol), tetrakistriphenylphosphine palladium (0) (0.533 g, 0.461 mmol) and Na$_2$CO$_3$ (2.64 g, 24.9 mmol) was flushed with nitrogen. Toluene (24 mL) and methanol (8 mL) were added and the reaction was heated at 110° C. for 23 h. This was partitioned between EtOAc and aq. sat. sodium bicarbonate solution. The organic phase was washed with sat. aq. sodium bicarbonate solution and brine and then dried with sodium sulfate. Removal of the solvent followed by silica gel chromatography (step gradient elution with hexane containing 0 to 15% EtOAc afforded methyl 3-amino-2-(2-(benzyloxy)phenyl)-6-bromoisonicotinate (2.80 gm, 6.78 mmol, 74% yield) as a solid. This was quickly dissolved in TFA (40 mL) and the yellow solution cooled in an ice-bath. Sodium nitrite (0.935 g, 13.6 mmol) was added with stirring to give a dark red mixture. After 30 min, solid sodium azide (4.40 g, 67.8 mmol) was added over 5 min followed by Et$_2$O (40 mL). This was stirred in the ice-bath for 30 min and then partitioned between H$_2$O and EtOAc. The organic phase was separated and most of the solvent was removed. The residue was diluted with EtOAc, washed with aq. sat. NaHCO$_3$ solution and brine and then dried over sodium sulfate. The solution was concentrated to about 50 ml volume and the solid was with EtOAc, to leave methyl 3-azido-2-(2-(benzyloxy)phenyl)-6-bromoisonicotinate (2.70 gm, 4.39 mmol, 65% yield) as a solid. 1,2-Dichloroethane (3 mL), rhodium octanoate dimer (0.171 g, 0.220 mmol), and crushed 4A° molecular sieves (2.70 g) were added and the mixture was heated at 80° C. for 48 h. It was diluted with a mixture of 25% MeOH in DCM and filtered. The solid was washed with additional 25% MeOH in DCM and the solvents removed from the combined filtrates. The residue was suspended in MeOH and filtration followed by washing with MeOH left methyl 9-(benzyloxy)-2-bromo-5H-pyrido[3,2-b]indole-4-carboxylate (1.84 g, 97% yield) as a solid. MS (ESI) m/z 411.0 (M+H). $^1$H NMR (500 MHz, chloroform-d) d ppm 9.63 (1H, br. s.), 7.98 (1H, s), 7.77 (2H, d, J=7.32 Hz), 7.48 (3H, m), 7.34 (1H, m), 7.16 (1H, d, J=7.93 Hz), 6.85 (1H, d, J=7.93 Hz), 5.48 (2H, s), 4.09 (3H, s).

376B. Preparation of methyl 9-(benzyloxy)-2-phenyl-5H-pyrido[3,2-b]indole-4-carboxylate

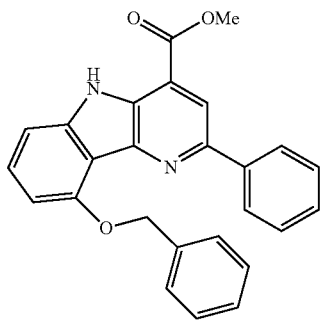 [SMILES: COC(=O)c1cc(-c2ccccc2)nc2c1[nH]c1cccc(OCc3ccccc3)c12]

A flask containing a mixture of phenylboronic acid (0.889 g, 7.29 mmol), methyl 9-(benzyloxy)-2-bromo-5H-pyrido[3,2-b]indole-4-carboxylate (1.50 g, 3.65 mmol), powdered potassium phosphate tribasic (2.48 g, 11 7 mmol), 2-dicyclohexylphosphino-2',4',6'-tri-iso-propyl-1,1'-biphenyl (0.348 g, 0.729 mmol), and Pd(OAc)$_2$ (0.082 g, 0.365 mmol) was flushed with nitrogen. THF (12 mL) was added and the mixture was heated at 80° C. for 2 hr. The reaction was diluted with EtOAc, washed with water, sat. aq. Na$_2$CO$_3$ solution, brine, and dried with sodium sulfate. The solvent was removed and the residue was suspended in a little EtOAc. Filtration and washing with EtOAc, afforded methyl 9-(benzyloxy)-2-phenyl-5H-pyrido[3,2-b]indole-4-carboxylate (1.47 g, 3.42 mmol, 94%). MS (ESI) m/z 408.9 (M+H). $^1$H NMR (500 MHz, DMSO-d$_6$) δ ppm 11.68 (1H, s), 8.33 (1H, s), 8.28 (2H, d, J=7.32 Hz), 7.87 (2H, d J=7.63 Hz), 7.37-7.57 (8H, m), 6.99 (1H, d, J=8.24 Hz), 5.45 (2H, s), 4.09 (3H, s).

376. Preparation of 9-hydroxy-2-phenyl-5H-pyrido[3,2-b]indole-4-carboxamide

A mixture of methyl 9-(benzyloxy)-2-phenyl-5H-pyrido[3,2-b]indole-4-carboxylate (1.28 g, 3.13 mmol), 10% Pd on carbon (0.567 g, 0.533 mmol) and ammonium formate (0.988 g, 15.7 mmol) in EtOH (8 mL) was heated at reflux for 1 hr. This was filtered and the solvent was removed from the filtrate to leave methyl 9-hydroxy-2-phenyl-5H-pyrido[3,2-b]indole-4-carboxylate (1.10 g) which was carried on. A suspension of methyl 9-hydroxy-2-phenyl-5H-pyrido[3,2-b]indole-4-carboxylate (1.1 g, 3.11 mmol) in 7 N NH$_3$ in MeOH (40 mL) in a sealed microwave vial was heated at 80° C. for 48 h. Filtration afford 9-hydroxy-2-phenyl-5H-pyrido[3,2-b]indole-4-carboxamide (675 mg, 1.78 mmol, 58% yield) as a solid. MS (ESI) m/z 304.12 (M+H). $^1$H NMR (500 MHz, MeOD) δ ppm 8.36 (1H, s), 8.07-8.11 (2H, m), 7.52-7.66 (4H, m), 7.24 (1H, d, J=7.93 Hz), 6.79 (1H, d, J=7.93 Hz).

EXAMPLE 377

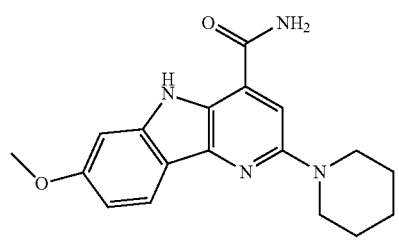 [SMILES: COc1ccc2c(c1)[nH]c1c(C(N)=O)cc(N3CCCCC3)nc12]

7-Methoxy-2-(piperidin-1-yl)-5H-pyrido[3,2-b]indole-4-carboxamide

377A. Preparation of methyl 5-benzyl-2-bromo-7-methoxy-5H-pyrido[3,2-b]indole-4-carboxylate

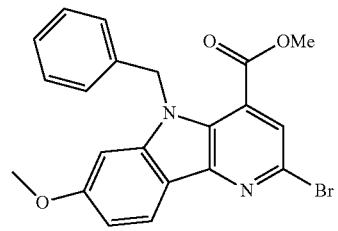 [SMILES: COC(=O)c1cc(Br)nc2c3ccc(OC)cc3n(Cc3ccccc3)c12]

Sodium hydride (81 mg, 2 0 mmol) was added to a solution of methyl 2-bromo-7-methoxy-5H-pyrido[3,2-b]indole-4-carboxylate (450 mg, 1.34 mmol) in THF (6 mL) in an ice bath. After 20 min this was removed from the bath and left stirring at RT for 0.5 h. Benzyl bromide (276 mg, 1.61 mmol) was added. After stirring at RT for 3 days, this was diluted with EtOAc, washed with water, brine, and dried over Na$_2$SO$_4$ Removal of the solvent followed by radial chromatography (elution with DCM) afforded methyl 5-benzyl-2-bromo-7-methoxy-5H-pyrido[3,2-b]indole-4-carboxylate (130 mg, 0.31 mmol, 23% yield). MS (ESI) m/z 425.0 (M+H). $^1$H NMR (500 MHz, chloroform-d) δ ppm 8.27 (1H, d, J=8.55 Hz), 7.59 (1H, s), 7.17-7.24 (3H, m), 6.97 (1H, dd, J=8.70, 1.98 Hz), 6.88-6.93 (2H, m), 6.84 (1H, d, J=1.83 Hz), 5.67 (2H, s), 3.86 (3H, s), 3.70 (3H, s).

377B. Preparation of methyl 5-benzyl-7-methoxy-2-(piperidin-1-yl)-5H-pyrido[3,2-b]indole-4-carboxylate

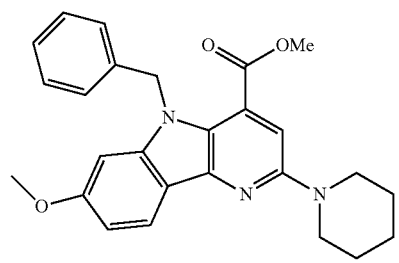 [SMILES: COC(=O)c1cc(N2CCCCC2)nc2c3ccc(OC)cc3n(Cc3ccccc3)c12]

A vial containing a mixture of methyl 5-benzyl-2-bromo-7-methoxy-5H-pyrido[3,2-b]indole-4-carboxylate (90 mg, 0.21 mmol), 9,9-dimethyl-4,5-bis(diphenylphosphino)xanthene (18 mg, 0.032 mmol), tris(dibenzylideneacetone)dipalladium-chloroform adduct (11 mg, 11 μmol), Cs$_2$CO$_3$ (56 mg, 0.53 mmol) was flushed with nitrogen. Dioxane (1 mL) and piperidine (0.042 mL, 0.42 mmol) was added and the vial was sealed and heated at 100° C. overnight. This was then diluted with EtOAc, washed with water and brine, and dried over Na$_2$SO$_4$. Removal of the solvent followed by radial silica gel chromatography (step gradient elution with DCM containing 0 to 2% MeOH) afforded methyl 5-benzyl-7-methoxy-2-(piperidin-1-yl)-5H-pyrido[3,2-b]indole-4-carboxylate (51 mg, 0.12 mmol, 56% yield) as a solid. MS (ESI) m/z 430.2 (M+H). $^1$H NMR (500 MHz, chloroform-d) δ ppm 8.15 (1H, d, J=8.55 Hz), 7.25 (1H, s), 7.15-7.21 (2H, m), 6.89-6.94 (3H, m), 6.87 (1H, dd, J=8.55, 2.14 Hz), 6.78 (1H, d, J=2.14 Hz), 5.59 (2H, s), 3.84 (3H, s), 3.66 (3H, s), 3.53-3.61 (4H, m), 1.68-1.76 (4H, m), 1.61-1.68 (2H, m).

377C. Preparation of methyl 7-methoxy-2-(piperidin-1-yl)-5H-pyrido[3,2-b]indole-4-carboxylate

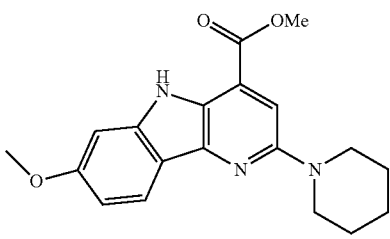 [SMILES: COC(=O)c1cc(N2CCCCC2)nc2c1[nH]c1cc(OC)ccc12]

A solution of methyl 5-benzyl-7-methoxy-2-(piperidin-1-yl)-5H-pyrido[3,2-b]indole-4-carboxylate (51 mg, 0.12 mmol) in TFA (2 mL) and two drops of trifluoromethanesulfonic acid was heated at reflux for 30 min. Another two drops of trifluoromethanesulfonic acid was added and heating continued for another 40 min. Preparative HPLC (100×30 mm Luna C18 column, Solvent A=10 mM NH$_4$OAc in 95% water:5% acetonitrile; B=10 mM NH$_4$OAc in 5% water:95% acetonitrile; gradient of 15 to 100% B over 20 min at 42 mL/min) followed by removal of the solvents afforded methyl 7-methoxy-2-(piperidin-1-yl)-5H-pyrido[3,2-b]indole-4-carboxylate (15 mg, 0.044 mmol, 37% yield). MS (ESI) m/z 340.2 (M+H). $^1$H NMR (500 MHz, chloroform-d) δ ppm 9.02 (1H, br. s.), 8.09 (1H, d, J=8.85 Hz), 7.22 (1H, s), 6.89 (1H, s), 6.85 (1H, d, J=8.55 Hz), 4.02 (3H, s), 3.90 (3H, s), 3.53-3.64 (4H, m), 1.69-1.80 (4H, m), 1.56-1.67 (2H, m).

377. Preparation of 7-methoxy-2-(piperidin-1-yl)-5H-pyrido[3,2-b]indole-4-carboxamide A mixture of methyl 7-methoxy-2-(piperidin-1-yl)-5H-pyrido[3,2-b]indole-4-carboxylate (15 mg, 0.044 mmol) and 7 N NH$_3$ in MeOH (1.5 mL) in a sealed microwave tube was heated at 75° C. for 40 h. Removal of solvent to afford 7-methoxy-2-(piperidin-1-yl)-5H-pyrido[3,2-b]indole-4-carboxamide (14 mg, 0.038 mmol, 87% yield) as a solid. MS (ESI) m/z 325.1 (M+H). $^1$H NMR (500 MHz, MeOD) δ ppm 8.04 (1H, d, J=8.85 Hz), 7.21 (1H, s), 7.06 (1H, d, J=2.14 Hz), 6.82 (1H, dd, J=8.70, 2.29 Hz), 3.91 (3H, s), 3.49-3.62 (4H, m), 1.74-1.82 (4H, m), 1.66-1.73 (2H, m).

EXAMPLE 378

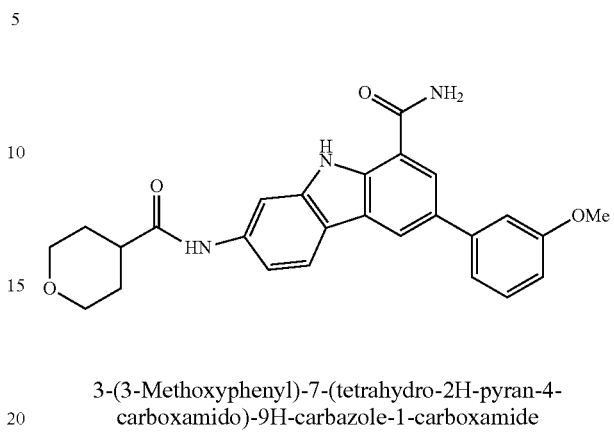

3-(3-Methoxyphenyl)-7-(tetrahydro-2H-pyran-4-carboxamido)-9H-carbazole-1-carboxamide Diisopropylethylamine (0.032 mL, 0.18 mmol), EDC (23 mg, 0.12 mmol) and HOBT (19 mg, 0.12 mmol) were added to a solution of tetrahydro-2H-pyran-4-carboxylic acid (15 mg, 0.12 mmol) in DMF (0.5 mL). This was stirred for 2 min and 7-amino-3-(3-methoxyphenyl)-9H-carbazole-1-carboxamide (20 mg, 0.060 mmol) was added. After stirring at RT overnight, additional EDC (23 mg, 0.12 mmol) and HOBT (19 mg, 0.12 mmol) were added and the reaction was left stirring over the weekend. Additional EDC (23 mg, 0.12 mmol), HOBT (19 mg, 0.12 mmol) and tetrahydro-2H-pyran-4-carboxylic acid (15 mg, 0.12 mmol) were added and the reaction was left stirring overnight.

Preparative HPLC (100×30 mm Luna C18 column, flow rate 42 ml permin, gradient elution starting with A:B=90:10 and ending with A:B=30:70 [A=10 mM NH$_4$OAc in 5% aqueous acetonitrile; B=10 mM NH$_4$OAc in 95% aqueous acetonitrile] over 20 min) Removal of the solvent left 3-(3-methoxyphenyl)-7-(tetrahydro-2H-pyran-4-carboxamido)-9H-carbazole-1-carboxamide (13 mg, 0.28 mmol, 47% yield) as a solid. MS (ESI) m/z 444.21 (M+H). $^1$H NMR (500 MHz, DMSO-d$_6$) δ ppm 11.33 (1H, s), 10.00 (1H, s), 8.55 (1H, s), 8.30 (1H, br. s.), 8.20 (1H, d, J=1.83 Hz), 8.13 (1H, d, J=8.24 Hz), 8.07 (1H, s), 7.39-7.53 (5H, m), 6.90-6.97 (1H, m), 3.91-3.99 (2H, m), 3.89 (3H, s), 3.34-3.44 (2H, m), 2.63-2.74 (1H, m), 1.63-1.81 (4H, m).

EXAMPLE 379

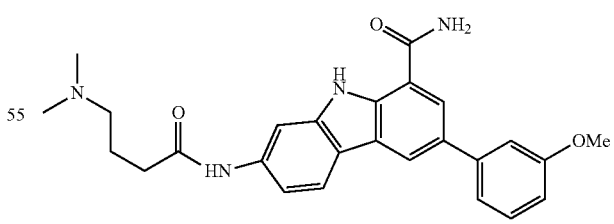

7-(4-(Dimethylamino)butanamido)-3-(3-methoxyphenyl)-9H-carbazole-1-carboxamide

This was similarly prepared from 7-amino-3-(3-methoxyphenyl)-9H-carbazole-1-carboxamide and 4-(dimethylamino)butanoic acid. MS (ESI) m/z 445.26 (M+H). $^1$H NMR (500 MHz, MeOD) δ ppm 8.45 (1H, d, J=1.83 Hz), 8.14 (1H, d, J=1.53 Hz), 8.10 (1H, d, J=8.55 Hz), 8.05 (1H, d, J=1.83 Hz), 7.35-7.39 (3H, m), 7.29 (1H, dd, J=8.39, 1.68 Hz), 6.93 (1H, dt, J=7.55, 2.02 Hz), 3.91 (3H, s), 2.54-2.61 (2H, m), 2.50 (2H, t, J=7.32 Hz), 2.40 (6H, s), 1.91-2.02 (2H, m).

EXAMPLE 380

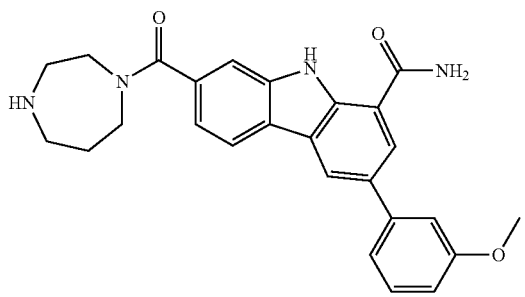 [SMILES: COc1cccc(-c2cc(C(N)=O)c3[nH]c4cc(C(=O)N5CCCNCC5)ccc4c3c2)c1]

7-(1,4-Diazepane-1-carbonyl)-3-(3-methoxyphenyl)-9H-carbazole-1-carboxamide

Trifluoroacetic acid (3 mL) was added to a solution of tert-butyl 4-(8-carbamoyl-6-(3-methoxyphenyl)-9H-carbazole-2-carbonyl)-1,4-diazepane-1-carboxylate (11 mg, 0.020 mmol) in DCM (5 mL). After 4 hr at RT, the solvents were removed and the residue was taken up in MeOH and applied onto a SCX cartridge. This was washed with MeOH and released 2 N NH$_3$ in MeOH to leave 7-(1,4-diazepane-1-carbonyl)-3-(3-methoxyphenyl)-9H-carbazole-1-carboxamide (8.5 mg, 0.019 mmol, 92% yield) as a solid. MS (ESI) m/z 443.23 (M+H). $^1$H NMR (500 MHz, MeOD) δ ppm 8.57 (1H, s), 8.28 (1H, d, J=8.24 Hz), 8.24 (1H, s), 7.71 (1H, s), 7.34-7.44 (3H, m), 7.29 (1H, d, J=7.93 Hz), 6.94 (1H, dt, J=7.55, 2.02 Hz), 3.92 (3H, s), 3.81-3.89 (2H, m), 3.55-3.65 (2H, m), 3.10-3.18 (1H, m), 2.94-3.04 (2H, m), 2.87-2.95 (1H, m), 1.96-2.08 (1H, m), 1.77-1.89(1H, m).

EXAMPLE 381

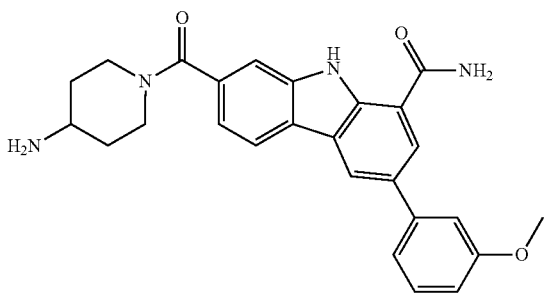 [SMILES: COc1cccc(-c2cc(C(N)=O)c3[nH]c4cc(C(=O)N5CCC(N)CC5)ccc4c3c2)c1]

7-(4-Aminopiperidine-1-carbonyl)-3-(3-methoxyphenyl)-9H-carbazole-1-carboxamide

This was similarly prepared from tert-butyl 1-(8-carbamoyl-6-(3-methoxyphenyl)-9H-carbazole-2-carbonyl)piperidin-4-ylcarbamate. MS (ESI) m/z 443.23 (M+H). $^1$H NMR (500 MHz, MeOD) δ ppm 8.56 (1H, d, J=1.53 Hz), 8.18-8.34 (2H, m), 7.68 (1H, s), 7.32-7.45 (3H, m), 7.26 (1H, d, J=7.93 Hz), 6.89-6.98 (1H, m), 4.52-4.75 (1H, m), 3.91 (3H, s), 3.74-3.88 (1H, m), 3.10-3.26 (1H, m), 2.89-3.11 (2H, m), 1.73-2.09 (2H, m), 1.26-1.56 (2H, m).

EXAMPLE 382

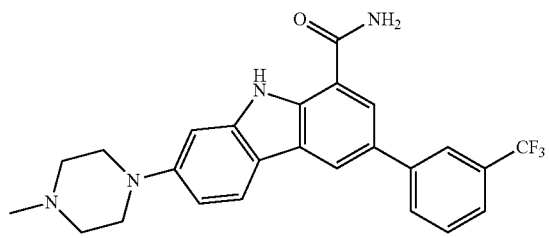 [SMILES: CN1CCN(c2ccc3c(c2)[nH]c2c(C(N)=O)cc(-c4cccc(C(F)(F)F)c4)cc23)CC1]

7-(4-Methylpiperazin-1-yl)-3-(3-(trifluoromethyl)phenyl)-9H-carbazole-1-carboxamide 382A. Preparation of methyl 4'-amino-4''-(4-methylpiperidin-1-yl)-3-trifluoromethyl-[1,1':3',1''-terphenyl]-5'-carboxylate

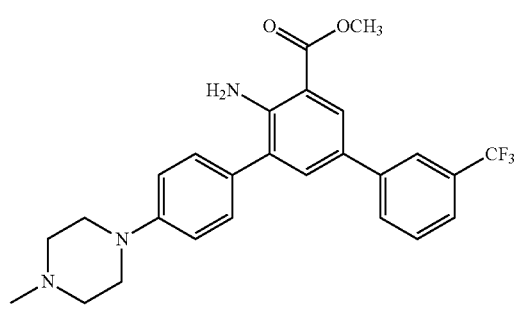 [SMILES: COC(=O)c1cc(-c2cccc(C(F)(F)F)c2)cc(-c2ccc(N3CCN(C)CC3)cc2)c1N]

N-Bromosuccinimide (13.5 g, 76.0 mmol) was added in portions over 1.5 h to a stirred solution of methyl 2-amino-5-iodobenzoate (20 g, 72 mmol) in CHCl$_3$ (320 mL) at RT. This was stirred overnight and then silica gel chromatography (step gradient elution with hexane containing 10 to 30% DCM) afforded impure methyl 2-amino-3-bromo-5-iodobenzoate (21 g) as a white solid that was used as such. A flask containing a mixture of 3- (trifluoromethyl)phenylboronic acid (3.73 g, 19 6 mmol), methyl 2-amino-3-bromo-5-iodobenzoate (7.0 g, 16 mmol), K$_2$CO$_3$ (6.85 g, 49 6 mmol), 1,1'-bis(diphenylphosphino)ferrocene-palladium(II)dichloride dichloromethane complex (1.4 g, 1 7 mmol), dioxane (140 mL), and water (28 mL) was degassed and flushed with N$_2$ twice and then heated at 70° C. for 3 h. It was cooled to RT, diluted with EtOAc, washed with water (2×), brine, and then dried over Na$_2$SO$_4$. Removal of the solvents followed by silica gel chromatography (step gradient elution with DCM containing 0 to 7% MeOH) afforded impure methyl 4-amino-5-bromo-3'-(trifluoromethyl)biphenyl-3-carboxylate (6.2 g, 10.44 mmol, 63.2% yield) as a white solid that was used as such. A mixture of 1-methyl-4-(4-(4,4,5,5-tetramethyl-1,3,2-dioxaborolan-2-yl)phenyl)piperazine (303 mg, 1.00 mmol), methyl 4-amino-5-bromo-3'-(trifluoromethyl)biphenyl-3-carboxylate (250 mg, 0.668 mmol), tetrakistriphenylphosphine palladium(0) (77 mg, 0.067 mmol), K$_2$CO$_3$ (369 mg, 2.67 mmol) in a microwave vial was flushed with nitrogen and DMF (2.7 mL) was added. The vial was sealed and heated at 100° C. overnight. The reaction was partitioned between EtOAc and water. The organic phase was washed with brine, dried over sodium sulfate, and the solvent removed. Silica gel chromatography (step gradient elution with hexane containing 0, to 20% EtOAc) afforded methyl 4'-amino-4"-(4-methylpiperidin-1-yl)-3-trifluoromethyl-[1,1':3',1"-terphenyl]-5'-carboxylate (150 mg, 0.532 mmol, 80% yield). MS (ESI) m/z 470.20 (M+H). $^1$H NMR (500 MHz, chloroform-d) δ ppm 8.16 (1H, d, J=2.14 Hz), 7.81 (1H, s), 7.73-7.78 (1H, m), 7.49-7.56 (3H, m), 7.37 (2H, d, J=8.55 Hz), 7.05 (2H, d, J=8.55 Hz), 6.15 (2H, br, s.), 3.95 (3H, s), 3.26-3.38 (4H, m), 2.60-2.69 (4H, m), 2.39 (3H, s).

382B. Preparation of methyl 4'-azido-4"-(4-methylpiperidin-1-yl)-3-trifluoromethyl-[1,1':3',1"-terphenyl]-5'-carboxylate

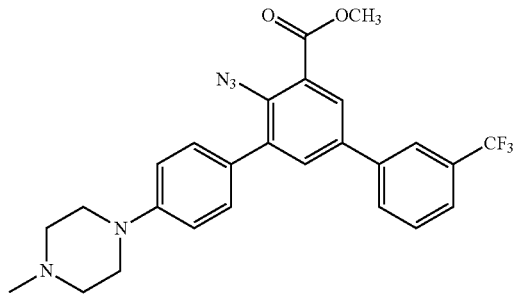 [SMILES: COC(=O)c1cc(-c2cccc(C(F)(F)F)c2)cc(-c2ccc(N3CCN(C)CC3)cc2)c1N=[N+]=[N-]]

A mixture of methyl 4'-amino-4"-(4-methylpiperidin-1-yl)-3-trifluoromethyl-[1,1':3',1"-terphenyl]-5'-carboxylate (250 mg, 0.532 mmol) in hydrochloric acid, (12 mL, 37% aqueous solution) was cooled in an ice bath and a solution of sodium nitrite (220 mg, 3.19 mmol) in water (2 mL) was added slowly. The orange-red solution was stirred for 30 min and a solution of sodium azide (208 mg, 3.19 mmol) in water (2 mL) was added dropwise. After 30 min this was partitioned between DCM and water. The organic phase washed with water and the combined organic phases were basified with 10 N aq. NaOH solution. This was extracted with DCM and the organic phases were washed with sat. NaHCO₃ solution, brine, and dried with sodium sulfate. Removal of the solvent followed by silica gel chromatography (step gradient elution with DCM containing 0 to 2% MeOH) afford methyl 4'-azido-4"-(4-methylpiperidin-1-yl)-3-trifluoromethyl-[1,1':3',1"-terphenyl]-5'-carboxylate (128 mg, 0.26 mmol, 49% yield) as a solid. $^1$H NMR (500 MHz, chloroform-d) δ ppm 8.02 (1H, d, J=2.44 Hz), 7.85 (1H, s), 7.79 (1H, d, J=7.63 Hz), 7.68 (1H, d, J=2.44 Hz), 7.64 (1H, d, J=7.63 Hz), 7.59 (1H, d, J=7.63 Hz), 7.42 (2H, d, J=8.55 Hz), 7.04 (2H, d, J=8.85 Hz), 4.03 (3H, s), 3.26-3.39 (4H, m), 2.57-2.69 (4H, m), 2.38 (3H, s).

382. Preparation of 7-(4-methylpiperazin-1-yl)-3-(3-(trifluoromethyl)phenyl)-9H-carbazole-1-carboxamide A solution of methyl 4'-azido-4"-(4-methylpiperidin-1-yl)-3-trifluoromethyl-[1,1':3',1"-terphenyl]-5'-carboxylate (98 mg, 0.20 mmol) in 1,2-dichlorobenzene (1 mL) in a vial was placed in a 180° C. oil bath for 10 min. It was cooled to RT, diluted with DCM (5 mL), captured on an SCX cartridge, washed with methanol, and released with a 1:1 mixture of 2 N NH₃ in methanol and DCM to leave crude methyl 7-(4-methylpiperazin-1-yl)-3-(3-(trifluoromethyl)phenyl)-9H-carbazole-1-carboxylate (98 mg). This was suspended in 7N NH₃ in MeOH (2 mL) and heated in a sealed microwave vial at 80° C. for 48 h. Preparative HPLC (100×30 mm Luna C18 column, flow rate 42 ml permin, gradient elution starting with A:B=90:10 and ending with A:B=30:70 [A=10 mM NH₄OAc in 5% aqueous acetonitrile; B=10 mM NH₄OAc in 95% aqueous acetonitrile] over 20 min) followed by SCX capture and release with 2 N NH₃ in MeOH left 7-(4-methylpiperazin-1-yl)-3-(3-(trifluoromethyl)phenyl)-9H-carbazole-1-carboxamide (9.2 mg, 0.020 mmol, 10% yield) as a solid. MS (ESI) m/z 451.4 (M–H). $^1$H NMR (500 MHz, MeOD) δ ppm 8.42 (1H, d, J=1.83 Hz), 8.13 (1H, d, J=1.83 (1H, d, J=1.83 Hz), 8.09 (1H, s), 8.02-8.08 (2H, m), 7.66 (2H, m), 7.15 (1H, d, J=1.83 Hz), 6.98 (1H, dd, J=8.55, 2.14 Hz), 3.30-3.35 (4H, m), 2.64-2.75 (4H, m), 2.39 (3H, s).

EXAMPLE 383

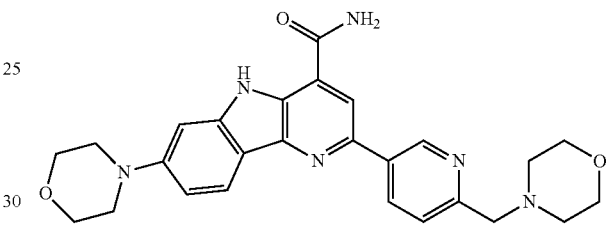

7-Morpholino-2-(6-(morpholinomethyl)pyridin-3-yl)-5H-pyrido[3,2-b]indole-4-carboxamide 383A. Preparation of 4-((5-bromopyridin-2-yl)methyl)morpholine

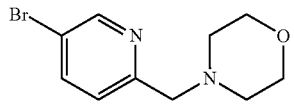

Sodium triacetoxyborohydride (1.6 gm, 7.5 mmol) was added to a solution of 5-bromopicolinaldehyde (1.0 g, 5.4 mmol) and morpholine (0.54 g, 6.2 mmol) in 1,2-dichloroethane (10 mL) and this was left stirring for 2 hr. Acetic acid (0.35 mL, 6.2 mmol) was added and the reaction was left stirring over the weekend. It was diluted with EtOAc and washed with sat. aq. NaHCO₃ followed by brine. This was concentrated, captured on a SCX column, washed with MeOH, and released with 2 N NH₃ in MeOH to give 4-((5-bromopyridin-2-yl)methyl)morpholine (537 mg, 2.09 mmol, 39% yield) as a brown oil. MS (ESI) m/z 256.96 (M+H). $^1$H NMR (500 MHz, chloroform-d) δ ppm 8.61 (1H, d, J=2.44 Hz), 7.77 (1H, dd, J=8.24, 2.44 Hz), 7.33 (1H, d, J=8.24 Hz), 3.67-3.77 (4H, m), 3.60 (2H, s), 2.42-2.57 (4H, m).

383. Preparation of 7-morpholino-2-(6-(morpholinomethyl)pyridin-3-yl)-5H-pyrido[3,2-b]indole-4-carboxamide A microwave vial containing a mixture of 4-((5-bromopyridin-2-yl)methyl)morpholine (537 mg, 2.09 mmol), 4,4,4', 4',5,5,5',5'-octamethyl-2,2'-bi(1,3,2-dioxaborolane) (583 mg, 2.30 mmol), KOAc (410 mg, 4.18 mmol) and PdCl₂(dppf)-CH₂Cl₂ adduct (85 mg, 0.10 mmol) was flushed with nitrogen, dioxane (5 mL) was added. and the vial was sealed and heated at 100° C. for 6 hr. The reaction was filtered and the solid was washed with EtOAc. The filtrate was and washed with water, brine, and dried over MgSO₄. Removal of the solvent left 750 mg of crude 4-((5-(4,4,5,5-tetramethyl-1,3,2-dioxaborolan-2-yl)pyridin-2-yl)methyl)morpholine (750 mg) as a brown thick oil that was used as such. A microwave vial containing a mixture of 2-bromo-7-morpholino-5H-pyrido[3,2-b]indole-4-carboxamide (60 mg, 0.14 mmol), 4-((5-(4,4,5,5-tetramethyl-1,3,2-dioxaborolan-2-yl)pyridin-2-yl)methyl)morpholine (130 mg, 0.171 mmol), PdCl₂(dppf)-CH₂Cl₂ adduct (12 mg, 0.014 mmol) was flushed with nitrogen. DME (2.5 mL) and Na₂CO₃ (0.36 mL, 0.72 mmol, 2.0 M aq. solution) were added and the vial was sealed and heated at 100° C. for 5 hr. Preparative HPLC (100×30 mm Luna C18 column, Solvent A=10% Methanol, 90% H₂O, 0.1% TFA; Solvent B=90% Methanol, 10% H₂O, 0.1% TFA; gradient of 0 to 60% B over 10 min at 42 mL/min) followed by SCX capture and release with 2 N NH₃ in MeOH gave 7-morpholino-2-(6-(morpholinomethyl)pyridin-3-yl)-5H-pyrido[3,2-b]indole-4-carboxamide (25 mg, 0.050 mmol, 35% yield) as a solid. MS (ESI) m/z 473.21 (M+H). ¹H NMR (500 MHz, Acetone) δ ppm 10.75 (1H, s), 9.36 (1H, d, J=2.14 Hz), 8.58 (1H, dd, J=8.09, 2.29 Hz), 8.35 (1H, s), 8.10-8.22 (2H, m), 7.62 (1H, d, J=7.93 Hz), 7.29 (1H, d, J=2.14 Hz), 7.18 (1H, br. s.), 7.07 (1H, dd, J=8.85, 2.14 Hz), 3.80-3.87 (4H, m), 3.71 (2H, s), 3.64-3.69 (4H, m), 3.28-3.35 (4H, m), 2.47-2.57 (4H, m).

EXAMPLE 384

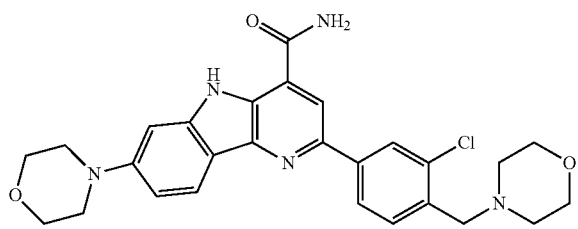 [SMILES: NC(=O)c1cc(-c2ccc(CN3CCOCC3)c(Cl)c2)nc2c1[nH]c1cc(N3CCOCC3)ccc12]

2-(3-Chloro-4-(morpholinomethyl)phenyl)-7-morpholino-5H-pyrido[3,2-b]indole-4-carboxamide This was similarly prepared from 2-chloro-4-bromobenzaldehyde and 2-bromo-7-morpholino-5H-pyrido[3,2-b]indole-4-carboxamide. MS (ESI) m/z 506.35 (M+H). ¹H NMR (500 MHz, DMSO-d₆) δ ppm 11.30 (1H, s), 8.54 (1H, s), 8.31-8.37 (2H, m), 8.24 (1H, dd, J=8.09, 1.68 Hz), 8.08 (1H, d, J=8.85 Hz), 7.84 (1H, s), 7.64 (1H, d, J=8.24 Hz), 7.23 (1H, d, J=2.14 Hz), 7.02 (1H, dd, J=8.85, 2.14 Hz), 3.78-3.87 (4H, m), 3.65 (2H, s), 3.60-3.64 (4H, m), 3.22-3.27 (4H, m), 2.45-2.50 (4H, m).

EXAMPLE 385

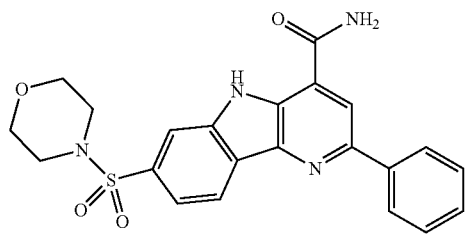 [SMILES: NC(=O)c1cc(-c2ccccc2)nc2c1[nH]c1cc(S(=O)(=O)N3CCOCC3)ccc12]

7-(Morpholinosulfonyl)-2-phenyl-5H-pyrido[3,2-b]indole-4-carboxamide

385A. Preparation of methyl 3-amino-6-bromo-2-(4-(morpholinosulfonyl)phenyl)isonicotinate

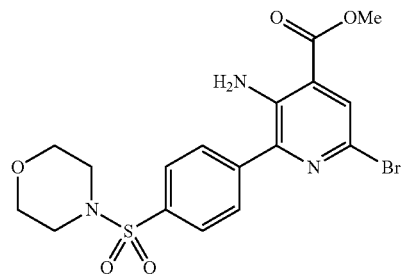 [SMILES: COC(=O)c1cc(Br)nc(-c2ccc(S(=O)(=O)N3CCOCC3)cc2)c1N]

A flask containing mixture of 4-(morpholinosulfonyl)-phenylboronic acid (0.920 g, 3.39 mmol), methyl 3-amino-2,6-dibromoisonicotinate (0.877 g, 2.83 mmol), tetrakistriphenylphosphine palladium(0) (0.196 g, 0.170 mmol), sodium carbonate (0.719 g, 6.79 mmol) was flushed with nitrogen. Toluene (7 mL), and MeOH (2.4 mL) were added and the reaction was heated at reflux under nitrogen for 24 hr. The reaction was partitioned between EtOAc and water. The organic phase was washed with brine, dried with sodium sulfate, and the solvent removed. Radial silica gel chromatography (step gradient elution with DCM containing 0 to 20% EtOAc) afforded methyl 3-amino-6-bromo-2-(4-(morpholinosulfonyl)phenyl)isonicotinate (982 mg, 2.15 mmol, 76% yield) as a yellow solid. MS (ESI) m/z 457.9 (M+H). ¹H NMR (500 MHz, chloroform-d) δ ppm 7.80-7.91 (5H, m), 5.94 (2H, br. s.), 3.94 (3H, s), 3.68-3.79 (4H, m), 2.98-3.07 (4H, m).

385B. Preparation of methyl 3-azido-6-bromo-2-(4-(morpholinosulfonyl)phenyl)isonicotinate

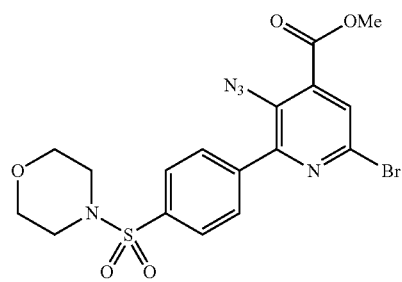 [SMILES: COC(=O)c1cc(Br)nc(-c2ccc(S(=O)(=O)N3CCOCC3)cc2)c1N=[N+]=[N-]]

Methyl 3-amino-6-bromo-2-(4-(morpholinosulfonyl)phenyl)-isonicotinate (0.988 g, 2.17 mmol) was dissolved in TFA (11 mL) and the yellow solution was cooled in an ice bath. Powdered sodium nitrite (0.299 g, 4.33 mmol) was added with stirring to give a dark red mixture with gas evolution. After 20 min, powdered sodium azide (1.41 g, 21.7 mmol) was added over 5 min followed by Et$_2$O (11 mL). A thick precipitate formed and, after 30 min, water was added and the mixture was extracted with EtOAc. The organic phase was washed with water (3×), brine (1×), saturated aqueous Na$_2$CO$_3$ solution (so that the aqueous phase was basic), and brine. After drying the solvent with sodium sulfate, the solvent was removed and silica gel chromatography (step gradient elution with DCM containing 0 to 10% EtOAc) afforded methyl 3-azido-6-bromo-2-(4-(morpholinosulfonyl)phenyl) isonicotinate (918 mg, 1.90 mmol, 88% yield). $^1$H NMR (500 MHz, chloroform-d) δ ppm 7.93-7.96 (2H, m), 7.87 (1H, s), 7.85 (2H, d, J=8.24 Hz), 4.03 (3H, s), 3.73-3.77 (4H, m), 3.03-3.07 (4H, m).

385C. Preparation of methyl 2-bromo-7-(morpholinosulfonyl)-5H-pyrido[3,2-b]indole-4-carboxylate

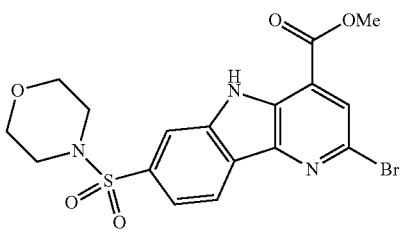 [SMILES: COC(=O)c1cc(Br)nc2c1[nH]c1cc(S(=O)(=O)N3CCOCC3)ccc12]

1,2-Dichloroethane (1.3 mL) was added to a mixture of methyl 3-azido-6-bromo-2-(4-(morpholinosulfonyl)phenyl) isonicotinate (918 mg, 1.90 mmol), rhodium octanoate dimer (74. mg, 0.095 mmol) and crushed 4A° molecular sieves (2.2 gm) and the reaction was heated at 80° C. overnight. It was then diluted with a mixture of DCM:MeOH (3:1) and filtered. The collected solid was washed with hot THF to extract any remaining product. The solvent was removed from the combined filtrates and the residue was suspended in MeOH. Filtration gave methyl 2-bromo-7-(morpholinosulfonyl)-5H-pyrido[3,2-b]indole-4-carboxylate (621 mg, 1.37 mmol, 72% yield) as a tan solid. $^1$H NMR (500 MHz, DMSO-d$_6$) δ ppm 12.15 (1H, s), 8.47 (1H, d, J=8.24 Hz), 8.19 (1H, s), 8.04 (1H, s), 7.65 (1H, dd, J=8.24, 1.53 Hz), 3.63-3.72 (4H, m), 2.87-3.02 (5H, m).

385D. Preparation of methyl 7-(morpholinosulfonyl)-2-phenyl-5H-pyrido[3,2-b]indole-4-carboxylate

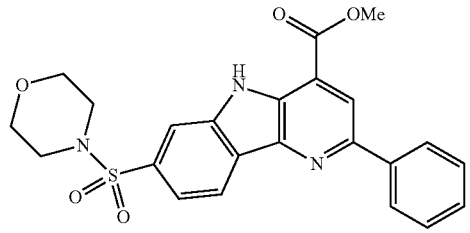 [SMILES: COC(=O)c1cc(-c2ccccc2)nc2c1[nH]c1cc(S(=O)(=O)N3CCOCC3)ccc12]

A mixture of phenylboronic acid (41.9 mg, 0.343 mmol), methyl 2-bromo-7-(morpholinosulfonyl)-5H-pyrido[3,2-b] indole-4-carboxylate (120 mg, 0.264 mmol), potassium phosphate tribasic (146 mg, 0.687 mmol), dicyclohexyl(2',6'-dimethoxybiphenyl-2-yl)phosphine (22 mg, 0.053 mmol), and Pd(OAc)$_2$ (5.9 mg, 0.026 mmol) in a microwave vial was flushed with nitrogen. THF (1.3 mL) was added, the vial was capped and the reaction was heated in a 70° C. for 18 hr. It was partitioned between EtOAc and water and the organic phase was separated and washed with brine. It was dried with sodium sulfate and the solvent were removed. The residue was dissolved in DCM and radial chromatography (step gradient elution with DCM containing 0 to 10% EtOAc) afforded methyl 7-(morpholinosulfonyl)-2-phenyl-5H-pyrido[3,2-b] indole-4-carboxylate (107 mg, 0.237 mmol, 90% yield) as a yellow solid. MS (ESI) m/z 450.0 (M−H). $^1$H NMR (500 MHz, DMSO-d$_6$) d ppm 12.04 (1H, s), 8.58 (1H, d, J=8.24 Hz), 8.47 (1H, s), 8.26 (2H, d, J=7.32 Hz), 8.19 (1H, d, J=1.22 Hz), 7.67 (1H, dd, J=8.24, 1.53 Hz), 7.58 (2H, t, J=7.63 Hz), 7.46-7.52 (1H, m), 4.11 (3H, s), 3.62-3.72 (4H, m), 2.92-3.00 (4H, m).

385. Preparation of 7-(morpholinosulfonyl)-2-phenyl-5H-pyrido[3,2-b]indole-4-carboxamide A suspension of methyl 7-(morpholinosulfonyl)-2-phenyl-5H-pyrido[3,2-b]indole-4-carboxylate (106 mg, 0.235 mmol) in 7 N NH$_3$ in MeOH (5 mL) in a sealed microwave vial was heated at 80° C. overnight. After cooling to RT, the precipitate was collected, washed with MeOH, and dried to leave 7-(morpholinosulfonyl)-2-phenyl-5H-pyrido[3,2-b]indole-4-carboxamide (67 mg, 0.15 mmol, 62% yield) as yellow fluffy solid. MS (ESI) m/z 435.1 (M−H). $^1$H NMR (400 MHz, DMSO-d$_6$) δ ppm 12.03 (1H, s), 8.70 (1H, s), 8.59 (1H, s), 8.52 (1H, d, J=8.06 Hz), 8.33 (2H, d, J=7.30 Hz), 8.21 (1H, d, J=1.01 Hz), 8.00 (1H, s), 7.52-7.64 (3H, m), 7.46 (1H, t, J=7.30 Hz), 3.60-3.69 (4H, m), 2.88-2.97 (4H, m).

The following compounds in Table 23 have been synthesized utilizing the procedures described for Example 144.

TABLE 23

| Ex. # | Structure | Name | Retention time (min) | MS (ESI) m/z* |
|---|---|---|---|---|
| 386 | 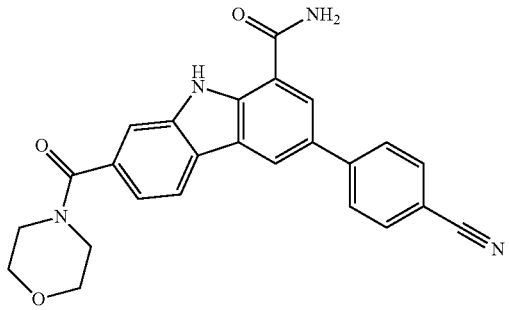 [SMILES: N#Cc1ccc(-c2cc(C(N)=O)c3[nH]c4cc(C(=O)N5CCOCC5)ccc4c3c2)cc1] | 3-(4-cyanophenyl)-7-(morpholine-4-carbonyl)-9H-carbazole-1-carboxamide | 9.87(a) | 425 |

TABLE 23-continued

| Ex. # | Structure | Name | Retention time (min) | MS (ESI) m/z* |
|---|---|---|---|---|
| 387 | 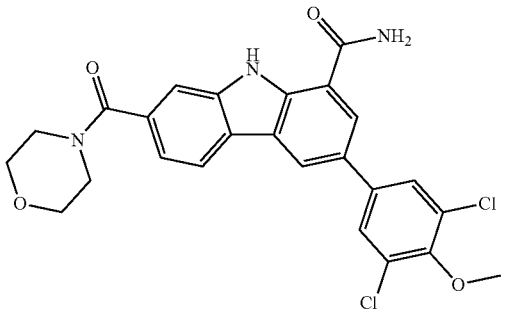 [SMILES: COc1c(Cl)cc(-c2cc(C(N)=O)c3[nH]c4cc(C(=O)N5CCOCC5)ccc4c3c2)cc1Cl] | 3-(3,5-dichloro-4-methoxyphenyl)-7-(morpholine-4-carbonyl)-9H-carbazole-1-carboxamide | 13.22(a) | 498/500/502 (**) |
| 388 | 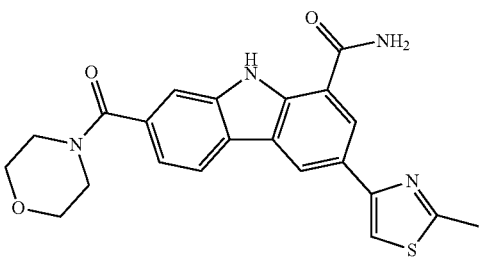 [SMILES: Cc1nc(-c2cc(C(N)=O)c3[nH]c4cc(C(=O)N5CCOCC5)ccc4c3c2)cs1] | 3-(2-methylthiazol-4-yl)-7-(morpholine-4-carbonyl)-9H-carbazole-1-carboxamide | 8.45(a) | 421 |
| 389 | 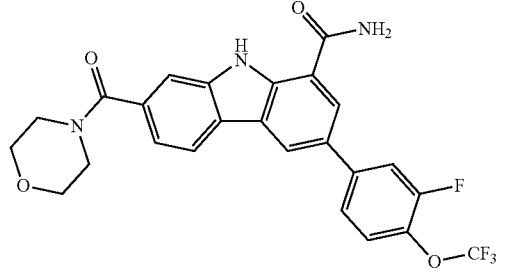 [SMILES: NC(=O)c1cc(-c2ccc(OC(F)(F)F)c(F)c2)cc2c1[nH]c1cc(C(=O)N3CCOCC3)ccc12] | 3-(3-fluoro-4-(trifluoromethoxy)phenyl)-7-(morpholine-4-carbonyl)-9H-carbazole-1-carboxamide | 13.18(a) | 502 |
| 390 | 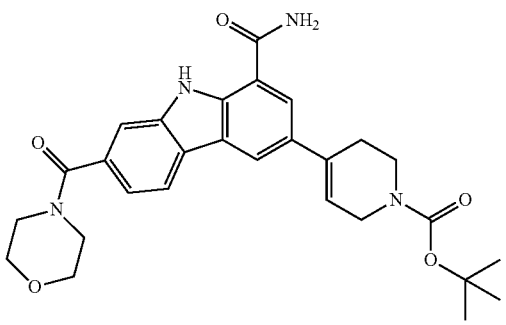 [SMILES: CC(C)(C)OC(=O)N1CC=C(c2cc(C(N)=O)c3[nH]c4cc(C(=O)N5CCOCC5)ccc4c3c2)CC1] | tert-butyl 4-(1-carbamoyl-7-(morpholine-4-carbonyl)-9H-carbazol-3-yl)-5,6-dihydropyridine-1(2H)-carboxylate | 12.08(a) | 505 |

HPLC condition a: Sunfire C18 3.5 μm, 4.6 × 150 mm column, 15 min gradient, 10-100% B, 1 mL/min. Solvent A: 5% $CH_3CN$ – 95% $H_2O$ – 0.1% TFA; Solvent B: 95% $CH_3CN$ – 5% $H_2O$ – 0.1% TFA.

*$(M + H)^+$ observed in all cases except the examples where specifically mentioned.

**Isotope pattern consistent with the presence of 2 chlorine atoms.

EXAMPLE 391

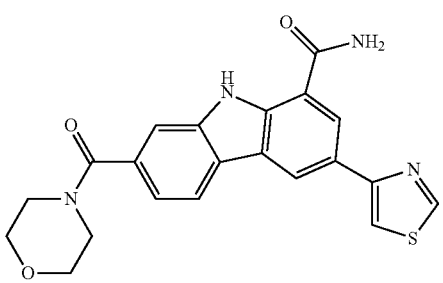 [SMILES: NC(=O)c1cc(-c2cscn2)cc2c1[nH]c1cc(C(=O)N3CCOCC3)ccc12]

7-(Morpholine-4-carbonyl)-3-(thiazol-4-yl)-9H-carbazole-1-carboxamide

3-Bromo-7-(morpholine-4-carbonyl)-9H-carbazole-1-carboxamide (50 mg, 0.112 mmol, Example 144A), Pd(Ph$_3$P)$_4$ (7 mg, 6.06 nmol), 4-(4,4,5,5-tetramethyl-1,3,2-dioxaborolan-2-yl)thiazole (37 mg, 0.175 mmol), aqueous Na$_2$CO$_3$ (0.15 mL, 0.300 mmol), MeOH (1 mL) and Toluene (2 mL) were combined in a 5 ml microwave vial. The vial was sealed, flushed with nitrogen and heated to 105° C. for 4 hours in an oil bath. Additional Pd(Ph$_3$P)$_4$ (20 mg, 15 nmol), 4-(4,4,5,5-tetramethyl-1,3,2-dioxaborolan-2-yl)thiazole (65 mg, 0.308 mmol) and aqueous Na$_2$CO$_3$ (0.30 mL, 0.60 mmol) were added, the vial flushed with nitrogen again and heat to 105° C. for 5 additional hours. The reaction mixture was evaporated to dryness, suspended in water and the crude product was collected by filtration through a medium porosity glass frit. The crude was washed with water, then dissolved off the frit with DMSO and purified by prep HPLC. Product containing fractions were combined and concentrated in vacuum to give 19.4 mg 7-(morpholine-4-carbonyl)-3-(thiazol-4-yl)-9H-carbazole-1-carboxamide. MS (ESI) m/e+ =407, m/e−=405, consistent with [M−H]$^-$ and [M+H]$^+$. $^1$H NMR (CD$_3$OD+CDCl$_3$) δ ppm 9.11 (d, 1H, J=2.1), 8.91 (d, 1H, J=1.5), 8.57 (d, 1H, J=1.5), 8.26 (d, 1H, J=8.0), 7.96 (d, 1H, J=1.8), 7.72 (s, 1H), 7.32 (dd, 1H, J=7.9, 1.2), 3.90-3.50 (b, 8H). HPLC retention time 8.02 min. (Sunfire C18 3.5 µm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA).

EXAMPLE 393

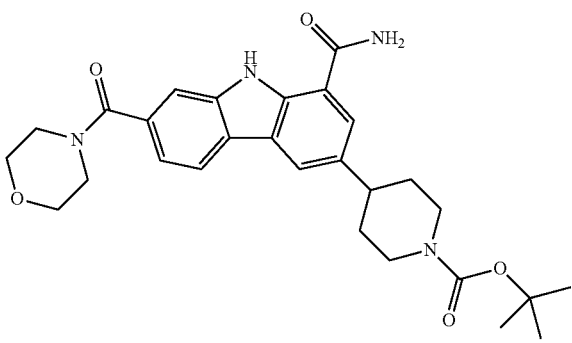 [SMILES: CC(C)(C)OC(=O)N1CCC(c2cc(C(N)=O)c3[nH]c4cc(C(=O)N5CCOCC5)ccc4c3c2)CC1]

tert-Butyl 4-(1-carbamoyl-7-(morpholine-4-carbonyl)-9H-carbazol-3-yl)piperidine-1-carboxylate tert-Butyl 4-(1-carbamoyl-7-(morpholine-4-carbonyl)-9H-carbazol-3-yl)-5,6-dihydropyridine-1(2H)-carboxylate (Example 390, 159 mg, 0.290 mmol) was dissolved in EtOH (50 ml) in a 500-ml PARR flask. The flask was flushed with nitrogen, than palladium (10% on carbon, 96 mg, 0.090 mmol) was added, the flask flushed with nitrogen again, then transferred onto PARR shaker and hydrogenated for 24 hours under 60 psi of hydrogen. The reaction mixture was filtered through a 0.45 uM nylon filter and concentrated in vacuum. 94.3 mg crude tert-butyl 4-(1-carbamoyl-7-(morpholine-4-carbonyl)-9H-carbazol-3-yl)piperidine-1-carboxylate (colorless film) was isolated. 44.3 mg of the crude were purified by preparative HPLC to give 21.5 mg tert-butyl 4-(1-carbamoyl-7-(morpholine-4-carbonyl)-9H-carbazol-3-yl)piperidine-1-carboxylate. MS m/e+=507, m/e−505 consistent with [M−H]$^-$ and [M+H]$^+$. $^1$H NMR (CD$_3$OD) δ ppm 8.21 (s, 1H), 8.20 (d, 1H, J=8.0), 7.86 (d, 1H, J=1.5), 7.67 (s, 1H), 7.26 (dd, 1H, J=8.0, 1.5), 4.29 (bd, 2H, J=13.3), 3.90-3.50 (b, 8H), 2.95 (m, 3H), 1.96 (br. d. 2H, J~12), 1.79 (dq, 2H, J=4.1, 12.6), 1.51 (s, 9H).

EXAMPLE 394

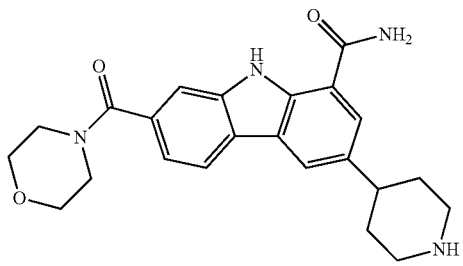 [SMILES: NC(=O)c1cc(C2CCNCC2)cc2c1[nH]c1cc(C(=O)N3CCOCC3)ccc12]

7-(Morpholine-4-carbonyl)-3-(piperidin-4-yl)-9H-carbazole-1-carboxamide tert-Butyl 4-(1-carbamoyl-7-(morpholine-4-carbonyl)-9H-carbazol-3-yl)piperidine-1-carboxylate (Example 393, 50 mg, 0.099 mmol) was dissolved in 1,2-Dichloroethane (3 ml) and trifluoroacetic acid (1 ml, 12.98 mmol) and stirred for 1 hour at room temperature. Evaporation of volatiles and purification by reversed phase preparative HPLC, followed by filtration of product containing fractions through a PHENOMENEX® Strata-X cartridge (2 g adsorbent), a wash with Methanol, and elution with 2M NH$_3$ in MeOH gave 21.9 mg 7-(morpholine-4-carbonyl)-3-(piperidin-4-yl)-9H-carbazole-1-carboxamide. MS (ESI) m/e−=405 and m/e=407 consistent with [M−H]$^-$ and [M+H]$^+$. HPLC retention time 7.61 min. (Sunfire C18 3.5 µm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (CD$_3$OD) δ ppm 8.21 (s, 1H), 8.20 (d, 1H, J=8.0), 7.87 (d, 1H, J=1.5), 7.69 (s, 1H), 7.27 (dd, 1H, J=8.0, 1.5), 3.90-3.50 (b, 8H), 3.23 (br. d., 2H, J~12), 2.91 (m, 1H), 2.83 (m, 2H), 1.97 (br. d., 2H, J~12), 1.85 (m, 2H).

EXAMPLE 395

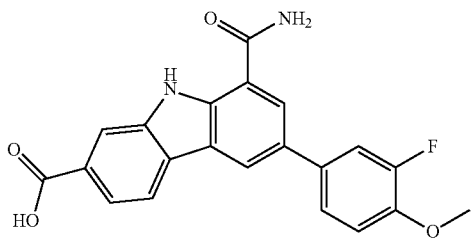 [SMILES: COc1ccc(-c2cc(C(N)=O)c3[nH]c4cc(C(=O)O)ccc4c3c2)cc1F]

8-Carbamoyl-6-(3-fluoro-4-methoxyphenyl)-9H-carbazole-2-carboxylate

395A. Preparation of ethyl 8-carbamoyl-6-(3-fluoro-4-methoxyphenyl)-9H-carbazole-2-carboxylate

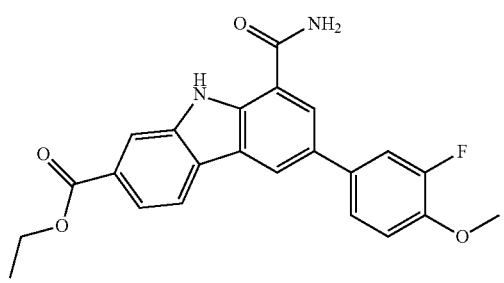 [SMILES: CCOC(=O)c1ccc2c(c1)[nH]c1c(C(N)=O)cc(-c3ccc(OC)c(F)c3)cc12]

A 250 ml pressure flask was loaded with ethyl 6-bromo-8-carbamoyl-9H-carbazole-2-carboxylate (1.39 g, 3.85 mmol, Example 58C), Pd(Ph$_3$P)$_4$ (280 mg, 0.242 mmol), 2-(3-fluoro-4-methoxyphenyl)-4,4,5,5-tetramethyl-1,3,2-dioxaborolane (1.30 g, 5.16 mmol), aqueous Na$_2$CO$_3$ (4.2 ml, 8.40 mmol), MeOH (21.00 ml) and Toluene (42 ml), flushed with nitrogen, sealed and heated to 105° C. for 4 hours in an oil bath. The reaction mixture was filtered and the collected solid washed with water. The filtrate was acidified with KHSO$_4$ (1M solution in water) and extracted with dichloromethane. The organic layer was washed with brine, dried over MgSO$_4$ and concentrated. The MgSO$_4$ was washed with THF and a MeOH+CH$_2$Cl$_2$ mixture. All wash liquids, the extracted product and the collected solid residue were combined to give 1.95 g crude ethyl 8-carbamoyl-6-(3-fluoro-4-methoxyphenyl)-9H-carbazole-2-carboxylate. (estimated purity ~75%). The crude product was used without further purification in the next reaction. MS (ESI) m/e–405 consistent with [M−H]$^−$ of product. HPLC retention time 2.13 min. (PHENOMENEX® Luna C18 S10, 3.0×50 mm column, 3 min gradient, 0-100% B, 4 mL/min. Solvent A: 5% CH$_3$CN—95% H$_2$O—10 mM NH$_4$OAc; Solvent B: 95% CH$_3$CN—5% H$_2$O—10 mM NH$_4$OAc), then isocratic at 100% B.

395. Preparation of 8-carbamoyl-6-(3-fluoro-4-methoxyphenyl)-9H-carbazole-2-carboxylate Ethyl 8-carbamoyl-6-(3-fluoro-4-methoxyphenyl)-9H-carbazole-2-carboxylate (Example 395A, 1.95 g, 3.60 mmol) was suspended in THF (100 ml). Methanol (25 ml) and sodium hydroxide (1 M solution in water) (25 ml, 25.00 mmol) were added and the mixture stirred at room temperature for 64 hours. The reaction mixture was partially concentrated (evaporate most of organic solvents), then acidified by addition of 1N aq. KHSO$_4$ solution. The product precipitated as dirty-yellow solid and was collected by filtration, washed with water and ether and dried under nitrogen stream. 1.1627 g 8-carbamoyl-6-(3-fluoro-4-methoxyphenyl)-9H-carbazole-2-carboxylate was isolated. (estimated purity ~90%). An analytical sample was purified by preparative reversed phase HPLC. MS (ESI) m/e–377 consistent with [M−H]$^−$ of product. HPLC retention time 10.03 min. (Sunfire C18 3.5 nm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (DMSO-d$_6$) δ ppm 11.68 (s, 1H), 8.75 (d, 1H, J=1.5), 8.39 (b, 1H), 8.38 (b, 1H), 8.35-8.30 (m, 2H), 7.83 (dd, 1H, J=13.2, 2.2), 7.81 (dd, 1H, J=8.3, 1.3), 7.72 (dd, 1H, J=9.8, 1.2), 7.59 (b, 1H), 7.31 (t, 1H, J=8.9), 3.92 (s, 3H).

EXAMPLE 396

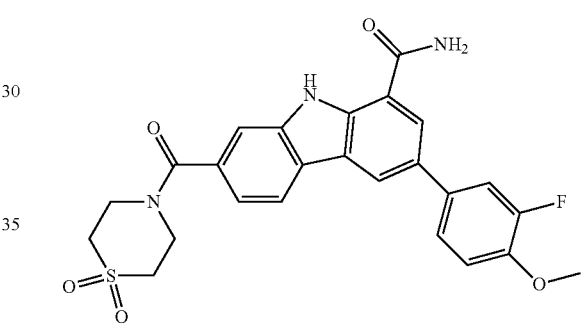

3-(3-Fluoro-4-methoxyphenyl)-7-(1,1-dioxo-thiomorpholine-4-carbonyl)-9H-carbazole-1-carboxamide 8-Carbamoyl-6-(3-fluoro-4-methoxyphenyl)-9H-carbazole-2-carboxylic acid (Example 395, 35 mg, 0.083 mmol), HATU (150 mg, 0.394 mmol), DMAP (50 mg, 0.409 mmol), Thiomorpholine-1,1-dioxide (90 mg, 0.666 mmol) and DMF (2 ml) were combined and stirred at room temperature for 3 days. The reaction mixture was filtered through a 0.45 um Nylon filter and purify by preparative HPLC. Product containing fractions were evaporated to give 26.3 mg 3-(3-fluoro-4-methoxyphenyl)-7-(1,1-dioxo-thiomorpholine-4-carbonyl)-9H-carbazole-1-carboxamide. MS (ESI) m/e+ =496, m/e−=494, consistent with [M+H]$^+$ and [M−H]$^−$ resp. HPLC retention time 9.61 min. (Sunfire C18 3.5 μm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (DMSO-d$_6$) δ ppm 11.60 (s, 1H), 8.73 (d, 1H, J=1.6), 8.39 (b, 1H), 8.34-8.30 (m, 2H), 7.86 (d, 1H, J=0.7), 7.81 (dd, 1H, J=13.3, 2.3), 7.71 (dd, 1H, J=8.5, 1.2), 7.60 (b, 1H), 7.35 (dd, 1H, J=8.1, 1.4), 7.31 (t, 1H, J=9.0), 3.92 (s, 3H), 4.2-3.7 (b, 4H), 3.35-3.25 (b, 4H).

EXAMPLE 397

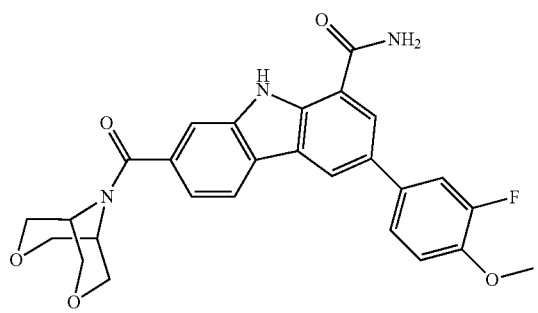 [SMILES: COc1ccc(-c2cc(C(N)=O)c3[nH]c4cc(C(=O)N5C6COCC5COC6)ccc4c3c2)cc1F]

7-(3,7-Dioxa-9-azabicyclo[3.3.1]nonane-9-carbonyl)-3-(3-fluoro-4-methoxyphenyl)-9H-carbazole-1-carboxamide 7-(3,7-Dioxa-9-azabicyclo[3.3.1]nonane-9-carbonyl)-3-(3-fluoro-4-methoxyphenyl)-9H-carbazole-1-carboxamide was synthesized following the procedure described for Example 396. MS (ESI) m/e+=490, m/e−=488, consistent with [M+H]+ and [M−H]− resp. HPLC retention time 9.12 min. (Sunfire C18 3.5 μm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (DMSO-d$_6$) δ ppm 11.59 (s, 1H), 8.72 (d, 1H, J=1.5), 8.39 (b, 1H), 8.32 (d, 1H, J~9), 8.31 (s, 1H), 7.86 (s, 1H), 7.82 (dd, 1H, J=13.3, 2.3), 7.71 (dd, 1H, J=8.5, 1.3), 7.60 (b, 1H), 7.33-7.28 (m, 2H), 4.33 (bs, 1H), 4.07 (bd, 1H, J=11.0), 3.92 (s, 3H), 3.91 (br. d., 2H, J~9.0), 3.84 (bd, 2H, J~9.4), 3.78 (bd, 2H, J~10.0), 3.68 (bs, 1H).

EXAMPLE 398

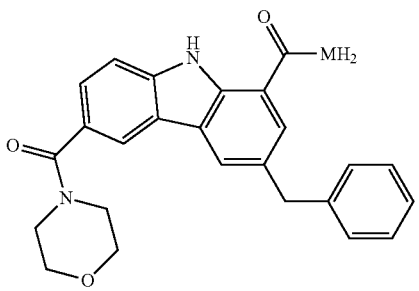

3-Benzyl-6-(morpholine-4-carbonyl)-9H-carbazole-1-carboxamide

398A. Preparation of 5-benzyl-2-(4-(morpholine-4-carbonyl)phenylamino)benzonitrile

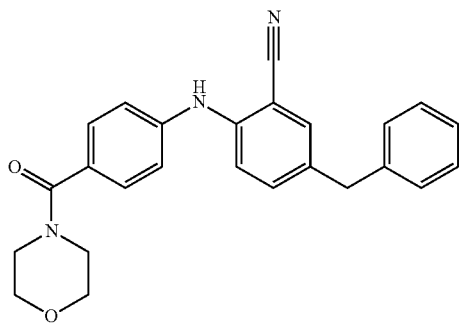 [SMILES: N#Cc1cc(Cc2ccccc2)ccc1Nc1ccc(C(=O)N2CCOCC2)cc1]

A 5 ml microwave vial was loaded with 5-bromo-2-(4-(morpholine-4-carbonyl)phenylamino)benzonitrile (125 mg, 0.259 mmol, Example 160A), 2-benzyl-4,4,5,5-tetramethyl-1,3,2-dioxaborolane (79 mg, 0.362 mmol) and Pd(Ph$_3$P)$_4$ (15 mg, 0.013 mmol). Toluene (1 mL), MeOH (0.500 mL) and a 2 molar solution of Na$_2$CO$_3$ (0.324 mL, 0.647 mmol) were added, the flask flushed with nitrogen, sealed and heat to 110° C. for 4 hours. LCMS after 4 hours showed product and starting material (1:2.5 ratio) (product m/e−=396, consistent with [M−H]−). Additional 2-benzyl-4,4,5,5-tetramethyl-1,3,2-dioxaborolane (400 mg, 1.834 mmol) and Pd(Ph$_3$P)$_4$ (30 mg, 0.026 mmol), Toluene (1 mL), MeOH (0.500 mL) and a 2 molar solution of Na$_2$CO$_3$ (0.324 mL, 0.647 mmol) were added. The flask was flushed with nitrogen, sealed and heated to 110° C. for additional 8 hours. The reaction mixture was poured into a separating funnel loaded with water and dichloromethane. The layers were separated and the aqueous layer extracted one more time with dichloromethane. The combined organic layers were washed with brine and dried over MgSO$_4$, filtered and concentrated in vacuum. The crude product was purified by column chromatography on silica, using a gradient from 100% CH$_2$Cl$_2$ to 50% CH$_2$Cl$_2$+50 EtOAc. Product containing fraction were combined and evaporated to dryness to give 42.3 mg 5-benzyl-2-(4-(morpholine-4-carbonyl)phenylamino)benzonitrile. (estimated purity 76%). The material was used without further purification. MS (ESI) m/e−=396, m/e+=398 consistent with [M−H]− and [M+H]+.

398. Preparation of 3-benzyl-6-(morpholine-4-carbonyl)-9H-carbazole-1-carboxamide A 5-ml microwave vial was loaded with 5-benzyl-2-(4-(morpholine-4-carbonyl)phenylamino)benzonitrile (42 mg, 0.080 mmol), acetic acid (4 mL) and palladium acetate (45.1 mg, 0.201 mmol). The flask was sealed and heated to 130° C. for 13 hours. The reaction mixture was filtered through a 0.45 um Nylon filter and concentrated in vacuum. The crude was filtered through a layer of BIOTAGE® Si-propylthiol resin (0.8 g in a 6 ml cartridge, to remove Pd) and rinsed with methanol. The pale yellow eluent was concentrated and purified by prep HPLC to give 7.0 mg 3-benzyl-6-(morpholine-4-carbonyl)-9H-carbazole-1-carboxamide. MS (ESI) m/e−412, m/e+=414 consistent with [M−H]− and [M+H]+ resp. HPLC retention time 9.14 min. (Sunfire C18 3.5 μm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (CD$_3$OD) δ ppm 8.18 (m, 2H), 7.87 (s, 1H), 7.65 (b, 1H), 7.52 (b, 1H), 7.30 (m, 4H), 7.20 (b, 1H), 4.21 (s, 2H), 3.90-3.50 (b, 8H).

EXAMPLE 399

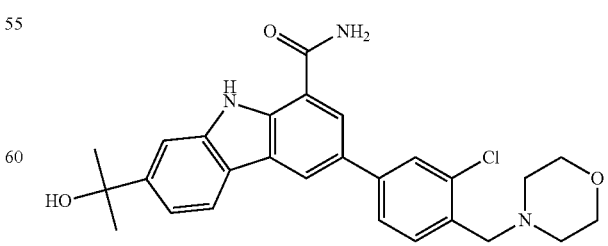

3-(3-Chloro-4-(morpholinomethyl)phenyl)-7-(2-hydroxypropan-2-yl)-9H-carbazole-1-carboxamide

399A. Preparation of 3-bromo-7-(2-hydroxypropan-2-yl)-9H-carbazole-1-carboxamide

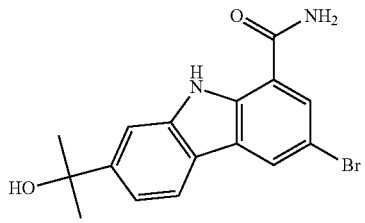 [SMILES: CC(C)(O)c1ccc2c(c1)[nH]c1c(C(N)=O)cc(Br)cc12]

Ethyl 6-bromo-8-carbamoyl-9H-carbazole-2-carboxylate (1.05 g, 2.471 mmol, Example 58C) was dissolved in THF (100 mL) in a 250-ml round bottom flask and cooled to 0° C. Methylmagnesium bromide (1.4 M solution in 25%THF+75%toluene) (26 mL, 36 4 mmol) was added and the mixture stirred at 0° C. for 1 hour, than the reaction was allowed to warm to room temperature during 1 hour. The reaction mixture was cooled to −78° C. and excess Grignard reagent quenched by the addition of acetone (5 mL, 68.1 mmol). The mixture was stirred for 30 minutes at -78° C., then quenched with sat. aq. NH$_4$Cl solution (at −78° C.). The flask was transferred into a water/ice bath and stirred for 10 minutes. The reaction mixture was poured into a separating funnel loaded with water and ethyl acetate. The layers were separated, the aqueous extracted once more with EtOAc (pH of aqueous ~9) The organic layer was washed once with water, once with brine, then dried over Na2SO4, filtered and concentrated in vacuum. (bath temp <30° C.). The crude product was purified by flash column chromatography on silica (25 g BIOTAGE® cartridge, eluent gradient from 5% EtOAc in DCM to 75% EtOAc in DCM during 96 fractions a 21 ml). Product eluted in fractions 57-80. Product containing fractions were combined and evaporated to give 395.5 mg 3-bromo-7-(2-hydroxypropan-2-yl)-9H-carbazole-1-carboxamide. $^1$H NMR (DMSO-d$_6$) δ ppm 11.38 (s, 1H), 8.48 (d, 1H, J=1.8), 8.22 (b, 1H), 8.09-8.09 (m, 2H), 7.88 (d, 1H, J=1.0), 7.54 (b, 1H), 7.33 (dd, 1H, J=8.3, 1.5), 5.05 (s, 1H), 1.52 (s, 6H). MS (ESI) m/e+=347/349 (1 Br isotope pattern) consistent with [M+H]$^+$ and m/e+=330/332 (1 Br isotope pattern) consistent with [M+H−NH$_3$]$^+$. HPLC retention time 9.89 min. (Sunfire C18 3.5 µm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA).

399. Preparation of 3-(3-chloro-4-(morpholinomethyl)phenyl)-7-(2-hydroxypropan-2-yl)-9H-carbazole-1-carboxamide A 20 ml microwave vial was loaded with 4-(2-chloro-4-(4,4,5,5-tetramethyl-1,3,2-dioxaborolan-2-yl)benzyl)morpholine (545 mg, 0.920 mmol, Example 477B) [crude material, reported to be 56% pure but may have been less, used without further purification], 3-bromo-7-(2-hydroxypropan-2-yl)-9H-carbazole-1-carboxamide (390 mg, 1.011 mmol, Example 399A), finely powdered potassium phosphate tribasic (780 mg, 3.67 mmol), 2-dicyclohexylphosphino-2',6'-dimethoxy-1,1'-biphenyl (S-Phos) (86 mg, 0.209 mmol), palladium(II) acetate (26 mg, 0.116 mmol) and THF (8 ml). The flask was sealed, flushed with nitrogen and heated to 85° C. for 4 hours. Additional 2-dicyclohexylphosphino-2',6'-dimethoxy-1,1'-biphenyl (S-Phos) (86 mg, 0.209 mmol) and palladium(II) acetate (26 mg, 0.116 mmol) were added and the reaction heated to 85° C. for additional 16 hours. Additional finely powdered potassium phosphate tribasic (780 mg, 3.67 mmol), 2-dicyclohexylphosphino-2',6'-dimethoxy-1,1'-biphenyl (S-Phos) (86 mg, 0.209 mmol) and palladium(II) acetate (26 mg, 0.116 mmol) were added and the mixture heat to 85° C. for additional 24 hours. The reaction was partitioned between aq. NH$_4$Cl solution and EtOAc. The organic phase was washed with aq. NaHCO$_3$, then brine, dried over MgSO$_4$, filtered and evaporated in vacuum. The crude product was dissolved in MeOH, filtered through 2.3 g thiol resin (SILICYCLE® Thiol-3, 1.27 mmol/g) and concentrated in vacuum. Purification by column chromatography on silica (Horizon station, 160g cartridge, gradient from 50% EtOAc+50% DCM to 40% EtOAc+40% DCM+20% MeOH during 190 fractions of 21 ml each. Product eluted in fractions 100-120 (~10% MeOH). Product containing fractions were combined and volatiles evaporated to give 71.7 mg 3-(3-chloro-4-(morpholinomethyl)phenyl)-7-(2-hydroxypropan-2-yl)-9H-carbazole-1-carboxamide. MS (ESI) m/e+=478 consistent with [M+H]$^+$. $^1$H NMR (DMSO-d$_6$) δ ppm 11.32 (s, 1H), 8.66 (d, 1H, J=1.3), 8.34 (b, 1H), 8.27 (d, 1H, J=1.7), 8.16 (d, 1H, J=8.3), 8.01 (d, 1H, 2.0), 7.90-7.85 (m, 2H), 7.61 (d, 1H, J=8.0), 7.51 (b, 1H), 7.35 (dd, 1H, J=8.2, 1.5), 5.04 (s, 1H), 3.67-3.60 (m, 6H), 2.49 (b, 4H), 1.54 (s, 6H). HPLC retention time 16.38 min. (Sunfire C18 3.5 µm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA).

EXAMPLE 400

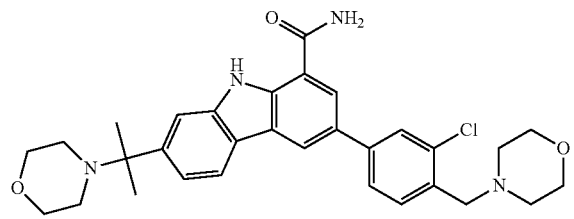 [SMILES: CC(C)(c1ccc2c(c1)[nH]c1c(C(N)=O)cc(-c3ccc(CN4CCOCC4)c(Cl)c3)cc12)N1CCOCC1]

3-(3-Chloro-4-(morpholinomethyl)phenyl)-7-(2-morpholinopropan-2-yl)-9H-carbazole-1-carboxamide 3-(3-Chloro-4-(morpholinomethyl)phenyl)-7-(2-hydroxypropan-2-yl)-9H-carbazole-1-carboxamide (40.3 mg, 0.080 mmol, Example 399) was suspended in HCl (1 M solution in diethyl ether) (5 ml, 5.00 mmol) and sonicated briefly. (not completely dissolved. DCM was added (5 ml) in an unsuccessful attempt to dissolve more). The suspension was stirred at room temperature for 1 hour, then cooled to 0° C. Morpholine (5 ml, 57 4 mmol) was added, the ice bath removed and the mixture stirred at room temperature for 3 days. The reaction mixture was poured into a separating funnel that is loaded with EtOAc and sat. aq. NaHCO$_3$ solution. Layers were separated, the aqueous extracted once more with EtOAc and the organic layer washed with brine, then dried over MgSO$_4$, filtered and evaporated. The crude was purified by prep HPLC. Product containing fractions were filtered through a Waters MCX cartridge (1 g adsorbent), washed with MeOH and the product eluted with a 2M solution of NH$_3$ in MeOH. Evaporation to dryness under a stream of nitrogen gave 10.8 mg white 3-(3-chloro-4-(morpholinomethyl)phenyl)-7-(2-morpholinopropan-2-yl)-9H-carbazole-1-carboxamide. MS (ESI) m/e-=545, m/e+=547 consistent with [M−H]$^-$ and [M+H]$^+$. HPLC retention time 5.60 min. (Sunfire C18 3.5 µm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA). $^1$H NMR (CD$_3$OD) δ ppm 8.50 (d, 1H, J=1.7), 8.17 (d, 1H, J=1.5), 8.12 (d, 1H, J=8.3), 7.87 (d, 1H, J=1.7), 7.80 (d, 1H, J=0.7), 7.74 (dd, 1H, J=8.0, 1.8), 7.61 (d, 1H, J=8.1), 7.52 (dd, 1H, J=8.2, 1.6), 3.75-3.68 (m, 10H), 2.61-2.54 (m, 8H), 1.49 (s, 6H).

EXAMPLE 402

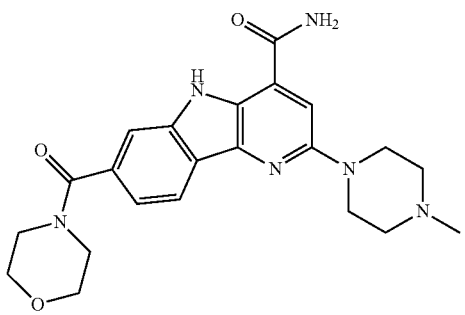 [SMILES: CN1CCN(c2cc(C(N)=O)c3[nH]c4cc(C(=O)N5CCOCC5)ccc4c3n2)CC1]

2-(4-Methylpiperazin-1-yl)-7-(morpholine-4-carbonyl)-5H-pyrido[3,2-b]indole-4-carboxamide 402A. Preparation of 2-bromo-7-(morpholine-4-carbonyl)-5H-pyrido[3,2-b]indole-4-carboxamide

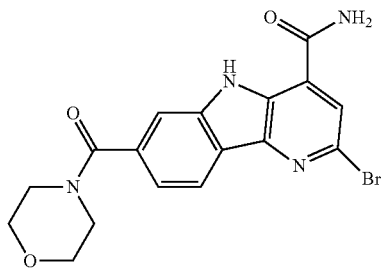 [SMILES: NC(=O)c1cc(Br)nc2c1[nH]c1cc(C(=O)N3CCOCC3)ccc12]

Methyl 2-bromo-7-(morpholine-4-carbonyl)-5H-pyrido[3,2-b]indole-4-carboxylate (1.008 g, 2.410 mmol, Example 212D) was suspended in NH$_3$/MeOH (7M) (18 mL, 126 mmol) in a sealed microwave vial. The mixture was heated at 105° C. for 8 hours in a microwave reactor. Product crystallized from reaction mixture upon cooling and was collected by filtration, washed with MeOH and dried in nitrogen stream to give 736.4 mg 2-bromo-7-(morpholine-4-carbonyl)-5H-pyrido[3,2-b]indole-4-carboxamide. $^1$H NMR (DMSO-d$_6$) δ ppm 11.4 (b, 1H), 8.56 (s, 1H), 8.22 (d, 1H, J=8.6), 7.81 (s, 1H), 7.31 (dd, 1H, J=7.9, 1.2), 3.75-3.35 (b, 10H). MS (ESI) m/e-=401/403, m/e+=403/405 (1 Br isotope pattern) consistent with [M−H]$^-$ and [M+H]$^+$. HPLC retention time 6.74 min. (Sunfire C18 3.5 μm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA).

402. Preparation of 2-(4-methylpiperazin-1-yl)-7-(morpholine-4-carbonyl)-5H-pyrido[3,2-b]indole-4-carboxamide A 0.5 ml microwave vial was loaded with 2-bromo-7-(morpholine-4-carbonyl)-5H-pyrido[3,2-b]indole-4-carboxamide (8 mg, 0.019 mmol), 1-Methylpiperazine (0.25 ml, 2.246 mmol) and NMP (0.25 ml), sealed and heated to 180° C. for 2 hours. Purification by prep HPLC, followed by filtration of the product containing fractions through gave a Waters MCX cartridge, washing with MeOH and elution with 2M NH$_3$ in MeOH and drying gave 6.3 mg 2-(4-methylpiperazin-1-yl)-7-(morpholine-4-carbonyl)-5H-pyrido[3,2-b]indole-4-carboxamid. MS (ESI) m/e+=423, m/e−=421 consistent with [M+H]$^+$ and [M−H]$^-$. HPLC retention time 5.42 min. (Sunfire C18 3.5 μm, 4.6×150 mm column, 15 min gradient, 10-100% B, 1 mL/min. Solvent A: 5% CH$_3$CN—95% H$_2$O—0.1% TFA; Solvent B: 95% CH$_3$CN—5% H$_2$O—0.1% TFA). $^1$H NMR (CD$_3$OD) δ ppm 8.25 (d, 1H, J=8.3), 7.67 (b, 1H), 7.42 (s, 1H), 7.26 (dd, 1H, J=8.0, 1.2), 3.90-3.50 (m, 12H), 2.74-2.66 (m, 4H), 2.41 (s, 3H).

The following compounds in Table 24 have been synthesized utilizing the procedures described for Example 402.

TABLE 24

| Ex. # | Structure | Name | Retention time (min) | MS (ESI) m/z* |
|---|---|---|---|---|
| 403 | 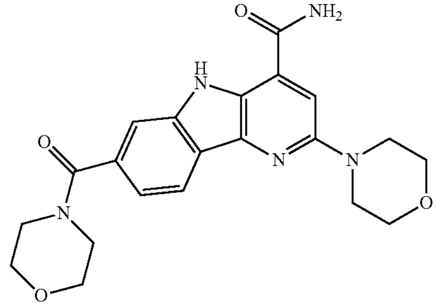 [SMILES: NC(=O)c1cc(N2CCOCC2)nc2c1[nH]c1cc(C(=O)N3CCOCC3)ccc12] | 7-(morpholine-4-carbonyl)-2-morpholino-5H-pyrido[3,2-b]indole-4-carboxamide | 9.75(b) | 410 |

TABLE 24-continued

| Ex. # | Structure | Name | Retention time (min) | MS (ESI) m/z* |
|---|---|---|---|---|
| 404 | 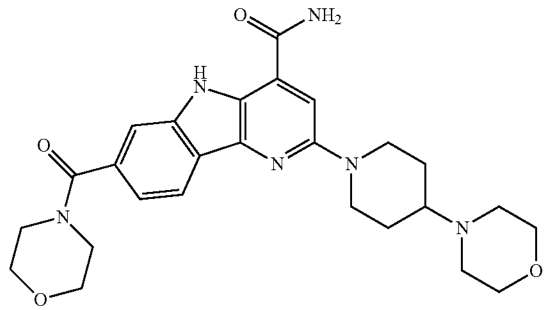 [SMILES: NC(=O)c1cc(N2CCC(N3CCOCC3)CC2)nc2c1[nH]c1cc(C(=O)N3CCOCC3)ccc12] | 7-(morpholine-4-carbonyl)-2-(4-morpholino-piperidin-1-yl)-5H-pyrido[3,2-b]indole-4-carboxamide | 10.34(b) | 493 |
| 405 | 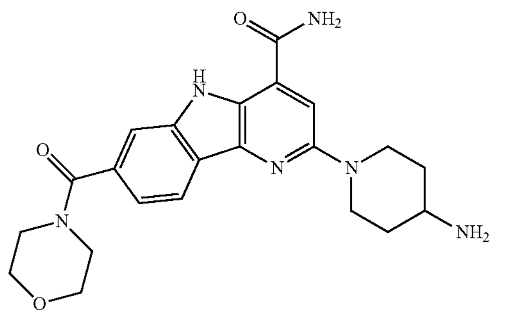 [SMILES: NC(=O)c1cc(N2CCC(N)CC2)nc2c1[nH]c1cc(C(=O)N3CCOCC3)ccc12] | 2-(4-aminopiperidin-1-yl)-7-(morpholine-4-carbonyl)-5H-pyrido[3,2-b]indole-4-carboxamide | 6.73(a) 7.50(b) | 423 (**) |

HPLC condition a: Sunfire C18 3.5 μm, 4.6 × 150 mm column, 15 min gradient, 10-100% B, 1 mL/min. Solvent A: 5% CH$_3$CN – 95% H$_2$O – 0.1% TFA; Solvent B: 95% CH$_3$CN – 5% H$_2$O – 0.1% TFA.
HPLC condition b: Xbridge C18 3.5 μm, 4.6 × 150 mm column, 15 min gradient, 10-100% B, 1 mL/min. Solvent A: 10 nM NH$_4$HCO$_3$ in 5% MeOH + 95% H$_2$O; Solvent B: 10 nM NH$_4$HCO$_3$ in 95% MeOH + 5% H$_2$O.
*(M + H)$^+$ observed in all cases except the examples where specifically mentioned.
**Structure confirmed by NOE experiment.

EXAMPLE 406

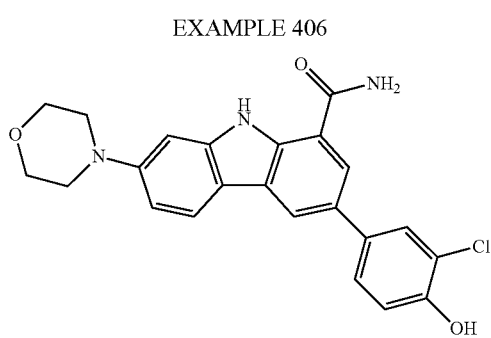

3-(3-Chloro-4-hydroxyphenyl)-7-morpholino-9H-carbazole-1-carboxamide

406A. Preparation of 7-amino-3-(3-chloro-4-hydroxyphenyl)-9H-carbazole-1-carboxamide

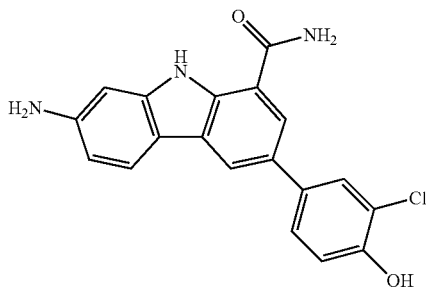 [SMILES: NC(=O)c1cc(-c2ccc(O)c(Cl)c2)cc2c1[nH]c1cc(N)ccc12]

A 250 ml pressure flask was loaded with 7-amino-3-bromo-9H-carbazole-1-carboxamide (2.02 g, 5.31 mmol, Example 480B), 3-chloro-4-hydroxyphenylboronic acid (1.00 g, 5.80 mmol), PdCl$_2$(dppf)-CH$_2$Cl$_2$ adduct (0.167 g, 0.204 mmol), Na$_2$CO$_3$ (2M) (8 mL, 16.00 mmol) and DME (80 mL). The flask was flushed with N2 and heated at 85° C. in an oil bath for 3 hours. LCMS after 2 h 20 min showed ~⅔ conversion. The temperature was increased to 100° C. and heating continued for 1 hour. LCMS showed small amount of remaining starting material. 3-Chloro-4-hydroxyphenylboronic acid (80 mg, 0.46 mmol) and PdCl$_2$(dppf)-CH$_2$Cl$_2$ adduct (0.050 g, 0.061 mmol) were added, the flask flushed with nitrogen again and heated to 100° C. for an additional 1 hour. The reaction mixture was partitioned between a saturated aqueous solution of NaCl and a 1:1 mixture of acetone and ethyl acetate. The aqueous layer was extracted once more with EtOAc+Acetone 1+1, the organic layer washed with brine, dried over MgSO$_4$, filtered and concentrated to dryness. A brown precipitate formed in the aqueous layer and between the layers during the extraction. It was collected by filtration through a pad of CELITE®. The CELITE® was washed with water, dried and the filter cake then washed with acetone. LCMS analysis of this showed a small amount of product in acetone solution. This material was combined with the extracted product. The collected MgSO$_4$ (from drying the organic layer) also had a brown precipitate mixed into it. This filter cake was washed with acetone. LCMS shows small amount of product in acetone solution. This solution was combine with main product fraction. Purification by flash column chromatography (gradient from 100% DCM to 25% DCM+75% acetone, then from (25% DCM+75% acetone) to (20% DCM+60% Acetone+20% MeOH). Product streaked badly, eluted from end of first gradient until end of second gradient. Product containing fractions were combined and evaporated to dryness to give 1.968 g 7-amino-3-(3-chloro-4-hydroxyphenyl)-9H-carbazole-1-carboxamide. HPLC retention time 6.17 min. (Sunfire C18 3.5 μm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA). HPLC purity ~55%. MS (ESI) m/e+=352/354 (isotope pattern consistent with 1 Cl) consistent with [M+H]$^+$. The material was used without further purification.

406B. Preparation of 2,2'-oxydiacetaldehyde

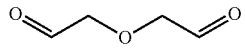

2,5-Dihydrofuran (350 mg, 4.99 mmol) was dissolved in Dichloromethane (35 ml) in a 250 ml round bottom flask and cooled to −78° C. Ozone was bubbled through the solution until a faint blue color persisted (~15 minutes). Nitrogen was bubbled through the mixture to purge excess ozone, then triphenylphosphine (2619 mg, 9.99 mmol) was added, the flask transferred into a freezer (−20° C.) and let sit for 1 hour. The solution of 2,2'-oxydiacetaldehyde was used without further purification.

406. Preparation of 3-(3-chloro-4-hydroxyphenyl)-7-morpholino-9H-carbazole-1-carboxamide 7-Amino-3-(3-chloro-4-hydroxyphenyl)-9H-carbazole-1-carboxamide (700 mg, 1.094 mmol, Example 406A) and sodium cyanoborohydride (400 mg, 6.37 mmol) were dissolved in methanol (20 mL)+THF (20.00 ml). Trimethyl orthoformate (10 ml, 90 mmol) and acetic acid (100 μl, 1.747 mmol) were added, followed by 28 ml of the crude reaction mixture from Example 406B (contained ~4 mmol of 2,2'-oxydiacetaldehyde in CH$_2$Cl$_2$). The reaction mixture was stirred at room temperature for 90 minutes, then filtered through a Waters MCX cartridge (18 g adsorbent). The cartridge was washed with water, methanol and dichloromethane, then the product was eluted with 2M NH$_3$ in MeOH. Evaporation of volatiles and purification by prep HPLC gave 149.0 mg 3-(3-chloro-4-hydroxyphenyl)-7-morpholino-9H-carbazole-1-carboxamide. MS (ESI) m/e+=422/424, m/e−=420/422 [1 Cl isotope pattern]. HPLC retention time 7.34 min. (Sunfire C18 3.5 μm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA). $^1$H NMR (DMSO-d$_6$) δ ppm 11.13 (s, 1H), 10.22 (b, 1H), 8.45 (d, 1H, J=1.5), 8.32 (b, 1H), 8.11 (d, 1H, J=1.7), 8.07 (d, 1H, J=8.8), 7.89 (d, 1H, J=2.3), 7.67 (dd, 1H, J=8.5, 2.3), 7.50 (b, 1H), 7.27 (d, 1H, J=1.0), 7.09 (d, 1H, J=8.5), 6.97 (dd, 1H, J=8.7, 1.7), 3.86-3.79 (m, 4H), 3.25-3.19 (m, 4H).

EXAMPLE 407

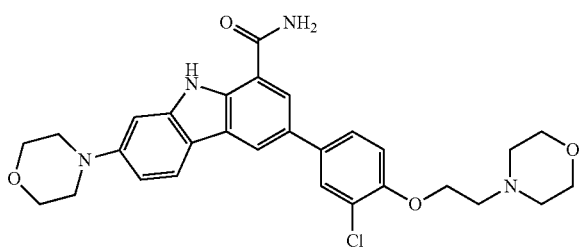 [SMILES: NC(=O)c1cc(-c2ccc(OCCN3CCOCC3)c(Cl)c2)cc2c1[nH]c1cc(N3CCOCC3)ccc12]

3-(3-Chloro-4-(2-morpholinoethoxy)phenyl)-7-morpholino-9H-carbazole-1-carboxamide 407A. Preparation of 3-(4-(2-bromoethoxy)-3-chlorophenyl)-7-morpholino-9H-carbazole-1-carboxamide

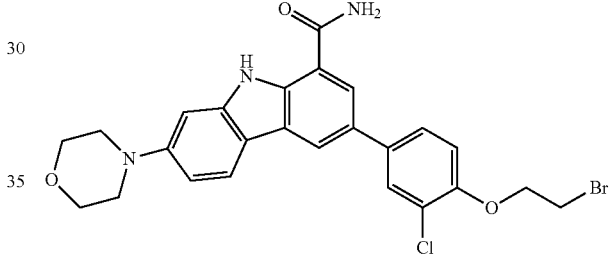

A 100 ml round bottom flask was loaded with 3-(3-chloro-4-hydroxyphenyl)-7-morpholino-9H-carbazole-1-carboxamide (114.9 mg, 0.245 mmol, Example 406), K$_2$CO$_3$ (386 mg, 2.79 mmol), DMF (10 ml) and 1,2-dibromoethane (0.24 ml, 2.79 mmol) and the mixture stirred at room temperature for 4 hours. The reaction mixture was partitioned between 500 ml water+citric acid (0.5 M solution in water) (20 ml, 10.00 mmol) and ethyl acetate. The organic layer was washed with dilute (1+5) aq. NaHCO$_3$ solution, then brine, dried over MgSO$_4$, filtered and evaporated to dryness to give 118.6 mg 3-(4-(2-bromoethoxy)-3-chlorophenyl)-7-morpholino-9H-carbazole-1-carboxamide. MS (ESI) m/e+=528/530/532, m/e−=526/528/530 consistent with isotope pattern for 1 Br and 1 Cl. $^1$H NMR (DMSO-d$_6$) δ ppm 11.14 (s, 1H), 8.50 (d, 1H, J=1.5), 8.34 (b, 1H), 8.15 (d, 1H, J=1.6), 8.07 (d, 1H, J=8.5), 8.01 (d, 1H, J=2.2), 7.83 (dd, 1H, J=8.6, 2.4), 7.52 (b, 1H), 7.31 (d, 1H, J=8.8), 7.24 (d, 1H, J=2.0), 6.95 (dd, 1H, J=8.8, 2.2), 4.50 (t, 2H, J=5.5),), 3.89 (t, 2H, J=5.5), 3.83-3.79 (m, 4H), 3.22-3.17 (m, 4H).

407. Preparation of 3-(3-chloro-4-(2-morpholinoethoxy)phenyl)-7-morpholino-9H-carbazole-1-carboxamide 3-(4-(2-Bromoethoxy)-3-chlorophenyl)-7-morpholino-9H-carbazole-1-carboxamide (110 mg, 0.146 mmol, Example 407A) was dissolved in DMF (5 ml). Morpholine (0.045 ml, 0.517 mmol) and K₂CO₃ (66 mg, 0.478 mmol) were added and the mixture heated to 75° C. for 1 hour. Additional morpholine (0.10 ml, 1.148 mmol) was added and the mixture heated for one additional hour. The mixture was concentrated to a volume of ~1 ml, then diluted with 3 ml DMSO+3 ml MeOH, filtered through a 0.45 um Nylon filter and purified by prep HPLC. Product containing fractions were evaporated to dryness to give 67.8 mg 3-(3-chloro-4-(2-morpholinoethoxy)phenyl)-7-morpholino-9H-carbazole-1-carboxamide. MS (ESI) m/e+=535/537, m/e−=533/535 [1 Cl isotope pattern]. HPLC retention time 15.81 min. (Sunfire C18 3.5 μm, 3.0×150 mm column, 15 min gradient, 10-100% B, 0.5 mL/min. Solvent A: 5% CH₃CN—95% H₂O—0.1% TFA; Solvent B: 95% CH₃CN—5% H₂O—0.1% TFA), then isocratic at 100% B. ¹H NMR (DMSO-d₆) δ ppm 11.13 (s, 1H), 8.49 (d, 1H, J=1.5), 8.34 (b, 1H), 8.14 (d, 1H, J=1.5), 8.07 (d, 1H, J=8.5), 7.99 (d, 1H, J=2.3), 7.82 (dd, 1H, J=8.6, 2.4), 7.51 (b, 1H), 7.31 (d, 1H, J=8.8), 7.24 (d, 1H, J=2.0), 6.94 (dd, 1H, J=8.8, 2.0), 4.26 (t, 2H, J=5.8), 3.83-3.79 (m, 4H), 3.64-3.59 (m, 4H), 3.22-3.17 (m, 4H), 2.79 (t, 2H, J=5.8), 2.58-2.54 (m, 4H).

EXAMPLE 408

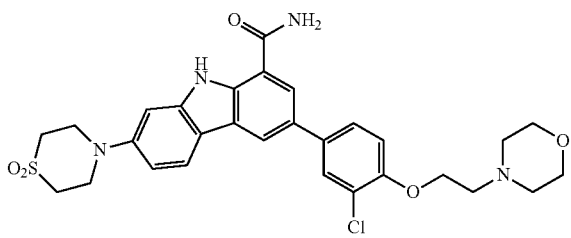 [SMILES: NC(=O)c1cc(-c2ccc(OCCN3CCOCC3)c(Cl)c2)cc2c1[nH]c1cc(N3CCS(=O)(=O)CC3)ccc12]

3-(3-Chloro-4-(2-morpholinoethoxy)phenyl)-7-(1,1-dioxo-thiomorpholino)-9H-carbazole-1-carboxamide

408A. Preparation of 2,2'-sulfonyldiacetaldehyde

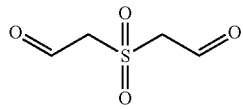

3-Sulfolene (CAS 77-79-2, 0.591 g, 5 mmol) was dissolved in dichloromethane (35 ml) in a 250 ml round bottom flask and cooled to −78° C. Ozone was bubbled through the solution until a faint blue color persisted (~15 minutes). Nitrogen was bubbled through the mixture to purge excess ozone, then dimethyl disulfide (1.479 ml, 20.00 mmol) was added, the flask transferred into a freezer (−20° C.) and let sit for 1 hour. The solution of 2,2'-sulfonyldiacetaldehyde was used without further purification.

408B. Preparation of 3-(3-chloro-4-hydroxyphenyl)-7-(1,1-dioxo-thiomorpholino)-9H-carbazole-1-carboxamide

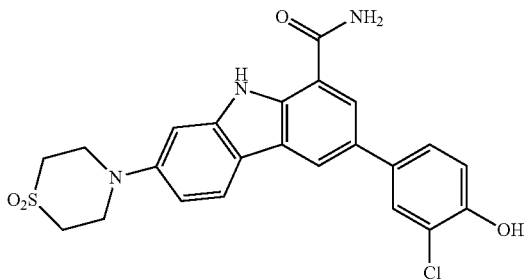 [SMILES: NC(=O)c1cc(-c2ccc(O)c(Cl)c2)cc2c1[nH]c1cc(N3CCS(=O)(=O)CC3)ccc12]

7-Amino-3-(3-chloro-4-hydroxyphenyl)-9H-carbazole-1-carboxamide (460 mg, 0.785 mmol, Example 406A) and sodium cyanoborohydride (560 mg, 8.91 mmol) were dissolved in methanol (20 mL)+THF (20.00 ml). Trimethyl orthoformate (5 ml, 45 mmol) and acetic acid (100 μl, 1.747 mmol) were added, followed by the crude reaction mixture from Example 408A (contained ~5 mmol of 2,2'-sulfonyldiacetaldehyde in CH₂Cl₂). The reaction mixture was stirred at room temperature for 90 minutes, then partitioned between ethyl acetate and dilute aqueous NH₄Cl solution (500 ml water+25 ml saturated solution). The aqueous layer was extracted once more with ethyl acetate. The combined organic layers were washed with brine, dried over MgSO₄, filtered and concentrated in vacuum. Attempted purification by reversed phase HPLC give 79.6 mg 3-(3-chloro-4-hydroxyphenyl)-7-(1,1-dioxo-thiomorpholino)-9H-carbazole-1-carboxamide of ~80% purity which was used without further purification. MS (ESI) m/e+=470/472, m/e−=468/470 [1 Cl isotope pattern].

408C. Preparation of 3-(4-(2-bromoethoxy)-3-chlorophenyl)-7-(1,1-dioxo-thiomorpholino)-9H-carbazole-1-carboxamide

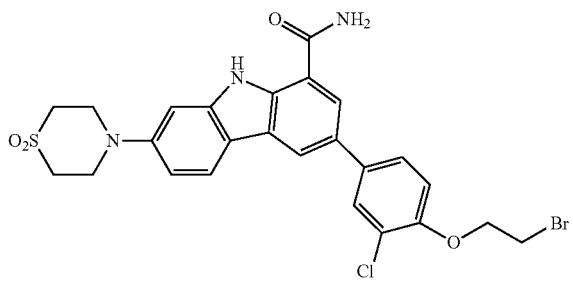 [SMILES: NC(=O)c1cc(-c2ccc(OCCBr)c(Cl)c2)cc2c1[nH]c1cc(N3CCS(=O)(=O)CC3)ccc12]

A 100 ml round bottom flask was loaded with 3-(3-chloro-4-hydroxyphenyl)-7-(1,1-dioxo-thiomorpholino)-9H-carbazole-1-carboxamide (49.4 mg, 0.084 mmol, Example 408B), K₂CO₃ (150 mg, 1.085 mmol), DMF (6 ml) and 1,2-dibromoethane (0.09 ml, 1.044 mmol) and stirred at room temperature for 4.5 hours. The reaction mixture was poured into a separating funnel that was loaded with 100 ml water+citric acid (0.5 M solution in water) (10 ml, 5.00 mmol) and extracted with ethyl acetate. The organic layer was washed with dilute (1+5) aq. NaHCO$_3$ solution, then brine, dried over MgSO$_4$, filtered and evaporated to dryness to give 48.6 mg 3-(4-(2-bromoethoxy)-3-chlorophenyl)-7-(1,1-dioxo-thiomorpholino)-9H-carbazole-1-carboxamide, which was used without further purification. Estimated purity (from LCMS) ~90%. MS (ESI) m/e+=576/578/580, m/e-=574/576/578 consistent with isotope pattern for 1 Br and 1 Cl.

408. Preparation of 3-(3-chloro-4-(2-morpholinoethoxy)phenyl)-7-(1,1-dioxo-thiomorpholino)-9H-carbazole-1-carboxamide 3-(4-(2-Bromoethoxy)-3-chlorophenyl)-7-(1,1-dioxo-thiomorpholino)-9H-carbazole-1-carboxamide (48.6 mg, 0.076 mmol, Example 408C) was dissolved in DMF (5 ml). Morpholine (0.1 ml, 1.15 mmol) and K$_2$CO$_3$ (40 mg, 0.29 mmol) were added and the mixture heated to 75° C. for 2 hour. The mixture was filtered through a 0.45 um Nylon filter and purified by prep HPLC. Product containing fractions were evaporated to dryness to give 43.0 mg 3-(3-chloro-4-(2-morpholinoethoxy)phenyl)-7-(1,1-dioxo-thiomorpholino)-9H-carbazole-1-carboxamide. MS (ESI) m/e+=583/585, m/e-=581/583 [1 Cl isotope pattern]. HPLC retention time 14.31 min. (Sunfire C18 3.5 μm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA), then isocratic at 100% B. $^1$H NMR (DMSO-d$_6$) δ ppm 11.12 (s, 1H), 8.53 (d, 1H, J=1.2), 8.35 (b, 1H), 8.16 (d, 1H, J=1.5), 8.11 (d, 1H, J=8.8), 7.99 (d, 1H, J=2.3), 7.82 (dd, 1H, J=8.5, 2.2), 7.53 (b, 1H), 7.34 (d, 1H, J=2.0), 7.31 (d, 1H, J=8.8), 7.00 (dd, 1H, J=8.8, 2.2), 4.26 (t, 2H, J=5.8), 3.85 (b, 4H), 3.64-3.59 (m, 4H), 3.23 (b, 4H), 2.79 (t, 2H, J=5.8), 2.58-2.54 (m, 4H).

EXAMPLE 409

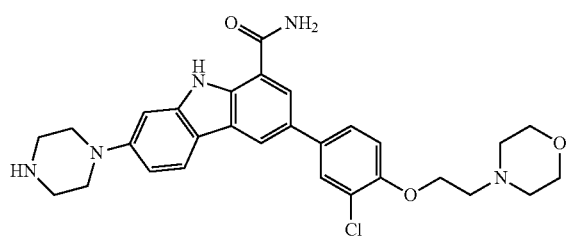 [SMILES: NC(=O)c1cc(-c2ccc(OCCN3CCOCC3)c(Cl)c2)cc2c1[nH]c1cc(N3CCNCC3)ccc12]

3-(3-Chloro-4-(2-morpholinoethoxy)phenyl)-7-(piperazine-1-yl)-9H-carbazole-1-carboxamide

409A. Preparation of tert-butyl bis(2-oxoethyl)carbamate

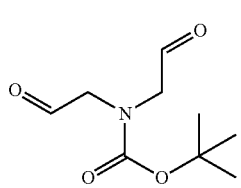

tert-Butyl 2,5-dihydro-1H-pyrrole-1-carboxylate (1.692 g, 10 mmol) was dissolved in dichloromethane (35 ml) in a 250 ml round bottom flask and cooled to −78° C. Ozone was bubbled through the solution until a faint blue color of dissolved ozone persisted. (~15 minutes). Nitrogen was bubbled through the solution until blue color disappeared, then dimethyl sulfide (2.96 ml, 40.0 mmol) was added, the flask transferred into a freezer (−20° C.) and let sit for 1 hour. The solution of tert-butyl bis(2-oxoethyl)carbamate was used without further purification.

409B. Preparation of tert-butyl 4-(8-carbamoyl-6-(3-chloro-4-hydroxyphenyl)-9H-carbazol-2-yl)piperazine-1-carboxylate

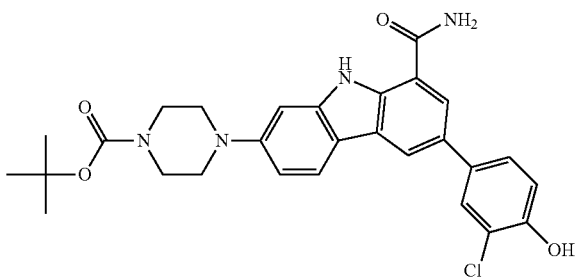 [SMILES: CC(C)(C)OC(=O)N1CCN(c2ccc3c(c2)[nH]c2c(C(N)=O)cc(-c4ccc(O)c(Cl)c4)cc23)CC1]

7-Amino-3-(3-chloro-4-hydroxyphenyl)-9H-carbazole-1-carboxamide (2.00 g, 3.41 mmol, Example 406A) and sodium cyanoborohydride (1.40 g, 22.3 mmol) were dissolved in methanol (40 mL)+THF (40.00 ml). Trimethyl orthoformate (24 ml, 109 mmol) and acetic acid (300 μl, 5.2 mmol) were added, followed by the crude reaction mixture from Example 409A (contained ~10 mmol of tert-butyl bis(2-oxoethyl)carbamate in CH$_2$Cl$_2$). The reaction mixture was stirred at room temperature for 90 minutes, then partitioned between ethyl acetate and dilute aqueous NH$_4$Cl solution (500 ml water+25 ml saturated solution). The aqueous layer was extracted once more with ethyl acetate. The combined organic layers were washed with brine, dried over MgSO$_4$, filtered and concentrated in vacuum. Purification by chromatography on silica (160 g cartridge, 800 ml EtOAc+DCM 1+1, then gradient from 0% to 10% MeOH in EtOAc+DCM 1+1) gave 365 mg tert-butyl 4-(8-carbamoyl-6-(3-chloro-4-hydroxyphenyl)-9H-carbazol-2-yl)piperazine-1-carboxylate of ~50% purity which was used without further purification. MS (ESI) m/e+=521/523, m/e-=519/521 [1 Cl isotope pattern].

409C. Preparation of tert-butyl 4-(6-(4-(2-bromoethoxy)-3-chlorophenyl)-8-carbamoyl-9H-carbazol-2-yl)piperazine-1-carboxylate

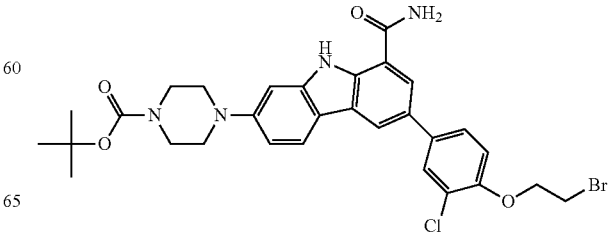

A 100 ml round bottom flask was loaded with tert-butyl 4-(8-carbamoyl-6-(3-chloro-4-hydroxyphenyl)-9H-carbazol-2-yl)piperazine-1-carboxylate (estimated purity ~50%, 365 mg, ~0.35 mmol, Example 409B), $K_2CO_3$ (1.12 g, 8.10 mmol), DMF (20 ml) and 1,2-dibromoethane (0.64 ml, 7.4 mmol) and stirred at room temperature for 17 hours. The reaction mixture was poured into a separating funnel that was loaded with 500 ml water+citric acid (0.5 M solution in water) (60 ml, 30 mmol) and extracted with ethyl acetate. The organic layer was washed with dilute (1+5) aq. $NaHCO_3$ solution, then brine, dried over $MgSO_4$, filtered and evaporated to dryness to give 342 mg tert-butyl 4-(6-(4-(2-bromoethoxy)-3-chlorophenyl)-8-carbamoyl-9H-carbazol-2-yl)piperazine-1-carboxylate, which was used without further purification. Estimated purity (from LCMS) ~55%. MS (ESI) m/e+=627/629/631, m/e−=625/627/629 consistent with isotope pattern for 1 Br and 1 Cl.

409D. Preparation of tert-butyl 4-(8-carbamoyl-6-(3-chloro-4-(2-morpholinoethoxy)phenyl)-9H-carbazol-2-yl)piperazine-1-carboxylate

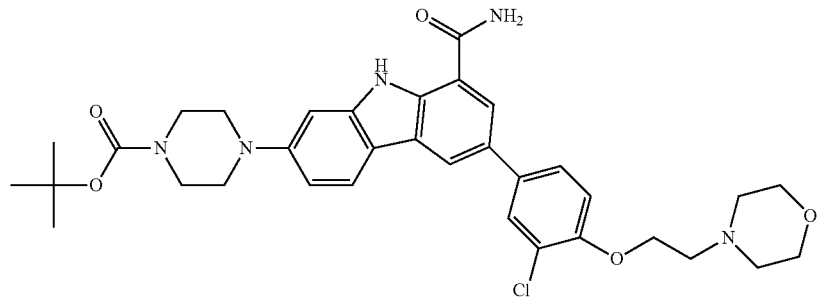 [SMILES: CC(C)(C)OC(=O)N1CCN(c2ccc3c(c2)[nH]c2c(C(N)=O)cc(-c4ccc(OCCN5CCOCC5)c(Cl)c4)cc23)CC1]

tert-Butyl 4-(6-(4-(2-bromoethoxy)-3-chlorophenyl)-8-carbamoyl-9H-carbazol-2-yl)piperazine-1-carboxylate (342 mg, estimated purity 55%, ~0.30 mmol, Example 409C) was dissolved in DMF (6 ml). Morpholine (0.5 ml, 5.7 mmol) and $K_2CO_3$ (160 mg, 1.16 mmol) were added and the mixture heated to 75° C. for 2 hour. The reaction mixture was poured into a separating funnel that was loaded with 100 ml water+25 ml saturated aq. $NH_4Cl$ solution and extracted with ethyl acetate. The organic layer was washed with brine, dried over $MgSO_4$, filtered and evaporated to dryness. Purification by prep HPLC gave 170 mg tert-butyl 4-(8-carbamoyl-6-(3-chloro-4-(2-morpholinoethoxy)phenyl)-9H-carbazol-2-yl)piperazine-1-carboxylate. MS (ESI) m/e+=634/636, m/e−=632/634 [1 Cl isotope pattern]. HPLC retention time 16.96 min. (Sunfire C18 3.5 μm, 3.0×150 mm column, 15 min gradient, 10-100% B, 0.5 mL/min. Solvent A: 5% $CH_3CN$—95% $H_2O$—0.1% TFA; Solvent B: 95% $CH_3CN$—5% $H_2O$—0.1% TFA), then isocratic at 100% B. $^1H$ NMR (DMSO-$d_6$) δ ppm 11.14 (s, 1H), 8.50 (d, 1H, J=1.3), 8.33 (b, 1H), 8.14 (d, 1H, J=1.5), 8.07 (d, 1H, J=8.8), 7.98 (d, 1H, J=2.3), 7.82 (dd, 1H, J=8.8, 2.3), 7.51 (b, 1H), 7.31 (d, 1H, J=8.8), 7.25 (d, 1H, J=2.0), 6.95 (dd, 1H, J=8.8, 2.0), 4.26 (t, 2H, J=5.8), 3.63-3.59 (m, 4H), 3.53 (b, 4H), 3.21-3.17 (m, 4H), 2.79 (t, 2H, J=5.8), 2.58-2.54 (m, 4H), 1.46 (s, 9H).

409. Preparation of 3-(3-chloro-4-(2-morpholinoethoxy)phenyl)-7-(piperazine-1-yl)-9H-carbazole-1-carboxamide tert-Butyl 4-(8-carbamoyl-6-(3-chloro-4-(2-morpholinoethoxy)phenyl)-9H-carbazol-2-yl)piperazine-1-carboxylate (124.3 mg, 0.171 mmol), $ClCH_2CH_2Cl$ (6 ml) and TFA (2 ml, 26.0 mmol) were combined and the mixture stirred at room temperature for 45 minutes. Volatiles were evaporated and the crude product dissolved in 6 ml MeOH. 2 ml each (⅓ of the crude product) was used in syntheses of Examples 410 and 411 below.

The remaining ⅓ was purified by prep HPLC. Product containing fractions were filtered through a Waters MCX cartridge, washed with MeOH, eluted with 2M $NH_3$ in MeOH and evaporated to dryness to give 19.4 mg 3-(3-chloro-4-(2-morpholinoethoxy)phenyl)-7-(piperazine-1-yl)-9H-carbazole-1-carboxamide. MS (ESI) m/e+=534/536, m/e−=532/534 [1 Cl isotope pattern]. HPLC retention time 4.72 min. (Sunfire C18 3.5 μm, 3.0×150 mm column, 15 min gradient, 10-100% B, 0.5 mL/min. Solvent A: 5% $CH_3CN$—95% $H_2O$—0.1% TFA; Solvent B: 95% $CH_3CN$—5% $H_2O$—0.1% TFA), then isocratic at 100% B. $^1H$ NMR ($CD_3OD$) δ ppm 8.33 (d, 1H, J=1.5), 8.04 (d, 1H, J=1.8), 8.02 (d, 1H, J=8.5), 7.84 (d, 1H, J=2.3), 7.68 (dd, 1H, J=8.5, 2.5), 7.19 (d, 1H, J=8.7), 7.15 (d, 1H, J=2.0), 6.98 (dd, 1H, J=8.8, 2.0), 4.28 (t, 2H, J=5.4), 3.76-3.73 (m, 4H), 3.40-3.25 (m, 4H, overlap with $CD_3OD$ signal), 3.09-3.04 (m, 4H), 2.91 (t, 2H, J=5.4), 2.73-2.69 (m, 4H).

EXAMPLE 410

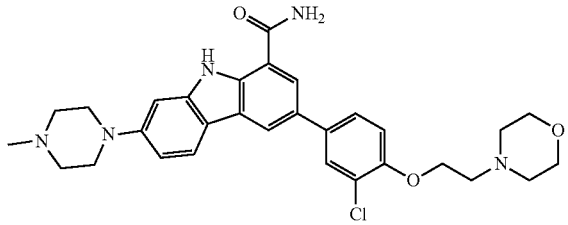 [SMILES: CN1CCN(c2ccc3c(c2)[nH]c2c(C(N)=O)cc(-c4ccc(OCCN5CCOCC5)c(Cl)c4)cc23)CC1]

3-(3-Chloro-4-(2-morpholinoethoxy)phenyl)-7-(4-methylpiperazin-1-yl)-9H-carbazole-1-carboxamide ⅓ of the crude product from Example 409 [contains 3-(3-chloro-4-(2-morpholinoethoxy)phenyl)-7-(piperazin-1-yl)-9H-carbazole-1-carboxamide (~30 mg, 0.057 mmol) as its TFA salt] was dissolved in MeOH (2 ml) and THF (2.0 ml). Potassium acetate (0.022 g, 0.224 mmol) was added and the pH checked to be ~4-5. Formaldehyde (aqueous solution, 37%) (0.05 ml, 0.672 mmol) followed by trimethyl orthoformate (1 ml, 9.05 mmol) were added and the mixture stirred for 5 minutes at room temperature. Sodium cyanoborohydride (15 mg, 0.239 mmol) was added and stirring continued for 1 hour at room temperature. The reaction mixture was partitioned between dilute aq. $NaHCO_3$ solution and EtOAc. The organic layer was washed one more time with dilute (1+5) aq.

NaHCO₃ solution, then brine, dried over MgSO₄, filtered and evaporated to dryness. The crude product was purified by prep HPLC to give 21.6 mg 3-(3-chloro-4-(2-morpholinoethoxy)phenyl)-7-(4-methylpiperazin-1-yl)-9H-carbazole-1-carboxamide. MS (ESI) m/e+=548/550 [1 Cl isotope pattern]. HPLC retention time 4.22 min. (Sunfire C18 3.5 µm, 3.0×150 mm column, 15 min gradient, 10-100% B, 0.5 mL/min. Solvent A: 5% CH₃CN—95% H₂O—0.1% TFA; Solvent B: 95% CH₃CN—5% H₂O—0.1% TFA), then isocratic at 100% B. ¹H NMR (CD₃OD) δ ppm 8.32 (d, 1H, J=1.7), 8.03 (d, 1H, J=1.8), 8.01 (d, 1H, J=8.5), 7.83 (d, 1H, 1.8), 7.67 (dd, 1H, J=8.5, 2.5), 7.18 (d, 1H, J=8.8), 7.14 (d, 1H, J=2.0), 6.97 (dd, 1H, J=8.8, 2.0), 4.27 (t, 2H, J=5.4), 3.76-3.73 (m, 4H), 3.36-3.25 (m, 4H, overlap with CD₃OD signal), 2.90 (t, 2H, J=5.3), 2.73-2.66 (m, 8H), 2.39 (s, 3H).

was washed one more time with dilute (1+5) aq. NaHCO₃ solution, then brine, dried over MgSO₄, filtered and evaporated to dryness. The crude product was purified by prep HPLC to give 26.0 mg 3-(3-chloro-4-(2-morpholinoethoxy)phenyl)-7-(4-(2-methoxyethyl)piperazin-1-yl)-9H-carbazole-1-carboxamide. MS (ESI) m/e+=592/594 [1 Cl isotope pattern]. HPLC retention time 5.69 min. (Sunfire C18 3.5 µm, 3.0×150 mm column, 15 min gradient, 10-100% B, 0.5 mL/min. Solvent A: 5% CH₃CN—95% H₂O—0.1% TFA; Solvent B: 95% CH₃CN—5% H₂O—0.1% TFA), then isocratic at 100% B. ¹H NMR (CD₃OD) δ ppm 8.33 (d, 1H, J=1.8), 8.03 (d, 1H, J=1.8), 8.01 (d, 1H, J=8.5), 7.83 (d, 1H, 2.2), 7.68 (dd, 1H, J=8.7, 2.4), 7.18 (d, 1H, J=8.5), 7.14 (d, 1H, J=2.1), 6.97 (dd, 1H, J=8.6, 2.2), 4.28 (t, 2H, J=5.4), 3.76-3.73 (m, 4H), 3.61 (t, 2H, J=5.6), 3.38 (s, 3H), 3.36-3.25 (m, 4H, overlap with CD₃OD signal), 2.90 (t, 2H, J=5.4), 2.79-2.75 (m, 4H), 2.73-2.67 (m, 6H).

EXAMPLE 411

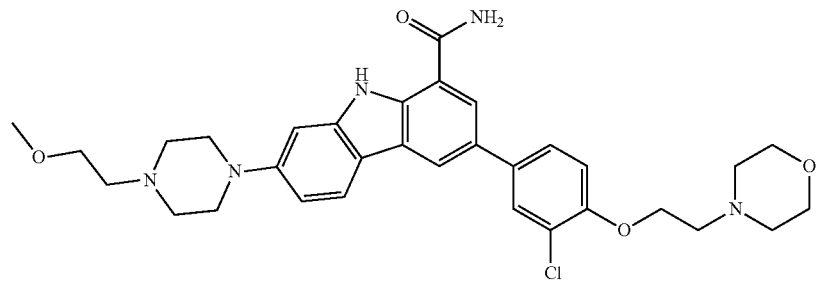 [SMILES: COCCN1CCN(c2ccc3c(c2)[nH]c2c(C(N)=O)cc(-c4ccc(OCCN5CCOCC5)c(Cl)c4)cc23)CC1]

3-(3-Chloro-4-(2-morpholinoethoxy)phenyl)-7-(4-(2-methoxyethyl)piperazin-1-yl)-9H-carbazole-1-carboxamide 411A. Preparation of 2-methoxyacetaldehyde

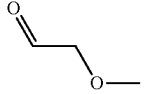

A 2 ml microwave vial was loaded with methoxyacetaldehyde dimethyl acetal (0.129 mL, 1 mmol) and HCl (1 M aqueous) (1.000 mL, 1.000 mmol), sealed and heated to 80° C. for 10 minutes. The reaction mixture was allow to cool to room temperature and used "as is" in the following experiment (Example 411).

411. Preparation of 3-(3-chloro-4-(2-morpholinoethoxy)phenyl)-7-(4-(2-methoxyethyl)piperazin-1-yl)-9H-carbazole-1-carboxamide ⅓ of the crude product from Example 409 [contains 3-(3-chloro-4-(2-morpholinoethoxy)phenyl)-7-(piperazin-1-yl)-9H-carbazole-1-carboxamide (~30 mg, 0.057 mmol) as its TFA salt] was dissolved in MeOH (2 ml) and THF (2.0 ml). Potassium acetate (0.250 g, 2.55 mmol) and the crude reaction mixture from Example 411A (contains ~1 mmol 2-methoxyacetaldehyde in 1 ml aq. 1 N HCl) was added and the pH checked to be ~4-5. Trimethyl orthoformate (2 ml, 18.1 mmol) was added and the mixture stirred for 5 minutes at room temperature. Sodium cyanoborohydride (18 mg, 0.286 mmol) was added and stirring continued for 1 hour at room temperature. The reaction mixture was partitioned between dilute aq. NaHCO₃ solution and EtOAc. The organic layer

EXAMPLE 412

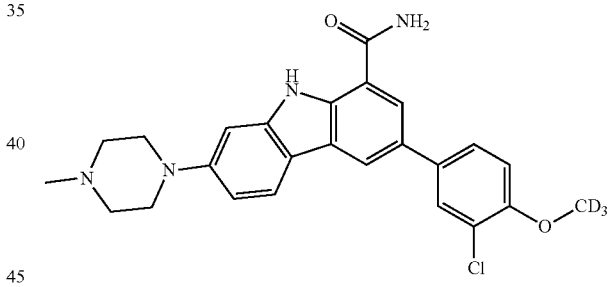

3-(3-Chloro-4-trideuteromethoxyphenyl)-7-(4-methylpiperazin-1-yl)-9H-carbazole-1-carboxamide 412A. Preparation of tert-butyl 4-(8-carbamoyl-6-(3-chloro-4-trideuteromethoxyphenyl)-9H-carbazol-2-yl)piperazine-1-carboxylate

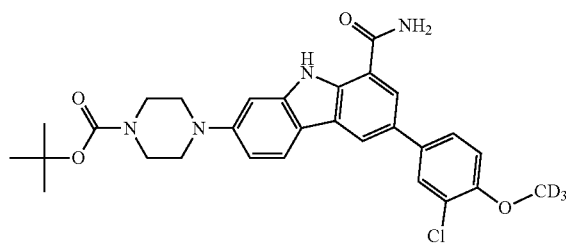 [SMILES: [2H]C([2H])([2H])Oc1ccc(-c2cc(C(N)=O)c3[nH]c4cc(N5CCN(C(=O)OC(C)(C)C)CC5)ccc4c3c2)cc1Cl]

A 100 ml round bottom flask was loaded with tert-butyl 4-(8-carbamoyl-6-(3-chloro-4-hydroxyphenyl)-9H-carbazol-2-yl)piperazine-1-carboxylate (0.29 g, 0.167 mmol, Example 409B), K$_2$CO$_3$ (0.40 g, 2.89 mmol) and DMF (20 ml). Iodomethane-d3 (0.17 ml, 2.73 mmol) was added and the mixture stirred at room temperature for 18 hours. The reaction mixture was poured into 500 ml water+25 ml sat. aq. NH$_4$Cl solution and extracted with ethyl acetate. The organic layer was washed twice with dilute (1+5) aq. NaHCO$_3$ solution, then once with brine, dried over MgSO$_4$, filtered and evaporated to dryness. The crude product was dissolved in DMSO+MeOH and purified by prep HPLC. Product containing fractions were filtered through a Waters MCX cartridge (5 g adsorbent), the cartridge washed with MeOH, and the product eluted with a 1:1 mixture of 2M NH$_3$ in MeOH and dichloromethane. Evaporation of volatiles gave 31.0 mg tert-butyl 4-(8-carbamoyl-6-(3-chloro-4-trideuteromethoxyphenyl)-9H-carbazol-2-yl)piperazine-1-carboxylate. MS (ESI) m/e+=538/540, 1-Cl-isotope pattern, consistent with [M+H]$^+$. $^1$H NMR (CDCl$_3$) δ ppm 10.24 (s, 1H), 8.23 (d, 1H, J=1.2), 7.98 (d, 1H, J=8.3), 7.69 (d, 1H, J=2.3), 7.63 (d, 1H, J=1.0), 7.52 (dd, 1H, J=8.5, 2.3), 7.03 (d, 1H, J=8.3), 6.98-6.94 (m, 2H), 3.67-3.62 (m, 4H), 3.29-3.23 (b, 4H), 1.52 (s, 9H).

412B. Preparation of 3-(3-chloro-4-trideuteromethoxyphenyl)-7-(piperazin-1-yl)-9H-carbazole-1-carboxamide

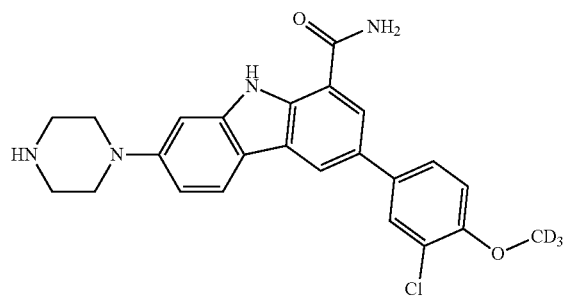 [SMILES: [2H]C([2H])([2H])Oc1ccc(-c2cc(C(N)=O)c3[nH]c4cc(N5CCNCC5)ccc4c3c2)cc1Cl]

tert-Butyl 4-(8-carbamoyl-6-(3-chloro-4-(trideuteromethoxy)phenyl)-9H-carbazol-2-yl)piperazine-1-carboxylate (31 mg, 0.058 mmol) was dissolved in ClCH$_2$CH$_2$Cl (10 ml). TFA (2 ml, 26.0 mmol) was added and the mixture stirred at room temperature for 1 hour. The reaction was evaporated to dryness and the crude product used without further purification. MS (ESI) m/e+=438/440 (1 Cl isotope pattern).

412 Preparation of 3-(3-chloro-4-trideuteromethoxyphenyl)-7-(4-methylpiperazin-1-yl)-9H-carbazole-1-carboxamide The crude product from Example 412B [contains <=0.058 mmol 3-(3-chloro-4-(trideuteriomethoxy)phenyl)-7-(piperazin-1-yl)-9H-carbazole-1-carboxamide as its TFA salt] was dissolved in MeOH (2 ml) and THF (2 ml). Potassium acetate (0.022 g, 0.224 mmol) was added and the pH checked to be ~4-5. Formaldehyde (aqueous solution, 37%) (0.050 ml, 0.672 mmol) followed by trimethyl orthoformate (1 ml, 9.05 mmol) were added and the mixture stirred for 5 minutes at room temperature. Sodium cyanoborohydride (15 mg, 0.239 mmol) was added and the mixture stirred at room temperature for 2 hours. The reaction mixture was partitioned between dilute aq. NaHCO$_3$ solution and EtOAc. The aqueous layer was washed once more with EtOAc. The combined organic layers were washed once with brine, dried over MgSO$_4$, filtered and evaporated to dryness. The crude product was purified by prep HPLC. Product containing fractions were filtered through a Waters MCX cartridge (1 g), the cartridge washed with MeOH, the product eluted with 2M NH$_3$ in MeOH+CH$_2$Cl$_2$ and evaporated to dryness to give 13.8 mg 3-(3-chloro-4-trideuteromethoxyphenyl)-7-(4-methylpiperazin-1-yl)-9H-carbazole-1-carboxamide. MS (ESI) m/e+=452/454 (1 Cl isotope pattern) consistent with the desired product. HPLC retention time 8.03 min. (Sunfire C18 3.5 µm, 3.0×150 mm column, 15 min gradient, 10-100% B, 0.5 mL/min. Solvent A: 5% CH$_3$CN—95% H$_2$O—0.1% TFA; Solvent B: 95% CH$_3$CN—5% H$_2$O—0.1% TFA), then isocratic at 100% B. $^1$H NMR (CDCl$_3$) δ ppm 10.21 (s, 1H), 8.23 (d, 1H, J=1.2), 7.97 (d, 1H, J=8.3), 7.70 (d, 1H, J=2.3), 7.61 (d, 1H, J=1.5), 7.53 (dd, 1H, J=8.5, 2.3), 7.04 (d, 1H, J=8.5), 7.00-6.95 (m, 2H), 3.38-3.34 (m, 4H), 2.69-2.64 (m, 4H), 2.41 (s, 3H).

EXAMPLE 413

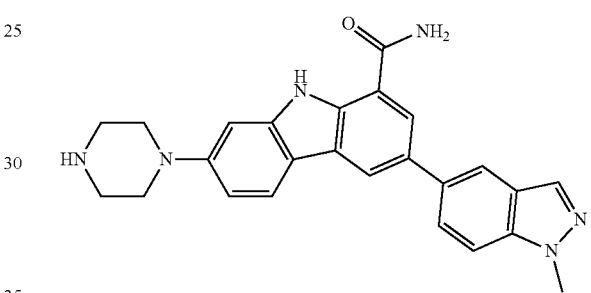

3-(1-Methyl-1H-indazol-5-yl)-7-(piperazin-1-yl)-9H-carbazole-1-carboxamide

413A. Preparation of tert-butyl 4-(6-bromo-8-carbamoyl-9H-carbazol-2-yl)piperazine-1-carboxylate

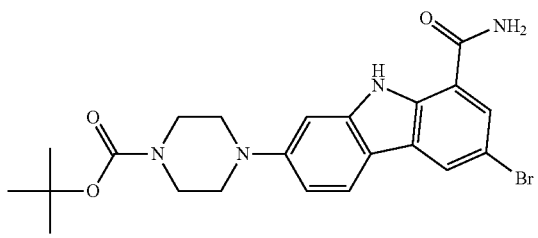 [SMILES: CC(C)(C)OC(=O)N1CCN(c2ccc3c(c2)[nH]c2c(C(N)=O)cc(Br)cc23)CC1]

7-Amino-3-bromo-9H-carbazole-1-carboxamide (0.78 g, 1.282 mmol, Example 480B) was dissolved in methanol (40 mL)+THF (20.0 ml). potassium acetate (0.126 g, 1.282 mmol) acetate was added until pH ~4-5. Trimethyl orthoformate (6 ml, 54 mmol) was added, followed by a solution of ~2.9 mmol of tert-butyl bis(2-oxoethyl)carbamate in 10 ml CH$_2$Cl$_2$ (Example 409A). The reaction mixture was stirred at room temperature for 5 minutes, then sodium cyanoborohydride (503 mg, 8 mmol) was added and the mixture stirred at room temperature for 18 hours. The reaction mixture was partitioned between ethyl acetate and diluted aqueous NaHCO$_3$ solution (500 ml water+25 ml saturated solution).

The aqueous layer was extracted once more with ethyl acetate. The combined organic layers were washed with brine, dried over MgSO₄, filtered and concentrated in vacuum. The crude product was dissolved in MeOH+DCM, filtered through a Strata X-C strong cation exchange cartridge (2×5 g adsorbent). The cartridge was washed with methanol and the product eluted with 1+1 mixture of 2M NH₃ in MeOH and DCM to give 0.49 g tert-butyl 4-(6-bromo-8-carbamoyl-9H-carbazol-2-yl)piperazine-1-carboxylate. Estimated purity ~50%. The material was used "as is" in the next reaction. MS (ESI) m/e+=473/475 (1 Br isotope pattern).

413B. Preparation of tert-butyl 4-(8-carbamoyl-6-(1-methyl-1H-indazol-5-yl)-9H-carbazol-2-yl)piperazine-1-carboxylate

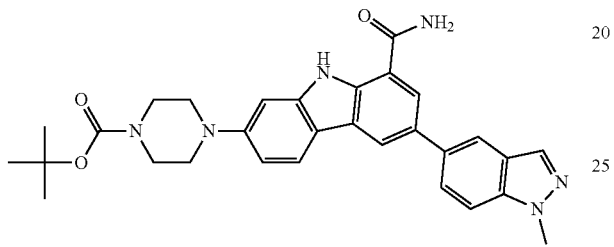

A 20 ml microwave vial was loaded with tert-butyl 4-(6-bromo-8-carbamoyl-9H-carbazol-2-yl)piperazine-1-carboxylate (0.49 g, 0.518 mmol), 1-methyl-1H-indazol-5-ylboronic acid (0.255 g, 1.377 mmol), DME (15 mL), PdCl₂(dppf)-CH₂Cl₂ adduct (40 mg, 0.049 mmol) and Na₂CO₃ (2M) (1.55 mL, 3.10 mmol). The vial was sealed, flushed with nitrogen for 15 minutes, then heated to 100° C. for 2 hours. LCMS showed partial conversion of bromide starting material. 1-Methyl-1H-indazol-5-ylboronic acid (0.115 g, 0.621 mmol), PdCl₂(dppf)-CH₂Cl₂ adduct (30 mg, 0.037 mmol) and Na₂CO₃ (2M) (1.0 mL, 2.0 mmol) were added and heating continued for 4 hours at 100° C. The reaction mixture was poured into a separating funnel that is loaded with 100 ml water+25 ml sat. aq. NH₄Cl solution and extracted with EtOAc (2×). The organic layers were washed once with dilute NaHCO₃ solution, then brine, then dried over MgSO₄+3 g SILICYCLE® thiol resin [to capture Pd and ferrocene] overnight. Filtration and evaporation to dryness gave the crude product, which was purified by chromatography on silica. (Gradient from 100% dichloromethane to 50% DCM+50% EtOAc (85 fractions a 12 ml, fractions A), then gradient from 50% DCM+50% EtOAc to 40% DCM+40% EtOAc+20% MeOH (85 fractions a 12 ml, fractions B). Product containing fractions (B20-B27) were combined and evaporated to dryness to give 168 mg tert-butyl 4-(8-carbamoyl-6-(1-methyl-1H-indazol-5-yl)-9H-carbazol-2-yl)piperazine-1-carboxylate. Estimated purity ~50% (contains significant amount of 1-methyl-1H-indazol-5-ylboronic acid). MS (ESI) m/e+=525.

413. Preparation of 3-(1-methyl-1H-indazol-5-yl)-7-(piperazin-1-yl)-9H-carbazole-1-carboxamide The crude product from Example 413B [168 mg, contains ~0.16 mmol tert-butyl 4-(8-carbamoyl-6-(1-methyl-1H-indazol-5-yl)-9H-carbazol-2-yl)piperazine-1-carboxylate was suspended in ClCH₂CH₂Cl (20 ml). Addition of TFA (2 ml, 26.0 mmol) resulted in complete dissolution. The reaction mixture was stirred at room temperature for 2.5 hours, then evaporated to dryness. The product was purified by prep HPLC to give 62.6 mg 3-(1-methyl-1H-indazol-5-yl)-7-(piperazin-1-yl)-9H-carbazole-1-carboxamide. The "free base product" was suspended in MeOH. Addition of 1.0 equiv. HCl (147 ul of a 1.00 M aq. solution) resulted in complete dissolution. Evaporate to dryness gave 67.8 mg 3-(1-methyl-1H-indazol-5-yl)-7-(piperazin-1-yl)-9H-carbazole-1-carboxamide as its mono-HCl salt. MS (ESI) m/e+=425. HPLC retention time 5.82 min. (Sunfire C18 3.5 μm, 3.0×150 mm column, 15 min gradient, 10-100% B, 0.5 mL/min. Solvent A: 5% CH₃CN—95% H₂O—0.1% TFA; Solvent B: 95% CH₃CN—5% H₂O—0.1% TFA), then isocratic at 100% B. ¹H NMR (CD₃OD) δ ppm 8.46 (d, 1H, J=1.5), 8.17 (d, 1H, J=1.7), 8.13 (b, 1H), 8.11-8.07 (m, 2H), 7.91 (dd, 1H, J=1.8, 8.8), 7.67 (d, 1H, J=8.8), 7.23 (d, 1H, J=2.0), 7.03 (dd, 1H, J=8.5, 2.0), 4.12 (s, 3H), 3.56-3.52 (m, 4H), 3.47-3.43 (m, 4H).

EXAMPLE 414

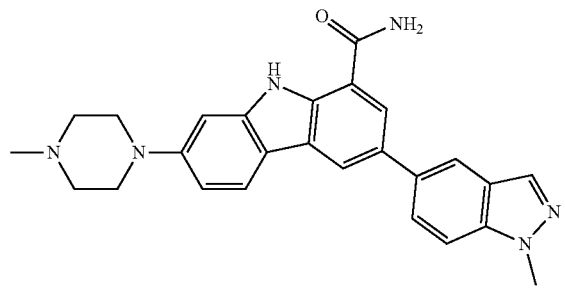 [SMILES: CN1CCN(c2ccc3c(c2)[nH]c2c(C(N)=O)cc(-c4ccc5c(cnn5C)c4)cc23)CC1]

3-(1-Methyl-1H-indazol-5-yl)-7-(4-methylpiperazin-1-yl)-9H-carbazole-1-carboxamide 3-(1-Methyl-1H-indazol-5-yl)-7-(piperazin-1-yl)-9H-carbazole-1-carboxamide, HCl (44 mg, 0.091 mmol, Example 413) was dissolved in MeOH (7 ml). pH was checked and found to be ~4-5. Formaldehyde (aqueous solution, 37%) (0.050 ml, 0.672 mmol) was added, followed by trimethyl orthoformate (1 ml, 9.05 mmol). After 5 minutes of stirring at room temperature sodium cyanoborohydride (20 mg, 0.318 mmol) was added and the reaction stirred at room temperature for 1 hour, then concentrated to dryness. The crude product was purified by prep HPLC. Product containing fractions were filtered through a PHENOMENEX® X-C cartridge (2 g), the cartridge washed with MeOH and the product eluted with 2M NH₃ in MeOH+CH₂Cl₂. Evaporation to dryness gave 22.0 mg 3-(1-methyl-1H-indazol-5-yl)-7-(4-methylpiperazin-1-yl)-9H-carbazole-1-carboxamide ("free base"). The product was suspended in 10 ml MeOH, 50 ul 1.00 N aq. HCl (1.00 equiv.) was added (resulted in complete dissolution) and volatiles evaporated to give 21.3 mg 3-(1-methyl-1H-indazol-5-yl)-7-(4-methylpiperazin-1-yl)-9H-carbazole-1-carboxamide HCl salt. MS (ESI) m/e+=439. HPLC retention time 5.86 min. (Sunfire C18 3.5 μm, 3.0×150 mm column, 15 min gradient, 10-100% B, 0.5 mL/min. Solvent A: 5% CH₃CN—95% H₂O—0.1% TFA; Solvent B: 95% CH₃CN—5% H₂O—0.1% TFA), then isocratic at 100% B. ¹H NMR (CD₃OD) δ ppm 8.45 (d, 1H, J=1.8), 8.17 (d, 1H, J=1.7), 8.12 (b, 1H), 8.11-8.07 (m, 2H), 7.91 (dd, 1H, J=1.5, 8.7), 7.67 (d, 1H, J=8.8), 7.23 (d, 1H, J=2.0), 7.02 (dd, 1H, J=8.7, 2.2), 4.12 (s, 3H), 4.01-3.94 (m, 4H), 3.71-3.64 (m, 4H), 3.02 (s, 3H).

The following compounds in Table 25 have been synthesized utilizing the procedures described for Example 144.

TABLE 25

| Ex. # | Structure | Name | Retention time (min) | MS (ESI) m/z* |
|---|---|---|---|---|
| 415 | 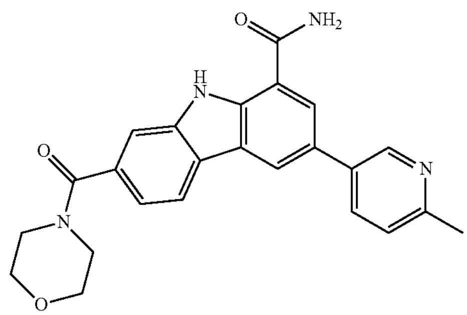 [SMILES: Cc1ccc(-c2cc(C(N)=O)c3[nH]c4cc(C(=O)N5CCOCC5)ccc4c3c2)cn1] | 3-(6-methylpyridin-3-yl)-7-(morpholine-4-carbonyl)-9H-carbazole-1-carboxamide | 1.24(a) | 415.16 |
| 416 | 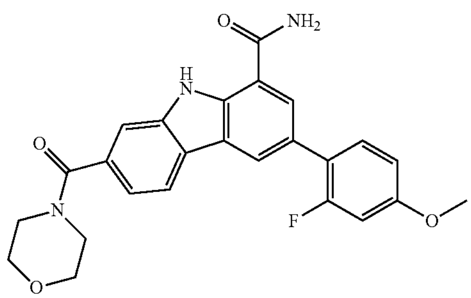 [SMILES: COc1ccc(-c2cc(C(N)=O)c3[nH]c4cc(C(=O)N5CCOCC5)ccc4c3c2)c(F)c1] | 3-(2-fluoro-4-methoxyphenyl)-7-(morpholine-4-carbonyl)-9H-carbazole-1-carboxamide | 1.55(a) | 448.14 |
| 417 | 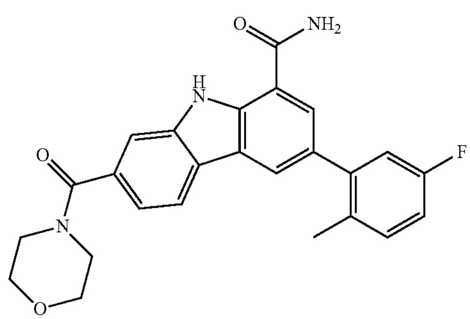 [SMILES: Cc1ccc(F)cc1-c1cc(C(N)=O)c2[nH]c3cc(C(=O)N4CCOCC4)ccc3c2c1] | 3-(5-fluoro-2-methylphenyl)-7-(morpholine-4-carbonyl)-9H-carbazole-1-carboxamide | 1.61(b) | 432.17 |
| 418 | 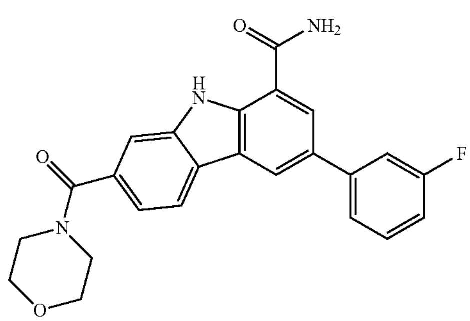 [SMILES: NC(=O)c1cc(-c2cccc(F)c2)cc2c1[nH]c1cc(C(=O)N3CCOCC3)ccc12] | 3-(3-fluorophenyl)-7-(morpholine-4-carbonyl)-9H-carbazole-1-carboxamide | 1.56(b) | 418.18 |

HPLC condition a: XTERRA ® C18 3.0 × 50 mm S7 column, 3 min gradient, 0-100% B, 4 mL/min. Solvent A: 5% $CH_3CN$ – 95% $H_2O$ – 10 mm $NH_4OAc$; Solvent B: 95% $CH_3CN$ – 5% $H_2O$ – 10 mm $NH_4OAc$.

HPLC condition b: Luna C18 3.0 × 50 mm S10 column, 3 min gradient, 0-100% B, 4 mL/min. Solvent A: 5% $CH_3CN$ – 95% $H_2O$ – 10 mm $NH_4OAc$; Solvent B: 95% $CH_3CN$ – 5% $H_2O$ – 10 mm $NH_4OAc$.

EXAMPLE 420

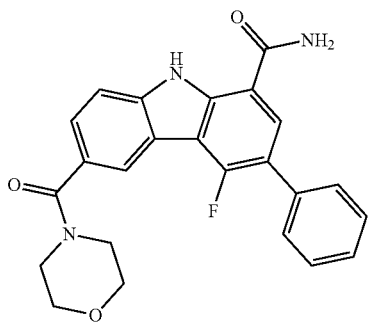 [SMILES: NC(=O)c1cc(-c2ccccc2)c(F)c2c1[nH]c1ccc(C(=O)N3CCOCC3)cc12]

4-Fluoro-6-(morpholine-4-carbonyl)-3-phenyl-9H-carbazole-1-carboxamide

420A. Preparation of 4-fluoro-2-(4-(morpholine-4-carbonyl)phenylamino)benzonitrile

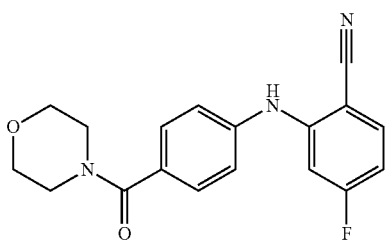 [SMILES: N#Cc1ccc(F)cc1Nc1ccc(C(=O)N2CCOCC2)cc1]

KOtBu (0.968 g, 8.63 mmol) was dissolved into DMSO (3 ml) in a 100 ml round bottom flask. (4-aminophenyl)(morpholino)methanone (1.631 g, 7.91 mmol) in 7 ml of DMSO was added. The mixture was stirred for 15 mins at r.t. 2,4-difluorobenzonitrile (1 g, 7.19 mmol) in 3 ml DMSO was added slowly into the mixture for about 5 mins. The resulting mixture was stirred for 1.5 hrs at r.t. The mixture was diluted with ethyl acetate and extracted with aqueous NH$_4$Cl solution. The organic layer was then washed with water (4×), brine, dried with MgSO$_4$ and concentrated. 2.54 g crude 4-fluoro-2-(4-(morpholine-4-carbonyl)phenylamino)benzonitrile (80% by LC/MS) was obtained. MS (ESI) m/z 326.11 (M+H)$^+$.

420B. Preparation of 4-fluoro-6-(morpholine-4-carbonyl)-9H-carbazole-1-carboxamide

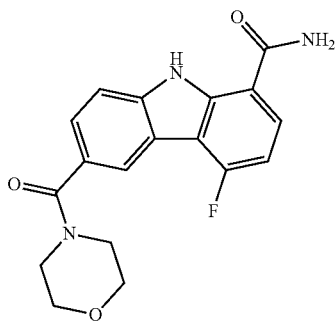 [SMILES: NC(=O)c1ccc(F)c2c1[nH]c1ccc(C(=O)N3CCOCC3)cc12]

4-Fluoro-2-(4-(morpholine-4-carbonyl)phenylamino)benzonitrile (100 mg, 0.246 mmol) was mixed with Pd(OAc)$_2$ (138 mg, 0.615 mmol) in AcOH (7 mL) in a sealed microwave tube. The mixture was heated in microwave at 160° C. for 90 mins. The mixture was filtered and washed with 5 ml AcOH. The filtrate was concentrated and purified using preparative HPLC to give 4-fluoro-6-(morpholine-4-carbonyl)-9H-carbazole-1-carboxamide. MS (ESI) m/z 342.13 (M+H). $^1$H NMR (DMSO-d$_6$) δ ppm 11.87 (s, 1H), 8.19 (s, 1H), 8.11 (s, 1H), 8.03 (dd, 1H, J=8.3, 5.0), 7.83(d, 1H, J=8.6), 7.53 (m, 2H), 7.08(m, 1H), 3.64-3.57 (bm, 8H).

420C. Preparation of 3-bromo-4-fluoro-6-(morpholine-4-carbonyl)-9H-carbazole-1-carboxamide

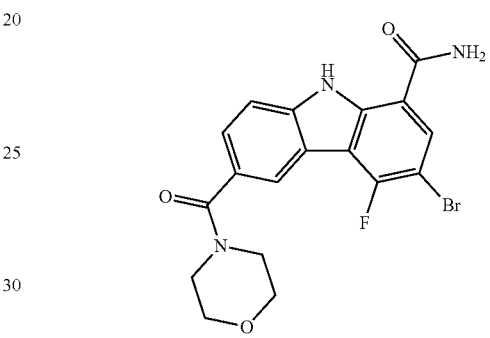

4-Fluoro-6-(morpholine-4-carbonyl)-9H-carbazole-1-carboxamide (9 mg, 0.026 mmol) was mixed with NBS (5.5 mg, 0.031 mmol) in DMF (1.5 mL). The mixture was stirred at 80° C. for 20 mins More NBS (3 mg, 0.017 mmol) was added to the mixture and heated at 80° C. for another 20 mins. The mixture was concentrated and purified using preparative HPLC to give 3-bromo-4-fluoro-6-(morpholine-4-carbonyl)-9H-carbazole-1-carboxamide. MS (ESI) m/z 420 (M+H)$^+$. $^1$H NMR (DMSO-d$_6$) δ ppm 11.72 (s, 1H), 8.32 (d, 1H, J=6.5), 8.28 (bs, 1H), 8.13 (s, 1H), 7.85(d, 1H, J=8.3), 7.64 (bs, 1H), 7.58(dd, 1H, J=8.5, 1.6), 3.7-3.5 (bm, 8H).

420. Preparation of 4-fluoro-6-(morpholine-4-carbonyl)-3-phenyl-9H-carbazole-1-carboxamide 3-Bromo-4-fluoro-6-(morpholine-4-carbonyl)-9H-carbazole-1-carboxamide (25 mg, 0.059 mmol), phenylboronic acid (10.88 mg, 0.089 mmol), Pd(Ph$_3$P)$_4$ (6.87 mg, 5.95 μmol) and Na$_2$CO$_3$(2M) (0.074 mL, 0.149 mmol) were mixed with toluene (2 mL) and MeOH (1 mL) in a sealed microwave tube. The mixture was stirred at 105° C. for 3 hrs. The mixture was filtered through a ACRODISC® PTFE membrane (0.45 um) and purified using preparative HPLC to give 9.7 mg of 4-fluoro-6-(morpholine-4-carbonyl)-3-phenyl-9H-carbazole-1-carboxamide. MS (ESI) m/z 418.06 (M+H)$^+$. $^1$H NMR (DMSO-d$_6$) δ ppm 11.9 (bs, 1H), 8.32 (bs, 1H), 8.19 (d, 1H, J=7.1), 8.15 (s, 1H), 7.84 (d, 1H, J=8.6), 7.72 (d, 2H, J=7.3), 7.62-7.53(m, 4H), 7.43 (t, 1H, J=7.3), 3.7-3.5 (bm, 8H).

EXAMPLE 421

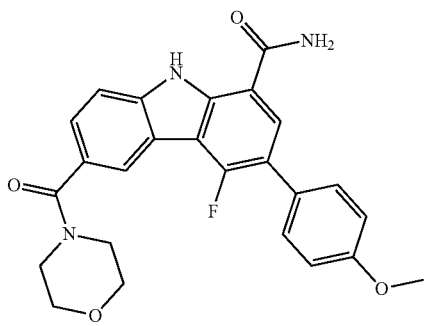 [SMILES: COc1ccc(-c2cc(C(N)=O)c3[nH]c4ccc(C(=O)N5CCOCC5)cc4c3c2F)cc1]

4-Fluoro-3-(4-methoxyphenyl)-6-(morpholine-4-carbonyl)-9H-carbazole-1-carboxamide 3-Bromo-4-fluoro-6-(morpholine-4-carbonyl)-9H-carbazole-1-carboxamide (25 mg, 0.059 mmol), 4-methoxyphenylboronic acid (13.56 mg, 0.089 mmol), Pd(Ph$_3$P)$_4$ (6.87 mg, 5.95 μmol) and Na$_2$CO$_3$(2M) (0.074 mL, 0.149 mmol) were mixed with toluene (2 mL) and MeOH (1 mL) in a sealed microwave tube. The mixture was stirred at 105° C. for 3 hrs. The mixture was filtered through an ACRODISC® PTFE membrane (0.45 um) and purified using preparative HPLC to give 12.2 mg of titled product. MS (ESI) m/z 448.06 (M+H)$^+$. $^1$H NMR (DMSO-d$_6$) δ ppm 11.86 (bs, 1H), 8.31 (bs, 1H), 8.16 (d, 1H, J=9.1), 8.14 (s, 1H), 7.83 (d, 1H, J=8.6), 7.66 (d, 2H, J=8.2), 7.55(m, 2H), 7.11 (d, 2H, J=8.5), 3.84 (s, 3H), 3.7-3.5 (bm, 8H).

EXAMPLE 422

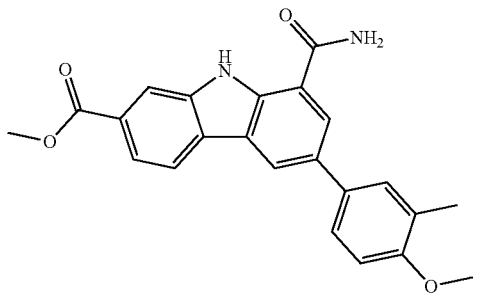

Methyl 8-carbamoyl-6-(4-methoxy-3-methylphenyl)-9H-carbazole-2-carboxylate

Following the procedure described in Example 144, the titled product was isolated as side product from making Example 153. MS (ESI) m/z 387.15 (M–H)$^-$. $^1$H NMR (DMSO-d$_6$) δ ppm 11.69 (s, 1H), 8.68 (s, 1H), 8.41-8.35 (m, 3H), 8.31 (s, 1H), 7.81 (d, 1H, J=8.2), 7.71 (m, 2H), 7.58(bs, 1H), 7.07 (d, 1H, J=8.2), 3.91 (s, 3H), 3.86 (s, 3H), 2.28 (s, 3H).

EXAMPLE 423

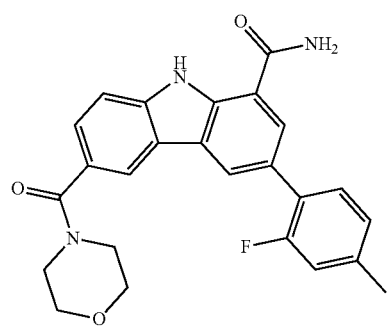 [SMILES: Cc1ccc(-c2cc(C(N)=O)c3[nH]c4ccc(C(=O)N5CCOCC5)cc4c3c2)c(F)c1]

3-(2-Fluoro-4-methylphenyl)-6-(morpholine-4-carbonyl)-9H-carbazole-1-carboxamide 423A. Preparation of 2'-fluoro-4'-methyl-4-(4-(morpholine-4-carbonyl)phenylamino)biphenyl-3-carbonitrile

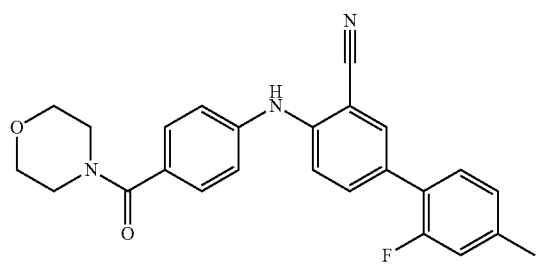 [SMILES: Cc1ccc(-c2ccc(Nc3ccc(C(=O)N4CCOCC4)cc3)c(C#N)c2)c(F)c1]

Following the procedure described in Example 160B, using 2-fluoro-4-methylphenylboronic acid instead of 3,4-dimethylphenylboronic acid. MS (ESI) m/z 416.21 (M+H)$^+$.

423. Preparation of 3-(2-fluoro-4-methylphenyl)-6-(morpholine-4-carbonyl)-9H-carbazole-1-carboxamide Following the procedure described in Example 160. MS (ESI) m/z 432.18 (M+H)$^+$. $^1$H NMR (DMSO-d$_6$) δ ppm 11.66 (s, 1H), 8.55 (s, 1H), 8.33 (s, 1H), 8.28 (s, 1H), 8.14 (s, 1H), 7.78(d, 1H, J=8.6), 7.6-7.55 (m, 2H), 7.49(d, 1H, J=8.5), 7.18(m, 2H), 3.7-3.5 (bm, 8H), 2.4 (s, 3H).

EXAMPLE 424

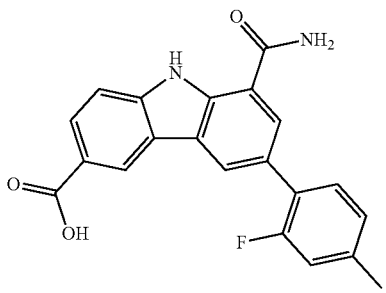 [SMILES: Cc1ccc(-c2cc(C(N)=O)c3[nH]c4ccc(C(=O)O)cc4c3c2)c(F)c1]

8-Carbamoyl-6-(2-fluoro-4-methylphenyl)-9H-carbazole-3-carboxylic acid

424. Preparation of 8-carbamoyl-6-(2-fluoro-4-methylphenyl)-9H-carbazole-3-carboxylic acid This title product was isolated as a side product from making Example 423. MS (ESI) m/z 361.19 (M−H)⁻. ¹H NMR (MeOD-d4) δ ppm 8.86 (s, 1H), 8.50 (s, 1H), 8.17 (dd, 1H, J=8.6, 1.8), 8.13 (s, 1H), 7.67(d, 1H, J=8.5), 7.56 (m, 1H), 7.09-7.17(m, 2H), 2.45 (s, 3H).

EXAMPLE 425

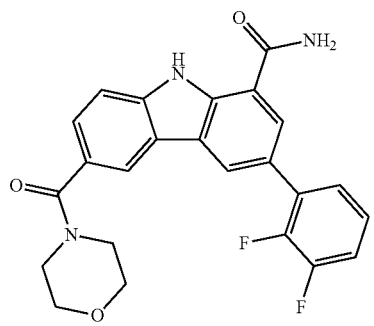 [SMILES: NC(=O)c1cc(-c2cccc(F)c2F)cc2c1[nH]c1ccc(C(=O)N3CCOCC3)cc12]

3-(2,3-Difluorophenyl)-6-(morpholine-4-carbonyl)-9H-carbazole-1-carboxamide

425A. Preparation of 2',3'-difluoro-4-(4-(morpholine-4-carbonyl)phenylamino)biphenyl-3-carbonitrile

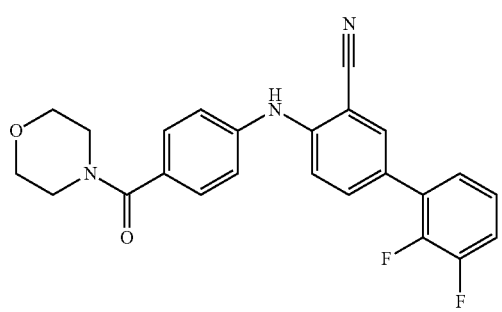 [SMILES: N#Cc1cc(-c2cccc(F)c2F)ccc1Nc1ccc(C(=O)N2CCOCC2)cc1]

Following the procedure described in Example 160B, using 2,3-difluorophenylboronic acid instead of 3,4-dimethylphenylboronic acid. MS (ESI) m/z 420.14 (M+H)⁺.

425. Preparation of 3-(2,3-difluorophenyl)-6-(morpholine-4-carbonyl)-9H-carbazole-1-carboxamide Following the procedure described in Example 160. MS (ESI) m/z 436.16 (M+H)⁺. ¹H NMR (DMSO-d₆) δ ppm 11.73 (s, 1H), 8.65 (s, 1H), 8.36 (s, 1H), 8.30 (s, 1H), 8.20 (s, 1H), 7.80(d, 1H, J=8.2), 7.6 (s, 1H), 7.56-7.35(m, 4H), 3.7-3.5 (bm, 8 H).

EXAMPLE 426

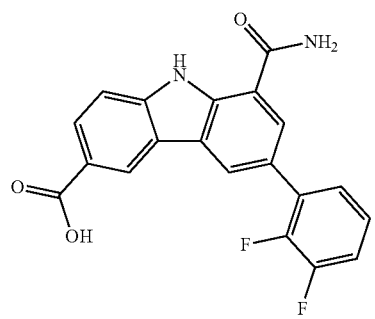 [SMILES: NC(=O)c1cc(-c2cccc(F)c2F)cc2c1[nH]c1ccc(C(=O)O)cc12]

8-Carbamoyl-6-(2,3-difluorophenyl)-9H-carbazole-3-carboxylic acid

426. Preparation of 8-carbamoyl-6-(2,3-difluorophenyl)-9H-carbazole-3-carboxylic acid This title product was isolated as a side product from making Example 425. MS (ESI) m/z 365.12 (M−H)⁻. ¹H NMR (MeOD-d4) δ ppm 8.88 (s, 1H), 8.55 (s, 1H), 8.19-8.17 (m, 2H), 7.68(d, 1H, J=8.6), 7.51-7.47 (m, 1H), 7.32-7.29(m, 2H).

EXAMPLE 427

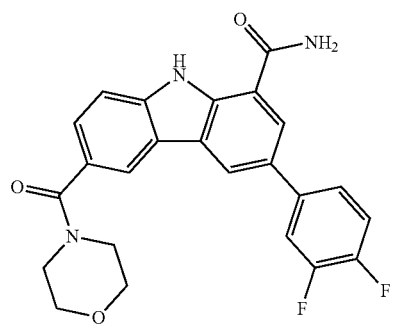 [SMILES: NC(=O)c1cc(-c2ccc(F)c(F)c2)cc2c1[nH]c1ccc(C(=O)N3CCOCC3)cc12]

3-(3,4-Difluorophenyl)-6-(morpholine-4-carbonyl)-9H-carbazole-1-carboxamide

427A. Preparation of 3',4'-difluoro-4-(4-(morpholine-4-carbonyl)phenylamino)biphenyl-3-carbonitrile

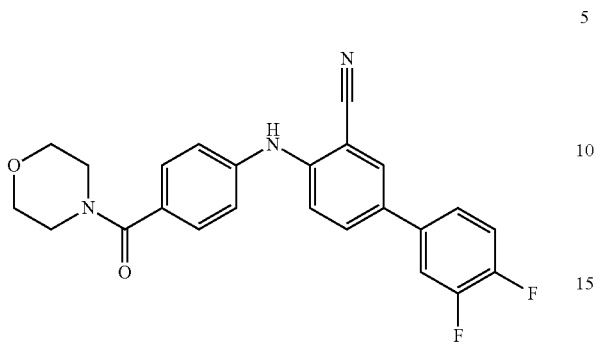

Following the procedure described in Example 160B, using 3,4-difluorophenylboronic acid instead of 3,4-dimethylphenylboronic acid. MS (ESI) m/z 420.15 (M+H)+.

427. Preparation of 3-(3,4-difluorophenyl)-6-(morpholine-4-carbonyl)-9H-carbazole-1-carboxamide Following the procedure described in Example 160. MS (ESI) m/z 436.14 (M+H)+. $^1$H NMR (DMSO-$d_6$) δ ppm 11.66 (s, 1H), 8.84 (s, 1H), 8.38 (s, 2H), 8.34 (s, 1H), 8.06-8.01 (m, 1H), 7.81-7.77(m, 2H), 7.62-7.57(m, 2H), 7.5(d, 1H, J=8.6), 3.7-3.5 (bm, 8H).

EXAMPLE 427

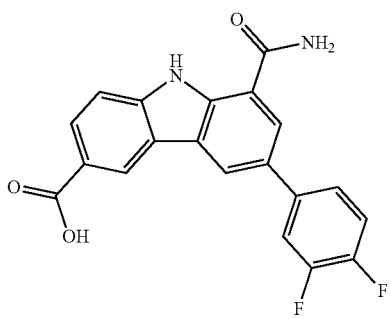 [SMILES: NC(=O)c1cc(-c2ccc(F)c(F)c2)cc2c1[nH]c1ccc(C(=O)O)cc12]

8-Carbamoyl-6-(3,4-difluorophenyl)-9H-carbazole-3-carboxylic acid

428. Preparation of 8-carbamoyl-6-(3,4-difluorophenyl)-9H-carbazole-3-carboxylic acid This title product was isolated as a side product from making Example 427. MS (ESI) m/z 365.14 (M–H)−. $^1$H NMR (MeOD-d4) δ ppm 8.89 (s, 1H), 8.64 (s, 1H), 8.22 (s, 1H), 8.17 (dd, 1H, J=8.5, 1.8), 7.82-7.77(m, 1H), 7.67-7.64 (m, 2H), 7.43-7.38(m, 1H).

EXAMPLE 429

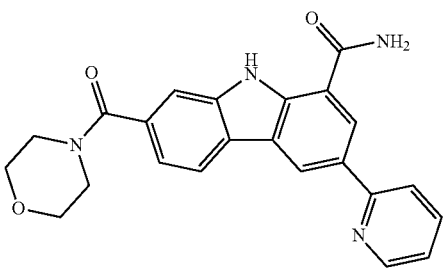 [SMILES: NC(=O)c1cc(-c2ccccn2)cc2c1[nH]c1cc(C(=O)N3CCOCC3)ccc12]

7-(Morpholine-4-carbonyl)-3-(pyridin-2-yl)-9H-carbazole-1-carboxamide

429A. Preparation of 7-(morpholine-4-carbonyl)-3-(4,4,5,5-tetramethyl-1,3,2-dioxaborolan-2-yl)-9H-carbazole-1-carboxamide

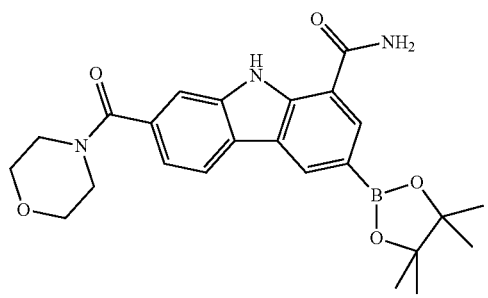 [SMILES: CC1(C)OB(c2cc(C(N)=O)c3[nH]c4cc(C(=O)N5CCOCC5)ccc4c3c2)OC1(C)C]

3-Bromo-7-(morpholine-4-carbonyl)-9H-carbazole-1-carboxamide 144A (250 mg, 0.559 mmol), 4,4,4',4',5,5,5',5'-octamethyl-2,2'-bi(1,3,2-dioxaborolane) (568 mg, 2.237 mmol), PdCl$_2$(dppf)-CH$_2$Cl$_2$ adduct (91 mg, 0.112 mmol) and potassium acetate (274 mg, 2.80 mmol) were mixed with Dioxane (7 mL) in a sealed microwave tube. The mixture was degassed and filled with N2, then stirred in an oil bath at 100° C. for 10 hrs. The mixture was filtered through CELITE®, rinsed with MeOH and concentrated. 300 ml of water was added and the mixture was extracted with CH$_2$Cl$_2$. The organic layer was dried over MgSO$_4$ and filtered and concentrated. The crude product was used as it is. MS (ESI) m/z 450.12 (M+H)+.

429. Preparation of 7-(morpholine-4-carbonyl)-3-(pyridin-2-yl)-9H-carbazole-1-carboxamide 2-Bromopyridine (0.1 mL, 1.025 mmol), 7-(morpholine-4-carbonyl)-3-(4,4,5,5-tetramethyl-1,3,2-dioxaborolan-2-yl)-9H-carbazole-1-carboxamide 429A (140 mg, 0.125 mmol), Pd(Ph$_3$P)$_4$ (76 mg, 0.066 mmol) and Na$_2$CO$_3$ (2M) (0.8 mL, 1.600 mmol) were mixed with toluene (2 mL) and MeOH (1 mL) in a sealed microwave tube. The mixture was degassed and heated at 100° C. for 12 hrs. The mixture was concentrated and purified using preparative HPLC to give titled product. MS (ESI) m/z 401.16 (M+H)+. $^1$H NMR (DMSO-$d_6$) δ ppm 11.66 (s, 1H), 9.13 (d, 1H, J=1.5), 8.73 (d, 1H, J=4.8), 8.71 (d, 1H, J=1.5), 8.40 (s, 1H), 8.33 (d, 1H, J=8.0), 8.21 (d, 1H, J=8.0), 7.95 (td, 1H, J=7.8, 1.8), 7.83 (s, 1H), 7.57 (s, 1H), 7.37 (m, 1H), 7.27(dd, 1H, J=8.1, 1.5), 3.7-3.5 (bm, 8 H).

EXAMPLE 430

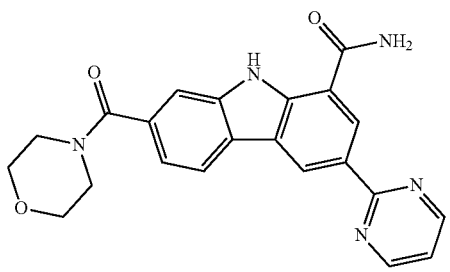 [SMILES: NC(=O)c1cc(-c2ncccn2)cc2c1[nH]c1cc(C(=O)N3CCOCC3)ccc12]

7-(Morpholine-4-carbonyl)-3-(pyrimidin-2-yl)-9H-carbazole-1-carboxamide

2-Bromopyrimidine (250 g, 1.572 mmol), 7-(morpholine-4-carbonyl)-3-(4,4,5,5-tetramethyl-1,3,2-dioxaborolan-2-yl)-9H-carbazole-1-carboxamide 429A (140 mg, 0.125 mmol), Pd(Ph$_3$P)$_4$ (76 mg, 0.066 mmol) and Na$_2$CO$_3$ (2M) (0.8 mL, 1.600 mmol) were mixed with toluene (2 mL) and MeOH (1 mL) in a sealed microwave tube. The mixture was degassed and heated at 100° C. for 12 hrs. The mixture was concentrated and purified using preparative HPLC to give titled product. MS (ESI) m/z 402.16 (M+H)$^+$. $^1$H NMR (DMSO-d$_6$) δ ppm 11.76 (s, 1H), 9.35 (s, 1H), 9.01 (d, 1H, J=1.5), 8.95 (d, 2H, J=4.9), 8.43 (s, 1H), 8.34 (d, 1H, J=7.9), 7.82 (s, 1H), 7.58 (s, 1H), 7.45 (t, 1H, J=4.7), 7.26(dd, 1H, J=8.0, 1.5), 3.7-3.5 (bm, 8 H).

EXAMPLE 431

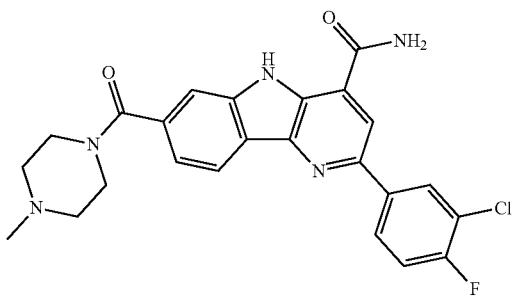 [SMILES: CN1CCN(C(=O)c2ccc3c(c2)[nH]c2c(C(N)=O)cc(-c4ccc(F)c(Cl)c4)nc23)CC1]

2-(3-Chloro-4-fluorophenyl)-7-(4-methylpiperazine-1-carbonyl)-5H-pyrido[3,2-b]indole-4-carboxamide 431A. Preparation of 7-isopropyl 4-methyl 2-(3-chloro-4-fluorophenyl)-5H-pyrido[3,2-b]indole-4,7-dicarboxylate

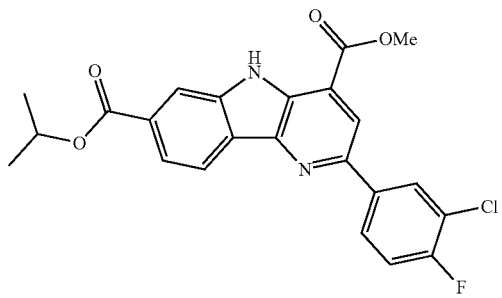 [SMILES: COC(=O)c1cc(-c2ccc(F)c(Cl)c2)nc2c1[nH]c1cc(C(=O)OC(C)C)ccc12]

Following the procedure described in Example 288D. MS (ESI) m/z 441.17 (M+H)$^+$. $^1$H NMR (500 MHz, chloroform-d) δ ppm 9.71 (s, 1H,), 8.50 (d, 1H, J=8.3), 8.31 (m, 3H), 8.09 (m, 2H), 7.31 (t, 1H, J=8.5), 5.36 (m, 1H), 4.15 (s, 3H), 1.46 (d, 6H, J=6.1).

431B. Preparation of 2-(3-chloro-4-fluorophenyl)-7-(isopropoxycarbonyl)-5H-pyrido[3,2-b]indole-4-carboxylic acid

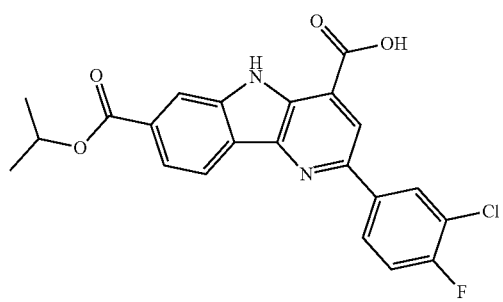 [SMILES: CC(C)OC(=O)c1ccc2c(c1)[nH]c1c(C(=O)O)cc(-c3ccc(F)c(Cl)c3)nc12]

Following the procedure described in Example 288E. MS (ESI) m/z 426.93 (M+H)$^+$.

431C. Preparation of isopropyl 4-carbamoyl-2-(3-chloro-4-fluorophenyl)-5H-pyrido[3,2-b]indole-7-carboxylate

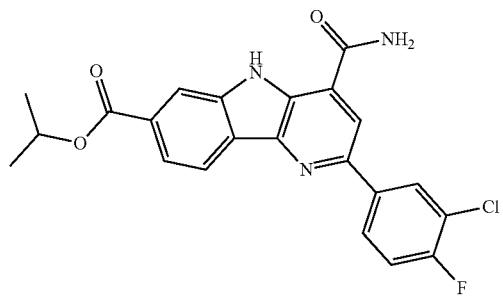

Following the procedure described in Example 288F. MS (ESI) m/z 426.23 (M+H)$^+$.

431D. Preparation of 4-carbamoyl-2-(3-chloro-4-fluorophenyl)-5H-pyrido[3,2-b]indole-7-carboxylic acid

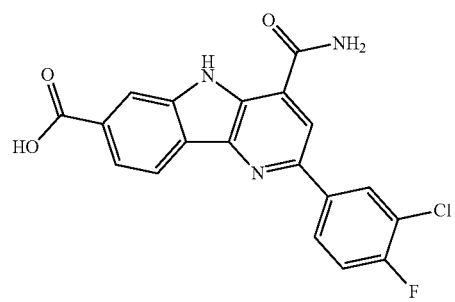 [SMILES: NC(=O)c1cc(-c2ccc(F)c(Cl)c2)nc2c1[nH]c1cc(C(=O)O)ccc12]

Following the procedure described in Example 288G. MS (ESI) m/z 384.13 (M+H)$^+$. $^1$H NMR (DMSO-d$_6$) δ ppm 11.94

(s, 1H), 8.64 (s, 1H), 8.56 (s, 1H), 8.51 (dd, 1H, J=7.4, 2.1), 8.42 (s, 1H), 8.37 (m, 2H), 8.00 (s, 1H), 7.88 (dd, 1H, J=8.2, 1.2), 7.63 (t, 1H, J=8.9).

431. Preparation of 2-(3-chloro-4-fluorophenyl)-7-(4-methylpiperazine-1-carbonyl)-5H-pyrido[3,2-b]indole-4-carboxamide A mixture of 4-carbamoyl-2-(3-chloro-4-fluorophenyl)-5H-pyrido[3,2-b]indole-7-carboxylic acid 431D (55 mg, 0.143 mmol), 1-methylpiperazine (0.032 mL, 0.287 mmol), N,N-diisopropylethylamine (0.075 mL, 0.430 mmol) and HATU (109 mg, 0.287 mmol) in DMF (1 mL) was stirred for overnight. The mixture was concentrated and purified using preparative HPLC to give titled product. MS (ESI) m/z 466.16 (M+H)+. 1H NMR (DMSO-d6) δ ppm 11.82 (s, 1H), 8.62 (s, 1H), 8.53 (s, 1H), 8.50 (dd, 1H, J=7.1, 2.1), 8.34 (m, 2H), 7.99 (s, 1H), 7.79 (s, 1H), 7.62 (t, 1H, J=8.8), 7.28(d, 1H, J=8.0), 3.67 (bs, 4H), 2.37 (bs, 4H), 2.22 (s, 3H).

The following compounds in Table 26 have been synthesized utilizing the procedures described for Example 431

TABLE 26

| Ex. # | Structure | Name | Retention time (min) | MS (ESI) m/z* |
|---|---|---|---|---|
| 432 | 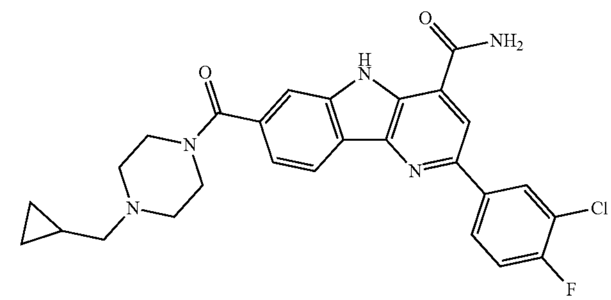 [SMILES: NC(=O)c1cc(-c2ccc(F)c(Cl)c2)nc2c1[nH]c1cc(C(=O)N3CCN(CC4CC4)CC3)ccc12] | 2-(3-chloro-4-fluorophenyl)-7-(4-(cyclopropylmethyl)piperazine-1-carbonyl)-5H-pyrido[3,2-b]indole-4-carboxamide | 1.895(a) | 506.23 |
| 433 | 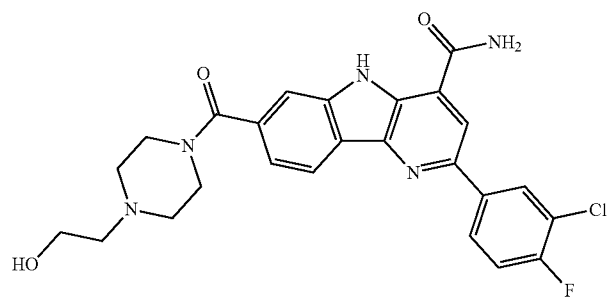 [SMILES: NC(=O)c1cc(-c2ccc(F)c(Cl)c2)nc2c1[nH]c1cc(C(=O)N3CCN(CCO)CC3)ccc12] | 2-(3-chloro-4-fluorophenyl)-7-(4-(2-hydroxyethyl)piperazine-1-carbonyl)-5H-pyrido[3,2-b]indole-4-carboxamide | 1.627(a) | 496.25 |
| 434 | 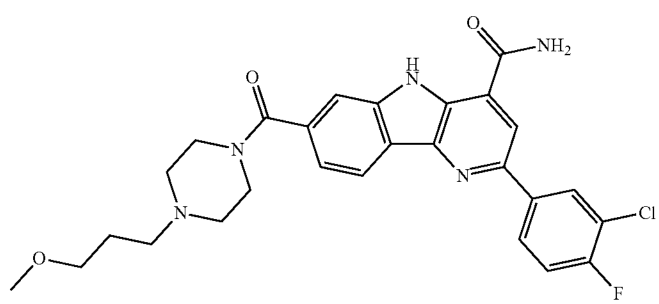 [SMILES: COCCCN1CCN(C(=O)c2ccc3c(c2)[nH]c2c(C(N)=O)cc(-c4ccc(F)c(Cl)c4)nc23)CC1] | 2-(3-chloro-4-fluorophenyl)-7-(4-(3-methoxypropyl)piperazine-1-carbonyl)-5H-pyrido[3,2-b]indole-4-carboxamide | 1.807(a) | 524.24 |
| 435 | 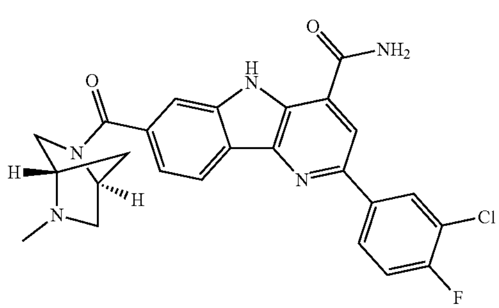 [SMILES: CN1C[C@@H]2C[C@H]1CN2C(=O)c1ccc2c(c1)[nH]c1c(C(N)=O)cc(-c3ccc(F)c(Cl)c3)nc12] | 2-(3-chloro-4-fluorophenyl)-7-((1S,4S)-5-methyl-2,5-diazabicyclo[2.2.1]heptane-2-carbonyl)-5H-pyrido[3,2-b]indole-4-carboxamide | 1.790(a) | 478.24 |

TABLE 26-continued

| Ex. # | Structure | Name | Retention time (min) | MS (ESI) m/z* |
|---|---|---|---|---|
| 436 | 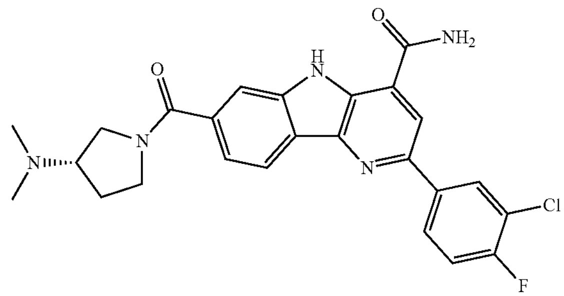 [SMILES: CN(C)[C@H]1CCN(C(=O)c2ccc3c(c2)[nH]c2c(C(N)=O)cc(-c4ccc(F)c(Cl)c4)nc23)C1] | (S)-2-(3-chloro-4-fluorophenyl)-7-(3-(dimethyl-amino)pyrrolidine-1-carbonyl)-5H-pyrido[3,2-b]indole-4-carboxamide | 1.813(a) | 480.19 |
| 437 | 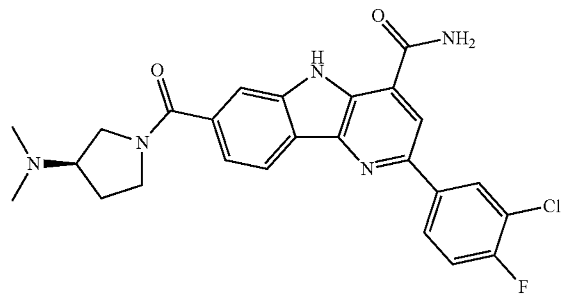 [SMILES: CN(C)[C@@H]1CCN(C(=O)c2ccc3c(c2)[nH]c2c(C(N)=O)cc(-c4ccc(F)c(Cl)c4)nc23)C1] | (R)-2-(3-chloro-4-fluorophenyl)-7-(3-(dimethyl-amino)pyrrolidine-1-carbonyl)-5H-pyrido[3,2-b]indole-4-carboxamide | 1.817(a) | 480.19 |
| 438 | 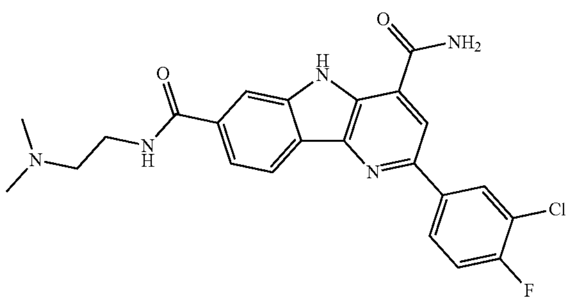 [SMILES: CN(C)CCNC(=O)c1ccc2c(c1)[nH]c1c(C(N)=O)cc(-c3ccc(F)c(Cl)c3)nc12] | 2-(3-chloro-4-fluorophenyl)-N$^7$-(2-(dimethylamino)ethyl)-5H-pyrido[3,2-b]indole-4,7-dicarboxamide | 1.853(a) | 454.16 |
| 439 | 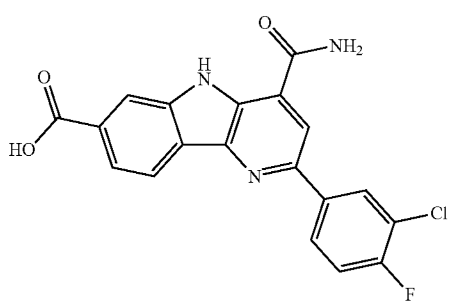 [SMILES: NC(=O)c1cc(-c2ccc(F)c(Cl)c2)nc2c1[nH]c1cc(C(=O)O)ccc12] | 4-carbamoyl-2-(3-chloro-4-fluorophenyl)-5H-pyrido[3,2-b]indole-7-carboxylic acid | 1.520(a) | 384.13 |
| 440 | 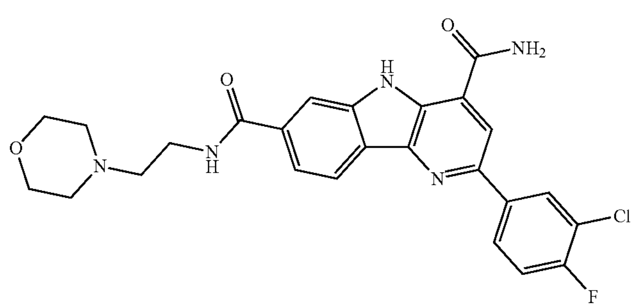 [SMILES: NC(=O)c1cc(-c2ccc(F)c(Cl)c2)nc2c1[nH]c1cc(C(=O)NCCN3CCOCC3)ccc12] | 2-(3-chloro-4-fluorophenyl)-N$^7$-(2-morpholinoethyl)-5H-pyrido[3,2-b]indole-4,7-dicarboxamide | 1.75(a) | 496.18 |

TABLE 26-continued

| Ex. # | Structure | Name | Retention time (min) | MS (ESI) m/z* |
|---|---|---|---|---|
| 441 | 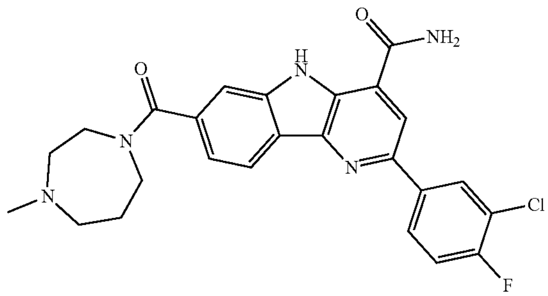 [SMILES: CN1CCCN(C(=O)c2ccc3c(c2)[nH]c2c(C(N)=O)cc(-c4ccc(F)c(Cl)c4)nc23)CC1] | 2-(3-chloro-4-fluorophenyl)-7-(4-methyl-1,4-diazepane-1-carbonyl)-5H-pyrido[3,2-b]indole-4-carboxamide | 1.793(a) | 480.19 |
| 442 | 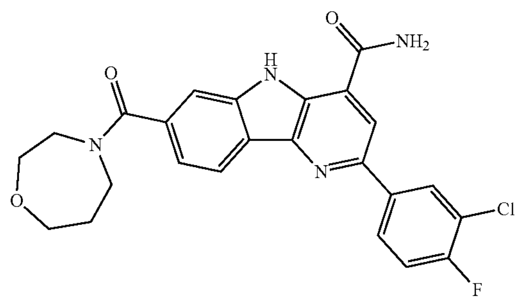 [SMILES: NC(=O)c1cc(-c2ccc(F)c(Cl)c2)nc2c1[nH]c1cc(C(=O)N3CCCOCC3)ccc12] | 2-(3-chloro-4-fluorophenyl)-7-(1,4-oxazepane-4-carbonyl)-5H-pyrido[3,2-b]indole-4-carboxamide | 1.827(a) | 467.14 |
| 443 | 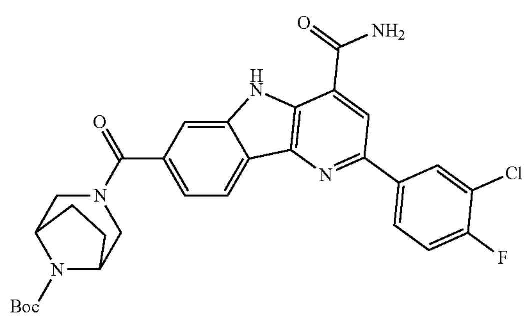 [SMILES: CC(C)(C)OC(=O)N1C2CCC1CN(C(=O)c1ccc3c(c1)[nH]c1c(C(N)=O)cc(-c4ccc(F)c(Cl)c4)nc13)C2] | tert-butyl 3-(4-carbamoyl-2-(3-chloro-4-fluorophenyl)-5H-pyrido[3,2-b]indole-7-carbonyl)-3,8-diazabicyclo[3.2.1]octane-8-carboxylate | 2.310(a) | 578.34 |
| 444 | 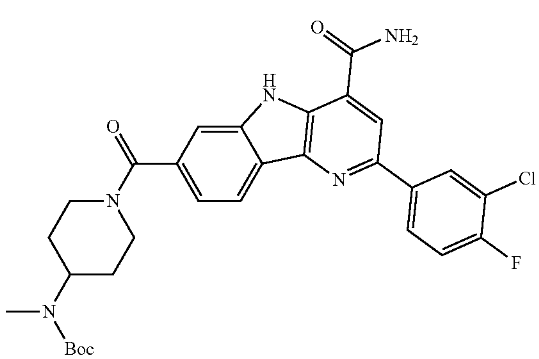 [SMILES: CN(C(=O)OC(C)(C)C)C1CCN(C(=O)c2ccc3c(c2)[nH]c2c(C(N)=O)cc(-c4ccc(F)c(Cl)c4)nc23)CC1] | tert-butyl 1-(4-carbamoyl-2-(3-chloro-4-fluorophenyl)-5H-pyrido[3,2-b]indole-7-carbonyl)piperidin-4-yl(methyl)carbamate | 2.355(a) | 580.37 |

TABLE 26-continued

| Ex. # | Structure | Name | Retention time (min) | MS (ESI) m/z* |
|---|---|---|---|---|
| 445 | 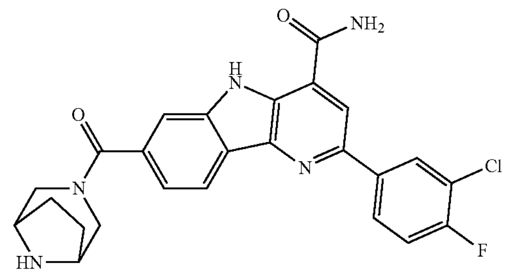 [SMILES: NC(=O)c1cc(-c2ccc(F)c(Cl)c2)nc2c1[nH]c1cc(C(=O)N3CC4CCC(C3)N4)ccc12] | 7-(3,8-diazabicyclo[3.2.1]octane-3-carbonyl)-2-(3-chloro-4-fluorophenyl)-5H-pyrido[3,2-b]indole-4-carboxamide | 1.847(a) | 478.17 |

HPLC condition a: XTERRA ® C18 3.0 × 50 mm S7 column, 3 min gradient, 0-100% B, 4 mL/min. Solvent A: 5% CH$_3$CN – 95% H$_2$O – 10 mm NH$_4$OAc; Solvent B: 95% CH$_3$CN – 5% H$_2$O – 10 mm NH$_4$OAc.

EXAMPLE 446

8-(Morpholine-4-carbonyl)-2-phenyl-5H-pyrido[3,2-b]indole-4-carboxamide

446A. Preparation of methyl 3-amino-6-bromo-2-(3-(morpholine-4-carbonyl)phenyl)isonicotinate

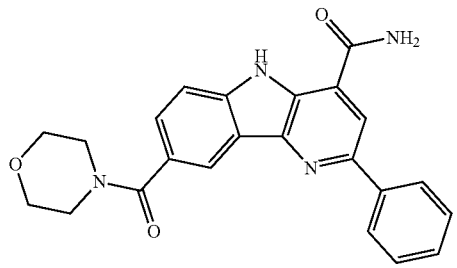 [SMILES: NC(=O)c1cc(-c2ccccc2)nc2c1[nH]c1ccc(C(=O)N3CCOCC3)cc12]

Following the procedure described in Example 212C. MS (ESI) m/z 420.03 (M+H)$^+$.

446B. Preparation of methyl 3-azido-6-bromo-2-(3-(morpholine-4-carbonyl)phenyl)isonicotinate

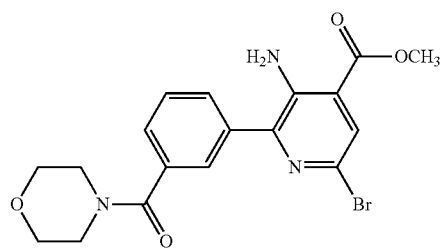 [SMILES: COC(=O)c1cc(Br)nc(-c2cccc(C(=O)N3CCOCC3)c2)c1N]

Following the procedure described in Example 212D. MS (ESI) m/z 446.03 (M+H)$^+$.

446C. Preparation of methyl 2-bromo-8-(morpholine-4-carbonyl)-5H-pyrido[3,2-b]indole-4-carboxylate

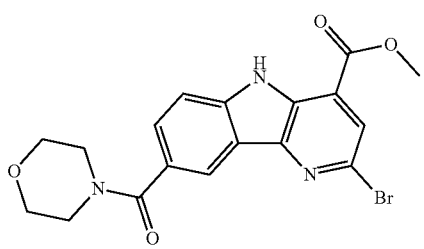 [SMILES: COC(=O)c1cc(Br)nc2c1[nH]c1ccc(C(=O)N3CCOCC3)cc12]

Following the procedure described in Example 212E. MS (ESI) m/z 418 (M+H)$^+$. $^1$H NMR (DMSO-d$_6$) δ ppm 12.03 (s, 1H), 8.23 (s, 1H), 7.97 (s, 1H), 7.82(d, 1H, J=8.6), 7.69(d, 1H, J=8.5), 4.05 (s, 3H), 3.7-3.5 (bm, 8H).

446D. Preparation of 2-bromo-8-(morpholine-4-carbonyl)-5H-pyrido[3,2-b]indole-4-carboxamide

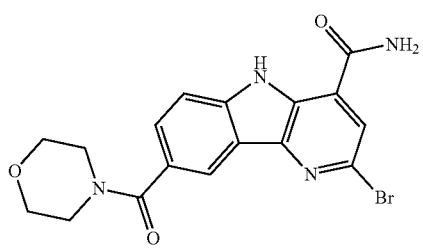 [SMILES: NC(=O)c1cc(Br)nc2c1[nH]c1ccc(C(=O)N3CCOCC3)cc12]

Methyl 2-bromo-8-(morpholine-4-carbonyl)-5H-pyrido[3,2-b]indole-4-carboxylate (220 mg, 0.526 mmol) was mixed with NH$_3$/MeOH(7N) (18 mL, 126 mmol) in a sealed microwave vial. The mixture was heated at 105° C. for 2.5 hrs in microwave. The mixture was concentrated to give 205 mg crude product. MS (ESI) m/z 402.95 (M+H)$^+$.

446. Preparation of 8-(morpholine-4-carbonyl)-2-phenyl-5H-pyrido[3,2-b]indole-4-carboxamide 2-Bromo-8-(morpholine-4-carbonyl)-5H-pyrido[3,2-b]indole-4-carboxamide (100 mg, 0.248 mmol), phenylboronic acid (60.5 mg, 0.496 mmol), potassium phosphate tribasic (168 mg, 0.794 mmol), 2-Dicyclohexylphosphino-2',4',6'-triisopropylbiphenyl (23.64 mg, 0.050 mmol) and palladium(II) acetate (5.57 mg, 0.025 mmol) were mixed with THF (4 mL) in a sealed microwave tube. The mixture was heated in microwave at 85° C. for 3 hrs. The mixture was concentrated and purified using preparative HPLC to give titled product. MS (ESI) m/z 401.2 (M+H)+. $^1$H NMR (DMSO-d$_6$) δ ppm 11.8 (s, 1H), 8.65 (s, 1H), 8.5 (s, 1H), 8.32 (m, 3H), 7.94 (s, 1H), 7.81(d, 1H, J=8.2), 7.60(m, 3H), 7.44 (t, 1H, J=7), 3.7-3.5 (bm, 8H).

EXAMPLE 447

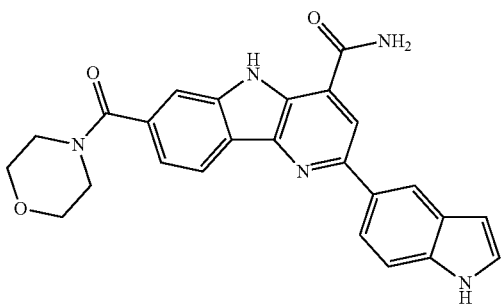 [SMILES: NC(=O)c1cc(-c2ccc3[nH]ccc3c2)nc2c1[nH]c1cc(C(=O)N3CCOCC3)ccc12]

2-(1H-Indol-5-yl)-7-(morpholine-4-carbonyl)-5H-pyrido[3,2-b]indole-4-carboxamide 2-Bromo-7-(morpholine-4-carbonyl)-5H-pyrido[3,2-b]indole-4-carboxamide (60 mg, 0.149 mmol), 5-(4,4,5,5-tetramethyl-1,3,2-dioxaborolan-2-yl)-1H-indole (72.3 mg, 0.298 mmol), Potassium phosphate tribasic (134 mg, 0.476 mmol), 2-dicyclohexylphosphino-2',6'-dimethoxy-1,1'-biphenyl (24.43 mg, 0.060 mmol) and Pd(OAc)$_2$ (6.68 mg, 0.030 mmol) were mixed with THF (2 mL) in a sealed microwave vial. The mixture was flushed with N2 and heated at 85° C. in an oil bath for 3.5 hr. LC/MS showed there was trace amount of product formed. The reaction mixture was blown to dryness under N2 blower. To the mixture was added Pd(Ph$_3$P)$_4$ (34.4 mg, 0.030 mmol), Toluene (3 mL), MeOH (1.5 mL) and Na$_2$CO$_3$ (2M) (0.149 mL, 0.298 mmol). The mixture was then heated at 100° C. for 3 hrs. The mixture was concentrated and purified using preparative HPLC to give titled product. MS (ESI) m/z 440.3 (M+H)+. $^1$H NMR (DMSO-d$_6$) δ ppm 11.65 (s, 1H), 11.20 (s, 1H), 8.67 (s, 1H), 8.5 (m, 2H), 8.32 (d, 1H, J=8.2), 8.12 (d, 1H, J=8.5), 7.9 (s, 1H), 7.8 (s, 1H), 7.53(d, 1H, J=8.0), 7.41(m, 1H), 7.30 (d, 1H, J=8.0), 6.57 (s, 1H), 3.66 (bs, 8H).

The following compounds in Table 27 have been synthesized utilizing the procedures described for Example 447

TABLE 27

| Ex. # | Structure | Name | Retention time (min) | MS (ESI) m/z* |
|---|---|---|---|---|
| 448 | 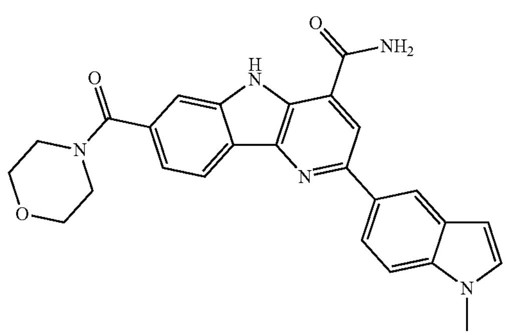 [SMILES: Cn1ccc2cc(-c3cc(C(N)=O)c4[nH]c5cc(C(=O)N6CCOCC6)ccc5c4n3)ccc21] | 2-(1-methyl-1H-indol-5-yl)-7-(morpholine-4-carbonyl)-5H-pyrido[3,2-b]indole-4-carboxamide | 1.307(b) | 454.3 |
| 449 | 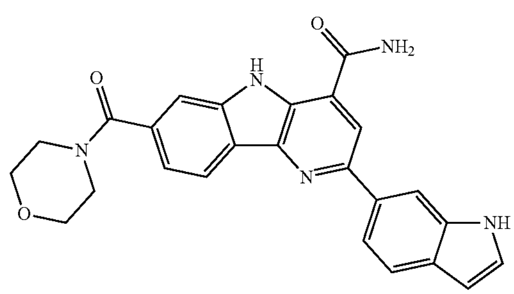 [SMILES: NC(=O)c1cc(-c2ccc3cc[nH]c3c2)nc2c1[nH]c1cc(C(=O)N3CCOCC3)ccc12] | 2-(1H-indol-6-yl)-7-(morpholine-4-carbonyl)-5H-pyrido[3,2-b]indole-4-carboxamide | 1.977(a) | 440.14 |

TABLE 27-continued

| Ex. # | Structure | Name | Retention time (min) | MS (ESI) m/z* |
|---|---|---|---|---|
| 450 | 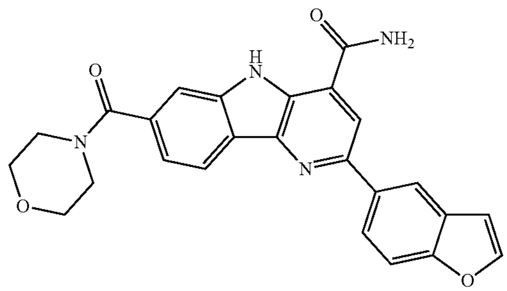 [SMILES: NC(=O)c1cc(-c2ccc3occc3c2)nc2c1[nH]c1cc(C(=O)N3CCOCC3)ccc12] | 2-(benzofuran-5-yl)-7-(morpholine-4-carbonyl)-5H-pyrido[3,2-b]indole-4-carboxamide | 2.148(a) | 441.12 |
| 451 | 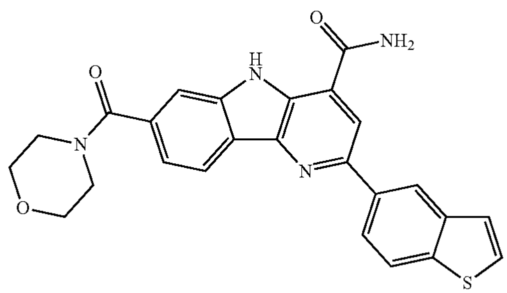 [SMILES: NC(=O)c1cc(-c2ccc3sccc3c2)nc2c1[nH]c1cc(C(=O)N3CCOCC3)ccc12] | 2-(benzo[b]thiophen-5-yl)-7-(morpholine-4-carbonyl)-5H-pyrido[3,2-b]indole-4-carboxamide | 2.315(a) | 457.03 |
| 452 | 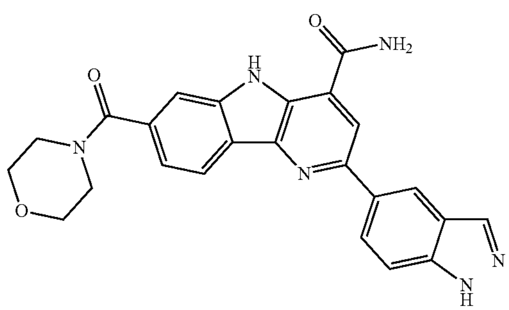 [SMILES: N=Cc1cc(-c2cc(C(N)=O)c3[nH]c4cc(C(=O)N5CCOCC5)ccc4c3n2)ccc1N] | 2-(1H-indazol-5-yl)-7-(morpholine-4-carbonyl)-5H-pyrido[3,2-b]indole-4-carboxamide | 1.767(a) | 441.12 |
| 453 | 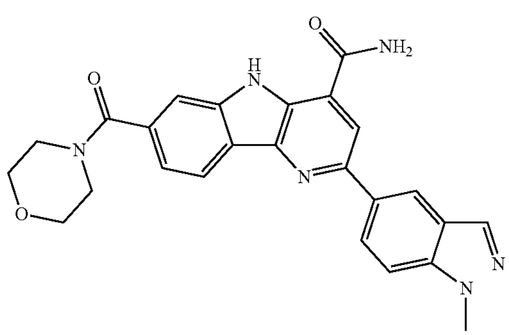 [SMILES: CNc1ccc(-c2cc(C(N)=O)c3[nH]c4cc(C(=O)N5CCOCC5)ccc4c3n2)cc1C=N] | 2-(1-methyl-1H-indazol-5-yl)-7-(morpholine-4-carbonyl)-5H-pyrido[3,2-b]indole-4-carboxamide | 1.513(c) | 455.1 |
| 454 | 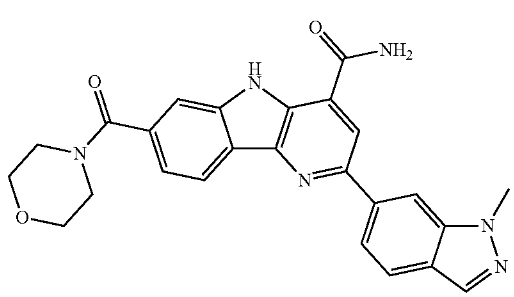 [SMILES: Cn1ncc2ccc(-c3cc(C(N)=O)c4[nH]c5cc(C(=O)N6CCOCC6)ccc5c4n3)cc21] | 2-(1-methyl-1H-indazol-6-yl)-7-(morpholine-4-carbonyl)-5H-pyrido[3,2-b]indole-4-carboxamide | 2.002(a) | 455.15 |

TABLE 27-continued

| Ex. # | Structure | Name | Retention time (min) | MS (ESI) m/z* |
|---|---|---|---|---|
| 455 | 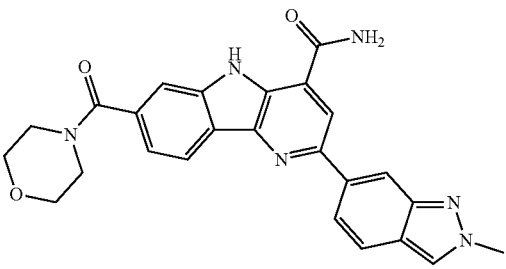 [SMILES: Cn1cc2ccc(-c3cc(C(N)=O)c4[nH]c5cc(C(=O)N6CCOCC6)ccc5c4n3)cc2n1] | 2-(2-methyl-2H-indazol-6-yl)-7-(morpholine-4-carbonyl)-5H-pyrido[3,2-b]indole-4-carboxamide | 1.903(a) | 455.13 |
| 456 | 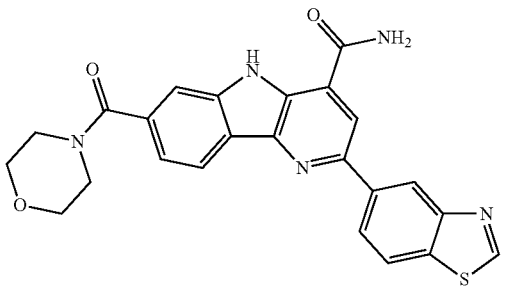 [SMILES: NC(=O)c1cc(-c2ccc3scnc3c2)nc2c1[nH]c1cc(C(=O)N3CCOCC3)ccc12] | 2-(benzo[d]thiazol-5-yl)-7-(morpholine-4-carbonyl)-5H-pyrido[3,2-b]indole-4-carboxamide | 2.033(a) | 458.08 |
| 457 | 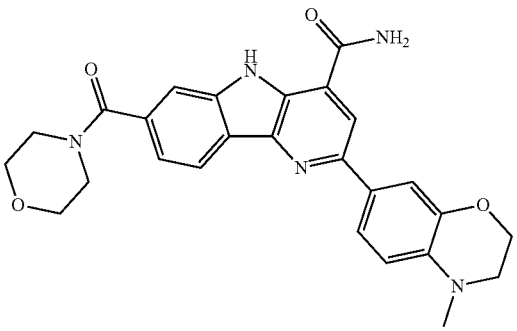 [SMILES: CN1CCOc2cc(-c3cc(C(N)=O)c4[nH]c5cc(C(=O)N6CCOCC6)ccc5c4n3)ccc21] | 2-(4-methyl-3,4-dihydro-2H-benzo[b][1,4]oxazin-7-yl)-7-(morpholine-4-carbonyl)-5H-pyrido[3,2-b]indole-4-carboxamide | 2.062(a) | 472.12 |

HPLC condition a: Luna C18 3.0 × 50 mm S10 column, 3 min gradient, 0-100% B, 4 mL/min. Solvent A: 5% MeOH – 95% H₂O – 10 mm NH₄OAc; Solvent B: 95% MeOH – 5% H₂O – 10 mm NH₄OAc.
HPLC condition b: Luna C18 3.0 × 50 mm S10 column, 3 min gradient, 0-100% B, 4 mL/min. Solvent A: 5% CH₃CN – 90% H₂O – 0.1% TFA; Solvent B: 90% CH₃CN – 10% H₂O – 0.1% TFA.
HPLC condition c: Luna C18 30 × 2, 3u column, 3 min gradient, 0-100% B, 4 mL/min. Solvent A: 5% CH₃CN – 95% H₂O – 10 mm NH₄OAc; Solvent B: 95% CH₃CN – 5% H₂O – 10 mm NH₄OAc.

EXAMPLE 458

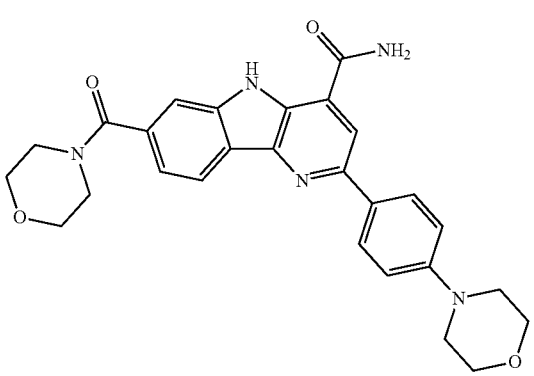 [SMILES: NC(=O)c1cc(-c2ccc(N3CCOCC3)cc2)nc2c1[nH]c1cc(C(=O)N3CCOCC3)ccc12]

7-(Morpholine-4-carbonyl)-2-(4-morpholinophenyl)-5H-pyrido[3,2-b]indole-4-carboxamide 2-Bromo-7-(morpholine-4-carbonyl)-5H-pyrido[3,2-b]indole-4-carboxamide (60 mg, 0.149 mmol), 4-(4-(4,4,5,5-tetramethyl-1,3,2-dioxaborolan-2-yl)phenyl)morpholine (86 mg, 0.298 mmol), PdCl₂(dppf)-CH₂Cl₂ adduct (12.15 mg, 0.015 mmol), and Na₂CO₃ (2M) (0.223 mL, 0.446 mmol) were mixed with DME (4 mL) in a sealed microwave vial. The mixture was flushed with N2 and heated at 100° C. in an oil bath for 4 hrs. The mixture was concentrated and purified using preparative HPLC to give titled product. MS (ESI) m/z 486.13 (M+H)⁺. ¹H NMR (DMSO-d₆) δ ppm 11.65 (s, 1H), 8.63 (s, 1H), 8.4 (s, 1H), 8.29 (d, 1H, J=7.9), 8.20 (d, 2H, J=8.9), 7.9 (s, 1H), 7.79 (s, 1H), 7.29(dd, 1H, J=8.0, 1.5), 7.11 (d, 2H, J=9.2), 3.79 (t, 4H, J=4.9), 3.65-3.45 (bm, 8H), 3.23 (t, 4H, J=4.9).

The following compounds in Table 28 have been synthesized utilizing the procedures described for Example 459.

TABLE 28

| Ex. # | Structure | Name | Retention time (min) | MS (ESI) m/z* |
|---|---|---|---|---|
| 459 | 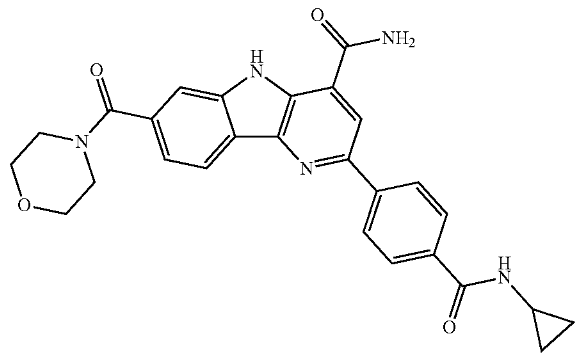 [SMILES: NC(=O)c1cc(-c2ccc(C(=O)NC3CC3)cc2)nc2c1[nH]c1cc(C(=O)N3CCOCC3)ccc12] | 2-(4-(cyclopropyl-carbamoyl)phenyl)-7-(morpholine-4-carbonyl)-5H-pyrido[3,2-b]indole-4-carboxamide | 1.855(a) | 484.13 |
| 460 | 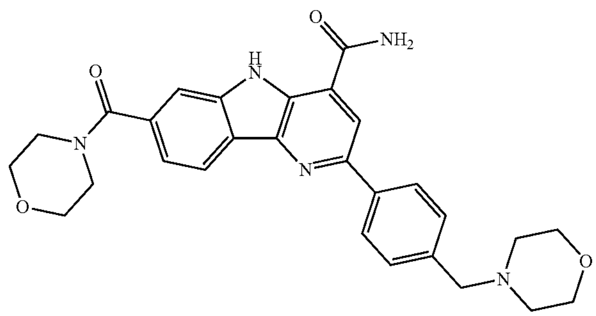 [SMILES: NC(=O)c1cc(-c2ccc(CN3CCOCC3)cc2)nc2c1[nH]c1cc(C(=O)N3CCOCC3)ccc12] | 7-(morpholine-4-carbonyl)-2-(4-(morpholino-methyl)phenyl)-5H-pyrido[3,2-b]indole-4-carboxamide | 2.005(a) | 500.16 |
| 461 | 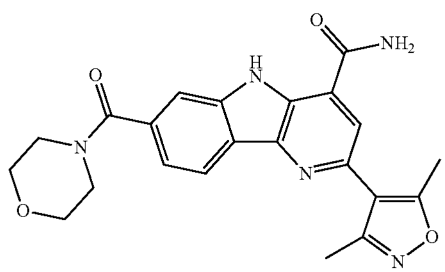 [SMILES: Cc1noc(C)c1-c1cc(C(N)=O)c2[nH]c3cc(C(=O)N4CCOCC4)ccc3c2n1] | 2-(3,5-dimethylisoxazol-4-yl)-7-(morpholine-4-carbonyl)-5H-pyrido[3,2-b]indole-4-carboxamide | 1.710(a) | 420.1 |
| 462 | 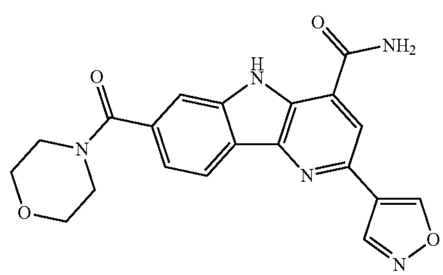 [SMILES: NC(=O)c1cc(-c2cnoc2)nc2c1[nH]c1cc(C(=O)N3CCOCC3)ccc12] | 2-(isoxazol-4-yl)-7-(morpholine-4-carbonyl)-5H-pyrido[3,2-b]indole-4-carboxamide | 1.648(a) | 392.03 |
| 463 | 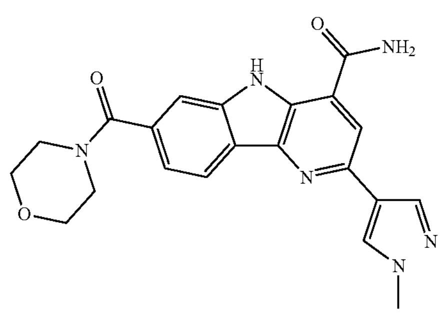 [SMILES: CN/C=C(\C=N)c1cc(C(N)=O)c2[nH]c3cc(C(=O)N4CCOCC4)ccc3c2n1] | 2-(1-methyl-1H-pyrazol-4-yl)-7-(morpholine-4-carbonyl)-5H-pyrido[3,2-b]indole-4-carboxamide | 1.595(a) | 405.1 |

TABLE 28-continued

| Ex. # | Structure | Name | Retention time (min) | MS (ESI) m/z* |
|---|---|---|---|---|
| 464 | 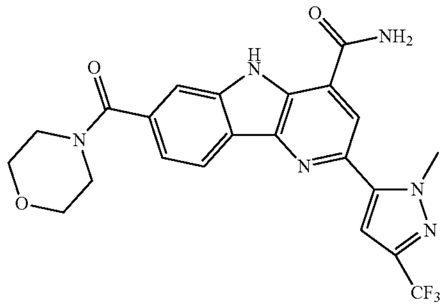 [SMILES: Cn1nc(C(F)(F)F)cc1-c1cc(C(N)=O)c2[nH]c3cc(C(=O)N4CCOCC4)ccc3c2n1] | 2-(1-methyl-3-(trifluoromethyl)-1H-pyrazol-5-yl)-7-(morpholine-4-carbonyl)-5H-pyrido[3,2-b]indole-4-carboxamide | 2.152(a) | 473.08 |
| 465 | 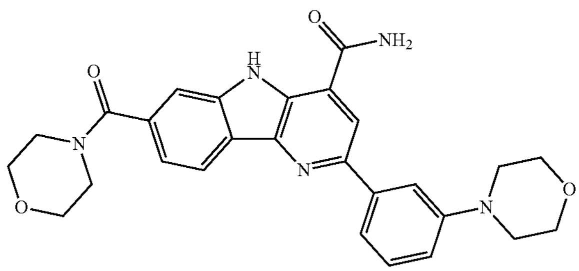 [SMILES: NC(=O)c1cc(-c2cccc(N3CCOCC3)c2)nc2c1[nH]c1cc(C(=O)N3CCOCC3)ccc12] | 7-(morpholine-4-carbonyl)-2-(3-morpholinophenyl)-5H-pyrido[3,2-b]indole-4-carboxamide | 1.948(a) | 486.19 |
| 466 | 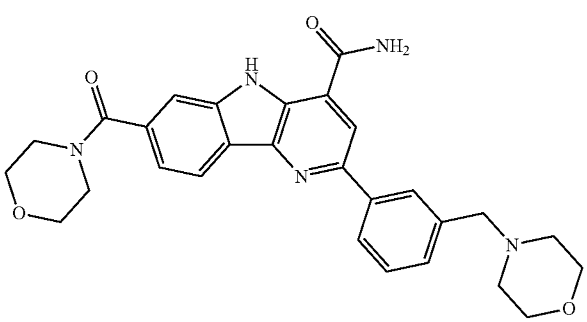 [SMILES: NC(=O)c1cc(-c2cccc(CN3CCOCC3)c2)nc2c1[nH]c1cc(C(=O)N3CCOCC3)ccc12] | 7-(morpholine-4-carbonyl)-2-(3-(morpholinomethyl)phenyl)-5H-pyrido[3,2-b]indole-4-carboxamide | 2.047(a) | 500.22 |
| 467 | 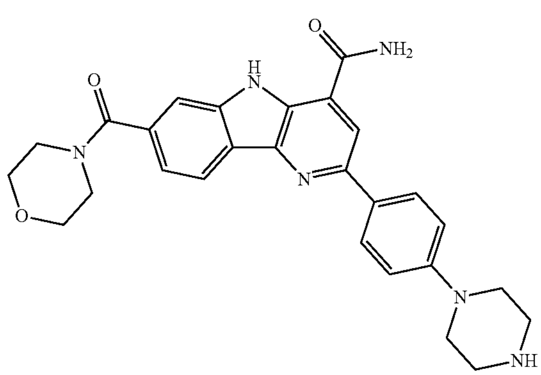 [SMILES: NC(=O)c1cc(-c2ccc(N3CCNCC3)cc2)nc2c1[nH]c1cc(C(=O)N3CCOCC3)ccc12] | 7-(morpholine-4-carbonyl)-2-(4-(piperazin-1-yl)phenyl)-5H-pyrido[3,2-b]indole-4-carboxamide | 1.890(a) | 485.18 |

TABLE 28-continued

| Ex. # | Structure | Name | Retention time (min) | MS (ESI) m/z* |
|---|---|---|---|---|
| 468 | 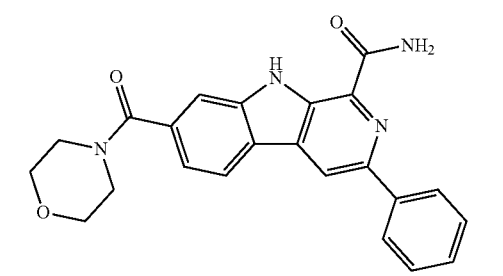 [SMILES: NC(=O)c1nc(-c2ccccc2)cc2c1[nH]c1cc(C(=O)N3CCOCC3)ccc12] | 2-(4-(4-methylpiperazin-1-yl)phenyl)-7-(morpholine-4-carbonyl)-5H-pyrido[3,2-b]indole-4-carboxamide | 2.022(a) | 499.23 |

HPLC condition a: Luna C18 3.0 × 50 mm S10 column, 3 min gradient, 0-100% B, 4 mL/min. Solvent A: 5% MeOH – 95% H₂O – 10 mm NH₄OAc; Solvent B: 95% MeOH – 5% H₂O – 10 mm NH₄OAc.

EXAMPLE 469

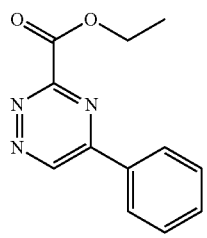 [SMILES: CCOC(=O)c1nncc(-c2ccccc2)n1]

7-(Morpholine-4-carbonyl)-3-phenyl-9H-pyrido[3,4-b]indole-1-carboxamide

469A. Preparation of ethyl 5-phenyl-1,2,4-triazine-3-carboxylate

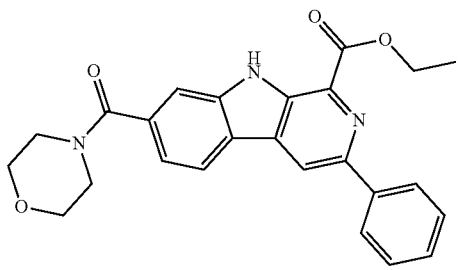 [SMILES: CCOC(=O)c1nc(-c2ccccc2)cc2c1[nH]c1cc(C(=O)N3CCOCC3)ccc12]

In a 500 mL three-neck round bottom flask, ethyl 2-amino-2-thioxoacetate (2.5 g, 18.77 mmol) was mixed with ethanol (25 mL). To this orange solution was added via addition funnel a solution of hydrazine (0.590 mL, 18.77 mmol) in Ethanol (15 mL) over 5 minutes. The reaction mixture was stirred for 1 hr. 2-oxo-2-phenylacetaldehyde hydrate (2.86 g, 18.77 mmol) was added to the above mixture and the mixture was stirred overnight at r.t. under N2. The mixture was concentrated and diluted with 10 ml CH₂Cl₂ and purified by BIOTAGE® with 0-20% EtOAc in CH₂Cl₂. The fractions containing the product were concentrated to give 2.52 g titled product. MS (ESI) m/z 229.95 (M+H)⁺. ¹H NMR (DMSO-d₆) δ ppm 9.82 (s, 1H), 8.30 (d, 2H, J=8.6), 7.7-7.6 (m, 3H), 4.65 (q, 2H, J=7.1), 1.55 (t, 3H, J=7.1).

469B. Preparation of ethyl 7-(morpholine-4-carbonyl)-3-phenyl-9H-pyrido[3,4-b]indole-1-carboxylate (1H-Indol-6-yl)(morpholino)methanone (200 mg, 0.869 mmol), ethyl 5-phenyl-1,2,4-triazine-3-carboxylate (299 mg, 1.303 mmol) and 1-methoxy-2-(2-methoxyethoxy)ethane (556 μL, 3.91 mmol) were mixed in a sealed microwave vial. The mixture was heated in microwave at 185° C. for 8 hrs. The mixture was purified using preparative HPLC to give titled product. MS (ESI) m/z 430.09 (M+H)⁺. ¹H NMR (DMSO-d₆) δ ppm 11.82 (s, 1H), 9.13 (s, 1H), 8.47 (d, 1H, J=7.9), 8.27 (d, 2H, J=7.7), 7.81 (s, 1H), 7.56(t, 2H, J=7.6), 7.44 (t, 1H, J=7.3), 7.36 (d, 1H, J=7.9), 4.57 (q, 2H, J=7.1), 3.67-3.45 (bm, 8H), 1.47 (t, 3H, J=7.1). NOE and ghmbc were used to confirm the structure.

469. Preparation of 7-(morpholine-4-carbonyl)-3-phenyl-9H-pyrido[3,4-b]indole-1-carboxamide Ethyl 7-(morpholine-4-carbonyl)-3-phenyl-9H-pyrido[3,4-b]indole-1-carboxylate (15 mg, 0.035 mmol) and 7N NH₃/MeOH (1.5 mL, 10.50 mmol) were mixed in a sealed microwave tube and heated in microwave at 135° C. for 3.5 hrs. The mixture was concentrated and purified using preparative HPLC to give titled product. MS (ESI) m/z 401.07 (M+H)⁺. ¹H NMR (DMSO-d₆) δ ppm 11.83 (s, 1H), 9.07 (s, 1H), 8.43 (m, 4H), 7.89 (s, 1H), 7.84 (s, 1H), 7.53(t, 2H, J=7.6), 7.42 (t, 1H, J=7.3), 7.32 (dd, 1H, J=7.9, 1.5), 3.67-3.43 (bm, 8H).

EXAMPLE 470

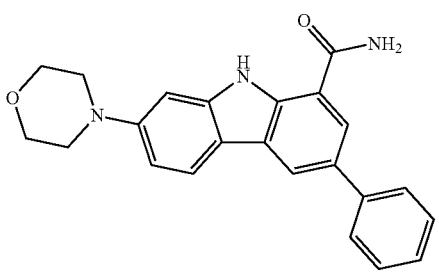 [SMILES: NC(=O)c1cc(-c2ccccc2)cc2c1[nH]c1cc(N3CCOCC3)ccc12]

7-Morpholino-3-phenyl-9H-carbazole-1-carboxamide

470A. Preparation of tert-butyl 6-bromo-8-carbamoyl-9H-carbazol-2-ylcarbamate

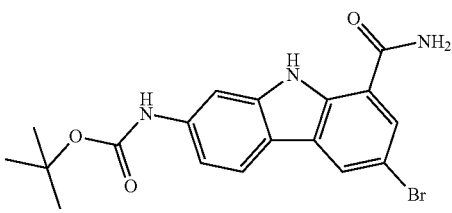 [SMILES: CC(C)(C)OC(=O)Nc1ccc2c(c1)[nH]c1c(C(N)=O)cc(Br)cc12]

6-Bromo-8-carbamoyl-9H-carbazole-2-carboxylic acid 58D (20 g, 60.0 mmol) was mixed with molecular sieve 4A (20 g, 60.0 mmol) in dioxane (500 mL). To the mixture was added Et3N (20.67 mL, 148 mmol) and diphenyl phosphorazidate (32.1 mL, 148 mmol). The mixture was stirred at 55° C. for 2 hrs. tBuOH (57.4 mL, 600 mmol) was added to the mixture and stirred at 80° C. for 16 hrs. The mixture was diluted with 500 ml MeOH, 500 ml CH$_2$Cl$_2$, and filtered through CELITE®. The filtrate was concentrated to dryness. 100 ml MeOH was added, light brown solid was formed and collected by filtration to give 11.2 g titled product. MS (ESI) m/z 402.1 (M−H)$^−$.

470B. Preparation of 7-amino-3-bromo-9H-carbazole-1-carboxamide

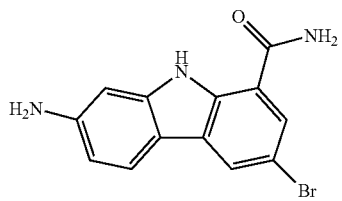 [SMILES: NC(=O)c1cc(Br)cc2c1[nH]c1cc(N)ccc12]

tert-Butyl 6-bromo-8-carbamoyl-9H-carbazol-2-ylcarbamate (2.2 g, 5.44 mmol) was suspended into CH$_2$Cl$_2$ (30 mL). TFA (11 mL, 143 mmol) was added. The mixture was stirred for 1 hr at r.t. The mixture was concentrated to dryness. Saturated NaHCO$_3$ water solution was added and stirred for 30 mins and filtered. The off white solid was collected and washed with water 2× and air-dried overnight to give the titled product. MS (ESI) m/z 303.95 (M−H)$^−$.

470C. Preparation of 3-bromo-7-morpholino-9H-carbazole-1-carboxamide

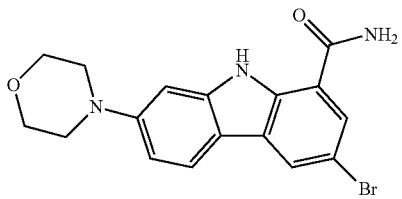 [SMILES: NC(=O)c1cc(Br)cc2c1[nH]c1cc(N3CCOCC3)ccc12]

7-Amino-3-bromo-9H-carbazole-1-carboxamide (250 mg, 0.822 mmol), 1-chloro-2-(2-chloroethoxy)ethane (0.387 mL, 3.29 mmol), sodium carbonate (697 mg, 6.58 mmol) were mixed in DMF (4 mL) in a sealed microwave vial. The vial was degassed and filled with N2. The mixture was heated in microwave at 200° C. for 2 hrs. The mixture was purified using preparative HPLC to give titled product. MS (ESI) m/z 374.01 (M+H)$^+$.

470. Preparation of 7-morpholino-3-phenyl-9H-carbazole-1-carboxamide

3-Bromo-7-morpholino-9H-carbazole-1-carboxamide (34 mg, 0.091 mmol), phenylboronic acid (22.16 mg, 0.182 mmol), PdCl$_2$(dppf)-CH$_2$Cl$_2$ adduct (7.42 mg, 9.09 μmol), and Na$_2$CO$_3$ (2M) (0.182 mL, 0.363 mmol) were mixed with DME (1 mL) in a sealed microwave vial. The mixture was flushed with N2 and heated at 105° C. in an oil bath for 1.5 hrs. The mixture was purified using preparative HPLC to give titled product. MS (ESI) m/z 372.13 (M+H)$^+$. $^1$H NMR (DMSO-d$_6$) δ ppm 11.12 (s, 1H), 8.47 (s, 1H), 8.30 (s, 1H), 8.16 (s, 1H), 8.05 (d, 1H, J=8.5), 7.87 (d, 2H, J=8.3), 7.50(m, 3H), 7.34 (t, 1H, J=7.4), 7.24 (s, 1H), 6.93 (dd, 1H, J=8.5, 1.9), 3.8 (m, 4H), 3.19 (m, 4H).

The following compounds in Table 29 have been synthesized utilizing the procedures described for Example 470.

TABLE 29

| Ex. # | Structure | Name | Retention time (min) | MS (ESI) m/z* |
|---|---|---|---|---|
| 471 | 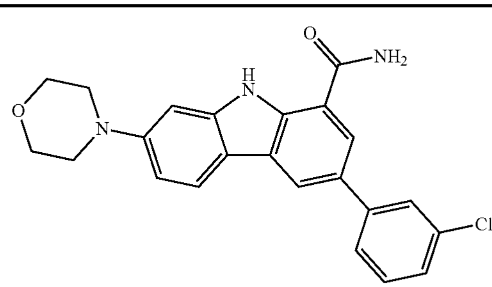 | 3-(3-chlorophenyl)-7-morpholino-9H-carbazole-1-carboxamide | 2.713(a) | 406.1 |

TABLE 29-continued

| Ex. # | Structure | Name | Retention time (min) | MS (ESI) m/z* |
|---|---|---|---|---|
| 472 | 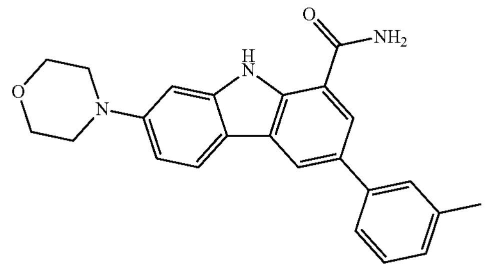 [SMILES: Cc1cccc(-c2cc(C(N)=O)c3[nH]c4cc(N5CCOCC5)ccc4c3c2)c1] | 7-morpholino-3-m-tolyl-9H-carbazole-1-carboxamide | 2.651(a) | 386.17 |
| 473 | 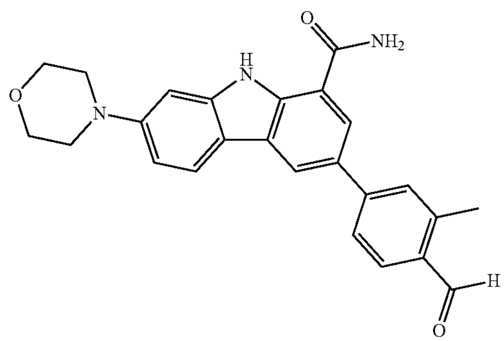 [SMILES: Cc1cc(-c2cc(C(N)=O)c3[nH]c4cc(N5CCOCC5)ccc4c3c2)ccc1C=O] | 3-(4-formyl-3-methylphenyl)-7-morpholino-9H-carbazole-1-carboxamide | 2.395(a) | 414.17 |

HPLC condition a: Luna C18 3.0 × 50 mm S10 column, 3 min gradient, 0-100% B, 4 mL/min. Solvent A: 5% MeOH – 95% H₂O – 10 mm NH₄OAc; Solvent B: 95% MeOH – 5% H₂O – 10 mm NH₄OAc.

EXAMPLE 474

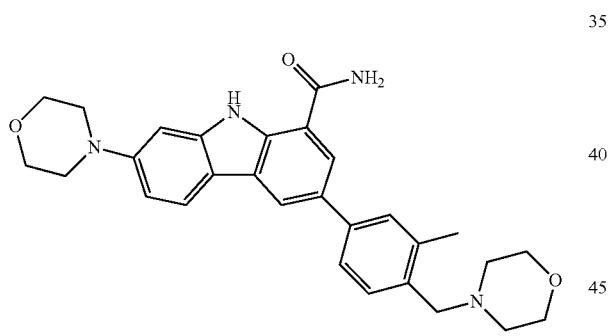

3-(3-Methyl-4-(morpholinomethyl)phenyl)-7-morpholino-9H-carbazole-1-carboxamide 3-(4-formyl-3-methylphenyl)-7-morpholino-9H-carbazole-1-carboxamide (20 mg, 0.034 mmol), morpholine (0.05 mL, 0.574 mmol), sodium triacetoxyborohydride (100 mg, 0.472 mmol) were mixed with THF (5 mL) and $CH_2Cl_2$ (2 mL) in a sealed microwave vial. The mixture was stirred for 3 hr at r.t. The mixture was concentrated and purified using preparative HPLC to give titled product. MS (ESI) m/z 485.25 (M+H)⁺. ¹H NMR (DMSO-d₆) δ ppm 11.10 (s, 1H), 8.44 (s, 1H), 8.28 (s, 1H), 8.13 (s, 1H), 8.04 (d, 1H, J=8.6), 7.67 (s, 1H), 7.62 (d, 1H, J=8.0), 7.47(s, 1H), 7.33 (d, 1H, J=7.6), 7.24 (s, 1H), 6.93 (dd, 1H, J=8.6, 1.9), 3.8 (t, 4H, J=4.7), 3.58 (bs, 4H), 3.49 (s, 2H). 3.19 (t, 4H, J=4.6), 2.45 (s, 3H), 2.4 (bs, 4H).

EXAMPLE 475

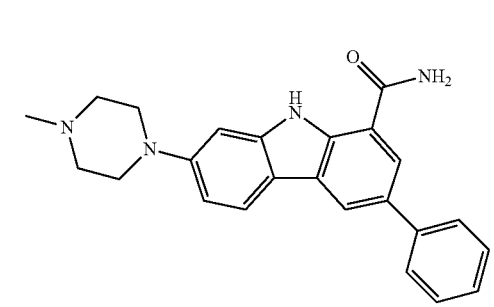 [SMILES: CN1CCN(c2ccc3c(c2)[nH]c2c(C(N)=O)cc(-c4ccccc4)cc23)CC1]

7-(4-Methylpiperazin-1-yl)-3-phenyl-9H-carbazole-1-carboxamide

475A. Preparation of 3-bromo-7-(4-methylpiperazin-1-yl)-9H-carbazole-1-carboxamide

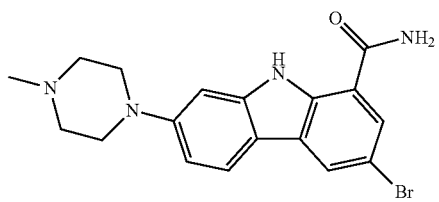 [SMILES: CN1CCN(c2ccc3c(c2)[nH]c2c(C(N)=O)cc(Br)cc23)CC1]

7-Amino-3-bromo-9H-carbazole-1-carboxamide 470B (250 mg, 0.822 mmol), 2-chloro-N-(2-chloroethyl)-N-methylethanamine hydrochloride, Mechlorethamine HCl (316 mg, 1.644 mmol) and sodium carbonate (436 mg, 4.11 mmol) were mixed in t-BuOH (5 mL) in a sealed microwave vial. The vial was degassed and filled with N2. The mixture was heated at 80° C. for 16 hrs in an oil bath. 6 ml of DMF was added to the mixture and the mixture was heated in microwave at 160° C. for 1 hr. The mixture was concentrated and purified using preparative HPLC to give titled product. MS (ESI) m/z 387.04 (M+H)+.

475. Preparation of 7-(4-methylpiperazin-1-yl)-3-phenyl-9H-carbazole-1-carboxamide 3-Bromo-7-(4-methylpiperazin-1-yl)-9H-carbazole-1-carboxamide (35 mg, 0.090 mmol), phenylboronic acid (22.04 mg, 0.181 mmol), PdCl$_2$(dppf)-CH$_2$Cl$_2$ adduct (7.38 mg, 9.04 μmol), and Na$_2$CO$_3$ (2M) (0.181 mL, 0.362 mmol) were mixed with DME (1 mL) in a sealed microwave vial. The mixture was flushed with N2 and heated at 105° C. in an oil bath for 1.5 hrs. The mixture was concentrated and purified using preparative HPLC to give titled product. MS (ESI) m/z 385.19 (M+H)+. $^1$H NMR (DMSO-d$_6$) δ ppm 11.08 (s, 1H), 8.46 (s, 1H), 8.29 (s, 1H), 8.15 (s, 1H), 8.02 (d, 1H, J=8.5), 7.87 (d, 2H, J=7.4), 7.50(m, 3H), 7.34 (t, 1H, J=7.3), 7.23 (s, 1H), 6.92 (dd, 1H, J=8.8, 2.1), 3.25-3.15 (m, 8H), 2.25 (s, 3H).

EXAMPLE 476

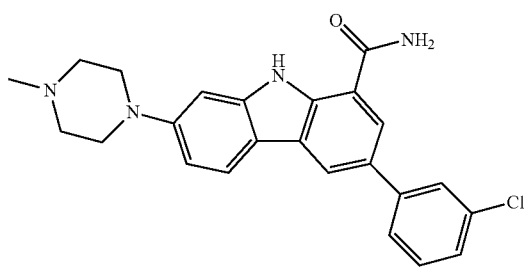 [SMILES: CN1CCN(c2ccc3c(c2)[nH]c2c(C(N)=O)cc(-c4cccc(Cl)c4)cc23)CC1]

3-(3-Chlorophenyl)-7-(4-methylpiperazin-1-yl)-9H-carbazole-1-carboxamide

The titled compound was synthesized utilizing the procedures described for Example 475. MS (ESI) m/z 419.15 (M+H)+. $^1$H NMR (DMSO-d$_6$) δ ppm 11.13 (s, 1H), 8.54 (d, 1H, J=1.5), 8.33 (s, 1H), 8.18 (d, 1H, J=1.6), 8.04 (d, 1H, J=8.9), 7.97 (t, 1H, J=1.8), 7.86 (d, 1H, J=7.9), 7.52 (m, 2H), 7.40 (dd, 1H, J=8.0, 1.2), 7.23 (d, 1H, J=2.1), 6.93 (dd, 1H, J=8.5, 2.1), 3.25-3.15 (m, 8H), 2.25 (s, 3H).

EXAMPLE 477

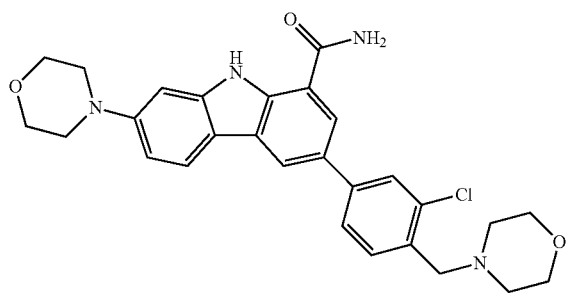 [SMILES: NC(=O)c1cc(-c2ccc(CN3CCOCC3)c(Cl)c2)cc2c1[nH]c1cc(N3CCOCC3)ccc12]

3-(3-Chloro-4-(morpholinomethyl)phenyl)-7-morpholino-9H-carbazole-1-carboxamide

477A. Preparation of 4-(4-bromo-2-chlorobenzyl)morpholine

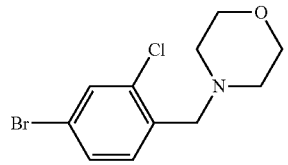 [SMILES: Clc1cc(Br)ccc1CN1CCOCC1]

4-Bromo-2-chlorobenzaldehyde (1 g, 4.56 mmol), morpholine (0.457 mL, 5.24 mmol), acetic acid (0.300 mL, 5.24 mmol) and sodium triacetoxyborohydride (1.45 g, 6.84 mmol) were mixed with THF (4 mL) in a sealed microwave vial. The mixture was stirred at r.t. for 2 hrs. The mixture was diluted with EtOAc, washed with H$_2$O. The organic layer was washed with brine, dried over MgSO$_4$ and concentrated. The crude was purified on BIOTAGE® with 0-20% of EtOAc in hexane. The fractions containing the desired product was collected and concentrated to give 1.01 g titled product. MS (ESI) m/z 289.9 (M+H)+.

477B. Preparation of 4-(2-chloro-4-(4,4,5,5-tetramethyl-1,3,2-dioxaborolan-2-yl)benzyl)morpholine

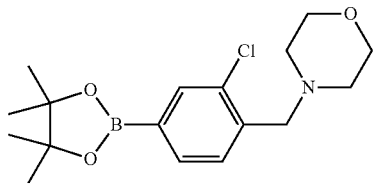 [SMILES: CC1(C)OB(c2ccc(CN3CCOCC3)c(Cl)c2)OC1(C)C]

4-(4-Bromo-2-chlorobenzyl)morpholine (500 mg, 1.721 mmol), 4,4,4',4',5,5,5',5'-octamethyl-2,2'-bi(1,3,2-dioxaborolane) (481 mg, 1.893 mmol), potassium acetate (338 mg, 3.44 mmol) and PdCl$_2$(dppf)-CH$_2$Cl$_2$ adduct (70.3 mg, 0.086 mmol) were mixed with dioxane (5 mL) in a sealed microwave tube. The mixture was flushed with N2 and heated at 100° C. for 4 hrs. The mixture was filtered, washed with EtOAc. The filtrate was diluted with EtOAc and washed with H$_2$O, brine. The organic layer was dried over MgSO$_4$ and concentrated to give 680 g of crude product. MS (ESI) m/z 338.04 (M+H)+.

477. Preparation of 3-(3-chloro-4-(morpholinomethyl)phenyl)-7-morpholino-9H-carbazole-1-carboxamide The titled compound was synthesized utilizing the procedures described for Example 475. MS (ESI) m/z 505.09 (M+H)+.

EXAMPLE 478

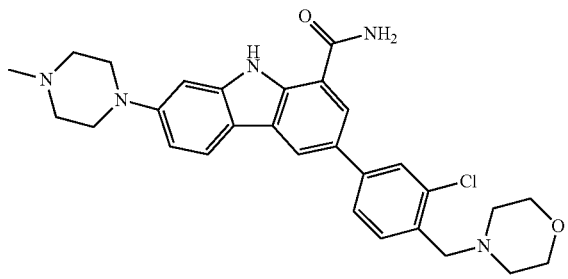 [SMILES: CN1CCN(c2ccc3c(c2)[nH]c2c(C(N)=O)cc(-c4ccc(CN5CCOCC5)c(Cl)c4)cc23)CC1]

3-(3-Chloro-4-(morpholinomethyl)phenyl)-7-(4-methylpiperazin-1-yl)-9H-carbazole-1-carboxamide The titled compound was synthesized utilizing the procedures described for Example 475. MS (ESI) m/z 518.26 (M+H)+. 1H NMR (DMSO-d6) δ ppm 11.13 (s, 1H), 8.52 (s, 1H), 8.32 (s, 1H), 8.17 (s, 1H), 8.03 (d, 1H, J=8.8), 7.97 (s, 1H), 7.84 (d, 1H, J=7.9), 7.58 (d, 1H, J=8.0), 7.50(s, 1H), 7.23 (s, 1H), 6.93 (d, 1H, J=8.8), 3.62 (bm, 10H), 3.22 (bm, 4H), 2.46 (bm, 4H), 2.27 (s, 3H).

EXAMPLE 479

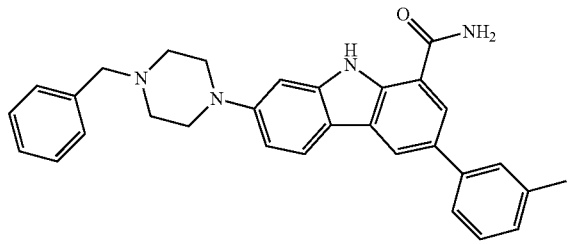 [SMILES: Cc1cccc(-c2cc(C(N)=O)c3[nH]c4cc(N5CCN(Cc6ccccc6)CC5)ccc4c3c2)c1]

7-(4-Benzylpiperazin-1-yl)-3-m-tolyl-9H-carbazole-1-carboxamide

479A. Preparation of 7-(4-benzylpiperazin-1-yl)-3-bromo-9H-carbazole-1-carboxamide

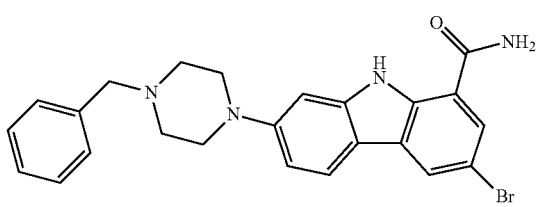 [SMILES: NC(=O)c1cc(Br)cc2c1[nH]c1cc(N3CCN(Cc4ccccc4)CC3)ccc12]

7-Amino-3-bromo-9H-carbazole-1-carboxamide 470B (400 mg, 1.315 mmol), N-benzyl-2-chloro-N-(2-chloroethyl)ethanamine hydrochloride (707 mg, 2.63 mmol) and sodium carbonate (697 mg, 6.58 mmol) were mixed in DMF (8 mL) in a sealed microwave vial. The vial was degassed and filled with N2. The mixture was heated at 80° C. for 16 hrs in an oil bath. The mixture was then heated in microwave at 200 C for 1 hr. The mixture was purified using preparative HPLC to give titled product. MS (ESI) m/z 463.07 (M+H)+.

479. Preparation of 7-(4-benzylpiperazin-1-yl)-3-m-tolyl-9H-carbazole-1-carboxamide 7-(4-Benzylpiperazin-1-yl)-3-bromo-9H-carbazole-1-carboxamide (100 mg, 0.216 mmol), m-tolylboronic acid (58.7 mg, 0.432 mmol), PdCl2(dppf)-CH2Cl2 adduct (17.62 mg, 0.022 mmol), and Na2CO3 (2M) (0.432 mL, 0.863 mmol) were mixed with DME (4 mL) in a sealed microwave vial. The mixture was flushed with N2 and heated at 100° C. in an oil bath for 4 hrs. The mixture was purified using preparative HPLC to give titled product. MS (ESI) m/z 475.12 (M+H)+. 1H NMR (DMSO-d6) δ ppm 11.07 (s, 1H), 8.44 (s, 1H), 8.28 (s, 1H), 8.12 (s, 1H), 8.02 (d, 1H, J=8.6), 7.69 (s, 1H), 7.65 (d, 1H, J=7.0), 7.47(s, 1H), 7.36 (m, 5H), 7.28 (m, 1H), 7.21 (s, 1H), 7.16 (d, 1H, J=7.9), 6.90 (dd, 1H, J=8.5, 2.1), 3.56 (s, 2H), 3.22 (bm, 4H), 2.57 (bm, 4H), 2.42 (s, 3H).

EXAMPLE 480

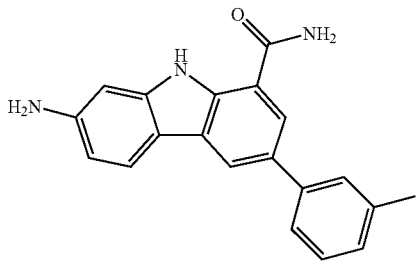 [SMILES: Cc1cccc(-c2cc(C(N)=O)c3[nH]c4cc(N)ccc4c3c2)c1]

7-Amino-3-m-tolyl-9H-carbazole-1-carboxamide

7-Amino-3-bromo-9H-carbazole-1-carboxamide 470B (350 mg, 1.151 mmol), m-tolylboronic acid (313 mg, 2.302 mmol), PdCl2(dppf)-CH2Cl2 adduct (94 mg, 0.115 mmol), and Na2CO3 (2M) (2.88 mL, 5.75 mmol) were mixed with DME (15 mL) in a sealed microwave vial. The mixture was flushed with N2 and heated at 100° C. in an oil bath for 4 hrs. The mixture was purified using preparative HPLC to give titled product. MS (ESI) m/z 316.04 (M+H)+. 1H NMR (DMSO-d6) δ ppm 10.89 (s, 1H), 8.30 (s, 1H), 8.23 (s, 1H), 8.03 (s, 1H), 7.82 (d, 1H, J=8.2), 7.67 (s, 1H), 7.63 (d, 1H, J=7.6), 7.41(s, 1H), 7.36 (t, 1H, J=7.6), 7.14 (d, 1H, J=7.6), 6.81 (s, 1H), 6.5 (d, 1H, J=8.3), 5.24 (bs, 2H), 2.42 (s, 3H).

EXAMPLE 481

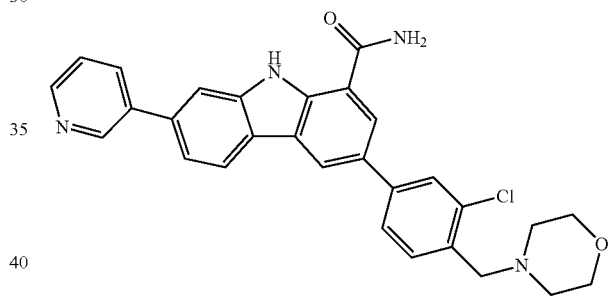

3-(3-Chloro-4-(morpholinomethyl)phenyl)-7-(pyridin-3-yl)-9H-carbazole-1-carboxamide 481A. Preparation of 3-bromo-7-iodo-9H-carbazole-1-carboxamide

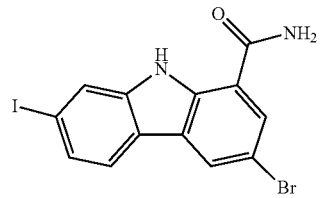 [SMILES: NC(=O)c1cc(Br)cc2c1[nH]c1cc(I)ccc12]

To a mixture of 7-amino-3-bromo-9H-carbazole-1-carboxamide 470B (1 g, 2.79 mmol) and CH2I2 (15 mL) was slowly added isopentyl nitrite (1 mL, 7.48 mmol). The mixture was heated in microwave at 60° C. for 45 mins copper(I) iodide (0.266 g, 1.397 mmol) was added to the reaction mixture and heated in microwave at 55° C. for additional 30 mins The mixture was concentrated. EtOAc(50 ml) was added and stirred for 10 mins and filtered. The collected solid was washed with H2O 2×50 ml. The remaining solid was purified using preparative HPLC to give titled product. MS (ESI) m/z 412.82 (M−H)−.

481B. Preparation of 3-bromo-7-(pyridin-3-yl)-9H-carbazole-1-carboxamide

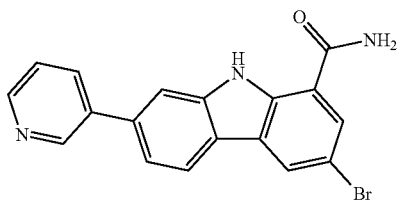 [SMILES: NC(=O)c1cc(Br)cc2c1[nH]c1cc(-c3cccnc3)ccc12]

3-Bromo-7-iodo-9H-carbazole-1-carboxamide (100 mg, 0.241 mmol), pyridin-3-ylboronic acid (35.5 mg, 0.289 mmol), PdCl$_2$(dppf)-CH$_2$Cl$_2$ adduct (39.4 mg, 0.048 mmol), and Na$_2$CO$_3$ (2M) (0.482 mL, 0.964 mmol) were mixed with DME (4 mL) in a sealed microwave vial. The mixture was flushed with N2 and heated at 105° C. in an oil bath for 5 hrs. The mixture was used as it is. MS (ESI) m/z 365.88 (M+H)$^+$.

481. Preparation of 3-(3-chloro-4-(morpholinomethyl)phenyl)-7-(pyridin-3-yl)-9H-carbazole-1-carboxamide To the reaction mixture above (481B) was added 4-(2-chloro-4-(4,4,5,5-tetramethyl-1,3,2-dioxaborolan-2-yl)benzyl)morpholine 477B (0.098 g, 0.289 mmol) and additional PdCl$_2$(dppf)-CH$_2$Cl$_2$ adduct (0.020 g, 0.024 mmol). The mixture was heated in microwave at 105° C. for 1 hr. The mixture was filtered and then purified using preparative HPLC to give titled product. MS (ESI) m/z 495.19 (M−H)$^-$.

EXAMPLE 482

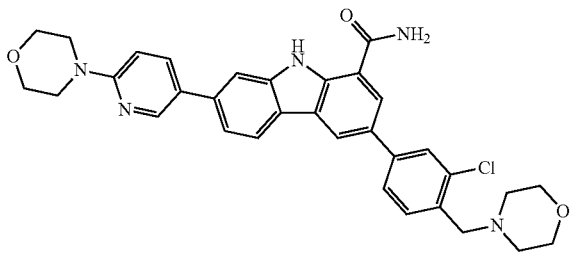 [SMILES: NC(=O)c1cc(-c2ccc(CN3CCOCC3)c(Cl)c2)cc2c1[nH]c1cc(-c3ccc(N4CCOCC4)nc3)ccc12]

3-(3-Chloro-4-(morpholinomethyl)phenyl)-7-(6-morpholinopyridin-3-yl)-9H-carbazole-1-carboxamide

482A. Preparation of 3-bromo-7-(6-morpholinopyridin-3-yl)-9H-carbazole-1-carboxamide

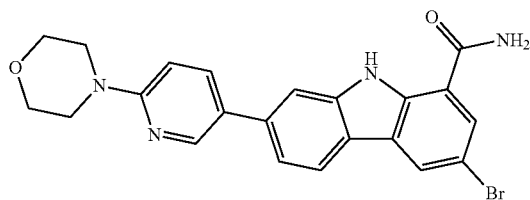 [SMILES: NC(=O)c1cc(Br)cc2c1[nH]c1cc(-c3ccc(N4CCOCC4)nc3)ccc12]

3-Bromo-7-iodo-9H-carbazole-1-carboxamide 481A (100 mg, 0.241 mmol), 4-(5-(4,4,5,5-tetramethyl-1,3,2-dioxaborolan-2-yl)pyridin-2-yl)morpholine (84 mg, 0.289 mmol), PdCl$_2$(dppf)-CH$_2$Cl$_2$ adduct (39.4 mg, 0.048 mmol), and Na$_2$CO$_3$ (2M) (0.602 mL, 1.205 mmol) were mixed with DME (4 mL) in a sealed microwave vial. The mixture was flushed with N2 and heated at 105° C. in an oil bath for 5 hrs. The mixture was used as it is. MS (ESI) m/z 450.97 (M+H)$^+$.

482. Preparation of 3-(3-chloro-4-(morpholinomethyl)phenyl)-7-(6-morpholinopyridin-3-yl)-9H-carbazole-1-carboxamide To the reaction mixture above (482A) was added 4-(2-chloro-4-(4,4,5,5-tetramethyl-1,3,2-dioxaborolan-2-yl)benzyl)morpholine 477B (0.098 g, 0.289 mmol) and additional PdCl$_2$(dppf)-CH$_2$Cl$_2$ adduct (0.020 g, 0.024 mmol). The mixture was heated in microwave at 105° C. for 1 hr. The mixture was filtered and then purified using preparative HPLC to give titled product. MS (ESI) m/z 582.21 (M+H)$^+$.

EXAMPLE 483

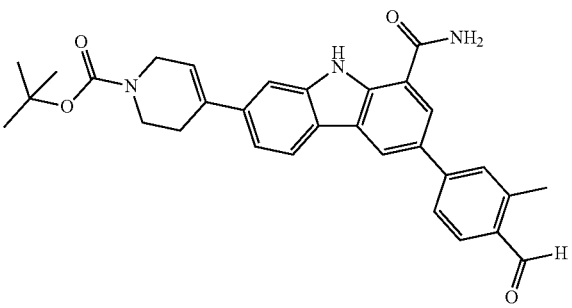 [SMILES: Cc1cc(-c2cc(C(N)=O)c3[nH]c4cc(C5=CCN(C(=O)OC(C)(C)C)CC5)ccc4c3c2)ccc1C=O]

tert-Butyl 4-(8-carbamoyl-6-(4-formyl-3-methylphenyl)-9H-carbazol-2-yl)-5,6-dihydropyridine-1(2H)-carboxylate

483A. Preparation of tert-butyl 4-(6-bromo-8-carbamoyl-9H-carbazol-2-yl)-5,6-dihydropyridine-1(2H)-carboxylate

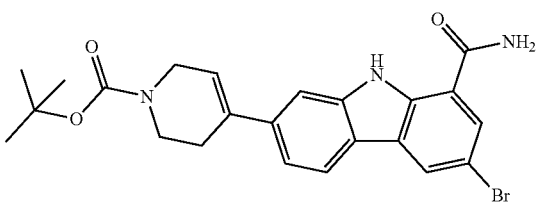 [SMILES: CC(C)(C)OC(=O)N1CC=C(c2ccc3c(c2)[nH]c2c(C(N)=O)cc(Br)cc23)CC1]

3-Bromo-7-iodo-9H-carbazole-1-carboxamide 481A (200 mg, 0.482 mmol), tert-butyl 4-(4,4,5,5-tetramethyl-1,3,2-dioxaborolan-2-yl)-5,6-dihydropyridine-1(2H)-carboxylate (194 mg, 0.626 mmol), Pd(Ph$_3$P)$_4$ (35 mg, 0.030 mmol), and Na$_2$CO$_3$ (2M) (0.964 mL, 1.928 mmol) were mixed with toluene (10 mL) and MeOH (5 mL) in a sealed microwave vial. The mixture was flushed with N2 and heated at 105° C. in an oil bath for 4 hrs. The mixture was used as it is. MS (ESI) m/z 468.22 (M−H)$^-$.

483. Preparation of tert-butyl 4-(8-carbamoyl-6-(4-formyl-3-methylphenyl)-9H-carbazol-2-yl)-5,6-dihydropyridine-1(2H)-carboxylate To the reaction mixture above (483A) was added 4-formyl-3-methylphenylboronic acid (103 mg, 0.627 mmol), Pd(Ph$_3$P)$_4$ (11.14 mg, 9.64 μmol) and Na$_2$CO$_3$ (0.482 mL, 0.964 mmol). The mixture was stirred at 105 C for 4 hrs. The mixture was filtered and then purified using preparative HPLC to give titled product. MS (ESI) m/z 508.31 (M–H)$^-$.

EXAMPLE 484

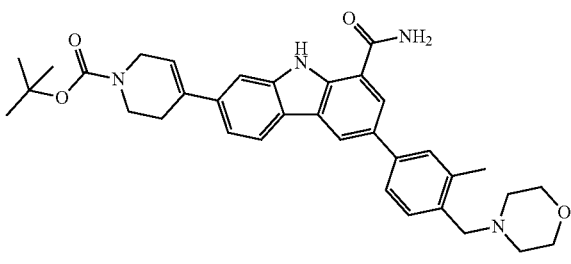 [SMILES: Cc1cc(-c2cc(C(N)=O)c3[nH]c4cc(C5=CCN(C(=O)OC(C)(C)C)CC5)ccc4c3c2)ccc1CN1CCOCC1]

tert-Butyl 4-(8-carbamoyl-6-(3-methyl-4-(morpholinomethyl)phenyl)-9H-carbazol-2-yl)-5,6-dihydropyridine-1(2H)-carboxylate The titled compound was synthesized utilizing the procedures described for Example 474. MS (ESI) m/z 581.24 (M+H)$^+$.

EXAMPLE 485

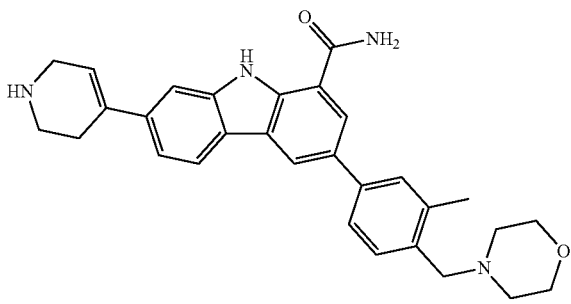 [SMILES: Cc1cc(-c2cc(C(N)=O)c3[nH]c4cc(C5=CCNCC5)ccc4c3c2)ccc1CN1CCOCC1]

3-(3-Methyl-4-(morpholinomethyl)phenyl)-7-(1,2,3,6-tetrahydropyridin-4-yl)-9H-carbazole-1-carboxamide tert-Butyl 4-(8-carbamoyl-6-(3-methyl-4-(morpholinomethyl)phenyl)-9H-carbazol-2-yl)-5,6-dihydropyridine-1(2H)-carboxylate 484 (3 mg, 5.17 μmol) was mixed with TFA (0.2 mL, 2.60 mmol) in 1,2-Dichloroethane (0.4 mL). The mixture was stirred at r.t. for 1 hr. The mixture was concentrated to give the titled product as TFA salt. MS (ESI) m/z 481.07 (M+H)$^+$. $^1$H NMR (MeOD-d4) δ ppm 8.60 (d, 1H, J=1.8), 8.27 (d, 1H, J=1.8), 8.21 (d, 1H, J=8.2), 7.87 (s, 1H), 7.82 (dd, 1H, J=7.9, 1.5), 7.75 (d, 1H, J=1.3), 7.63 (d, 1H, J=7.9), 7.43 (dd, 1H, J=8.2, 1.5), 6.31 (bs, 1H), 4.51 (s, 2H), 4.1-3.85 (m, 6H), 3.56 (t, 2H, J=6.1), 3.47-3.2 (m, 4H), 2.98 (bs, 2H), 2.63 (s, 3H).

EXAMPLE 486

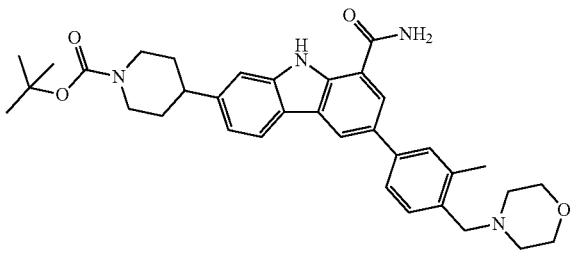 [SMILES: Cc1cc(-c2cc(C(N)=O)c3[nH]c4cc(C5CCN(C(=O)OC(C)(C)C)CC5)ccc4c3c2)ccc1CN1CCOCC1]

tert-Butyl 4-(8-carbamoyl-6-(3-methyl-4-(morpholinomethyl)phenyl)-9H-carbazol-2-yl)piperidine-1-carboxylate tert-Butyl 4-(8-carbamoyl-6-(3-methyl-4-(morpholinomethyl)phenyl)-9H-carbazol-2-yl)-5,6-dihydropyridine-1(2H)-carboxylate 484 (12 mg, 0.021 mmol) and palladium on carbon (20 mg, 0.019 mmol) were mixed with MeOH (10 ml) in a sealed microwave tube. The mixture was stirred at r.t. with H2 in a balloon overnight. The mixture was filtered and then purified using preparative HPLC (MeOH/H$_2$O/TFA) to give titled product. MS (ESI) m/z 583.19 (M+H)$^+$.

EXAMPLE 487

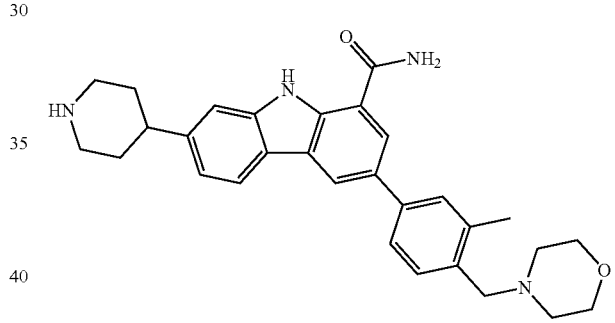

3-(3-Methyl-4-(morpholinomethyl)phenyl)-7-(piperidin-4-yl)-9H-carbazole-1-carboxamide The titled product was detected and isolated during the preparative HPLC purification of Example 486. MS (ESI) m/z 483.20 (M+H)$^+$.

EXAMPLE 488

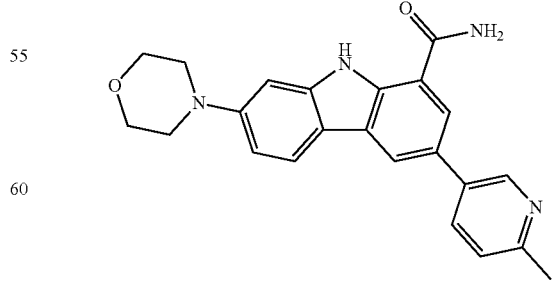

3-(6-Methylpyridin-3-yl)-7-morpholino-9H-carbazole-1-carboxamide

488A. Preparation of 7-amino-3-(6-methylpyridin-3-yl)-9H-carbazole-1-carboxamide

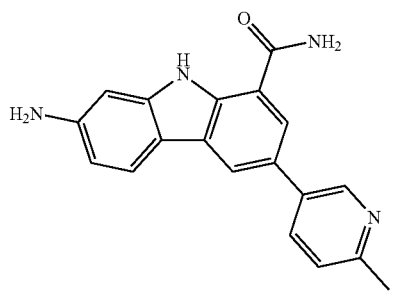 [SMILES: Cc1ccc(-c2cc(C(N)=O)c3[nH]c4cc(N)ccc4c3c2)cn1]

The titled compound was synthesized utilizing the procedures described for Example 480, using 6-methylpyridin-3-ylboronic acid. MS (ESI) m/z 316.96 (M+H)+.

488. Preparation of 3-(6-methylpyridin-3-yl)-7-morpholino-9H-carbazole-1-carboxamide 7-Amino-3-(6-methylpyridin-3-yl)-9H-carbazole-1-carboxamide (134 mg, 0.284 mmol), 1-chloro-2-(2-chloroethoxy)ethane (101 mg, 0.709 mmol) and $Na_2CO_3$ (180 mg, 1.703 mmol) were mixed with DMF (4 mL) in a sealed microwave vial. The mixture was heated in microwave at 200° C. for 2 hrs. The mixture was filtered and then purified using preparative HPLC to give titled product. MS (ESI) m/z 387.00 (M+H)+. $^1$H NMR (DMSO-$d_6$) δ ppm 11.16 (s, 1H), 8.97 (s, 1H), 8.53 (s, 1H), 8.3 (s, 1H), 8.18 (s, 1H), 8.15 (dd, 1H, J=8.0, 2.5), 8.05 (d, 1H, J=8.5), 7.51 (s, 1H), 7.37 (d, 1H, J=8.2), 7.24 (s, 1H), 6.94 (d, 1H, J=8.6), 3.8 (m, 4H), 3.19 (m, 4H), 2.53(s, 3H).

EXAMPLE 489

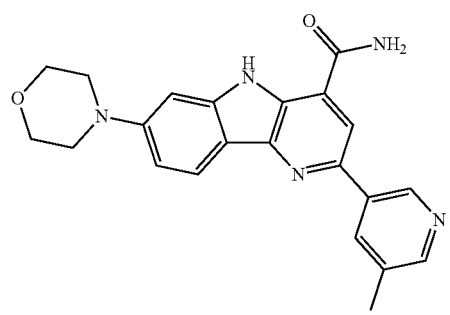 [SMILES: Cc1cncc(-c2cc(C(N)=O)c3[nH]c4cc(N5CCOCC5)ccc4c3n2)c1]

2-(5-Methylpyridin-3-yl)-7-morpholino-5H-pyrido[3,2-b]indole-4-carboxamide

2-Bromo-7-morpholino-5H-pyrido[3,2-b]indole-4-carboxamide 325D (100 mg, 0.267 mmol), 5-methylpyridin-3-ylboronic acid (51.1 mg, 0.373 mmol), $PdCl_2$(dppf)-$CH_2Cl_2$ adduct (10.88 mg, 0.013 mmol), and $Na_2CO_3$ (2M) (0.666 mL, 1.333 mmol) were mixed with DME (4 mL) in a sealed microwave vial. The mixture was flushed with N2 and heated at 110° C. in microwave for 1 hr. The mixture was filtered and then purified using preparative HPLC to give titled product. MS (ESI) m/z 387.97 (M+H)+. $^1$H NMR (DMSO-$d_6$) δ ppm 11.33 (s, 1H), 9.25 (s, 1H), 8.52 (s, 1H), 8.44 (s, 1H), 8.43 (s, 1H), 8.36 (s, 1H), 8.09 (d, 1H, J=8.6), 7.87 (s, 1H), 7.23 (s, 1H), 7.03 (dd, 1H, J=8.9, 2.1), 3.81 (m, 4H), 3.25 (m, 4H), 2.44(s, 3H).

The following compounds in Table 30 have been synthesized utilizing the procedures described for Example 489.

TABLE 30

| Ex. # | Structure | Name | Retention time (min) | MS (ESI) m/z* |
|---|---|---|---|---|
| 490 | 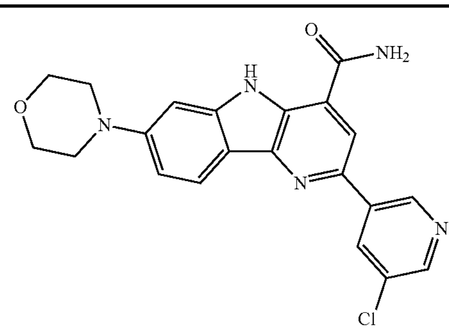 | 2-(5-chloropyridin-3-yl)-7-morpholino-5H-pyrido[3,2-b]indole-4-carboxamide | 2.422(a) | 407.93 |
| 491 | 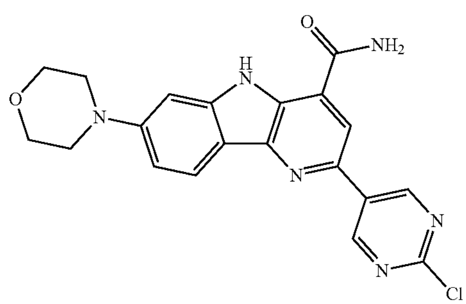 [SMILES: NC(=O)c1cc(-c2cnc(Cl)nc2)nc2c1[nH]c1cc(N3CCOCC3)ccc12] | 2-(2-chloropyrimidin-5-yl)-7-morpholino-5H-pyrido[3,2-b]indole-4-carboxamide | 2.222(a) | 409.03 |

TABLE 30-continued

| Ex. # | Structure | Name | Retention time (min) | MS (ESI) m/z* |
|---|---|---|---|---|
| 492 | 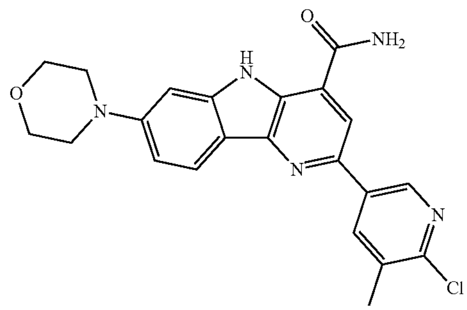 [SMILES: Cc1cc(-c2cc(C(N)=O)c3[nH]c4cc(N5CCOCC5)ccc4c3n2)cnc1Cl] | 2-(6-chloro-5-methylpyridin-3-yl)-7-morpholino-5H-pyrido[3,2-b]indole-4-carboxamide | 2.447(a) | 422.05 |
| 493 | 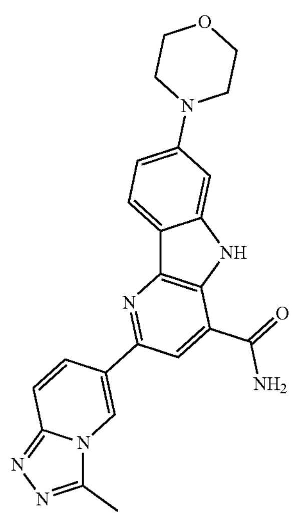 [SMILES: Cc1nnc2ccc(-c3cc(C(N)=O)c4[nH]c5cc(N6CCOCC6)ccc5c4n3)cn12] | 2-(3-methyl-[1,2,4]triazolo[4,3-a]pyridin-6-yl)-7-morpholino-5H-pyrido[3,2-b]indole-4-carboxamide | 1.973(a) | 428.07 |
| 494 | 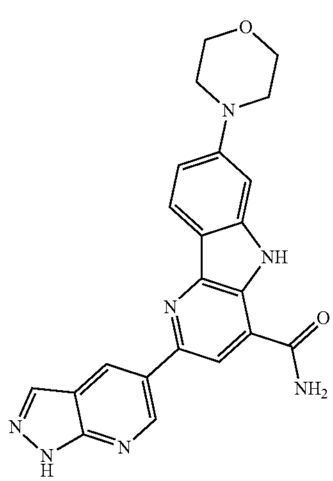 [SMILES: NC(=O)c1cc(-c2cnc3[nH]ncc3c2)nc2c1[nH]c1cc(N3CCOCC3)ccc12] | 7-morpholino-2-(1H-pyrazolo[3,4-b]pyridin-5-yl)-5H-pyrido[3,2-b]indole-4-carboxamide | 1.985(a) | 414.05 |

TABLE 30-continued

| Ex. # | Structure | Name | Retention time (min) | MS (ESI) m/z* |
|---|---|---|---|---|
| 495 | 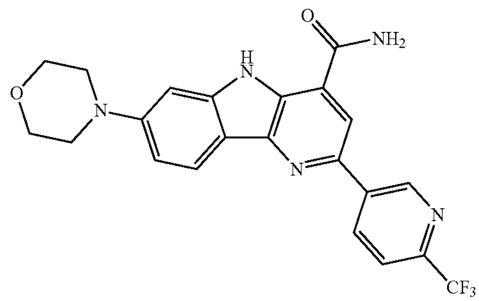 [SMILES: NC(=O)c1cc(-c2ccc(C(F)(F)F)nc2)nc2c1[nH]c1cc(N3CCOCC3)ccc12] | 7-morpholino-2-(6-(trifluoromethyl)pyridin-3-yl)-5H-pyrido[3,2-b]indole-4-carboxamide | 2.432(a) | 442.02 |
| 496 | 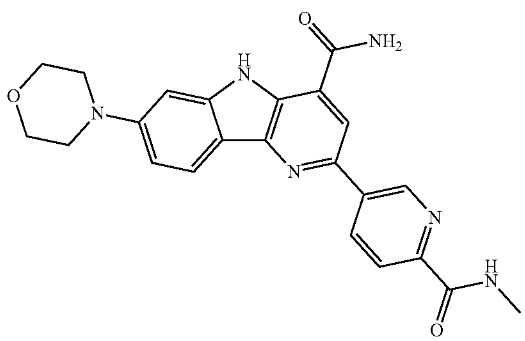 [SMILES: CNC(=O)c1ccc(-c2cc(C(N)=O)c3[nH]c4cc(N5CCOCC5)ccc4c3n2)cn1] | 2-(6-(methylcarbamoyl)pyridin-3-yl)-7-morpholino-5H-pyrido[3,2-b]indole-4-carboxamide | 2.042(a) | 431.06 |
| 497 | 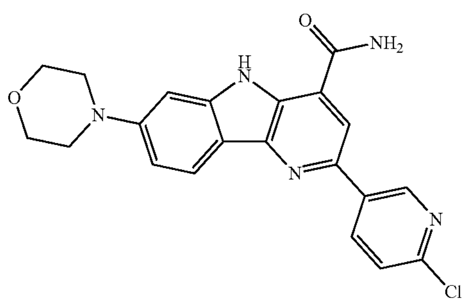 [SMILES: NC(=O)c1cc(-c2ccc(Cl)nc2)nc2c1[nH]c1cc(N3CCOCC3)ccc12] | 2-(6-chloropyridin-3-yl)-7-morpholino-5H-pyrido[3,2-b]indole-4-carboxamide | 2.282(a) | 408.02 |
| 498 | 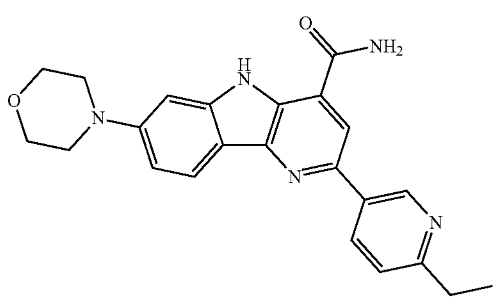 [SMILES: CCc1ccc(-c2cc(C(N)=O)c3[nH]c4cc(N5CCOCC5)ccc4c3n2)cn1] | 2-(6-ethylpyridin-3-yl)-7-morpholino-5H-pyrido[3,2-b]indole-4-carboxamide | 2.290(a) | 402.12 |
| 499 | 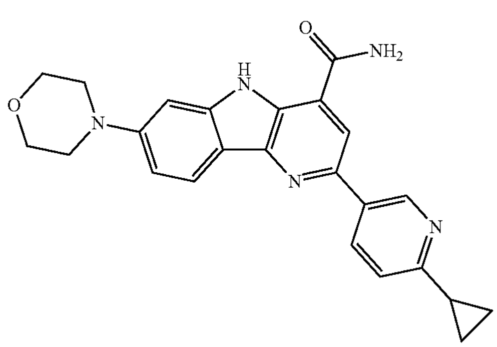 [SMILES: NC(=O)c1cc(-c2ccc(C3CC3)nc2)nc2c1[nH]c1cc(N3CCOCC3)ccc12] | 2-(6-cyclopropylpyridin-3-yl)-7-morpholino-5H-pyrido[3,2-b]indole-4-carboxamide | 2.325(a) | 414.11 |

TABLE 30-continued

| Ex. # | Structure | Name | Retention time (min) | MS (ESI) m/z* |
|---|---|---|---|---|
| 500 | 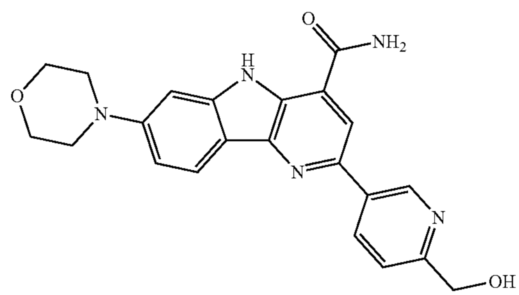 [SMILES: NC(=O)c1cc(-c2ccc(CO)nc2)nc2c1[nH]c1cc(N3CCOCC3)ccc12] | 2-(6-(hydroxymethyl)pyridin-3-yl)-7-morpholino-5H-pyrido[3,2-b]indole-4-carboxamide | 1.857(a) | 404.06 |
| 501 | 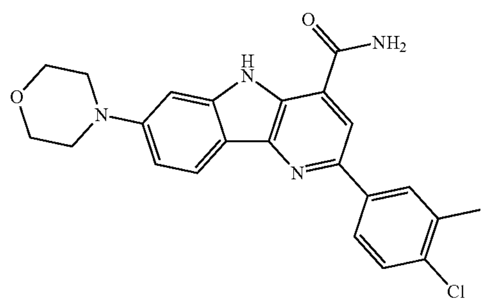 [SMILES: Cc1cc(-c2cc(C(N)=O)c3[nH]c4cc(N5CCOCC5)ccc4c3n2)ccc1Cl] | 2-(4-chloro-3-methylphenyl)-7-morpholino-5H-pyrido[3,2-b]indole-4-carboxamide | 2.545(a) | 421.01 |
| 502 | 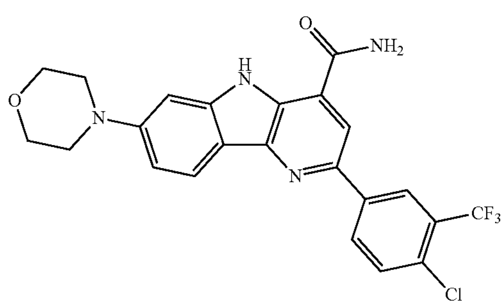 [SMILES: NC(=O)c1cc(-c2ccc(Cl)c(C(F)(F)F)c2)nc2c1[nH]c1cc(N3CCOCC3)ccc12] | 2-(4-chloro-3-(trifluoromethyl)phenyl)-7-morpholino-5H-pyrido[3,2-b]indole-4-carboxamide | 2.741(a) | 474.96 |
| 503 | 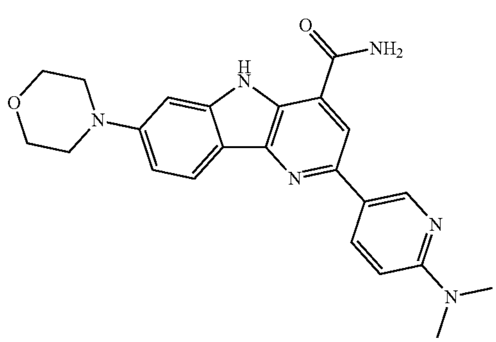 [SMILES: CN(C)c1ccc(-c2cc(C(N)=O)c3[nH]c4cc(N5CCOCC5)ccc4c3n2)cn1] | 2-(6-(dimethylamino)pyridin-3-yl)-7-morpholino-5H-pyrido[3,2-b]indole-4-carboxamide | 2.205(a) | 417.10 |

TABLE 30-continued

| Ex. # | Structure | Name | Retention time (min) | MS (ESI) m/z* |
|---|---|---|---|---|
| 504 | 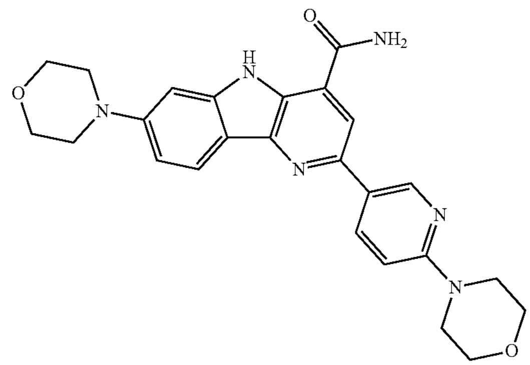 [SMILES: NC(=O)c1cc(-c2ccc(N3CCOCC3)nc2)nc2c1[nH]c1cc(N3CCOCC3)ccc12] | 7-morpholino-2-(6-morpholinopyridin-3-yl)-5H-pyrido[3,2-b]indole-4-carboxamide | 2.133(a) | 459.10 |
| 505 | 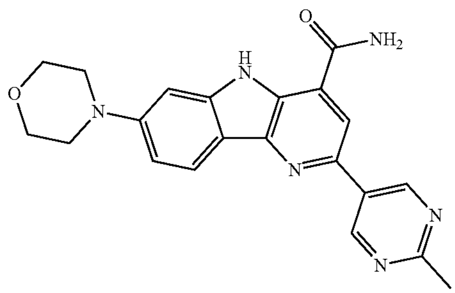 [SMILES: Cc1ncc(-c2cc(C(N)=O)c3[nH]c4cc(N5CCOCC5)ccc4c3n2)cn1] | 2-(2-methylpyrimidin-5-yl)-7-morpholino-5H-pyrido[3,2-b]indole-4-carboxamide | 1.983(a) | 389.08 |
| 506 | 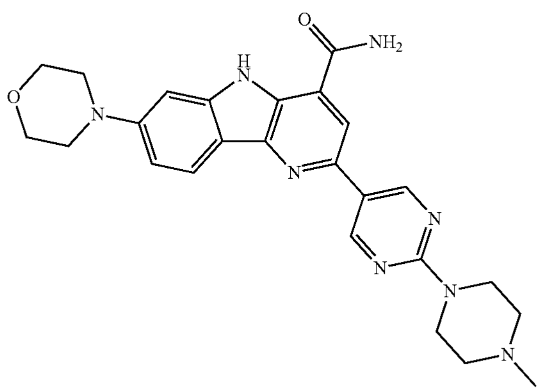 [SMILES: CN1CCN(c2ncc(-c3cc(C(N)=O)c4[nH]c5cc(N6CCOCC6)ccc5c4n3)cn2)CC1] | 2-(2-(4-methylpiperazin-1-yl)pyrimidin-5-yl)-7-morpholino-5H-pyrido[3,2-b]indole-4-carboxamide | 2.338(a) | 473.08 |

HPLC condition a: Luna C18 3.0 × 50 mm S10 column, 3 min gradient, 0-100% B, 4 mL/min.
Solvent A: 5% MeOH - 95% H₂O - 10 mM NH₄OAc;
Solvent B: 95% MeOH - 5% H₂O - 10 mM NH₄OAc.

EXAMPLE 507

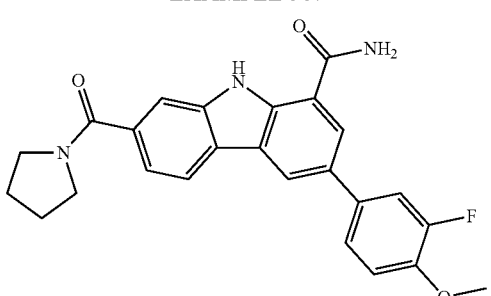

3-(3-Fluoro-4-methoxyphenyl)-7-(pyrrolidine-1-carbonyl)-9H-carbazole-1-carboxamide 8-Carbamoyl-6-(3-fluoro-4-methoxyphenyl)-9H-carbazole-2-carboxylic acid (16 mg, 0.042 mmol, Example 395), HATU (24.12 mg, 0.063 mmol) and DIPEA (0.022 mL, 0.127 mmol) were dissolved in DMF (1 mL) and stirred for 10 minutes. Pyrrolidine (9.2 mg, 0.13 mmol) was added and the mixture shaken over night. Purification by prep HPLC gave 9.4 mg 3-(3-fluoro-4-methoxyphenyl)-7-(pyrrolidine-1-carbonyl)-9H-carbazole-1-carboxamide. HPLC retention time 4.36 min. (Ascentis 4.6×50 mm 5 um C18, 2 ml/min, 0 to 100% B in 8 minutes, then 100% B for 1 minute. Solvent A: 5% CH₃CN—95% H₂O—10 mM NH₄OAc; Solvent B: 95% CH₃CN—5% H₂O—10 mM NH₄OAc). MS (ESI) m/e+=432 [M+H]⁺.

The following compounds in Table 31 have been synthesized utilizing the procedures described for Example 507. The crude reaction products for Examples 514, 523 and 528 were dried and de-protected by TFA in DCM (DCM, 0.5 mL, TFA, 0.5 mL) for 2 hours at RT before purification.

TABLE 31

| Ex. # | Structure | Name | Retention time (min) | MS (ESI) m/z* |
|---|---|---|---|---|
| 508 | 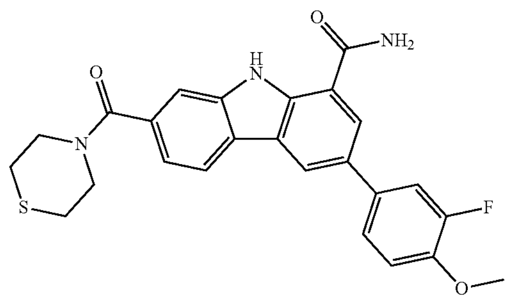 [SMILES: COc1ccc(-c2cc(C(N)=O)c3[nH]c4cc(C(=O)N5CCSCC5)ccc4c3c2)cc1F] | 3-(3-fluoro-4-methoxyphenyl)-7-(thiomorpholine-4-carbonyl)-9H-carbazole-1-carboxamide | 4.51(a) | 464 |
| 509 | 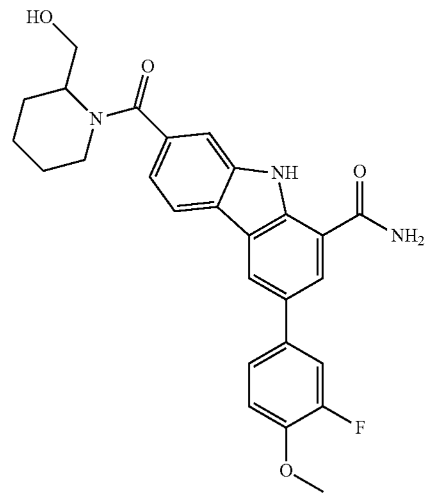 [SMILES: COc1ccc(-c2cc(C(N)=O)c3[nH]c4cc(C(=O)N5CCCCC5CO)ccc4c3c2)cc1F] | 3-(3-fluoro-4-methoxyphenyl)-7-(2-(hydroxymethyl)piperidine-1-carbonyl)-9H-carbazole-1-carboxamide | 4.08(a) | 476 |
| 510 | 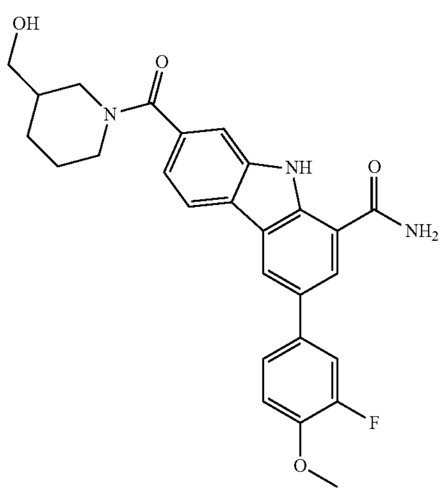 [SMILES: COc1ccc(-c2cc(C(N)=O)c3[nH]c4cc(C(=O)N5CCCC(CO)C5)ccc4c3c2)cc1F] | 3-(3-fluoro-4-methoxyphenyl)-7-(3-(hydroxymethyl)piperidine-1-carbonyl)-9H-carbazole-1-carboxamide | 3.88(a) | 476 |
| 511 | 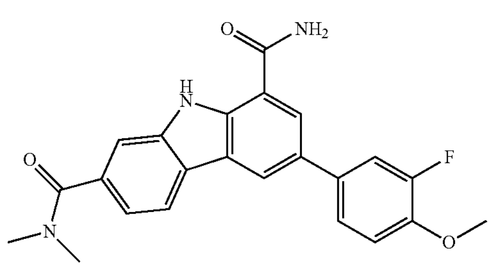 | 3-(3-fluoro-4-methoxyphenyl)-$N^7,N^7$-dimethyl-9H-carbazole-1,7-dicarboxamide | 4.06(a) | 406 |

TABLE 31-continued
| Ex. # | Structure | Name | Retention time (min) | MS (ESI) m/z* |
|---|---|---|---|---|
| 512 | 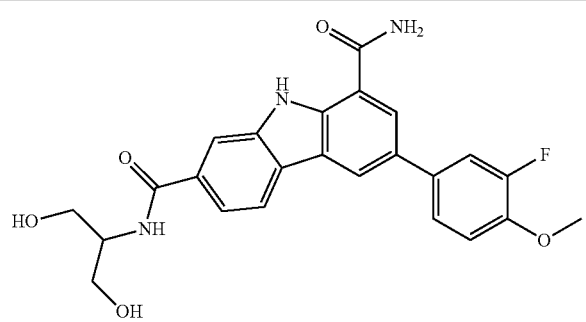 [SMILES: COc1ccc(-c2cc(C(N)=O)c3[nH]c4cc(C(=O)NC(CO)CO)ccc4c3c2)cc1F] | N⁷-(1,3-dihydroxypropan-2-yl)-3-(3-fluoro-4-methoxyphenyl)-9H-carbazole-1,7-dicarboxamide | 3.18(a) | 452 |
| 513 | 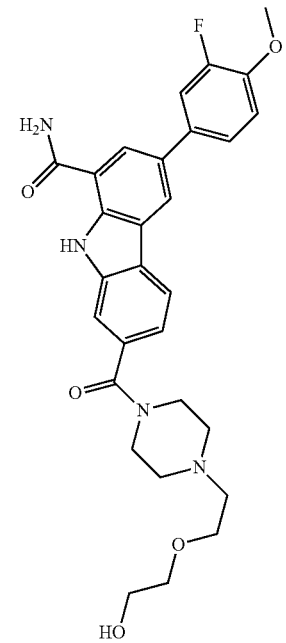 [SMILES: COc1ccc(-c2cc(C(N)=O)c3[nH]c4cc(C(=O)N5CCN(CCOCCO)CC5)ccc4c3c2)cc1F] | 3-(3-fluoro-4-methoxyphenyl)-7-((4-(2-(2-hydroxyethoxy)ethyl)-1-piperazinyl)carbonyl)-9H-carbazole-1-carboxamide | 3.53(a) | 535 |
| 514 | 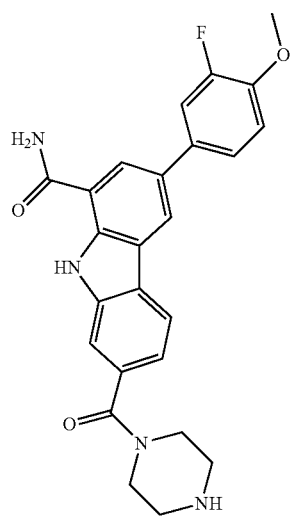 [SMILES: COc1ccc(-c2cc(C(N)=O)c3[nH]c4cc(C(=O)N5CCNCC5)ccc4c3c2)cc1F] | 3-(3-fluoro-4-methoxyphenyl)-7-(1-piperazinylcarbonyl)-9H-carbazole-1-carboxamide | 3.76(a) | 447 |

TABLE 31-continued
| Ex. # | Structure | Name | Retention time (min) | MS (ESI) m/z* |
|---|---|---|---|---|
| 515 | 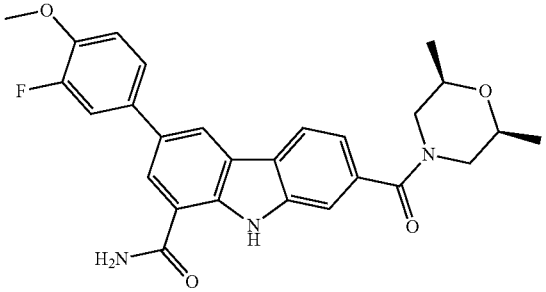 | 7-(((2R,6S)-2,6-dimethyl-4-morpholinyl)carbonyl)-3-(3-fluoro-4-methoxyphenyl)-9H-carbazole-1-carboxamide | 4.54(a) | 476 |
| 516 | 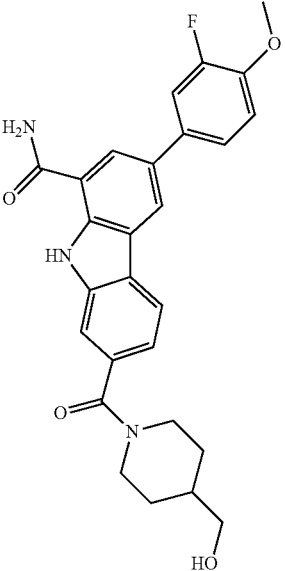 [SMILES: COc1ccc(-c2cc(C(N)=O)c3[nH]c4cc(C(=O)N5CCC(CO)CC5)ccc4c3c2)cc1F] | 3-(3-fluoro-4-methoxyphenyl)-7-((4-(hydroxymethyl)-1-piperidinyl)carbonyl)-9H-carbazole-1-carboxamide | 3.64(a) | 476 |
| 517 | 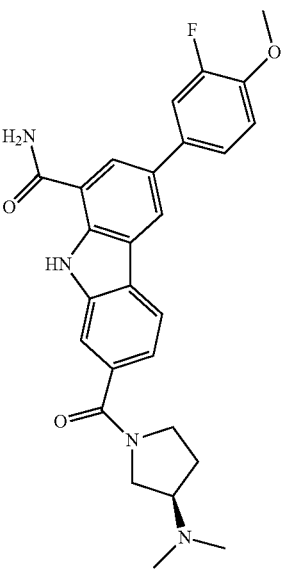 [SMILES: COc1ccc(-c2cc(C(N)=O)c3[nH]c4cc(C(=O)N5CC[C@@H](N(C)C)C5)ccc4c3c2)cc1F] | 7-(((3R)-3-(dimethylamino)-1-pyrrolidinyl)carbonyl)-3-(3-fluoro-4-methoxyphenyl)-9H-carbazole-1-carboxamide | 3.91(a) | 475 |

TABLE 31-continued
| Ex. # | Structure | Name | Retention time (min) | MS (ESI) m/z* |
|---|---|---|---|---|
| 518 | 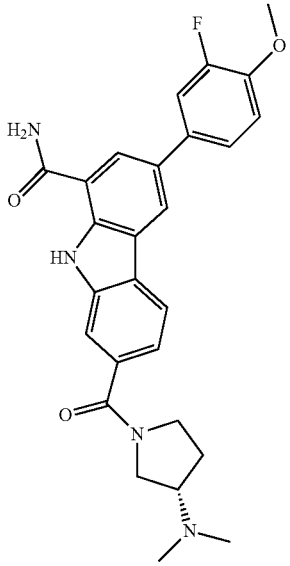 [SMILES: COc1ccc(-c2cc(C(N)=O)c3[nH]c4cc(C(=O)N5CC[C@H](N(C)C)C5)ccc4c3c2)cc1F] | 7-(((3S)-3-(dimethylamino)-1-pyrrolidinyl)carbonyl)-3-(3-fluoro-4-methoxyphenyl)-9H-carbazole-1-carboxamide | 3.94(a) | 475 |
| 519 | 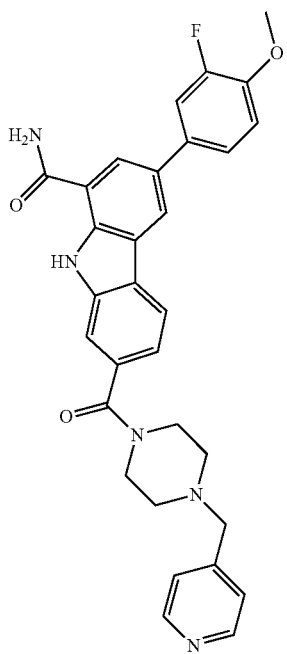 [SMILES: COc1ccc(-c2cc(C(N)=O)c3[nH]c4cc(C(=O)N5CCN(Cc6ccncc6)CC5)ccc4c3c2)cc1F] | 3-(3-fluoro-4-methoxyphenyl)-7-((4-(4-pyridinylmethyl)-1-piperazinyl)carbonyl)-9H-carbazole-1-carboxamide | 4.07(a) | 538 |

TABLE 31-continued

| Ex. # | Structure | Name | Retention time (min) | MS (ESI) m/z* |
|---|---|---|---|---|
| 520 | 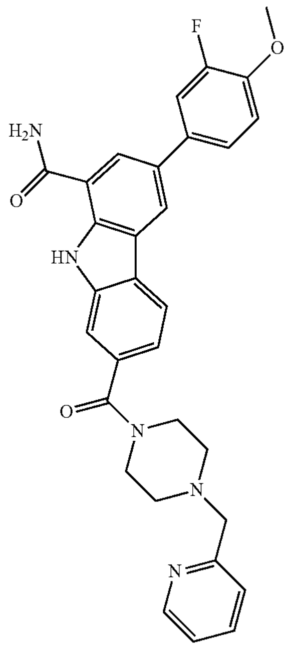 [SMILES: COc1ccc(-c2cc(C(N)=O)c3[nH]c4cc(C(=O)N5CCN(Cc6ccccn6)CC5)ccc4c3c2)cc1F] | 3-(3-fluoro-4-methoxyphenyl)-7-((4-(2-pyridinylmethyl)-1-piperazinyl)carbonyl)-9H-carbazole-1-carboxamide | 3.98(a) | 538 |
| 521 | 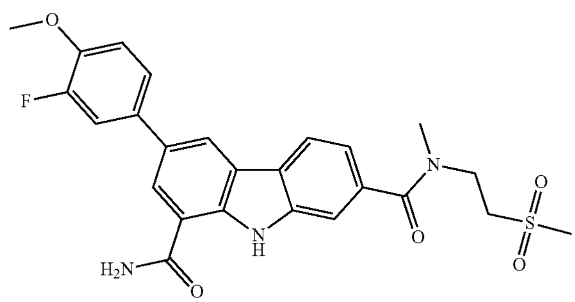 | 3-(3-fluoro-4-methoxyphenyl)-N$^7$-methyl-N$^7$-(2-(methylsulfonyl)ethyl)-9H-carbazole-1,7-dicarboxamide | 3.83(a) | 498 |
| 522 | 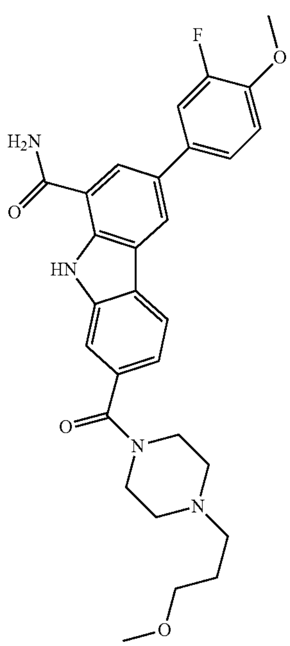 [SMILES: COCCCN1CCN(C(=O)c2ccc3c(c2)[nH]c2c(C(N)=O)cc(-c4ccc(OC)c(F)c4)cc23)CC1] | 3-(3-fluoro-4-methoxyphenyl)-7-((4-(3-methoxypropyl)-1-piperazinyl)carbonyl)-9H-carbazole-1-carboxamide | 4.01(a) | 519 |

TABLE 31-continued

| Ex. # | Structure | Name | Retention time (min) | MS (ESI) m/z* |
|---|---|---|---|---|
| 523 | 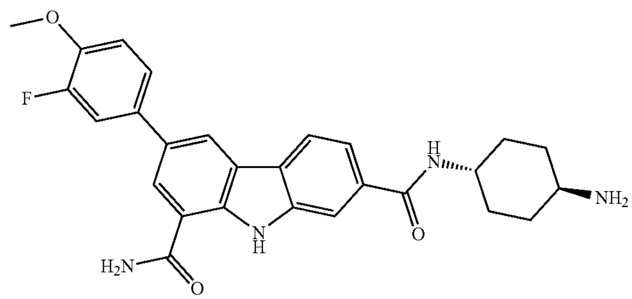 [SMILES: COc1ccc(-c2cc(C(N)=O)c3[nH]c4cc(C(=O)N[C@H]5CC[C@H](N)CC5)ccc4c3c2)cc1F] | N⁷-(trans-4-aminocyclohexyl)-3-(3-fluoro-4-methoxyphenyl)-9H-carbazole-1,7-dicarboxamide | 3.81(a) | 475 |
| 524 | 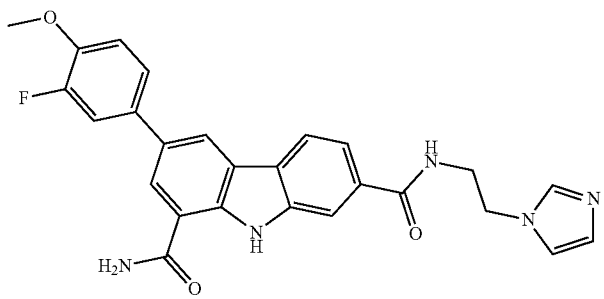 [SMILES: COc1ccc(-c2cc(C(N)=O)c3[nH]c4cc(C(=O)NCCn5ccnc5)ccc4c3c2)cc1F] | 3-(3-fluoro-4-methoxyphenyl)-N⁷-(2-(1H-imidazol-1-yl)ethyl)-9H-carbazole-1,7-dicarboxamide | 3.61(a) | 472 |
| 525 | 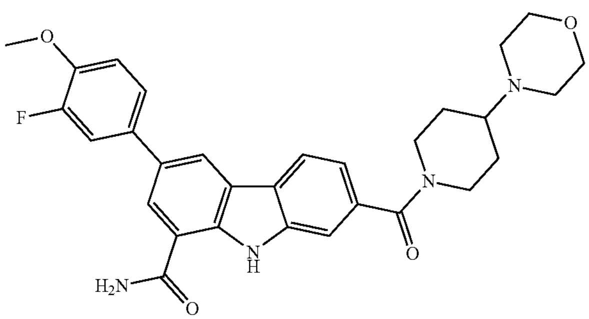 [SMILES: COc1ccc(-c2cc(C(N)=O)c3[nH]c4cc(C(=O)N5CCC(N6CCOCC6)CC5)ccc4c3c2)cc1F] | 3-(3-fluoro-4-methoxyphenyl)-7-((4-(4-morpholinyl)-1-piperidinyl)carbonyl)-9H-carbazole-1-carboxamide | 3.84(a) | 531 |
| 526 | 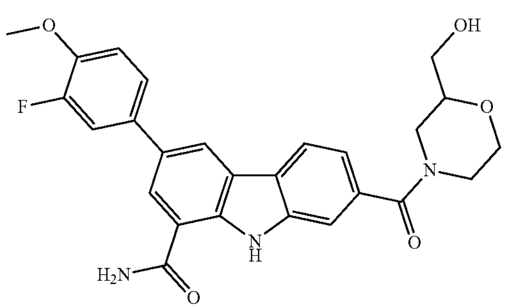 [SMILES: COc1ccc(-c2cc(C(N)=O)c3[nH]c4cc(C(=O)N5CCOC(CO)C5)ccc4c3c2)cc1F] | 3-(3-fluoro-4-methoxyphenyl)-7-((2-(hydroxymethyl)-4-morpholinyl)carbonyl)-9H-carbazole-1-carboxamide | 3.51(a) | 478 |
| 527 | 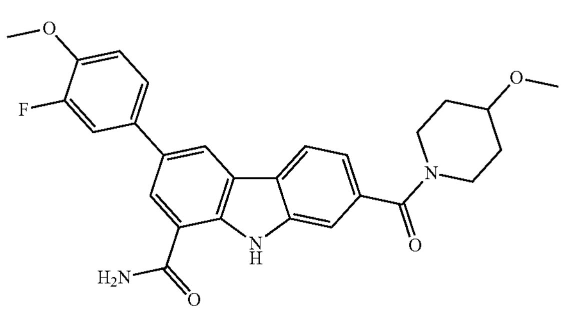 | 3-(3-fluoro-4-methoxyphenyl)-7-((4-methoxy-1-piperidinyl)carbonyl)-9H-carbazole-1-carboxamide | 4.32(a) | 476 |

TABLE 31-continued

| Ex. # | Structure | Name | Retention time (min) | MS (ESI) m/z* |
|---|---|---|---|---|
| 528 | 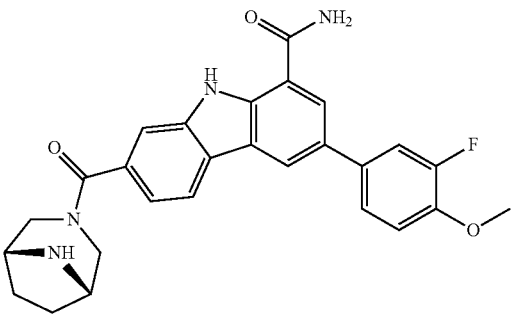 [SMILES: COc1ccc(-c2cc(C(N)=O)c3[nH]c4cc(C(=O)N5C[C@H]6CC[C@@H](C5)N6)ccc4c3c2)cc1F] | 7-((1R,5S)-3,8-diazabicyclo[3.2.1]oct-3-ylcarbonyl)-3-(3-fluoro-4-methoxyphenyl)-9H-carbazole-1-carboxamide | 3.91(a) | 473 |
| 529 | 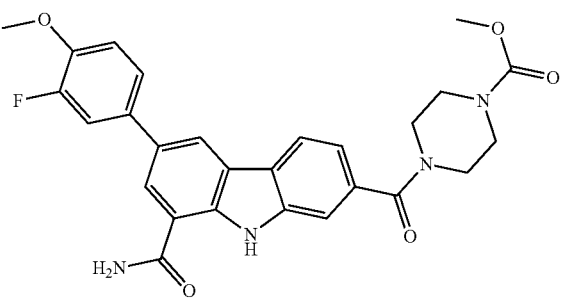 [SMILES: COC(=O)N1CCN(C(=O)c2ccc3c(c2)[nH]c2c(C(N)=O)cc(-c4ccc(OC)c(F)c4)cc23)CC1] | methyl 4-((8-carbamoyl-6-(3-fluoro-4-methoxyphenyl)-9H-carbazol-2-yl)carbonyl)-1-piperazinecarboxylate | 4.11(a) | 505 |
| 530 | 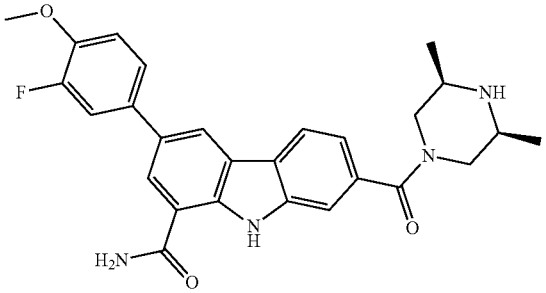 | 7-(((3R,5S)-3,5-dimethyl-1-piperazinyl)carbonyl)-3-(3-fluoro-4-methoxyphenyl)-9H-carbazole-1-carboxamide | 3.62(b) | 475 |
| 531 | 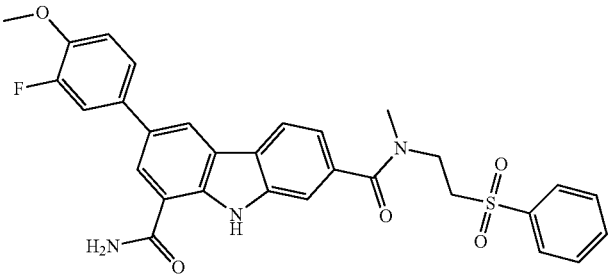 [SMILES: COc1ccc(-c2cc(C(N)=O)c3[nH]c4cc(C(=O)N(C)CCS(=O)(=O)c5ccccc5)ccc4c3c2)cc1F] | 3-(3-fluoro-4-methoxyphenyl)-N$^7$-methyl-N$^7$-(2-(phenylsulfonyl)ethyl)-9H-carbazole-1,7-dicarboxamide | 4.41(b) | 560 |
| 532 | 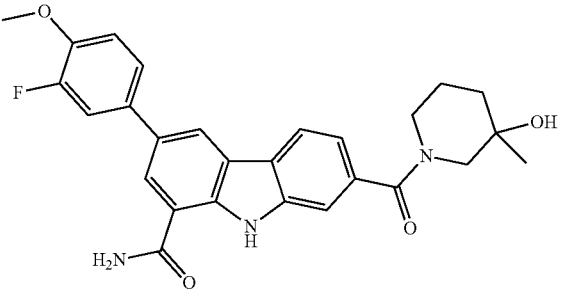 | 3-(3-fluoro-4-methoxyphenyl)-7-((3-hydroxy-3-methyl-1-piperidinyl)carbonyl)-9H-carbazole-1-carboxamide | 3.41(b) | 494 [M + H$_2$O + H]$^+$ |

TABLE 31-continued

| Ex. # | Structure | Name | Retention time (min) | MS (ESI) m/z* |
|---|---|---|---|---|
| 533 | 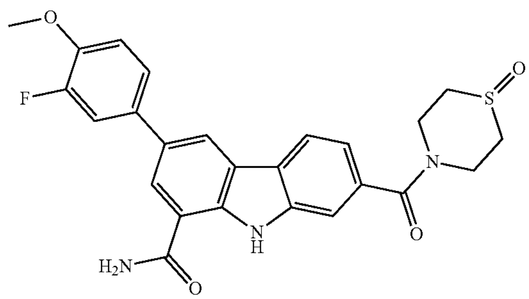 [SMILES: COc1ccc(-c2cc(C(N)=O)c3[nH]c4cc(C(=O)N5CCS(=O)CC5)ccc4c3c2)cc1F] | 3-(3-fluoro-4-methoxyphenyl)-7-((thiomorpholine-S-oxide)-4-carbonyl)-9H-carbazole-1-carboxamide | 3.40(b) | 480 |
| 534 | 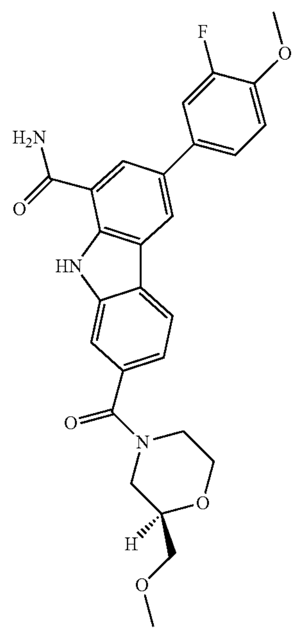 [SMILES: COC[C@H]1CN(C(=O)c2ccc3c(c2)[nH]c2c(C(N)=O)cc(-c4ccc(OC)c(F)c4)cc23)CCO1] | 3-(3-fluoro-4-methoxyphenyl)-7-(((2R)-2-(methoxymethyl)-4-morpholinyl)carbonyl)-9H-carbazole-1-carboxamide | 3.99(b) | 492 |
| 535 | 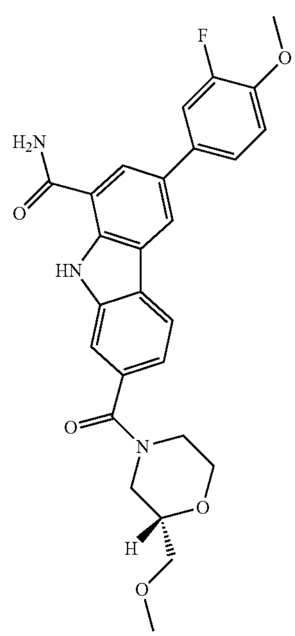 [SMILES: COC[C@@H]1CN(C(=O)c2ccc3c(c2)[nH]c2c(C(N)=O)cc(-c4ccc(OC)c(F)c4)cc23)CCO1] | 3-(3-fluoro-4-methoxyphenyl)-7-(((2S)-2-(methoxymethyl)-4-morpholinyl)carbonyl)-9H-carbazole-1-carboxamide | 4.09(b) | 492 |

TABLE 31-continued

| Ex. # | Structure | Name | Retention time (min) | MS (ESI) m/z* |
|---|---|---|---|---|
| 536 | 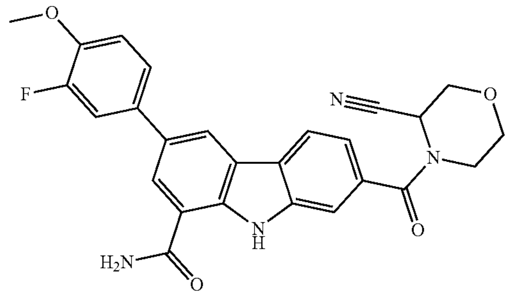 [SMILES: COc1ccc(-c2cc(C(N)=O)c3[nH]c4cc(C(=O)N5CCOCC5C#N)ccc4c3c2)cc1F] | 7-((3-cyano-4-morpholinyl)carbonyl)-3-(3-fluoro-4-methoxyphenyl)-9H-carbazole-1-carboxamide | 4.32(b) | 473 |
| 537 | 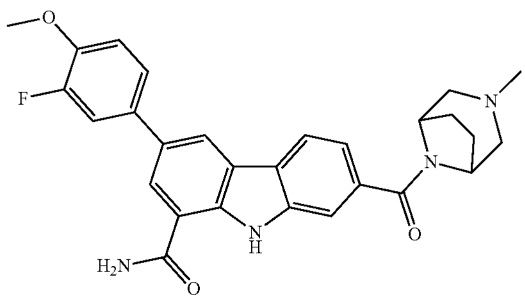 | 3-(3-fluoro-4-methoxyphenyl)-7-((3-methyl-3,8-diazabicyclo[3.2.1]oct-8-yl)carbonyl)-9H-carbazole-1-carboxamide | 4.17(b) | 487 |
| 538 | 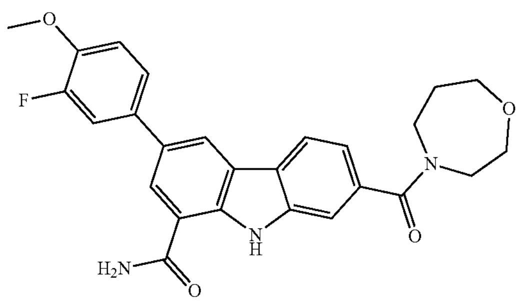 [SMILES: COc1ccc(-c2cc(C(N)=O)c3[nH]c4cc(C(=O)N5CCCOCC5)ccc4c3c2)cc1F] | 3-(3-fluoro-4-methoxyphenyl)-7-(1,4-oxazepan-4-ylcarbonyl)-9H-carbazole-1-carboxamide | 3.93(b) | 462 |
| 539 | 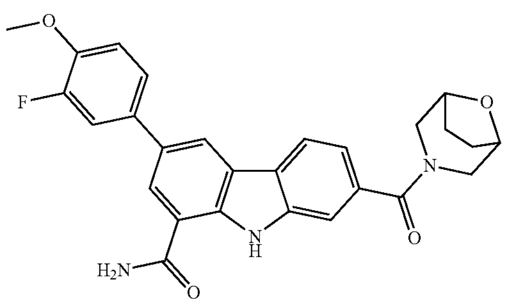 [SMILES: COc1ccc(-c2cc(C(N)=O)c3[nH]c4cc(C(=O)N5CC6CCC(C5)O6)ccc4c3c2)cc1F] | 3-(3-fluoro-4-methoxyphenyl)-7-(8-oxa-3-azabicyclo[3.2.1]oct-3-ylcarbonyl)-9H-carbazole-1-carboxamide | 4.15(b) | 474 |
| 540 | 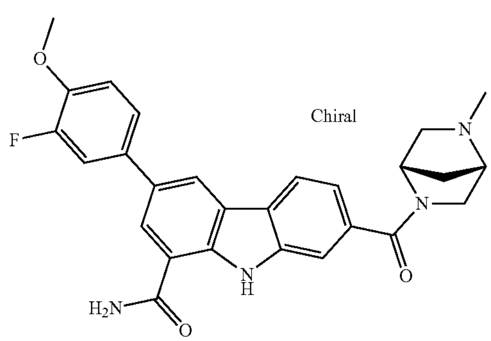 [SMILES: COc1ccc(-c2cc(C(N)=O)c3[nH]c4cc(C(=O)N5C[C@@H]6C[C@H]5CN6C)ccc4c3c2)cc1F] | 3-(3-fluoro-4-methoxyphenyl)-7-((1S,4S)-5-methyl-2,5-diazabicyclo[2.2.1]heptane-2-carbonyl)-9H-carbazole-1-carboxamide | 3.79(b) | 473 |

TABLE 31-continued

| Ex. # | Structure | Name | Retention time (min) | MS (ESI) m/z* |
|---|---|---|---|---|
| 541 | 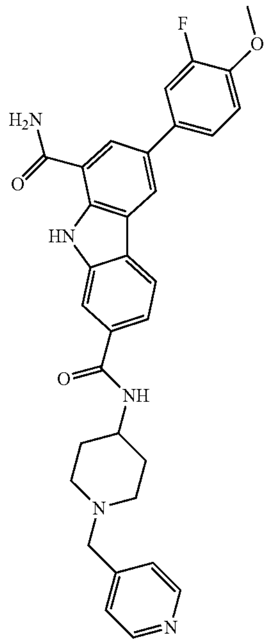 [SMILES: COc1ccc(-c2cc(C(N)=O)c3[nH]c4cc(C(=O)NC5CCN(Cc6ccncc6)CC5)ccc4c3c2)cc1F] | 3-(3-fluoro-4-methoxyphenyl)-$N^7$-(1-(4-pyridinylmethyl)-4-piperidinyl)-9H-carbazole-1,7-dicarboxamide | 4.06(b) | 552 |
| 542 | 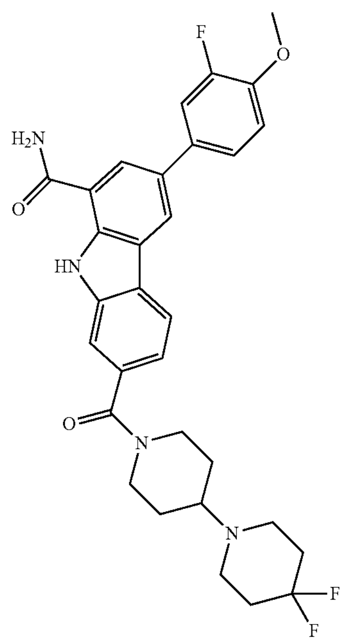 [SMILES: COc1ccc(-c2cc(C(N)=O)c3[nH]c4cc(C(=O)N5CCC(N6CCC(F)(F)CC6)CC5)ccc4c3c2)cc1F] | 7-((4,4-difluoro-1,4'-bipiperidin-1'-yl)carbonyl)-3-(3-fluoro-4-methoxyphenyl)-9H-carbazole-1-carboxamide | 4.62(b) | 565 |
| 543 | 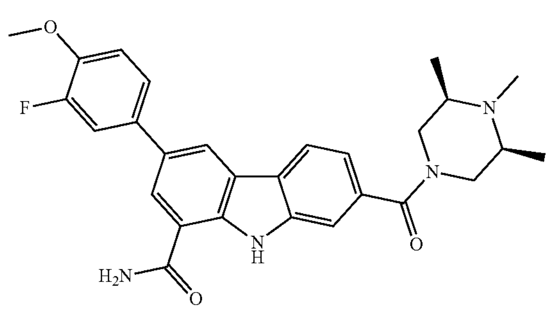 | 3-(3-fluoro-4-methoxyphenyl)-7-(((3R,5S)-3,4,5-trimethyl-1-piperazinyl)carbonyl)-9H-carbazole-1-carboxamide | 3.99(b) | 489 |

TABLE 31-continued

| Ex. # | Structure | Name | Retention time (min) | MS (ESI) m/z* |
|---|---|---|---|---|
| 544 | 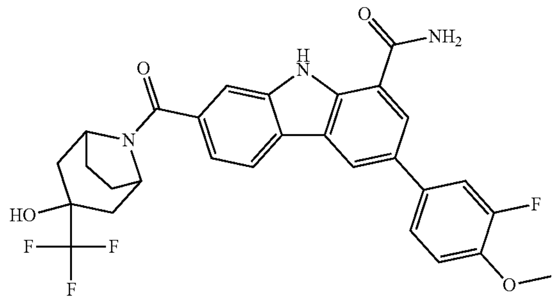 [SMILES: COc1ccc(-c2cc(C(N)=O)c3[nH]c4cc(C(=O)N5C6CCC5CC(O)(C(F)(F)F)C6)ccc4c3c2)cc1F] | 3-(3-fluoro-4-methoxyphenyl)-7-((3-hydroxy-3-(trifluoromethyl)-8-azabicyclo[3.2.1]oct-8-yl)carbonyl)-9H-carbazole-1-carboxamide | 4.47(a) | 556 |

HPLC condition a: Ascentis 4.6 × 50 mm 5 um C18, 2 ml/min, 0 to 100% B in 8 minutes, then 100% B for 1 minute.
Solvent A: 5% CH$_3$CN - 95% H$_2$O - 10 mM NH$_4$OAc;
Solvent B: 95% CH$_3$CN - 5% H$_2$O - 10 mM NH$_4$OAc.
HPLC condition b: SUPELCO ® Ascentis Express 4.6 × 50 mm 2.7 um C18, 2 ml/min, 0 to 100% B in 8 minutes, then 100% B for 1 minute.
Solvent A: 5% CH$_3$CN - 95% H$_2$O - 10 mM NH$_4$OAc;
Solvent B: 95% CH$_3$CN - 5% H$_2$O - 10 mM NH$_4$OAc.

Observed MS signals are consistent with [M+H]$^+$ except the examples where specifically mentioned.

EXAMPLE 545

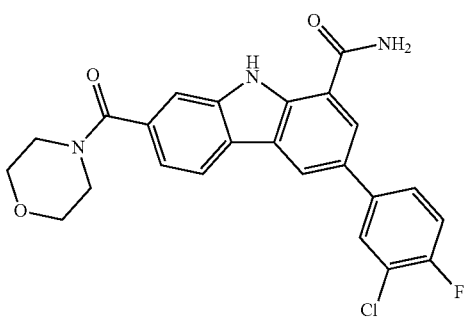 [SMILES: NC(=O)c1cc(-c2ccc(F)c(Cl)c2)cc2c1[nH]c1cc(C(=O)N3CCOCC3)ccc12]

3-(3-Chloro-4-fluorophenyl)-7-(morpholine-4-carbonyl)-9H-carbazole-1-carboxamide 3-Bromo-7-(morpholine-4-carbonyl)-9H-carbazole-1-carboxamide (33 mg, 0.075 mmol, Example 144A) was dissolved in MeOH (0.6 mL) and added into a microwave vial containing 3-chloro-4-fluorophenylboronic acid (55.7 mg, 0.32 mmol), followed by addition of Na$_2$CO$_3$ (0.12 mL of a 2M aq. solution) and PdCl$_2$(dppf)-CH$_2$Cl$_2$ (6.12 mg, 7.50 µmol) and Toluene (1.2 mL). The vial was sealed and heated in a BIOTAGE® microwave reactor for 15 minutes at 160° C. The reaction mixture was evaporated to dryness, dissolved in DMF+isopropanol and purified by preparative HPLC. Product containing fractions were combined and evaporated to dryness to give 6.0 mg 3-(3-chloro-4-fluorophenyl)-7-(morpholine-4-carbonyl)-9H-carbazole-1-carboxamide. HPLC retention time 4.72 min. (SUPELCO® Ascentis Express 4.6× 50 mm 2.7 um C18, 2 ml/min, 0 to 100% B in 8 minutes, then 100% B for 1 minute. Solvent A: 5% CH$_3$CN—95% H$_2$O—10 mM NH$_4$OAc; Solvent B: 95% CH$_3$CN—5% H$_2$O—10 mM NH$_4$OAc). MS (ESI) m/e+=452 [M+H]$^+$.

The following compounds in Table 32 have been synthesized utilizing the procedures described for Example 545.

TABLE 32

| Ex. # | Structure | Name | Retention time (min) | MS (ESI) m/z* |
|---|---|---|---|---|
| 546 | 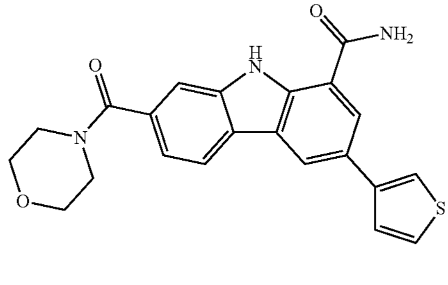 [SMILES: NC(=O)c1cc(-c2ccsc2)cc2c1[nH]c1cc(C(=O)N3CCOCC3)ccc12] | 7-(4-morpholinylcarbonyl)-3-(3-thienyl)-9H-carbazole-1-carboxamide | 4.04 | 406 |

TABLE 32-continued

| Ex. # | Structure | Name | Retention time (min) | MS (ESI) m/z* |
|---|---|---|---|---|
| 547 | 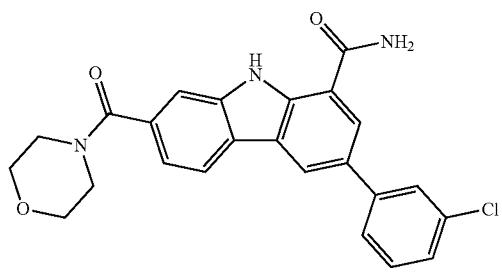 [SMILES: NC(=O)c1cc(-c2cccc(Cl)c2)cc2c1[nH]c1cc(C(=O)N3CCOCC3)ccc12] | 3-(3-chlorophenyl)-7-(4-morpholinylcarbonyl)-9H-carbazole-1-carboxamide | 4.65 | 434 |
| 548 | 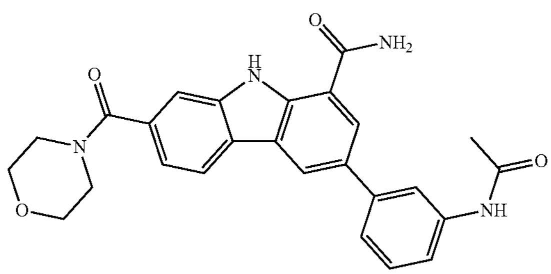 [SMILES: CC(=O)Nc1cccc(-c2cc(C(N)=O)c3[nH]c4cc(C(=O)N5CCOCC5)ccc4c3c2)c1] | 3-(3-acetamidophenyl)-7-(4-morpholinylcarbonyl)-9H-carbazole-1-carboxamide | 3.26 | 457 |
| 549 | 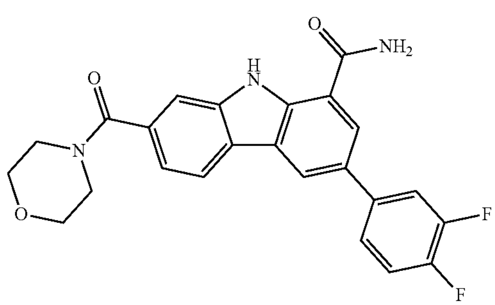 [SMILES: NC(=O)c1cc(-c2ccc(F)c(F)c2)cc2c1[nH]c1cc(C(=O)N3CCOCC3)ccc12] | 3-(3,4-difluorophenyl)-7-(4-morpholinylcarbonyl)-9H-carbazole-1-carboxamide | 4.47 | 436 |
| 551 | 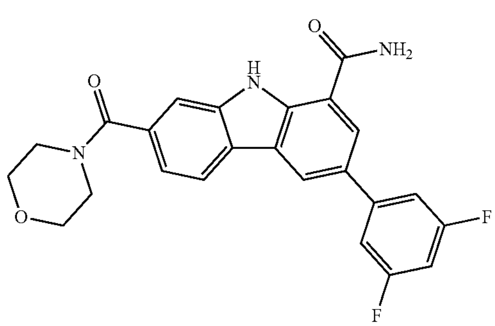 [SMILES: NC(=O)c1cc(-c2cc(F)cc(F)c2)cc2c1[nH]c1cc(C(=O)N3CCOCC3)ccc12] | 3-(3,5-difluorophenyl)-7-(4-morpholinylcarbonyl)-9H-carbazole-1-carboxamide | 4.53 | 436 |
| 553 | 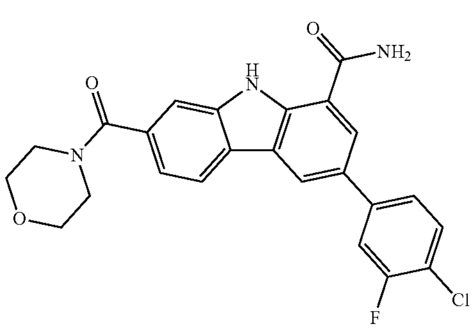 [SMILES: NC(=O)c1cc(-c2ccc(Cl)c(F)c2)cc2c1[nH]c1cc(C(=O)N3CCOCC3)ccc12] | 3-(4-chloro-3-fluorophenyl)-7-(4-morpholinylcarbonyl)-9H-carbazole-1-carboxamide | 4.79 | 452 |

TABLE 32-continued

| Ex. # | Structure | Name | Retention time (min) | MS (ESI) m/z* |
|---|---|---|---|---|
| 554 | 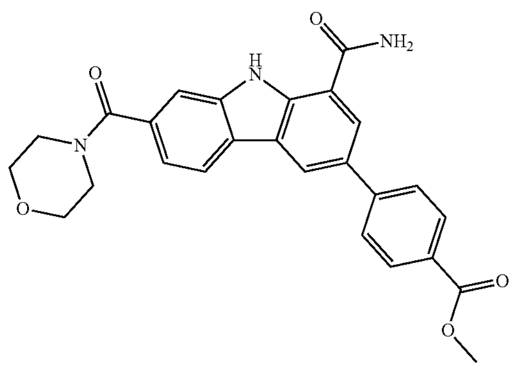 [SMILES: COC(=O)c1ccc(-c2cc(C(N)=O)c3[nH]c4cc(C(=O)N5CCOCC5)ccc4c3c2)cc1] | methyl 4-(1-carbamoyl-7-(4-morpholinylcarbonyl)-9H-carbazol-3-yl)benzoate | 4.08 | 458 |
| 556 | 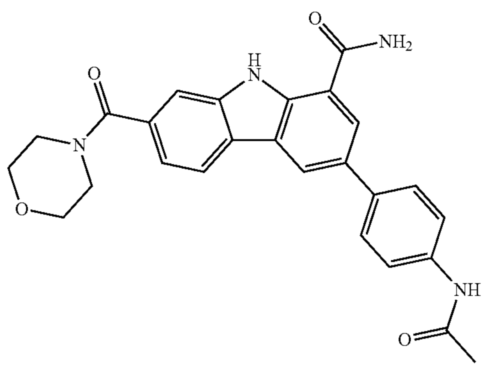 [SMILES: CC(=O)Nc1ccc(-c2cc(C(N)=O)c3[nH]c4cc(C(=O)N5CCOCC5)ccc4c3c2)cc1] | 3-(4-acetamidophenyl)-7-(4-morpholinylcarbonyl)-9H-carbazole-1-carboxamide | 3.12 | 457 |
| 557 | 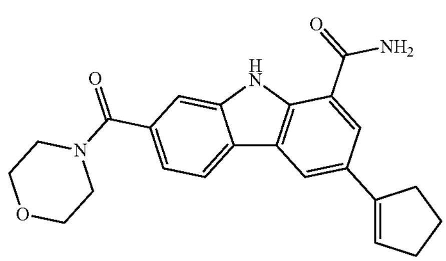 [SMILES: NC(=O)c1cc(C2=CCCC2)cc2c1[nH]c1cc(C(=O)N3CCOCC3)ccc12] | 3-(1-cyclopenten-1-yl)-7-(4-morpholinylcarbonyl)-9H-carbazole-1-carboxamide | 4.36 | 390 |
| 558 | 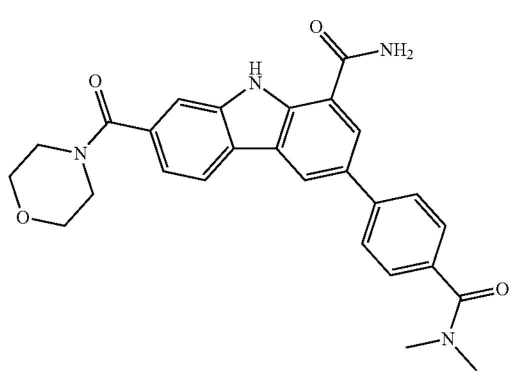 [SMILES: CN(C)C(=O)c1ccc(-c2cc(C(N)=O)c3[nH]c4cc(C(=O)N5CCOCC5)ccc4c3c2)cc1] | 3-(4-(dimethylcarbamoyl)phenyl)-7-(4-morpholinylcarbonyl)-9H-carbazole-1-carboxamide | 3.22 | 471 |

TABLE 32-continued

| Ex. # | Structure | Name | Retention time (min) | MS (ESI) m/z* |
|---|---|---|---|---|
| 559 | 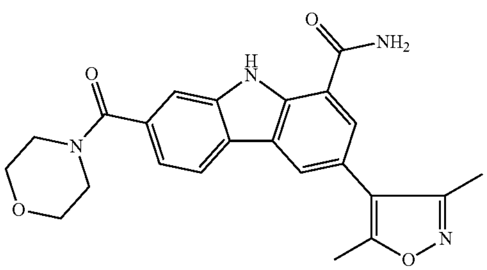 [SMILES: Cc1noc(C)c1-c1cc(C(N)=O)c2[nH]c3cc(C(=O)N4CCOCC4)ccc3c2c1] | 3-(3,5-dimethyl-4-isoxazolyl)-7-(4-morpholinylcarbonyl)-9H-carbazole-1-carboxamide | 3.40 | 419 |
| 560 | 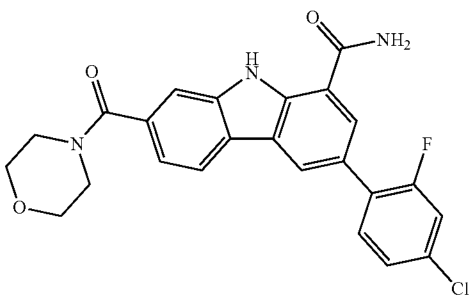 [SMILES: NC(=O)c1cc(-c2ccc(Cl)cc2F)cc2c1[nH]c1cc(C(=O)N3CCOCC3)ccc12] | 3-(4-chloro-2-fluorophenyl)-7-(4-morpholinylcarbonyl)-9H-carbazole-1-carboxamide | 4.71 | 452 |
| 561 | 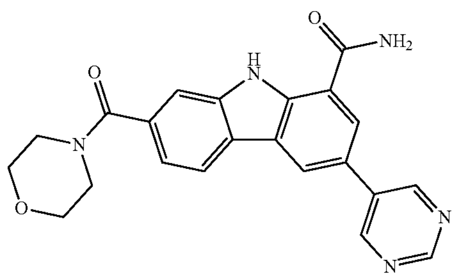 [SMILES: NC(=O)c1cc(-c2cncnc2)cc2c1[nH]c1cc(C(=O)N3CCOCC3)ccc12] | 7-(4-morpholinylcarbonyl)-3-(5-pyrimidinyl)-9H-carbazole-1-carboxamide | 2.68 | 402 |
| 562 | 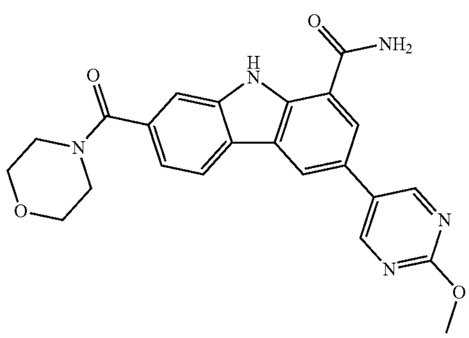 [SMILES: COc1ncc(-c2cc(C(N)=O)c3[nH]c4cc(C(=O)N5CCOCC5)ccc4c3c2)cn1] | 3-(2-methoxy-5-pyrimidinyl)-7-(4-morpholinylcarbonyl)-9H-carbazole-1-carboxamide | 3.13 | 432 |
| 563 | 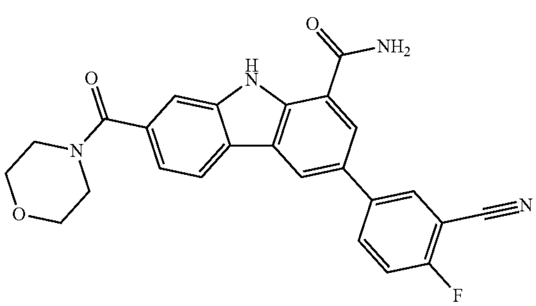 [SMILES: N#Cc1cc(-c2cc(C(N)=O)c3[nH]c4cc(C(=O)N5CCOCC5)ccc4c3c2)ccc1F] | 3-(3-cyano-4-fluorophenyl)-7-(4-morpholinylcarbonyl)-9H-carbazole-1-carboxamide | 4.22 | 443 |

TABLE 32-continued

| Ex. # | Structure | Name | Retention time (min) | MS (ESI) m/z* |
|---|---|---|---|---|
| 564 | 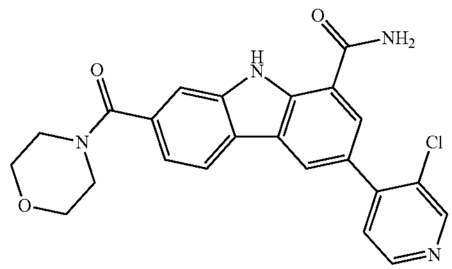 [SMILES: NC(=O)c1cc(-c2ccncc2Cl)cc2c1[nH]c1cc(C(=O)N3CCOCC3)ccc12] | 3-(3-chloro-4-pyridinyl)-7-(4-morpholinylcarbonyl)-9H-carbazole-1-carboxamide | 3.36 | 435 |
| 565 | 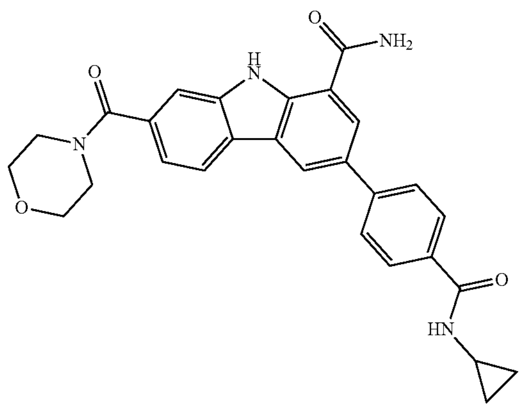 [SMILES: NC(=O)c1cc(-c2ccc(C(=O)NC3CC3)cc2)cc2c1[nH]c1cc(C(=O)N3CCOCC3)ccc12] | 3-(4-(cyclopropylcarbamoyl)phenyl)-7-(4-morpholinylcarbonyl)-9H-carbazole-1-carboxamide | 3.31 | 483 |
| 567 | 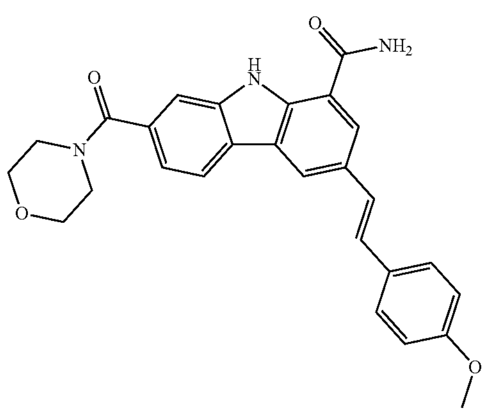 [SMILES: COc1ccc(/C=C/c2cc(C(N)=O)c3[nH]c4cc(C(=O)N5CCOCC5)ccc4c3c2)cc1] | 3-((E)-2-(4-methoxyphenyl)vinyl)-7-(4-morpholinylcarbonyl)-9H-carbazole-1-carboxamide | 4.56 | 456 |
| 568 | 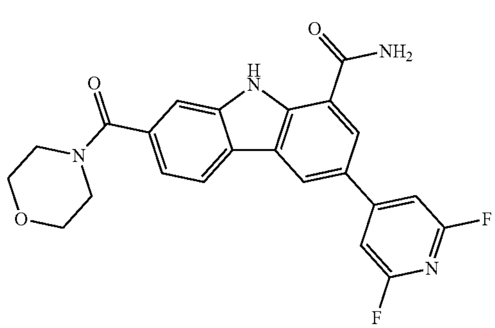 [SMILES: NC(=O)c1cc(-c2cc(F)nc(F)c2)cc2c1[nH]c1cc(C(=O)N3CCOCC3)ccc12] | 3-(2,6-difluoro-4-pyridinyl)-7-(4-morpholinylcarbonyl)-9H-carbazole-1-carboxamide | 4.10 | 437 |

TABLE 32-continued

| Ex. # | Structure | Name | Retention time (min) | MS (ESI) m/z* |
|---|---|---|---|---|
| 569 | 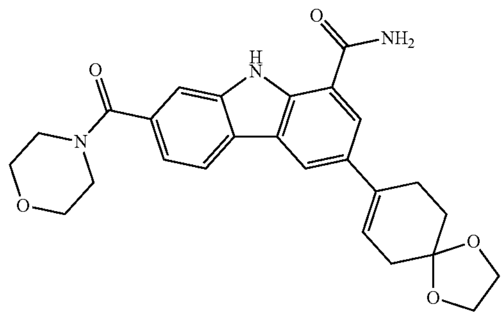 [SMILES: NC(=O)c1cc(C2=CCC3(CC2)OCCO3)cc2c1[nH]c1cc(C(=O)N3CCOCC3)ccc12] | 3-(1,4-dioxaspiro[4.5]dec-7-en-8-yl)-7-(4-morpholinylcarbonyl)-9H-carbazole-1-carboxamide | 3.59 | 462 |

HPLC conditions: SUPELCO ® Ascentis Express 4.6 × 50 mm 2.7 um C18, 2 ml/min, 0 to 100% B in 8 minutes, then 100% B for 1 minute.
Solvent A: 5% CH$_3$CN - 95% H$_2$O - 10 mM NH$_4$OAc;
Solvent B: 95% CH$_3$CN - 5% H$_2$O - 10 mM NH$_4$OAc.

All observed MS signals are consistent with [M+H]$^+$.

EXAMPLE 570

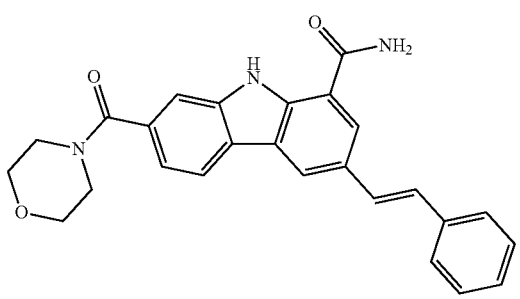 [SMILES: NC(=O)c1cc(/C=C/c2ccccc2)cc2c1[nH]c1cc(C(=O)N3CCOCC3)ccc12]

(E)-7-(Morpholine-4-carbonyl)-3-styryl-9H-carbazole-1-carboxamide

3-Bromo-7-(morpholine-4-carbonyl)-9H-carbazole-1-carboxamide (40 mg, 0.10 mmol, Example 144A) and dicyclohexy(2',6'-dimethoxybiphenyl-2)phosphine (8.2 mg) were dissolved in dioxane (1.5 mL) and added into a 2-ml microwave vial containing (E)-styrylboronic acid (37 mg, 0.25 mmol), followed by addition of potassium phosphate (64 mg in 0.15 mL water) into above vials. Pd(OAc)$_2$ (4.49 mg, 20.00 µmol) was added as solid. The vial was sealed and heated to 130° C. for 10 minutes. The crude reaction mixture was evaporated to dryness, dissolved in DMF+MeOH (1.2 mL+0.4 mL), filtered and purified by preparative HPLC. Product containing fractions were combined and evaporated to dryness to give 1.4 mg (E)-7-(morpholine-4-carbonyl)-3-styryl-9H-carbazole-1-carboxamide. HPLC retention time 4.39 min. (SUPELCO® Ascentis Express 4.5×50 mm 3 um C18, 2 ml/min, 5 to 95% B in 8 minutes, then 95% B for 1 minute. Solvent A: 5% CH$_3$CN—95% H$_2$O—10 mM NH$_4$OAc; Solvent B: 95% CH$_3$CN—5% H$_2$O—10 mM NH$_4$OAc). MS (ESI) m/e+=426 [M+H]$^+$.

The following compounds in Table 33 have been synthesized utilizing the procedures described for Example 570.

TABLE 33

| Ex. # | Structure | Name | Retention time (min) | MS (ESI) m/z* |
|---|---|---|---|---|
| 571 | 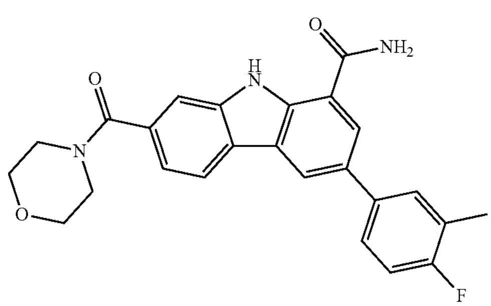 [SMILES: Cc1cc(-c2cc(C(N)=O)c3[nH]c4cc(C(=O)N5CCOCC5)ccc4c3c2)ccc1F] | 3-(4-fluoro-3-methylphenyl)-7-(4-morpholinylcarbonyl)-9H-carbazole-1-carboxamide | 4.38 | 432 |

TABLE 33-continued

| Ex. # | Structure | Name | Retention time (min) | MS (ESI) m/z* |
|---|---|---|---|---|
| 572 | 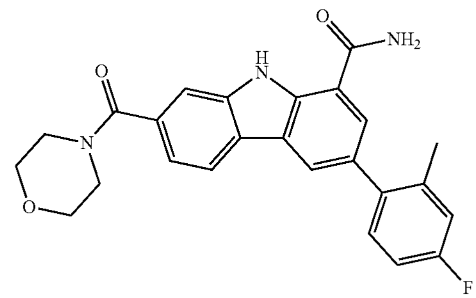 [SMILES: Cc1cc(F)ccc1-c1cc(C(N)=O)c2[nH]c3cc(C(=O)N4CCOCC4)ccc3c2c1] | 3-(4-fluoro-2-methylphenyl)-7-(4-morpholinylcarbonyl)-9H-carbazole-1-carboxamide | 4.27 | 432 |
| 573 | 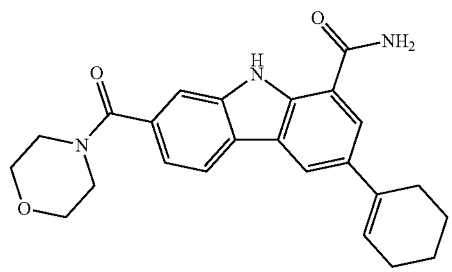 [SMILES: NC(=O)c1cc(C2=CCCCC2)cc2c1[nH]c1cc(C(=O)N3CCOCC3)ccc12] | 3-(1-cyclohexen-1-yl)-7-(4-morpholinylcarbonyl)-9H-carbazole-1-carboxamide | 4.32 | 404 |
| 574 | 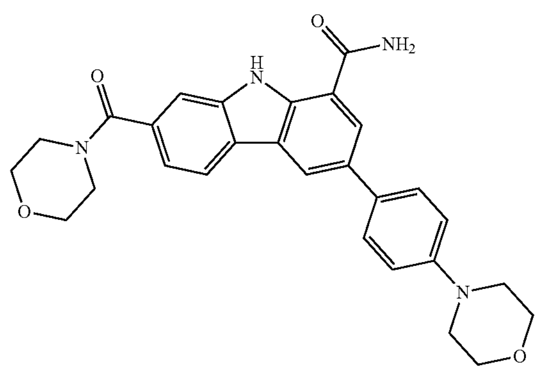 [SMILES: NC(=O)c1cc(-c2ccc(N3CCOCC3)cc2)cc2c1[nH]c1cc(C(=O)N3CCOCC3)ccc12] | 7-(4-morpholinylcarbonyl)-3-(4-(4-morpholinyl)phenyl)-9H-carbazole-1-carboxamide | 3.63 | 485 |
| 575 | 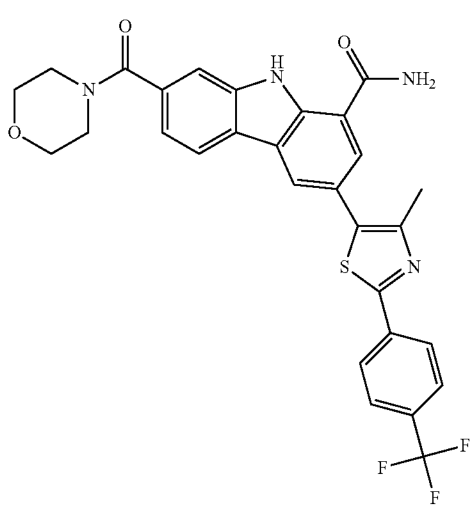 [SMILES: Cc1nc(-c2ccc(C(F)(F)F)cc2)sc1-c1cc(C(N)=O)c2[nH]c3cc(C(=O)N4CCOCC4)ccc3c2c1] | 3-(4-methyl-2-(4-(trifluoromethyl)phenyl)-1,3-thiazol-5-yl)-7-(4-morpholinylcarbonyl)-9H-carbazole-1-carboxamide | 5.22 | 565 |

TABLE 33-continued

| Ex. # | Structure | Name | Retention time (min) | MS (ESI) m/z* |
|---|---|---|---|---|
| 576 | 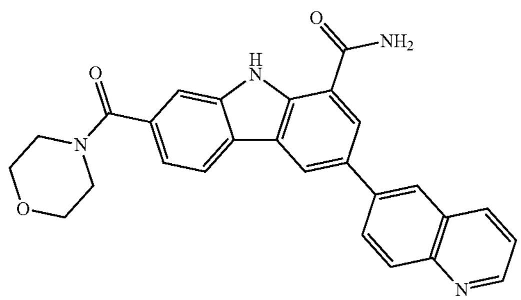 [SMILES: NC(=O)c1cc(-c2ccc3ncccc3c2)cc2c1[nH]c1cc(C(=O)N3CCOCC3)ccc12] | 7-(4-morpholinylcarbonyl)-3-(6-quinolinyl)-9H-carbazole-1-carboxamide | 3.34 | 451 |
| 577 | 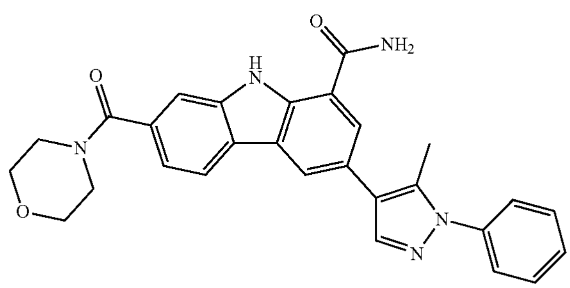 [SMILES: Cc1c(-c2cc(C(N)=O)c3[nH]c4cc(C(=O)N5CCOCC5)ccc4c3c2)cnn1-c1ccccc1] | 3-(5-methyl-1-phenyl-1H-pyrazol-4-yl)-7-(4-morpholinylcarbonyl)-9H-carbazole-1-carboxamide | 3.80 | 480 |
| 578 | 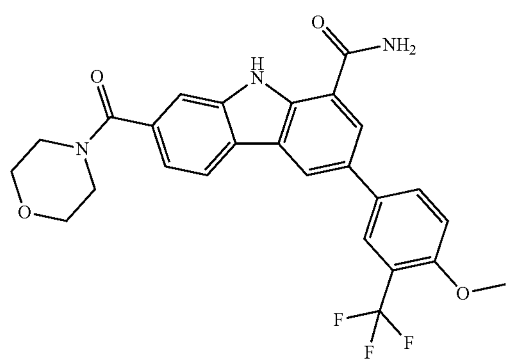 [SMILES: COc1ccc(-c2cc(C(N)=O)c3[nH]c4cc(C(=O)N5CCOCC5)ccc4c3c2)cc1C(F)(F)F] | 3-(4-methoxy-3-(trifluoromethyl)phenyl)-7-(4-morpholinylcarbonyl)-9H-carbazole-1-carboxamide | 4.41 | 498 |
| 579 | 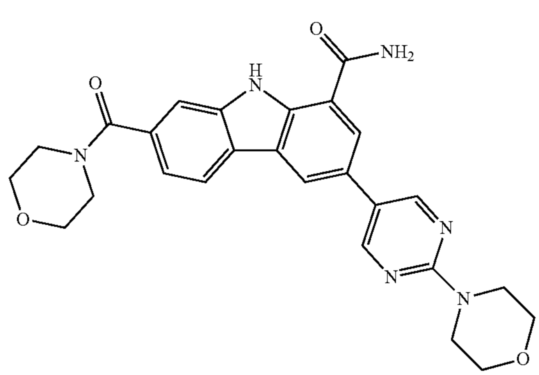 [SMILES: NC(=O)c1cc(-c2cnc(N3CCOCC3)nc2)cc2c1[nH]c1cc(C(=O)N3CCOCC3)ccc12] | 7-(4-morpholinylcarbonyl)-3-(2-(4-morpholinyl)-5-pyrimidinyl)-9H-carbazole-1-carboxamide | 3.25 | 487 |

TABLE 33-continued

| Ex. # | Structure | Name | Retention time (min) | MS (ESI) m/z* |
|---|---|---|---|---|
| 580 | 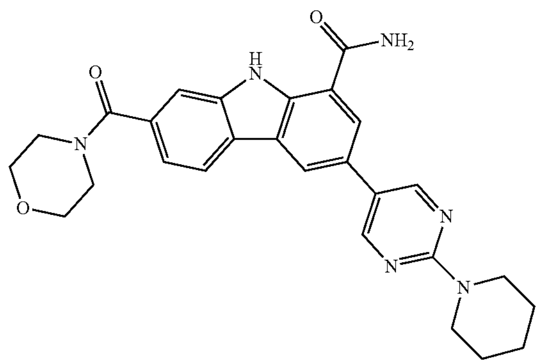 [SMILES: NC(=O)c1cc(-c2cnc(N3CCCCC3)nc2)cc2c1[nH]c1cc(C(=O)N3CCOCC3)ccc12] | 7-(4-morpholinylcarbonyl)-3-(2-(1-piperidinyl)-5-pyrimidinyl)-9H-carbazole-1-carboxamide | 4.26 | 485 |
| 581 | 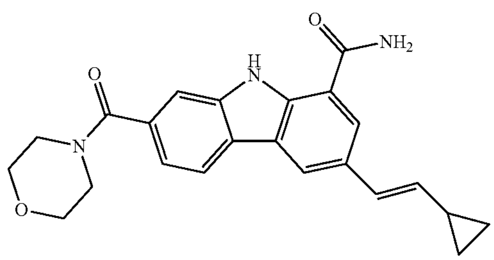 [SMILES: NC(=O)c1cc(/C=C/C2CC2)cc2c1[nH]c1cc(C(=O)N3CCOCC3)ccc12] | 3-((E)-2-cyclopropylvinyl)-7-(4-morpholinylcarbonyl)-9H-carbazole-1-carboxamide | 4.01 | 390 |
| 582 | 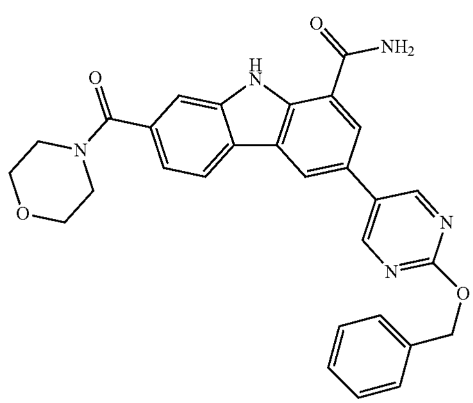 [SMILES: NC(=O)c1cc(-c2cnc(OCc3ccccc3)nc2)cc2c1[nH]c1cc(C(=O)N3CCOCC3)ccc12] | 3-(2-(benzyloxy)-5-pyrimidinyl)-7-(4-morpholinylcarbonyl)-9H-carbazole-1-carboxamide | 4.14 | 508 |
| 583 | 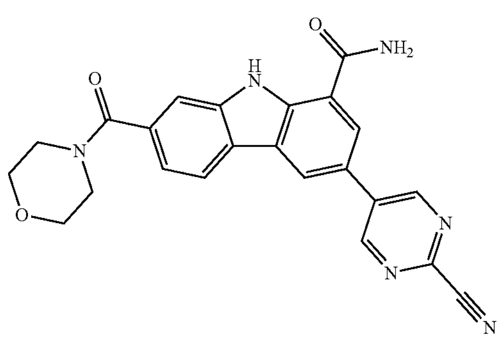 [SMILES: N#Cc1ncc(-c2cc(C(N)=O)c3[nH]c4cc(C(=O)N5CCOCC5)ccc4c3c2)cn1] | 3-(2-cyano-5-pyrimidinyl)-7-(4-morpholinylcarbonyl)-9H-carbazole-1-carboxamide | 5.43 | 427 |

| Ex. # | Structure | Name | Retention time (min) | MS (ESI) m/z* |
|---|---|---|---|---|
| 584 | 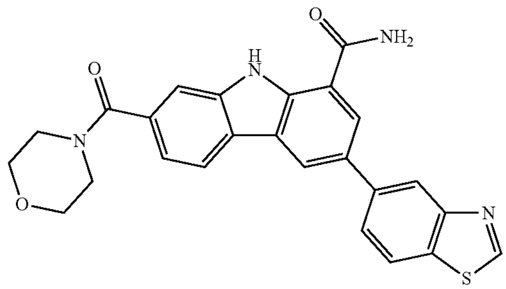 [SMILES: NC(=O)c1cc(-c2ccc3scnc3c2)cc2c1[nH]c1cc(C(=O)N3CCOCC3)ccc12] | 3-(1,3-benzothiazol-5-yl)-7-(4-morpholinylcarbonyl)-9H-carbazole-1-carboxamide | 3.60 | 457 |
| 585 | 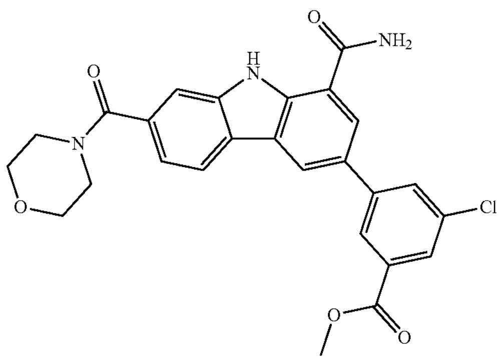 [SMILES: COC(=O)c1cc(Cl)cc(-c2cc(C(N)=O)c3[nH]c4cc(C(=O)N5CCOCC5)ccc4c3c2)c1] | methyl 3-(1-carbamoyl-7-(4-morpholinylcarbonyl)-9H-carbazol-3-yl)-5-chlorobenzoate | 4.46 | 492 |
| 586 | 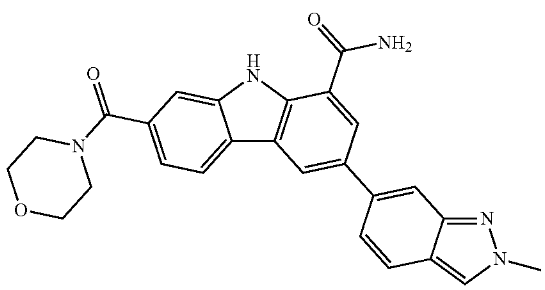 [SMILES: Cn1cc2ccc(-c3cc(C(N)=O)c4[nH]c5cc(C(=O)N6CCOCC6)ccc5c4c3)cc2n1] | 3-(2-methyl-2H-indazol-6-yl)-7-(4-morpholinylcarbonyl)-9H-carbazole-1-carboxamide | 3.21 | 454 |
| 587 | 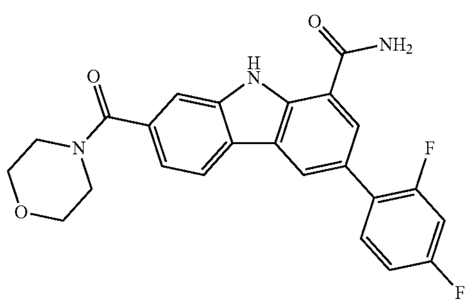 [SMILES: NC(=O)c1cc(-c2ccc(F)cc2F)cc2c1[nH]c1cc(C(=O)N3CCOCC3)ccc12] | 3-(2,4-difluorophenyl)-7-(4-morpholinylcarbonyl)-9H-carbazole-1-carboxamide | 4.02 | 436 |
| 588 | 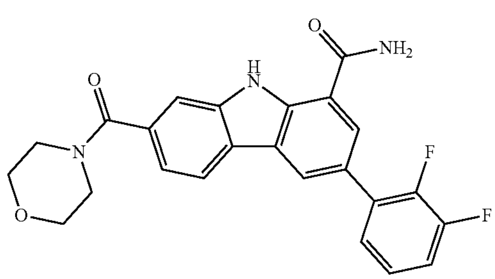 [SMILES: NC(=O)c1cc(-c2cccc(F)c2F)cc2c1[nH]c1cc(C(=O)N3CCOCC3)ccc12] | 3-(2,3-difluorophenyl)-7-(4-morpholinylcarbonyl)-9H-carbazole-1-carboxamide | 4.04 | 436 |

TABLE 33-continued

| Ex. # | Structure | Name | Retention time (min) | MS (ESI) m/z* |
|---|---|---|---|---|
| 589 | 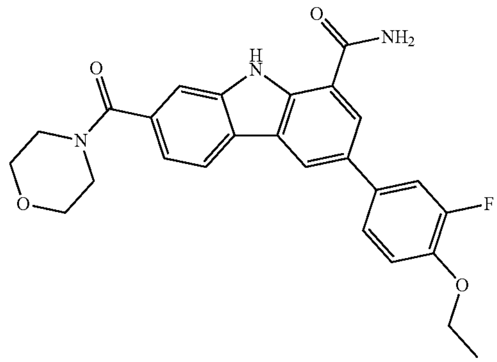 [SMILES: CCOc1ccc(-c2cc(C(N)=O)c3[nH]c4cc(C(=O)N5CCOCC5)ccc4c3c2)cc1F] | 3-(4-ethoxy-3-fluorophenyl)-7-(4-morpholinylcarbonyl)-9H-carbazole-1-carboxamide | 4.31 | 462 |
| 590 | 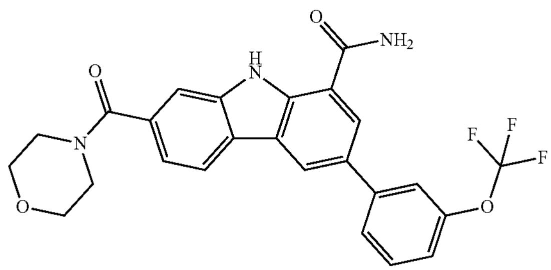 [SMILES: NC(=O)c1cc(-c2cccc(OC(F)(F)F)c2)cc2c1[nH]c1cc(C(=O)N3CCOCC3)ccc12] | 7-(4-morpholinylcarbonyl)-3-(3-(trifluoromethoxy)phenyl)-9H-carbazole-1-carboxamide | 4.63 | 484 |

HPLC conditions: SUPELCO ® Ascentis Express 4.5 × 50 mm 3 um C18, 2 ml/min, 5 to 95% B in 8 minutes, then 95% B for 1 minute.
Solvent A: 5% CH$_3$CN - 95% H$_2$O - 10 mM NH$_4$OAc;
Solvent B: 95% CH$_3$CN - 5% H$_2$O - 10 mM NH$_4$OAc.

All observed MS signals are consistent with [M+H]$^+$.

What is claimed is:

1. A compound of formula I

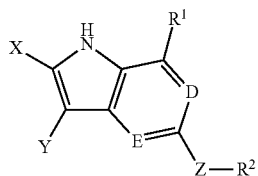

stereoisomers or pharmaceutically acceptable salts, thereof, wherein:
the compound of formula (I) is selected from

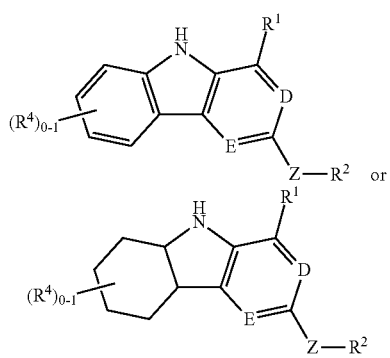

$R^1$ is —CONH$_2$;
D is N or CR$_5$;
E is n or CR$_6$;
Z is a bond, NR, CRR, O, or S;
$R^2$ is $C_{3-8}$ cycloalkyl optionally substituted with 0-3 $R^a$, $C_{6-10}$ aryl substituted with 0-3 $R^a$, or a 5-10 membered heterocyclic system containing 1-4 heteroatoms selected from N, O, and S, substituted with 0-3 $R^a$;
$R^4$ is independently halo, —CO—NR$^7$—R$^8$, —CO—NR$^7$—SO$_2$—R$^8$, —(CH$_2$)$_r$O—R$^{10}$, —(CH$_2$)$_r$OC(O)—R$^{10}$, —NR$^7$R$^8$, —NR—CO—R$^{10}$, —NR—CO—O—R$^9$, NR—CO—O—NR$^7$—R$^8$, or —CO—O—R;
$R^5$ and $R^6$ are independently H, or $C_{1-4}$ alkyl;
R is independently H or $C_{1-4}$ alkyl;
$R^7$ and $R^8$ are independently hydrogen, $C_{1-6}$ alkyl substituted with 0-2 $R^{7a}$, $C_{3-6}$ cycloalkyl substituted with 0-2 $R^{7a}$, a 5-7 membered heterocyclic system containing 1-2 heteroatoms selected from N, O, and S, substituted with 0-2 $R^{7a}$; or a 5-6 membered heteroaryl containing 1-2 heteroatoms selected from N, O, and S, substituted with 0-2 $R^{7a}$; alternatively $R^7$ and $R^8$, along with the nitrogen atom to which they are attached, join to form a 5-10 membered heterocyclic ring containing 0-1 additional heteroatoms selected from N, O or S, substituted with 0-2 $R^{7a}$;
$R^{7a}$ is hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{12}$, —(CH$_2$)$_r$C(O)NR$^{11}$R$^{12}$, —(CH$_2$)$_r$NR$^b$C(O)R$^c$, —(CH$_2$)$_r$NR$^b$C(O)OR$^c$, —NR$^b$C(O)NR$^{11}$R$^{12}$, —S(O)$_p$NR$^{11}$R$^{12}$, —NR$^b$S(O)$_p$R$^c$, —S(O)R$^c$, —S(O)$_2$R$^c$, $C_{1-6}$ alkyl substituted with 0-2 $R^a$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$ substituted with 0-1 $R^a$, alternatively two $R^{7a}$ on adjacent or the same carbon atom form a cyclic acetal of the formula —O—$(CH_2)_n$—O—, wherein n is selected from 1 or 2 and p is selected from 1 or 2;

$R^9$ is $C_{1-6}$ alkyl optionally substituted with 0-1$R^a$, $C_{3-6}$ cycloalkyl optionally substituted with $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^{10}$ is hydrogen, $C_{1-6}$ alkyl optionally substituted with 0-1 $R^a$, $C_{3-6}$ cycloalkyl optionally substituted with 0-1 $R^a$, $C_{6-10}$ aryl substituted with 0-3 $R^a$, or a 5-10 membered heterocyclic system containing 1-4 heteroatoms selected from N, O, and S, substituted with 0-3 $R^a$;

$R^{11}$ and $R^{12}$ are independently hydrogen, $C_{1-6}$ alkyl substituted with 0-1 $R^d$, $C_{3-6}$ cycloalkyl substituted with 0-1 $R^d$, or $(CH_2)_r$-phenyl substituted with 0-1 $R^d$; alternatively $R^{11}$ and $R^{12}$, along with the nitrogen atom to which they are attached, join to form a 5-10 membered heterocyclic ring containing 1-4 heteroatoms selected from N, O, and S;

$R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$, alternatively two $R^a$ on adjacent or the same carbon atom form a cyclic acetal of the formula —O—$(CH_2)_n$—O—, or —O—$CF_2$—O—, wherein n is selected from 1 or 2 and p is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, $NO_2$, —$OR^e$, —$(CH_2)_rC(O)R^b$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

r is 0, 1, 2, 3, or 4.

2. The compound according to claim 1, wherein

D is $CR_5$;
E is N or $CR_6$;
Z is a bond;
$R^2$ is phenyl, naphthyl, pyridyl, or benzodioxolyl, any of which are substituted with 0-3 $R^a$;
$R^4$ is independently halo, —CO—$NR^7$—$R^8$, —$(CH_2)_r$—O—$R^{10}$, —$NR^7R^8$, —NH—CO—$R^{10}$, —NH—CO—O—$R^9$, NH—CO—$NR^7$—$R^8$, or —CO—O—R;
$R^5$ and $R^6$ are H;
$R^7$ and $R^8$ are independently hydrogen; methyl, ethyl, or propyl substituted with 0-2 $R^{7a}$; cyclohexyl substituted with 0-2 $R^{7a}$; piperidinyl, pyrrolidinyl, azetidinyl, tetrahydropyranyl, oxaazobicyclooctanyl, piperidinyl, morpholinyl, ozazabicycloheptanyl, piperazinyl, or diazapenyl substituted with 0-2 $R^{7a}$; the heterocyclic ring being selected from oxaazobicyclooctanyl, piperidinyl, morpholinyl, oxazabicycloheptanyl, piperazinyl, diazapenyl, pyrrolidinyl,

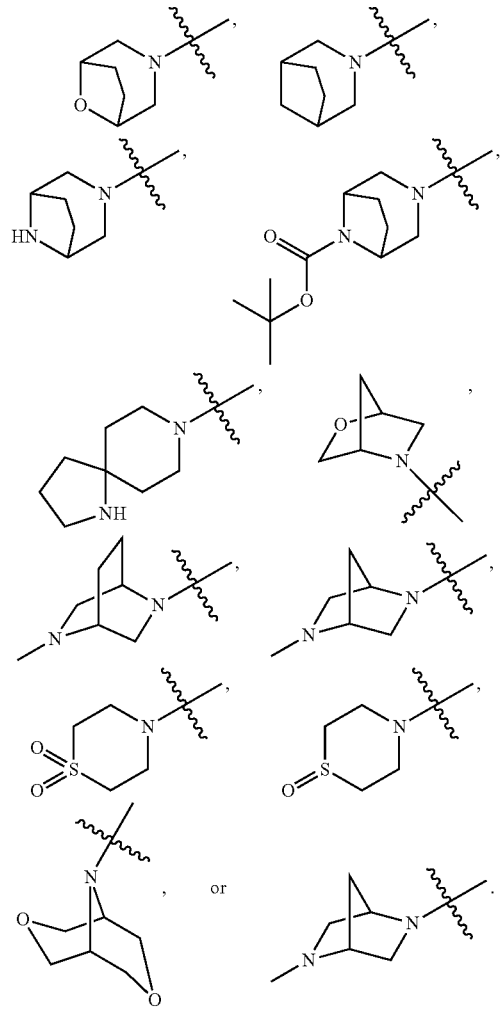

$R^{7a}$ is hydrogen, =O, F, Cl, Br, $CF_3$, CN, $NO_2$, —$(CH_2)_rOR^b$, —$(CH_2)_rC(O)R^b$, —$C(O)OR^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$S(O)_2R^c$, $C_{1-6}$ alkyl, —$(CH_2)_r$-phenyl substituted with 0-1 $R^a$, or —$(CH_2)_r$-5-7 membered heterocycle, wherein the heterocycle is selected from piperidinyl, pyridinyl, pyrrolyl, morpholinyl, piperazinyl, or imidazolyl; alternatively two $R^{7a}$ on adjacent or the same carbon atom form a cyclic acetal of the formula —O—$(CH_2)_n$—O—, wherein n is selected from 1 or 2 and p is selected from 1 or 2;

$R^9$ is selected from methyl, ethyl, propyl, isopropyl, butyl, and t-butyl optionally substituted with 0-1 $R^a$; or piperidinyl; and $R^{10}$ is hydrogen, methyl, ethyl, propyl, isopropyl or butyl; or piperidinyl substituted with 0-1 $R^a$.

3. The compound according to claim 2, wherein $R^a$ is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-14 membered carbocycle, or —$(CH_2)_r$-5-7 membered heterocycle, wherein the heterocycle is selected from pyrrolidinyl, morpholinyl, pyridinyl, or piperizinyl substituted with 0-2 $R^b$, alternatively two $R^a$ on adjacent or the same carbon atom form a cyclic acetal of the formula —O—$(CH_2)_n$—O—, or —O—$CF_2$—O—, wherein n is selected from 1 or 2 and p is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, $NO_2$, —$OR^e$, —$(CH_2)_rC(O)R^b$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

r is 0, 1, 2, or 3.

4. The compound according to claim 3, wherein the compound of formula (I) is

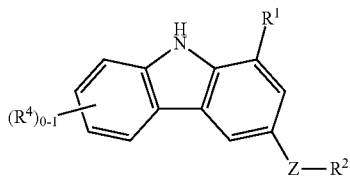

or pharmaceutically acceptable salt thereof.

5. The compound according to claim 1, wherein the compound of formula (I) is

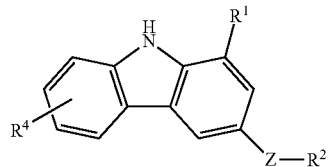

or pharmaceutically acceptable salt thereof, wherein Z is a bond;

$R^2$ is phenyl substituted with 0-3 $R^a$, or a 5-10 membered heterocyclic system, wherein the heterocyclic system is pyridyl, indazolyl, pyrazolyl, furanyl, thiazolyl, indolyl, or thiophenyl substituted with 0-3 $R^a$;

$R^4$ is independently halo, —CO—$NR^7$—$R^8$, —CO—$NR^7$—$SO_2$—$R^8$, —$(CH_2)_rOC(O)$—$R^{10}$, —$NR^7R^8$, —NR—CO—$R^{10}$, —NR—CO—O—$R^9$, NR—CO—$NR^7$—$R^8$, —CO—O—R;

$R^{7a}$ is hydrogen, F, Cl, Br, CN, $NO_2$, —$(CH_2)_rOR^b$, —$C(O)R^b$, —$C(O)OR^b$, —$(CH_2)_rNR^{11}R^{12}$, —$NR^bC(O)OR^c$, $C_{1-6}$ alkyl substituted with 0-2 $R^a$, or —$(CH_2)_r$-phenyl substituted with 0-1 $R^a$, or morpholinyl or piperidinyl substituted with 0-2 $R^a$, alternatively two $R^{7a}$ on adjacent or the same carbon atom form a cyclic acetal of the formula —O—$(CH_2)_n$—O—, wherein n is selected from 1 or 2;

$R^{11}$ and $R^{12}$ are independently hydrogen, or $C_{1-4}$ alkyl substituted with 0-1 $R^d$;

$R^a$ is hydrogen, F, Cl, Br, $OCF_3$, $CF_3$, $CHF_2$, CN, —$(CH_2)_rOR^b$, —$C(O)R^b$, —$C(O)OR^b$, $OC(O)R^b$, —$(CH_2)_rNR^{11}R^{12}$, —$(CH_2)_rC(O)NR^{11}R^{12}$, —$(CH_2)_rNR^bC(O)R^c$, —$(CH_2)_rNR^bC(O)OR^c$, —$NR^bC(O)NR^{11}R^{12}$, —$S(O)_pNR^{11}R^{12}$, —$NR^bS(O)_pR^c$, —$S(O)R^c$, —$S(O)_2R^c$, $C_{1-6}$ alkyl, $C_{1-6}$ haloalkyl, cyclopropyl, cyclohexyl, pyrrolidinyl, morpholinyl, pyridinyl, or piperizinyl substituted with 0-2 $R^b$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is hydrogen, $C_{1-6}$ alkyl substituted with 0-2 $R^d$, $C_{1-6}$ halolalkyl, $C_{3-6}$ cycloalkyl substituted with 0-2 $R^d$, or $(CH_2)_r$-phenyl substituted with 0-2 $R^d$; and r is 0, 1, 2, or 3.

6. A pharmaceutical composition comprising one or more compounds of claim 1 and a pharmaceutically acceptable carrier therefore.

* * * * *